(12) United States Patent
Kiyoto et al.

(10) Patent No.: US 8,367,831 B2
(45) Date of Patent: Feb. 5, 2013

(54) HETEROCYCLIC COMPOUND OR SALT THEREOF AND INTERMEDIATE THEREOF

(75) Inventors: Taro Kiyoto, Toyama (JP); Junichi Ando, Toyama (JP); Tadashi Tanaka, Toyama (JP); Yasuhiro Tsutsui, Toyama (JP); Mai Yokotani, Toyama (JP); Toshiya Noguchi, Toshima-ku (JP); Fumihito Ushiyama, Toshima-ku (JP); Hiroki Urabe, Toshima-ku (JP); Hiromasa Horikiri, Toshima-ku (JP)

(73) Assignees: Toyama Chemical Co., Ltd., Tokyo (JP); Taisho Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 13/468,140

(22) Filed: May 10, 2012

(65) Prior Publication Data

US 2012/0226035 A1 Sep. 6, 2012

Related U.S. Application Data

(62) Division of application No. 12/302,451, filed as application No. PCT/JP2007/060606 on May 24, 2007, now Pat. No. 8,211,908.

(30) Foreign Application Priority Data

May 26, 2006 (JP) .................................. 2006-146588

(51) Int. Cl.
C07D 471/04 (2006.01)
(52) U.S. Cl. ...................................................... 546/123
(58) Field of Classification Search .................... 546/123
See application file for complete search history.

(56) References Cited

U.S. PATENT DOCUMENTS

| | | | |
|---|---|---|---|
| 5,801,183 | A | 9/1998 | Keana et al. |
| 6,696,565 | B2 | 2/2004 | Fenniri |
| 7,875,715 | B2 | 1/2011 | Breault et al. |
| 8,211,908 | B2 | 7/2012 | Kiyoto et al. |
| 2002/0151556 | A1 | 10/2002 | Fenniri |
| 2005/0131230 | A1 | 6/2005 | Fenniri |
| 2006/0189604 | A1 | 8/2006 | Axten et al. |
| 2006/0229336 | A1 | 10/2006 | Kazmierski et al. |
| 2010/0168418 | A1 | 7/2010 | Kiyoto et al. |
| 2010/0249417 | A1 | 9/2010 | Kiyoto et al. |

FOREIGN PATENT DOCUMENTS

| | | |
|---|---|---|
| CA | 1088659 | 10/1980 |
| WO | WO 99/07682 | 2/1999 |
| WO | WO 02/066482 | 8/2002 |
| WO | WO 02/096907 A1 | 12/2002 |
| WO | WO 2004/002490 | 1/2004 |
| WO | WO 2004/002992 | 1/2004 |
| WO | WO 2004/054974 | 7/2004 |
| WO | WO 2005/077050 | 8/2005 |
| WO | WO 2006/012396 A1 | 2/2006 |
| WO | WO 2006/014580 A1 | 2/2006 |
| WO | WO 2006/017468 A2 | 2/2006 |
| WO | WO 2006/017468 A3 | 2/2006 |
| WO | WO 2006/046552 | 5/2006 |
| WO | WO 2006/125974 A1 | 11/2006 |
| WO | WO 2006/134378 A1 | 12/2006 |
| WO | WO 2006/137485 | 12/2006 |
| WO | WO 2008/009700 A1 | 1/2008 |
| WO | WO 2008/071962 A1 | 6/2008 |
| WO | WO 2008/071964 A1 | 6/2008 |
| WO | WO 2009/001126 A1 | 12/2008 |

OTHER PUBLICATIONS

U.S. Appl. No. 13/463,434, filed May 3, 2012, Kiyoto, et al.
Australian Office Action issued Jan. 10, 2012, in Patent Application No. 2007268749.
CAS Registry No. 28252-73-5, Nov. 16, 1984.
CAS Registry No. 788765-24-2, Nov. 25, 2004.
CAS Registry No. 767571-26-6, Oct. 22, 2004.

*Primary Examiner* — Rebecca Anderson
*Assistant Examiner* — Samantha Shterengarts
(74) *Attorney, Agent, or Firm* — Oblon, Spivak, McClelland, Maier & Neustadt, L.L.P.

(57) ABSTRACT

Disclosed is a compound represented by the general formula:

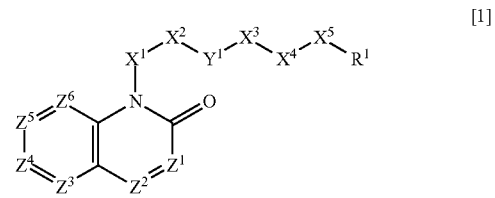

[1]

wherein $R^1$ represents an aryl or heterocyclic group which may be substituted or the like; $X^1$ represents a $C_2$-$C_4$ alkylene group or the like; $X^2$, $X^3$ and $X^5$ independently represent NH, a bond or the like; $X^4$ represents a lower alkylene group, a bond or the like; $Y^1$ represents a bivalent alicyclic hydrocarbon residue which may be substituted or a bivalent alicyclic amine residue which may be substituted; and $Z^1$, $Z^2$, $Z^3$, $Z^4$, $Z^5$ and $Z^6$ independently represent a nitrogen atom, a group represented by the formula: CH, or the like, provided that at least one of $Z^3$, $Z^4$, $Z^5$ and $Z^6$ represents a nitrogen atom, or a salt thereof, which is useful as an antibacterial agent.

6 Claims, No Drawings

HETEROCYCLIC COMPOUND OR SALT THEREOF AND INTERMEDIATE THEREOF

CROSS-REFERENCE TO RELATED APPLICATIONS

The present application is division of U.S. Pat. No. 12/302,451, filed Nov. 25, 2008, which is a National Stage (371) of PCT/JP2007/060606, filed on May 24, 2007, and claims priority to JP 2006-146588, filed on May 26, 2006.

TECHNICAL FIELD

The present invention relates to novel compounds or salts thereof that have strong antimicrobial activity against gram-positive bacteria, gram-negative bacteria and resistant bacteria, and relates to antimicrobial agents containing such compounds or salts. The present invention further relates to intermediates useful for producing such compounds.

BACKGROUND ART

In clinical practice, various types of antibiotics and synthetic antimicrobial agents have been used for treating infectious diseases. However, recently, resistant bacteria such as methicillin-resistant *Staphylococcus aureus* (MRSA), vancomycin-resistant *Enterococcus* (VRE), and penicillin-resistant *Streptococcus pneumoniae* (PRSP) have been reported, and therapeutic treatment of patients infected with such resistant bacteria is a critical issue. In addition, multidrug-resistant bacteria, which have developed resistance to a plurality of drugs, have appeared. Infectious diseases due to multidrug-resistant bacteria are intractable and are severe problems worldwide.

The development of antibiotics effective on these resistant bacteria has been strongly desired, and, for example, International Patent Publication No. WO 99/07682 (Patent Document 1) discloses quinolone compounds that are effective against MRSA. International Patent Publication No. WO 2004/002490 (Patent Document 2) and WO 2004/002992 (Patent Document 3) disclose compounds of which the working mechanisms are different from those of conventional medicaments.

Patent Document 1: International Patent Publication No. WO 99/07682

Patent Document 2: International Patent Publication No. WO 2004/002490

Patent Document 3: International Patent Publication No. WO 2004/002992

DISCLOSURE OF THE INVENTION

The development of a medicament having strong antimicrobial activity against gram-positive bacteria, gram-negative bacteria, and resistant bacteria and having high safety has been desired. Furthermore, an intermediate useful for producing this medicament is highly desired.

Under such circumstances, the present inventors have conducted intensive studies and, as a result, have found that a compound represented by a general formula [1]:

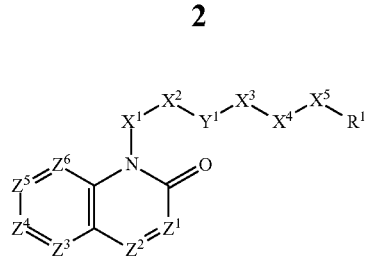

(wherein $R^1$ denotes an optionally substituted $C_2$-$C_{12}$ alkyl, aryl or heterocyclic group; $X^1$ denotes an optionally substituted $C_2$-$C_4$ alkylene group; $X^2$ denotes a group represented by a general formula $NR^2$ (where $R^2$ denotes a hydrogen atom, an optionally substituted lower alkyl group or an imino-protecting group) or a bond; $X^3$ denotes a group represented by a general formula $NR^3$ or $CR^4R^5NR^3$ (where $R^3$ denotes a hydrogen atom, an optionally substituted lower alkyl group or an imino-protecting group; and $R^4$ and $R^5$ are the same or different and are each a hydrogen atom or an optionally substituted lower alkyl group, or $R^4$ and $R^5$ together form an oxo group) or a bond; $X^4$ denotes an optionally substituted lower alkylene, lower alkenylene or lower alkynylene group or a bond; $X^5$ denotes an oxygen atom, a sulfur atom, a sulfinyl group, a sulfonyl group, a group represented by a general formula $NR^6$ (where $R^6$ denotes a hydrogen atom, an optionally substituted lower alkyl, lower alkenyl or lower alkynyl group or an imino-protecting group) or a bond; $Y^1$ denotes an optionally substituted bivalent alicyclic hydrocarbon residue or an optionally substituted bivalent alicyclic amine residue; $Z^1$, $Z^2$, $Z^3$, $Z^4$, $Z^5$ and $Z^6$ are the same or different and are each a nitrogen atom or a group represented by a general formula $CR^7$ (where $R^7$ denotes a hydrogen atom, a halogen atom, a hydroxyl group, a cyano group, a nitro group, a formyl group, an optionally protected or substituted amino group, an optionally substituted lower alkyl, cycloalkyl, aryl, lower alkoxy, cycloalkyloxy, aralkyloxy, alkanoyl, ureido or monocyclic heterocyclic group, or a group represented by a general formula $Q^1CONR^8R^9$, $Q^1CO_2R^{10}$ or $Q^1CN$ (where $R^8$ and $R^9$ are the same or different and are each a hydrogen atom, an optionally substituted lower alkyl, cycloalkyl, aralkyl, aryl, lower alkoxy, alkanesulfonyl or monocyclic heterocyclic group, or form, together with the nitrogen atom to which $R^8$ and $R^9$ bind, an optionally substituted cyclic amino group; $R^{10}$ denotes a hydrogen atom or a carboxyl-protecting group; and $Q^1$ denotes an optionally substituted lower alkylene or lower alkenylene group or a bond)), provided that at least one of $Z^3$, $Z^4$, $Z^5$ and $Z^6$ is a nitrogen atom) or a salt thereof has strong antimicrobial activity and high safety; and that a compound represented by a general formula [2]:

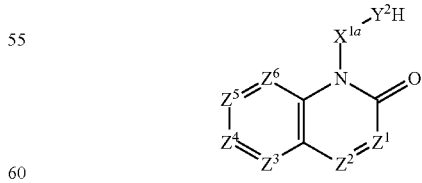

(wherein $X^{1a}$ denotes an optionally substituted $C_1$-$C_3$ alkylene group; $Y^2$ denotes an optionally protected carbonyl group; $Z^1$, $Z^2$, $Z^3$, $Z^4$, $Z^5$ and $Z^6$ have the same meanings as mentioned above; and at least one of $Z^3$, $Z^4$, $Z^5$ and $Z^6$ denotes a nitrogen atom) and a compound represented by a general formula [3]:

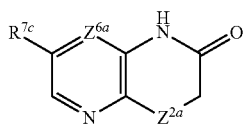

(wherein $R^{7c}$ denotes a halogen atom, a hydroxyl group, a cyano group, a nitro group, a formyl group, an optionally protected or substituted amino group, an optionally substituted lower alkyl, cycloalkyl, aryl, lower alkoxy, cycloalkyloxy, aralkyloxy, alkanoyl, ureido or monocyclic heterocyclic group, or a group represented by a general formula $Q^1CONR^8R^9$, $Q^1CO_2R^{10}$ or $Q^1CN$ (where $R^8$, $R^9$, $R^{10}$, and $Q^1$ have the same meanings as mentioned above); $Z^{2a}$ and $Z^{6a}$ are the same or different and are each a nitrogen atom or a group represented by a general formula $CR^2$ (where $R^7$ has the same meaning as mentioned above)) are useful intermediates for the production of the compound of the general formula [1]. The present invention has been accordingly completed.

The compound of the general formula [1] or a salt thereof has strong antimicrobial activity against gram-positive bacteria, gram-negative bacteria and resistant bacteria, and has high safety and is therefore useful as an excellent antimicrobial agent.

The compounds of the general formulas [2] and [3] are useful as intermediates for producing the compound of the general formula [1].

BEST MODE FOR CARRYING OUT THE INVENTION

The compound of the present invention will be described in detail.

In this description, unless otherwise specified, a halogen atom denotes a fluorine atom, a chlorine atom, a bromine atom or a iodine atom; an alkyl group denotes, for example, a straight-chain or branched-chain $C_{1-12}$ alkyl group such as methyl, ethyl, propyl, isopropyl, butyl, sec-butyl, isobutyl, tert-butyl, pentyl, hexyl and octyl; a $C_2$-$C_{12}$ alkyl group denotes, for example, a straight-chain or branched-chain $C_{2-12}$ alkyl group such as ethyl, propyl, isopropyl, butyl, sec-butyl, isobutyl, tert-butyl, pentyl, hexyl and octyl; a lower alkyl group denotes, for example, a straight-chain or branched-chain $C_{1-6}$ alkyl group such as methyl, ethyl, propyl, isopropyl, butyl, sec-butyl, isobutyl, tert-butyl, pentyl and isopentyl; an alkenyl group denotes, for example, a straight-chain or branched-chain $C_{2-12}$ alkenyl group such as vinyl, allyl, propenyl, isopropenyl, butenyl, isobutenyl, pentenyl, hexenyl, heptenyl and octenyl; a lower alkenyl group denotes, for example, a straight-chain or branched-chain $C_{2-6}$ alkenyl group such as vinyl, allyl, propenyl, isopropenyl, butenyl, isobutenyl, pentenyl and hexenyl; a lower alkynyl group denotes, for example, a straight-chain or branched-chain $C_{2-6}$ alkynyl group such as ethynyl, 2-propynyl and 2-butynyl;

A cycloalkyl group denotes, for example, a $C_{3-8}$ cycloalkyl group such as cyclopropyl, cyclobutyl, cyclopentyl and cyclohexyl; an aryl group denotes, for example, such a group as phenyl, naphthyl, anthracenyl and phenanthrenyl; an aralkyl group denotes, for example, an ar-$C_{1-8}$ alkyl group such as benzyl, diphenylmethyl, trityl, phenethyl and naphthylmethyl;

A lower alkoxy group denotes, for example, a straight-chain or branched-chain $C_{1-6}$ alkyloxy group such as methoxy, ethoxy, propoxy, isopropoxy, butoxy, isobutoxy, sec-butoxy, tert-butoxy, pentyloxy and isopentyloxy; a cycloalkyloxy group denotes, for example, a $C_{3-8}$ cycloalkyloxy group such as cyclopropyloxy, cyclobutyloxy, cyclopentyloxy and cyclohexyloxy; an aralkyloxy group denotes, for example, an ar-$C_{1-6}$ alkyloxy group such as benzyloxy and phenethyloxy; an alkoxyalkyl group denotes, for example, a $C_{1-6}$ alkyloxy $C_{1-6}$ alkyl group such as methoxymethyl and 1-ethoxyethyl; an aralkyloxyalkyl group denotes, for example, an ar-$C_{1-6}$ alkyloxy $C_{1-6}$ alkyl group such as benzyloxymethyl and phenethyloxymethyl;

A lower alkylene group denotes, for example, a $C_{1-6}$ alkylene group such as methylene, ethylene, propylene, butylene and hexylene; a $C_2$-$C_4$ alkylene group denotes, for example, a $C_{2-4}$ alkylene group such as ethylene, propylene and butylene; a $C_1$-$C_3$ alkylene group denotes, for example, a $C_{1-3}$ alkylene group such as methylene, ethylene and propylene; a lower alkenylene group denotes, for example, a $C_{2-6}$ alkenylene group such as vinylene, propenylene, butenylene and pentenylene; a lower alkynylene group denotes, for example, a $C_{2-6}$ alkynylene group such as ethynylene, propynylene, butynylene and pentynylene;

An alkanoyl group denotes, for example, a straight-chain or branched-chain $C_{2-12}$ alkanoyl group such as acetyl, propionyl, butyryl, isovaleryl and pivaloyl; an acyl group denotes, for example, a formyl group, a straight-chain or branched-chain $C_{2-12}$ alkanoyl group such as acetyl, propionyl, butyryl, isovaleryl and pivaloyl, an ar-$C_{1-6}$ alkylcarbonyl group such as benzylcarbonyl, a cyclic hydrocarbon-carbonyl group such as benzoyl and naphthoyl, a heterocyclic carbonyl group such as nicotinoyl, thenoyl, pyrrolidinocarbonyl and furoyl, a succinyl group, a glutaryl group, a maleoyl group, a phthaloyl group, and a straight-chain or branched-chain α-aminoalkanoyl group having an optionally protected N-terminal, which is derived from an amino acid (the amino acid is, for example, glycine, alanine, valine, leucine, isoleucine, serine, threonine, cysteine, methionine, aspartic acid, glutamic acid, asparagine, glutamine, arginine, lysine, histidine, hydroxylysine, phenylalanine, tyrosine, tryptophan, proline and hydroxyproline);

An acylalkyl group denotes, for example, such a group as acetylmethyl, benzoylmethyl, p-nitrobenzoylmethyl, p-bromobenzoylmethyl, p-methoxybenzoylmethyl and 1-benzoylethyl; an acyloxy group denotes, for example, a straight-chain or branched-chain $C_{2-6}$ alkanoyloxy group such as acetyloxy and propionyloxy, and an aroyloxy group such as benzoyloxy; an acyloxyalkyl group denotes, for example, such a group as acetoxymethyl, propionyloxymethyl and pivaloyloxymethyl;

An alkyloxycarbonyl group denotes, for example, a straight-chain or branched-chain $C_{1-12}$ alkyloxycarbonyl group such as methoxycarbonyl, ethoxycarbonyl, 1,1-dimethylpropoxycarbonyl, isopropoxycarbonyl, 2-ethylhexyloxycarbonyl, tert-butoxycarbonyl and tert-pentyloxycarbonyl; an aralkyloxycarbonyl group denotes, for example, an ar-$C_{1-6}$ alkyloxycarbonyl group such as benzyloxycarbonyl and phenethyloxycarbonyl; an aryloxycarbonyl group denotes, for example, a phenyloxycarbonyl group;

An alkylthio group denotes, for example, a $C_{1-6}$ alkylthio group such as methylthio, ethylthio and propylthio; an arylthio group denotes, for example, a phenylthio group; an alkylthioalkyl group denotes, for example, a $C_{1-6}$ alkylthio $C_{1-6}$ alkyl group such as methylthiomethyl, ethylthiomethyl and propylthiomethyl; an arylthioalkyl group denotes, for example, such a group as (phenylthio)methyl and 2-(p-nitrophenylthio)ethyl; an alkanesulfonyl group denotes, for example, a $C_{1-6}$ alkanesulfonyl group such as methanesulfonyl, trifluoromethanesulfonyl, ethanesulfonyl and propanesulfonyl; an arylsulfonyl group denotes, for example, such a group as benzenesulfonyl, toluenesulfonyl and naphthalenesulfonyl;

An arylsulfonylalkyl group denotes, for example, a p-toluenesulfonylethyl group; an alkanesulfonyloxy group denotes a $C_{1-6}$ alkanesulfonyloxy group such as methanesulfonyloxy, trifluoromethanesulfonyloxy and ethanesulfonyloxy; an arylsulfonyloxy group denotes, for example, such a group as benzenesulfonyloxy and toluenesulfonyloxy;

A lower alkylamino group denotes, for example, a mono-$C_{1-6}$ alkylamino group such as methylamino, ethylamino, propylamino, isopropylamino, butylamino, tert-butylamino and pentylamino, a $C_{3-6}$ cycloalkylamino group such as cyclopropylamino, cyclobutylamino and cyclopentylamino, and a di-$C_{1-6}$ alkylamino group such as dimethylamino, diethylamino, dipropylamino and dibutylamino; a cyclic amino group denotes, for example, such a group as piperazinyl, piperidinyl, morpholino and pyrrolidinyl; an oxygen-containing heterocyclic group denotes, for example, such a group as 2-tetrahydropyranyl and 2-tetrahydrofuranyl; a sulfur-containing heterocyclic group denotes, for example, a tetrahydrothiopyranyl group;

An oxygen-containing heterocyclic alkyl group denotes, for example, a 5-methyl-2-oxo-2H-1,3-dioxol-4-ylmethyl group; a nitrogen-containing heterocyclic alkyl group denotes, for example, such a group as phthalimidomethyl and succinimidomethyl; a heterocyclicoxycarbonyl group denotes, for example, such a group as 2-furfuryloxycarbonyl and 8-quinolyloxycarbonyl;

A cycloalkylidene group denotes, for example, such a group as cyclopentylidene and cyclohexylidene; an aralkylidene group denotes, for example, such a group as benzylidene and naphthylmethylene; a dialkylaminoalkylidene group denotes, for example, such a group as N,N-dimethylaminomethylene and N,N-diethylaminomethylene; a nitrogen-containing heterocyclic alkylidene group denotes, for example, a 3-hydroxy-4-pyridylmethylene group;

A diarylphosphoryl group denotes, for example, a diphenylphosphoryl group; a di(aralkyl)phosphoryl group denotes, for example, a dibenzylphosphoryl group; a substituted silyl group denotes, for example, such a group as trimethylsilyl, triethylsilyl and tributylsilyl; an alkylsilylalkyl group denotes, for example, a 2-(trimethylsilyl)ethyl group;

A monocyclic heterocyclic group denotes, for example, such a group as furyl, furfuryl, thienyl, 2-thenyl, 2-pyrrolyl, imidazolyl, 3-pyrazolyl, thiazolyl, isothiazolyl, oxazolyl, isoxazolyl, thiadiazolyl, furazonyl, pyrrolidinyl, imidazolidinyl, pyridyl, pyrimidinyl, pyridazinyl, pyrazinyl, piperazinyl, 2-piperidyl, 3-piperidyl, 4-piperidyl, 2-piperazinyl, 2-morpholinyl, 2-thiomorpholinyl and pyranyl; a bicyclic heterocyclic group denotes, for example, such a group as benzofuranyl, isobenzofuranyl, benzothienyl, indolyl, isoindolyl, indolizinyl, benzimidazolyl, benzoxazolyl, benzisoxazolyl, benzothiazolyl, 1H-indazolyl, purinyl, coumarinyl, chromenyl, quinolyl, isoquinolyl, phthalazinyl, naphthyridinyl, quinoxalinyl, quinazolinyl, cinnolinyl, chromanyl, isochromanyl, quinuclidinyl, 1,3-benzodioxanyl, 1,4-benzodioxanyl, benzomorpholinyl, benzomorpholonyl, 2,3-dihydro(1,4)dioxino(2,3-c)pyridin-7-yl, 3,4-dihydro-2H-pyrido(4,3-b)(1,4)oxazin-7-yl, 3-oxo-3,4-dihydro-2H-pyrido(3,2-b)(1,4)oxazin-6-yl, 3-oxo-3,4-dihydro-2H-pyrido(3,2-b)(1,4)thiazin-6-yl, 3-oxo-3,4-dihydro-2H-benzothiazin-6-yl, 3,4-dihydro-2H-pyrano(2,3-c)pyridin-6-yl, 3,4-dihydro-2H-(1,4)dioxepino(2,3-c)pyridin-8-yl, (1,3)dioxolo(4,5-c)pyridin-6-yl, 6-oxide-2,3-dihydro(1,4)dioxino(2,3-c)pyridin-7-yl, 7-oxo-5,6,7,8-tetrahydro-1,8-naphthyridin-2-yl and 5,6,7,8-tetrahydroquinoxalin-2-yl; a tricyclic heterocyclic group denotes, for example, such a group as thianthren-2-yl, xanthen-2-yl, phenoxathiin-2-yl, 4aH-carbazol-2-yl, carbazol-2-yl, phenanthridin-3-yl, acridin-2-yl, perimidin-2-yl, phenanthrolin-3-yl, phenazin-1-yl, phenothiazin-2-yl, phenoxazin-2-yl and 2,3-dihydro-5-oxo-(1H,5H)-benzo(IJ)quinolin-6-yl; a heterocyclic group denotes, for example, the above-mentioned monocyclic heterocyclic, bicyclic heterocyclic or tricyclic heterocyclic group;

A protected carbonyl group denotes, for example, a group composed of a carbonyl group and an alcohol, such as (hydroxy)(methoxy)methylene, (hydroxy)(ethoxy)methylene, (hydroxy)(propoxy)methylene, (hydroxy)(isopropoxy)methylene, (hydroxy)(butoxy)methylene, (hydroxy)(pentyloxy)methylene, (hydroxy)(hexyloxy)methylene, (hydroxy)(heptyloxy)methylene, (hydroxy)(octyloxy)methylene, (hydroxy)(1,1-dimethylpropoxy)methylene, dimethoxymethylene, diethoxymethylene, dipropoxymethylene, diisopropoxymethylene, dibutoxymethylene, bis(benzyloxy)methylene, 1,3-dioxolan-2-ylidene and 1,3-dioxan-2-ylidene, a group composed of a carbonyl group and a thiol, such as bis(methylthio)methylene, bis(ethylthio)methylene, bis(benzylthio)methylene, 1,3-dithiolan-2-ylidene and 1,3-dithian-2-ylidene, and such a group as oxazolin-2-ylidene, imidazolidin-2-ylidene and thiazolidin-2-ylidene;

A bivalent alicyclic hydrocarbon residue denotes, for example, a $C_{3-8}$ cycloalkylene residue such as 1,2-cyclobutylene, 1,3-cyclobutylene, 1,2-cyclopentylene, 1,3-cyclopentylene, 1,2-cyclohexylene, 1,3-cyclohexylene, and 1,4-cyclohexylene, and a cross-linked $C_{3-6}$ cycloalkylene residue such as bicyclo(3.2.1)octylene, bicyclo(2.2.0)hexylene and bicyclo(5.2.0)nonylene; a bivalent 4-, 5- or 6-membered alicyclic hydrocarbon residue denotes, for example, a $C_{4-6}$ cycloalkylene residue such as 1,2-cyclobutylene, 1,3-cyclobutylene, 1,2-cyclopentylene, 1,3-cyclopentylene, 1,2-cyclohexylene, 1,3-cyclohexylene, and 1,4-cyclohexylene, and a cross-linked $C_{4-6}$ cycloalkylene residue such as bicyclo(3.2.1)octylene and bicyclo(2.2.0)hexylene;

A bivalent alicyclic amine residue denotes, for example, a 4-membered alicyclic amine residue such as azetidine-1,2-diyl and azetidine-1,3-diyl, a monocyclic 5-membered alicyclic amine residue such as pyrrolidine-1,2-diyl and pyrrolidine-1,3-diyl, a cross-linked 5-membered alicyclic amine residue such as 3-azabicyclo(3.1.0)hexane-3,5-diyl, 3-azabicyclo(3.1.0)hexane-3,6-diyl, 8-azabicyclo(3.2.1)octane-3,8-diyl, octahydrocyclopenta(c)pyrrole-2,4-diyl, octahydrocyclopenta(c)pyrrole-2,5-diyl, octahydropyrrolo(3,4-c)pyrrole-2,4-diyl and octahydropyrrolo(3,4-c)pyrrole-2,5-diyl, a monocyclic 6-membered alicyclic amine residue such as piperidine-1,3-diyl, piperidine-1,4-diyl, piperazine-1,3-diyl, piperazine-1,4-diyl, morpholine-2,4-diyl and thiomorpholine-2,4-diyl, a cross-linked 6-membered alicyclic amine residue such as 3-azabicyclo(4.1.0)heptane-3,6-diyl and hexahydroimidazo(1,5-a)pyrazine-2,7-diyl, and a homopiperazine-1,4-diyl group;

A bivalent 5-membered alicyclic amine residue denotes, for example, a monocyclic 5-membered alicyclic amine residue such as pyrrolidine-1,2-diyl and pyrrolidine-1,3-diyl, and a cross-linked 5-membered alicyclic amine residue such as 3-azabicyclo(3.1.0)hexane-3,5-diyl, 3-azabicyclo(3.1.0)hexane-3,6-diyl, 8-azabicyclo(3.2.1)octane-3,8-diyl, octahydrocyclopenta(c)pyrrole-2,4-diyl, octahydrocyclopenta(c)pyrrole-2,5-diyl, octahydropyrrolo(3,4-c)pyrrole-2,4-diyl and octahydropyrrolo(3,4-c)pyrrole-2,5-diyl; and a bivalent 6-membered alicyclic amine residue denotes, for example, a monocyclic 6-membered alicyclic amine residue such as piperidine-1,3-diyl, piperidine-1,4-diyl, piperazine-1,3-diyl, piperazine-1,4-diyl, morpholine-2,4-diyl and thiomorpholine-2,4-diyl, and a cross-linked 6-membered alicyclic amine residue such as 3-azabicyclo(4.1.0)heptane-3,6-diyl and hexahydroimidazo(1,5-a)pyrazine-2,7-diyl.

Examples of an imino-protecting group include all groups that can be generally used as an imino-protecting group, for example, those disclosed in W. Greene, et al., Protective Groups in Organic Synthesis, 3rd Ed., pp. 494-653, 1999, John Wiley & Sons, INC. More specific examples include an acyl group, an alkyloxycarbonyl group, an aralkyloxycarbonyl group, an aryloxycarbonyl group, an aralkyl group, an alkoxyalkyl group, an aralkyloxyalkyl group, an arylthio group, an alkanesulfonyl group, an arylsulfonyl group, a diarylphosphoryl group, a di(aralkyl)phosphoryl group, an oxygen-containing heterocyclic alkyl group and a substituted silyl group.

Examples of an amino-protecting group include all groups that can be generally used as an amino-protecting group, for example, those disclosed in W. Greene, et al., Protective Groups in Organic Synthesis, 3rd Ed., pp. 494-653, 1999, John Wiley & Sons, INC. More specific examples include an acyl group, an alkyloxycarbonyl group, an aralkyloxycarbonyl group, an aryloxycarbonyl group, an aralkyl group, an alkoxyalkyl group, an aralkyloxyalkyl group, an arylthio group, an alkanesulfonyl group, an arylsulfonyl group, a dialkylaminoalkylidene group, an aralkylidene group, a nitrogen-containing heterocyclic alkylidene group, a cycloalkylidene group, a diarylphosphoryl group, a di(aralkyl)phosphoryl group, an oxygen-containing heterocyclic alkyl group and a substituted silyl group.

Examples of a hydroxyl-protecting group include all groups that can be generally used as a hydroxyl-protecting group, for example, those disclosed in W. Greene, et al., Protective Groups in Organic Synthesis, 3rd Ed., pp. 17-245, 1999, John Wiley & Sons, INC. More specific examples include an acyl group, an alkyloxycarbonyl group, an aralkyloxycarbonyl group, a heterocyclicoxycarbonyl group, an alkyl group, an alkenyl group, an aralkyl group, an oxygen-containing heterocyclic group, a sulfur-containing heterocyclic group, an alkoxyalkyl group, an aralkyloxyalkyl group, an alkanesulfonyl group, an arylsulfonyl group and a substituted silyl group.

Examples of a carboxyl-protecting group include all groups that can be generally used as a carboxyl-protecting group, for example, those disclosed in W. Greene, et al., Protective Groups in Organic Synthesis, 3rd Ed., pp. 369-453, 1999, John Wiley & Sons, INC. More specific examples include an alkyl group, an aryl group, an aralkyl group, an acylalkyl group, an arylthioalkyl group, an arylsulfonylalkyl group, an oxygen-containing heterocyclic group, an alkylsilylalkyl group, an acyloxyalkyl group, a nitrogen-containing heterocyclic alkyl group, a cycloalkyl group, an alkoxyalkyl group, an aralkyloxyalkyl group, an alkylthioalkyl group, an alkenyl group and a substituted silyl group.

A leaving group is, for example, a halogen atom, an alkanesulfonyloxy group, an arylsulfonyloxy group and an acyloxy group.

In general, the salt of the compound of the general formula [1] includes commonly known salts formed from a basic group such as an amino group, or from an acid group such as a phenolic hydroxyl group or a carboxyl group.

Examples of the salts formed from a basic group include salts with mineral acids such as hydrochloric acid, hydrobromic acid and sulfuric acid; salts with organic carboxylic acids such as tartaric acid, formic acid, acetic acid, citric acid, trichloroacetic acid and trifluoroacetic acid; and salts with sulfonic acids such as methanesulfonic acid, benzenesulfonic acid, p-toluenesulfonic acid, mesitylenesulfonic acid and naphthalenesulfonic acid.

Examples of the salts formed from an acid group include salts with alkali metals such as sodium and potassium; salts with alkaline-earth metals such as calcium and magnesium; ammonium salts; and salts with nitrogen-containing organic bases such as trimethylamine, triethylamine, tributylamine, pyridine, N,N-dimethylaniline, N-methylpiperidine, N-methylmorpholine, diethylamine, dicyclohexylamine, procaine, dibenzylamine, N-benzyl-β-phenethylamine and N,N'-dibenzylethylenediamine.

Furthermore, among the above-mentioned salts, pharmacologically acceptable salts are preferable as salts of the compound of the general formula [1].

For example, 1-(2-(4-((2,3-dihydro(1,4)dioxino(2,3-c)pyridin-7-ylmethyl)amino)piperidin-1-yl)ethyl)-7-fluoro-1,5-naphthyridin-2(1H)-one trihydrochloride is nonhygroscopic and is a particularly preferable salt.

Examples of substituents for the $C_2$-$C_{12}$ alkyl group, aryl group and heterocyclic group of $R^1$ include one or more groups selected from a halogen atom, optionally protected hydroxyl and carboxyl groups, lower alkyl, lower alkenyl, lower alkynyl and lower alkoxy groups which may be substituted by one or more halogen atoms, a hydroxyimino group, an acyl group, a protected amino group, an amino group, a lower alkylamino group, an alkylthio group, an aryl group, a monocyclic heterocyclic group, an oxo group, and the like. Examples of the preferred substituents include one or more groups selected from a halogen atom, optionally protected hydroxyl and carboxyl groups, lower alkyl, lower alkenyl and lower alkoxy groups which may be substituted by one or more halogen atoms, a lower alkylamino group, an aryl group, a monocyclic heterocyclic group, and an oxo group. Examples of the more preferred substituents include one or more groups selected from a halogen atom, a hydroxyl group, a carboxyl group, a methyl group, an ethyl group, a tert-butyl group, a trifluoromethyl group, a vinyl group, a methoxy group, an ethoxy group, a trifluoromethoxy group, a dimethylamino group, a phenyl group, a thienyl group, a pyrrolidinyl group and an oxo group. Examples of the further preferred substituents include one or more groups selected from a halogen atom, a methyl group, an ethyl group, a thienyl group and an oxo group.

Examples of substituents for the lower alkyl groups of $R^2$, $R^3$, $R^4$ and $R^5$ and for the lower alkyl group, lower alkenyl group and lower alkynyl group of $R^6$ include one or more groups selected from a halogen atom, optionally protected hydroxyl and carboxyl groups, lower alkyl, lower alkenyl, lower alkynyl and lower alkoxy groups which may be substituted by one or more halogen atoms, lower alkyl, lower alkenyl and lower alkynyl groups which may be substituted by one or more aryl groups, an aryl group, a monocyclic heterocyclic group, and the like. Examples of the preferred substituents include one or more groups selected from a halogen atom, optionally protected hydroxyl and carboxyl groups, a lower alkyl group which may be substituted by one or more halogen atoms, and a lower alkynyl group which may be substituted by one or more aryl groups. Examples of the more preferred substituents include one or more groups selected from a halogen atom, a hydroxyl group, a carboxyl group, a methyl group, an ethyl group, a trifluoromethyl group, a 2-phenylethynyl group and an oxo group. Examples of further preferred substituents include a carboxyl group and a 2-phenylethynyl group.

Examples of substituents for the lower alkyl group, cycloalkyl group, aryl group, lower alkoxy group, cycloalkyloxy group, aralkyloxy group, alkanoyl group, ureido group and monocyclic heterocyclic group of $R^7$, for the lower alkyl group and lower alkoxy group of $R^{7a}$, for the lower alkyl group and lower alkoxy group of $R^{7b}$, for the lower alkyl group, cycloalkyl group, aryl group, lower alkoxy group, cycloalkyloxy group, aralkyloxy group, alkanoyl group, ureido group and monocyclic heterocyclic group of $R^{7c}$, for the lower alkyl group and lower alkoxy group of $R^{7d}$, and for the lower alkyl group, cycloalkyl group, aralkyl group, aryl group, lower alkoxy group, alkanesulfonyl group and monocyclic heterocyclic group of $R^8$ and $R^9$ include one or more groups selected from a halogen atom, optionally protected hydroxyl and carboxyl groups, lower alkyl, lower alkenyl, lower alkynyl and lower alkoxy groups which may be substituted by one or more halogen atoms, a hydroxyimino group, an aryl group, a monocyclic heterocyclic group, and the like. Examples of the preferred substituents include one or more groups selected from a halogen atom, optionally protected hydroxyl and carboxyl groups, lower alkyl and lower alkoxy groups which may be substituted by one or more halogen atoms, and a monocyclic heterocyclic group. Examples of the more preferred substituents include one or more groups selected from a halogen atom, a hydroxyl group, a carboxyl group, a methyl group and a methoxy group.

Examples of substituents for the amino group of $R^7$ include one or more groups selected from lower alkyl, lower alkenyl, lower alkynyl and lower alkoxy groups which may be substituted by one or more halogen atoms, an acyl group, an aryl group, a monocyclic heterocyclic group, and the like. Examples of the preferred substituents include one or more groups selected from lower alkyl and lower alkenyl groups which may be substituted by one or more halogen atoms, an acyl group, and an aryl group. Examples of the more preferred substituents include one or more groups selected from a methyl group, an ethyl group, a trifluoromethyl group, a vinyl group, a formyl group, an acetyl group, a benzoyl group and a phenyl group. Examples of the further preferred substituents include one or more groups selected from a methyl group, an ethyl group, an acetyl group and a phenyl group.

Examples of substituents for the cyclic amino group formed by $R^8$ and $R^9$ together with the nitrogen atom to which they bind include one or more groups selected from a halogen atom, optionally protected hydroxyl and carboxyl groups, lower alkyl, lower alkenyl, lower alkynyl and lower alkoxy groups which may be substituted by one or more halogen atoms, a hydroxyimino group, an acyl group, an amino group, a lower alkylamino group, an alkylthio group, an aryl group, a monocyclic heterocyclic group which may be substituted by one or more aralkyl groups, an oxo group, and the like. Examples of the preferred substituents include one or more groups selected from a halogen atom, optionally protected hydroxyl and carboxyl groups, lower alkyl, lower alkenyl and lower alkoxy groups which may be substituted by one or more halogen atoms, an alkanoyl group, a lower alkylamino group, an alkylthio group, an aryl group, a monocyclic heterocyclic group which may be substituted by one or more aralkyl groups, and an oxo group. Examples of the more preferred substituents include one or more groups selected from a halogen atom, a hydroxyl group, a carboxyl group, a methyl group, an ethyl group, a methoxy group, an ethoxy group, a dimethylamino group, a phenyl group and an oxo group.

Examples of substituents for the lower alkylene group and lower alkenylene group of $Q^1$ include one or more groups selected from an oxo group, optionally protected hydroxyl and carboxyl groups, a lower alkyl group, a lower alkenyl group, a lower alkynyl group, a lower alkoxy group, an aryl group, and the like. Examples of the preferred substituents include one or more groups selected from an oxo group, optionally protected hydroxyl and carboxyl groups, a lower alkyl group, a lower alkoxy group, and an aryl group. Examples of the more preferred substituents include one or more groups selected from an oxo group, a hydroxyl group, a carboxyl group, a methyl group, a methoxy group and a phenyl group.

Examples of substituents for the $C_2$-$C_4$ alkylene group of $X^1$, for the $C_1$-$C_3$ alkylene group of $X^{1a}$, and for the lower alkylene group, lower alkenylene group and lower alkynylene group of $X^4$ include one or more groups selected from an oxo group, optionally protected hydroxyl and carboxyl groups, a lower alkyl group, a lower alkenyl group, a lower alkynyl group, a lower alkoxy group, an aryl group, and the like. Examples of the preferred substituents include one or more groups selected from an oxo group and a lower alkyl group. Examples of the more preferred substituents include one or more groups selected from an oxo group and a methyl group.

Examples of substituents for the bivalent alicyclic hydrocarbon residue and bivalent alicyclic amine residue of $Y^1$ include one or more groups selected from a halogen atom, optionally protected hydroxyl and carboxyl groups, lower alkyl, lower alkenyl, lower alkynyl and lower alkoxy groups which may be substituted by one or more halogen atoms, a hydroxyimino group, an acyl group, an amino group, a lower alkylamino group, an alkylthio group, an aryl group, a monocyclic heterocyclic group which may be substituted by one or more aralkyl groups, an oxo group, and the like. Examples of the preferred substituents include one or more groups selected from a halogen atom, optionally protected hydroxyl and carboxyl groups, lower alkyl, lower alkenyl and lower alkoxy groups which may be substituted by one or more halogen atoms, an alkanoyl group, a lower alkylamino group, an alkylthio group, an aryl group, a monocyclic heterocyclic group which may be substituted by one or more aralkyl groups, and an oxo group. Examples of the more preferred substituents include one or more groups selected from a halogen atom, a hydroxyl group, a carboxyl group, a methyl group, an ethyl group, a methoxy group, an ethoxy group, a dimethylamino group, a phenyl group and an oxo group.

In the compounds of the general formula [1] of the present invention, examples of the preferred compounds are as follows:

Preferred are the compounds wherein $R^1$ is an optionally substituted aryl or heterocyclic group. More preferred are the compounds wherein $R^1$ is 3-fluoro-4-methylphenyl, 3-fluoro-4-(trifluoromethyl)phenyl, 3-fluoro-4-methylpyridyl, 5-fluoro-6-methylpyridyl, 4-ethylphenyl, naphthyl, benzo(b)thiophen-2-yl, benzo(b)thiophen-5-yl, benzo(b)thiophen-6-yl, 5-(thiophen-2-yl)isoxazol-2-yl, 2,3-dihydro-1,4-benzodithiin-6-yl, 2,3-dihydrobenzo(1,4)dioxin-6-yl, 2,3-dihydro(1,4)dioxino(2,3-c)pyridin-7-yl, 3-oxo-3,4-dihydro-2H-pyrido(3,2-b)(1,4)oxazin-6-yl, 7-chloro-3-oxo-3,4-dihydro-2H-pyrido(3,2-b)(1,4)thiazin-6-yl, 3-oxo-3,4-dihydro-2H-pyrido(3,2-b)(1,4)thiazin-6-yl or 3-oxo-3,4-dihydro-2H-benzothiazin-6-yl. Further preferred are the compounds wherein $R^1$ is 2,3-dihydrobenzo(1,4)dioxin-6-yl, 2,3-dihydro(1,4)dioxino(2,3-c)pyridin-7-yl or 3,4-dihydro-2H-pyrano(2,3-c)pyridin-6-yl, and further more preferred are the compounds wherein $R^1$ is 2,3-dihydro(1,4)dioxino(2,3-c)pyridin-7-yl.

Preferred are the compounds wherein $X^1$ is an optionally substituted ethylene group, and more preferred are the compounds wherein $X^1$ is an ethylene group.

Preferred are the compounds wherein $X^2$ is NH or a bond, and more preferred are the compounds wherein $X^2$ is a bond.

Preferred are the compounds wherein $X^3$ is NH, CH$_2$NH or a bond, and more preferred are the compounds wherein $X^3$ is NH or a bond, and further preferred are the compounds wherein $X^3$ is NH.

Preferred are the compounds wherein $X^4$ is an optionally substituted lower alkylene group or a bond, and more preferred are the compounds wherein $X^4$ is a lower alkylene group, and further preferred are the compounds wherein $X^4$ is a methylene group.

Preferred are the compounds wherein $X^5$ is an oxygen atom, a sulfur atom, NH or a bond, and more preferred are the compounds wherein $X^5$ is a bond.

Preferred are the compounds wherein $Y^1$ is an optionally substituted bivalent 4-, 5- or 6-membered alicyclic hydrocarbon residue or an optionally substituted bivalent 5- or 6-membered alicyclic amine residue. More preferred are the compounds wherein $Y^1$ is an optionally substituted bivalent 6-membered alicyclic hydrocarbon residue or an optionally substituted bivalent 6-membered alicyclic amine residue, and further preferred are the compounds wherein $Y^1$ is an optionally substituted cyclohexylene, piperazinediyl or piperidinediyl group, and further more preferred are the compounds wherein $Y^1$ is a piperidine-1,4-diyl group (the nitrogen atom in the 1-position binds to $X^2$).

Preferred are the compounds wherein $Z^1$ has the general formula CR$^7$ (where R$^7$ has the same meaning as mentioned above), and more preferred are the compounds wherein $Z^1$ has the general formula CR$^{7a}$ (where R$^{7a}$ denotes a hydrogen atom, a halogen atom, a hydroxyl group, an optionally substituted lower alkyl or lower alkoxy group), and further preferred are the compounds wherein $Z^1$ is CH.

Preferred are the compounds wherein $Z^2$ has the general formula CR$^7$ (where R$^7$ has the same meaning as mentioned above), and more preferred are the compounds wherein $Z^2$ is a group represented by the general formula CR$^{7a}$ (where R$^{7a}$ has the same meaning as mentioned above), and further preferred are the compounds wherein $Z^2$ is CH.

Preferred are the compounds wherein $Z^3$ is a nitrogen atom or a group represented by the general formula CR$^{7a}$ (where R$^{7a}$ has the same meaning as mentioned above), and more preferred are the compounds wherein $Z^3$ is a nitrogen atom or CH, and further preferred are the compounds wherein $Z^3$ is a nitrogen atom.

Preferred are the compounds wherein $Z^4$ is a nitrogen atom or a group represented by the general formula CR$^{7a}$ (where R$^{7a}$ has the same meaning as mentioned above), and more preferred are the compounds wherein $Z^4$ is a nitrogen atom or CH, and further preferred are the compounds wherein $Z^4$ is CH.

Preferred are the compounds wherein $Z^5$ has the general formula CR$^7$ (where R$^7$ has the same meaning as mentioned above), and more preferred are the compounds wherein $Z^5$ has the general formula CR$^{7b}$ (where R$^{7b}$ denotes a hydrogen atom, a halogen atom, an optionally substituted lower alkyl or lower alkoxy group), and further preferred are the compounds wherein $Z^5$ has the general formula CR$^{7d}$ (where R$^{7d}$ denotes a halogen atom, an optionally substituted lower alkyl or lower alkoxy group), and further more preferred are the compounds wherein $Z^5$ has the general formula CR$^{7e}$ (where R$^{7e}$ denotes a halogen atom, a lower alkyl group or a lower alkoxy group).

Preferred are the compounds wherein $Z^6$ is a nitrogen atom or a group represented by the general formula CR$^{7a}$ (where R$^{7a}$ has the same meaning as mentioned above), and more preferred are the compounds wherein $Z^6$ is a nitrogen atom or CH.

Examples of the most preferable compounds of the general formula [1] of the present invention are:
7-Chloro-1-(2-(4-((2,3-dihydro(1,4)dioxino(2,3-c)pyridin-7-ylmethyl)amino)piperidin-1-yl)ethyl)-1,5-naphthyridin-2(1H)-one, 1-(2-(4-((2,3-dihydro(1,4)dioxino(2,3-c)pyridin-7-ylmethyl)amino)piperidin-1-yl)ethyl)-7-fluoro-1,5-naphthyridin-2(1H)-one, 1-(2-(4-((2,3-dihydro(1,4)dioxino(2,3-c)pyridin-7-ylmethyl)amino)piperidin-1-yl)ethyl)-7-methoxy-1,5-naphthyridin-2(1H)-one, and 5-(2-(4-((2,3-dihydro(1,4)dioxino(2,3-c)pyridin-7-ylmethyl)amino)piperidin-1-yl)ethyl)-3-methoxypyrido(2,3-b)pyrazin-6(5H)-one.

Examples of typical compounds of the general formula [1] of the present invention are those shown in Tables 1A to 3B.

TABLE 1A

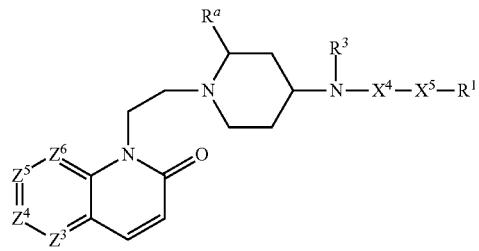

| $Z^3$ | $Z^4$ | $Z^5$ | $Z^6$ | $R^3$ | $R^a$ | $X^4$—$X^5$—$R^1$ |
|---|---|---|---|---|---|---|
| CH | CH | C (OCH$_3$) | N | H | H | 2,3-dihydro-1,4-benzodioxin-6-ylmethyl |
| CH | CH | C (OCH$_3$) | N | H | H | 2,3-dihydro(1,4)dioxino(2,3-c)pyridin-7-ylmethyl |
| CH | CH | CH | N | H | H | 2,3-dihydro-1,4-benzodioxin-6-ylmethyl |
| CH | CH | CH | N | H | H | 7-chloro-2H-pyrido(3,2-b)(1,4)thiazin-3(4H)-on-6-ylmethyl |
| CH | CH | CH | N | H | H | 2H-1,4-benzoxazin-3(4H)-on-6-ylmethyl |
| CH | CH | N | CH | H | H | 1-benzothiophen-2-ylmethyl |
| CH | CH | N | CH | H | H | 2-naphthylmethyl |
| CH | CH | N | CH | H | H | 3-fluoro-4-methylbenzyl |
| CH | CH | N | CH | H | H | 4-ethylbenzyl |
| CH | CH | N | CH | H | H | 5-(2-thienyl)isoxazol-3-ylmethyl |
| CH | CH | N | CH | H | H | 7-chloro-2H-pyrido(3,2-b) (1,4)thiazin-3(4H)-on-6-ylmethyl |
| CH | CH | N | CH | H | H | 2H-pyrido(3,2-b) (1,4)thiazin-3(4H)-on-6-ylmethyl |
| CH | CH | N | CH | H | H | 2,3-dihydro-1,4-benzodioxin-6-ylmethyl |

TABLE 1A-continued

| $Z^3$ | $Z^4$ | $Z^5$ | $Z^6$ | $R^3$ | $R^a$ | $X^4$—$X^5$—$R^1$ |
|---|---|---|---|---|---|---|
| CH | CH | N | CH | H | H | 2,3-dihydro(1,4)dioxino(2,3-c)pyridin-7-ylmethyl |
| CH | CH | N | CH | H | H | CH$_2$C≡CC$_6$H$_5$ |
| CH | CH | N | CH | H | H | 2H-1,4-benzoxazin-3(4H)-on-6-ylmethyl |
| CH | CH | N | CHCH$_2$C≡CC$_6$H$_5$ | H | H | CH$_2$C≡CC$_6$H$_5$ |
| CH | N | CH | CH | H | H | 2,3-dihydro-1,4-benzodioxin-6-ylmethyl |
| N | CH | C (OCH$_3$) | CH | H | H | 3-fluoro-4-methylbenzyl |
| N | CH | C (OCH$_3$) | CH | H | H | 3-oxo-3,4-dihydro-2H-pyrido[3,2-b] [1,4]-oxazin-6-ylmethyl |
| N | CH | C (OCH$_3$) | CH | H | H | 2,3-dihydro(1,4)dioxino(2,3-b)pyridin-7-ylmethyl |
| N | CH | C (OCH$_3$) | CH | H | H | 2,3-dihydro(1,4)dioxino(2,3-c)pyridin-7-ylmethyl |
| N | CH | C (OCH$_3$) | CH | H | H | 5,6,7,8-tetrahydroquinoxalin-2-ylmethyl |
| N | CH | C (OCH$_3$) | CH | CH$_2$CO$_2$H | H | 2,3-dihydro(1,4)dioxino(2,3-c)pyridin-7-ylmethyl |
| N | CH | C (OCH$_3$) | CH | H | CH$_3$ | 2,3-dihydro(1,4)dioxino(2,3-c)pyridin-7-ylmethyl |
| N | CH | C (OCH$_3$) | N | H | H | 2,3-dihydro(1,4)dioxino(2,3-c)pyridin-7-ylmethyl |
| N | CH | CCH$_3$ | CH | H | H | 2,3-dihydro(1,4)dioxino(2,3-c)pyridin-7-ylmethyl |
| N | CH | CH | CH | H | H | 2,3-dihydro-1,4-benzodioxin-6-ylmethyl |
| N | CH | CH | CH | H | H | 2,3-dihydro(1,4)dioxino(2,3-c)pyridin-7-ylmethyl |
| N | CH | CH | CH | H | H | 2H-pyrido(3,2-b) (1,4)thiazin-3(4H)-on-6-ylmethyl |
| N | CH | CCH=CHCO$_2$C$_2$H$_5$ | CH | H | H | 2,3-dihydro(1,4)dioxino(2,3-c)pyridin-7-ylmethyl |
| N | CH | CCl | CH | H | H | 2,3-dihydro(1,4)dioxino(2,3-c)pyridin-7-ylmethyl |
| N | CH | CCN | CH | H | H | 2,3-dihydro(1,4)dioxino(2,3-c)pyridin-7-ylmethyl |
| N | CH | CF | CH | H | H | 2,3-dihydro(1,4)dioxino(2,3-c)pyridin-7-ylmethyl |

TABLE 1B

| $Z^3$ | $Z^4$ | $Z^5$ | $Z^6$ | $R^3$ | $R^a$ | $X^4$—$X^5$—$R^1$ |
|---|---|---|---|---|---|---|
| N | CH | C (OCH$_3$) | CH | H | H | (5-fluoro-2-methylpyridin-3-yl)methyl |
| N | CH | C (OCH$_3$) | CH | H | H | 4-fluoro-3-methylbenzyl |
| N | CH | C (OCH$_3$) | CH | H | H | 2H-pyrido(3,2-b) (1,4)thiazin-3(4H)-on-6-yl |
| N | CH | C-Im | CH | H | H | 2,3-dihydro(1,4)dioxino(2,3-c)pyridin-7-ylmethyl |
| N | CH | C (OCH$_3$) | CH | H | H | (5-fluoro-6-methylpyridin-3-yl)methyl |
| N | CH | C (OCH$_3$) | N | H | H | (5-fluoro-6-methylpyridin-3-yl)methyl |
| CH | N | C (OCH$_3$) | N | H | H | 2,3-dihydro(1,4)dioxino(2,3-c)pyridin-7-ylmethyl |
| N | CH | CF | CH | H | H | (5-fluoro-6-methoxypyridin-3-yl)methyl |
| N | CH | CF | CH | H | H | (5-fluoro-2,6-dimethylpyridin-3-yl)methyl |
| N | CH | CF | CH | H | H | (3,4-dihydro-2H-pyrano(2,3-c)pyridin-6-yl)methyl |
| N | CH | CF | CH | H | H | (5-fluoro-6-methylpyridin-3-yl)methyl |
| N | CH | CF | CH | H | H | (3,4-dihydro-2H-(1,4)dioxepino(2,3-c)pyridin-8-yl)methyl |
| N | CH | CF | CH | H | H | ((1,3)dioxolo(4,5-c)pyridin-6-yl)methyl |
| N | CH | C (NHCH$_3$) | CH | H | H | 2,3-dihydro(1,4)dioxino(2,3-c)pyridin-7-ylmethyl |
| N | CH | CF | CH | H | H | (3,4-dihydro-2H-pyrido(4,3-b) (1,4)oxazin-7-yl)methyl |
| N | CH | CF | CH | H | H | 3-(pyrazin-2-yl)prop-2-in-1-yl |
| N | CH | C (OCH$_3$) | CH | H | H | (3,4-dihydro-2H-(1,4)dioxepino(2,3-c)pyridin-8-yl)methyl |
| N | CH | C (OCH$_3$) | CH | H | H | (6-oxido-2,3-dihydro(1,4)dioxino(2,3-c)pyridin-7-yl)methyl |
| N | CH | C (OCH$_3$) | CH | H | H | (5-ethylpyridin-2-yl)methyl |
| N | CH | CF | CH | H | H | 3-fluoro-4-methylbenzoyl |
| N | CH | CF | CH | H | H | (2,3-dihydro(1,4)dioxino(2,3-c)pyridin-7-yl)carbonyl |
| N | CH | C (OCH$_3$) | CH | H | H | (7-oxo-5,6,7,8-tetrahydro-1,8-naphthyridin-2-yl)methyl |

TABLE 1B-continued

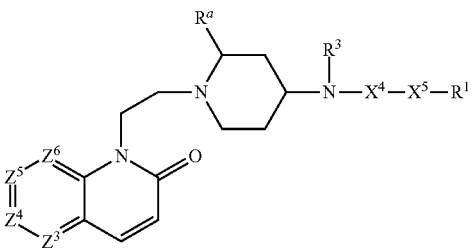

| $Z^3$ | $Z^4$ | $Z^5$ | $Z^6$ | $R^3$ | $R^a$ | $X^4$—$X^5$—$R^1$ |
|---|---|---|---|---|---|---|
| N | CH | C (OCH$_3$) | CH | H | H | (4-methoxy-5-methylpyridin-2-yl)methyl |
| N | CH | C (OCH$_3$) | CH | H | H | (5-ethyl-4-methoxypyridin-2-yl)methyl |
| N | CH | C (OCH$_3$) | CH | H | H | (5-methoxy-4-methylpyridin-2-yl)methyl |
| N | CH | C (OCH$_3$) | CH | H | H | (5-(3-thienyl)isoxazol-3-yl)methyl |
| N | CH | C (OCH$_3$) | CH | H | H | 6-(3-thienyl)pyridin-2-yl)methyl |
| N | CH | C (OCH$_3$) | CH | H | H | (5-fluoro-6-methoxypyridin-3-yl)methyl |
| N | CH | C (OCH$_3$) | CH | H | H | (6-ethyl-5-fluoropyridin-3-yl)methyl |
| N | CH | C (OCH$_3$) | CH | H | H | (5-fluoro-6-(pyrrolidin-1-yl)pyridin-3-yl)methyl |
| N | CH | C (OCH$_3$) | CH | H | H | (5-(2-furyl)isoxazol-3-yl)methyl |
| N | CH | C (OCH$_3$) | CH | H | H | (5-(2-thienyl)pyridin-3-yl)methyl |
| N | CH | C (OCH$_3$) | CH | H | H | (6-(2-thienyl)pyridin-3-yl)methyl |
| N | CH | CF | CH | H | H | (5-(2-furyl)isoxazol-3-yl)methyl |
| N | CH | C (OCH$_3$) | CH | H | H | (3,4-dihydro-2H-pyrano(2,3-c)pyridin-6-yl)methyl |
| N | CH | C (OCH$_3$) | CH | H | H | (5-(2-furyl)pyridin-3-yl)methyl |
| N | CH | C (OCHF$_2$) | CH | H | H | 2,3-dihydro(1,4)dioxino(2,3-c)pyridin-7-ylmethyl |
| N | CH | C (OCH$_3$) | CH | H | H | (1,5-naphthyridin-3-yl)methyl |
| N | CH | C (OCH$_3$) | CH | H | H | (6-(2-furyl)pyrazin-2-yl)methyl |
| N | CH | C-Oxa | CH | H | H | 2,3-dihydro(1,4)dioxino(2,3-c)pyridin-7-ylmethyl |
| N | CH | C-Thia | CH | H | H | 2,3-dihydro(1,4)dioxino(2,3-c)pyridin-7-ylmethyl |
| N | CH | CF | CH | H | H | (5,6,7,8-tetrahydroquinoxalin-2-yl)methyl |
| N | CH | CF | CH | H | H | (5-(2-furyl)-1,3-oxazol-2-yl)methyl |
| N | CH | CF | CH | H | H | (3,4-dihydro-2H-pyrano(3,2-c)pyridin-7-yl)methyl |
| N | CH | C (OCH$_3$) | CH | H | H | (3,4-dihydro-2H-pyrano(3,2-c)pyridin-7-yl)methyl |
| N | CH | C (CF$_3$) | CH | H | H | 2,3-dihydro(1,4)dioxino(2,3-c)pyridin-7-ylmethyl |
| N | CMe | CF | CH | H | H | 2,3-dihydro(1,4)dioxino(2,3-c)pyridin-7-ylmethyl |
| N | CMe | C (OCH$_3$) | CH | H | H | 2,3-dihydro(1,4)dioxino(2,3-c)pyridin-7-ylmethyl |
| N | CH | CF | CH | H | H | (2,3-dihydro(1,4)dioxino(2,3-b)pyridin-7-yl)methyl |
| N | CH | CBr | CH | H | H | 2,3-dihydro(1,4)dioxino(2,3-c)pyridin-7-ylmethyl |
| N | CH | CNH$_2$ | CH | H | H | 2,3-dihydro(1,4)dioxino(2,3-c)pyridin-7-ylmethyl |
| N | CH | C (OCH$_3$) | CH | H | H | (5-methyl-4-oxo-4H-pyran-2-yl)methyl |
| N | CH | C (OCH$_3$) | CH | H | H | (5-aminopyrazin-2-yl)methyl |

Im: 1H-imidazol-1-yl,
Oxa: 1,3-oxazol-2-yl,
Thia: 1,3-thiazol-2-yl

TABLE 2

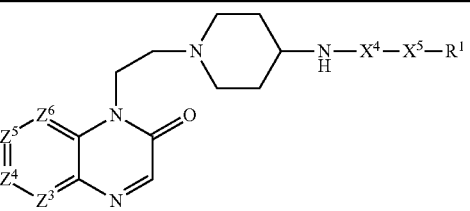

| $Z^3$ | $Z^4$ | $Z^5$ | $Z^6$ | $X^4$—$X^5$—$R^1$ |
|---|---|---|---|---|
| CH | N | CH | CH | 2,3-dihydro-1,4-benzodioxin-6-ylmethyl |
| CH | CH | CH | N | 2,3-dihydro-1,4-benzodioxin-6-ylmethyl |
| N | CH | CH | CH | 2,3-dihydro-1,4-benzodioxin-6-ylmethyl |
| CH | CH | C (OCH$_3$) | N | 2,3-dihydro(1,4)dioxino(2,3-c)pyridin-7-ylmethyl |
| CH | CH | N | CH | 2,3-dihydro-1,4-benzodioxin-6-ylmethyl |
| CH | CH | C (OCH$_3$) | N | 2H-pyrido(3,2-b) (1,4)thiazin-3(4H)-on-6-ylmethyl |
| N | CH | C (OCH$_3$) | CH | 3,4-dihydro-2H-(1,4)dioxepino(2,3-c)pyridin-8-ylmethyl |
| CH | CH | CF | N | 2,3-dihydro(1,4)dioxino(2,3-c)pyridin-7-ylmethyl |
| N | CH | C (OCH$_3$) | CH | 2,3-dihydro(1,4)dioxino(2,3-c)pyridin-7-ylmethyl |
| CH | CH | CNH2 | N | 2,3-dihydro(1,4)dioxino(2,3-c)pyridin-7-ylmethyl |
| CH | CH | C-Tri | N | 2,3-dihydro(1,4)dioxino(2,3-c)pyridin-7-ylmethyl |

Tri: 1,2,4-triazol-1-yl

TABLE 3A

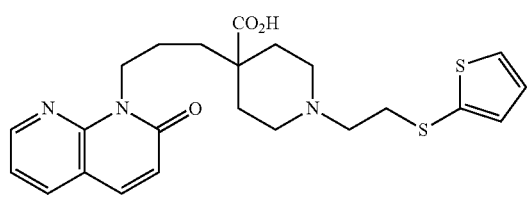 [SMILES: O=C(O)C1(CCCn2c(=O)ccc3cccnc32)CCN(CCSc2cccs2)CC1]

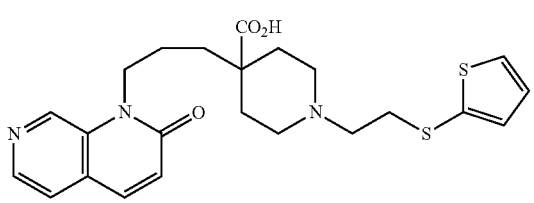 [SMILES: O=C(O)C1(CCCn2c(=O)ccc3ccncc32)CCN(CCSc2cccs2)CC1]

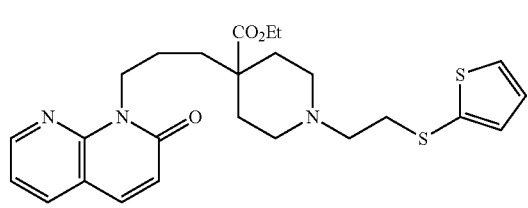

TABLE 3B

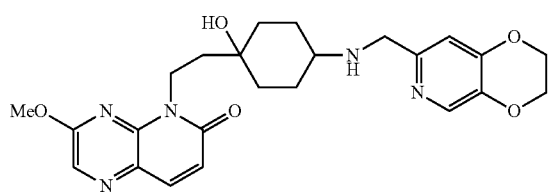 [SMILES: COc1cnc2ccc(=O)n(CCC3(O)CCC(NCc4cc5c(cn4)OCCO5)CC3)c2n1]

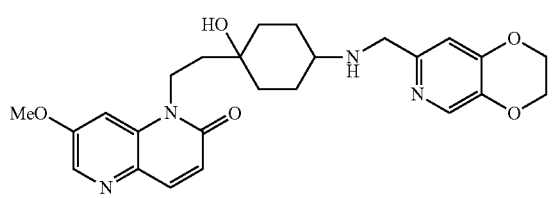 [SMILES: COc1cnc2ccc(=O)n(CCC3(O)CCC(NCc4cc5c(cn4)OCCO5)CC3)c2c1]

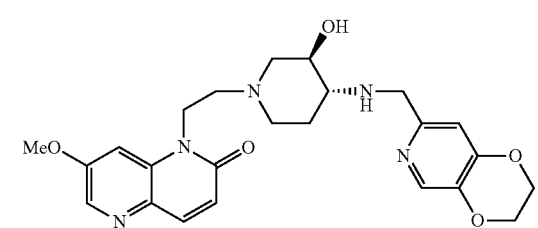 [SMILES: COc1cnc2ccc(=O)n(CCN3CC[C@@H](NCc4cc5c(cn4)OCCO5)[C@H](O)C3)c2c1]

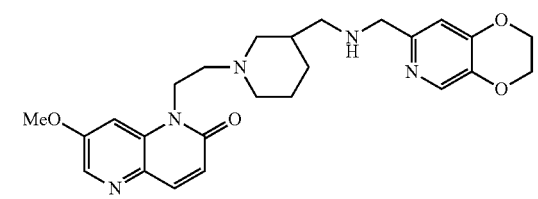 [SMILES: COc1cnc2ccc(=O)n(CCN3CCCC(CNCc4cc5c(cn4)OCCO5)C3)c2c1]

TABLE 3B-continued

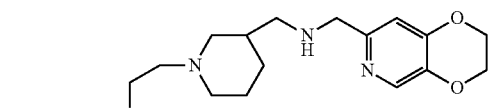

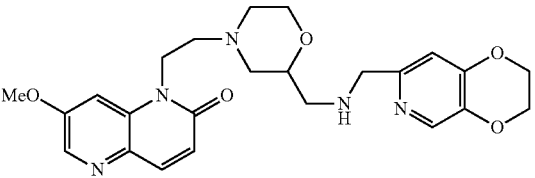 [SMILES: COc1cnc2ccc(=O)n(CCN3CCOC(CNCc4cc5c(cn4)OCCO5)C3)c2c1]

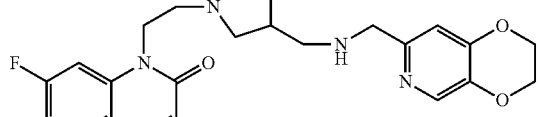

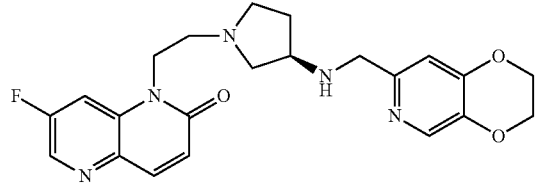 [SMILES: O=c1ccc2ncc(F)cc2n1CCN1CC[C@@H](NCc2cc3c(cn2)OCCO3)C1]

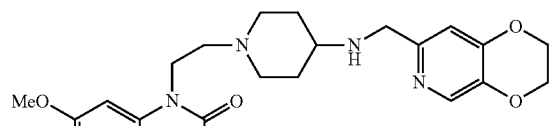

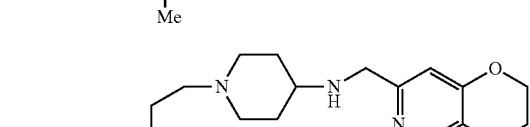

In the compounds of the general formula [2] of the present invention, examples of the preferred compounds are as follows:

Preferred are the compounds wherein $X^{1a}$ is a methylene group or an ethylene group, and more preferred are the compounds wherein $X^{1a}$ is a methylene group.

Preferred are the compounds wherein $Y^2$ is a 1,3-dioxolan-2-ylidene group, a (hydroxy)(methoxy)methylene group, a dimethoxymethylene group or a carbonyl group, and more preferred are compounds wherein $Y^2$ is a 1,3-dioxolan-2-ylidene group, a dimethoxymethylene group or a carbonyl group, and further preferred are the compounds wherein $Y^2$ is a dimethoxymethylene group or a carbonyl group, and further more preferred are the compounds wherein $Y^2$ is a carbonyl group.

Preferred are the compounds wherein $Z^1$ has the general formula $CR^7$ (where $R^7$ has the same meaning as mentioned above), and more preferred are the compounds wherein $Z^1$ is a group represented by the general formula $CR^{7a}$ (where $R^{7a}$ has the same meaning as mentioned above), and further preferred are the compounds wherein $Z^1$ is CH.

Preferred are the compounds wherein $Z^2$ has the general formula $CR^7$ (where $R^7$ has the same meaning as mentioned above), and more preferred are the compounds wherein $Z^2$ is a group represented by the general formula $CR^{7a}$ (where $R^{7a}$ has the same meaning as mentioned above), and further preferred are the compounds wherein $Z^2$ is CH.

Preferred are the compounds wherein $Z^3$ is a nitrogen atom or a group represented by the general formula $CR^{7a}$ (where $R^{7a}$ has the same meaning as mentioned above), and more preferred are the compounds wherein $Z^3$ is a nitrogen atom or CH, and further preferred are the compounds wherein $Z^3$ is a nitrogen atom.

Preferred are the compounds wherein $Z^4$ is a nitrogen atom or a group represented by the general formula $CR^{7a}$ (where $R^{7a}$ has the same meaning as mentioned above), and more preferred are the compounds wherein $Z^4$ is a nitrogen atom or CH, and further preferred are the compounds wherein $Z^4$ is CH.

Preferred are the compounds wherein $Z^5$ has the general formula $CR^7$ (where $R^7$ has the same meaning as mentioned above), and more preferred are the compounds wherein $Z^5$ has the general formula $CR^{7a}$ (where $R^{7a}$ has the same meaning as mentioned above), and further preferred are the compounds wherein $Z^5$ has the general formula $CR^{7d}$ (where $R^{7d}$ has the same meaning as mentioned above), and furthermore preferred are the compounds wherein $Z^5$ has the general formula $CR^{7e}$ (where $R^{7e}$ has the same meaning as mentioned above).

Preferred are the compounds wherein $Z^6$ is a nitrogen atom or a group represented by the general formula $CR^{7a}$ (where $R^{7a}$ has the same meaning as mentioned above), and more preferred are the compounds wherein $Z^6$ is a nitrogen atom or CH.

Examples of the typical compounds of the general formula [2] of the present invention are those shown in Tables 4A to 4B.

TABLE 4A

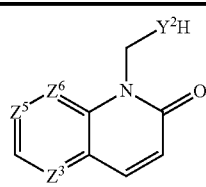

| $Z^3$ | $Z^5$ | $Z^6$ | $Y^2$ |
|---|---|---|---|
| N | CH | CH | CO |
| N | CF | CH | CO |
| N | CCH$_3$ | CH | CO |
| N | C(OCH$_3$) | CH | CO |
| CH | CH | N | CO |
| CH | CF | N | CO |
| CH | CCH$_3$ | N | CO |
| CH | C(OCH$_3$) | N | CO |
| N | CH | N | CO |
| N | CF | N | CO |
| N | CCH$_3$ | N | CO |
| N | C(OCH$_3$) | N | CO |
| N | CH | CH | 1,3-dioxolan-2-ylidene |
| N | CF | CH | 1,3-dioxolan-2-ylidene |
| N | CCH$_3$ | CH | 1,3-dioxolan-2-ylidene |

TABLE 4A-continued

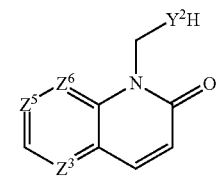

| $Z^3$ | $Z^5$ | $Z^6$ | $Y^2$ |
|---|---|---|---|
| N | C(OCH$_3$) | CH | 1,3-dioxolan-2-ylidene |
| CH | CH | N | 1,3-dioxolan-2-ylidene |
| CH | CF | N | 1,3-dioxolan-2-ylidene |
| CH | CCH$_3$ | N | 1,3-dioxolan-2-ylidene |
| CH | C(OCH$_3$) | N | 1,3-dioxolan-2-ylidene |
| N | CH | N | 1,3-dioxolan-2-ylidene |
| N | CF | N | 1,3-dioxolan-2-ylidene |
| N | CCH$_3$ | N | 1,3-dioxolan-2-ylidene |
| N | C(OCH$_3$) | N | 1,3-dioxolan-2-ylidene |

TABLE 4B

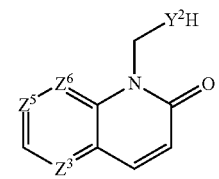

| $Z^3$ | $Z^5$ | $Z^6$ | $Y^2$ |
|---|---|---|---|
| N | CH | CH | dimethoxymethylene |
| N | CF | CH | dimethoxymethylene |
| N | CCH$_3$ | CH | dimethoxymethylene |
| N | C(OCH$_3$) | CH | dimethoxymethylene |
| CH | CH | N | dimethoxymethylene |
| CH | CF | N | dimethoxymethylene |
| CH | CCH$_3$ | N | dimethoxymethylene |
| CH | C(OCH$_3$) | N | dimethoxymethylene |
| N | CH | N | dimethoxymethylene |
| N | CF | N | dimethoxymethylene |
| N | CCH$_3$ | N | dimethoxymethylene |
| N | C(OCH$_3$) | N | dimethoxymethylene |
| N | CH | CH | (hydroxy)(methoxy)methylene |
| N | CF | CH | (hydroxy)(methoxy)methylene |
| N | CCH$_3$ | CH | (hydroxy)(methoxy)methylene |
| N | C(OCH$_3$) | CH | (hydroxy)(methoxy)methylene |
| CH | CH | N | (hydroxy)(methoxy)methylene |
| CH | CF | N | (hydroxy)(methoxy)methylene |
| CH | CCH$_3$ | N | (hydroxy)(methoxy)methylene |
| CH | C(OCH$_3$) | N | (hydroxy)(methoxy)methylene |
| N | CH | N | (hydroxy)(methoxy)methylene |
| N | CF | N | (hydroxy)(methoxy)methylene |
| N | CCH$_3$ | N | (hydroxy)(methoxy)methylene |
| N | C(OCH$_3$) | N | (hydroxy)(methoxy)methylene |

In the compounds of the general formula [3] of the present invention, examples of the preferred compounds are as follows:

Preferred are the compounds wherein $R^{7c}$ is a halogen atom or an optionally substituted lower alkyl or lower alkoxy group.

Preferred are the compounds wherein $Z^{2a}$ has the general formula $CR^7$ (where $R^7$ has the same meaning as mentioned above), and more preferred are the compounds wherein $Z^{2a}$ is CH.

Preferred are the compounds wherein $Z^{6a}$ is a nitrogen atom or CH.

Examples of the typical compounds of the general formula [3] of the present invention are those shown in Table 5.

TABLE 5

| $Z^{6a}$ | $R^{7c}$ |
|---|---|
| CH | F |
| CH | $CH_3$ |
| CH | $OCH_3$ |
| N | F |
| N | $CH_3$ |
| N | $OCH_3$ |

Methods of producing the compounds of the present invention will now be described.

The compounds of the general formula [1] of the present invention can be produced by a combination of known methods. For example, the compounds can be produced by the following production methods.

Production Method 1

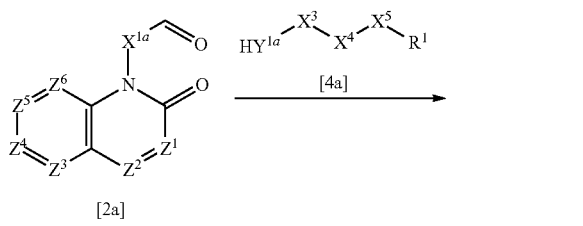

(In the formulas, $Y^{1a}$ denotes an optionally substituted bivalent alicyclic amine residue wherein one nitrogen atom in the ring binds to an adjacent group and another atom in the ring binds to $X^3$; and $R^1$, $X^{1a}$, $X^3$, $X^4$, $X^5$, $Z^1$, $Z^2$, $Z^3$, $Z^4$, $Z^5$ and $Z^6$ have the same meanings as mentioned above.)

Examples of known compounds of the general formula [4a] include 4-((1-phenylethyl)amino)-piperidine, tert-butyl (3-aminobenzyl)(4-piperidinyl)carbamate and phenyl-N-(4-piperidinyl)carboxamide.

A compound of the general formula [1a] can be produced by reacting a compound of the general formula [2a] with the compound of the general formula [4a] in the presence of a reducing agent.

This reaction may be carried out by the method described in, for example, International Patent Publication Nos. WO 02/50061 and WO 02/56882, Jerry March, Advanced Organic Chemistry, 4th Ed., pp. 898-900, 1992, John Wiley & Sons, INC., or Richard C. Larock, Comprehensive Organic Transformations, pp. 421-425, 1989, VCH Publishers, INC. or a method according to the method.

In this reaction, any solvent that does not adversely affect the reaction can be used, and examples thereof include alcohols such as methanol, ethanol, 2-propanol, and 2-methyl-2-propanol; halogenated hydrocarbons such as methylene chloride, chloroform, and dichloroethane; aromatic hydrocarbons such as benzene, toluene, and xylene; ethers such as dioxane, tetrahydrofuran, anisole, ethylene glycol dimethyl ether, diethylene glycol dimethyl ether, diethylene glycol diethyl ether, and ethylene glycol monomethyl ether; sulfoxides such as dimethyl sulfoxide; esters such as ethyl acetate; amides such as N,N-dimethylformamide, N,N-dimethylacetamide, and 1-methyl-2-pyrrolidone; and water. These solvents may be used as a mixture thereof.

Examples of the reducing agent used in this reaction include hydride complex compounds such as lithium aluminum hydride, sodium triacetoxyborohydride, sodium cyanoborohydride, and sodium borohydride; borane, sodium, and sodium amalgam. In addition, electrolysis reduction using a copper or platinum anode, catalytic reduction using Raney nickel, platinum oxide, or palladium black, or reduction using "zinc-acid" can be employed.

In this reaction, the amounts of the compound of the general formula [4a] and the reducing agent may be 1 to 50-fold moles, preferably 1 to 5-fold moles to that of the compound of the general formula [2a].

This reaction may be carried out at −30 to 150° C., preferably at 0 to 100° C., for 10 minutes to 120 hours.

Production Method 2

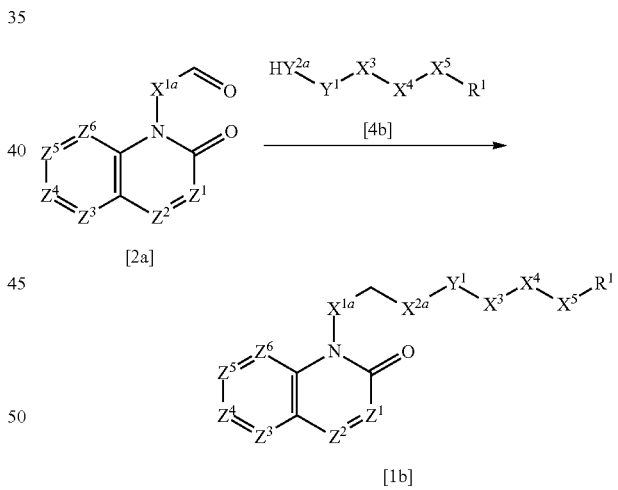

(In the formulas, $X^{2a}$ is a group represented by a general formula $NR^{2a}$ (where $R^{2a}$ denotes a hydrogen atom or an optionally substituted lower alkyl group); and $R^1$, $X^{1a}$, $X^3$, $X^4$, $X^5$, $Y^1$, $Z^1$, $Z^2$, $Z^3$, $Z^4$, $Z^5$ and $Z^6$ have the same meanings as mentioned above.)

Examples of known compounds of the general formula [4b] include 4-amino-1-(1-oxo-2-phenylethyl)piperidine and 4-amino-1-(2-phenylethyl)piperidine.

A compound of the general formula [1b] can be produced by reacting the compound of the general formula [2a] with a compound of the general formula [4b] in the presence of a reducing agent. This reaction may be carried out according to the production method 1.

Production Method 3

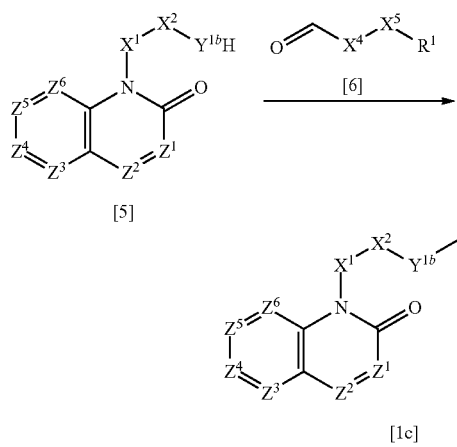

(In the formulas, $Y^{1b}$ denotes an optionally substituted bivalent alicyclic amine residue wherein one nitrogen atom in the ring binds to an adjacent group and another atom in the ring binds to $X^2$; and $R^1$, $X^1$, $X^2$, $X^4$, $X^5$, $Z^1$, $Z^2$, $Z^3$, $Z^4$, $Z^5$ and $Z^6$ have the same meanings as mentioned above.)

Examples of known compounds of the general formula [6] include 1,4-benzodioxane-6-carbaldehyde and (2,3-dihydro-1,4-benzodioxin-6-yl)acetaldehyde.

A compound of the general formula [1c] can be produced by reacting a compound of the general formula [5] with the compound of the general formula [6] in the presence of a reducing agent. This reaction may be carried out according to the production method 1.

Production Method 4

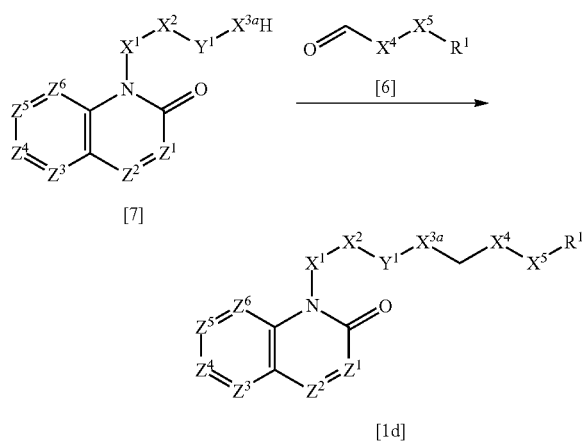

(In the formulas, $X^{3a}$ is a group represented by a general formula $NR^{3a}$ or $CR^4R^5NR^{3a}$ (where $R^{3a}$ denotes a hydrogen atom or an optionally substituted lower alkyl group; and $R^4$ and $R^5$ have the same meanings as mentioned above); and $R^1$, $X^1$, $X^2$, $X^4$, $X^5$, $Y^1$, $Z^1$, $Z^2$, $Z^3$, $Z^4$, $Z^5$ and $Z^6$ have the same meanings as mentioned above.)

A compound of the general formula [1d] can be produced by reacting a compound of the general formula [7] with the compound of the general formula [6] in the presence of a reducing agent. This reaction may be carried out according to the production method 1.

Production Method 5

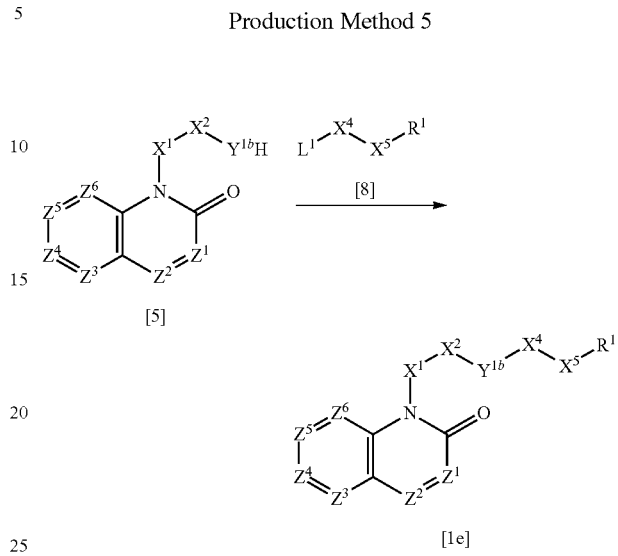

(In the formulas, $L^1$ denotes a leaving group; and $R^1$, $X^1$, $X^2$, $X^4$, $Y^{1b}$, $Z^1$, $Z^2$, $Z^3$, $Z^4$, $Z^5$ and $Z^6$ have the same meanings as mentioned above.)

Examples of known compounds of the general formula [8] include 2-(3-oxo-3,4-dihydro-2H-benzothiazin-6-yl)ethyl methanesulfonate, 2-(benzo[1,3]dioxol-5-yl)ethyl methanesulfonate, 2-((2-bromoethyl)thio)thiophene and 2-bromo-N-(pyridin-2-yl)acetamide.

A compound of the general formula [1e] can be produced by reacting the compound of the general formula [5] with a compound of the general formula [8] in the presence or absence of a base. This reaction may be carried out by the method described in, for example, U.S. Pat. No. 6,603,005 or a method according to the method.

In this reaction, any solvent that does not adversely affect the reaction can be used, and examples thereof include alcohols such as methanol, ethanol, 2-propanol, and 2-methyl-2-propanol; halogenated hydrocarbons such as methylene chloride, chloroform, and dichloroethane; aromatic hydrocarbons such as benzene, toluene, and xylene; ethers such as dioxane, tetrahydrofuran, anisole, ethylene glycol dimethyl ether, diethylene glycol dimethyl ether, diethylene glycol diethyl ether, and ethylene glycol monomethyl ether; sulfoxides such as dimethyl sulfoxide; ketones such as acetone and 2-butanone; esters such as ethyl acetate; amides such as N,N-dimethylformamide, N,N-dimethylacetamide, and 1-methyl-2-pyrrolidone; and water. These solvents may be used as a mixture thereof.

In this reaction, examples of the base used according to need include organic bases such as pyridine, dimethylaminopyridine, and triethylamine; and inorganic bases such as sodium hydroxide, potassium hydroxide, sodium hydrogen carbonate, potassium carbonate, and sodium carbonate.

In this reaction, the amounts of the compound of the general formula [8] and the base used according to need may be 1 to 20-fold moles to that of the compound of the general formula [5].

This reaction may be carried out at 0 to 200° C., preferably at 0 to 150° C., for 30 minutes to 48 hours.

Production Method 6

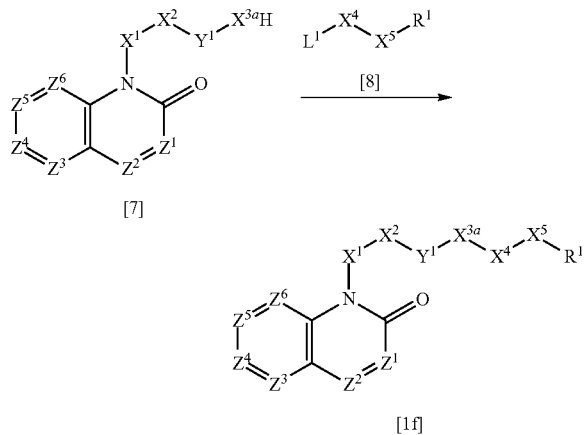

(In the formulas, $R^1$, $L^1$, $X^1$, $X^2$, $X^{3a}$, $X^4$, $X^5$, $Y^1$, $Z^1$, $Z^2$, $Z^3$, $Z^4$, $Z^5$ and $Z^6$ have the same meanings as mentioned above.)

A compound of the general formula [1f] can be produced by reacting the compound of the general formula [7] with a compound of the general formula [8] in the presence or absence of a base. This reaction may be carried out according to the production method 5.

Production Method 7

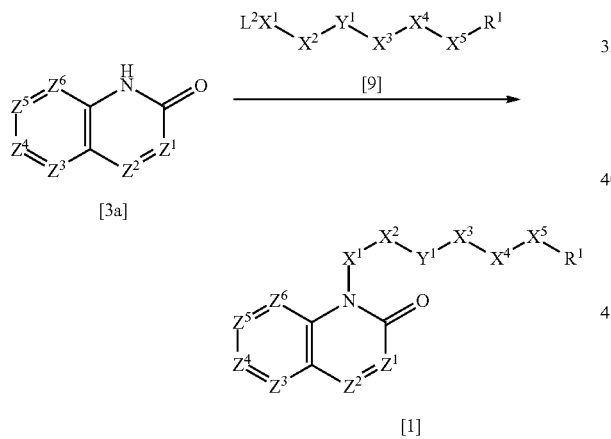

(In the formulas, $L^2$ denotes a leaving group; and $R^1$, $X^1$, $X^2$, $X^3$, $X^4$, $X^5$, $Y^1$, $Z^1$, $Z^2$, $Z^3$, $Z^4$, $Z^5$ and $Z^6$ have the same meanings as mentioned above.)

Examples of known compounds of the general formula [9] include 2-(4-(phenylacetyl)piperazin-1-yl)ethyl chloride and 2-chloro-1-(4-phenethylpiperazin-1-yl)ethanone.

The compound of the general formula [1] can be produced by reacting a compound of the general formula [3a] with the compound of the general formula [9] in the presence or absence of a base.

In this reaction, any solvent that does not adversely affect the reaction can be used, and examples thereof include amides such as N,N-dimethylformamide, N,N-dimethylacetamide, and 1-methyl-2-pyrrolidone; halogenated hydrocarbons such as methylene chloride, chloroform, and dichloroethane; aromatic hydrocarbons such as benzene, toluene, and xylene; ethers such as dioxane, tetrahydrofuran, anisole, ethylene glycol dimethyl ether, diethylene glycol dimethyl ether, diethylene glycol diethyl ether, and ethylene glycol monomethyl ether; sulfoxides such as dimethyl sulfoxide; esters such as ethyl acetate; and water. These solvents may be used as a mixture thereof.

In this reaction, examples of the base used according to need include organic bases such as pyridine, dimethylaminopyridine, and triethylamine; and inorganic bases such as sodium hydride, sodium hydroxide, potassium hydroxide, sodium hydrogen carbonate, potassium carbonate, sodium carbonate, and cesium carbonate.

In this reaction, the amounts of the base used according to need and the compound of the general formula [9] may be 1 to 50-fold moles, preferably 1 to 5-fold moles to that of the compound of the general formula [3a].

This reaction may be carried out at −30 to 150° C., preferably at 0 to 100° C., for 30 minutes to 48 hours.

The compounds of the general formulas [1], [1a], [1b], [1c], [1d], [1e] and [1f] prepared in the production methods 1 to 7 or salts thereof can be derived to other compounds of the general formula [1] or salts thereof by a known reaction such as condensation, addition, oxidation, reduction, rearrangement, substitution, halogenation, dehydration, or hydrolysis, or by a proper combination of such reactions.

In the compounds in the above-mentioned production methods, when isomers (for example, enantiomers, geometric isomers, or tautomers) exist, these isomers also can be used. Furthermore, solvates, hydrates, and various forms of crystals can be used.

The compounds of the general formula [2] of the present invention can be produced by a combination of known methods. For example, the compounds can be produced by the following production methods.

Production Method 8

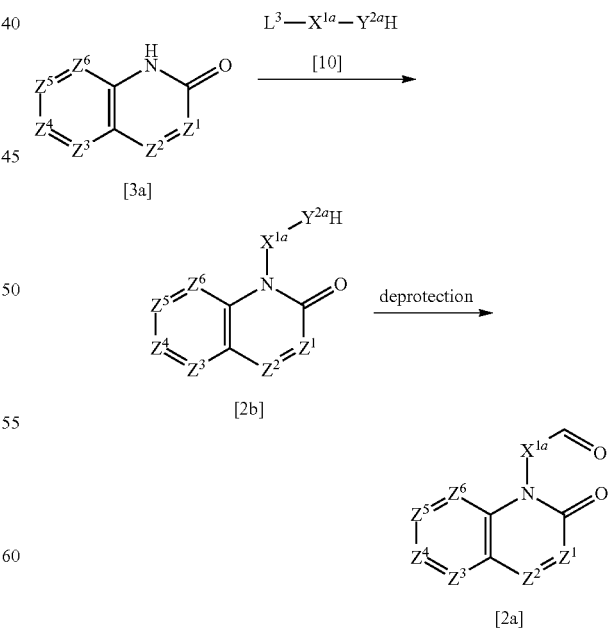

(In the formulas, $Y^{2a}$ denotes a protected carbonyl group; $L^3$ denotes a leaving group; and $X^{1a}$, $Z^1$, $Z^2$, $Z^3$, $Z^4$, $Z^5$ and $Z^6$ have the same meanings as mentioned above.)

Examples of known compounds of the general formula [10] include 2-(2-bromomethyl)-1,3-dioxolane, 2-(2-bromoethyl)-1,3-dioxolane and 2-(2-bromoethyl)-1,3-dioxane.

(8-1) A compound of the general formula [2b] can be produced by reacting the compound of the general formula [3a] with a compound of the general formula [10] in the presence or absence of a base. This reaction may be carried out according to the production method 7.

(8-2) The compound of the general formula [2a] can be produced by deprotecting the compound of the general formula [2b]. This reaction may be carried out by the method described in, for example, Protective Groups in Organic Synthesis, 3rd Ed., pp. 293-368, 1999, John Wiley & Sons, INC. or a method according to the method.

Production Method 9

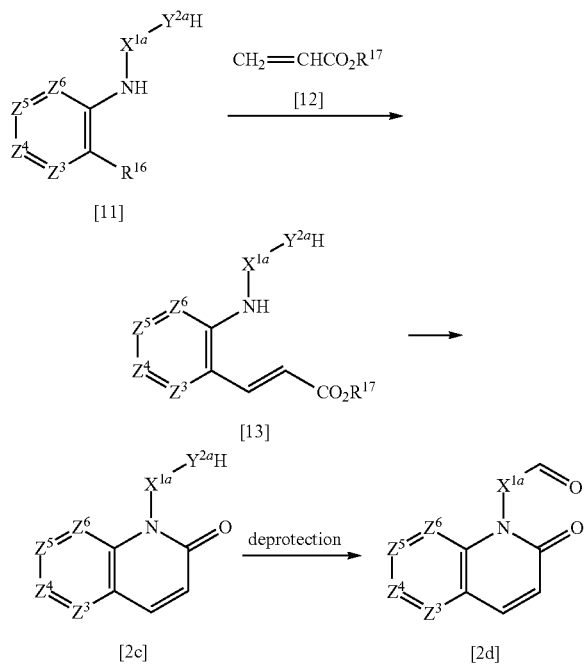

(In the formulas, $R^{16}$ denotes a chlorine atom, a bromine atom, a iodine atom, or an optionally substituted alkanesulfonyloxy group; $R^{17}$ denotes a carboxyl-protecting group; and $X^{1a}, Y^{2a}, Z^3, Z^4, Z^5$ and $Z^6$ have the same meanings as mentioned above.)

An example of a compound of the general formula [11] is 2-chloro-N-(2,2-dimethoxyethyl)pyridine-3-amine.

Examples of a compound of the general formula [12] include methyl acrylate, ethyl acrylate and tert-butyl acrylate.

(9-1) A compound of the general formula [13] can be produced by reacting the compound of the general formula [11] with the compound of the general formula [12] in the presence of a catalyst, in the presence or absence of a base, and in the presence or absence of a ligand. This reaction may be carried out by the method described in, for example, Tsuji, et al., Sen-i Kinzoku ga Hiraku Yuki Gosei (Organic synthesis using transition metal), pp. 19-22, 1997, Maruzen and Chem. Pharm. Bull., vol. 33, pp. 4764-4768, 1985 or a method according to the method.

In this reaction, any solvent that does not adversely affect the reaction can be used, and examples thereof include alcohols such as methanol, ethanol, 2-propanol, and 2-methyl-2-propanol; amides such as N,N-dimethylformamide, N,N-dimethylacetamide, and 1-methyl-2-pyrrolidone; halogenated hydrocarbons such as methylene chloride, chloroform, and dichloroethane; aromatic hydrocarbons such as benzene, toluene, and xylene; ethers such as dioxane, tetrahydrofuran, anisole, ethylene glycol dimethyl ether, diethylene glycol dimethyl ether, diethylene glycol diethyl ether, and ethylene glycol monomethyl ether; sulfoxides such as dimethyl sulfoxide; ketones such as acetone and 2-butanone; esters such as ethyl acetate; nitriles such as acetonitrile; and water. These solvents may be used as a mixture thereof. This reaction may be carried out in the absence of a solvent.

Examples of the catalyst used in this reaction include tetrakis(triphenylphosphine)palladium(0), palladium(II) acetate, palladium(II) chloride, bis(tri-tert-butylphosphine) palladium(0), and tris(dibenzylideneacetone)dipalladium(0).

In this reaction, examples of the base used according to need include organic bases such as pyridine, dimethylaminopyridine, triethylamine, N,N-dimethylbenzylamine, sodium acetate, and potassium acetate; and inorganic bases such as sodium hydroxide, potassium hydroxide, sodium hydrogen carbonate, potassium carbonate, and sodium carbonate.

In this reaction, examples of the ligand used according to need include trialkylphosphines such as trimethylphosphine and tri-tert-butylphosphine; tricycloalkylphosphines such as tricyclohexylphosphine; triarylphosphines such as triphenylphosphine and tritolylphosphine; trialkylphosphites such as trimethylphosphite, triethylphosphite, and tributylphosphite; tricycloalkylphosphites such as tricyclohexylphosphite; triarylphosphites such as triphenylphosphite; imidazolium salts such as 1,3-bis(2,4,6-trimethylphenyl) imidazolium chloride; diketones such as acetylacetone and octafluoroacetylacetone; amines such as trimethylamine, triethylamine, tripropylamine, and triisopropylamine; and 1,1'-bis(diphenylphosphino)ferrocene, 2,2'-bis(diphenylphosphino)-1,1'-binaphthyl, 2-dicyclohexylphosphino-2',6'-dimethoxybiphenyl, 2-dicyclohexylphosphino-2',4',6'-triisopropylbiphenyl, 2-(di-tert-butylphosphino)-2',4',6'-triisopropylbiphenyl, and 2-(di-tert-butylphosphino) biphenyl. These ligands may be used as a combination thereof.

In this reaction, the amount of the compound of the general formula [12] is 1 to 10-fold moles, preferably 1 to 5-fold moles to that of the compound of the general formula [11].

In this reaction, the amount of the catalyst is 0.001 to 10-fold moles, preferably 0.01 to 2-fold moles to that of the compound of the general formula [11].

In this reaction, the amount of the base used according to need is 1 to 10-fold moles, preferably 1 to 5-fold moles to that of the compound of the general formula [11].

In this reaction, the amount of the ligand used according to need is 0.00001 to 1-fold moles, preferably 0.001 to 0.1-fold moles to that of the compound of the general formula [11].

This reaction may be carried out at −30 to 200° C., preferably at 0 to 100° C., for 30 minutes to 48 hours.

(9-2) A compound of the general formula [2c] can be produced by ring-closing the compound of the general formula [13] in the presence or absence of a base. This reaction may be carried out by the method described in, for example, Chem. Pharm. Bull., vol. 33, pp. 4764-4768, 1985 or a method according to the method.

In this reaction, any solvent that does not adversely affect the reaction can be used, and examples thereof include alcohols such as methanol, ethanol, 2-propanol, and 2-methyl-2-propanol; amides such as N,N-dimethylformamide, N,N- dimethylacetamide, and 1-methyl-2-pyrrolidone; aromatic hydrocarbons such as benzene, toluene, and xylene; ethers such as dioxane, tetrahydrofuran, anisole, ethylene glycol dimethyl ether, diethylene glycol dimethyl ether, diethylene glycol diethyl ether, and ethylene glycol monomethyl ether; sulfoxides such as dimethyl sulfoxide; ketones such as acetone and 2-butanone; esters such as ethyl acetate; nitriles such as acetonitrile; and water. These solvents may be used as a mixture thereof.

In this reaction, examples of the base used according to need include organic bases such as pyridine, dimethylaminopyridine, and triethylamine; and inorganic bases such as sodium methoxide, sodium ethoxide, sodium hydroxide, potassium hydroxide, sodium hydrogen carbonate, potassium carbonate, and sodium carbonate.

In this reaction, the amount of the base used according to need may be 1 to 20-fold moles to that of the compound of the general formula [13].

This reaction may be carried out at 0 to 200° C., preferably at 0 to 150° C., for 30 minutes to 48 hours.

(9-3) A compound of the general formula [2d] can be produced by deprotecting the compound of the general formula [2c]. This reaction may be carried out according to the production method 8-2.

Production Method 10

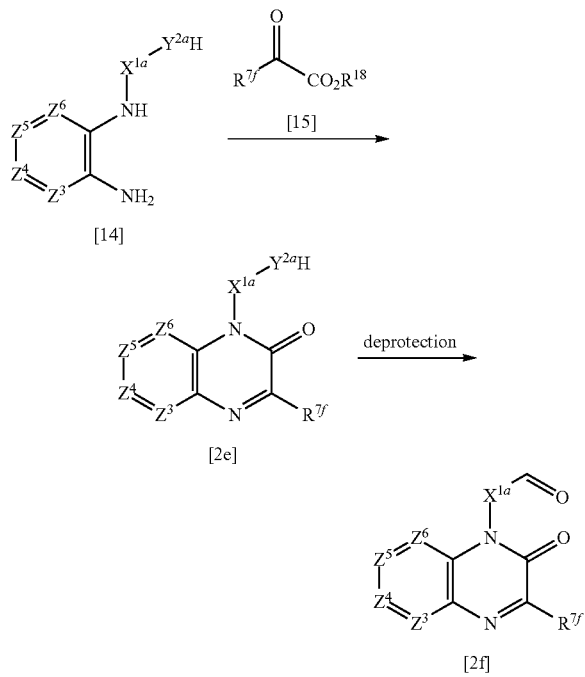

(In the formulas, $R^{7f}$ denotes a hydrogen atom or an optionally substituted lower alkyl, cycloalkyl or aryl group; $R^{18}$ denotes a hydrogen atom or a carboxyl-protecting group; $X^{1a}$, $Y^{2a}$, $Z^3$, $Z^4$, $Z^5$ and $Z^6$ have the same meanings as mentioned above.)

An example of a compound of the general formula [15] is ethyl glyoxylate. In this reaction, the compound of the general formula [15] may be a hydrate (hemiacetal) thereof. An example of the hydrate (hemiacetal) of the compound of the general formula [15] is ethyl glyoxylate hemiacetal.

(10-1) A compound of the general formula [2e] can be produced by reacting a compound of the general formula [14] with the compound of the general formula [15]. This reaction may be carried out by the method described in, for example, J. Chem. Soc., pp. 5156-5166, 1963 or a method according to the method.

(10-2) A compound of the general formula [2f] can be produced by deprotecting the compound of the general formula [2e]. This reaction may be carried out according to the production method 8-2.

The compounds of the general formula [3] of the present invention can be produced by a combination of known methods. For example, the compounds can be produced by the following production methods.

Production Method 11

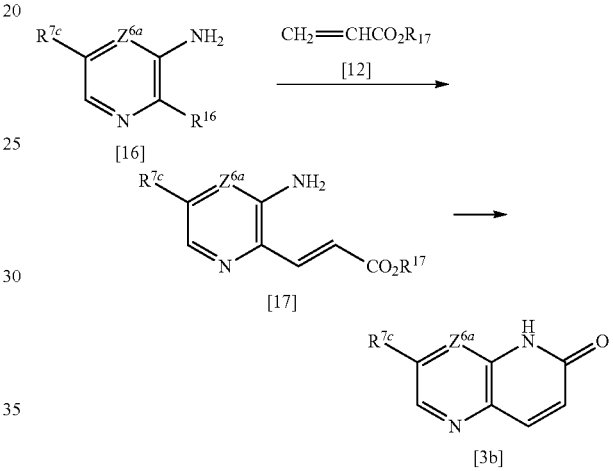

(In the formulas, $R^{7c}$, $R^{16}$, $R^{17}$, and $Z^{6a}$ have the same meanings as mentioned above.)

Examples of a compound of the general formula [16] include 3-amino-2-chloro-5-methoxypyridine and 3-amino-2-chloro-5-methoxypyrazine.

(11-1) A compound of the general formula [17] can be produced by reacting the compound of the general formula [16] with the compound of the general formula [12] in the presence of a catalyst and in the presence or absence of a base. This reaction may be carried out according to the production method 9-1.

(11-2) The compound of the general formula [3b] can be produced by ring-closing the compound of the general formula [17] in the presence or absence of a base. This reaction may be carried out according to the production method 9-2.

Production Method 12

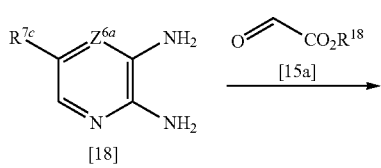

-continued

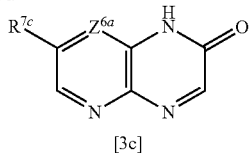

[3c]

(In the formulas, $R^{7c}$, $R^{18}$ and $Z^{6a}$ have the same meanings as mentioned above.)

A compound of the general formula [3c] can be produced by reacting a compound of the general formula [18] with a compound of the general formula [15a]. This reaction may be carried out according to the production method 10-1.

Production Method 13

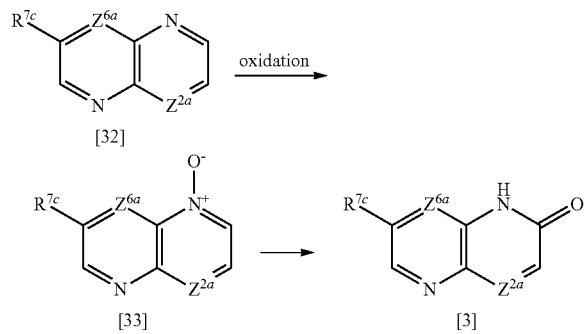

(In the formulas, $Z^{2a}$, $Z^{6a}$, and $R^{7c}$ have the same meanings as mentioned above.)

(13-1) A compound of the general formula [33] can be produced by oxidizing a compound of the general formula [32].

This reaction may be carried out by the method described in, for example, Heterocycles, vol. 32, pp. 1579-1586, 1991 or Heterocycles, vol. 34, pp. 1055-1063, 1992 or a method according to the method.

In this reaction, any solvent that does not adversely affect the reaction can be used, and examples thereof include halogenated hydrocarbons such as methylene chloride, chloroform, and dichloroethane; aromatic hydrocarbons such as benzene, toluene, and xylene; sulfoxides such as dimethyl sulfoxide; and water. These solvents may be used as a mixture thereof.

Examples of the oxidant used in this reaction are m-chloroperbenzoic acid and peracetic acid.

In this reaction, the amount of the oxidant may be 1 to 10-fold moles to that of the compound of the general formula [32].

This reaction may be carried out at 0 to 200° C., preferably at 0 to 50° C., for 30 minutes to 48 hours.

(13-2) The compound of the general formula [3] can be produced by reacting the compound of the general formula [33] with a sulfonyl chloride and then hydrating the resulting product.

This reaction may be carried out by the method described in, for example, Heterocycles, vol. 32, pp. 1579-1586, 1991 or Heterocycles, vol. 34, pp. 1055-1063, 1992 or a method according to the method.

In this reaction, any solvent that does not adversely affect the reaction can be used together with water, and examples thereof include halogenated hydrocarbons such as methylene chloride, chloroform, and dichloroethane; aromatic hydrocarbons such as benzene, toluene, and xylene; sulfoxides such as dimethyl sulfoxide; nitriles such as acetonitrile. These solvents may be used as a mixture thereof.

Examples of the sulfonyl chlorides used in this reaction include p-toluenesulfonyl chloride and benzenesulfonyl chloride.

In this reaction, the amount of the sulfonyl chloride may be 1 to 10-fold moles to that of the compound of the general formula [33].

This reaction may be carried out at 0 to 200° C., preferably at 0 to 50° C., for 30 minutes to 48 hours.

The compounds of the general formula [1] of the present invention can be also produced by the following production methods.

Production Method 14

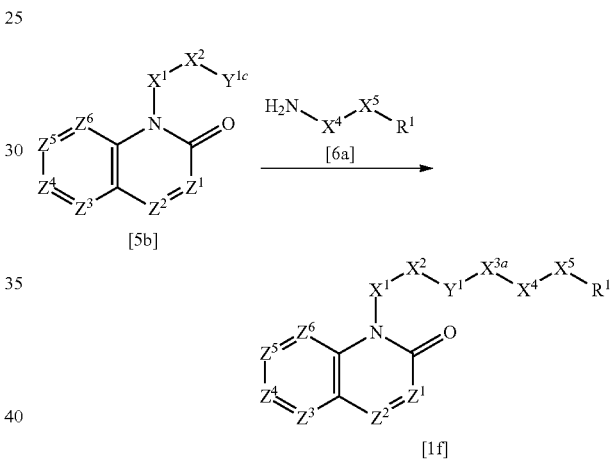

(In the formulas, $Y^{1c}$ denotes an optionally substituted bivalent alicyclic hydrocarbon residue wherein one carbon atom in the ring or of a substituent is substituted with an oxo group or denotes an optionally substituted bivalent alicyclic amine residue wherein one carbon atom in the ring or of a substituent is substituted with an oxo group; and $R^1$, $X^1$, $X^2$, $X^{3a}$, $X^4$, $X^5$, $Y^1$, $Z^1$, $Z^2$, $Z^3$, $Z^4$, $Z^5$ and $Z^6$ have the same meanings as mentioned above.)

An example of known compounds of the general formula [6a] is 1-(2,3-dihydro(1,4)dioxino(2,3-c) pyridin-7-yl) methaneamine.

The compound of the general formula [1f] can be produced by reacting a compound of the general formula [5b] with the compound of the general formula [6a] in the presence of a reducing agent. This reaction may be carried out according to the production method 1.

Next, methods of producing the compounds of the general formulas [5], [7] and [14], which are raw materials for producing the compounds of the general formulas [1], [2] and [3] of the present invention, will be described. These compounds can be produced by a combination of known methods. For example, the compounds can be produced by the following production methods.

Production Method A

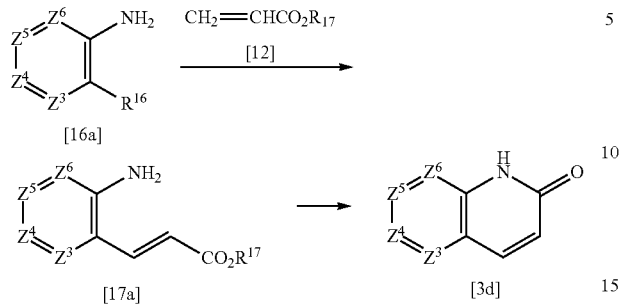

(In the formulas, $R^{16}$, $R^{17}$, $Z^3$, $Z^4$, $Z^5$ and $Z^6$ have the same meanings as mentioned above.)

Examples of a compound of the general formula [16a] include 3-amino-2-chloro-5-methoxypyridine and 3-amino-2-chloro-5-methoxypyrazine.

(A-1) A compound of the general formula [17a] can be produced by reacting the compound of the general formula [16a] with the compound of the general formula [12] in the presence of a catalyst and in the presence or absence of a base. This reaction may be carried out according to the production method 9-1.

(A-2) A compound of the general formula [3d] can be produced by ring-closing the compound of the general formula [17a] in the presence or absence of a base. This reaction may be carried out according to the production method 9-2.

Production method B

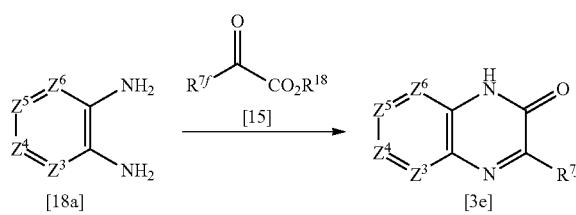

(In the formulas, $R^{7f}$, $R^{18}$, $Z^3$, $Z^4$, $Z^5$ and $Z^6$ have the same meanings as mentioned above.)

A compound of the general formula [3e] can be produced by reacting a compound of the general formula [18a] with the compound of the general formula [15]. This reaction may be carried out according to the production method 10-1.

Production Method C

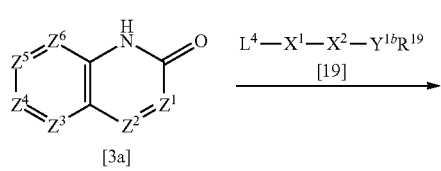

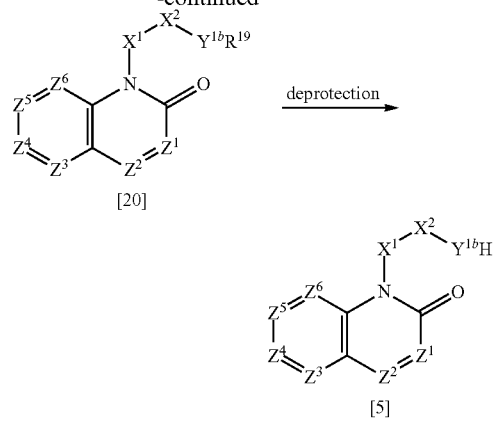

(In the formulas, $R^{19}$ denotes an imino-protecting group; $L^4$ denotes a leaving group; and $X^1$, $X^2$, $Y^{1b}$, $Z^1$, $Z^2$, $Z^3$, $Z^4$, $Z^5$ and $Z^6$ have the same meanings as mentioned above.)

An example of known compounds of the general formula [19] is 1-tert-butyl 4-ethyl 4-(2-(methanesulfonyloxy)ethyl)-1,4-piperidinedicarboxylate.

(C-1) A compound of the general formula [20] can be produced by reacting the compound of the general formula [3a] with the compound of the general formula [19] in the presence or absence of a base. This reaction may be carried out according to the production method 7.

(C-2) The compound of the general formula [5] can be produced by deprotecting the compound of the general formula [20]. This reaction may be carried out by the method described in, for example, Protective Groups in Organic Synthesis, 3rd Ed., pp. 494-653, 1999, John Wiley & Sons, INC. or a method according to the method.

Production Method D

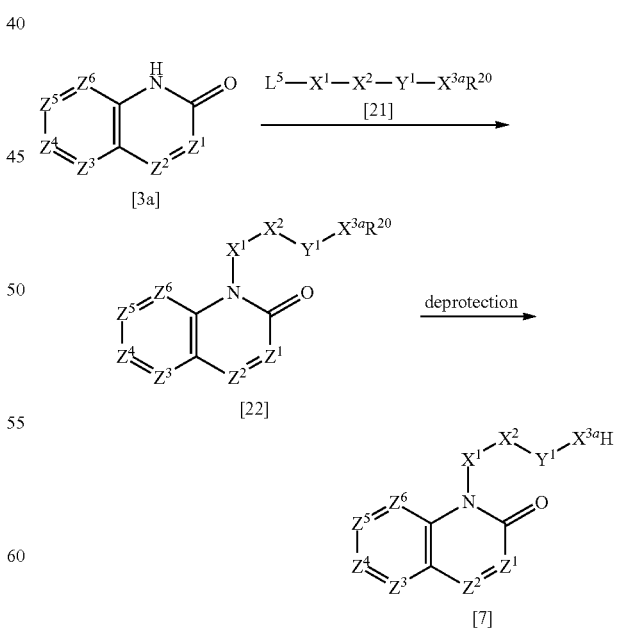

(In the formulas, $R^{20}$ denotes an imino-protecting group; $L^5$ denotes a leaving group; $X^2$, $X^2$, $X^{3a}$, $Y^1$, $Z^1$, $Z^2$, $Z^3$, $Z^4$, $Z^5$ and $Z^6$ have the same meanings as mentioned above.)

An example of known compounds of the general formula [21] is tert-butyl ((1-(2-chloroacetyl)-4-(3-(trifluoromethyl)phenyl)-4-piperidyl)methyl)(methyl)carbamate.

(D-1) A compound of the general formula [22] can be produced by reacting the compound of the general formula [3a] with the compound of the general formula [21] in the presence or absence of a base. This reaction may be carried out according to the production method 7.

(D-2) The compound of the general formula [7] can be produced by deprotecting the compound of the general formula [22]. This reaction may be carried out according to the production method C-2.

Production Method E

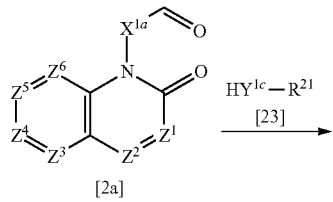

[2a]

[20a]

[5a]

(In the formulas, $R^{21}$ denotes an imino-protecting group; $Y^{1c}$ denotes an optionally substituted bivalent alicyclic amine residue wherein two nitrogen atoms in the ring bind to each other's adjacent groups; and $X^{1a}$, $Z^1$, $Z^2$, $Z^3$, $Z^4$, $Z^5$ and $Z^6$ have the same meanings as mentioned above.)

Examples of a compound of the general formula [23] include 1-(tert-butoxycarbonyl)piperazine and methyl 4-(tert-butoxycarbonyl)piperazine-2-carboxylate.

(E-1) A compound of the general formula [20a] can be produced by reacting the compound of the general formula [2a] with a compound of the general formula [23] in the presence of a reducing agent. This reaction may be carried out according to the production method 1.

(E-2) A compound of the general formula [5a] can be produced by deprotecting the compound of the general formula [20a]. This reaction may be carried out according to the production method C-2.

Production Method F

[2a]

[22a]

[7a]

(In the formulas, $R^{22}$ denotes an imino-protecting group; $X^{1a}$, $X^{3a}$, $Y^{1a}$, $Z^1$, $Z^2$, $Z^3$, $Z^4$, $Z^5$ and $Z^6$ have the same meanings as mentioned above.)

An example of a compound of the general formula [24] is 4-((benzyloxycarbonyl)amino)-4-methylpiperidine.

(F-1) A compound of the general formula [22a] can be produced by reacting the compound of the general formula [2a] with the compound of the general formula [24] in the presence of a reducing agent. This reaction may be carried out according to the production method 1.

(F-2) A compound of the general formula [7a] can be produced by deprotecting the compound of the general formula [22a]. This reaction may be carried out according to the production method C-2.

Production Method G

[25]

[26]

[4c]

(In the formulas, $R^{23}$ denotes an imino-protecting group; and $R^1$, $X^4$, $X^5$, and $Y^{1c}$ have the same meanings as mentioned above.)

(G-1) A compound of the general formula [26] can be produced by reacting a compound of the general formula [25] with the compound of the general formula [6] in the presence of a reducing agent. This reaction may be carried out according to the production method 1.

(G-2) A compound of the general formula [4c] can be produced by deprotecting the compound of the general formula [26]. This reaction may be carried out according to the production method C-2.

Production Method H

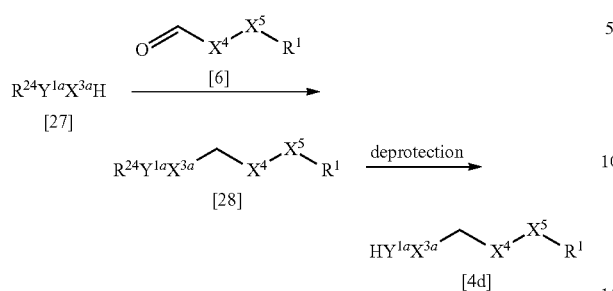

(In the formulas, $R^{24}$ denotes an imino-protecting group; and $R^1$, $X^{3a}$, $X^4$, $X^5$, and $Y^{1a}$ have the same meanings as mentioned above.)

(H-1) A compound of the general formula [28] can be produced by reacting a compound of the general formula [27] with the compound of the general formula [6] in the presence of a reducing agent. This reaction may be carried out according to the production method 1.

(H-2) A compound of the general formula [4d] can be produced by deprotecting the compound of the general formula [28]. This reaction may be carried out according to the production method C-2.

Production Method I

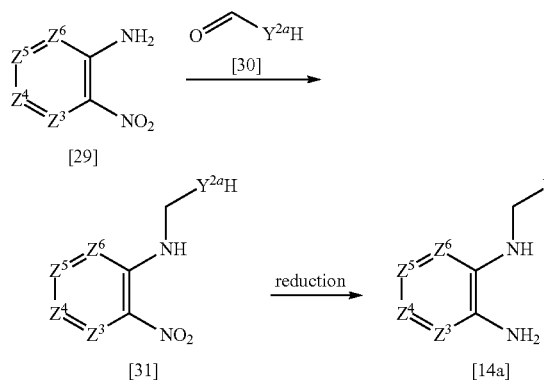

(In the formulas, $Y^{2a}$, $Z^3$, $Z^4$, $Z^5$ and $Z^6$ have the same meanings as mentioned above.)

Examples of a compound of the general formula [29] include 3-nitropyridin-2-amine and 3-amino-2-nitropyridine.

Examples of a compound of the general formula [30] include 2,2-dimethoxyacetaldehyde and 2,2-diethoxyacetaldehyde.

(I-1) A compound of the general formula [31] can be produced by reacting the compound of the general formula [29] with the compound of the general formula [30] in the presence of a reducing agent. This reaction may be carried out according to the production method 1.

(I-2) A compound of the general formula [14a] can be produced by reducing the compound of the general formula [31]. This reaction may be carried out by the method described in, for example, Richard C. Larock, Comprehensive Organic Transformations, pp. 411-415, 1989, VCH Publishers, INC. or a method according to the method.

Production Method J

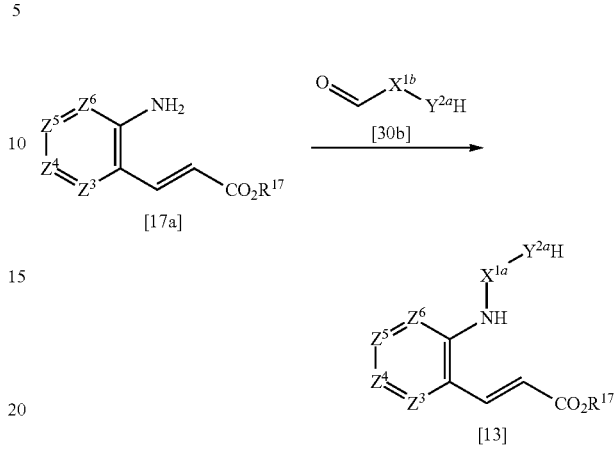

(In the formulas, $X^{1b}$ denotes an optionally substituted methylene or ethylene group or a bond; and $R^{17}$, $X^{1a}$, $Y^{2a}$, $Z^3$, $Z^4$, $Z^5$ and $Z^6$ have the same meanings as mentioned above.)

The compound of the general formula [13] can be produced by reacting the compound of the general formula [17a] with a compound of the general formula [30b] in the presence of a reducing agent. This reaction may be carried out according to the production method 1.

Production Method K

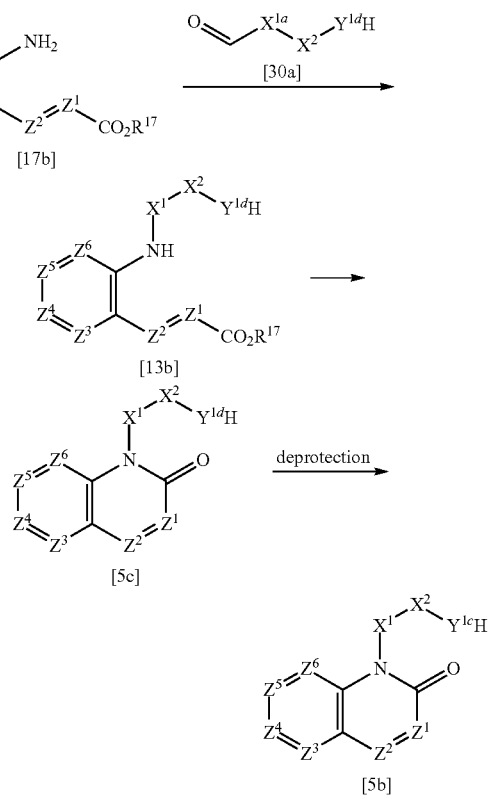

(In the formulas, $Y^{1d}$ denotes an optionally substituted bivalent alicyclic hydrocarbon residue wherein one carbon atom in the ring or of a substituent is that of a protected carbonyl group or denotes an optionally substituted bivalent alicyclic amine residue wherein one carbon atom in the ring or of a substituent is that of a protected carbonyl group; and $R^{17}$, $X^1$, $X^{1a}$, $X^2$, $Y^{1c}$, $Z^1$, $Z^2$, $Z^3$, $Z^4$, $Z^5$ and $Z^6$ have the same meanings as mentioned above.)

(K-1) A compound of the general formula [13b] can be produced by reacting a compound of the general formula [17b] with a compound of the general formula [30a] in the presence of a reducing agent. This reaction may be carried out according to the production method 1.

(K-2) A compound of the general formula [5c] can be produced by ring-closing the compound of the general formula [13b] in the presence or absence of a base. This reaction may be carried out according to the production method 9-2.

(K-3) A compound of the general formula [5b] can be produced by deprotecting the compound of the general formula [5c] in the presence or absence of a base. This reaction may be carried out according to the production method 8-2.

The compounds prepared in the production methods 1 to 14 and the production methods A to K can be derived to other compounds by a known reaction such as condensation, addition, oxidation, reduction, rearrangement, substitution, halogenation, dehydration, or hydrolysis, or by a proper combination of such reactions.

When an imino, amino, hydroxyl, or carboxyl group exists in the compounds prepared in the production methods 1 to 14 and the production methods A to K and intermediates thereof, the reactions can be carried out with such groups appropriately protected with their protecting groups.

In the production methods 1 to 14 and the production methods A to K, when a compound having a carbonyl group is used in a reaction, a compound having a protected carbonyl group can be used instead of the compound having a carbonyl group.

When the compound of the general formula [1] of the present invention is used as a drug, in general, formulation additives, for example, a carrier, an excipient, and a diluent, which are used in preparation, may be appropriately mixed with the compound. These mixtures can be administered, in the usual manner, orally or parenterally in forms of, for example, tablets, capsules, powder, syrup, granules, pills, suspensions, emulsions, solutions, powdered medicine, suppositories, eye-drops, nose-drops, ear drops, plasters, ointment or injections. The administration route, dose, and frequency can be appropriately determined depending on the age, body weight, and symptoms of a patient. In general, the compound may be administered to an adult orally or parenterally (for example, injection, infusion, or administration into the rectum) in an amount of 0.01 to 1000 mg/kg per day at once or in several divided doses.

The compound of the general formula [1] of the present invention has strong antimicrobial activity against, for example, gram-positive bacteria including resistant bacteria such as multidrug-resistant *Staphylococcus aureus*, multidrug-resistant pneumococcus, and vancomycin-resistant *Enterococcus*, gram-negative bacteria, anaerobes, or atypical mycobacteria.

More specifically, the compound of the general formula [1] of the present invention has strong antimicrobial activity against, for example, bacteria selected from *Staphylococcus aureus* (*Staphylococcus aureus* Smith, *Staphylococcus aureus* F-3095 (MDRSA), and *Staphylococcus aureus* F-2161 (MDRSA)), pneumococcus (*Streptococcus pneumoniae* IID553, *Streptococcus pneumoniae* D-1687 (QRSP) and *Streptococcus pneumoniae* D-4249 (MDRSP)), *Enterococcus faecalis* (*Enterococcus faecalis* ATCC29212, *Enterococcus faecalis* IID682, *Enterococcus faecalis* D-2648 (VCM-R), and *Enterococcus faecalis* EF-210 (VanA)), *Enterococcus faecium* (*Enterococcus faecium* NBRC 13712 and *Enterococcus faecium* EF-211 (VanA)), *Corynebacterium diphtheriae* (*Corynebacterium diphtheriae* ATCC 27010), *Escherichia coli* (*Escherichia coli* NIHJ), *Serratia marcescens* (*Serratia marcescens* IID 5218), *Haemophilus influenzae* (*Haemophilus influenzae* ATCC 49247), *Moraxella catarrhalis* (*Moraxella catarrhalis* ATCC 25238), *Pseudomonas aeruginosa* (*Pseudomonas aeruginosa* IF03445), *Enterobacter cloacae* (*Enterobacter cloacae* IID 977), *Citrobacter freundii* (*Citrobacter freundii* NBRC 12681), *Gardnerella vaginalis* (*Gardnerella vaginalis* ATCC 14018), *Neisseria gonorrhoeae* (*Neisseria gonorrhoeae* ATCC 19424), *Peptostreptococcus asaccharolyticus* (*Peptostreptococcus asaccharolyticus* ATCC 14963), *Propionibacterium acnes* (*Propionibacterium acnes* JCM 6425), *Clostridium perfringens* (*Clostridium perfringens* ATCC 13124), *Bacteroides fragilis* (*Bacteroides fragilis* ATCC 25285), *Porphyromonas gingivalis* (*Porphyromonas gingivalis* JCM 8525), *Prevotella intermedia* (*Prevotella intermedia* JCM 7365), *Fusobacterium nucleatum* (*Fusobacterium nucleatum* JCM 8532), *Legionella pneumophilia* (*Legionella pneumophilia* ATCC33153, *Legionella pneumophilia* subsp. *pneumophilia* ATCC33155, *Legionella pneumophilia* subsp. *pneumophilia* ATCC33215, and *Legionella pneumophilia* subsp. *fraseri* ATCC33216), *Mycoplasma pneumoniae* (*Mycoplasma pneumoniae* ATCC15531), and the like.

The compound of the general formula [1] of the present invention has excellent safety. The safety can be evaluated by various tests, for example, by various types of safety tests selected from a cytotoxicity test, a selectivity test against DNA gyrase of human and various bacteria, a selectivity test against topoisomerase IV of human and various bacteria, an hERG test, a repeat-dose toxicity test, a cytochrome P450 (CYP) activity inhibition test, a metabolic dependence inhibition test, an in vivo mouse micronucleus test, an in vivo rat liver UDS test, and the like.

The compound of the general formula [1] of the present invention has excellent metabolic stability. The metabolic stability can be evaluated by various tests, for example, by various types of stability tests selected from a human liver microsome metabolic stability test, a human S9 stability test, and the like.

In particular, the compounds in Examples 2, 4, 77 and 85 of the present invention exhibited higher antimicrobial activity and safety and further higher metabolic stability and tissue distribution.

Furthermore, usefulness of the compounds of the general formula [1] of the present invention will now be described with reference to the following test examples.

Test Example 1

Susceptibility Test 1

Test substances were initially dissolved in dimethylsulfoxide. Antibacterial activities (MICs) of the same compounds were determined by the micro-dilution method as recommended by the Japanese Society of Chemotherapy.

*Staphylococcus aureus* (*S. aureus* FDA209P, F-3095) was used as the test organism. The bacteria cultured on Mueller-Hinton agar (MHA) plates at 35° C. overnight were suspended in sterile physiological saline in a concentration that was equivalent to 0.5 McFarland. The bacterial inoculum was prepared by 10-fold dilution of this suspension. Approximately 0.005 mL of the bacterial inoculum was inoculated into Cation-adjusted Mueller-Hinton broth (CAMHB, 100 µL/well) containing the test substance and was incubated at 35° C. overnight. The lowest concentration of the test substance at which no bacterial growth was macroscopically observed was determined as the MIC. Table 6 shows the results.

TABLE 6

| Test substance | MIC (μg/mL) | |
|---|---|---|
| (Example No.) | S. aureus FDA209P | S. aureus F-3095 |
| 2 | 0.0313 | 0.0313 |
| 4 | 0.0313 | 0.0313 |
| 8 | 0.0313 | 0.0313 |
| 10 | 0.0156 | 0.0156 |
| 17 | 0.0039 | 0.0313 |
| 30 | 0.0313 | 0.0313 |
| 33 | 0.0313 | 0.0313 |
| 35 | 0.0313 | 0.0313 |
| 44 | 0.0313 | 0.0313 |
| 45 | 0.0313 | 0.0625 |
| 55 | 0.0039 | 0.0078 |
| 77 | 0.0313 | 0.0625 |
| 79 | 0.0078 | 0.0156 |
| 80 | 0.0078 | 0.0156 |
| 85 | 0.0313 | 0.0313 |
| 90 | 0.0313 | 0.0313 |
| 93 | 0.0625 | 0.0313 |
| 95 | 0.0313 | 0.0625 |
| 96 | 0.0625 | 0.0625 |
| 103 | 0.0625 | 0.0625 |
| 118 | 0.0625 | 0.0625 |
| 119B | 0.0625 | 0.0625 |
| 123 | 0.0313 | 0.125 |
| 133 | 0.0078 | 0.0156 |
| 137 | 0.0313 | 0.0625 |
| 140 | 0.0156 | 0.0156 |
| 141 | 0.0313 | 0.0313 |
| 143 | 0.0313 | 0.0313 |
| 144 | 0.0313 | 0.0313 |
| 146 | 0.0625 | 0.0625 |
| 147 | 0.0313 | 0.0625 |
| 149 | 0.0313 | 0.0313 |
| 151 | 0.0313 | 0.125 |
| 152 | 0.0625 | 0.0625 |
| 162 | 0.0313 | 0.0625 |
| 163 | 0.0313 | 0.0313 |

Test Example 2

S. aureus Infection Experiment

ICR mice (male, SPF grade, 4-week old, five mice per group) were used. A bacterial inoculum was prepared by suspending Staphylococcus aureus (S. aureus Smith), which was cultured on a Mueller-Hinton agar plate at 37° C. overnight, in sterile physiological saline, preparing a bacterial solution of about $4 \times 10^8$ CFU/mL, and diluting the solution 10-fold in 5.6% mucin-phosphate buffer. ICR mice were intraperitoneally administered with the bacterial inoculum (approximately $2 \times 10^7$ CFU/mouse) to induce infection. Test substances were dissolved in 10% hydroxypropyl-β-cyclodextrin and 0.05 mol/L hydrochloric acid. Each of the test substance solutions was subcutaneously administered once in an amount of 3 mg/kg to the mice after 1 hour of the infection. The number of surviving mice was recorded on 5 days after the infection.

As the result, all mice of the control group which were not administered with the test substance died. However, all mice of the administration groups of Example Nos. 2, 4, 68, 77, 93, 103, 119B, 140, 149 and 151 survived. Similarly, the compound of Example 85 was administered in an amount of 1 mg/kg. As the result, four mice out of five survived.

Test Example 3

Cytotoxicity Test

Each test substance was dissolved in dimethyl sulfoxide and was prepared to each concentration with E-MEM containing 10% FBS, and then 0.1 mL of this solution was dispensed into each well of a 96-well microplate. A vero cell suspension containing $3 \times 10^4$ cells/mL was prepared with E-MEM containing 10% FBS, and 0.1 mL of the suspension was inoculated to each well. After incubation in 5% $CO_2$ at 37° C. for 3 days, 50 μL of E-MEM containing 1 mg/mL of 2,3-bis-(2-methoxy-4-nitro-5-sulfophenyl)-5-[(phenylamino)carbonyl]-2H-tetrazolium, inner salt, monosodium salt (XTT) and 25 μM of phenazine methosulfate (PMS) was added to each well. After about 2 hours, the absorbance at 450 nm was measured with a microplate reader.

The absorbance ratio of each well supplied with the test substance and the control not containing the test substance was calculated, and the concentration of each compound when cell proliferation was inhibited by 50% ($CC_{50}$; μg/mL) was calculated.

As the result, the $CC_{50}$ values of all compounds of Example Nos. 2, 4, 8, 10, 30, 33, 35, 55, 68, 77, 79, 80, 85, 90, 93, 95, 96 and 103 were 51.2 μg/mL or more.

The present invention will be then described with reference to Reference Examples and Examples; however, the present invention is not limited to these Examples.

Unless otherwise stated, the carrier used in silica gel column chromatography is B. W. silica gel, BW-127ZH, manufactured by Fuji Silysia Chemical Ltd.; the carrier used in basic silica gel column chromatography is silica gel, FL100D, manufactured by Fuji Silysia Chemical Ltd.; and the carrier used in reversed phase silica gel column chromatography is ODS-AM120-S50, manufactured by YMC Co., Ltd.

Flash column chromatography is performed with a medium pressure liquid chromatograph, YFLC-Wprep2XY.N, manufactured by YAMAZEN CORPORATION. Unless otherwise stated, a silica gel column is a Hi-Flash column, W001, W002, W003 or W004, manufactured by YAMAZEN CORPORATION; and a basic silica gel column is a Hi-Flash column, W091, W092 or W093, manufactured by YAMAZEN CORPORATION.

A mixing ratio for an eluent is indicated as a volume ratio.

In Examples, respective abbreviations stand for the following meanings:
Ac: acetyl, Boc: tert-butoxycarbonyl, Bu: butyl, Et: ethyl, Me: methyl, MOM: methoxymethyl, Tf: trifluoromethylsulfonyl, THP: tetrahydro-2H-pyran-2-yl, Z: benzyloxycarbonyl, and DMSO-$d_6$: deuterated dimethylsulfoxide.

Reference Example 1

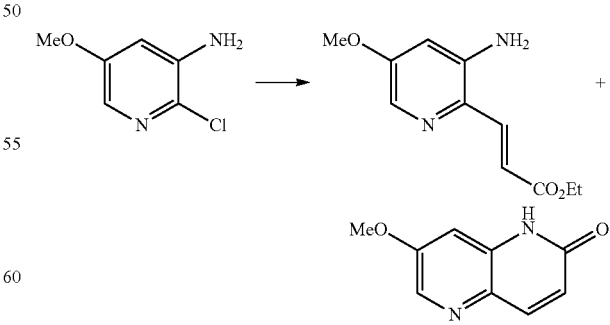

To 1.0 g of 2-chloro-5-methoxypyridin-3-amine, 0.82 mL of ethyl acrylate, 4.2 mL of triethylamine, and 0.16 g of bis(tri-tert-butylphosphine)palladium(0) were added, and the mixture was stirred at an external temperature of 150 to 160° C. for 6 hours in a sealed tube. The reaction mixture was cooled to room temperature and the solvent was distilled off under reduced pressure. The resultant residue was purified by flash silica gel column chromatography using gradient elution with chloroform:methanol=100:0 to 90:10 to obtain 0.41 g of ethyl (2E)-3-(3-amino-5-methoxypyridin-2-yl)acrylate and 0.25 g of 7-methoxy-1,5-naphthyridin-2(1H)-one as light brown solids.

Ethyl (2E)-3-(3-amino-5-methoxypyridin-2-yl)acrylate
$^1$H-NMR (CDCl$_3$) δ: 1.32 (3H, t, J=7.2 Hz), 3.83 (3H, s), 3.96-4.04 (2H, m), 4.25 (2H, q, J=7.2 Hz), 6.46 (1H, d, J=2.7 Hz), 6.78 (1H, d, J=15.1 Hz), 7.74 (1H, d, J=15.1 Hz), 7.83 (1H, d, J=2.7 Hz)

7-methoxy-1,5-naphthyridin-2(1H)-one $^1$H-NMR (DMSO-d$_6$) δ: 3.88 (3H, s), 6.54 (1H, d, J=9.8 Hz), 7.13 (1H, d, J=2.6 Hz), 7.86 (1H, d, J=9.8 Hz), 8.21 (1H, d, J=2.6 Hz), 11.78 (1H, s)

Reference Example 2

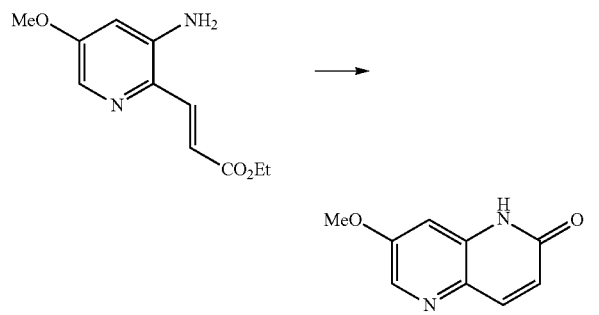

To a solution of 0.51 g of ethyl (2E)-3-(3-amino-5-methoxypyridin-2-yl)acrylate in 6 mL of methanol, 0.53 g of a 28% sodium methoxide/methanol solution was added at room temperature, and the mixture was heated under reflux while stirring for 2 hours 20 minutes. Thereto was added 0.53 g of a 28% sodium methoxide/methanol solution, and the mixture was heated under reflux while stirring for 1 hour 45 minutes. Thereto was further added 0.53 g of a 28% sodium methoxide/methanol solution, and the mixture was heated under reflux while stirring for 1 hour 15 minutes. The reaction mixture was cooled to room temperature, the solvent was then distilled off under reduced pressure, and the resultant residue was charged with ethyl acetate and water and adjusted to pH 7.2 with 1 mol/L hydrochloric acid. The solvent was distilled off under reduced pressure, and the solid was filtered off and washed with water and diethyl ether to obtain 0.25 g of 7-methoxy-1,5-naphthyridin-2(1H)-one as a light brown solid.

Reference Example 3

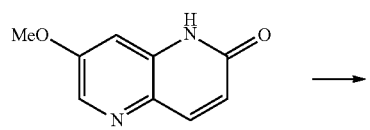

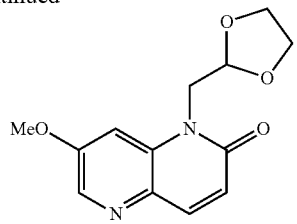

To a suspension of 0.23 g of 7-methoxy-1,5-naphthyridin-2(1H)-one in 3 mL of N,N-dimethylformamide, 79 mg of 60% sodium hydride was added at room temperature, the temperature was increased to 50° C., and the mixture was stirred for 15 minutes. Thereto was added 0.41 mL of 2-bromomethyl-1,3-dioxolan, the temperature of the reaction mixture was increased to 90 to 100° C., and the reaction mixture was stirred for 3 hours. The reaction mixture was cooled to room temperature, and water and ethyl acetate were added thereto. The organic layer was separated, and the aqueous layer was extracted with ethyl acetate. The organic layer and the extract were combined, the resultant solution was dried over anhydrous magnesium sulfate, and the solvent was distilled off under reduced pressure. The resultant residue was purified by flash silica gel column chromatography using gradient elution with hexane:ethyl acetate=100:0 to 33:67, then gradient elution with chloroform:methanol=100:0 to 90:10 to obtain 0.11 g of 1-(1,3-dioxolan-2-ylmethyl)-7-methoxy-1,5-naphthyridin-2(1H)-one as a light brown solid.
$^1$H-NMR (CDCl$_3$) δ: 3.83-4.07 (4H, m), 3.97 (3H, s), 4.50 (2H, d, J=4.1 Hz), 5.20 (1H, t, J=4.1 Hz), 6.77 (1H, d, J=9.8 Hz), 7.40 (1H, d, J=2.4 Hz), 7.86 (1H, d, J=9.8 Hz), 8.28 (1H, d, J=2.4 Hz)

Reference Example 4

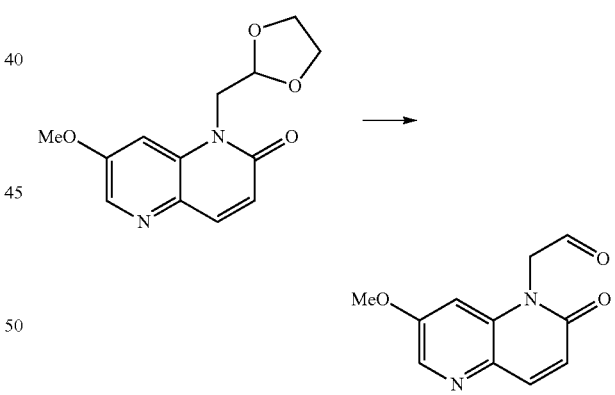

To 0.11 g of 1-(1,3-dioxolan-2-ylmethyl)-7-methoxy-1,5-naphthyridin-2(1H)-one, 6.0 mL of an 80% aqueous trifluoroacetic acid solution was added, and the mixture was stirred at 60 to 70° C. for 1 hour. Thereto was added 4.0 mL of an 80% aqueous trifluoroacetic acid solution, and the mixture was stirred at 60 to 70° C. for 1 hour. The reaction mixture was cooled to room temperature, and the solvent was distilled off under reduced pressure. The resultant residue was charged with ethyl acetate and water and adjusted to pH 7.0 with a 1 mol/L aqueous sodium hydroxide solution. The organic layer was separated, and the aqueous layer was extracted with ethyl acetate. The organic layer and the extract were combined and the resultant solution was dried over anhydrous magnesium sulfate, and the solvent was distilled off under reduced pressure to obtain 0.11 g of (7-methoxy-2-oxo-1,5-naphthyridin-1(2H)-yl)acetaldehyde as a light brown foam.

$^1$H-NMR (DMSO-d$_6$) δ: 3.92 (3H, s), 5.28 (2H, s), 6.70 (1H, d, J=9.6 Hz), 7.36 (1H, d, J=2.4 Hz), 7.94 (1H, d, J=9.6 Hz), 8.29 (1H, d, J=2.4 Hz), 9.68 (1H, s)

Reference Example 5

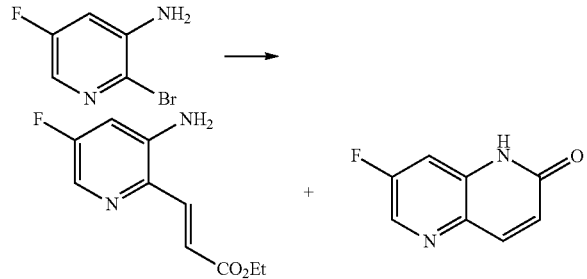

To 0.99 g of 2-bromo-5-fluoropyridin-3-amine, 0.67 mL of ethyl acrylate, 3.5 mL of triethylamine, and 0.13 g of bis(tri-tert-butylphosphine)palladium(0) were added, and the mixture was stirred at an external temperature of 145 to 150° C. for 5 hours in a sealed tube. The reaction mixture was cooled to room temperature and the solvent was distilled off under reduced pressure. The resultant residue was purified by flash silica gel column chromatography using gradient elution with chloroform:methanol=100:0 to 90:10 to obtain 0.37 g of ethyl (2E)-3-(3-amino-5-fluoropyridin-2-yl)acrylate and 0.15 g of 7-fluoro-1,5-naphthyridin-2(1H)-one as light brown solids.

Ethyl (2E)-3-(3-amino-5-fluoropyridin-2-yl)acrylate
$^1$H-NMR (CDCl$_3$) δ: 1.33 (3H, t, J=7.1 Hz), 4.02-4.12 (2H, broad), 4.27 (2H, q, J=7.1 Hz), 6.71 (1H, dd, J=9.8, 2.4 Hz), 6.85 (1H, d, J=15.1 Hz), 7.71 (1H, d, J=15.1 Hz), 7.94 (1H, d, J=2.4 Hz) 7-fluoro-1,5-naphthyridin-2(1H)-one $^1$H-NMR (DMSO-d$_6$) δ: 6.72 (1H, dd, J=9.8, 1.7 Hz), 7.47 (1H, dd, J=9.6, 2.5 Hz), 7.94 (1H, d, J=9.8 Hz), 8.50 (1H, d, J=2.5 Hz), 11.99 (1H, s)

Reference Example 6

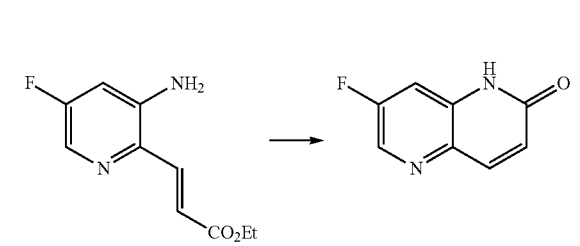 [SMILES: CCOC(=O)/C=C/c1ncc(F)cc1N ; O=c1ccc2ncc(F)cc2[nH]1]

To a solution of 0.36 g of ethyl (2E)-3-(3-amino-5-fluoropyridin-2-yl)acrylate in 3 mL of methanol, 0.37 g of a 28% sodium methoxide/methanol solution was added at room temperature, and the mixture was heated under reflux while stirring for 2 hours 40 minutes. Thereto was added 72 mg of a 28% sodium methoxide/methanol solution, and the mixture was heated under reflux while stirring for 1 hour. The reaction mixture was cooled to room temperature, the solvent was then distilled off under reduced pressure, and the resultant residue was charged with ethyl acetate and water and adjusted to pH 6.7 with 1 mol/L hydrochloric acid. The solvent was distilled off under reduced pressure, the solid was filtered off and washed with water and diethyl ether to obtain 0.17 g of 7-fluoro-1,5-naphthyridin-2(1H)-one as a light brown solid.

$^1$H-NMR (DMSO-d$_6$) δ: 6.72 (1H, d, J=9.8 Hz), 7.47 (1H, dd, J=9.6, 2.4 Hz), 7.94 (1H, d, J=9.8 Hz), 8.50 (1H, d, J=2.4 Hz), 11.99 (1H, brs)

Reference Example 7

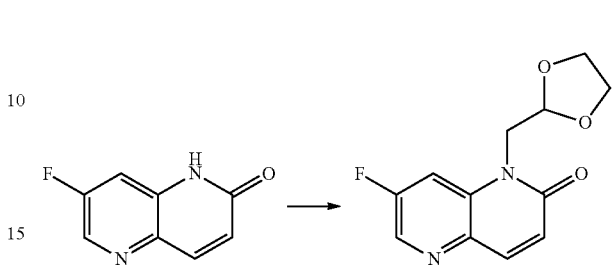

To a suspension of 0.32 g of 7-fluoro-1,5-naphthyridin-2(1H)-one in 3 mL of N,N-dimethylformamide, 0.12 g of 60% sodium hydride was added at room temperature, and the mixture was stirred at 50 to 60° C. for 1 hour. Thereto was added 0.60 mL of 2-bromomethyl-1,3-dioxolan, the temperature was increased to 85 to 95° C., and the reaction mixture was stirred for 4 hours. The reaction mixture was cooled to room temperature, and water and ethyl acetate were then added thereto. The organic layer was separated, and the aqueous layer was extracted with ethyl acetate. The organic layer and the extract were combined, the resultant solution was dried over anhydrous magnesium sulfate, and the solvent was distilled off under reduced pressure. To the resultant residue, chloroform was added, the solid was filtered off and purified by flash silica gel column chromatography using gradient elution with hexane:ethyl acetate=100:0 to 30:70 to obtain 0.23 g of 1-(1,3-dioxolan-2-ylmethyl)-7-fluoro-1,5-naphthyridin-2(1H)-one as a light yellow solid.

$^1$H-NMR (CDCl$_3$) δ: 3.84-3.93 (2H, m), 3.96-4.05 (2H, m), 4.45 (2H, d, J=4.2 Hz), 5.19 (1H, t, J=4.2 Hz), 6.88 (1H, d, J=9.8 Hz), 7.69 (1H, dd, J=10.5, 2.4 Hz), 7.90 (1H, d, J=9.8 Hz), 8.41 (1H, d, J=2.4 Hz)

Reference Example 8

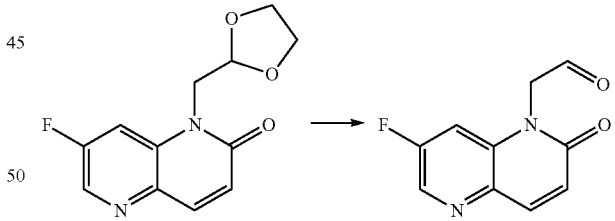

To 0.21 g of 1-(1,3-dioxolan-2-ylmethyl)-7-fluoro-1,5-naphthyridin-2(1H)-one, 3 mL of an 80% aqueous trifluoroacetic acid solution was added, and the mixture was stirred at room temperature for 20 minutes, and then stirred at 50 to 60° C. for 1 hour. Thereto was added 3 mL of an 80% aqueous trifluoroacetic acid solution, the mixture was stirred at 80 to 90° C. for 1 hour 45 minutes, then, 3 mL of an 80% aqueous trifluoroacetic acid solution was further added thereto, and the mixture was stirred at the same temperature for 1 hour. The reaction mixture was cooled to room temperature, and the solvent was then distilled off under reduced pressure. The resultant residue was charged with chloroform and water and adjusted to pH 7.4 with a 20% aqueous sodium hydroxide solution. The organic layer was separated, and the aqueous layer was extracted with chloroform. The organic layer and the extract were combined, the resultant solution was dried over anhydrous magnesium sulfate, and the solvent was distilled off under reduced pressure to obtain 0.20 g of 7-fluoro-2-oxo-1,5-naphthyridin-1(2H)-yl)acetaldehyde as a yellow oily substance.

$^1$H-NMR (CDCl$_3$) δ: 5.12 (2H, s), 6.93 (1H, d, J=9.9 Hz), 7.04 (1H, dd, J=9.6, 2.3 Hz), 7.98 (1H, d, J=9.9 Hz), 8.46 (1H, d, J=2.3 Hz), 9.77 (1H, s)

Reference Example 9

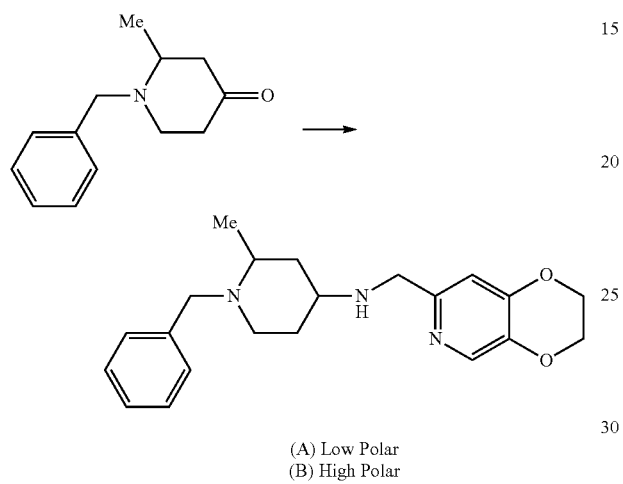

(A) Low Polar
(B) High Polar

By the same technique as in Reference Example 21, 0.22 g of (A) 1-benzyl-N-(2,3-dihydro(1,4)dioxino(2,3-c)pyridin-7-ylmethyl)-2-methylpiperidin-4-amine as a colorless oily substance and 0.13 g of (B) 1-benzyl-N-(2,3-dihydro(1,4)dioxino(2,3-c)pyridin-7-ylmethyl)-2-methylpiperidin-4-amine as a colorless oily substance were obtained from 0.24 g of 1-benzyl-2-methylpiperidin-4-one and 0.20 g of 1-(2,3-dihydro(1,4)dioxino(2,3-c)pyridin-7-yl)methanamine.

(A) $^1$H-NMR (CDCl$_3$) δ: 1.07 (3H, d, J=6.6 Hz), 1.40-1.85 (4H, m), 2.40-2.60 (2H, m), 2.80-3.00 (2H, m), 3.42 (1H, d, J=13.7 Hz), 3.69-3.82 (3H, m), 4.24-4.35 (4H, m), 6.83 (1H, s), 7.18-7.36 (5H, m), 8.10 (1H, s)

(B) $^1$H-NMR (CDCl$_3$) δ: 1.19-1.40 (2H, m), 1.22 (3H, d, J=6.1 Hz), 1.76-1.84 (1H, m), 1.86-1.97 (2H, m), 2.20-2.30 (1H, m), 2.40-2.55 (1H, m), 2.75-2.85 (1H, m), 3.14 (1H, d, J=13.5 Hz), 3.78 (2H, s), 4.07 (1H, d, J=13.5 Hz), 4.24-4.34 (4H, m), 6.81 (1H, s), 7.20-7.40 (5H, m), 8.09 (1H, s)

Reference Example 10

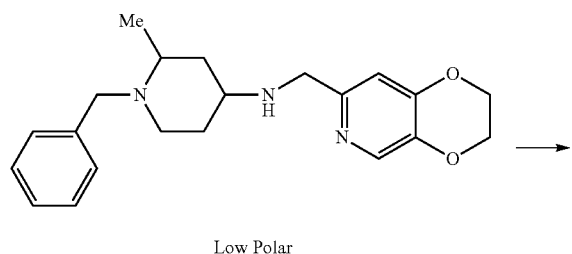

Low Polar

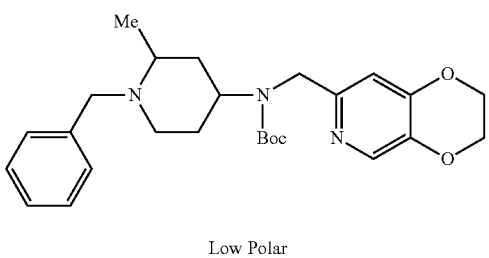

Low Polar

By the same technique as in Reference Example 61, tert-butyl (1-benzyl-2-methylpiperidin-4-yl)(2,3-dihydro(1,4)dioxino(2,3-c)pyridin-7-ylmethyl)carbamate was obtained from 1-benzyl-N-(2,3-dihydro(1,4)dioxino(2,3-c)pyridin-7-ylmethyl)-2-methylpiperidin-4-amine.

$^1$H-NMR (CDCl$_3$) δ: 1.00-1.13 (3H, m), 1.35-1.65 (12H, s), 1.78-1.92 (1H, m), 2.48-2.60 (2H, m), 3.09-3.20 (1H, m), 3.48 (1H, d, J=13.5 Hz), 3.59 (1H, d, J=13.5 Hz), 4.20-4.66 (7H, m), 6.73 (1H, s), 7.20-7.30 (5H, m), 8.05 (1H, s)

Reference Example 11

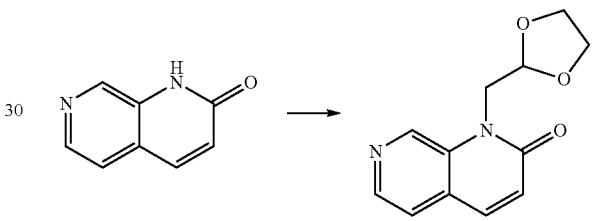

To a suspension of 6.0 g of 1,7-naphthyridin-2(1H)-one in 60 mL of N,N-dimethylformamide, 2.5 g of 60% sodium hydride was added at room temperature, and the mixture was stirred at 50 to 60° C. for 1 hour. Thereto was added 6.4 mL of 2-bromomethyl-1,3-dioxolan, the temperature was increased to 90 to 95° C., and the reaction mixture was stirred for 2 hours 30 minutes. The temperature was further increased to 95 to 100° C., and the mixture was stirred for 4 hours. Thereto were added 0.82 g of 60% sodium hydride and 2.1 mL of 2-bromomethyl-1,3-dioxolan and the mixture was further stirred at the same temperature for 2 hours. Thereto were added 0.49 g of 60% sodium hydride and 1.3 mL of 2-bromomethyl-1,3-dioxolan and the mixture was stirred at 90 to 100° C. for 2 hours. Thereto were further added 0.49 g of 60% sodium hydride and 1.3 mL of 2-bromomethyl-1,3-dioxolan and the mixture was stirred at the same temperature for 4 hours. The reaction mixture was cooled to 5° C., and ethyl acetate and ice water were then added thereto. The organic layer was separated, and the aqueous layer was extracted with ethyl acetate. The organic layer and the extract were combined, the resultant solution was dried over anhydrous magnesium sulfate, and the solvent was distilled off under reduced pressure. The resultant residue was purified by flash silica gel column chromatography using gradient elution with hexane:ethyl acetate=100:0 to 0:100 and then, using gradient elution with chloroform:methanol=100:0 to 90:10 to obtain 3.1 g of 1-(1,3-dioxolan-2-ylmethyl)-1,7-naphthyridin-2(1H)-one as a brown solid.

$^1$H-NMR (CDCl$_3$) δ: 3.85-3.94 (2H, m), 3.99-4.08 (2H, m), 4.58 (2H, d, J=4.5 Hz), 5.29 (1H, t, J=4.5 Hz), 6.91 (1H, d, J=9.4 Hz), 7.41 (1H, d, J=5.1 Hz), 7.67 (1H, d, J=9.4 Hz), 8.45 (1H, d, J=5.1 Hz), 9.05 (1H, s)

Reference Example 12

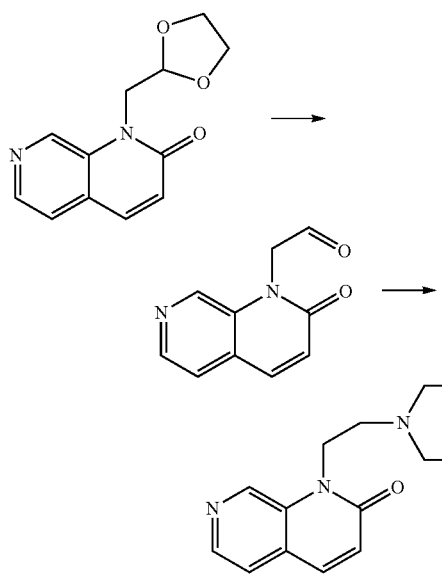

(1) To 3.1 g of 1-(1,3-dioxolan-2-ylmethyl)-1,7-naphthyridin-2(1H)-one, 30 mL of an 80% aqueous trifluoroacetic acid solution was added, and the mixture was stirred at 70 to 80° C. for 2 hours. The reaction mixture was cooled to room temperature, then 30 mL of an 80% aqueous trifluoroacetic acid solution was added thereto, the mixture was stirred at 70 to 80° C. for 3 hours 30 minutes, and the temperature was increased to 75 to 85° C. and the mixture was stirred for 2 hours. Thereto was further added 30 mL of an 80% aqueous trifluoroacetic acid solution, and the mixture was stirred at 80 to 90° C. for 2 hours 30 minutes. The reaction mixture was cooled to room temperature, and then left overnight. The solvent was distilled off under reduced pressure, and the resultant residue was charged with chloroform and water and adjusted to pH 10.4 with a 20% aqueous sodium hydroxide solution. Sodium chloride was added thereto, the organic layer was separated, and the aqueous layer was extracted with chloroform. The organic layer and the extract were combined, the resultant solution was dried over anhydrous magnesium sulfate, and the solvent was distilled off under reduced pressure to obtain 2.5 g of (2-oxo-1,7-naphthyridin-1(2H)-yl)acetaldehyde as a yellow oily substance.

(2) To a solution of 2.5 g of (2-oxo-1,7-naphthyridin-1(2H)-yl)acetaldehyde in 25 mL of dichloromethane, 2.6 g of tert-butyl (piperidin-4-yl)carbamate and 0.76 mL of acetic acid, and 4.2 g of sodium triacetoxyborohydride were added, and the mixture was stirred at room temperature for 4 hours and then left overnight. Thereto was added chloroform and the reaction mixture was adjusted to pH 9.1 with a saturated aqueous sodium hydrogen carbonate solution and a 20% aqueous sodium hydroxide solution. The organic layer was separated, and the aqueous layer was extracted with chloroform. The organic layer and the extract were combined, and the resultant solution was washed sequentially with water and a saturated aqueous sodium chloride solution and dried over anhydrous magnesium sulfate, and the solvent was distilled off under reduced pressure. To the resultant residue, diethyl ether was added, and the solid was filtered off to obtain 2.8 g of tert-butyl (1-(2-(2-oxo-1,7-naphthyridin-1(2H)-yl)ethyl)piperidin-4-yl)carbamate as a slightly yellow solid.

$^1$H-NMR (CDCl$_3$) δ: 1.35-1.51 (2H, m), 1.44 (9H, s), 1.89-1.98 (2H, m), 2.23-2.32 (2H, m), 2.67-2.74 (2H, m), 2.90-2.98 (2H, m), 3.41-3.55 (1H, m), 4.37-4.50 (3H, m), 6.89 (1H, d, J=9.5 Hz), 7.42 (1H, d, J=5.0 Hz), 7.65 (1H, d, J=9.5 Hz), 8.45 (1H, d, J=5.0 Hz), 8.89 (1H, s)

Reference Example 13

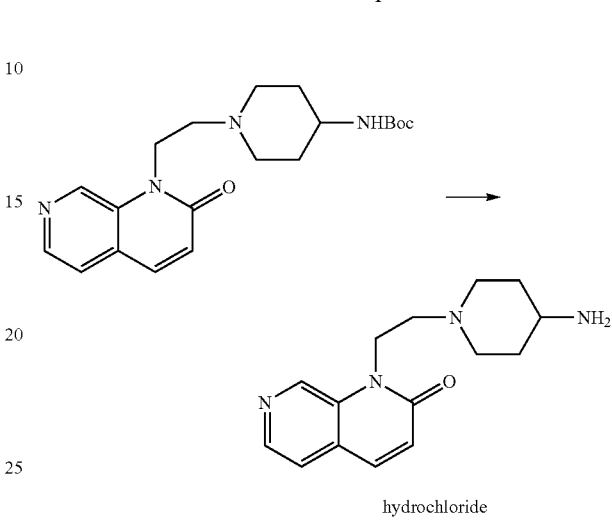

To a solution of 2.8 g of tert-butyl (1-(2-(2-oxo-1,7-naphthyridin-1(2H)-yl)ethyl)piperidin-4-yl)carbamate in 20 mL of ethanol, 60 mL of a 6.2 mol/L hydrogen chloride/ethanol solution was added at room temperature, and the mixture was stirred for 2 hours. Thereto was further added 60 mL of a 6.2 mol/L hydrogen chloride/ethanol solution, and the mixture was stirred for 4 hours and then left for 4 days. The solvent was distilled off under reduced pressure, diethyl ether was added to the resultant residue, and the solid was filtered off to obtain 2.8 g of 1-(2-(4-aminopiperidin-1-yl)ethyl)-1,7-naphthyridin-2(1H)-one as a yellow solid.

$^1$H-NMR (D$_2$O) δ: 1.94-2.09 (2H, m), 2.36-2.45 (2H, m), 3.23-3.37 (2H, m), 3.54-3.70 (3H, m), 3.92-4.03 (2H, m), 4.81-4.87 (2H, m), 7.25 (1H, d, J=9.6 Hz), 8.20 (1H, d, J=9.6 Hz), 8.27 (1H, d, J=5.9 Hz), 8.64 (1H, d, J=5.9 Hz), 9.18 (1H, s)

Reference Example 14

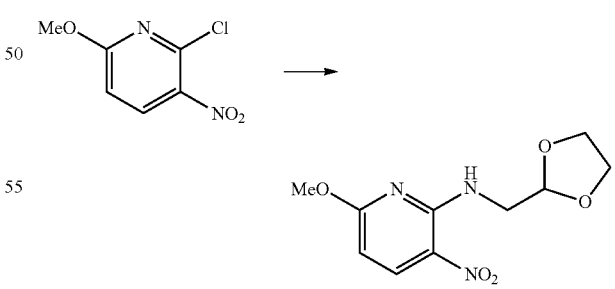

To a solution of 1.1 g of 1-(1,3-dioxolan-2-yl)methanamine in 10 mL of N,N-dimethylformamide, 1.6 mL of triethylamine and 2.0 g of 2-chloro-6-methoxy-3-nitropyridine were added at room temperature, and the mixture was stirred at 55 to 65° C. for 1 hour. The reaction mixture was cooled to room temperature, and ethyl acetate and water were then added thereto. The organic layer was separated, and the aqueous layer was extracted with ethyl acetate. The organic layer and the extract were combined, the resultant solution was washed sequentially with water and a saturated aqueous sodium chloride solution and dried over anhydrous magnesium sulfate, and the solvent was distilled off under reduced pressure to obtain 2.7 g of N-(1,3-dioxolan-2-ylmethyl)-6-methoxy-3-nitropyridin-2-amine as a yellow solid.

$^1$H-NMR (CDCl$_3$) δ: 3.90 (2H, dd, J=5.6, 3.5 Hz), 3.92-3.99 (2H, m), 3.97 (3H, s), 4.01-4.10 (2H, m), 5.17 (1H, t, J=3.5 Hz), 6.07 (1H, d, J=9.1 Hz), 8.31 (1H, d, J=9.1 Hz), 8.76-8.85 (1H, broad)

Reference Example 15

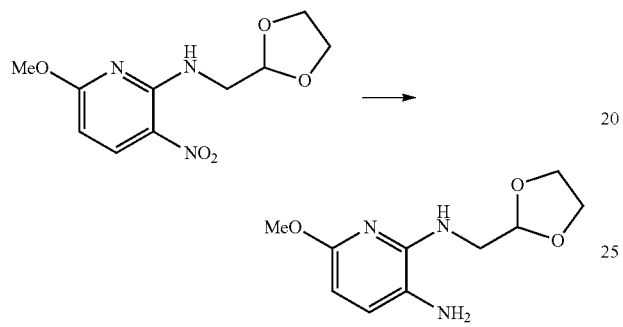

To a solution of 2.7 g of N-(1,3-dioxolan-2-ylmethyl)-6-methoxy-3-nitropyridin-2-amine in 30 mL of ethanol, 0.81 g of 10% palladium-carbon was added at room temperature, and mixture was stirred at 40° C. for 2 hours 30 minutes under a hydrogen atmosphere. The reaction mixture was cooled to room temperature, the insoluble substance was filtered off, and the filtration residue was washed with diethyl ether. The solvent was distilled off under reduced pressure to obtain 2.4 g of 3-amino-2-(1,3-dioxolan-2-ylmethyl)amino-6-methoxypyridine as a purple solid.

$^1$H-NMR (CDCl$_3$) δ: 2.30-2.80 (2H, broad), 3.62-3.76 (2H, m), 3.84 (3H, s), 3.86-4.08 (4H, m), 4.30-5.10 (1H, broad), 5.15 (1H, t, J=4.4 Hz), 5.93 (1H, d, J=7.8 Hz), 6.91 (1H, d, J=7.8 Hz)

Reference Example 16

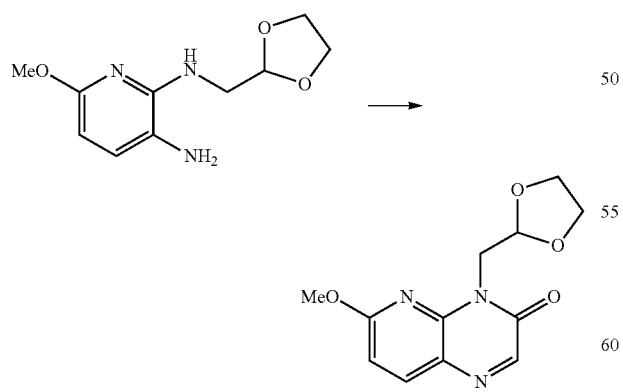

To a solution of 0.20 g of 3-amino-2-(1,3-dioxolan-2-ylmethyl)amino-6-methoxypyridine in 2 mL of dioxane, 0.22 g of a 45 to 50% toluene solution of ethyl oxoacetate was added, and the mixture was stirred at room temperature for 2 hours and then left overnight. Thereto was added 36 mg of 60% sodium hydride, and the mixture was stirred at room temperature for 30 minutes. To the reaction mixture, water and ethyl acetate were added. The organic layer was separated and the aqueous layer was extracted with ethyl acetate. The organic layer and the extract were combined, the resultant solution was washed with a saturated aqueous sodium chloride solution and dried over anhydrous magnesium sulfate, and the solvent was distilled off under reduced pressure. The resultant residue was purified by flash silica gel column chromatography using gradient elution with hexane:ethyl acetate=100:0 to 50:50 to obtain 36 mg of 4-(1,3-dioxolan-2-ylmethyl)-6-methoxypyrido (2,3-b)pyrazin-3(4H)-one as a light brown solid.

$^1$H-NMR (CDCl$_3$) δ: 3.87-3.96 (2H, m), 4.04 (3H, s), 4.06-4.15 (2H, m), 4.60 (2H, d, J=5.1 Hz), 5.57 (1H, t, J=5.1 Hz), 6.73 (1H, d, J=8.8 Hz), 8.01 (1H, d, J=8.8 Hz), 8.18 (1H, s)

Reference Example 17

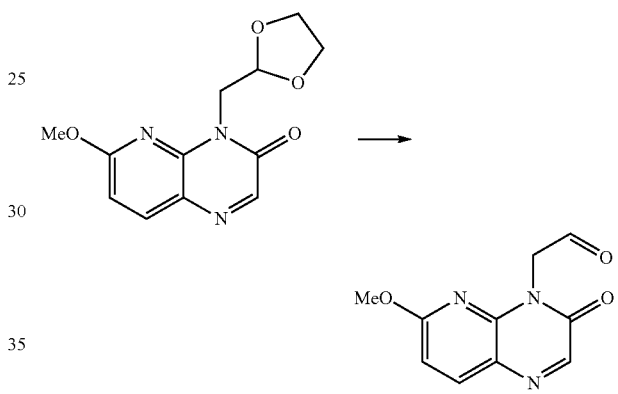

To 0.21 g of 4-(1,3-dioxolan-2-ylmethyl)-6-methoxypyrido(2,3-b)pyrazin-3(4H)-one, 10 mL of an 80% aqueous trifluoroacetic acid solution was added, and the mixture was stirred at room temperature for 5 hours and then left overnight. The solvent was distilled off under reduced pressure. The resultant residue was charged with ethyl acetate and water and adjusted to pH 7.0 with a 1 mol/L aqueous sodium hydroxide solution. The organic layer was separated, and the aqueous layer was extracted with ethyl acetate. The organic layer and the extract were combined, the resultant solution was dried over anhydrous magnesium sulfate, and the solvent was distilled off under reduced pressure to obtain 0.18 g of (6-methoxy-3-oxopyrido(2,3-b)pyrazin-4(3H)-yl)acetaldehyde as a light brown foam.

$^1$H-NMR (CDCl$_3$) δ: 3.94 (3H, s), 5.22 (2H, s), 6.76 (1H, d, J=8.8 Hz), 8.07 (1H, d, J=8.8 Hz), 8.24 (1H, s), 9.70 (1H, s)

Reference Example 18

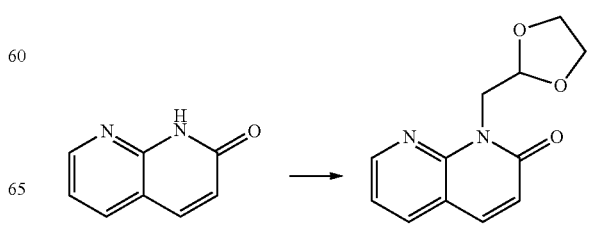

To a solution of 1.2 g of 1,8-naphthyridin-2(1H)-one in 18 mL of N,N-dimethylformamide, 0.36 g of 60% sodium hydride was added, and the mixture was stirred at 50 to 60° C. for 7 minutes. Thereto was added 0.94 mL of 2-bromomethyl-1,3-dioxolan, and the mixture was stirred at 95 to 105° C. for 3 hours. The reaction mixture was cooled to room temperature, water and ethyl acetate were then added thereto, and the organic layer was separated. The aqueous layer was extracted with ethyl acetate and chloroform. The organic layer and the extract were combined, the resultant solution was dried over anhydrous magnesium sulfate, and the solvent was distilled off under reduced pressure. The resultant residue was purified by silica gel column chromatography using an eluent of hexane:ethyl acetate=1:1 to obtain 1.2 g of 1-(1,3-dioxolan-2-ylmethyl)-1,8-naphthyridin-2(1H)-one as a white solid.

$^1$H-NMR (CDCl$_3$) δ: 3.83-3.93 (2H, m), 3.95-4.17 (2H, m), 4.72 (1H, d, J=5.1 Hz), 5.56 (1H, t, J=5.1 Hz), 6.72 (1H, d, J=9.5 Hz), 7.17 (1H, dd, J=7.6, 4.7 Hz), 7.64 (1H, d, J=9.5 Hz), 7.86 (1H, dd, J=7.6, 1.8 Hz), 8.57 (1H, dd, J=4.7, 1.8 Hz)

Reference Example 19

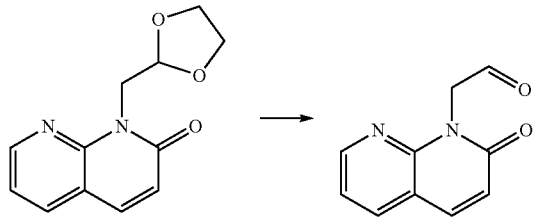 [SMILES: O=c1ccc2cccnc2n1CC1OCCO1 ; O=CCn1c(=O)ccc2cccnc21]

To 1.1 g of 1-(1,3-dioxolan-2-ylmethyl)-1,8-naphthyridin-2(1H)-one, 11 mL of a 90% aqueous trifluoroacetic acid solution was added, and the mixture was stirred at room temperature for 2 hours. Then, 1.1 mL of water was added thereto and the mixture was stirred for 13 hours, and thereto was further added 1.1 mL of water and the mixture was stirred for 3 hours 30 minutes, and stirred at 50 to 70° C. for 1 hour 30 minutes. The solvent was distilled off under reduced pressure, and to the resultant residue, a saturated aqueous sodium hydrogen carbonate solution, water and chloroform were added. The organic layer was separated, and the aqueous layer was extracted with chloroform. The organic layer and the extract were combined, the resultant solution was washed with a saturated aqueous sodium chloride solution and dried over anhydrous magnesium sulfate, and the solvent was distilled off under reduced pressure to obtain 0.75 g of (2-oxo-1,8-naphthyridin-1(2H)-yl)acetaldehyde as a yellow solid.

$^1$H-NMR (CDCl$_3$) δ: 5.36 (2H, s), 6.80 (1H, d, J=9.5 Hz), 7.20 (1H, dd, J=7.6, 4.8 Hz), 7.72 (1H, d, J=9.5 Hz), 7.91 (1H, dd, J=7.6, 1.8 Hz), 8.51 (1H, dd, J=4.8, 1.8 Hz), 9.72 (1H, s)

Reference Example 20

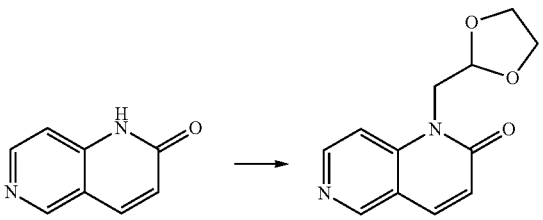 [SMILES: O=c1ccc2cnccc2[nH]1 ; O=c1ccc2cnccc2n1CC1OCCO1]

To a solution of 1.0 g of 1,6-naphthyridin-2(1H)-one in 10 mL of N,N-dimethylformamide, 0.30 g of 60% sodium hydride was added, and the mixture was stirred at 50 to 60° C. for 1 hour. Thereto was added 0.78 mL of 2-bromomethyl-1,3-dioxolan, and the reaction mixture was stirred at 90 to 100° C. for 30 minutes. Thereto were further added 0.30 g of 60% sodium hydride and 0.78 mL of 2-bromomethyl-1,3-dioxolan, and the reaction mixture was stirred at 90 to 108° C. for 5 hours 30 minutes. The reaction mixture was cooled to room temperature, water and chloroform were then added thereto, the organic layer was separated, and the aqueous layer was extracted with chloroform. The organic layer and the extract were combined, the resultant solution washed with a saturated aqueous sodium chloride solution and dried over anhydrous magnesium sulfate, and the solvent was distilled off under reduced pressure. The resultant residue was purified by silica gel column chromatography using an eluent of chloroform:methanol=100:1 to obtain 0.60 g of 1-(1,3-dioxolan-2-ylmethyl)-1,6-naphthyridin-2(1H)-one as a yellow solid.

$^1$H-NMR (CDCl$_3$) δ: 3.84-3.94 (2H, m), 3.98-4.07 (2H, m), 4.48 (2H, d, J=4.3 Hz), 5.23 (1H, t, J=4.3 Hz), 6.75 (1H, d, J=9.5 Hz), 7.47 (1H, d, J=6.2 Hz), 7.78 (1H, d, J=9.5 Hz), 8.58 (1H, d, J=6.2 Hz), 8.76 (1H, s)

Reference Example 21

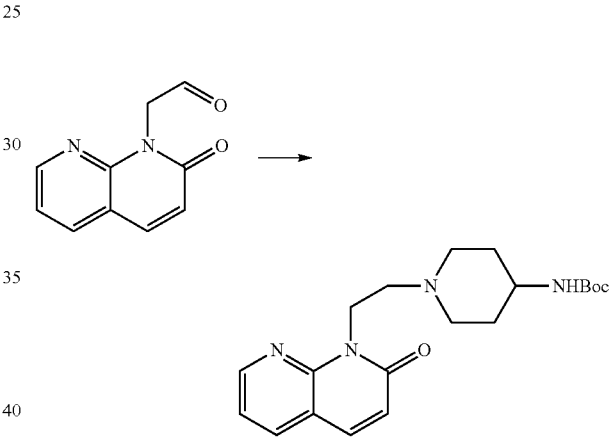

To a solution of 0.29 g of (2-oxo-1,8-naphthyridin-1(2H)-yl)acetaldehyde in 10 mL of methylene chloride, 0.30 g of tert-butyl (piperidin-4-yl)carbamate and 87 μL of acetic acid were added, the mixture was stirred for 10 minutes, and to the reaction mixture, 0.48 g of sodium triacetoxyborohydride was then added and the mixture was stirred at room temperature for 4 hours. Thereto were added water, a saturated aqueous sodium hydrogen carbonate solution and chloroform, the organic layer was separated, and the aqueous layer was extracted with chloroform. The organic layer and the extract were combined, and the resultant solution was washed with a saturated aqueous sodium chloride solution and dried over anhydrous magnesium sulfate, and the solvent was distilled off under reduced pressure. The resultant residue was purified by silica gel column chromatography using an eluent of chloroform:methanol=100:1 to obtain 0.27 g of tert-butyl (1-(2-(2-oxo-1,8-naphthyridin-1(2H)-yl)ethyl)piperidin-4-yl)carbamate as a light brown oily substance.

$^1$H-NMR (CDCl$_3$) δ: 1.36-1.51 (11H, m), 1.88-1.96 (2H, m), 2.19-2.28 (2H, m), 2.66-2.72 (2H, m), 2.98-3.06 (2H, m), 3.41-3.56 (1H, m), 4.50-4.60 (1H, m), 4.65-4.70 (2H, m), 6.74 (1H, d, J=9.5 Hz), 7.17 (1H, dd, J=7.7, 4.8 Hz), 7.63 (1H, d, J=9.5 Hz), 7.86 (1H, dd, J=7.7, 1.8 Hz), 8.58 (1H, dd, J=4.8, 1.8 Hz)

Reference Example 22

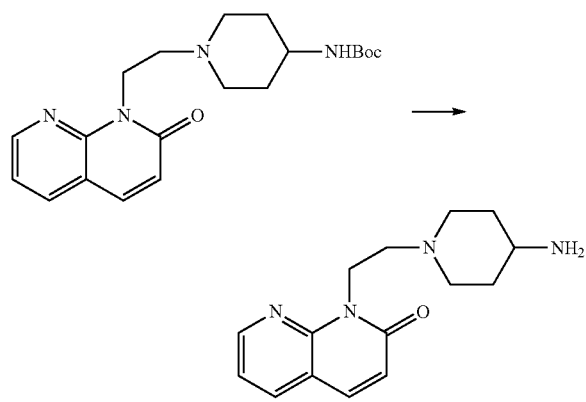

To a solution of 0.26 g of tert-butyl (1-(2-(2-oxo-1,8-naphthyridin-1(2H)-yl)ethyl)piperidin-4-yl)carbamate in 4 mL of dichloromethane, 2 mL of trifluoroacetic acid was added, and the mixture was stirred at room temperature for 2 hours. The solvent was distilled off under reduced pressure, water and diethyl ether was added to the resultant residue, and the aqueous layer was separated and washed with diethyl ether, and then, thereto was added a 20% aqueous sodium hydroxide solution and the reaction mixture was adjusted to pH 13 to 14. Thereto were added dichloromethane and sodium chloride, the organic layer was separated, and the aqueous layer was extracted with chloroform while being salted out. The organic layer and the extract were combined, the resultant solution was dried over anhydrous magnesium sulfate, and the solvent was distilled off under reduced pressure to obtain 0.15 g of 1-(2-(4-aminopiperidin-1-yl)ethyl)-1,8-naphthyridin-2(1H)-one as a yellow oily substance.

$^1$H-NMR (CDCl$_3$) δ: 1.31-1.43 (2H, m), 1.77-1.91 (4H, m), 2.13-2.22 (2H, m), 2.62-2.73 (3H, m), 3.03-3.10 (2H, m), 4.66-4.72 (2H, m), 6.74 (1H, d, J=9.4 Hz), 7.17 (1H, dd, J=7.6, 4.6 Hz), 7.63 (1H, d, J=9.4 Hz), 7.86 (1H, dd, J=7.6, 1.9 Hz), 8.59 (1H, dd, J=4.6, 1.9 Hz)

Reference Example 23

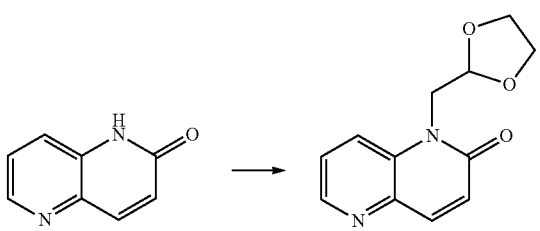 [SMILES: O=c1ccc2ncccc2[nH]1 ; O=c1ccc2ncccc2n1CC1OCCO1]

To a solution of 1.2 g of 1,5-naphthyridin-2(1H)-one in 24 mL of N,N-dimethylformamide, 0.82 g of 60% sodium hydride was added at 60° C., and the mixture was stirred at the same temperature for 20 minutes, and then stirred at 55 to 80° C. for 30 minutes. Thereto was added 1.3 mL of 2-bromomethyl-1,3-dioxolan at 60° C., the temperature of the reaction mixture was increased to 100° C. over 4 hours, and to the reaction mixture, 2.3 g of potassium carbonate was added, and the mixture was stirred at the same temperature for 3 hours. After leaving overnight, 0.85 mL of 2-bromomethyl-1,3-dioxolan and 0.33 g of 60% sodium hydride were added thereto, and the mixture was stirred at 70 to 75° C. for 1 hour 30 minutes. The reaction mixture was cooled to room temperature, water, sodium chloride and chloroform were then added thereto, and the organic layer was separated. The aqueous layer was extracted with chloroform. The organic layer and the extract were combined, the resultant solution was dried over anhydrous magnesium sulfate, and the solvent was distilled off under reduced pressure. The resultant residue was purified by silica gel column chromatography using an eluent of chloroform:methanol=49:1 to obtain 1.1 g of 1-(1,3-dioxolan-2-ylmethyl)-1,5-naphthyridin-2(1H)-one as a light yellow solid.

$^1$H-NMR (CDCl$_3$) δ: 3.82-3.94 (2H, m), 3.96-4.05 (2H, m), 4.52 (2H, d, J=4.2 Hz), 5.22 (1H, t, J=4.2 Hz), 6.94 (1H, d, J=9.8 Hz), 7.45 (1H, dd, J=8.6, 4.5 Hz), 7.90-7.98 (2H, m), 8.54 (1H, dd, J=4.5, 1.2 Hz)

Reference Example 24

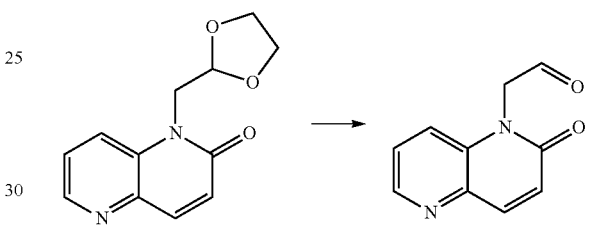

To 1.0 g of 1-(1,3-dioxolan-2-ylmethyl)-1,5-naphthyridin-2(1H)-one, 5 mL of an 80% aqueous trifluoroacetic acid solution was added, and the mixture was stirred at 60 to 70° C. for 30 minutes, and then stirred at 70 to 90° C. for 4 hours. Thereto was further added 5 mL of an 80% aqueous trifluoroacetic acid solution, and the mixture was stirred for 2 hours. The solvent was distilled off under reduced pressure, a saturated aqueous sodium hydrogen carbonate solution, sodium chloride and chloroform were added to the resultant residue, and the organic layer was separated, and the aqueous layer was extracted with chloroform. The organic layer and the extract were combined, the resultant solution was dried over anhydrous magnesium sulfate, and the solvent was distilled off under reduced pressure to obtain 0.73 g of (2-oxo-1,5-naphthyridin-1(2H)-yl)acetaldehyde as an orange oily substance.

$^1$H-NMR (CDCl$_3$) δ: 5.15 (2H, s), 6.99 (1H, d, J=10.0 Hz), 7.43-7.49 (1H, m), 7.96-8.03 (2H, m), 8.56-8.62 (1H, m), 9.76 (1H, s)

Reference Example 25

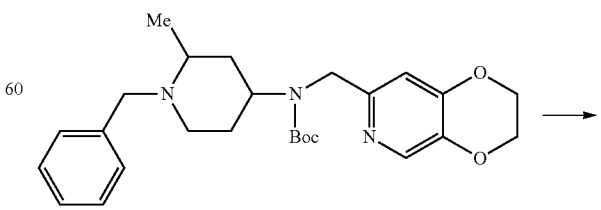

Low Polar

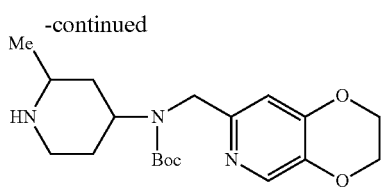

Low Polar

To a solution of 0.24 g of tert-butyl (1-benzyl-2-methylpiperidin-4-yl)(2,3-dihydro(1,4)dioxino(2,3-c)pyridin-7-ylmethyl)carbamate in 3 mL of methanol, 90 μL of acetic acid and 0.32 g of 20% palladium hydroxide were added. The reaction mixture was stirred for 4 hours 30 minutes under a hydrogen atmosphere. The insoluble substance was filtered off, and the solvent was distilled off under reduced pressure to obtain 0.16 g of tert-butyl (2,3-dihydro(1,4)dioxino(2,3-c)pyridin-7-ylmethyl)(2-methylpiperidin-4-yl)carbamate as a yellow foam.

$^1$H-NMR (CDCl$_3$) δ: 1.36-1.45 (9H, m), 1.50 (3H, d, J=6.8 Hz), 1.67-1.75 (1H, m), 1.86-1.95 (1H, m), 2.03-2.14 (1H, m), 2.18-2.30 (1H, m), 3.04-3.17 (1H, m), 3.26-3.35 (1H, m), 3.83-3.93 (1H, m), 4.27-4.51 (7H, m), 6.71-6.83 (1H, m), 8.08 (1H, s), 9.40-9.60 (1H, m)

Reference Example 26

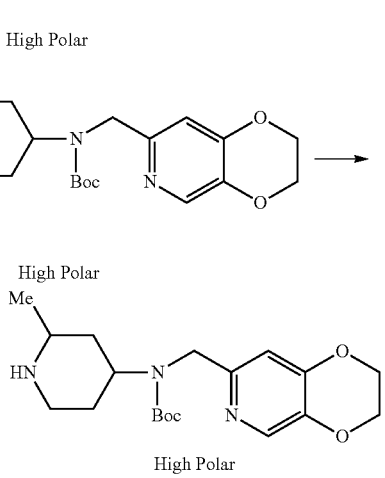

High Polar

High Polar (1) By the same technique as in Reference Example 61, tert-butyl (1-benzyl-2-methylpiperidin-4-yl)(2,3-dihydro(1,4)dioxino(2,3-c)pyridin-7-ylmethyl)carbamate was obtained from 1-benzyl-N-(2,3-dihydro(1,4)dioxino(2,3-c)pyridin-7-ylmethyl)-2-methylpiperidin-4-amine.

(2) By the same technique as in Reference Example 25, tert-butyl (2,3-dihydro(1,4)dioxino(2,3-c)pyridin-7-ylmethyl)(2-methylpiperidin-4-yl)carbamate was obtained from tert-butyl (1-benzyl-2-methylpiperidin-4-yl)(2,3-dihydro(1,4)dioxino(2,3-c)pyridin-7-ylmethyl)carbamate.

$^1$H-NMR (CDCl$_3$) δ: 1.27-1.57 (14H, m), 1.82-2.00 (2H, m), 2.83-2.97 (1H, m), 3.14-3.27 (1H, m), 3.40-3.53 (1H, m), 4.26-4.61 (7H, m), 6.62-7.02 (1H, m), 8.05-8.13 (1H, m), 9.84-10.06 (1H, m)

Reference Example 27

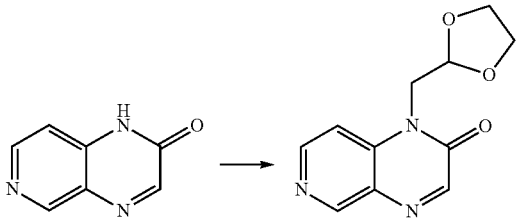 [SMILES: O=c1cnc2cnccc2[nH]1 ; O=c1cnc2cnccc2n1CC1OCCO1]

By the same technique as in Reference Example 3, 1-(1,3-dioxolan-2-ylmethyl)pyrido(3,4-b)pyrazin-2(1H)-one was obtained from pyrido(3,4-b)pyrazin-2(1H)-one and 2-bromomethyl-1,3-dioxolan.

$^1$H-NMR (CDCl$_3$) δ: 3.84-4.02 (4H, m), 4.44 (2H, d, J=4.0 Hz), 5.24 (1H, t, J=4.0 Hz), 7.43 (1H, d, J=6.0 Hz), 8.33 (1H, s), 8.63 (1H, d, J=6.0 Hz), 9.07 (1H, s)

Reference Example 28

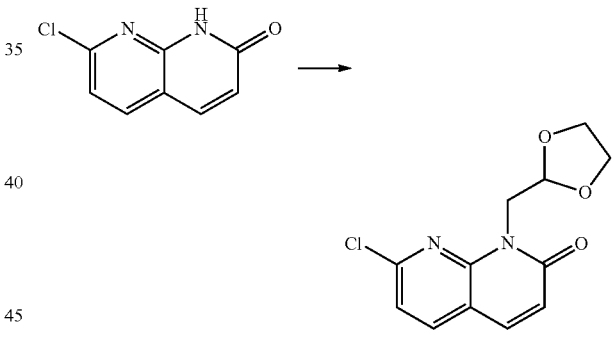

To a solution of 3.2 g of 7-chloro-1,8-naphthyridin-2(1H)-one in 32 mL of N,N-dimethylformamide, 3.7 g of potassium carbonate was added, and the mixture was stirred at 50 to 60 C.° for 23 minutes, and then, thereto was added 2.2 mL of 2-bromomethyl-1,3-dioxolan, and the mixture was stirred at 60 to 78° C. for 25 minutes. Thereto were added 16 mL of N,N-dimethylformamide and 1.1 mL of 2-bromomethyl-1,3-dioxolan, the mixture was stirred at 90 to 95° C. for 2 hours 15 minutes, 3.7 g of potassium carbonate was added thereto, and the mixture was stirred for 20 minutes. The reaction mixture was cooled to room temperature, water and ethyl acetate were then added thereto, the organic layer was separated, and the aqueous layer was extracted with ethyl acetate. The organic layer and the extract were combined, the resultant solution was dried over anhydrous magnesium sulfate, and the solvent was distilled off under reduced pressure. The resultant residue was purified by silica gel column chromatography using an eluent of hexane:ethyl acetate=1:1 to obtain 3.6 g of 7-chloro-1-(1,3-dioxolan-2-ylmethyl)-1,8-naphthyridin-2(1H)-one as a yellow solid.

$^1$H-NMR (CDCl$_3$) δ: 3.86-3.96 (2H, m), 4.10-4.20 (2H, m), 4.63 (2H, t, J=5.4 Hz), 5.60 (1H, t, J=5.4 Hz), 6.75 (1H, d, J=9.6 Hz), 7.17 (1H, d, J=8.0 Hz), 7.62 (1H, d, J=9.6 Hz), 7.79 (1H, d, J=8.0 Hz)

Reference Example 29

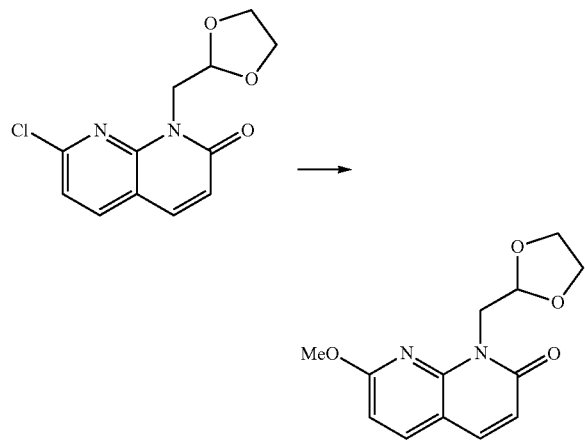

To a solution of 2.5 g of 7-chloro-1-(1,3-dioxolan-2-ylmethyl)-1,8-naphthyridin-2(1H)-one in 30 mL of methanol, 5.4 g of a 28% sodium methoxide/methanol solution was added, and the mixture was heated under reflux while stirring for 3 hours 40 minutes. The reaction mixture was cooled to room temperature, then water was added thereto, and the solvent was then distilled off under reduced pressure. To the resultant residue, water, a saturated aqueous ammonium chloride solution and chloroform were added, the organic layer was separated, and the aqueous layer was extracted with chloroform. The organic layer and the extract were combined, and the resultant solution was washed with a saturated aqueous sodium chloride solution and dried over anhydrous magnesium sulfate, and the solvent was distilled off under reduced pressure to obtain 2.9 g of 1-(1,3-dioxolan-2-ylmethyl)-7-methoxy-1,8-naphthyridin-2(1H)-one as a yellow oily substance.

$^1$H-NMR (CDCl$_3$) δ: 3.84-3.94 (2H, m), 4.00 (3H, s), 4.05-4.15 (2H, m), 4.65 (2H, d, J=5.1 Hz), 5.56 (1H, t, J=5.1 Hz), 6.55 (1H, d, J=9.3 Hz), 6.57 (1H, d, J=8.6 Hz), 7.55 (1H, d, J=9.3 Hz), 7.69 (1H, d, J=8.6 Hz)

Reference Example 30

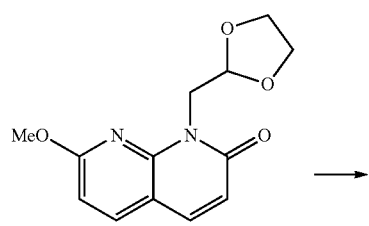

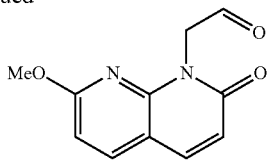

To 2.8 g of 1-(1,3-dioxolan-2-ylmethyl)-7-methoxy-1,8-naphthyridin-2(1H)-one, 20 mL of an 80% aqueous trifluoroacetic acid solution was added, and the mixture was stirred at 60 to 72° C. for 3 hours 20 minutes, and at 80 to 85° C. for 2 hours 20 minutes, 4 mL of water was then added thereto and the mixture was further stirred for 4 hours. The reaction mixture was cooled to room temperature and then left overnight, and the solvent was distilled off under reduced pressure. To the resultant residue, a saturated aqueous sodium hydrogen carbonate solution and chloroform were added, the organic layer was separated, and the aqueous layer was extracted with chloroform. The organic layer and the extract were combined, the resultant solution was dried over anhydrous magnesium sulfate, and the solvent was distilled off under reduced pressure to obtain 1.8 g of (7-methoxy-2-oxo-1,8-naphthyridin-1(2H)-yl)acetaldehyde as a yellow solid.

$^1$H-NMR (CDCl$_3$) δ: 3.92 (3H, s), 5.23 (2H, d, J=0.7 Hz), 6.63-6.67 (2H, m), 7.66 (1H, d, J=9.5 Hz), 7.78 (1H, d, J=8.3 Hz), 9.65-9.67 (1H, m)

Reference Example 31

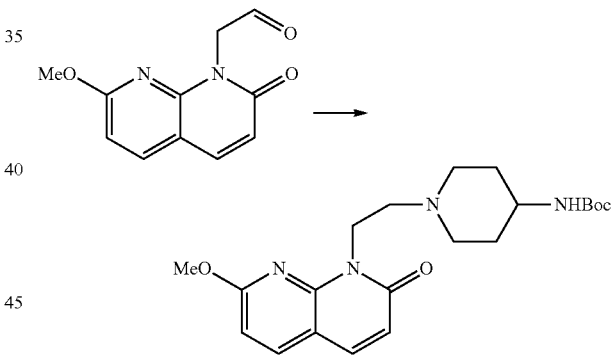

To a solution of 1.6 g of (7-methoxy-2-oxo-1,8-naphthyridin-1(2H)-yl)acetaldehyde in 70 mL of dichloromethane, 1.5 g of tert-butyl (piperidin-4-yl)carbamate and 0.42 mL of acetic acid were added, the mixture was stirred for 20 minutes, then 2.3 g of sodium triacetoxyborohydride was added to the reaction mixture and the mixture was stirred at room temperature for 2 hours 10 minutes. Thereto were added water, a saturated aqueous sodium hydrogen carbonate solution and chloroform, the organic layer was separated, and the aqueous layer was extracted with chloroform. The organic layer and the extract were combined, the resultant solution was washed with a saturated aqueous sodium chloride solution and dried over anhydrous magnesium sulfate, and the solvent was distilled off under reduced pressure. The resultant residue was purified by silica gel column chromatography using an eluent of chloroform:methanol=50:1 to obtain 2.8 g of tert-butyl (1-(2-(7-methoxy-2-oxo-1,8-naphthyridin-1(2H)-yl)ethyl)piperidin-4-yl)carbamate as a white foam.

¹H-NMR (CDCl₃) δ: 1.38-1.51 (11H, m), 1.88-1.98 (2H, m), 2.22-2.31 (2H, m), 2.69-2.75 (2H, m), 2.98-3.06 (2H, m), 3.41-3.52 (1H, m), 4.01 (3H, s), 4.38-4.47 (1H, m), 4.61-4.66 (2H, m), 6.57 (1H, d, J=9.3 Hz), 6.61 (1H, d, J=8.5 Hz), 7.56 (1H, d, J=9.3 Hz), 7.72 (1H, d, J=8.5 Hz)

Reference Example 32

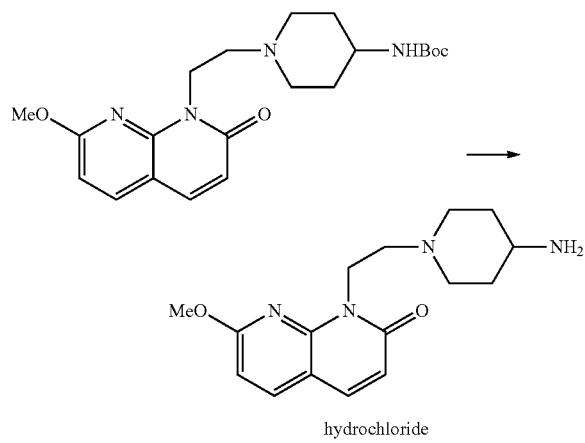

To 2.8 g of tert-butyl (1-(2-(7-methoxy-2-oxo-1,8-naphthyridin-1(2H)-yl)ethyl)piperidin-4-yl)carbamate, 50 mL of a 4 mol/L hydrogen chloride/ethyl acetate solution was added, and the mixture was stirred at room temperature for 29 hours. The solvent was distilled off under reduced pressure, ethyl acetate was added to the solid thus obtained, and a crystal was filtered off and washed with ethyl acetate to obtain 2.3 g of 1-(2-(4-aminopiperidin-1-yl)ethyl)-7-methoxy-1,8-naphthyridin-2(1H)-one hydrochloride as a light yellow solid.

¹H-NMR (D₂O) δ: 1.90-2.05 (2H, m), 2.34-2.43 (2H, m), 3.17-3.30 (2H, m), 3.55-3.67 (3H, m), 3.93-4.02 (2H, m), 4.04 (3H, s), 4.88-4.94 (2H, m), 6.62 (1H, d, J=9.5 Hz), 6.83 (1H, d, J=8.5 Hz), 7.93 (1H, d, J=9.5 Hz), 8.01 (1H, d, J=8.5 Hz)

Reference Example 33

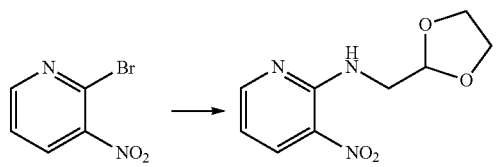 [SMILES: O=[N+]([O-])c1cccnc1Br ; O=[N+]([O-])c1cccnc1NCC1OCCO1]

By the same technique as in Reference Example 14, N-(1,3-dioxolan-2-ylmethyl)-3-nitropyridin-2-amine was obtained from 2-bromo-3-nitropyridine and 1-(1,3-dioxolan-2-yl)methanamine.

¹H-NMR (CDCl₃) δ: 3.90-4.10 (6H, m), 5.17 (1H, t, J=3.4 Hz), 6.64-6.69 (1H, m), 8.36-8.44 (3H, m)

Reference Example 34

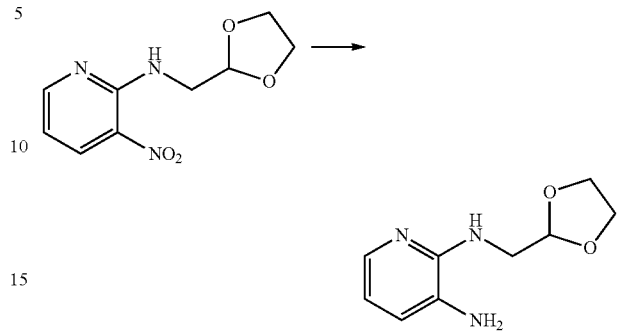

By the same technique as in Reference Example 15, 3-amino-2-(1,3-dioxolan-2-ylmethyl)aminopyridine was obtained from N-(1,3-dioxolan-2-ylmethyl)-3-nitropyridin-2-amine.

¹H-NMR (CDCl₃) δ: 3.20-3.60 (2H, broad), 3.70-3.74 (2H, m), 3.87-4.08 (4H, m), 4.76-4.88 (1H, broad), 5.16 (1H, t, J=4.1 Hz), 6.55 (1H, dd, J=7.4, 5.2 Hz), 6.86 (1H, dd, J=7.4, 1.3 Hz), 7.70 (1H, dd, J=5.2, 1.3 Hz)

Reference Example 35

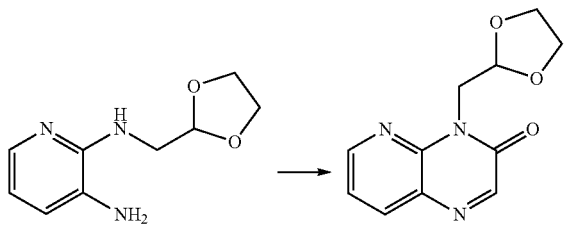 [SMILES: Nc1cccnc1NCC1OCCO1 ; O=c1cnc2cccnc2n1CC1OCCO1]

To a solution of 0.20 g of 3-amino-2-(1,3-dioxolan-2-ylmethyl)aminopyridine in 2 mL of ethanol, 0.25 g of a 45 to 50% toluene solution of ethyl oxoacetate was added, and the mixture was heated under reflux while stirring for 1 hour 30 minutes. The reaction mixture was cooled to room temperature, and thereto were added water and ethyl acetate. The organic layer was separated and the aqueous layer was extracted with ethyl acetate. The organic layer and the extract were combined, the resultant solution was washed with a saturated aqueous sodium chloride solution and dried over anhydrous magnesium sulfate, and the solvent was distilled off under reduced pressure. The resultant residue was purified by flash silica gel column chromatography using gradient elution with chloroform:methanol=100:0 to 90:10 to obtain 0.16 g of 4-(1,3-dioxolan-2-ylmethyl)pyrido(2,3-b)pyrazin-3(4H)-one as a light brown solid.

¹H-NMR (CDCl₃) δ: 3.85-3.95 (2H, m), 4.06-4.16 (2H, m), 4.66 (2H, d, J=5.2 Hz), 5.56 (1H, t, J=5.2 Hz), 7.33 (1H, dd, J=7.9, 4.7 Hz), 8.17 (1H, dd, J=7.9, 1.7 Hz), 8.35 (1H, s), 8.60 (1H, dd, J=4.7, 1.7 Hz)

Reference Example 36

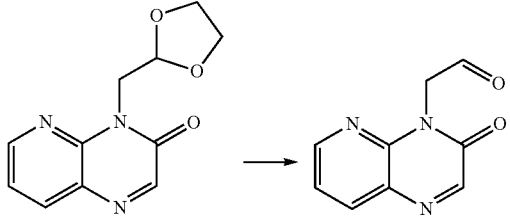 [SMILES: O=c1cnc2cccnc2n1CC1OCCO1 ; O=CCn1c(=O)cnc2cccnc21]

By the same technique as in Reference Example 4, (3-oxopyrido(2,3-b)pyrazin-4(3H)-yl)acetaldehyde was obtained from 4-(1,3-dioxolan-2-ylmethyl)pyrido(2,3-b)pyrazin-3(4H)-one.

$^1$H-NMR (CDCl$_3$) δ: 5.33 (2H, s), 7.35 (1H, dd, J=7.9, 4.7 Hz), 8.22 (1H, dd, J=7.9, 1.7 Hz), 8.40 (1H, s), 8.52 (1H, dd, J=4.7, 1.7 Hz), 9.75 (1H, s)

Reference Example 37

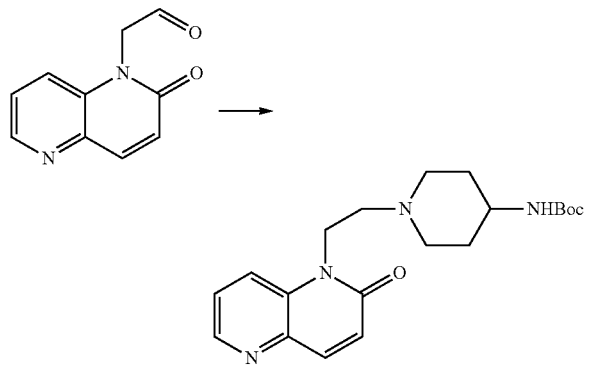

By the same technique as in Reference Example 42, tert-butyl (1-(2-(2-oxo-1,5-naphthyridin-1(2H)-yl)ethyl)piperidin-4-yl)carbamate was obtained from (2-oxo-1,5-naphthyridin-1(2H)-yl)acetaldehyde and tert-butyl (piperidin-4-yl)carbamate.

$^1$H-NMR (CDCl$_3$, D$_2$O) δ: 1.24-1.46 (11H, m), 1.90-1.98 (2H, m), 2.21-2.30 (2H, m), 2.62-2.68 (2H, m), 2.88-2.97 (2H, m), 4.35-4.55 (3H, m), 6.92 (1H, d, J=9.7 Hz), 7.47 (1H, dd, J=8.5, 4.5 Hz), 7.74-7.78 (1H, m), 7.92 (1H, d, J=9.7 Hz), 8.55 (1H, dd, J=4.5, 1.1 Hz)

Reference Example 38

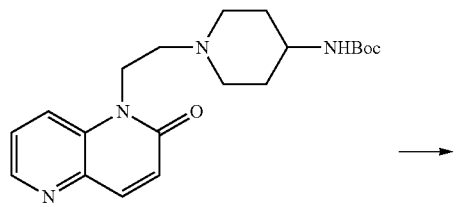

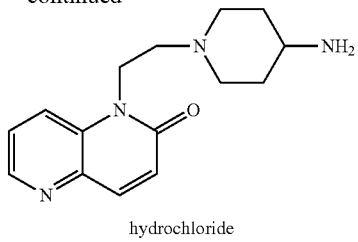

hydrochloride

By the same technique as in Reference Example 13, 1-(2-(4-aminopiperidin-1-yl)ethyl)1,5-naphthyridin-2(1H)-one hydrochloride was obtained from tert-butyl (1-(2-(2-oxo-1,5-naphthyridin-1(2H)-yl)ethyl)piperidin-4-yl)carbamate.

$^1$H-NMR (D$_2$O) δ: 1.80-2.10 (2H, m), 2.26-2.48 (2H, m), 3.10-3.40 (2H, m), 3.53-3.70 (3H, m), 3.90-4.10 (2H, m), 4.84-4.90 (2H, m), 7.31 (1H, d, J=10.0 Hz), 8.21 (1H, dd, J=9.0, 5.5 Hz), 8.26 (1H, d, J=10.0 Hz), 8.72 (1H, d, J=9.0 Hz), 8.81 (1H, d, J=5.5 Hz)

Reference Example 39

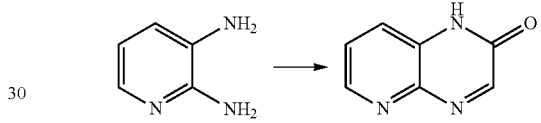

To a suspension of 3.8 g of pyridine-2,3-diamine in 100 mL of dioxane, 7.1 g of a 45 to 50% toluene solution of ethyl oxoacetate was added, and the mixture was stirred at room temperature for 1 hour, and then heated under reflux while stirring for 1 hour. The reaction mixture was cooled with ice bath, and diethyl ether was added thereto. The solid was filtered off to obtain 3.9 g of pyrido(2,3-b)pyrazin-2(1H)-one as a light brown solid.

$^1$H-NMR (DMSO-d$_6$) δ: 7.58 (1H, dd, J=8.2, 4.5 Hz), 7.73 (1H, dd, J=8.2, 1.6 Hz), 8.37 (1H, s), 8.53 (1H, dd, J=4.5, 1.6 Hz)

Reference Example 40

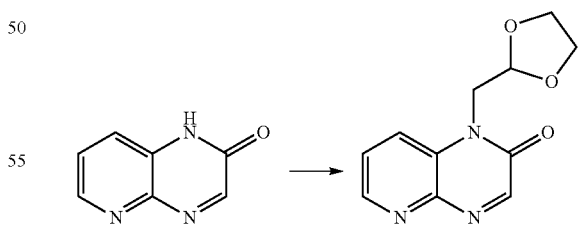

By the same technique as in Reference Example 3, 1-(1,3-dioxolan-2-ylmethyl)pyrido(2,3-b)pyrazin-2(1H)-one was obtained from pyrido(2,3-b)pyrazin-2(1H)-one and 2-bromomethyl-1,3-dioxolan.

$^1$H-NMR (CDCl$_3$) δ: 3.83-4.00 (4H, m), 4.49 (2H, d, J=4.0 Hz), 5.23 (1H, t, J=4.0 Hz), 7.52 (1H, dd, J=8.5, 4.4 Hz), 7.99 (1H, dd, J=8.5, 1.5 Hz), 8.56 (1H, s), 8.66 (1H, dd, J=4.4, 1.5 Hz)

Reference Example 41

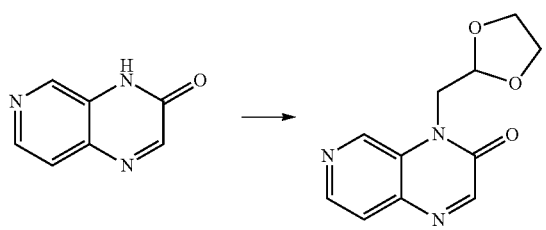 [SMILES: O=c1cnc2ccncc2[nH]1 ; O=c1cnc2ccncc2n1CC1OCCO1]

By the same technique as in Reference Example 3, 4-(1,3-dioxolan-2-ylmethyl)pyrido(3,4-b)pyrazin-3(4H)-one was obtained from pyrido(3,4-b)pyrazin-3(4H)-one and 2-bromomethyl-1,3-dioxolan.

$^1$H-NMR (CDCl$_3$) δ: 3.85-4.05 (4H, m), 4.53 (2H, d, J=4.2 Hz), 5.29 (1H, t, J=4.2 Hz), 7.73 (1H, d, J=5.2 Hz), 8.49 (1H, s), 8.59 (1H, d, J=5.2 Hz), 9.05 (1H, s)

Reference Example 42

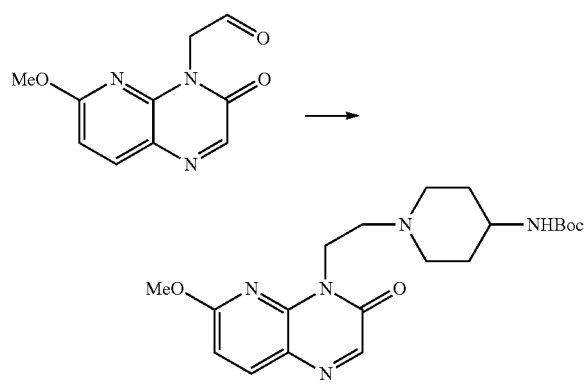

To a solution of 0.18 g of (6-methoxy-3-oxopyrido(2,3-b)pyrazin-4(3H)-yl)acetaldehyde in 4 mL of dichloromethane, 0.16 g of tert-butyl (piperidin-4-yl)carbamate and 47 μL of acetic acid and 0.26 g of sodium triacetoxyborohydride were added, and the mixture was stirred at room temperature for 3 hours. Chloroform and a saturated aqueous sodium hydrogen carbonate solution were added to the reaction mixture, the organic layer was separated, and the aqueous layer was extracted with chloroform. The organic layer and the extract were combined, the resultant solution was washed with a saturated aqueous sodium chloride solution and dried over anhydrous magnesium sulfate, and the solvent was distilled off under reduced pressure. To the resultant residue, diethyl ether, methanol and hexane were added, and the solid was filtered off to obtain 0.23 g of tert-butyl (1-(2-(6-methoxy-3-oxopyrido(2,3-b)pyrazin-4(3H)-yl)ethyl)piperidin-4-yl)carbamate as a light brown solid.

$^1$H-NMR (CDCl$_3$) δ: 1.25-1.47 (2H, m), 1.44 (9H, s), 1.86-1.95 (2H, m), 2.18-2.28 (2H, m), 2.70-2.77 (2H, m), 2.93-3.02 (2H, m), 3.38-3.52 (1H, broad), 4.02 (3H, s), 4.35-4.44 (1H, m), 4.53-4.59 (2H, m), 6.73 (1H, d, J=8.8 Hz), 8.01 (1H, d, J=8.8 Hz), 8.15 (1H, s)

Reference Example 43

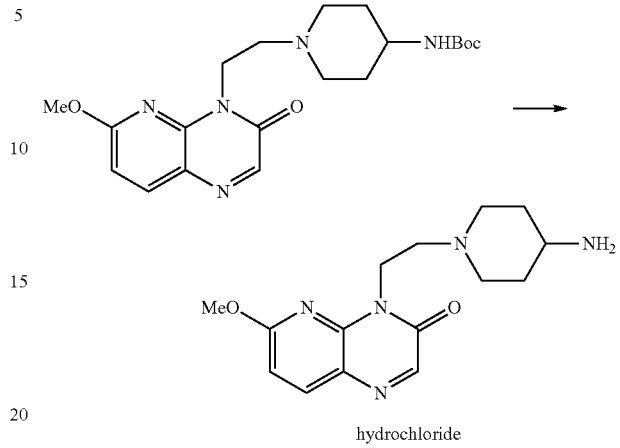

hydrochloride

To a suspension of 0.23 g of tert-butyl (1-(2-(6-methoxy-3-oxopyrido(2,3-b)pyrazin-4(3H)-yl)ethyl)piperidin-4-yl)carbamate in 3 mL of ethyl acetate, 4.0 mL of a 4.0 mol/L hydrogen chloride/ethyl acetate solution was added at room temperature. The mixture was stirred at the same temperature for 5 hours, and then left overnight. The solvent was distilled off under reduced pressure, diethyl ether was added to the resultant residue, and the solid was filtered off to obtain 0.23 g of 4-(2-(4-aminopiperidin-1-yl)ethyl)-6-methoxypyrido(2,3-b)pyrazin-3(4H)-one hydrochloride as a light brown solid.

$^1$H-NMR (D$_2$O) δ: 1.88-2.03 (2H, m), 2.32-2.43 (2H, m), 3.18-3.32 (2H, m), 3.52-3.74 (3H, m), 3.91-4.04 (2H, m), 4.07 (3H, s), 4.87-4.93 (2H, m), 6.98 (1H, d, J=8.9 Hz), 8.17 (1H, d, J=8.9 Hz), 8.18 (1H, s)

Reference Example 44

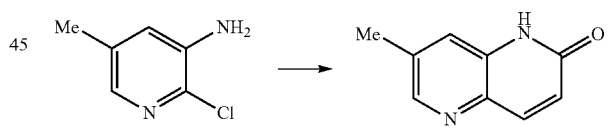

By the same technique as in Reference Example 1, 7-methyl-1,5-naphthyridin-2(1H)-one was obtained from 2-chloro-5-methylpyridin-3-amine and ethyl acrylate.

$^1$H-NMR (DMSO-d$_6$) δ: 2.39 (3H, s), 6.66 (1H, d, J=9.8 Hz), 7.43-7.47 (1H, m), 7.89 (1H, d, J=9.8 Hz), 8.32-8.34 (1H, m), 11.81-11.85 (1H, broad)

Reference Example 45

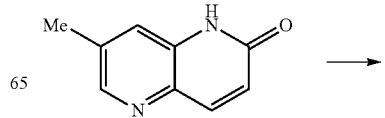

-continued

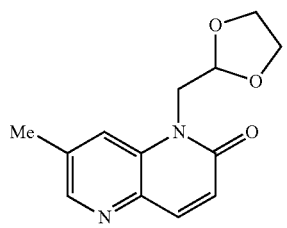

By the same technique as in Reference Example 3, 1-(1,3-dioxolan-2-ylmethyl)-7-methyl-1,5-naphthyridin-2(1H)-one was obtained from 7-methyl-1,5-naphthyridin-2(1H)-one and 2-bromomethyl-1,3-dioxolan.

$^1$H-NMR (CDCl$_3$) δ: 2.50 (3H, s), 3.84-3.93 (2H, m), 3.97-4.07 (2H, m), 4.50 (2H, d, J=4.2 Hz), 5.22 (1H, t, J=4.2 Hz), 6.87 (1H, d, J=9.8 Hz), 7.69-7.73 (1H, m), 7.89 (1H, d, J=9.8 Hz), 8.38 (1H, d, J=1.5 Hz)

Reference Example 46

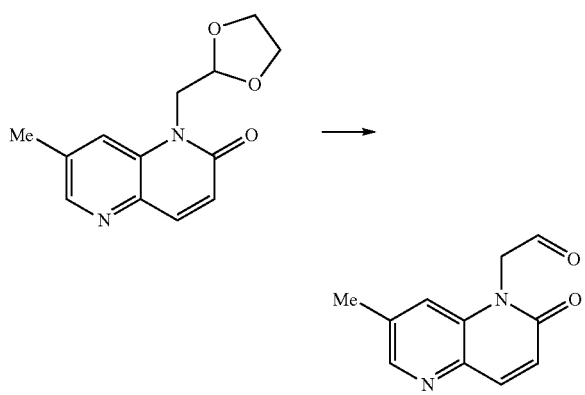

By the same technique as in Reference Example 4, (7-methyl-2-oxo-1,5-naphthyridin-1(2H)-yl)acetaldehyde was obtained from 1-(1,3-dioxolan-2-ylmethyl)-7-methyl-1,5-naphthyrdin-2(1H)-one.

$^1$H-NMR (DMSO-d$_6$) δ: 2.41 (3H, s), 5.25 (2H, s), 6.83 (1H, d, J=9.8 Hz), 7.73-7.78 (1H, m), 7.97 (1H, d, J=9.8 Hz), 8.38-8.42 (1H, m), 9.70 (1H, s)

Reference Example 47

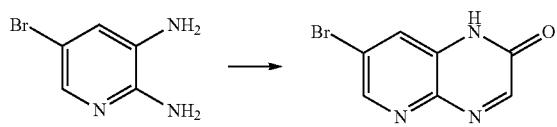 [SMILES: Nc1cc(Br)cnc1N ; O=c1cnc2ncc(Br)cc2[nH]1]

By the same technique as in Reference Example 39, 7-bromopyrido(2,3-b)pyrazin-2(1H)-one was obtained from 5-bromopyridine-2,3-diamine and ethyl oxoacetate.

$^1$H-NMR (DMSO-d$_6$) δ: 7.86 (1H, d, J=2.2 Hz), 8.39 (1H, s), 8.60 (1H, d, J=2.2 Hz), 12.56-12.64 (1H, broad)

Reference Example 48

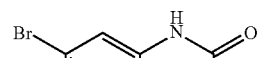
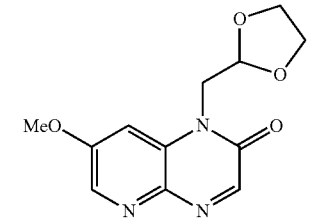

To a suspension of 4.0 g of 7-bromopyrido(2,3-b)pyrazin-2(1H)-one in 40 mL of N,N-dimethylformamide, 8.2 g of a 28% sodium methoxide/methanol solution and 0.25 g of copper (I) bromide were added at room temperature, and the mixture was stirred at 80 to 90° C. for 3 hours under a nitrogen atmosphere. The reaction mixture was cooled to 55° C., thereto was added 2.8 mL of 2-bromomethyl-1,3-dioxolan, and the mixture was stirred at 80 to 90° C. for 1 hour 30 minutes under a nitrogen atmosphere. The reaction mixture was cooled to room temperature and then left overnight. The mixture was further stirred at 80 to 90° C. for 1 hour, and then stirred at 90 to 100° C. for 1 hour 30 minutes. The reaction mixture was cooled to room temperature, and then ethyl acetate and water were added thereto. The insoluble substance was filtered off, the organic layer was separated, and the aqueous layer was extracted with ethyl acetate. The organic layer and the extract were combined, the resultant solution was dried over anhydrous magnesium sulfate, and the solvent was then distilled off under reduced pressure. The resultant residue was purified by flash silica gel column chromatography using gradient elution with chloroform:methanol=100:0 to 95:5, ethyl acetate was added to the orange oily substance thus obtained, and the solid was filtered off to obtain 0.12 g of 1-(1,3-dioxolan-2-ylmethyl)-7-methoxypyrido(2,3-b)pyrazin-2(1H)-one as an orange solid.

$^1$H-NMR (CDCl$_3$) δ: 3.84-3.93 (2H, m), 3.93-4.02 (2H, m), 3.99 (3H, s), 4.47 (2H, d, J=3.8 Hz), 5.21 (1H, t, J=3.8 Hz), 7.39 (1H, d, J=2.7 Hz), 8.36 (1H, d, J=2.7 Hz), 8.38 (1H, s)

Reference Example 49

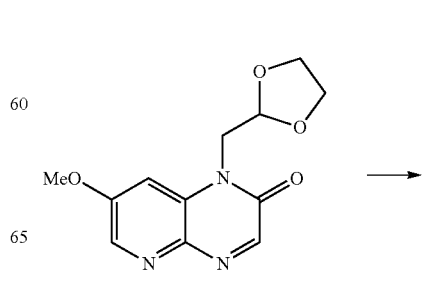

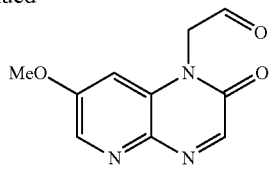

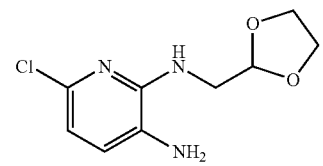

By the same technique as in Reference Example 4, (7-methoxy-2-oxopyrido(2,3-b)pyrazin-1(2H)-yl)acetaldehyde was obtained from 1-(1,3-dioxolan-2-ylmethyl)-7-methoxypyrido(2,3-b)pyrazin-2(1H)-one.

$^1$H-NMR (DMSO-d$_6$) δ: 3.94 (3H, s), 5.31 (2H, s), 7.48 (1H, d, J=2.7 Hz), 8.32 (1H, s), 8.33 (1H, d, J=2.7 Hz), 9.68 (1H, s)

Reference Example 50

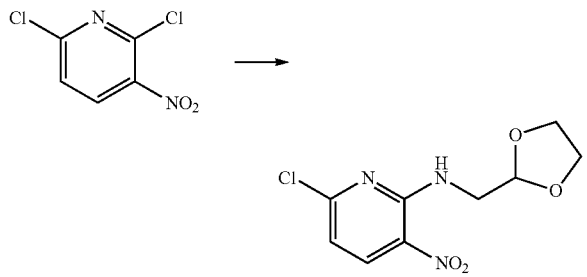

To a solution of 0.50 g of 2,6-dichloro-3-nitropyridine in 5 mL of acetonitrile, 0.43 g of potassium carbonate was added, thereto was added a solution of 0.24 mL of 2-aminomethyl-1,3-dioxolan in 3 mL of acetonitrile under cooling with ice, and the mixture was stirred for 2 hours under cooling with ice. Thereto was further added 80 μL of 2-aminomethyl-1,3-dioxolan, and the mixture was stirred for 2 hours under cooling with ice. Water and ethyl acetate were added thereto under cooling with ice, the organic layer was separated, washed with a saturated aqueous sodium chloride solution and dried over anhydrous sodium sulfate, and the solvent was distilled off under reduced pressure. The resultant residue was purified by basic silica gel column chromatography using an eluent of hexane:ethyl acetate=20:1 to obtain 0.44 g of 6-chloro-N-(1,3-dioxolan-2-ylmethyl)-3-nitropyridin-2-amine as a yellow solid.

$^1$H-NMR (CDCl$_3$) δ: 3.90-4.00 (2H, m), 4.00-4.12 (2H, m), 5.16 (1H, t, J=3.3 Hz), 6.63 (1H, d, J=8.7 Hz), 8.35 (1H, d, J=8.7 Hz), 8.40-8.60 (1H, broad)

Reference Example 51

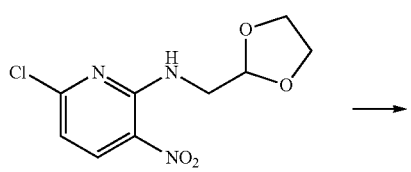

To a suspension of 13 g of iron powder in 650 mL of ethanol and 350 mL of water, 14 g of sodium chloride was added, and the mixture was heated under reflux while stirring for 20 minutes. Thereto was added 10 g of 6-chloro-N-(1,3-dioxolan-2-ylmethyl)-3-nitropyridin-2-amine at 65° C., and the mixture was heated under reflux while stirring for 30 minutes. The insoluble substance was filtered off, the solvent was distilled off to be 300 mL under reduced pressure, ethyl acetate was added thereto, the organic layer was separated, and the aqueous layer was extracted with ethyl acetate. The organic layer and the extract were combined, the resultant solution was dried over anhydrous sodium sulfate, and the solvent was distilled off under reduced pressure. The resultant residue was purified by basic silica gel column chromatography using an eluent of ethyl acetate to obtain 6.5 g of 3-amino-6-chloro-2-(1,3-dioxolan-2-ylmethyl)aminopyridine as a light purple solid.

$^1$H-NMR (CDCl$_3$) δ: 3.15 (2H, s), 3.68 (2H, dd, J=6.0, 4.2 Hz), 3.88-3.98 (2H, m), 3.98-4.06 (2H, m), 4.50-4.60 (1H, m), 5.14 (1H, t, J=4.2 Hz), 6.51 (1H, d, J=7.7 Hz), 6.80 (1H, d, J=7.7 Hz)

Reference Example 52

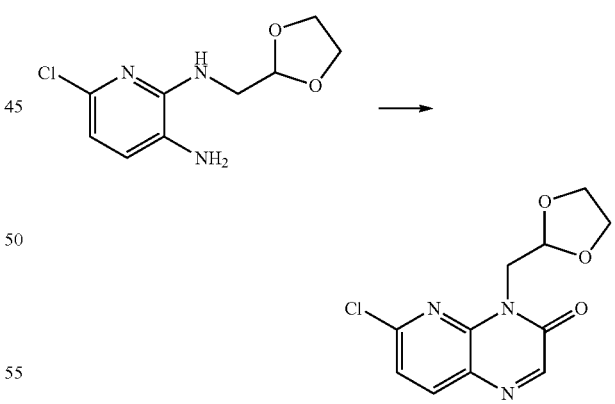

By the same technique as in Reference Example 16, 6-chloro-4-(1,3-dioxolan-2-ylmethyl)pyrido(2,3-b)pyrazin-3(4H)-one was obtained from 3-amino-6-chloro-2-(1,3-dioxolan-2-ylmethyl)aminopyridine and ethyl oxoacetate.

$^1$H-NMR (CDCl$_3$) δ: 3.87-3.96 (2H, m), 4.08-4.18 (2H, m), 4.56 (2H, d, J=5.4 Hz), 5.58 (1H, t, J=5.4 Hz), 7.30 (1H, d, J=8.3 Hz), 8.10 (1H, d, J=8.3 Hz), 8.32 (1H, s)

Reference Example 53

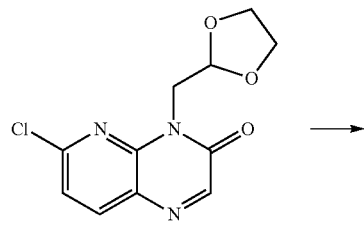

To a solution of 0.10 g of 6-chloro-4-(1,3-dioxolan-2-yl-methyl)pyrido(2,3-b)pyrazin-3(4H)-one in 3 mL of N,N-dimethylformamide, 0.57 g of cesium fluoride was added, and the mixture was stirred at 90 to 100° C. for 1 hour 10 minutes. Thereto was further added 0.57 g of cesium fluoride, and the mixture was stirred at 90 to 100° C. for 1 hour 30 minutes. Thereto were added ethyl acetate and water, the organic layer was separated, and the aqueous layer was extracted with ethyl acetate. The organic layer and the extract were combined, the resultant solution was washed sequentially with diluted hydrochloric acid and a saturated aqueous sodium chloride solution, and dried over anhydrous magnesium sulfate, and the solvent was distilled off under reduced pressure. The resultant residue was purified by silica gel column chromatography using an eluent of chloroform:methanol=50:1 to obtain 60 mg of 4-(1,3-dioxolan-2-ylm-ethyl)-6-fluoropyrido(2,3-b)pyrazin-3(4H)-one as a light yellow solid.

$^1$H-NMR (CDCl$_3$) δ: 3.86-3.96 (2H, m), 4.06-4.16 (2H, m), 4.53 (2H, d, J=5.4 Hz), 5.54 (1H, t, J=5.4 Hz), 6.91 (1H, dd, J=8.4, 2.4 Hz), 8.25 (1H, dd, J=8.4, 7.3 Hz), 8.30 (1H, s)

Reference Example 54

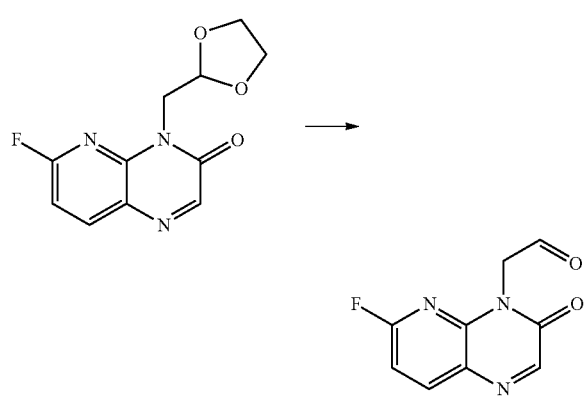

By the same technique as in Reference Example 4, (6-fluoro-3-oxopyrido(2,3-b)pyrazin-4(3H)-yl)acetaldehyde was obtained from 4-(1,3-dioxolan-2-ylmethyl)-6-fluoropyrido(2,3-b)pyrazin-3(4H)-one.

$^1$H-NMR (CDCl$_3$) δ: 5.27 (2H, s), 6.93 (1H, dd, J=8.5, 2.4 Hz), 8.30 (1H, dd, J=8.5, 7.1 Hz), 8.34 (1H, s), 9.75 (1H, s)

Reference Example 55

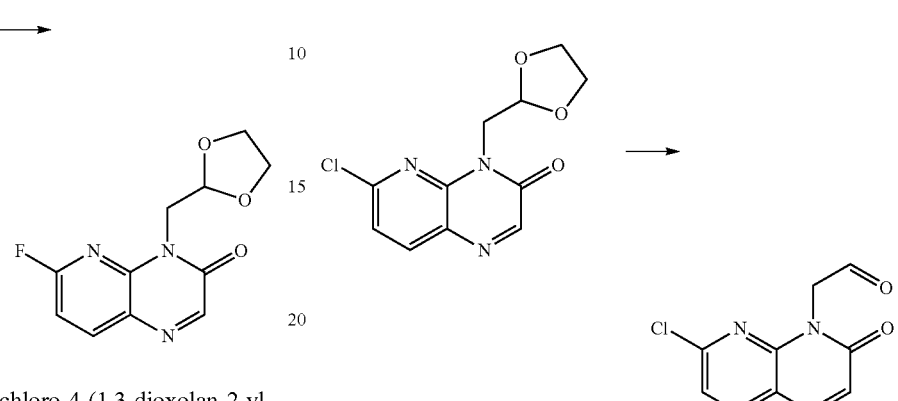

By the same technique as in Reference Example 4, (6-chloro-3-oxopyrido(2,3-b)pyrazin-4(3H)-yl)acetaldehyde was obtained from 6-chloro-4-(1,3-dioxolan-2-ylm-ethyl)pyrido(2,3-b)pyrazin-3(4H)-one.

$^1$H-NMR (CDCl$_3$) δ: 5.31 (2H, s), 7.32 (1H, d, J=8.3 Hz), 8.15 (1H, d, J=8.3 Hz), 8.36 (1H, s), 9.76 (1H, s)

Reference Example 56

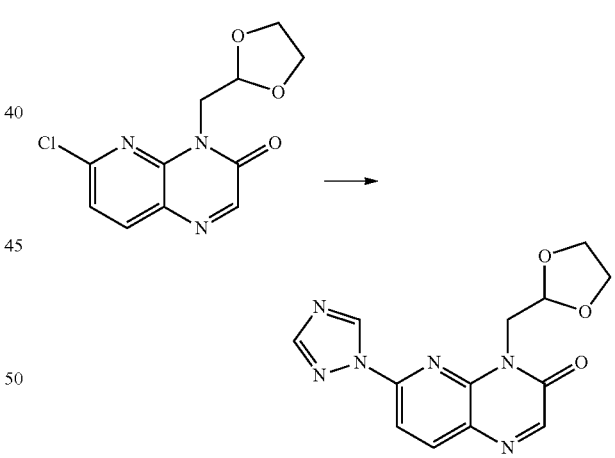

To a solution of 0.30 g of 6-chloro-4-(1,3-dioxolan-2-yl-methyl)pyrido(2,3-b)pyrazin-3(4H)-one and 78 mg of 1,2,4-triazole in 9 mL of N,N-dimethylformamide, 48 mg of 60% sodium hydride was added, and the mixture was stirred at 40 to 50° C. for 1 hour 30 minutes. Thereto was further added 78 mg of 1,2,4-triazole and 48 mg of 60% sodium hydride, and the mixture was stirred at 40 to 50° C. for 1 hour 30 minutes, and stirred at 60 to 70° C. for 20 minutes. The reaction mixture was charged with a mixed solution of ethyl acetate and water and neutralized with 2.0 mol/L hydrochloric acid, and the insoluble substance was filtered off. The organic layer was separated and the aqueous layer was extracted with ethyl acetate. The organic layer and the extract were combined, the resultant solution was washed sequentially with water and a saturated aqueous sodium chloride solution and dried over anhydrous magnesium sulfate, and the solvent was distilled off under reduced pressure. The resultant residue was purified by flash silica gel column chromatography using gradient elution with hexane:ethyl acetate=80:20 to 30:70 and washed with diisopropyl ether to obtain 77 mg of 4-(1,3-dioxolan-2-ylmethyl)-6-(1H-1,2,4-triazole-1-yl)pyrido(2,3-b)pyrazin-3(4H)-one as a light red solid.

$^1$H-NMR (CDCl$_3$) δ: 3.86-3.96 (2H, m), 4.04-4.14 (2H, m), 4.67 (2H, d, J=4.9 Hz), 5.47 (1H, t, J=4.9 Hz), 7.93 (1H, d, J=8.5 Hz), 8.16 (1H, s), 8.34-8.37 (2H, m), 9.19 (1H, s)

Reference Example 57

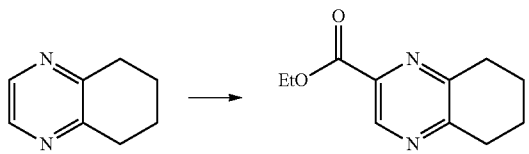 [SMILES: c1cnc2c(n1)CCCC2 ; CCOC(=O)c1cnc2c(n1)CCCC2]

To a solution of 1.0 g of monoethyl oxalate in 14 mL of dichloromethane, 0.47 g of 5,6,7,8-tetrahydroquinoxaline, 91 μL of concentrated sulfuric acid, 1.7 g of sodium persulfate, and a suspension of 60 mg of silver nitrate in 14 mL of water were added, and the mixture was heated under reflux while stirring for 1 hour 30 minutes. To the reaction mixture, 1.7 g of sodium persulfate and 60 mg of silver nitrate were further added, and the mixture was heated under reflux for 1 hour 50 minutes. The reaction mixture was charged with chloroform and adjusted to pH 7.5 with a saturated aqueous sodium hydrogen carbonate solution, the insoluble substance was filtered off, and the organic layer was separated. The organic layer was washed with a saturated aqueous sodium chloride solution, and dried over anhydrous magnesium sulfate, and the solvent was distilled off under reduced pressure. The resultant residue was purified by flash silica gel column chromatography using gradient elution with hexane:ethyl acetate=90:10 to 67:33 to obtain 0.16 g of ethyl 5,6,7,8-tetrahydroquinoxaline-2-carboxylate as a yellow oily substance.

$^1$H-NMR (CDCl$_3$) δ: 1.44 (3H, t, J=7.1 Hz), 1.92-2.00 (4H, m), 3.00-3.10 (4H, m), 4.50 (2H, q, J=7.1 Hz), 9.02 (1H, s)

Reference Example 58

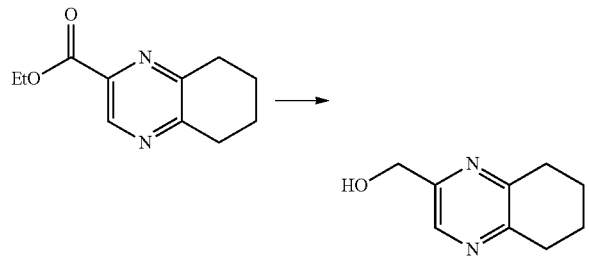

To a solution of 0.16 g of ethyl 5,6,7,8-tetrahydroquinoxaline-2-carboxylate in 1.5 mL of tetrahydrofuran, 29 mg of lithium aluminum hydride was added under cooling with ice, the mixture was stirred for 45 minutes, 29 mg of lithium aluminum hydride was further added thereto, and the mixture was stirred for 30 minutes. Thereto were added ethyl acetate and water, the insoluble substance was filtered off, sodium chloride was added to a filtrate, the organic layer was separated, and the aqueous layer was extracted with ethyl acetate. The organic layer and the extract were combined, the resultant solution was washed with a saturated aqueous sodium chloride solution, and dried over anhydrous magnesium sulfate, and the solvent was distilled off under reduced pressure to obtain 0.10 g of (5,6,7,8-tetrahydroquinoxalin-2-yl)methanol as a brown solid.

$^1$H-NMR (CDCl$_3$) δ: 1.89-1.98 (4H, m), 2.92-3.01 (4H, m), 4.76 (2H, s), 8.33 (1H, s)

Reference Example 59

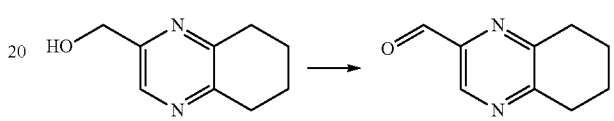

By the same technique as in Reference Example 67, 5,6,7,8-tetrahydroquinoxaline-2-carbaldehyde was obtained from (5,6,7,8-tetrahydroquinoxalin-2-yl)methanol.

$^1$H-NMR (CDCl$_3$) δ: 1.96-2.01 (4H, m), 3.03-3.10 (4H, m), 8.91 (1H, s), 10.09 (1H, s)

Reference Example 60

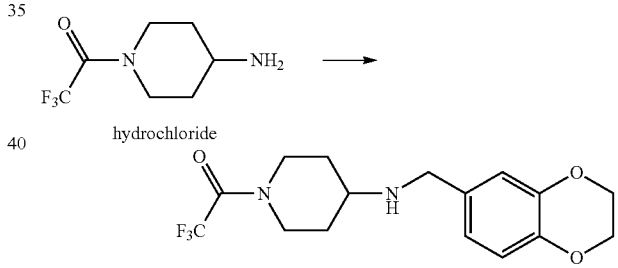

To a suspension of 1.0 g of 1-(trifluoroacetyl)piperidin-4-amine hydrochloride in 20 mL of dichloromethane, 0.71 g of 2,3-dihydro-1,4-benzodioxine-6-carbaldehyde and 0.25 mL of acetic acid were added, and the mixture was stirred at room temperature for 2 hours. To the reaction mixture, 1.37 g of sodium triacetoxyborohydride was added, and the mixture was stirred at the same temperature for 30 minutes. The solvent was distilled off under reduced pressure, water and ethyl acetate were then added thereto, and the mixture was adjusted to pH 1.5 with 1 mol/L hydrochloric acid. The aqueous layer was separated and washed with ethyl acetate, thereto was added ethyl acetate, and the aqueous layer was adjusted to pH 7.8 with a saturated aqueous sodium hydrogen carbonate solution. The organic layer was separated, and the aqueous layer was extracted with ethyl acetate. The organic layer and the extract were combined, the resultant solution was washed with a saturated aqueous sodium chloride solution and dried over anhydrous magnesium sulfate, and the solvent was distilled off under reduced pressure to obtain 1.4 g of N-(2,3-dihydro-1,4-benzodioxin-6-ylmethyl)-1-(trifluoroacetyl)piperidin-4-amine as a colorless oily substance.

¹H-NMR (CDCl₃) δ: 1.35-1.50 (2H, m), 1.90-2.00 (2H, m), 2.80-2.88 (1H, m), 3.02-3.12 (1H, m), 3.18-3.28 (1H, m), 3.71 (2H, s), 3.90-4.00 (1H, m), 4.25 (4H, s), 4.25-4.32 (1H, m), 6.75-6.83 (3H, m)

Reference Example 61

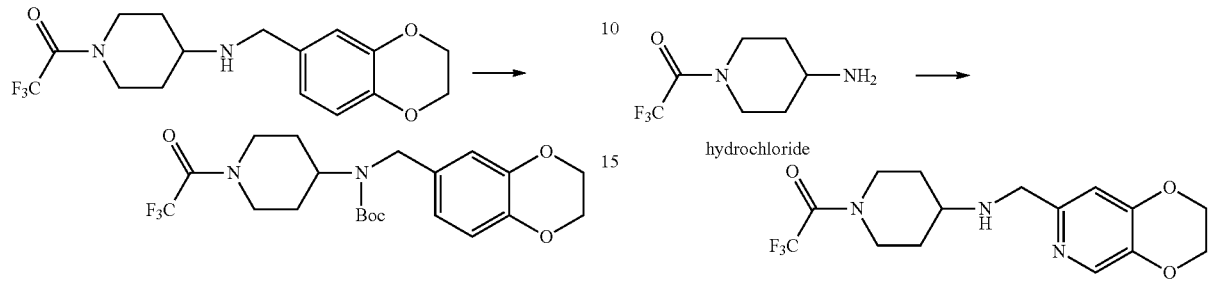

To a solution of 1.4 g of N-(2,3-dihydro-1,4-benzodioxin-6-ylmethyl)-1-(trifluoroacetyl)piperidin-4-amine in 20 mL of dichloromethane, 0.88 g of di-tert-butyl dicarbonate was added, and the mixture was stirred at room temperature for 30 minutes. Thereto was added 0.28 mL of triethylamine, the mixture was stirred at the same temperature for 10 minutes, and then 0.44 g of di-tert-butyl dicarbonate was added and the mixture was stirred for 10 minutes. After stirring at 40° C. for 30 minutes, the solvent was distilled off under reduced pressure, and the resultant residue was purified by silica gel column chromatography using an eluent of hexane:ethyl acetate=1:1 to obtain 1.4 g of tert-butyl (2,3-dihydro-1,4-benzodioxin-6-ylmethyl) (1-(trifluoroacetyl)piperidin-4-yl) carbamate as a white foam.

¹H-NMR (CDCl₃) δ: 1.44 (9H, s), 1.60-1.82 (4H, m), 2.60-2.80 (1H, m), 3.00-3.20 (1H, m), 3.95-4.05 (1H, m), 4.15-4.40 (3H, m), 4.25 (4H, s), 4.50-4.65 (1H, m), 6.60-6.75 (2H, m), 6.70-6.73 (1H, m), 6.79 (1H, d, J=8.3 Hz)

Reference Example 62

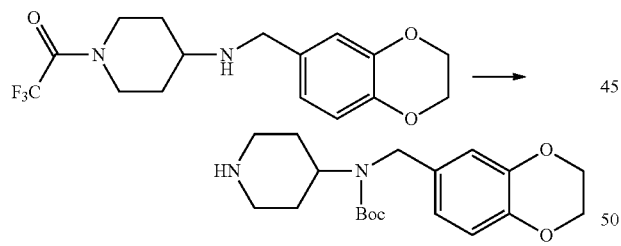

To a solution of 1.4 g of tert-butyl (2,3-dihydro-1,4-benzodioxin-6-ylmethyl)(1-(trifluoroacetyl)piperidin-4-yl)carbamate in 20 mL of methanol, 5 mL of water and 0.53 g of potassium carbonate were added, and the mixture was stirred at room temperature for 1 hour 15 minutes. The solvent was distilled off under reduced pressure, and ethyl acetate and water were added thereto. The organic layer was separated, and the aqueous layer was extracted with ethyl acetate. The organic layer and the extract were combined, the resultant solution was washed sequentially with water and a saturated aqueous sodium chloride solution and dried over anhydrous magnesium sulfate, and the solvent was distilled off under reduced pressure to obtain 1.0 g of tert-butyl (2,3-dihydro-1,4-benzodioxin-6-ylmethyl)(piperidin-4-yl)carbamate as a light yellow oily substance.

¹H-NMR (CDCl₃) δ: 1.42 (9H, s), 1.35-1.70 (4H, m), 2.55-2.70 (2H, m), 3.05-3.15 (2H, m), 4.15-4.35 (3H, m), 4.24 (4H, s), 6.66-6.71 (1H, m), 6.73-6.75 (1H, m), 6.78 (1H, d, J=8.3 Hz)

Reference Example 63

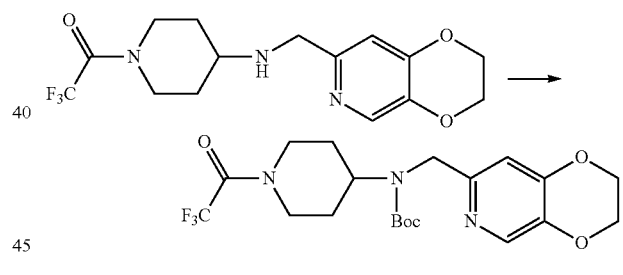

By the same technique as in Reference Example 60, N-(2,3-dihydro-1,4-dioxino(2,3-c)pyridin-7-ylmethyl)-1-(trifluoroacetyl)piperidin-4-amine was obtained from 1-(trifluoroacetyl)piperidin-4-amine hydrochloride and 2,3-dihydro-1,4-dioxino(2,3-c)pyridine-7-carbaldehyde.

¹H-NMR (CDCl₃) δ: 1.39-1.51 (2H, m), 1.93-2.01 (2H, m), 2.79-2.88 (1H, m), 3.02-3.10 (1H, m), 3.19-3.27 (1H, m), 3.80 (2H, s), 3.90-3.99 (1H, m), 4.25-4.35 (5H, m), 6.80 (1H, s), 8.11 (1H, s)

Reference Example 64

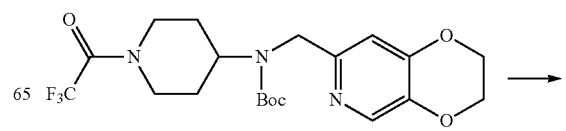

By the same technique as in Reference Example 61, tert-butyl (2,3-dihydro-1,4-dioxino(2,3-c)pyridin-7-ylmethyl)(1-(trifluoroacetyl)piperidin-4-yl)carbamate was obtained from N-(2,3-dihydro-1,4-dioxino(2,3-c)pyridin-7-ylmethyl)-1-(trifluoroacetyl)piperidin-4-amine.

¹H-NMR (CDCl₃) δ: 1.43 (9H, s), 1.37-1.84 (4H, m), 2.60-2.80 (1H, m), 3.00-3.20 (1H, m), 3.98-4.06 (1H, m), 4.25-4.41 (7H, m), 4.54-4.62 (1H, m), 6.74 (1H, s), 8.05 (1H, s)

Reference Example 65

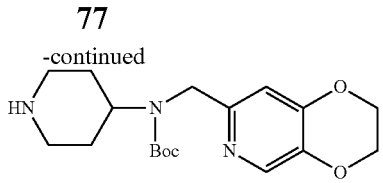

By the same technique as in Reference Example 62, tert-butyl (2,3-dihydro-1,4-dioxino(2,3-c)pyridin-7-ylmethyl)(piperidin-4-yl)carbamate was obtained from tert-butyl (2,3-dihydro-1,4-dioxino(2,3-c)pyridin-7-ylmethyl)(1-(trifluoroacetyl)piperidin-4-yl)carbamate.

$^1$H-NMR (CDCl$_3$) δ: 1.39 (9H, s), 1.34-1.71 (4H, m), 2.52-2.70 (2H, m), 3.04-3.11 (2H, m), 4.11-4.48 (7H, m), 6.75 (1H, s), 8.05 (1H, s)

Reference Example 66

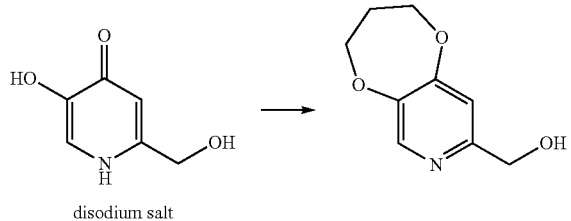 [SMILES: O=c1cc(CO)[nH]cc1O ; OCc1cc2c(cn1)OCCCO2]

disodium salt

To a solution of 0.11 kg of 5-hydroxy-2-(hydroxymethyl)-1,4-dihydropyridin-4-one disodium salt in 600 mL of dimethyl sulfoxide, 0.25 kg of potassium carbonate and 81 mL of 1-bromo-3-chloropropane were added, and the mixture was stirred at 80 to 90° C. for 3 hours 20 minutes, at 90 to 100° C. for 45 minutes, and further at 80 to 95° C. for 5 hours. The reaction mixture was cooled to room temperature, water and chloroform were then added thereto, and the insoluble substance was filtered off. The organic layer was separated and the aqueous layer was extracted with chloroform. The organic layer and the extract were combined, the resultant solution was dried over anhydrous magnesium sulfate, and the solvent was distilled off under reduced pressure. The resultant residue was purified by silica gel column chromatography using an eluent of chloroform:methanol=10:1 to obtain 31 g of (3,4-dihydro-2H-(1,4)dioxepino(2,3-c)pyridin-8-yl)methanol as a brown oily substance.

$^1$H-NMR (CDCl$_3$) δ: 2.23-2.30 (2H, m), 4.24-4.28 (2H, m), 4.33-4.37 (2H, m), 4.63 (2H, s), 6.82 (1H, s), 8.19 (1H, s)

Reference Example 67

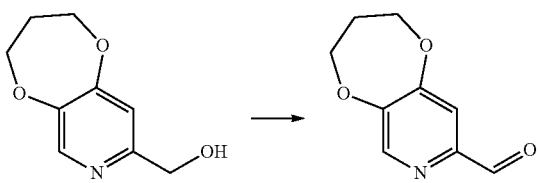 [SMILES: OCc1cc2c(cn1)OCCCO2 ; O=Cc1cc2c(cn1)OCCCO2]

To a solution of 13 g of (3,4-dihydro-2H-(1,4)dioxepino(2,3-c)pyridin-8-yl)methanol in 250 mL of chloroform, 13 g of manganese dioxide was added, and the mixture was stirred at room temperature for 30 minutes. Thereto was further added 20 g of manganese dioxide dividedly, the mixture was then stirred at room temperature for 20 minutes and at 60 to 70° C. for 1 hour 30 minutes. The reaction mixture was cooled to room temperature, the insoluble substance was then filtered off, and the solvent was distilled off under reduced pressure. The resultant residue was purified by silica gel column chromatography using an eluent of hexane:ethyl acetate=1:1 to obtain 2.2 g of 3,4-dihydro-2H-(1,4)dioxepino(2,3-c)pyridine-8-carbaldehyde as a light yellowish white solid.

$^1$H-NMR (CDCl$_3$) δ: 2.28-2.35 (2H, m), 4.36-4.43 (4H, m), 7.53 (1H, s), 8.36 (1H, s), 9.94 (1H, s)

Reference Example 68

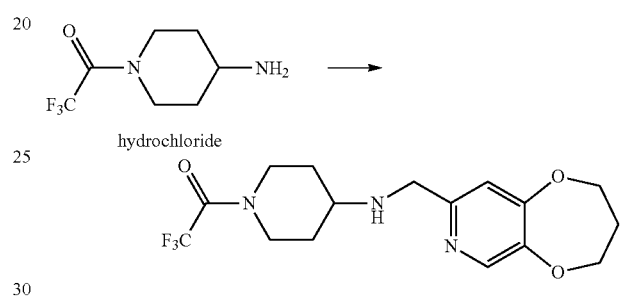

hydrochloride

By the same technique as in Reference Example 60, N-(3,4-dihydro-2H-(1,4)dioxepino(2,3-c)pyridin-8-ylmethyl)-1-(trifluoroacetyl)piperidin-4-amine was obtained from 1-(trifluoroacetyl)piperidin-4-amine hydrochloride and 3,4-dihydro-2H-(1,4)dioxepino(2,3-c)pyridine-8-carbaldehyde.

$^1$H-NMR (CDCl$_3$) δ: 1.39-1.52 (2H, m), 1.93-2.01 (2H, m), 2.12-2.30 (2H, m), 2.80-2.88 (1H, m), 3.01-3.11 (1H, m), 3.18-3.28 (1H, m), 3.81 (2H, s), 3.90-3.99 (1H, m), 4.21-4.38 (5H, m), 6.85 (1H, s), 8.18 (1H, s)

Reference Example 69

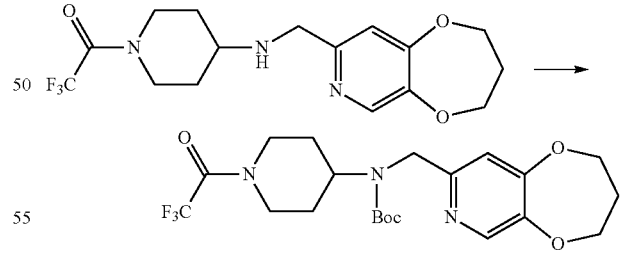

By the same technique as in Reference Example 61, tert-butyl (3,4-dihydro-2H-(1,4)dioxepino(2,3-c)pyridin-8-ylmethyl)(1-(trifluoroacetyl)piperidin-4-yl)carbamate was obtained from N-(3,4-dihydro-2H-(1,4)dioxepino(2,3-c)pyridin-8-ylmethyl)-1-(trifluoroacetyl)piperidin-4-amine.

$^1$H-NMR (CDCl$_3$) δ: 1.41 (9H, s), 1.55-1.90 (4H, m), 2.20-2.30 (2H, m), 2.65-2.80 (1H, m), 3.04-3.21 (1H, m), 3.70-4.50 (8H, m), 4.55-4.64 (1H, m), 6.78 (1H, s), 8.13 (1H, s)

Reference Example 70

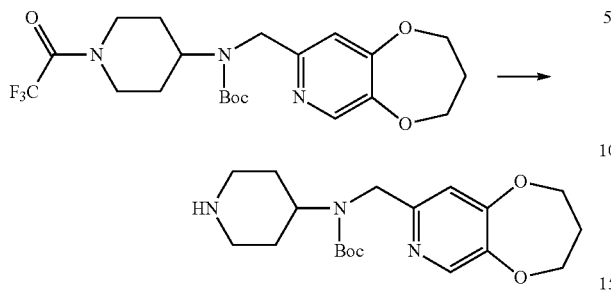

By the same technique as in Reference Example 62, tert-butyl (3,4-dihydro-2H-(1,4)dioxepino(2,3-c)pyridin-8-ylmethyl)(piperidin-4-yl)carbamate was obtained from tert-butyl (3,4-dihydro-2H-(1,4)dioxepino(2,3-c)pyridin-8-ylmethyl)(1-(trifluoroacetyl)piperidin-4-yl)carbamate.

$^1$H-NMR (CDCl$_3$) δ: 1.40-1.72 (13H, m), 2.17-2.28 (2H, m), 2.50-2.70 (2H, m), 3.01-3.11 (2H, m), 4.10-4.50 (7H, m), 6.79 (1H, s), 8.13 (1H, s)

Reference Example 71

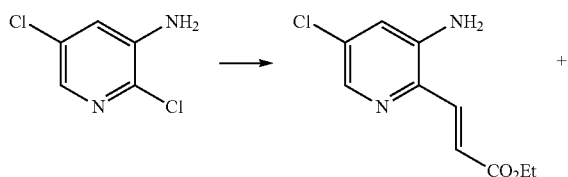

By the same technique as in Reference Example 1, ethyl (2E)-3-(3-amino-5-chloropyridin-2-yl)acrylate and ethyl (2E)-3-(6-oxo-5,6-dihydro-1,5-naphthyridin-3-yl)acrylate were obtained from 2,5-dichloropyridin-3-amine and ethyl acrylate.

Ethyl (2E)-3-(3-amino-5-chloropyridin-2-yl)acrylate $^1$H-NMR (CDCl$_3$) δ: 1.33 (3H, t, J=7.1 Hz), 4.04 (2H, s), 4.27 (2H, q, J=7.1 Hz), 6.91 (1H, d, J=15.2 Hz), 7.01 (1H, d, J=2.0 Hz), 7.71 (1H, d, J=15.2 Hz), 8.00 (1H, d, J=2.0 Hz)

Ethyl (2E)-3-(6-oxo-5,6-dihydro-1,5-naphthyridin-3-yl)acrylate $^1$H-NMR (DMSO-d$_6$) δ: 1.28 (3H, t, J=7.1 Hz), 4.22 (2H, q, J=7.1 Hz), 6.77 (1H, d, J=16.0 Hz), 6.78 (1H, d, J=9.5 Hz), 7.75 (1H, d, J=16.0 Hz), 7.80-7.84 (1H, m), 7.94 (1H, d, J=9.5 Hz), 8.82-8.87 (1H, m), 11.98 (1H, s)

Reference Example 72

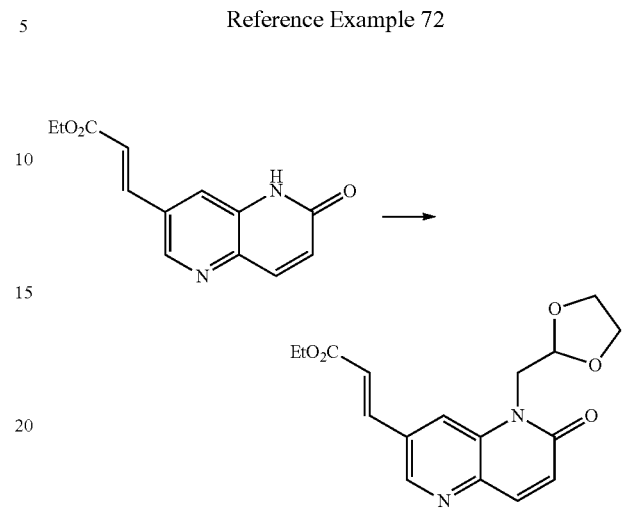

By the same technique as in Reference Example 3, ethyl (2E)-3-(5-(1,3-dioxolan-2-ylmethyl)-6-oxo-5,6-dihydro-1,5-naphthyridin-3-yl)acrylate was obtained from ethyl (2E)-3-(6-oxo-5,6-dihydro-1,5-naphthyridin-3-yl)acrylate and 2-bromomethyl-1,3-dioxolan.

$^1$H-NMR (CDCl$_3$) δ: 1.38 (3H, t, J=7.1 Hz), 3.84-3.93 (2H, m), 3.96-4.06 (2H, m), 4.32 (2H, q, J=7.1 Hz), 4.53 (2H, d, J=4.1 Hz), 5.20 (1H, t, J=4.1 Hz), 6.63 (1H, d, J=16.1 Hz), 6.96 (1H, d, J=9.8 Hz), 7.77 (1H, d, J=16.1 Hz), 7.91 (1H, d, J=9.8 Hz), 8.03-8.06 (1H, m), 8.68 (1H, d, J=1.7 Hz)

Reference Example 73

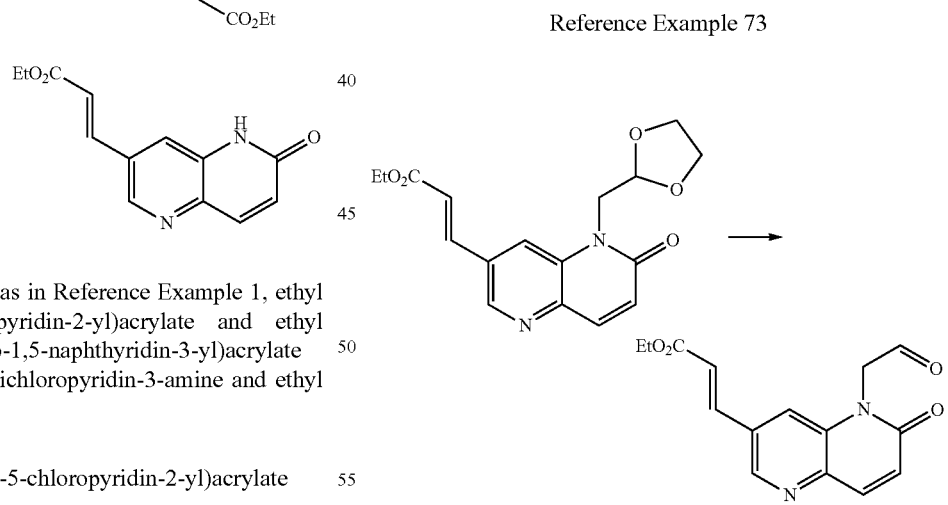

By the same technique as in Reference Example 4, ethyl (2E)-3-(6-oxo-5-(2-oxoethyl)-5,6-dihydro-1,5-naphthyridin-3-yl)acrylate was obtained from ethyl (2E)-3-(5-(1,3-dioxolan-2-ylmethyl)-6-oxo-5,6-dihydro-1,5-naphthyridin-3-yl)acrylate.

$^1$H-NMR (CDCl$_3$) δ: 1.36 (3H, t, J=7.2 Hz), 4.30 (2H, q, J=7.2 Hz), 5.19 (2H, s), 6.59 (1H, d, J=16.1 Hz), 7.00 (1H, d, J=9.8 Hz), 7.34-7.38 (1H, m), 7.71 (1H, d, J=16.1 Hz), 7.99 (1H, d, J=9.8 Hz), 8.72 (1H, d, J=1.5 Hz), 9.79 (1H, s)

Reference Example 74

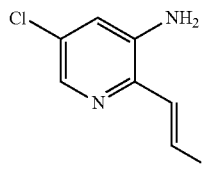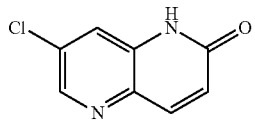

By the same technique as in Reference Example 2, 7-chloro-1,5-naphthyridin-2(1H)-one was obtained from ethyl (2E)-3-(3-amino-5-chloropyridin-2-yl)acrylate.

$^1$H-NMR (DMSO-d$_6$) δ: 6.77 (1H, d, J=9.8 Hz), 7.70-7.73 (1H, m), 7.94 (1H, d, J=9.8 Hz), 8.49 (1H, d, J=2.2 Hz), 11.95-12.05 (1H, broad)

Reference Example 75

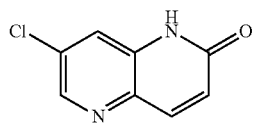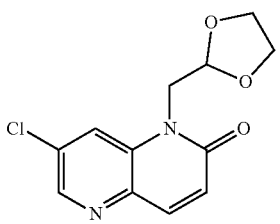

By the same technique as in Reference Example 3, 7-chloro-1-(1,3-dioxolan-2-ylmethyl)-1,5-naphthyridin-2(1H)-one was obtained from 7-chloro-1,5-naphthyridin-2(1H)-one and 2-bromomethyl-1,3-dioxolan.

$^1$H-NMR (CDCl$_3$) δ: 3.84-4.06 (4H, m), 4.46 (2H, d, J=4.2 Hz), 5.20 (1H, t, J=4.2 Hz), 6.92 (1H, d, J=9.8 Hz), 7.89 (1H, d, J=9.8 Hz), 7.96 (1H, d, J=2.0 Hz), 8.46 (1H, d, J=2.0 Hz)

Reference Example 76

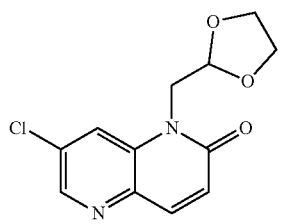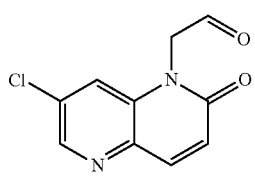

By the same technique as in Reference Example 4, (7-chloro-2-oxo-1,5-naphthyridin-1(2H)-yl)acetaldehyde was obtained from 7-chloro-1-(1,3-dioxolan-2-ylmethyl)-1,5-naphthyridin-2(1H)-one.

$^1$H-NMR (CDCl$_3$) δ: 5.13 (2H, s), 6.96 (1H, d, J=9.9 Hz), 7.31-7.33 (1H, m), 7.96 (1H, d, J=9.9 Hz), 8.51 (1H, d, J=2.0 Hz), 9.78 (1H, s)

Reference Example 77

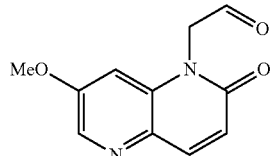

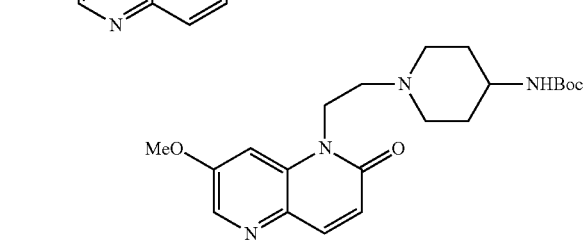

To a solution 0.16 g of (7-methoxy-2-oxo-1,5-naphthyridin-1(2H)-yl)acetaldehyde in 2 mL of dichloromethane, 0.14 g of tert-butyl (piperidin-4-yl)carbamate, 41 μL of acetic acid and 0.23 g of sodium triacetoxyborohydride were added, and the mixture was stirred at room temperature for 1 hour 30 minutes. The reaction mixture was charged with chloroform and a saturated aqueous sodium hydrogen carbonate solution and adjusted to pH 8.5, the organic layer was separated, and the aqueous layer was extracted with chloroform. The organic layer and the extract were combined, the resultant solution was washed sequentially with water and a saturated aqueous sodium chloride solution and dried over anhydrous magnesium sulfate, and the solvent was distilled off under reduced pressure. The resultant residue was purified by basic silica gel column chromatography using an eluent of chloroform:methanol=19:1 to obtain 0.23 g of tert-butyl (1-(2-(7-methoxy-2-oxo-1,5-naphthyridin-1(2H)-yl)ethyl)piperidin-4-yl)carbamate as a yellow oily substance.

$^1$H-NMR (CDCl$_3$) δ: 1.36-1.48 (2H, m), 1.45 (9H, s), 1.91-1.99 (2H, m), 2.22-2.31 (2H, m), 2.61-2.68 (2H, m), 2.90-2.97 (2H, m), 3.42-3.54 (1H, m), 3.98 (3H, s), 4.32-4.47 (3H, m), 6.74 (1H, d, J=9.8 Hz), 7.18 (1H, d, J=2.3 Hz), 7.84 (1H, d, J=9.8 Hz), 8.28 (1H, d, J=2.3 Hz)

Reference Example 78

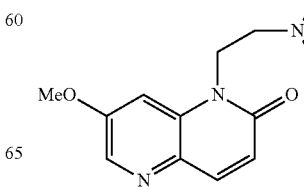

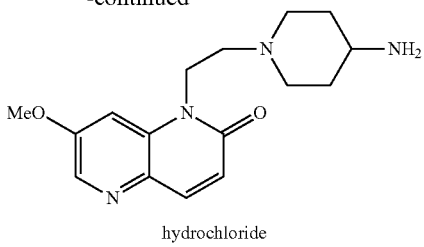

hydrochloride

To a solution of 0.23 g of tert-butyl (1-(2-(7-methoxy-2-oxo-1,5-naphthyridin-1(2H)-yl)ethyl)piperidin-4-yl)carbamate in 5 mL of ethanol, 5 mL of a 6.0 mol/L hydrogen chloride/ethanol solution was added at room temperature and the mixture was stirred for 1 hour. The solvent was distilled off under reduced pressure, diethyl ether was added to the resultant residue, and the solid was filtered off to obtain 0.22 g of 1-(2-(4-aminopiperidin-1-yl)ethyl)-7-methoxy-1,5-naphthyridin-2(1H)-one hydrochloride as a light yellow solid.

$^1$H-NMR (D$_2$O) δ: 1.93-2.07 (2H, m), 2.34-2.44 (2H, m), 3.20-3.33 (2H, m), 3.57-3.67 (3H, m), 3.90-4.01 (2H, m), 4.05 (3H, s), 4.73-4.85 (2H, m), 6.89 (1H, d, J=9.8 Hz), 7.50 (1H, d, J=2.3 Hz), 8.06 (1H, d, J=9.8 Hz), 8.42 (1H, d, J=2.3 Hz)

Reference Example 79

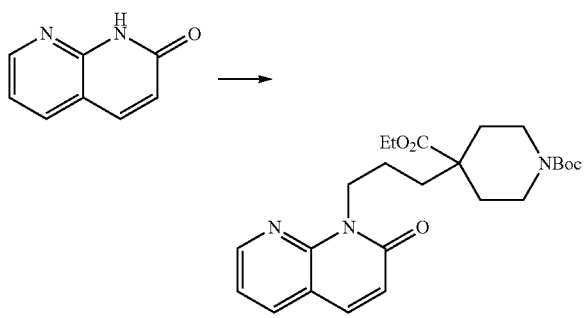

To a solution of 0.15 g of 1,8-naphthyridin-2(1H)-one in 2 mL of N,N-dimethylformamide, 45 mg of 60% sodium hydride was added, and the mixture was stirred at 50 to 65° C. for 1 hour. Thereto was added a solution of 0.44 g of 1-tert-butyl 4-ethyl 4-(3-((methylsulfonyl)oxy)propyl)piperidine-1,4-dicarboxylate in 1.2 mL of N,N-dimethylformamide, and the reaction mixture was stirred at 80 to 90° C. for 1 hour 30 minutes and cooled to room temperature, and water and ethyl acetate were then added thereto. The organic layer was separated, and the aqueous layer was extracted with ethyl acetate. The organic layer and the extract were combined, the resultant solution was washed with a saturated aqueous sodium chloride solution and dried over anhydrous magnesium sulfate, and the solvent was distilled off under reduced pressure. The resultant residue was purified by silica gel column chromatography using an eluent of hexane:ethyl acetate=3:2 to obtain 0.29 g of 1-tert-butyl 4-ethyl 4-(3-(2-oxo-1,8-naphthyridin-1(2H)-yl)propyl)piperidine-1,4-dicarboxylate as a colorless oily substance.

$^1$H-NMR (CDCl$_3$) δ: 1.22 (3H, t, J=7.1 Hz), 1.32-1.41 (2H, m), 1.44 (9H, s), 1.65-1.72 (4H, m), 2.05-2.11 (2H, m), 2.80-3.00 (2H, m), 3.75-4.00 (2H, m), 4.13 (2H, q, J=7.1 Hz), 4.43-4.48 (2H, m), 6.72 (1H, d, J=9.5 Hz), 7.18 (1H, dd, J=7.7, 4.7 Hz), 7.65 (1H, d, J=9.5 Hz), 7.88 (1H, dd, J=7.7, 1.8 Hz), 8.57 (1H, dd, J=4.7, 1.8 Hz)

Reference Example 80

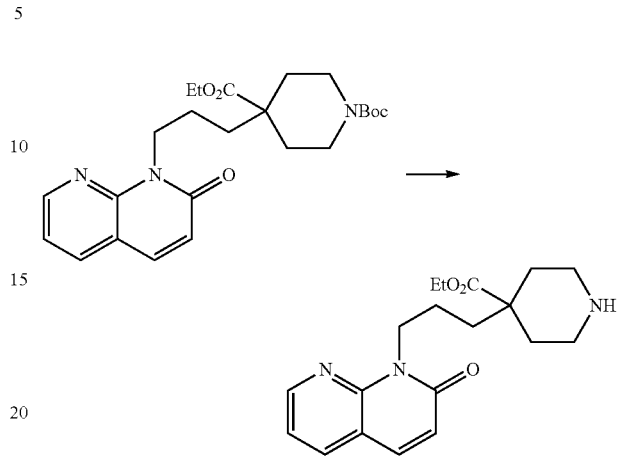

To a solution of 0.53 g of 1-tert-butyl 4-ethyl 4-(3-(2-oxo-1,8-naphthyridin-1(2H)-yl)propyl)piperidine-1,4-dicarboxylate in 6 mL of chloroform, 25 mL of trifluoroacetic acid was added, and the mixture was stirred at room temperature for 2 hours. The solvent was distilled off under reduced pressure, a saturated aqueous sodium hydrogen carbonate solution was added to the resultant residue and the mixture was neutralized, and chloroform was then added thereto. The organic layer was separated, and the aqueous layer was extracted with chloroform. The organic layer and the extract were combined, the resultant solution was washed with a saturated aqueous sodium chloride solution and dried over anhydrous magnesium sulfate, and the solvent was distilled off under reduced pressure to obtain 0.47 g of ethyl 4-(3-(2-oxo-1,8-naphthyridin-1(2H)-yl)propyl)piperidine-4-carboxylate as a colorless oily substance.

$^1$H-NMR (CDCl$_3$) δ: 1.22 (3H, t, J=7.1 Hz), 1.45-1.54 (2H, m), 1.64-1.71 (4H, m), 2.12-2.20 (2H, m), 2.67-2.78 (2H, m), 3.02-3.08 (2H, m), 4.14 (2H, q, J=7.1 Hz), 4.41-4.47 (3H, m), 6.73 (1H, d, J=9.5 Hz), 7.17 (1H, dd, J=7.6, 4.7 Hz), 7.64 (1H, d, J=9.5 Hz), 7.87 (1H, dd, J=7.6, 1.7 Hz), 8.57 (1H, dd, J=4.7, 1.7 Hz)

Reference Example 81

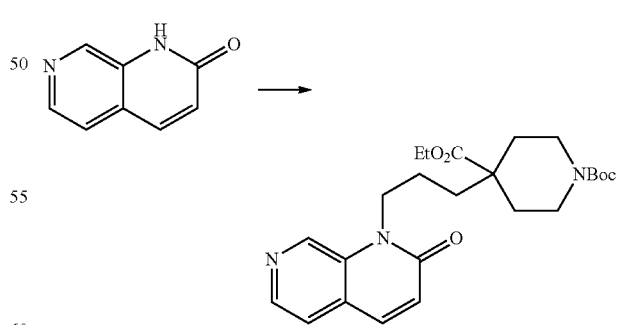

By the same technique as in Reference Example 79, 1-tert-butyl 4-ethyl 4-(3-(2-oxo-1,7-naphthyridin-1(2H)-yl)propyl)piperidine-1,4-dicarboxylate was obtained from 1,7-naphthyridin-2(1H)-one and 1-tert-butyl 4-ethyl 4-(3-((methanesulfonyl)oxy)propyl)piperidine-1,4-dicarboxylate.

¹H-NMR (CDCl₃) δ: 1.20-1.74 (9H, m), 1.44 (9H, s), 2.05-2.13 (2H, m), 2.74-2.95 (2H, m), 3.77-3.95 (2H, m), 4.14 (2H, q, J=7.1 Hz), 4.26-4.31 (2H, m), 6.89 (1H, d, J=9.5 Hz), 7.43 (1H, d, J=5.1 Hz), 7.65 (1H, d, J=9.5 Hz), 8.45 (1H, d, J=5.1 Hz), 8.74 (1H, s)

Reference Example 82

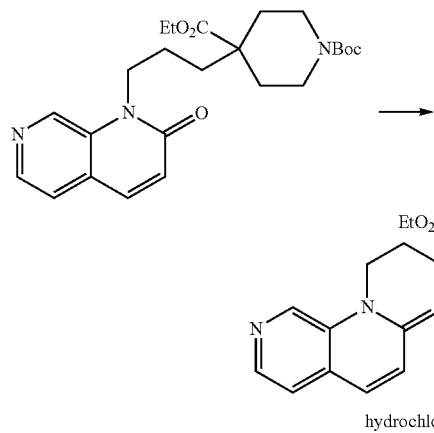

To a solution of 0.50 g of 1-tert-butyl 4-ethyl 4-(3-(2-oxo-1,7-naphthyridin-1(2H)-yl)propyl)piperidine-1,4-dicarboxylate in 3 mL of ethanol, 3.0 mL of a 4.0 mol/L hydrogen chloride/ethyl acetate solution was added, and the mixture was stirred at room temperature for 1 hour. Thereto was added 2.0 mL of a 4.0 mol/L hydrogen chloride/ethyl acetate solution, and the mixture was stirred at room temperature for 1 hour. The solid was filtered off to obtain 0.29 g of ethyl 4-(3-(2-oxo-1,7-naphthyridin-1(2H)-yl)propyl)piperidine-4-carboxylate hydrochloride as a light yellow solid.

¹H-NMR (DMSO-d₆) δ: 1.11 (3H, t, J=7.1 Hz), 1.48-1.58 (2H, m), 1.62-1.72 (4H, m), 2.03-2.11 (2H, m), 2.70-2.82 (2H, m), 3.14-3.25 (2H, m), 4.07 (2H, q, J=7.1 Hz), 4.24-4.30 (2H, m), 7.03 (1H, d, J=9.5 Hz), 8.02 (1H, d, J=5.4 Hz), 8.09 (1H, d, J=9.5 Hz), 8.54 (1H, d, J=5.4 Hz), 8.88-9.07 (2H, m), 9.17 (1H, s)

Reference Example 83

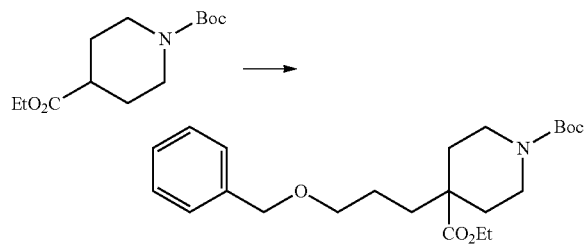

To a solution of 1.2 mL of diisopropylamine in 20 mL of tetrahydrofuran, 5.8 mL of a 1.6 mol/L butyryl lithium/hexane solution was dropped at −78° C., and the mixture was stirred at the same temperature for 1 hour. Thereto was dropped a solution of 2.0 g of 1-tert-butyl 4-ethyl piperidine-1,4-dicarboxylate in 2 mL of tetrahydrofuran, and the mixture was stirred for 1 hour. Thereto was added 1.7 mL of benzyl 3-bromopropyl ether, and the temperature of the reaction mixture was increased to room temperature and the mixture was stirred for 10 hours. The mixture was charged with water and adjusted to pH 2.0 with 6 mol/L hydrochloric acid. The organic layer was separated, and the aqueous layer was extracted with ethyl acetate. The organic layer and the extract were combined, the resultant solution was washed with a saturated aqueous sodium chloride solution, and dried over anhydrous magnesium sulfate, and the solvent was distilled off under reduced pressure. The resultant residue was purified by silica gel column chromatography using an eluent of hexane:ethyl acetate=10:1 to obtain 2.0 g of 1-tert-butyl 4-ethyl 4-(3-(benzyloxy)propyl)piperidine-1,4-dicarboxylate as a colorless oily substance.

¹H-NMR (CDCl₃) δ: 1.25 (3H, t, J=7.2 Hz), 1.25-1.45 (2H, m), 1.45 (9H, s), 1.50-1.65 (4H, m), 2.05-2.15 (2H, m), 2.75-3.00 (2H, m), 3.42 (2H, t, J=6.1 Hz), 3.75-3.95 (2H, m), 4.16 (2H, q, J=7.2 Hz), 4.47 (2H, s), 7.26-7.37 (5H, m)

Reference Example 84

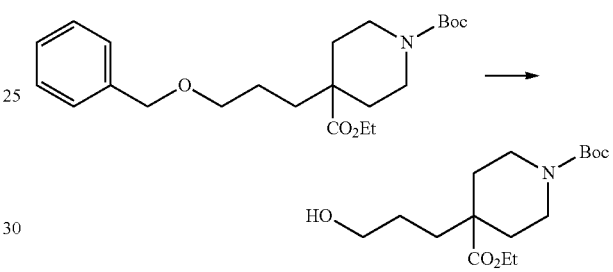

To a solution of 2.0 g of 1-tert-butyl 4-ethyl 4-(3-(benzyloxy)propyl)piperidine-1,4-dicarboxylate in 20 mL of ethanol, a suspension of 0.30 g of 10% palladium carbon in 2 mL of ethanol was added, and the mixture was stirred for 4 hours under a hydrogen atmosphere. The insoluble substance was filtered off, and the solvent was distilled off under reduced pressure to obtain 1.7 g of 1-tert-butyl 4-ethyl 4-(3-hydroxypropyl)piperidine-1,4-dicarboxylate as a colorless oily substance.

¹H-NMR (CDCl₃) δ: 1.27 (3H, t, J=7.2 Hz), 1.23-1.62 (6H, m), 1.45 (9H, s), 2.05-2.15 (2H, m), 2.80-2.95 (2H, m), 3.58-3.63 (2H, m), 3.75-3.95 (2H, m), 4.18 (2H, q, J=7.2 Hz)

Reference Example 85

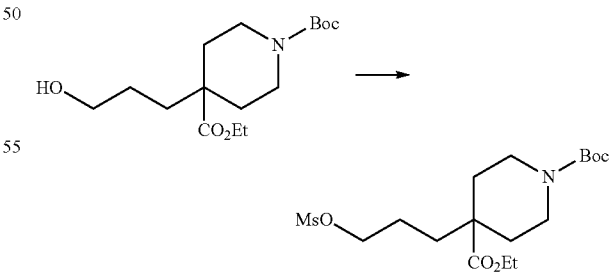

To a solution of 1.7 g of 1-tert-butyl 4-ethyl 4-(3-hydroxypropyl)piperidine-1,4-dicarboxylate in 20 mL of tetrahydrofuran, 0.82 mL of triethylamine and 0.58 mL of methanesulfonyl chloride were added at 5° C., and the mixture was stirred at room temperature for 1 hour. Thereto were added ethyl acetate and water.

The organic layer was separated and the aqueous layer was extracted with ethyl acetate. The organic layer and the extract were combined, the resultant solution was washed with a saturated aqueous sodium chloride solution and dried over anhydrous magnesium sulfate, and the solvent was distilled off under reduced pressure to obtain 1.9 g of 1-tert-butyl 4-ethyl 4-(3-((methanesulfonyl)oxy)propyl)piperidine-1,4-dicarboxylate as a colorless oily substance.

$^1$H-NMR (CDCl$_3$) δ: 1.25-1.75 (6H, m), 1.28 (3H, t, J=7.2 Hz), 1.45 (9H, s), 2.05-2.15 (2H, m), 2.80-2.95 (2H, m), 3.00 (3H, s), 3.80-3.95 (2H, m), 4.19 (2H, q, J=7.2 Hz), 4.15-4.22 (2H, m)

Reference Example 86

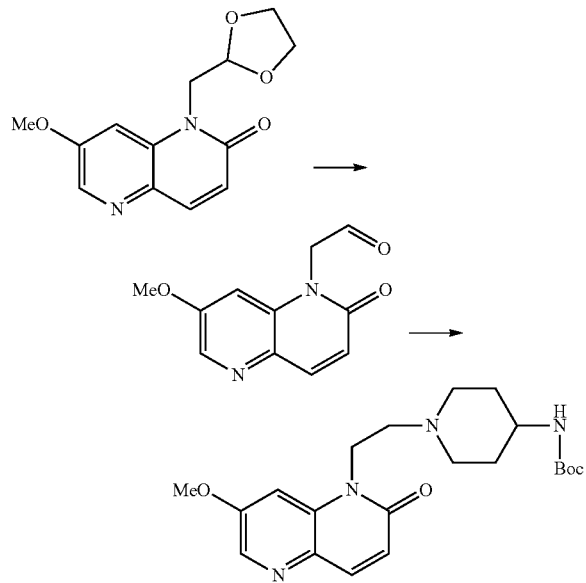

To 184 mL of 80% trifluoroacetic acid, 4.60 g of 1-(1,3-dioxolan-2-ylmethyl)-7-methoxy-1,5-naphthyridin-2(1H)-one was dissolved, and the resultant solution was stirred at room temperature for 11 hours and at 60° C. for 3.5 hours. The reaction mixture was charged with chloroform and alkalified with a 10% aqueous sodium hydroxide solution under cooling with ice. The organic layer was separated, and washed with an aqueous sodium chloride solution and dried over anhydrous magnesium sulfate, and the solvent was distilled off under reduced pressure to obtain (7-methoxy-2-oxo-1,5-naphthyridin-1(2H)-yl)acetaldehyde as a yellow solid.

To 58 mL of chloroform, the obtained (7-methoxy-2-oxo-1,5-naphthyridin-1(2H)-yl)acetaldehyde was dissolved, 2.67 g of tert-butyl (piperidin-4-yl)carbamate and 0.80 g of acetic acid were added, and the mixture was stirred at room temperature for 1.5 hours. To the reaction mixture, 4.23 g of sodium triacetoxyborohydride was added, and the mixture was stirred for 15 hours. Thereto was added a saturated aqueous sodium hydrogen carbonate solution, and the organic layer was separated. The organic layer was washed with a saturated aqueous sodium chloride solution and dried over anhydrous magnesium sulfate, and the solvent was distilled off under reduced pressure. The resultant residue was purified by silica gel column chromatography using silica gel; Silica Gel 60N made by KANTO CHEMICAL CO., INC. and an eluent of chloroform:methanol=10:1 to obtain 4.36 g of tert-butyl (1-(2-(7-methoxy-2-oxo-1,5-naphthyridin-1(2H)-yl)ethyl)piperidin-4-yl)carbamate as a white solid.

$^1$H-NMR (CDCl$_3$) δ: 1.38-1.44 (2H, m), 1.45 (9H, s), 1.90-2.00 (2H, m), 2.21-2.30 (2H, m), 2.59-2.70 (2H, m), 2.87-2.99 (2H, m), 3.43-3.54 (1H, m), 3.98 (3H, s), 4.29-4.38 (2H, m), 4.40-4.49 (1H, m), 6.74 (1H, d, J=9.6 Hz), 7.16-7.19 (1H, m), 7.84 (1H, d, J=9.6 Hz), 8.28 (1H, d, J=2.3 Hz)

Reference Example 87

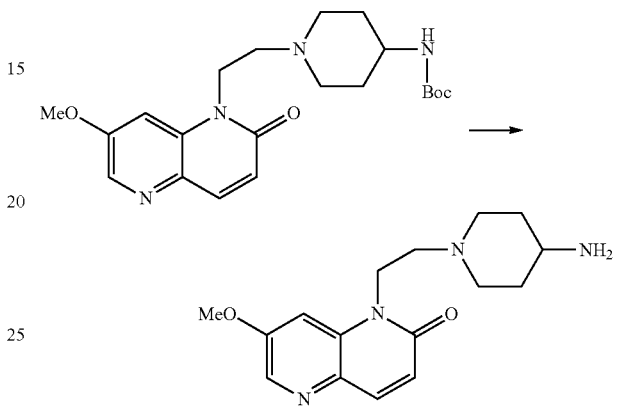

To a solution of 4.36 g of tert-butyl (1-(2-(7-methoxy-2-oxo-1,5-naphthyridin-1(2H)-yl)ethyl)piperidin-4-yl)carbamate in 50 mL of chloroform, 10 mL of trifluoroacetic acid was added, and the mixture was stirred at room temperature for 1 hour. After the solvent was distilled off under reduced pressure, the reaction mixture was alkalified with a saturated aqueous sodium hydrogen carbonate solution, the solvent was then distilled off under reduced pressure, and the resultant residue was purified by silica gel column chromatography using silica gel; Chromatorex-NH made by Fuji Silysia Chemical Ltd., and an eluent of chloroform:methanol=10:1 to obtain 2.16 g of 1-(2-(4-aminopiperidin-1-yl)ethyl)-7-methoxy-1,5-naphthyridin-2(1H)-one as a yellow oily substance.

$^1$H-NMR (CDCl$_3$) δ: 1.39 (4H, m), 1.81-1.86 (2H, m), 2.17-2.24 (2H, m), 2.63-2.73 (3H, m), 2.95-3.00 (2H, m), 3.98 (3H, s), 4.34-4.39 (2H, m), 6.75 (1H, d, J=9.6 Hz), 7.23 (1H, d, J=2.3 Hz), 7.84 (1H, d, J=9.6 Hz), 8.28 (1H, d, J=2.3 Hz)

Reference Example 88

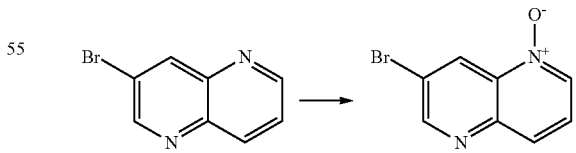

To 50 mL of chloroform, 5.00 g of 3-bromo-1,5-naphthyridin was dissolved, 6.40 g of m-chloroperbenzoic acid was added thereto, and the mixture was stirred at room temperature for 1.5 hours. To the reaction mixture, a 5% aqueous sodium thiosulfate solution and chloroform were added, and the organic layer was separated, washed sequentially with a 5% aqueous sodium hydroxide solution and a saturated aqueous sodium chloride solution and dried over anhydrous magnesium sulfate, and the solvent was distilled off under reduced pressure. The resultant residue was purified by silica gel column chromatography using silica gel; Chromatorex-NH made by Fuji Silysia Chemical Ltd., and an eluent of ethyl acetate:hexane=1:1 to obtain 1.95 g of 3-bromo-1,5-naphthyridin-5-oxide as a light yellow solid.

$^1$H-NMR (CDCl$_3$) δ: 7.55 (1H, dd, J=8.7, 6.0 Hz), 7.99 (1H, d, J=8.7 Hz), 8.55 (1H, d, J=6.0 Hz), 9.04 (1H, d, J=2.3 Hz), 9.23 (1H, d, J=2.3 Hz)

Reference Example 89

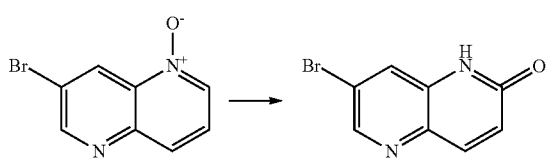

To a solution of 0.50 g of 3-bromo-1,5-naphthyridin-5-oxide in 10 mL of chloroform, 0.51 g of p-toluenesulfonyl chloride, 1.04 g of potassium carbonate and 3 mL of water were added, and the mixture was stirred at room temperature overnight. Thereto were added water and chloroform, and the solid was filtered off to obtain 0.39 g of 7-bromo-1,5-naphthyridin-2(1H)-one as a white solid.

$^1$H-NMR (DMSO-d$_6$) δ: 6.77 (1H, d, J=9.6 Hz), 7.85-7.87 (1H, m), 7.90 (1H, d, J=9.6 Hz), 8.53 (1H, d, J=1.8 Hz), 11.69-12.50 (1H, m)

Reference Example 90

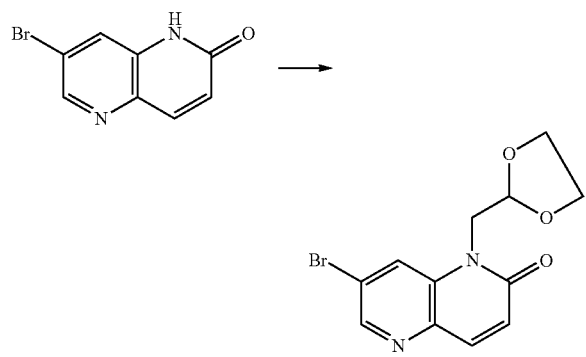

To 5 mL of N,N-dimethylformamide, 770 mg of 7-bromo-1,5-naphthyridin-2(1H)-one was dissolved, 278 mg of 60% sodium hydride was added, and the mixture was stirred at room temperature for 1 hour. Thereto was added 1.1 mL of 2-bromomethyl-1,3-dioxolan at 110° C. for 4 days. The reaction mixture was cooled to room temperature, and then ethyl acetate and 1 mol/L hydrochloric acid were added. The organic layer was separated, washed sequentially with water and a saturated aqueous sodium chloride solution and dried over anhydrous magnesium sulfate, and the solvent was distilled off under reduced pressure. The resultant residue was purified by silica gel column chromatography using silica gel; Silica Gel 60 made by KANTO CHEMICAL CO., INC., and an eluent of ethyl acetate:hexane 2:1 to obtain 467 mg of 7-bromo-1-(1,3-dioxolan-2-ylmethyl)-1,5-naphthyridin-2(1H)-one as a light yellow solid.

$^1$H-NMR (CDCl$_3$) δ: 3.87-3.91 (2H, m), 4.00-4.03 (2H, m), 4.46 (2H, d, J=4.1 Hz), 5.20 (1H, t, J=4.1 Hz), 6.94 (1H, d, J=9.6 Hz), 7.86-7.89 (1H, m), 8.11 (1H, d, J=1.8 Hz), 8.56 (1H, d, J=1.8 Hz)

Reference Example 91

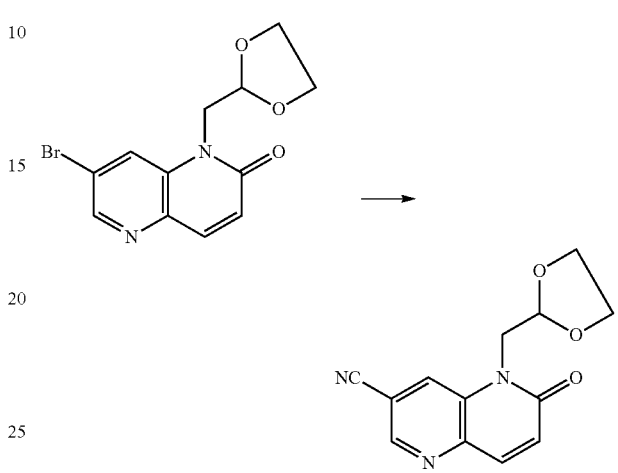

To 10 mL of 1-methyl-2-pyrrolidinone, 358 mg of 7-bromo-1-(1,3-dioxolan-2-ylmethyl)-1,5-naphthyridin-2(1H)-one and 183 mg of copper cyanide were suspended, and the suspension was heated under reflux for 70 minutes. The reaction mixture was cooled to room temperature, ethyl acetate was then added thereto, the mixture was washed sequentially with water and a saturated saline water and dried over anhydrous magnesium sulfate, and the solvent was distilled off under reduced pressure. The resultant residue was purified by silica gel column chromatography using silica gel; Silica Gel 60 made by KANTO CHEMICAL CO., INC., and an eluent of ethyl acetate:hexane 1:1 to obtain 145 mg of 7-cyano-1-(1,3-dioxolan-2-ylmethyl)-1,5-naphthyridin-2(1H)-one as a yellow solid.

$^1$H-NMR (CDCl$_3$) δ: 3.87-3.90 (2H, m), 3.98-4.02 (2H, m), 4.49 (2H, d, J=4.1 Hz), 5.17 (1H, t, J=4.1 Hz), 7.06 (1H, d, J=9.6 Hz), 7.95 (1H, d, J=9.6 Hz), 8.23-8.24 (1H, m), 8.72 (1H, d, J=1.8 Hz)

Reference Example 92

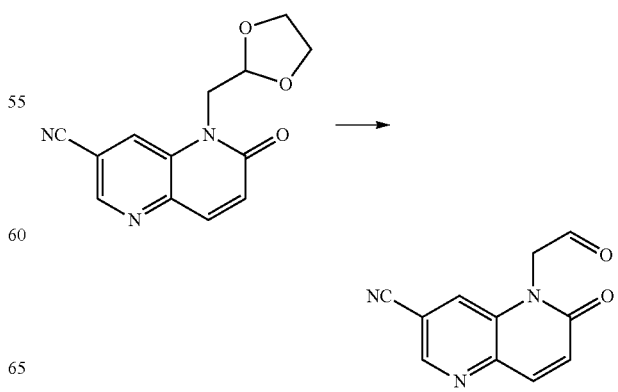

To 5 mL of 90% trifluoroacetic acid, 215 mg of 7-cyano-1-(1,3-dioxolan-2-ylmethyl)-1,5-naphthyridin-2(1H)-one was dissolved, and the resultant solution was stirred at 60° C. for 7 hours. After the reaction mixture was cooled to room temperature and alkalified with a 10% aqueous sodium hydroxide solution, the solvent was then distilled off under reduced pressure. The resultant residue was purified by silica gel column chromatography using silica gel; Silica Gel 60 made by KANTO CHEMICAL CO., INC., and an eluent of ethyl acetate:hexane=1:1, and washed with water to obtain 90 mg of (7-cyano-2-oxo-1,5-naphthyridin-1(2H)-yl)acetaldehyde as a light yellow solid.

$^1$H-NMR (CDCl$_3$) δ: 5.19 (2H, s), 7.09-7.11 (1H, m), 7.52-7.53 (1H, m), 8.02 (1H, d, J=9.6 Hz), 8.76 (1H, d, J=1.4 Hz), 9.83 (1H, s)

Reference Example 93

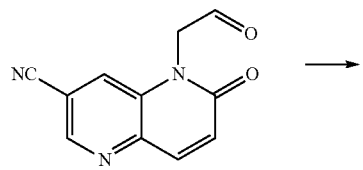

To a solution of 83 mg of (7-cyano-2-oxo-1,5-naphthyridin-1(2H)-yl)acetaldehyde and 80 mg of tert-butyl piperidin-4-yl-carbamate in 10 mL of chloroform, 24 μL of acetic acid was added, and the mixture was stirred at room temperature for 1.5 hours. To the reaction mixture, 136 mg of sodium triacetoxyborohydride was added, and the mixture was stirred for 1.5 hours. A saturated aqueous sodium hydrogen carbonate solution was added to the reaction mixture, and the solvent was distilled off under reduced pressure. The resultant residue was purified by silica gel column chromatography using silica gel; Chromatorex-NH made by Fuji Silysia Chemical Ltd., and an eluent of ethyl acetate:hexane=1:1 to obtain 76 mg of tert-butyl (1-(2-(7-cyano-2-oxo-1,5-naphthyridin-1(2H)-yl)ethyl)piperidin-4-yl)carbamate as a brown solid.

$^1$H-NMR (CDCl$_3$) δ: 1.33-1.39 (2H, m), 1.44 (9H, s), 1.92-1.97 (2H, m), 2.22-2.28 (2H, m), 2.64-2.68 (2H, m), 2.85-2.90 (2H, m), 3.46-3.51 (1H, m), 4.30-4.35 (2H, m), 4.41-4.45 (1H, m), 7.05 (1H, d, J=9.6 Hz), 7.94 (1H, d, J=9.6 Hz), 8.12-8.15 (1H, m), 8.72 (1H, d, J=1.4 Hz)

Reference Example 94

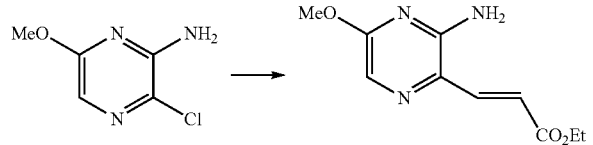 [SMILES: COc1cnc(Cl)c(N)n1 ; CCOC(=O)/C=C/c1ncc(OC)nc1N]

To a solution of 3.15 g of 3-chloro-6-methoxypyrazin-2-amine in 20 mL of triethylamine, 2.6 mL of ethyl acrylate and 0.50 g of bis(tri-tert-butylphosphine)palladium(0) were added, and the mixture was stirred at an external temperature of 120 to 130° C. for 2 hours in a sealed tube. Thereto was further added 5 mL of triethylamine, and the mixture was stirred at the same temperature for 4 hours 50 minutes. The reaction mixture was cooled to room temperature and left overnight, then 0.5 mL of ethyl acrylate and 0.25 g of bis(tri-tert-butylphosphine)palladium(0) were added thereto and the mixture was stirred at an external temperature of 115 to 125° C. for 9 hours 20 minutes in a sealed tube. The reaction mixture was cooled to room temperature, water and ethyl acetate were then added thereto, the organic layer was separated and the aqueous layer was extracted with ethyl acetate. The organic layer and the extract were combined, the resultant solution was washed with a saturated aqueous sodium chloride solution and dried over anhydrous magnesium sulfate, and the solvent was distilled off under reduced pressure. The resultant residue was purified by silica gel column chromatography using an eluent of hexane:ethyl acetate=4:1 to obtain 2.55 g of ethyl (2E)-3-(3-amino-5-methoxypyrazin-2-yl)acrylate as a yellow solid.

$^1$H-NMR (CDCl$_3$) δ: 1.32 (3H, t, J=7.1 Hz), 3.91 (3H, s), 4.26 (2H, q, J=7.1 Hz), 4.72 (2H, s), 6.73 (1H, d, J=15.1 Hz), 7.61-7.68 (2H, m)

Reference Example 95

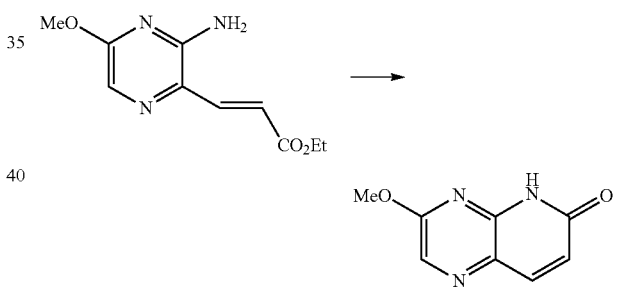

To a solution of 0.85 g of ethyl (2E)-3-(3-amino-5-methoxypyrazin-2-yl)acrylate in 40 mL of ethanol, 2.20 g of a 28% sodium methoxide/methanol solution was added, and the mixture was heated under reflux while stirring for 7 hours 30 minutes. The reaction mixture was cooled to room temperature, the solvent was then distilled off under reduced pressure, and to the resultant residue, water, a saturated aqueous ammonium chloride solution and chloroform were added, the organic layer was separated, and the aqueous layer was added with sodium chloride and extracted with chloroform. The organic layer and the extract were combined, the resultant solution was washed with a saturated aqueous sodium chloride solution and dried over anhydrous magnesium sulfate, and the solvent was distilled off under reduced pressure. Diethyl ether was added to the resultant residue, and the solid was filtered off and washed with diethyl ether to obtain 0.64 g of 3-methoxypyrido(2,3-b)pyrazin-6(5H)-one as a light yellow solid.

$^1$H-NMR (CDCl$_3$) δ: 4.06 (3H, s), 6.72 (1H, d, J=9.8 Hz), 7.92 (1H, d, J=9.8 Hz), 8.13 (1H, s), 9.68 (1H, s)

Reference Example 96

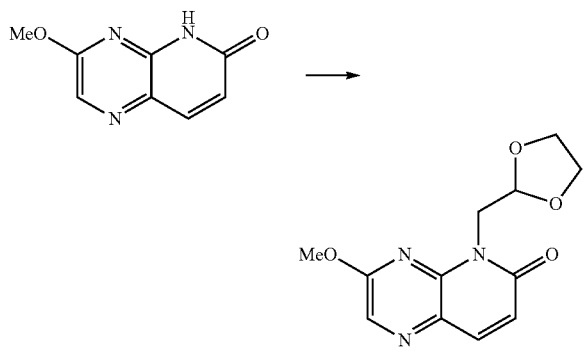

To a solution of 0.30 g of 3-methoxypyrido(2,3-b)pyrazin-6(5H)-one in 6 mL of N,N-dimethylformamide, 0.35 g of potassium carbonate was added, and the mixture was stirred at 65 to 75° C. for 10 minutes. Thereto was added 0.21 mL of 2-bromomethyl-1,3-dioxolan, and the mixture was stirred at 95 to 100° C. for 1 hour 30 minutes. Thereto were further added 0.05 mL of 2-bromomethyl-1,3-dioxolan and 120 mg of potassium carbonate, and the mixture was stirred at 95 to 100° C. for 2 hours 15 minutes. The reaction mixture was cooled to room temperature, and water and ethyl acetate were then added thereto, the organic layer was separated, and the aqueous layer was extracted with ethyl acetate. The organic layer and the extract were combined, and the resultant solution was washed with a saturated aqueous sodium chloride solution and dried over anhydrous magnesium sulfate, and the solvent was distilled off under reduced pressure. The resultant residue was purified by silica gel column chromatography using an eluent of hexane:ethyl acetate=2:1 to obtain 0.13 g of 5-(1,3-dioxolan-2-ylmethyl)-3-methoxypyrido(2,3-b)pyrazin-6(5H)-one as a yellow solid.

$^1$H-NMR (CDCl$_3$) δ: 3.88-3.92 (2H, m), 4.06-4.12 (5H, m), 4.63 (2H, d, J=5.1 Hz), 5.51 (1H, t, J=5.1 Hz), 6.78 (1H, d, J=9.8 Hz), 7.85 (1H, d, J=9.8 Hz), 8.12 (1H, s)

Reference Example 97

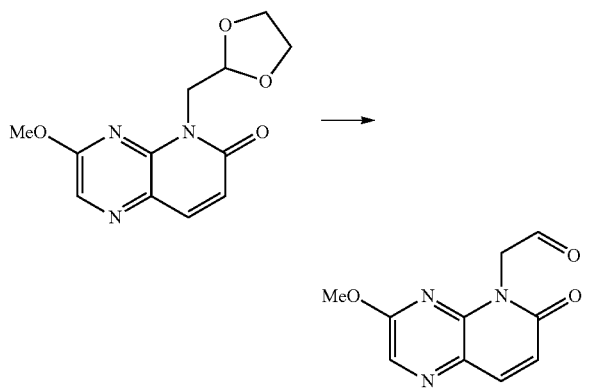

To 0.12 g of 5-(1,3-dioxolan-2-ylmethyl)-3-methoxypyrido(2,3-b)pyrazin-6(5H)-one, 5 mL of a 90% aqueous trifluoroacetic acid solution was added, and the mixture was stirred at room temperature for 3 hours 30 minutes. A saturated aqueous sodium hydrogen carbonate solution and chloroform were added to the reaction mixture, the organic layer was separated and the aqueous layer was extracted with chloroform. The organic layer and the extract were combined, the resultant solution was washed with a saturated aqueous sodium chloride solution and dried over anhydrous magnesium sulfate, and the solvent was distilled off under reduced pressure to obtain 0.12 g of (3-methoxy-6-oxopyrido(2,3-b)pyrazin-5(6H)-yl)acetaldehyde as a light yellow solid.

$^1$H-NMR (CDCl$_3$) δ: 3.99 (3H, s), 5.24 (2H, s), 6.82 (1H, d, J=9.8 Hz), 7.94 (1H, d, J=9.8 Hz), 8.15 (1H, s), 9.71 (1H, s)

Reference Example 98

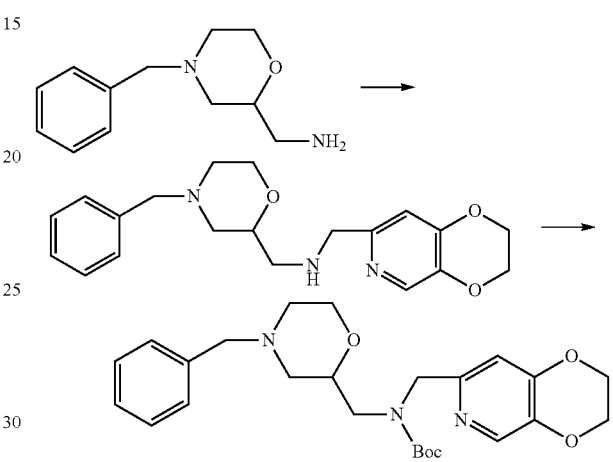

By the same technique as in Reference Example 60, 1-(4-benzylmorpholin-2-yl)-N-(2,3-dihydro(1,4)dioxino(2,3-c)pyridin-7-ylmethyl)methanamine was obtained from 1-(4-benzylmorpholin-2-yl)methanamine and 2,3-dihydro(1,4)dioxino(2,3-c)pyridine-7-carbaldehyde.

By the same technique as in Reference Example 61, tert-butyl ((4-benzylmorpholin-2-yl)methyl)(2,3-dihydro(1,4)dioxino(2,3-c)pyridin-7-ylmethyl)carbamate was obtained from 1-(4-benzylmorpholin-2-yl)-N-(2,3-dihydro(1,4)dioxino(2,3-c)pyridin-7-ylmethyl)methanamine.

$^1$H-NMR (CDCl$_3$) δ: 1.34-1.49 (9H, m), 1.81-1.93 (1H, m), 2.09-2.18 (1H, m), 2.56-2.66 (1H, m), 2.70-2.77 (1H, m), 3.20-3.85 (7H, m), 4.23-4.35 (4H, m), 4.37-4.64 (2H, m), 6.68-6.74 (1H, m), 7.20-7.36 (5H, m), 8.07 (1H, s)

Reference Example 99

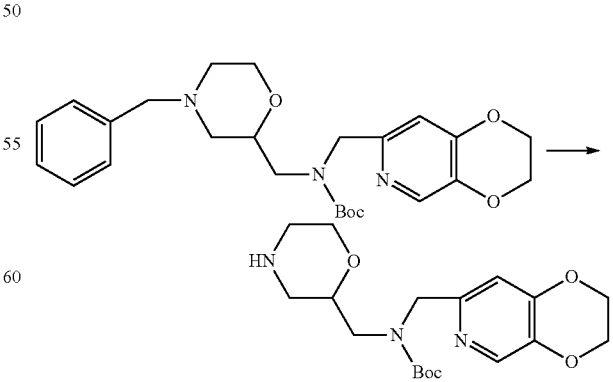

By the same technique as in Reference Example 25, tert-butyl (2,3-dihydro(1,4)dioxino(2,3-c)pyridin-7-ylmethyl)

(morpholin-2-ylmethyl)carbamate was obtained from tert-butyl ((4-benzylmorpholin-2-yl)methyl)(2,3-dihydro(1,4)dioxino(2,3-c)pyridin-7-ylmethyl)carbamate.

$^1$H-NMR (CDCl$_3$) δ: 1.35-1.57 (9H, m), 2.75-3.10 (2H, m), 3.25-3.56 (4H, m), 3.93-4.19 (3H, m), 4.25-4.44 (4H, m), 4.46-4.67 (2H, m), 6.70-6.92 (1H, m), 8.10-8.19 (1H, m), 9.80-10.4 (1H, broad)

Reference Example 100

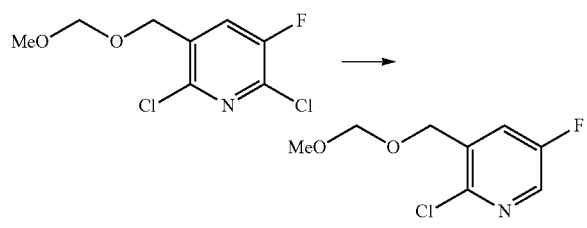

To a solution of 0.62 g of 2,6-dichloro-3-fluoro-5-((methoxymethoxy)methyl)pyridine in 18 mL of N,N-dimethylformamide, 0.54 mL of triethylamine, 0.15 mL of formic acid and 0.15 g of tetrakis(triphenylphosphine)palladium(0) were added, and the mixture was stirred at 90 to 100° C. for 4 hours 30 minutes under a nitrogen atmosphere. Thereto were added water and ethyl acetate, the insoluble substance was filtered off, the organic layer was separated, and the aqueous layer was extracted with ethyl acetate. The organic layer and the extract were combined, the resultant solution was washed sequentially with water and a saturated aqueous sodium chloride solution and dried over anhydrous magnesium sulfate, and the solvent was distilled off under reduced pressure. The resultant residue was purified by silica gel column chromatography using an eluent of hexane:ethyl acetate=8:1 to obtain 0.39 g of 2-chloro-5-fluoro-3-((methoxymethoxy)methyl)pyridine as a colorless oily substance.

$^1$H-NMR (CDCl$_3$) δ: 3.43 (3H, s), 4.65 (2H, d, J=0.8 Hz), 4.80 (2H, s), 7.66 (1H, dd, J=8.4, 3.0 Hz), 8.18 (1H, d, J=3.0 Hz)

Reference Example 101

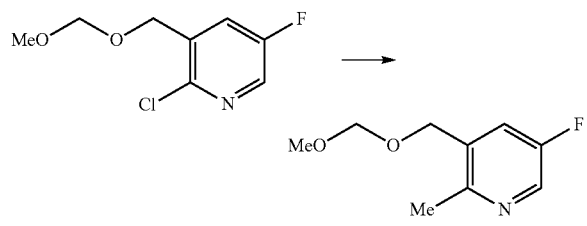

To a solution of 0.10 g of 2-chloro-5-fluoro-3-((methoxymethoxy)methyl)pyridine in 3 mL of dioxane, 0.20 g of potassium carbonate, 68 μL of trimethylboroxin and 56 mg of tetrakis(triphenylphosphine)palladium(0) were added, and the mixture was heated under reflux while stirring for 2 hours under a nitrogen atmosphere. Thereto were added 0.20 g of potassium carbonate, 68 μL of trimethylboroxin and 56 mg of tetrakis(triphenylphosphine)palladium(0), and the mixture was heated under reflux while stirring for 2 hours under a nitrogen atmosphere. Thereto were added 0.20 g of potassium carbonate, 68 μL of trimethylboroxin and 56 mg of tetrakis(triphenylphosphine)palladium(0), and the mixture was heated under reflux while stirring for 1 hour under a nitrogen atmosphere. The insoluble substance was filtered off, and the solvent was distilled off under reduced pressure. The resultant residue was purified by silica gel column chromatography using an eluent of chloroform:methanol=100:1 to obtain 93 mg of a colorless oily substance. The substance was purified by basic silica gel column chromatography using an eluent of chloroform to obtain 64 mg of 5-fluoro-3-((methoxymethoxy)methyl)-2-methylpyridine as a colorless oily substance.

$^1$H-NMR (CDCl$_3$) δ: 2.49 (3H, s), 3.42 (3H, s), 4.58 (2H, s), 4.76 (2H, s), 7.47 (1H, dd, J=9.2, 2.7 Hz), 8.27 (1H, d, J=2.7 Hz)

Reference Example 102

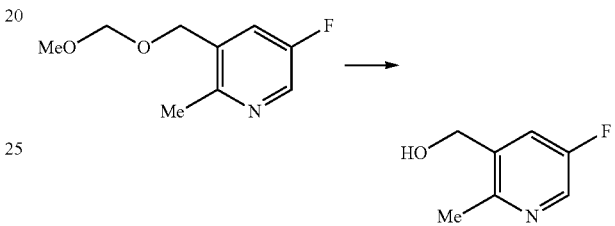

To a solution of 0.49 g of 5-fluoro-3-((methoxymethoxy)methyl)-2-methylpyridine in 20 mL of dioxane, 10 mL of 6.0 mol/L hydrochloric acid was added, and the mixture was stirred at 30 to 40° C. for 1 hour. Thereto were added water and ethyl acetate, and the mixture was adjusted to pH 5.5 with a 20% aqueous sodium hydroxide solution and a saturated aqueous sodium hydrogen carbonate solution. The organic layer was separated, and the aqueous layer was extracted with ethyl acetate twice. The organic layer and the extract were combined, the resultant solution was washed with water and a saturated aqueous sodium chloride solution and dried over anhydrous magnesium sulfate, and the solvent was distilled off under reduced pressure to obtain 0.41 g of (5-fluoro-2-methylpyridin-3-yl)methanol as a light yellow oily substance.

$^1$H-NMR (CDCl$_3$) δ: 2.40 (1H, t, J=5.2 Hz), 2.46 (3H, s), 4.72 (2H, d, J=5.2 Hz), 7.53 (1H, dd, J=9.1, 2.6 Hz), 8.24 (1H, d, J=2.6 Hz)

Reference Example 103

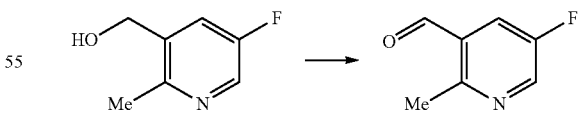

To a solution of 32 mg of (5-fluoro-2-methylpyridin-3-yl)methanol in 2 mL of dichloromethane, 80 mg of molecular sieves 3 A and 40 mg of 4-methylmorpholine N-oxide were added, and the mixture was stirred at room temperature for 30 minutes. Thereto was added 6.0 mg of tetrapropyl ammonium perruthenate, and the mixture was stirred at room temperature for 1 hour 30 minutes. The insoluble substance was filtered off, and the solvent was distilled off under reduced pressure. The resultant residue was purified by silica gel column chromatography using an eluent of chloroform:methanol=100:1 to obtain 20 mg of 5-fluoro-2-methylnicotinaldehyde as a colorless oily substance.

$^1$H-NMR (CDCl$_3$) δ: 2.87 (3H, d, J=1.0 Hz), 7.81 (1H, dd, J=8.0, 3.0 Hz), 8.56 (1H, d, J=3.0 Hz), 10.33 (1H, d, J=2.2 Hz)

Reference Example 104

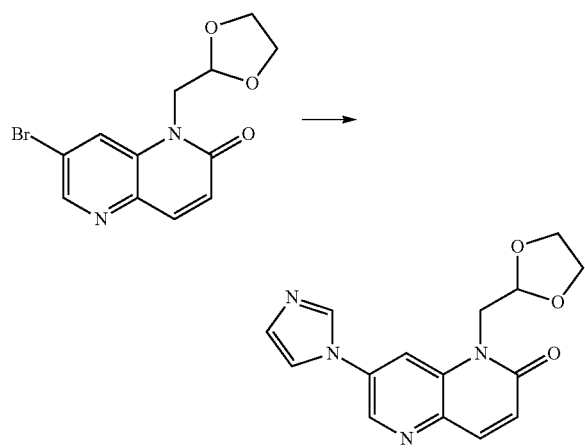

To a suspension of 77 mg of sodium hydride in 2 mL of N,N-dimethylformamide, 0.13 g of imidazole was added, and the mixture was stirred at room temperature for 10 minutes. To the reaction mixture, 0.20 g of 7-bromo-1-((1,3-dioxolan-2-yl)methyl)-1,5-naphthyridin-2(1H)-one was added dividedly, and then 18 mg of copper (II) oxide was added thereto. The reaction mixture was stirred at 135 to 140° C. for 30 minutes. The reaction mixture was cooled to room temperature, then chloroform and water were added thereto, the organic layer was separated, and the aqueous layer was extracted with chloroform. The organic layer and the extract were combined, the resultant solution was dried over anhydrous magnesium sulfate, and the solvent was distilled off under reduced pressure. To the resultant residue, a mixed solvent of diethyl ether: ethyl acetate (3:1) was added, and the solid was filtered off to obtain 0.12 g of 1-((1,3-dioxolan-2-yl)methyl)-7-(1H-imidazol-1-yl)-1,5-naphthyridin-2(1H)-one as a yellow solid.

$^1$H-NMR (CDCl$_3$) δ: 3.86-4.20 (4H, m), 4.55 (2H, d, J=4.0 Hz), 5.18 (1H, t, J=4.0 Hz), 6.97 (1H, d, J=9.9 Hz), 7.32 (1H, s), 7.40 (1H, s), 7.95 (1H, d, J=9.9 Hz), 7.98 (1H, s), 8.01 (1H, d, J=2.1 Hz), 8.65 (1H, d, J=2.1 Hz)

Reference Example 105

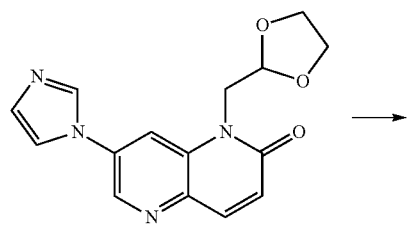

To 0.12 g of 1-((1,3-dioxolan-2-yl)methyl)-7-(1H-imidazol-1-yl)-1,5-naphthyridin-2(1H)-one, 2 mL of an 80% aqueous trifluoroacetic acid solution was added at room temperature, and the mixture was stirred at 50 to 60° C. for 1 hour 30 minutes. The reaction mixture was cooled to room temperature, and the solvent was then distilled off under reduced pressure. The resultant residue was charged with chloroform and water and adjusted to pH 7.8 with a 20% aqueous sodium hydroxide solution. The organic layer was separated and the aqueous layer was extracted with chloroform, and then further extracted with ethyl acetate. The organic layer and the extract were combined, the resultant solution was dried over anhydrous magnesium sulfate, and the solvent was distilled off under reduced pressure to obtain 0.12 g of (7-(1H-imidazol-1-yl)-2-oxo-1,5-naphthyridin-1(2H)-yl)acetaldehyde as a yellow solid.

$^1$H-NMR (DMSO-d$_6$) δ: 5.35 (2H, s), 6.92 (1H, d, J=9.8 Hz), 7.20 (1H, s), 7.22 (1H, s), 8.00 (1H, s), 8.05 (1H, d, J=9.8 Hz), 8.12 (1H, d, J=2.2 Hz), 8.96 (1H, d, J=2.2 Hz), 9.70 (1H, s)

Reference Example 106

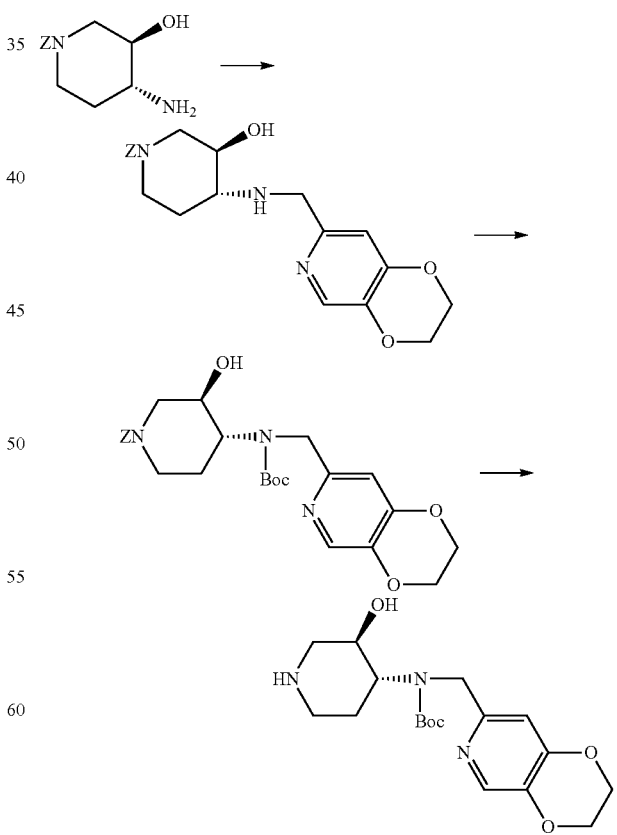

By the same technique as in Reference Example 60, benzyl (3R,4R)-4-((2,3-dihydro(1,4)dioxino(2,3-c)pyridin-7-ylmethyl)amino)-3-hydroxypiperidine-1-carboxylate was obtained from benzyl (3R,4R)-4-amino-3-hydroxypiperidine-1-carboxylate and 2,3-dihydro(1,4)dioxino(2,3-c)pyridine-7-carbaldehyde.

By the same technique as in Reference Example 61, benzyl (3R,4R)-4-((tert-butoxycarbonyl)(2,3-dihydro(1,4)dioxino(2,3-c)pyridin-7-ylmethyl)amino)-3-hydroxypiperidine-1-carboxylate was obtained from benzyl (3R,4R)-4-((2,3-dihydro(1,4)dioxino(2,3-c)pyridin-7-ylmethyl)amino)-3-hydroxypiperidine-1-carboxylate.

By the same technique as in Reference Example 25, tert-butyl (2,3-dihydro(1,4)dioxino(2,3-c)pyridin-7-ylmethyl)((3R,4R)-3-hydroxypiperidin-4-yl)carbamate was obtained from benzyl (3R,4R)-4-((tert-butoxycarbonyl)(2,3-dihydro(1,4)dioxino(2,3-c)pyridin-7-ylmethyl)amino)-3-hydroxypiperidine-1-carboxylate.

$^1$H-NMR (CDCl$_3$) δ: 1.28-1.57 (9H, m), 1.90-2.40 (2H, m), 2.70-3.10 (2H, m), 3.43-3.80 (2H, m), 4.00-4.35 (2H, m), 4.40-4.86 (6H, m), 7.20-7.40 (1H, m), 8.23-8.39 (1H, m), 9.10-9.90 (2H, m)

Reference Example 107

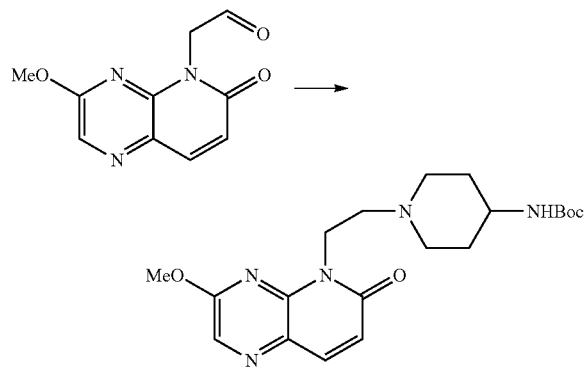

By the same technique as in Reference Example 42, tert-butyl (1-(2-(3-methoxy-6-oxopyrido(2,3-b)pyrazin-5(6H)-yl)ethyl)piperidin-4-yl)carbamate was obtained from (3-methoxy-6-oxopyrido(2,3-b)pyrazin-5(6H)-yl)acetaldehyde and tert-butyl piperidin-4-ylcarbamate.

$^1$H-NMR (CDCl$_3$) δ: 1.30-1.50 (11H, m), 1.87-1.96 (2H, m), 2.18-2.30 (2H, m), 2.66-2.74 (2H, m), 2.94-3.06 (2H, m), 3.39-3.52 (1H, m), 4.06 (3H, s), 4.34-4.46 (1H, m), 4.53-4.61 (2H, m), 6.76 (1H, d, J=9.6 Hz), 7.84 (1H, d, J=9.6 Hz), 8.11 (1H, s)

Reference Example 108

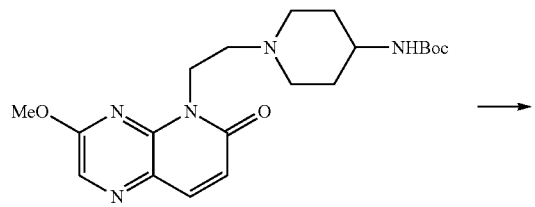

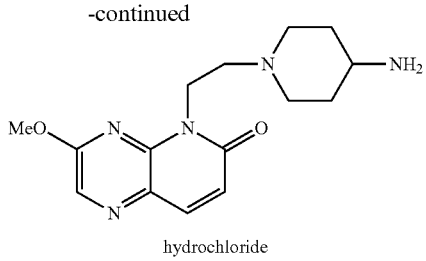

hydrochloride

By the same technique as in Reference Example 65, 5-(2-(4-aminopiperidin-1-yl)ethyl)-3-methoxypyrido(2,3-b)pyrazin-6(5H)-one hydrochloride was obtained from tert-butyl (1-(2-(3-methoxy-6-oxopyrido(2,3-b)pyrazin-5(6H)-yl)ethyl)piperidin-4-yl)carbamate.

$^1$H-NMR (DMSO-d$_6$) δ: 1.88-2.20 (4H, m), 3.05-3.19 (2H, m), 3.20-3.68 (3H, m), 3.71-3.82 (2H, m), 4.11 (3H, s), 4.68-4.78 (2H, m), 6.77 (1H, d, J=9.6 Hz), 8.01 (1H, d, J=9.6 Hz), 8.29 (1H, s), 8.30-8.38 (3H, broad), 10.58-10.70 (1H, broad)

Reference Example 109

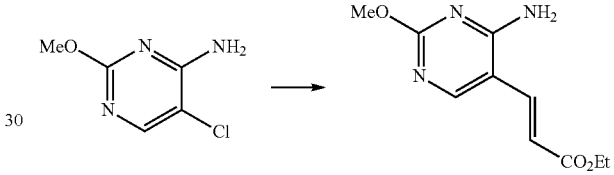

To 2.9 g of 5-chloro-2-methoxypyrimidin-4-amine, 2.35 mL of ethyl acrylate, 18 mL of triethylamine, and 0.46 g of bis(tri-tert-butylphosphine)palladium(0) were added, and the mixture was stirred at an external temperature of 115 to 130° C. for 5 hours in a sealed tube. Thereto were further added 5 mL of triethylamine, 0.30 g of bis(tri-tert-butylphosphine)palladium(0) and 0.5 mL of ethyl acrylate, and the mixture was stirred at an external temperature of 120 to 130° C. for 6 hours 30 minutes in a sealed tube. The reaction mixture was cooled to room temperature, and water and ethyl acetate were added thereto. The organic layer was separated, and the aqueous layer was extracted with chloroform and ethyl acetate. The organic layer and the extract were combined, the resultant solution was dried over anhydrous magnesium sulfate, and the solvent was distilled off under reduced pressure. The resultant residue was purified by silica gel column chromatography using an eluent of hexane:ethyl acetate=1:1 to obtain 0.89 g of ethyl (2E)-3-(4-amino-2-methoxypyrimidin-5-yl)acrylate as a yellow solid.

$^1$H-NMR (CDCl$_3$) δ: 1.33 (3H, t, J=7.1 Hz), 3.95 (3H, s), 4.26 (2H, q, J=7.1 Hz), 5.45 (2H, s), 6.28 (1H, d, J=16.1 Hz), 7.57 (1H, d, J=16.1 Hz), 8.29 (1H, s)

Reference Example 110

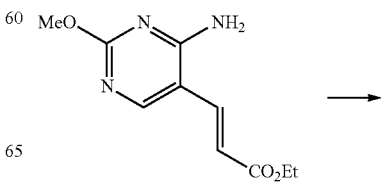

-continued

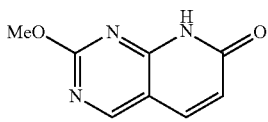

To a solution of 0.87 g of ethyl (2E)-3-(4-amino-2-methoxypyrimidin-5-yl)acrylate in 50 mL of methanol, 2.31 g of a 28% sodium methoxide/methanol solution was added at room temperature, and the mixture was heated under reflux while stirring for 4 hours. The reaction mixture was cooled to room temperature, and the solvent was then distilled off under reduced pressure. To the resultant residue, a saturated aqueous ammonium chloride solution and chloroform were added, the organic layer was separated, and the aqueous layer was extracted with chloroform. The organic layer and the extract were combined, the resultant solution was dried over anhydrous magnesium sulfate, and the solvent was distilled off under reduced pressure. The solid thus obtained was washed with diethyl ether to obtain 0.55 g of 2-methoxypyrido(2,3-d)pyrimidin-7(8H)-one as a yellow solid.

$^1$H-NMR (CDCl$_3$) δ: 4.07 (3H, s), 6.56 (1H, d, J=9.5 Hz), 7.68 (1H, d, J=9.5 Hz), 8.68 (1H, s), 9.32 (1H, s)

Reference Example 111

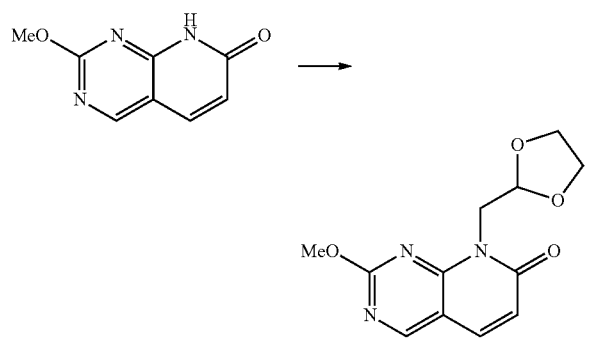

To a suspension of 0.50 g of 2-methoxypyrido(2,3-d)pyrimidin-7(8H)-one in 7.5 mL of N,N-dimethylformamide, 0.59 g of potassium carbonate was added at room temperature, the temperature was increased to 60 to 80° C., and the mixture was stirred for 1 hour. Thereto was added 0.35 mL of 2-bromomethyl-1,3-dioxolan at 80° C., the temperature of the reaction mixture was increased to 103° C., and the mixture was stirred for 3 hours 30 minutes. The reaction mixture was cooled to room temperature, and water and chloroform were added thereto. The organic layer was separated, and the aqueous layer was extracted with chloroform. The organic layer and the extract were combined, the resultant solution was washed with a saturated aqueous sodium chloride solution and dried over anhydrous magnesium sulfate, and the solvent was distilled off under reduced pressure. The resultant residue was purified by silica gel column chromatography using an eluent of chloroform:methanol=75:1 to obtain 0.60 g of 8-(1,3-dioxolan-2-ylmethyl)-2-methoxypyrido(2,3-d)pyrimidin-7(8H)-one as a yellow solid.

$^1$H-NMR (CDCl$_3$) δ: 3.87-3.95 (2H, m), 4.05-4.13 (2H, m), 4.09 (3H, s), 4.59 (2H, d, J=5.1 Hz), 5.52 (1H, d, J=5.1 Hz), 6.60 (1H, d, J=9.5 Hz), 7.62 (1H, d, J=9.5 Hz), 8.65 (1H, s)

Reference Example 112

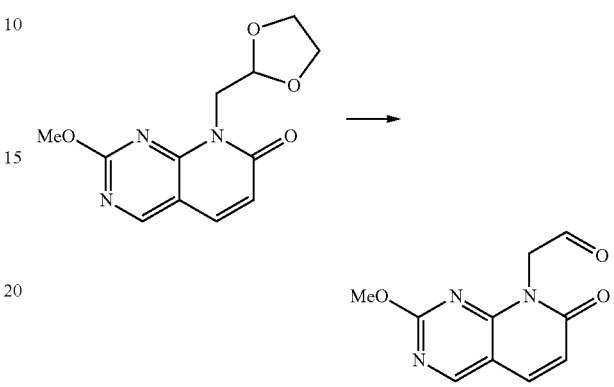

To 0.20 g of 8-(1,3-dioxolan-2-ylmethyl)-2-methoxypyrido(2,3-d)pyrimidin-7(8H)-one, 5 mL of an 80% aqueous trifluoroacetic acid solution was added, and the mixture was stirred at room temperature for 8 hours. To the reaction mixture, a saturated aqueous sodium hydrogen carbonate solution and chloroform were added. The organic layer was separated, and the aqueous layer was extracted with chloroform. The organic layer and the extract were combined, the resultant solution was washed with a saturated aqueous sodium chloride solution and dried over anhydrous magnesium sulfate, and the solvent was distilled off under reduced pressure to obtain 0.21 g of (2-methoxy-7-oxopyrido(2,3-d)pyrimidin-8(7H)-yl)acetaldehyde as a yellow oily substance.

$^1$H-NMR (CDCl$_3$) δ: 4.04 (3H, s), 5.25 (2H, s), 6.64 (1H, d, J=9.5 Hz), 7.72 (1H, d, J=9.5 Hz), 8.71 (1H, s), 9.72 (1H, s)

Reference Example 113

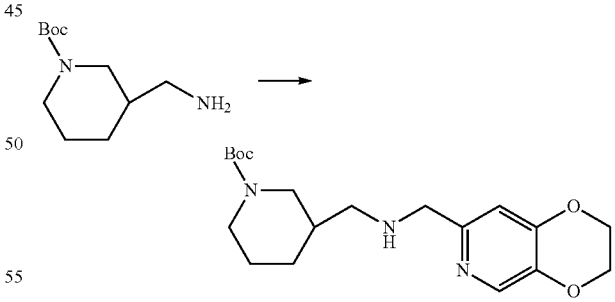

To a solution of 0.65 g of tert-butyl 3-(aminomethyl)piperidine-1-carboxylate in 5 mL of dichloromethane, 0.50 g of (2,3-dihydro(1,4)dioxino(2,3-c)pyridine-7-carbaldehyde and 0.17 mL of acetic acid were added. Subsequently, 0.96 g of sodium triacetoxyborohydride was added thereto and the mixture was stirred at room temperature for 1 hour 15 minutes. The reaction mixture was charged with chloroform and adjusted to pH 8.6 with a saturated aqueous sodium hydrogen carbonate solution and a 20% aqueous sodium hydroxide solution, the organic layer was separated, and the aqueous layer was extracted with chloroform. The organic layer and the extract were combined, the resultant solution was washed with water and a saturated aqueous sodium chloride solution and dried over anhydrous magnesium sulfate, and the solvent was distilled off under reduced pressure to obtain 1.3 g of tert-butyl 3-(((2,3-dihydro(1,4)dioxino(2,3-c)pyridin-7-ylmethyl)amino)methyl)piperidine-1-carboxylate as a yellow oily substance.

$^1$H-NMR (CDCl$_3$) δ: 1.12-1.92 (5H, m), 1.45 (9H, s), 2.20-2.72 (3H, m), 2.80-2.90 (1H, m), 3.78 (2H, s), 3.78-3.98 (2H, m), 4.22-4.35 (4H, m), 6.84 (1H, s), 8.10 (1H, s)

Reference Example 114

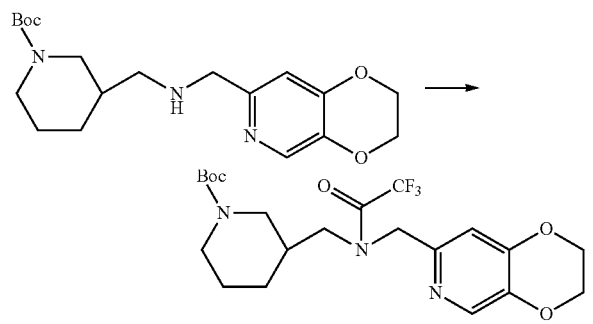

To a solution of 1.3 g of tert-butyl 3-(((2,3-dihydro(1,4)dioxino(2,3-c)pyridin-7-ylmethyl)amino)methyl)piperidine-1-carboxylate in 10 mL of methanol, 0.54 mL of ethyl trifluoroacetate was added, and a mixture was stirred at room temperature for 2 hours, and then stirred at 40 to 45° C. for 3 hours. Thereto was added 0.54 mL of ethyl trifluoroacetate, and the mixture was heated under reflux while stirring for 3 hours. The mixture was cooled to room temperature, and the solvent was then distilled off under reduced pressure. The resultant residue was purified by silica gel column chromatography using an eluent of hexane:ethyl acetate=1:1 to obtain 0.47 g of tert-butyl 3-(((2,3-dihydro(1,4)dioxino(2,3-c)pyridin-7-ylmethyl)(trifluoroacetyl)amino)-methyl)piperidine-1-carboxylate as a colorless oily substance.

$^1$H-NMR (CDCl$_3$) δ: 1.07-2.10 (5H, m), 1.44 (9H, s), 2.58-2.66 (1H, m), 2.70-2.79 (1H, m), 3.20-3.50 (2H, m), 3.80-4.00 (2H, m), 4.26-4.36 (4H, m), 4.58-4.68 (2H, m), 6.66 (1H, s), 8.11 (1H, s)

Reference Example 115

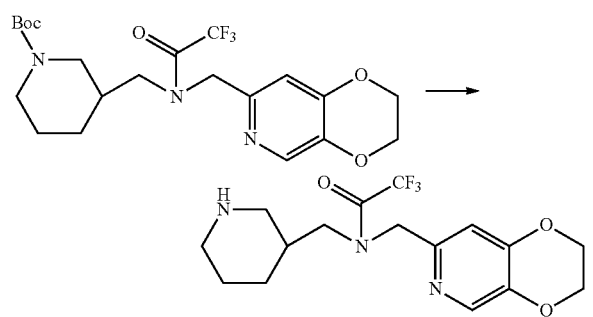

To a solution of 0.43 g of tert-butyl 3-(((2,3-dihydro(1,4)dioxino(2,3-c)pyridin-7-ylmethyl)(trifluoroacetyl)amino) methyl)piperidine-1-carboxylate in 3 mL of chloroform, 3 mL of trifluoroacetic acid was added, and the mixture was stirred at room temperature for 1 hour 40 minutes. The solvent was distilled off under reduced pressure. The resultant residue was charged with chloroform and water, and adjusted to pH 8.0 with an aqueous sodium hydrogen carbonate solution and a 20% aqueous sodium hydroxide solution. The organic layer was separated, and the aqueous layer was extracted with chloroform. The organic layer and the extract were combined, the resultant solution was washed with water and a saturated aqueous sodium chloride solution and dried over anhydrous magnesium sulfate, and the solvent was distilled off under reduced pressure to obtain 0.15 g of N-(2,3-dihydro(1,4)dioxino(2,3-c)pyridin-7-ylmethyl)-2,2,2-trifluoro-N-(piperidin-3-ylmethyl)acetamide as a light yellow oily substance.

$^1$H-NMR (CDCl$_3$) δ: 1.08-1.26 (1H, m), 1.48-1.62 (1H, m), 1.68-2.15 (3H, m), 2.32-2.47 (1H, m), 2.54-2.66 (1H, m), 3.00-3.12 (2H, m), 3.22-3.30 (1H, m), 3.32-3.44 (1H, m), 4.24-4.36 (4H, m), 4.61 (2H, s), 6.67 (1H, s), 8.11 (1H, s)

Reference Example 116

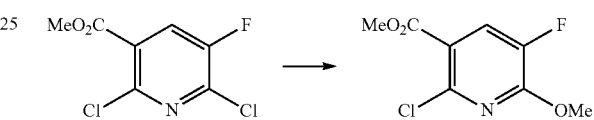

To a solution of 1.5 g of methyl 2,6-dichloro-5-fluoronicotinate in 12 mL of methanol, a solution of 1.3 g of 28% sodium methoxide/methanol in 3 mL of methanol was dropped, and the mixture was stirred at room temperature for 40 minutes. Thereto were added water and ethyl acetate, the organic layer was separated, and the aqueous layer was extracted with ethyl acetate. The organic layer and the extract were combined, the resultant solution was washed with water and a saturated aqueous sodium chloride solution and dried over anhydrous magnesium sulfate, and the solvent was distilled off under reduced pressure to obtain 1.2 g of methyl 2-chloro-5-fluoro-6-methoxynicotinate as a white solid.

$^1$H-NMR (CDCl$_3$) δ: 3.92 (3H, s), 4.09 (3H, s), 7.92 (1H, d, J=9.8 Hz)

Reference Example 117

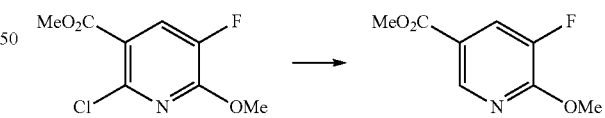

To a solution of 1.5 g of methyl 2-chloro-5-fluoro-6-methoxynicotinate in 15 mL of N,N-dimethylformamide, 0.38 g of tetrakis(triphenylphosphine)palladium(0), 1.4 mL of triethylamine, and 0.38 mL of formic acid were added at room temperature, and the mixture was stirred at 50 to 60° C. for 1 hour under a nitrogen atmosphere, and then stirred at 90 to 100° C. for 2 hours 20 minutes. Thereto were further added 1.4 mL of triethylamine, 0.38 g of tetrakis(triphenylphosphine)palladium(0) and 0.38 mL of formic acid at room temperature, and the mixture was stirred at 90 to 100° C. for 1 hour. After cooling to room temperature, the reaction mixture was charged with ethyl acetate and water, and adjusted to pH 4.8 with 2 mol/L hydrochloric acid. The organic layer was separated, and the aqueous layer was extracted with ethyl acetate. The organic layer and the extract were combined, and the resultant solution was washed with a saturated aqueous sodium chloride solution. A mixed solvent of chloroform:methanol was added to the organic layer to dissolve the insoluble substance, and dried over anhydrous magnesium sulfate, and the solvent was distilled off under reduced pressure. Ethyl acetate was added to the resultant residue, and the solid was filtered off to obtain 0.30 g of methyl 5-fluoro-6-methoxynicotinate as a yellow solid.

$^1$H-NMR (CDCl$_3$) δ: 3.92 (3H, s), 4.09 (3H, s), 7.88 (1H, dd, J=10.5, 2.0 Hz), 8.61 (1H, d, J=2.0 Hz)

Reference Example 118

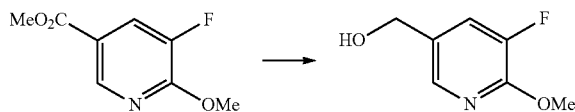 [SMILES: COC(=O)c1cnc(OC)c(F)c1 ; COc1ncc(CO)cc1F]

To a suspension of 0.24 g of lithium aluminum hydride in 6 mL of tetrahydrofuran, a solution of 0.58 g of methyl 5-fluoro-6-methoxynicotinate in 3.5 mL of tetrahydrofuran was dropped under cooling with ice. After warming to room temperature, the mixture was stirred for 30 minutes. Thereto was dropped a saturated aqueous sodium hydrogen carbonate solution under cooling with ice, after stirring for 10 minutes, the reaction mixture was filtered through celite, and the filtration residue was washed with ethyl acetate and water. The organic layer of the filtrate was separated, and the aqueous layer was extracted with ethyl acetate. The organic layer and the extract were combined, the resultant solution was washed with water and a saturated aqueous sodium chloride solution and dried over anhydrous magnesium sulfate, and the solvent was distilled off under reduced pressure to obtain 0.55 g of (5-fluoro-6-methoxypyridin-3-yl)methanol as a brown oily substance.

$^1$H-NMR (CDCl$_3$) δ: 1.72 (1H, t, J=5.7 Hz), 4.03 (3H, s), 4.65 (2H, d, J=5.7 Hz), 7.40 (1H, dd, J=10.7, 2.0 Hz), 7.89 (1H, d, J=2.0 Hz)

Reference Example 119

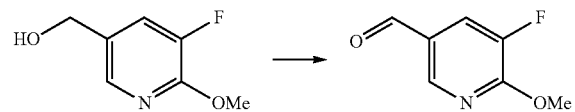 [SMILES: COc1ncc(CO)cc1F ; COc1ncc(C=O)cc1F]

To a solution of 0.54 g of (5-fluoro-6-methoxypyridin-3-yl)methanol in 5 mL of dichloromethane, 1.5 g of manganese dioxide was added. The mixture was stirred at room temperature for 3 hours, thereto were then added 0.89 g of manganese dioxide and 4 mL of dichloromethane, and the mixture was stirred for 1 hour. Thereto were further added 1.5 g of manganese dioxide and 2 mL of dichloromethane, and the mixture was stirred at room temperature for 2 hours 30 minutes. After leaving overnight, the insoluble substance was filtered off, and the filtration residue was washed with chloroform. The solvent was distilled off under reduced pressure to obtain 0.48 g of 5-fluoro-6-methoxynicotinaldehyde as a yellow solid.

$^1$H-NMR (CDCl$_3$) δ: 4.13 (3H, s), 7.78 (1H, dd, J=9.8, 1.8 Hz), 8.42 (1H, d, J=1.8 Hz), 9.97 (1H, d, J=2.7 Hz)

Reference Example 120

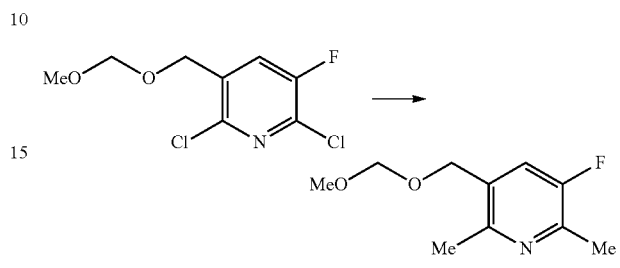

By the same technique as in Reference Example 101, 3-fluoro-5-((methoxymethoxy)methyl)-2,6-dimethylpyridine was obtained from 2,6-dichloro-3-fluoro-5-((methoxymethoxy)methyl)pyridine.

$^1$H-NMR (CDCl$_3$) δ: 2.47 (3H, s), 2.48 (3H, d, J=2.7 Hz), 3.42 (3H, s), 4.55 (2H, s), 4.73 (2H, s), 7.35 (1H, d, J=9.8 Hz)

Reference Example 121

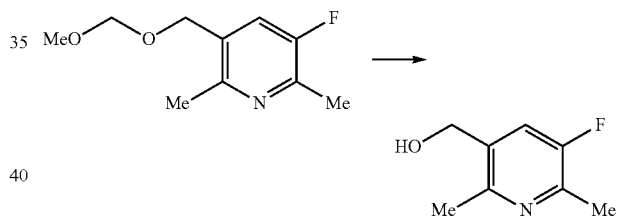

By the same technique as in Reference Example 102, (5-fluoro-2,6-dimethylpyridin-3-yl)methanol was obtained from 3-fluoro-5-((methoxymethoxy)methyl)-2,6-dimethylpyridine.

$^1$H-NMR (CDCl$_3$) δ: 1.99-2.20 (1H, broad), 2.45 (3H, s), 2.48 (3H, d, J=2.9 Hz), 4.68 (2H, s), 7.40 (1H, d, J=9.8 Hz)

Reference Example 122

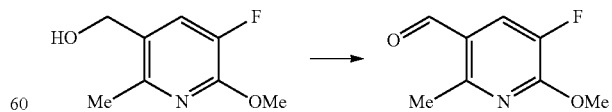

By the same technique as in Reference Example 103, 5-fluoro-2,6-dimethylnicotinaldehyde was obtained from (5-fluoro-2,6-dimethylpyridin-3-yl)methanol.

$^1$H-NMR (CDCl$_3$) δ: 2.57 (3H, d, J=2.9 Hz), 2.82 (3H, d, J=1.0 Hz), 7.72 (1H, d, J=9.0 Hz), 10.28 (1H, d, J=2.2 Hz)

Reference Example 123

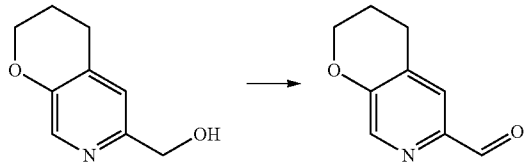 [SMILES: OCc1cc2c(cn1)OCCC2 ; O=Cc1cc2c(cn1)OCCC2]

To a solution of 0.25 g of (3,4-dihydro-2H-pyrano(2,3-c)pyridin-6-yl)methanol in 7.5 mL of chloroform, 0.66 g of manganese dioxide was added, and the mixture was heated under reflux while stirring for 4 hours 50 minutes. The reaction mixture was cooled to room temperature, the insoluble substance was then filtered off, and the solvent was distilled off under reduced pressure to obtain 0.24 g of 3,4-dihydro-2H-pyrano(2,3-c)pyridine-6-carbaldehyde as a light yellow oily substance.

$^1$H-NMR (CDCl$_3$) δ: 2.04-2.11 (2H, m), 2.85 (2H, t, J=6.5 Hz), 4.32 (2H, t, J=5.1 Hz), 7.72 (1H, s), 8.27 (1H, s), 9.94 (1H, s)

Reference Example 124

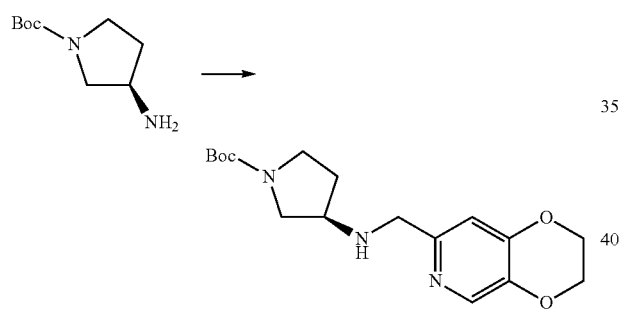

By the same technique as in Reference Example 60, tert-butyl (3S)-3-((2,3-dihydro(1,4)dioxino(2,3-c)pyridin-7-ylmethyl)amino)pyrrolidine-1-carboxylate was obtained from tert-butyl (3S)-3-aminopyrrolidine-1-carboxylate and 2,3-dihydro(1,4)dioxino(2,3-c)pyridine-7-carbaldehyde.

$^1$H-NMR (CDCl$_3$) δ: 1.43 (9H, s), 1.54-1.64 (1H, m), 2.18-2.42 (2H, m), 2.50-2.86 (3H, m), 3.62 (2H, s), 4.10-4.22 (1H, broad), 4.25-4.36 (4H, m), 4.86-4.94 (1H, m), 6.86 (1H, s), 8.10 (1H, s)

Reference Example 125

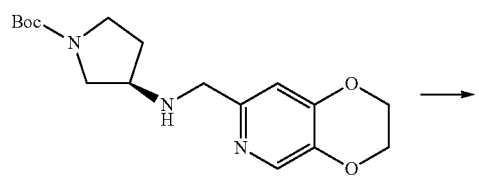

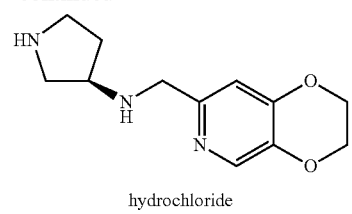

hydrochloride

By the same technique as in Reference Example 13, (3S)-N-(2,3-dihydro(1,4)dioxino(2,3-c)pyridin-7-ylmethyl)pyrrolidin-3-amine hydrochloride was obtained from tert-butyl (3S)-3-((2,3-dihydro(1,4)dioxino(2,3-c)pyridin-7-ylmethyl)amino)pyrrolidine-1-carboxylate.

$^1$H-NMR (DMSO-d$_6$) δ: 2.03-2.14 (1H, m), 2.30-2.40 (1H, m), 3.30-3.72 (4H, m), 3.92-4.05 (1H, m), 4.32-4.43 (4H, m), 4.45 (2H, s), 7.19 (1H, s), 8.22 (1H, s)

Reference Example 126

To 2.2 g of 1-(1,3-dioxolan-2-ylmethyl)-7-fluoro-1,5-naphthyridin-2(1H)-one, 20 mL of an 80% aqueous trifluoroacetic acid solution was added, and the mixture was stirred at 80 to 90° C. for 3 hours. Thereto was added 10 mL of an 80% aqueous trifluoroacetic acid solution, and the mixture was stirred at 80 to 90° C. for 2 hours, then, 10 mL of an 80% aqueous trifluoroacetic acid solution was further added, and the mixture was stirred at the same temperature for 9 hours. The reaction mixture was cooled to room temperature, and the solvent was then distilled off under reduced pressure. To the resultant residue, a 2 mol/L aqueous sodium hydroxide solution was added and adjusted to pH 8.0, and chloroform and methanol were added thereto. The organic layer was separated, and the aqueous layer was extracted with a mixed solution of chloroform and methanol twice. The organic layer and the extract were combined, the resultant solution was dried over anhydrous magnesium sulfate, and the solvent was distilled off under reduced pressure. Diethyl ether and hexane were added to the resultant residue, and the solid was filtered off to obtain 1.5 g of 7-fluoro-1-(2-hydroxy-2-methoxyethyl)-1,5-naphthyridin-2(1H)-one as a light brown solid.

¹H-NMR (DMSO-d₆) δ: 3.21 (3H, s), 4.19-4.31 (2H, m), 4.72-4.79 (1H, m), 6.53 (1H, d, J=7.1 Hz), 6.84 (1H, d, J=9.8 Hz), 7.97 (1H, d, J=9.8 Hz), 8.03 (1H, dd, J=11.5, 2.4 Hz), 8.55 (1H, d, J=2.4 Hz)

Reference Example 127

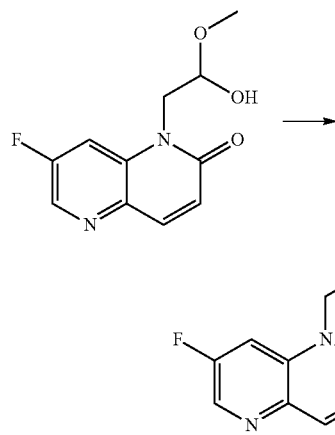

By the same technique as in Reference Example 77, tert-butyl (1-(2-(7-fluoro-2-oxo-1,5-naphthyridin-1(2H)-yl)ethyl)piperidin-4-yl)carbamate was obtained from 7-fluoro-1-(2-hydroxy-2-methoxyethyl)-1,5-naphthyridin-2(1H)-one and tert-butyl (piperidin-4-yl)carbamate.

¹H-NMR (CDCl₃) δ: 1.32-1.49 (2H, m), 1.44 (9H, s), 1.89-1.99 (2H, m), 2.20-2.30 (2H, m), 2.61-2.68 (2H, m), 2.86-2.95 (2H, m), 3.42-3.54 (1H, m), 4.27-4.35 (2H, m), 4.38-4.47 (1H, m), 6.86 (1H, d, J=9.8 Hz), 7.48-7.55 (1H, m), 7.89 (1H, d, J=9.8 Hz), 8.42 (1H, d, J=2.4 Hz)

Reference Example 128

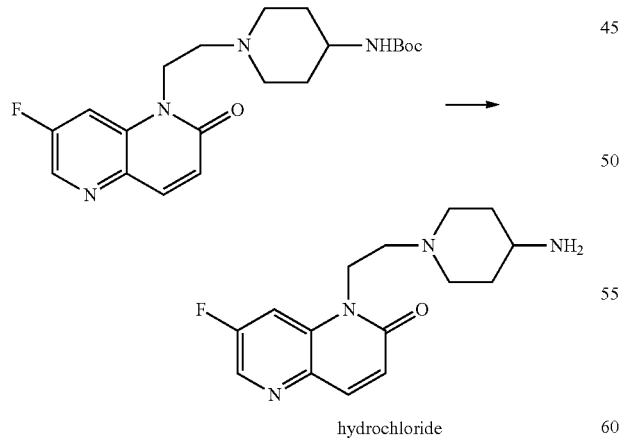

By the same technique as in Reference Example 78, 1-(2-(4-aminopiperidin-1-yl)ethyl)-7-fluoro-1,5-naphthyridin-2(1H)-one hydrochloride was obtained from tert-butyl (1-(2-(7-fluoro-2-oxo-1,5-naphthyridin-1(2H)-yl)ethyl)piperidin-4-yl)carbamate.

¹H-NMR (D₂O) δ: 1.92-2.08 (2H, m), 2.34-2.45 (2H, m), 3.17-3.35 (2H, m), 3.56-3.68 (3H, m), 3.91-4.03 (2H, m), 4.71-4.78 (2H, m), 6.99 (1H, d, J=9.9 Hz), 7.96 (1H, dd, J=10.0, 2.1 Hz), 8.09 (1H, d, J=9.9 Hz), 8.57 (1H, d, J=2.1 Hz)

Reference Example 129

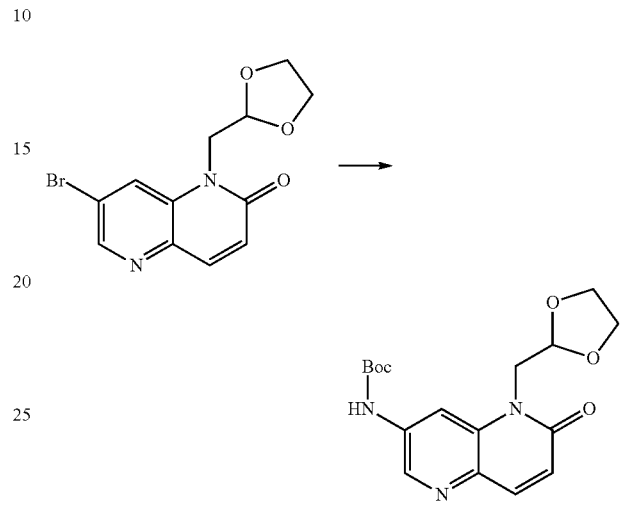

To a suspension of 0.40 g of 7-bromo-1-((1,3-dioxolan-2-yl)methyl)-1,5-naphthyridin-2(1H)-one in 4 mL of dioxane, 0.18 g of tert-butyl carbamate, 0.59 g of cesium carbonate, 22 mg of 4,5-bis(diphenylphosphino)-9,9-dimethylxanthene, and 18 mg of tris(dibenzylideneacetone)dipalladium(0) were added at room temperature, and the mixture was stirred at 90 to 95° C. for 4 hour 15 minutes. After cooling to the room temperature, chloroform and water were added to the reaction mixture, the organic layer was separated, and washed with water and a saturated aqueous sodium chloride solution. The organic layer was dried over anhydrous magnesium sulfate, the solvent was distilled off under reduced pressure, diethyl ether was added to the resultant residue and the solid was filtered off to obtain 0.29 g of tert-butyl (5-(1,3-dioxolan-2-yl)methyl-6-oxo-5,6-dihydro-1,5-naphthyridin-3-yl)carbamate as a light yellow solid.

¹H-NMR (CDCl₃) δ: 1.55 (9H, s), 3.86-3.94 (2H, m), 4.02-4.13 (2H, m), 4.46 (2H, d, J=4.6 Hz), 5.33 (1H, t, J=4.6 Hz), 6.80 (1H, d, J=9.6 Hz), 6.91 (1H, s), 7.83 (1H, d, J=9.6 Hz), 8.29 (1H, d, J=2.0 Hz), 8.43 (1H, s)

Reference Example 130

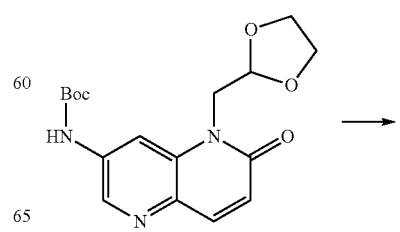

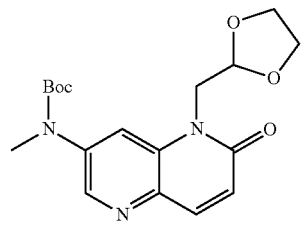

To a solution of 0.15 g of tert-butyl (5-(1,3-dioxolan-2-yl)methyl-6-oxo-5,6-dihydro-1,5-naphthyridin-3-yl)carbamate in 2 mL of N,N-dimethylformamide, 21 mg of 60% sodium hydride and 32 μL of methyl iodide were added, and the mixture was stirred at room temperature for 2 hours 20 minutes. Thereto were further added 9 mg of 60% sodium hydride and 13 μL of methyl iodide, and the mixture was stirred at room temperature for 1 hour. Ethyl acetate and water were added to the reaction mixture, and the organic layer was separated. The organic layer was washed with a saturated aqueous sodium chloride solution and dried over anhydrous magnesium sulfate, and the solvent was distilled off under reduced pressure. The resultant residue was purified by flash silica gel column chromatography using gradient elution with hexane:ethyl acetate=1:1 to 3:7 to obtain 0.13 g of tert-butyl (5-(1,3-dioxolan-2-yl)methyl-6-oxo-5,6-dihydro-1,5-naphthyridin-3-yl)(methyl)carbamate as a brown oily substance.

$^1$H-NMR (CDCl$_3$) δ: 1.50 (9H, s), 3.38 (3H, s), 3.85-3.94 (2H, m), 3.97-4.05 (2H, m), 4.48 (2H, d, J=4.3 Hz), 5.22 (1H, t, J=4.3 Hz), 6.87 (1H, d, J=9.8 Hz), 7.84-7.89 (2H, m), 8.51 (1H, d, J=2.0 Hz)

Reference Example 131

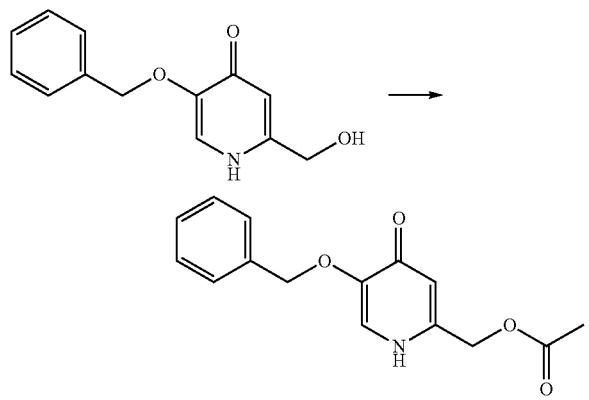

To a solution of 10 g of 5-(benzyloxy)-2-(hydroxymethyl)pyridin-4(1H)-one in 58 mL of pyridine, 4.6 mL of acetyl chloride was added under cooling with ice, and the mixture was stirred at 60 to 70° C. for 3 hours. The solvent was distilled off under reduced pressure, water was added thereto, and the mixture was stirred under cooling with ice. The solid was filtered off, chloroform was added thereto and the resultant was dried over anhydrous magnesium sulfate, the solvent was distilled off under reduced pressure. Thereto was added diethyl ether and the solid was filtered off to obtain 9.2 g of (5-(benzyloxy)-4-oxo-1,4-dihydropyridin-2-yl)methyl acetate as a light brown solid.

$^1$H-NMR (CDCl$_3$) δ: 2.08 (3H, s), 4.89 (2H, s), 5.00 (2H, s), 6.63 (1H, s), 7.28 (5H, s), 7.50 (1H, s)

Reference Example 132

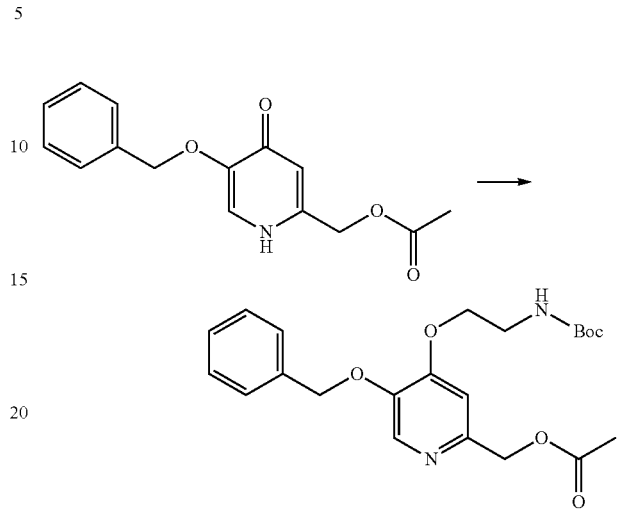

To a solution of 6.1 g of (5-(benzyloxy)-4-oxo-1,4-dihydropyridin-2-yl)methyl acetate in 50 mL of dimethyl sulfoxide, 5.0 g of tert-butyl (2-bromoethyl)carbamate and 10 g of potassium carbonate were added, and the mixture was stirred at 80 to 90° C. for 6 hours 30 minutes. The reaction mixture was cooled to room temperature, and ethyl acetate and water were then added thereto. The organic layer was separated, washed with water and dried over anhydrous magnesium sulfate, and the solvent was distilled off under reduced pressure. The resultant residue was purified by flash silica gel column chromatography using gradient elution with chloroform:methanol=99:1 to 98:2 obtain 3.8 g of (5-(benzyloxy)-4-(2-((tert-butoxycarbonyl)amino)ethoxy)pyridin-2-yl)methyl acetate as a brown oily substance.

$^1$H-NMR (CDCl$_3$) δ: 1.45 (9H, s), 2.15 (3H, s), 3.58 (2H, q, J=5.3 Hz), 4.13 (2H, t, J=5.3 Hz), 4.96 (1H, s), 5.10 (2H, s), 5.16 (2H, s), 6.89 (1H, s), 7.30-7.45 (5H, m), 8.16 (1H, s)

Reference Example 133

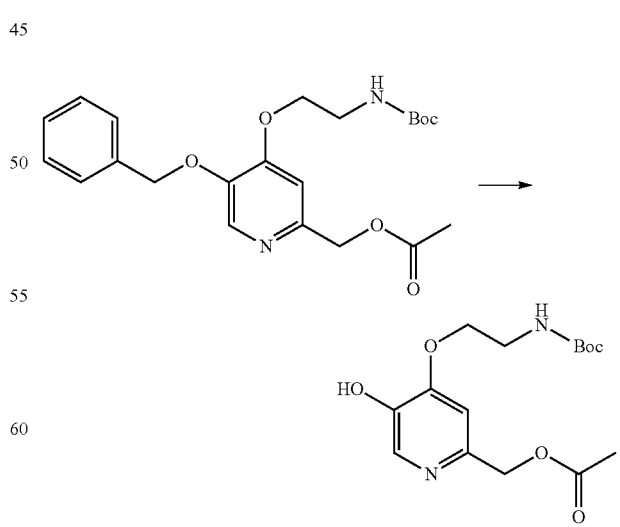

To a solution of 3.8 g of (5-(benzyloxy)-4-(2-((tert-butoxycarbonyl)amino)ethoxy)pyridin-2-yl)methyl acetate in 91 mL of ethanol, 1.1 g of 10% palladium carbon was added, and the mixture was stirred at room temperature for 5 hours under a hydrogen atmosphere. The insoluble substance was filtered off, and the solvent was distilled off under reduced pressure. Thereto were added chloroform and diethyl ether, and the solid was filtered off to obtain 2.1 g of (4-(2-((tert-butoxycarbonyl)amino)ethoxy)-5-hydroxypyridin-2-yl)methyl acetate as a light brown solid.

¹H-NMR (CDCl₃) δ: 1.45 (9H, s), 2.15 (3H, s), 3.61 (2H, q, J=4.8 Hz), 4.21 (2H, t, J=4.8 Hz), 5.20 (2H, s), 5.35 (1H, s), 6.94 (1H, s), 8.26 (1H, s)

Reference Example 134

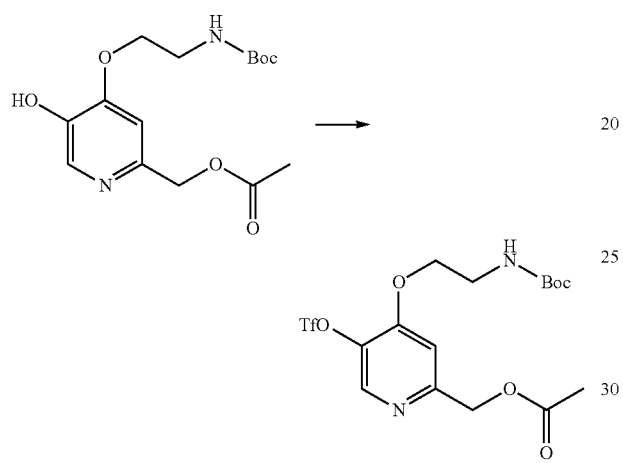

To a solution of 1.0 g of (4-(2-((tert-butoxycarbonyl)amino)ethoxy)-5-hydroxypyridin-2-yl)methyl acetate in 15 mL of dichloromethane, 0.86 mL of triethylamine and 0.78 mL of trifluoromethanesulfonic anhydride were added under cooling with ice, and the mixture was stirred for 30 minutes. Thereto were added a saturated aqueous sodium hydrogen carbonate solution and water, and the organic layer was separated and washed with a saturated aqueous sodium chloride solution. The organic layer was dried over anhydrous magnesium sulfate and the solvent was distilled off under reduced pressure. The resultant residue was purified by flash silica gel column chromatography using gradient elution with hexane:ethyl acetate=66:34 to 50:50 to obtain 1.3 g of (4-(2-((tert-butoxycarbonyl)amino)ethoxy)-5-(((trifluoromethyl)sulfonyl)oxy)pyridin-2-yl)methyl acetate as a colorless oily substance.

¹H-NMR (CDCl₃) δ: 1.45 (9H, s), 2.20 (3H, s), 3.60 (2H, q, J=5.2 Hz), 4.23 (2H, t, J=5.2 Hz), 5.05 (1H, s), 5.18 (2H, s), 7.04 (1H, s), 8.35 (1H, s)

Reference Example 135

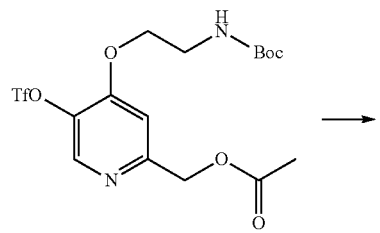

-continued

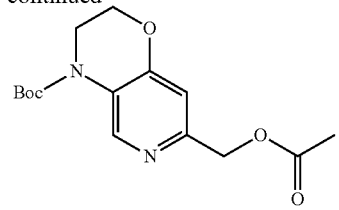

To a solution of 1.0 g of (4-(2-((tert-butoxycarbonyl)amino)ethoxy)-5-(((trifluoromethyl)sulfonyl)oxy)pyridin-2-yl)methyl acetate in 5.0 mL of dioxane, 1.0 g of cesium carbonate, 58 mg of tris(dibenzylideneacetone)dipalladium (0) and 76 mg of 4,5-bis(diphenylphosphino)-9,9-dimethylxanthene were added, and the mixture was heated under reflux while stirring for 2 hours. Ethyl acetate was added to the reaction mixture, the insoluble substance was filtered off, and the solvent was distilled off under reduced pressure. The resultant residue was purified by flash silica gel column chromatography using gradient elution with hexane:ethyl acetate=60:40 to 0:100 to obtain 0.29 g of tert-butyl 7-((acetoxy)methyl)-2,3-dihydro-4H-pyrido(4,3-b)(1,4)oxadine-4-carboxylate as a brown solid.

¹H-NMR (CDCl₃) δ: 1.56 (9H, s), 2.14 (3H, s), 3.85-3.89 (2H, m), 4.29-4.32 (2H, m), 5.11 (2H, s), 6.86 (1H, s), 8.88 (1H, s)

Reference Example 136

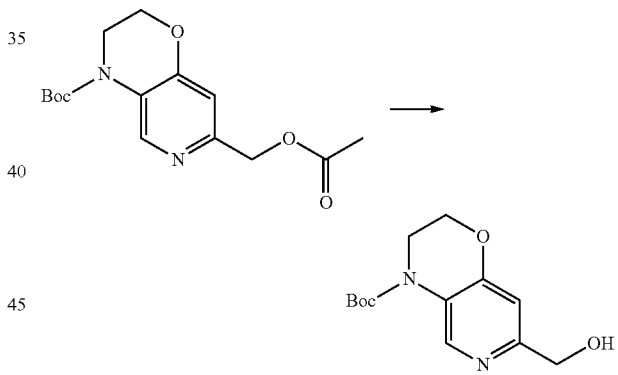

To a solution of 0.11 g of tert-butyl 7-((acetoxy)methyl)-2,3-dihydro-4H-pyrido(4,3-b)(1,4)oxadine-4-carboxylate in a mixture of 1.7 mL of tetrahydrofuran and 1.7 mL of water, 0.36 mL of a 2.0 mol/L aqueous sodium hydroxide solution was added, and the mixture was stirred at room temperature for 1 hour. The reaction solution was saturated with potassium carbonate, ethyl acetate was then added thereto, the organic layer was separated and the aqueous layer was extracted with ethyl acetate. The organic layer and the extract were combined, the resultant solution was washed with a saturated aqueous sodium chloride solution and dried over anhydrous magnesium sulfate, and the solvent was distilled off under reduced pressure to obtain 90 mg of tert-butyl 7-(hydroxymethyl)-2,3-dihydro-4H-pyrido(4,3-b)(1,4)oxadine-4-carboxylate as a brown oily substance.

¹H-NMR (CDCl₃) δ: 1.56 (9H, s), 3.32-3.41 (1H, m), 3.86-3.89 (2H, m), 4.29-4.32 (2H, m), 4.64 (2H, s), 6.76 (1H, s), 8.82-8.89 (1H, m)

Reference Example 137

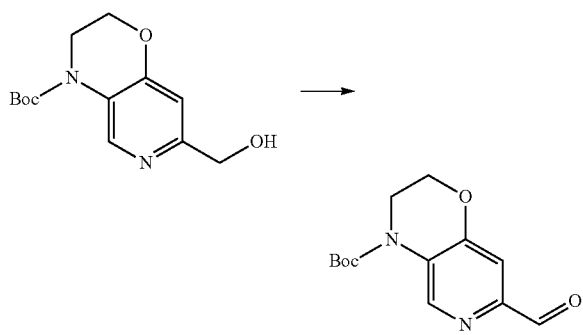

By the same technique as in Reference Example 67, tert-butyl 7-formyl-2,3-dihydro-4H-pyrido(4,3-b)(1,4)oxadine-4-carboxylate was obtained from tert-butyl 7-(hydroxymethyl)-2,3-dihydro-4H-pyrido(4,3-b)(1,4)oxadine-4-carboxylate.

$^1$H-NMR (CDCl$_3$) δ: 1.58 (9H, s), 3.91-3.94 (2H, m), 4.34-4.37 (2H, m), 7.48 (1H, s), 9.12-9.21 (1H, m), 9.96 (1H, s)

Reference Example 138

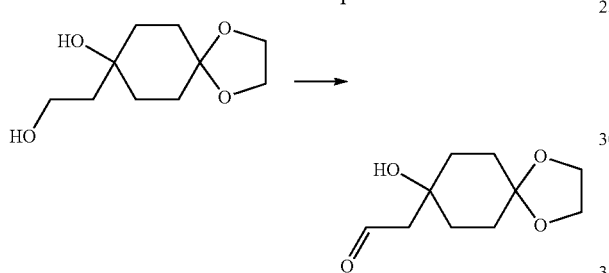

To a solution of 0.30 g of 8-(2-hydroxyethyl)-1,4-dioxaspiro(4.5)decan-8-al in 5 mL of dichloromethane, 0.76 g of Dess-Martin periodinane was added under cooling with ice, and the mixture was stirred at room temperature for 1 hour. To the reaction mixture, water was added under cooling with ice, and the organic layer was separated, and the aqueous layer was extracted with chloroform. The organic layer and the extract were combined, and the resultant solution was washed with a saturated aqueous sodium chloride solution, and dried over anhydrous magnesium sulfate. The solvent was distilled off under reduced pressure, chloroform was added thereto, and the insoluble substance was filtered off. The resultant residue was purified by flash silica gel column chromatography using gradient elution with hexane:ethyl acetate=35:65 to 25:75 to obtain 0.19 g of (8-hydroxy-1,4-dioxaspiro(4.5)deca-8-yl)acetaldehyde as a slightly yellow oily substance.

$^1$H-NMR (CDCl$_3$) δ: 1.53-1.64 (2H, m), 1.68 (2H, td, J=13.1, 4.3 Hz), 1.79-1.89 (2H, m), 1.95 (2H, dt, J=12.7, 4.3 Hz), 2.54-2.59 (1H, broad), 2.65 (2H, d, J=1.5 Hz), 3.90-4.00 (4H, m), 9.88 (1H, t, J=1.5 Hz)

Reference Example 139

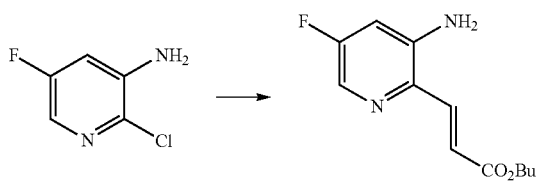

To a solution of 150 g of 2-chloro-5-fluoropyridin-3-amine in 600 mL of N,N-dimethylformamide, 190 mL of butyl acrylate and 287 mL of triethylamine were added under a nitrogen flow, and the mixture was stirred at 110° C. for 2 hours. The reaction mixture was cooled to 58° C., thereto were added 13.1 g of bis(tri-tert-butylphosphine)palladium (0), and the mixture was stirred at 110 to 120° C. for 40 minutes. The reaction mixture was cooled to 57° C., 13.1 g of bis(tri-tert-butylphosphine)palladium(0) was added thereto, and the mixture was stirred at 110 to 120° C. for 3 hours. The reaction mixture was cooled to room temperature, and water and ethyl acetate were added thereto. The insoluble substance was filtered off, the organic layer of the filtrate was separated, and the aqueous layer was extracted with ethyl acetate. The organic layer and the extract were combined, the resultant solution was washed sequentially with water and a saturated aqueous sodium chloride solution and dried over anhydrous magnesium sulfate, and the solvent was distilled off under reduced pressure. Cyclohexane and ethyl acetate were added to the resultant residue, and the solid was filtered off to obtain 200 g of butyl (2E)-3-(3-amino-5-fluoropyridin-2-yl)acrylate as a light brown solid.

$^1$H-NMR (CDCl$_3$) δ: 0.95 (3H, t, J=7.3 Hz), 1.38-1.48 (2H, m), 1.64-1.72 (2H, m), 4.13 (2H, s), 4.21 (2H, t, J=6.7 Hz), 6.71 (1H, dd, J=9.8, 2.3 Hz), 6.86 (1H, d, J=15.3 Hz), 7.72 (1H, d, J=15.3 Hz), 7.94 (1H, d, J=2.3 Hz)

Reference Example 140

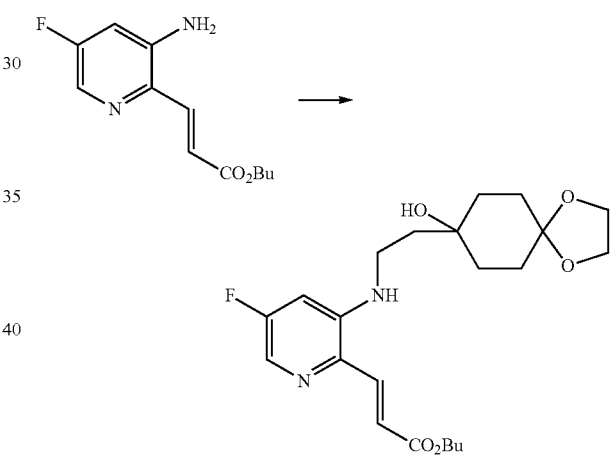

To a solution of 90 mg of butyl (2E)-3-(3-amino-5-fluoropyridin-2-yl)acrylate in 5 mL of dichloromethane, 90 mg of (8-hydroxy-1,4-dioxaspiro(4.5)deca-8-yl)acetaldehyde and 33 μL of acetic acid were added, and the mixture was stirred at room temperature for 4 hours and left overnight. To the reaction mixture, 80 mg of sodium triacetoxyborohydride was added, and the mixture was stirred at room temperature for 1 hour. Thereto were added a saturated aqueous sodium hydrogen carbonate solution and chloroform, the organic layer was separated, and the aqueous layer was extracted with chloroform. The organic layer and the extract were combined, the resultant solution was washed with a saturated aqueous sodium chloride solution and dried over anhydrous magnesium sulfate, and the solvent was distilled off under reduced pressure. The resultant residue was purified by flash silica gel column chromatography using gradient elution with hexane:ethyl acetate=60:40 to 50:50 to obtain 82 mg of butyl (2E)-3-(5-fluoro-3-((2-(8-hydroxy-1,4-dioxaspiro(4.5)deca-8-yl)ethyl)amino)pyridin-2-yl)acrylate as a yellow oily substance.

$^1$H-NMR (CDCl$_3$) δ: 0.95 (3H, t, J=7.4 Hz), 1.38-1.48 (2H, m), 1.55-2.00 (10H, m), 3.22-3.30 (2H, m), 3.90-4.02 (6H, m), 4.20 (2H, t, J=6.6 Hz), 5.40-5.47 (1H, m), 6.63 (1H, dd, J=11.2, 2.4 Hz), 6.83 (1H, d, J=15.2 Hz), 7.71 (1H, d, J=15.2 Hz), 7.82 (1H, d, J=2.4 Hz)

Reference Example 141

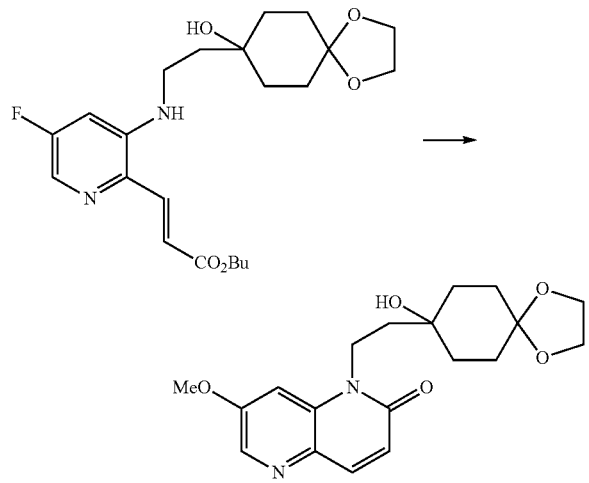

To a solution of 80 mg of butyl (2E)-3-(5-fluoro-3-((2-(8-hydroxy-1,4-dioxaspiro(4.5)deca-8-yl)ethyl)amino)pyridin-2-yl)acrylate in 4 mL of a mixture of methanol and tetrahydrofuran (1:1), 55 mg of a 28% sodium methoxide/methanol solution was added at room temperature, and the mixture was heated under reflux while stirring for 1 hour. The reaction mixture was cooled to room temperature, then, ethyl acetate and water were added thereto, and the organic layer was separated. The organic layer was washed with a saturated aqueous sodium chloride solution, and dried over anhydrous magnesium sulfate, and the solvent was distilled off under reduced pressure to obtain 65 mg of 1-(2-(8-hydroxy-1,4-dioxaspiro(4.5)deca-8-yl)ethyl)-7-methoxy-1,5-naphthyridin-2(1H)-one as a yellow oily substance.

$^1$H-NMR (CDCl$_3$) δ: 1.70-1.80 (4H, m), 1.87-1.96 (4H, m), 2.48-2.56 (2H, m), 3.92-4.00 (4H, m), 3.98 (3H, s), 4.38-4.45 (2H, m), 6.76 (1H, d, J=9.8 Hz), 7.24-7.32 (1H, m), 7.87 (1H, d, J=9.8 Hz), 8.30 (1H, d, J=2.4 Hz)

Reference Example 142

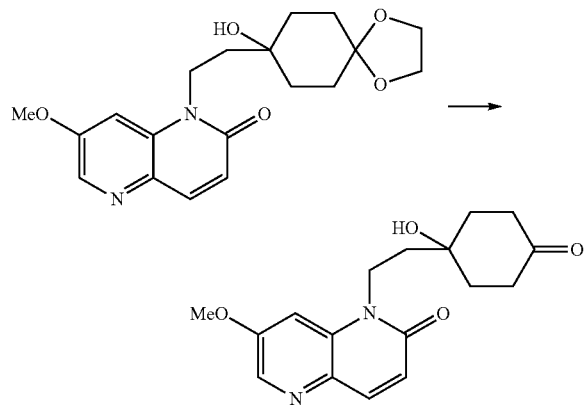

To 60 mg of 1-(2-(8-hydroxy-1,4-dioxaspiro(4.5)deca-8-yl)ethyl)-7-methoxy-1,5-naphthyridin-2(1H)-one, 3 mL of an 80% aqueous trifluoroacetic acid solution was added at room temperature, and the mixture was stirred for 8 hours 30 minutes. The solvent was distilled off under reduced pressure to the resultant residue, a saturated aqueous sodium hydrogen carbonate solution and ethyl acetate were added, the organic layer was separated, and the aqueous layer was extracted with ethyl acetate. The organic layer and the extract were combined, and the resultant solution was washed with a saturated aqueous sodium chloride solution, and dried over anhydrous magnesium sulfate. The solvent was distilled off under reduced pressure, and the resultant residue was purified by flash silica gel column chromatography using gradient elution with chloroform:methanol=100:0 to 99:1 to obtain 41 mg of 1-(2-(1-hydroxy-4-oxocyclohexyl)ethyl)-7-methoxy-1,5-naphthyridin-2(1H)-one as a yellow solid.

$^1$H-NMR (CDCl$_3$) δ: 1.60-2.12 (6H, m), 2.22-2.30 (2H, m), 2.73-2.83 (2H, m), 3.67-3.76 (1H, broad), 4.00 (3H, s), 4.47 (2H, t, J=6.7 Hz), 6.80 (1H, d, J=9.6 Hz), 7.16 (1H, d, J=2.3 Hz), 7.93 (1H, d, J=9.6 Hz), 8.35 (1H, d, J=2.3 Hz)

Reference Example 143

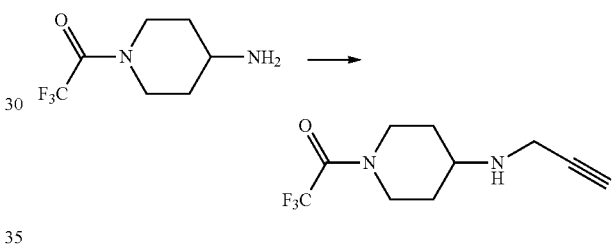

To a solution of 0.50 g of 1-(trifluoroacetyl)piperidin-4-amine in 10 mL of a mixed solvent of N,N-dimethylformamide and tetrahydrofuran (1:1), 0.41 g of potassium carbonate, 0.42 mL of propargyl bromide were added, and the mixture was heated under reflux while stirring for 2 hours. Thereto were added water and ethyl acetate, the organic layer was separated, and the aqueous layer was extracted with ethyl acetate. The organic layer and the extract were combined, the resultant solution was washed with water and a saturated aqueous sodium chloride solution, and dried over anhydrous magnesium sulfate, and the solvent was distilled off under reduced pressure to obtain 0.60 g of N-(2-propyn-1-yl)-1-(trifluoroacetyl)piperidin-4-amine as a crude product (crude product A). On the other hand, to a solution of 0.70 g of 1-(trifluoroacetyl)piperidin-4-amine in 7.2 mL of a mixed solvent of N,N-dimethylformamide and tetrahydrofuran (1:1), 0.59 g of potassium carbonate, and 0.30 mL of propargyl bromide were added, and the mixture was heated under reflux while stirring for 1 hour 50 minutes. Thereto were added water and ethyl acetate, and mixed with 0.60 g of the crude product A obtained above, and the mixture was adjusted to pH 1 with 6 mol/L hydrochloric acid. The aqueous layer was separated, and washed with ethyl acetate, ethyl acetate was added thereto, and the aqueous layer was saturated with potassium carbonate. The organic layer was separated, washed with a saturated aqueous sodium chloride solution, and dried over anhydrous magnesium sulfate, and the solvent was distilled off under reduced pressure to obtain 1.0 g of N-(2-propyn-1-yl)-1-(trifluoroacetyl)piperidin-4-amine as a brown oily substance.

¹H-NMR (CDCl₃) δ: 1.36-1.48 (2H, m), 1.90-1.98 (2H, m), 2.23 (1H, t, J=2.3 Hz), 3.03-3.34 (3H, m), 3.48 (2H, d, J=2.3 Hz), 3.90-3.98 (1H, m), 4.22-4.31 (1H, m)

Reference Example 144

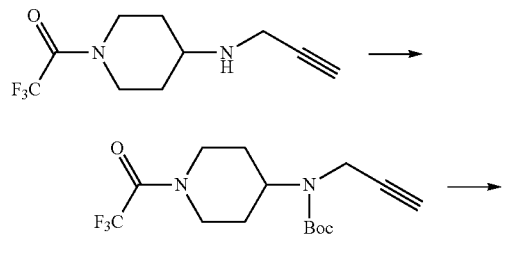

(1) To a solution of 0.60 g of N-(2-propyn-1-yl)-1-(trifluoroacetyl)piperidin-4-amine in 5.2 mL of dioxane, 0.56 g of di-tert-butyl dicarbonate was added and the mixture was stirred at room temperature for 1 hour 45 minutes. The solvent was distilled off under reduced pressure, and the resultant residue was purified by silica gel column chromatography using an elution with hexane:ethyl acetate=3:1 to obtain 0.70 g of tert-butyl (2-propyn-1-yl)(1-(trifluoroacetyl)piperidin-4-yl)carbamate as a colorless oily substance.

(2) To a solution of 0.20 g of tert-butyl (2-propyn-1-yl)(1-(trifluoroacetyl)piperidin-4-yl)carbamate in 6.0 mL of triethylamine, 59 μL of iodopyrazine, 0.57 mg of copper (I) iodide, and 4.2 mg of dichlorobis(triphenylphosphine)palladium(II) were added under a nitrogen atmosphere, and the mixture was stirred at 60 to 70° C. for 4 hours 30 minutes. The insoluble substance was filtered off, and the solvent was distilled off under reduced pressure. The resultant residue was purified by flash silica gel column chromatography using gradient elution with hexane:ethyl acetate=60:40 to 50:50 to obtain 0.17 g of tert-butyl (3-(pyrazin-2-yl)-2-propyn-1-yl)(1-(trifluoroacetyl)piperidin-4-yl)carbamate as a colorless oily substance.

¹H-NMR (CDCl₃) δ: 1.51 (9H, s), 1.76-2.02 (4H, m), 2.72-2.84 (1H, m), 3.12-3.22 (1H, m), 4.08-4.26 (4H, m), 4.64-4.72 (1H, m), 8.49 (1H, d, J=2.7 Hz), 8.53-8.56 (1H, m), 8.60 (1H, d, J=1.2 Hz)

Reference Example 145

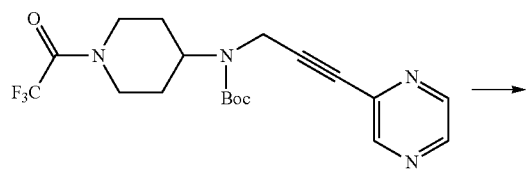

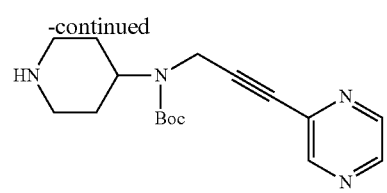

By the same technique as in Reference Example 62, tert-butyl (piperidin-4-yl)(3-pyrazin-2-yl)-2-propyn-1-yl)carbamate was obtained from tert-butyl (3-(pyrazin-2-yl)-2-propyn-1-yl)(1-(trifluoroacetyl)piperidin-4-yl)carbamate.

¹H-NMR (CDCl₃) δ: 1.51 (9H, s), 1.72-1.92 (4H, m), 2.66-2.76 (2H, m), 3.17-3.24 (2H, m), 3.96-4.30 (3H, m), 8.47 (1H, d, J=2.4 Hz), 8.51-8.54 (1H, m), 8.62 (1H, d, J=1.2 Hz)

Reference Example 146

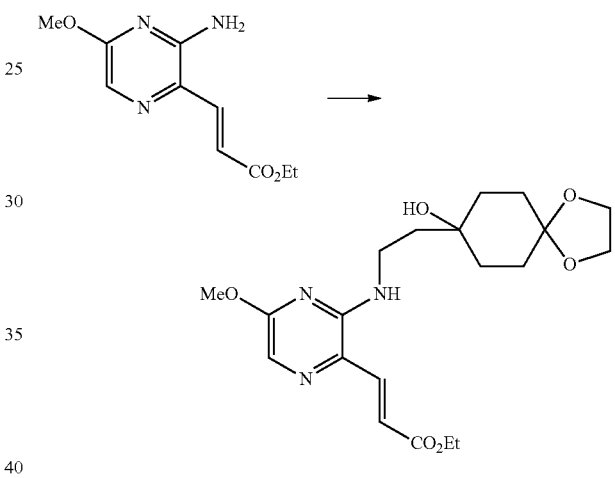

By the same technique as in Reference Example 140, ethyl (2E)-3-(3-((2-(8-hydroxy-1,4-dioxaspiro(4.5)deca-8-yl)ethyl)amino)-5-methoxypyrazin-2-yl)acrylate was obtained from 8-hydroxy-1,4-dioxaspiro(4.5)deca-8-yl)acetaldehyde and ethyl (2E)-3-(3-amino-5-methoxypyrazin-2-yl)acrylate.

¹H-NMR (CDCl₃) δ: 1.31 (3H, t, J=7.2 Hz), 1.71-1.90 (8H, m), 3.60-3.65 (2H, m), 3.90-4.00 (6H, m), 3.94 (3H, s), 4.24 (2H, q, J=7.2 Hz), 5.80-5.94 (1H, m), 6.68 (1H, d, J=15.1 Hz), 7.51 (1H, s), 7.63 (1H, d, J=15.1 Hz)

Reference Example 147

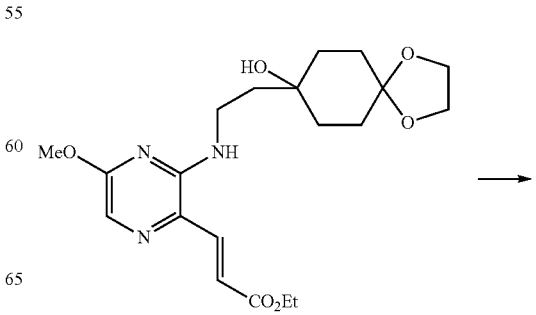

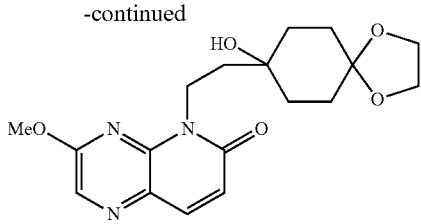

By the same technique as in Reference Example 2, 5-(2-(8-hydroxy-1,4-dioxaspiro(4.5)deca-8-yl)ethyl)-3-methoxypyrido(2,3-b)pyrazin-6(5H)-one was obtained from ethyl (2E)-3-(3-((2-(8-hydroxy-1,4-dioxaspiro(4.5)deca-8-yl)ethyl)amino)-5-methoxypyrazin-2-yl)acrylate.

$^1$H-NMR (CDCl$_3$) δ: 1.50-1.80 (6H, m), 1.90-2.00 (4H, m), 2.40-2.44 (1H, broad), 3.89-3.99 (4H, m), 4.08 (3H, s), 4.58-4.62 (2H, m), 6.78 (1H, d, J=9.6 Hz), 7.87 (1H, d, J=9.6 Hz), 8.14 (1H, s)

Reference Example 148

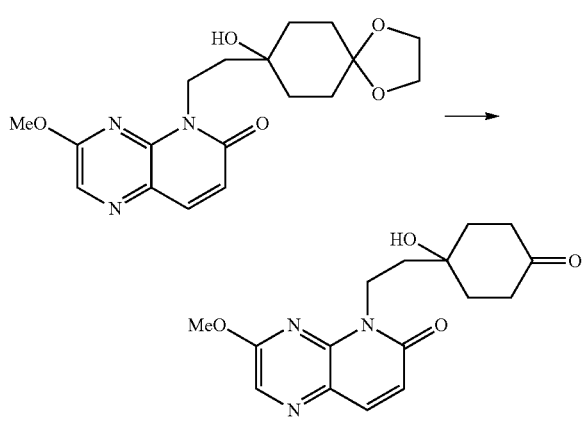

By the same technique as in Reference Example 142, 5-(2-(1-hydroxy-4-oxocyclohexyl)ethyl)-3-methoxypyrido(2,3-b)pyrazin-6(5H)-one was obtained from 5-(2-(8-hydroxy-1,4-dioxaspiro(4.5)deca-8-yl)ethyl)-3-methoxypyrido(2,3-b)pyrazin-6(5H)-one.

$^1$H-NMR (CDCl$_3$) δ: 1.79 (2H, td, J=13.8, 4.9 Hz), 2.04 (2H, t, J=6.8 Hz), 2.03-2.12 (2H, m), 2.20-2.29 (2H, m), 2.80 (2H, td, J=13.8, 6.2 Hz), 3.30-3.45 (1H, broad), 4.09 (3H, s), 4.65 (2H, t, J=6.8 Hz), 6.81 (1H, d, J=9.6 Hz), 7.92 (1H, d, J=9.6 Hz), 8.18 (1H, s)

Reference Example 149

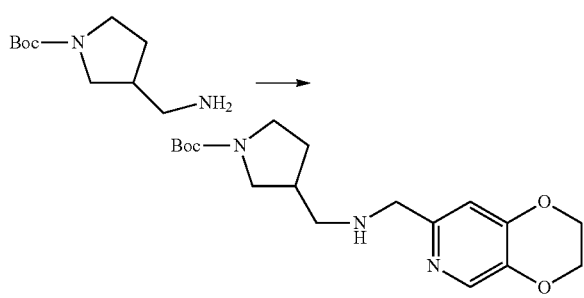

To a solution of 0.28 g of tert-butyl 3-(aminomethyl) pyrrolidine-1-carboxylate in a mixture of 7 mL of methanol and 20 mL of dichloromethane, 0.23 g of 2,3-dihydro(1,4)dioxino(2,3-c)pyridine-7-carbaldehyde and 0.50 g of molecular sieves 3 A were added, the mixture was stirred at room temperature for 3 hours, and then, the reaction mixture was charged with 79 mg of sodium borohydride and stirred at room temperature for 5 hours 30 minutes. Thereto was added water under cooling with ice, the organic layer was separated, and the aqueous layer was extracted with chloroform. The organic layer and the extract were combined, the resultant solution was washed with a saturated aqueous sodium chloride solution and dried over anhydrous magnesium sulfate, and the solvent was distilled off under reduced pressure to obtain 0.48 g of tert-butyl 3-(((2,3-dihydro(1,4)dioxino(2,3-c)pyridin-7-ylmethyl)amino)methyl)pyrrolidine-1-carboxylate as a colorless oily substance.

$^1$H-NMR (CDCl$_3$) δ: 1.45 (9H, s), 1.50-3.60 (9H, m), 3.77 (2H, s), 4.26-4.36 (4H, m), 6.81 (1H, s), 8.11 (1H, s)

Reference Example 150

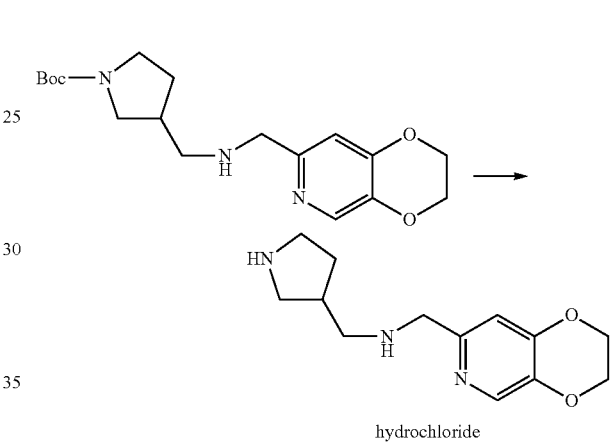

By the same technique as in Reference Example 13, 1-(2,3-dihydro(1,4)dioxino(2,3-c)pyridin-7-yl)-N-(pyrrolidin-3-ylmethyl)methanamine hydrochloride was obtained from tert-butyl 3-(((2,3-dihydro(1,4)dioxino(2,3-c)pyridin-7-ylmethyl)amino)methyl)pyrrolidine-1-carboxylate.

$^1$H-NMR (D$_2$O) δ: 1.76-1.89 (1H, m), 2.31-2.41 (1H, m), 2.73-2.87 (1H, m), 3.02-3.11 (1H, m), 3.28-3.40 (3H, m), 3.45-3.54 (1H, m), 3.64 (1H, dd, J=11.8, 8.2 Hz), 4.41-4.49 (4H, m), 4.54-4.60 (2H, m), 7.35-7.46 (1H, m), 8.30-8.36 (1H, m)

Reference Example 151

A solution of 2.0 g of 7-methyl-1,8-naphthyridin-2(1H)-one in 150 mL of ethanol, 1.0 g of 5% palladium-carbon was added, and the mixture was stirred at 40 to 50° C. for 17 hours under a hydrogen atmosphere. The reaction mixture was cooled to room temperature, the insoluble substance was filtered off, and the filtration residue was washed with methanol. The solvent was distilled off under reduced pressure, and the resultant residue was purified by silica gel column chromatography using an eluent of hexane:ethyl acetate=1:1 to obtain 0.92 g of 7-methyl-3,4-dihydro-1,8-naphthyridin-2 (1H)-one as a white solid.

¹H-NMR (CDCl₃) δ: 2.52 (3H, s), 2.61-2.68 (2H, m), 2.86-2.94 (2H, m), 6.78 (1H, d, J=7.6 Hz), 7.36 (1H, d, J=7.6 Hz), 9.86 (1H, s)

Reference Example 152

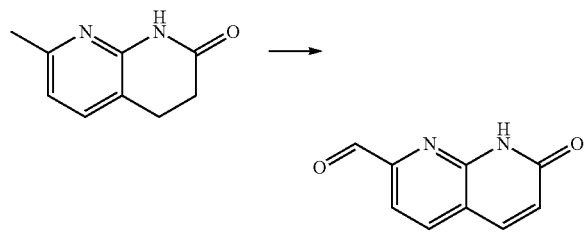

A solution of 0.90 g of 7-methyl-3,4-dihydro-1,8-naphthyridin-2(1H)-one in 150 mL of dioxane was heated under reflux while dividedly adding 25.7 g of selenium dioxide, and the mixture was stirred for 10 days. The insoluble substance was filtered off with celite, and the solvent was distilled off under reduced pressure. To the resultant residue, 2-propanol was added, and the solid was filtered off. The solid thus obtained was purified by silica gel column chromatography using an eluent of chloroform:methanol=20:1, and ethyl acetate was added thereto, and the solid was filtered off to obtain 0.48 g of 7-oxo-7,8-dihydro-1,8-naphthyridine-2-carbaldehyde as a light orange solid.

¹H-NMR (CDCl₃) δ: 6.87 (1H, d, J=9.6 Hz), 7.80 (1H, d, J=9.6 Hz), 7.85 (1H, dd, J=7.8, 1.0 Hz), 8.07 (1H, d, J=7.8 Hz), 10.11 (1H, s)

Reference Example 153

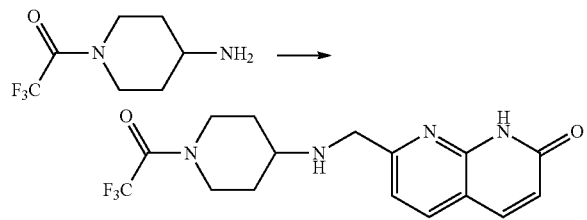

To a solution of 0.53 g of 1-(trifluoroacetyl)piperidin-4-amine in 100 mL of dichloromethane, 0.47 g of 7-oxo-7,8-dihydro-1,8-naphthyridine-2-carbaldehyde and 0.16 mL of acetic acid were added, and the mixture was stirred at room temperature for 45 minutes. The reaction mixture was added with 0.86 g of sodium triacetoxyborohydride and stirred at the same temperature for 5 hours. Thereto were added water, a saturated aqueous sodium hydrogen carbonate solution and chloroform, the organic layer was separated, and the aqueous layer was extracted with chloroform. Sodium chloride was further added to the aqueous layer, and the aqueous layer was extracted with chloroform. The organic layer and the extract were combined, the resultant solution was dried over anhydrous magnesium sulfate, and the solvent was distilled off under reduced pressure. The resultant residue was purified by silica gel column chromatography using an eluent of chloroform:methanol=20:1 to obtain 0.59 g of 7-(((1-(trifluoroacetyl)piperidin-4-yl)amino)methyl)-1,8-naphthyridin-2 (1H)-one as a light orange foam.

¹H-NMR (CDCl₃) δ: 1.42-1.56 (2H, m), 1.98-2.08 (2H, m), 2.85-2.94 (1H, m), 3.01-3.11 (1H, m), 3.19-3.29 (1H, m), 3.93-4.02 (1H, m), 4.06 (2H, s), 4.29-4.38 (1H, m), 6.70 (1H, d, J=9.4 Hz), 7.24 (1H, d, J=7.8 Hz), 7.72 (1H, d, J=9.4 Hz), 7.86 (1H, d, J=7.8 Hz)

Reference Example 154

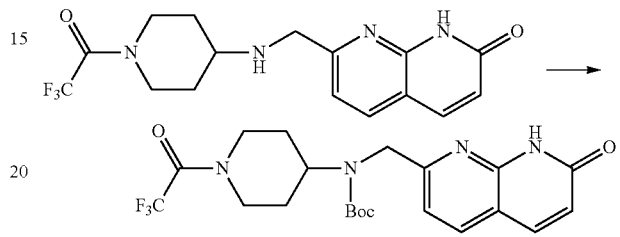

To a solution of 0.58 g of 7-(((1-(trifluoroacetyl)piperidin-4-yl)amino)methyl)-1,8-naphthyridin-2(1H)-one in 25 mL of chloroform, 0.43 g of di-tert-butyl dicarbonate was added, and the mixture was stirred at room temperature for 3 days. Water was added to the reaction mixture, the organic layer was separated, and the aqueous layer was extracted with chloroform. The organic layer and the extract were combined, the resultant solution was washed with a saturated aqueous sodium chloride solution, and dried over anhydrous magnesium sulfate, the solvent was distilled off under reduced pressure, and a mixed solvent of hexane:ethyl acetate (1:1) was added thereto, and the solid was filtered off to obtain 0.56 g of tert-butyl ((7-oxo-7,8-dihydro-1,8-naphthyridin-2-yl)methyl)(1-(trifluoroacetyl)piperidin-4-yl)carbamate as a light pinkish white solid.

¹H-NMR (CDCl₃) δ: 1.29-2.00 (13H, m), 2.67-2.84 (1H, m), 3.06-3.24 (1H, m), 4.06-4.20 (2H, m), 4.35-4.67 (3H, m), 6.69 (1H, d, J=9.5 Hz), 7.04-7.19 (1H, m), 7.70 (1H, d, J=9.5 Hz), 7.85 (1H, d, J=8.0 Hz), 9.69 (1H, s)

Reference Example 155

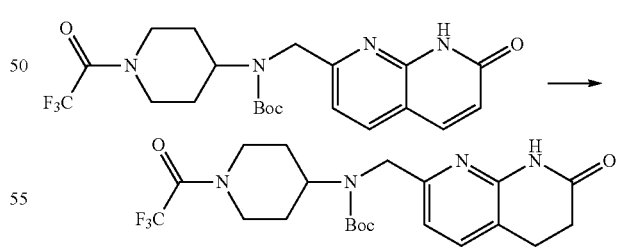

To a solution of 0.30 g of tert-butyl ((7-oxo-7,8-dihydro-1,8-naphthyridin-2-yl)methyl)(1-(trifluoroacetyl)piperidin-4-yl)carbamate in 40 mL of methanol, 0.10 g of 10% palladium-carbon was added, and the mixture was stirred at 45 to 50° C. for 9 hours 30 minutes under a hydrogen atmosphere. The reaction mixture was cooled to room temperature, the insoluble substance was filtered off, and the filtration residue was washed with methanol. The solvent was distilled off under reduced pressure, and the resultant residue was purified by silica gel column chromatography using an eluent of chloroform:methanol=100:3 to obtain 0.18 g of tert-butyl ((7-oxo-5,6,7,8-tetrahydro-1,8-naphthyridin-2-yl)methyl)(1-(trifluoroacetyl)piperidin-4-yl)carbamate as a colorless foam.

$^1$H-NMR (CDCl$_3$) δ: 1.24-1.88 (13H, m), 2.59-2.81 (3H, m), 2.87-2.98 (2H, m), 3.04-3.20 (1H, m), 3.98-4.08 (1H, m), 4.26-4.48 (3H, m), 4.54-4.63 (1H, m), 6.76-6.92 (1H, m), 7.43 (1H, d, J=7.6 Hz), 8.20-8.60 (1H, broad)

Reference Example 156

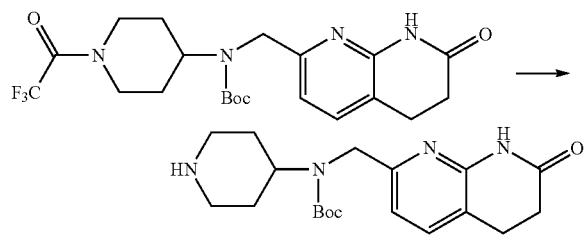

To a solution of 0.30 g of tert-butyl ((7-oxo-5,6,7,8-tetrahydro-1,8-naphthyridin-2-yl)methyl)(1-(trifluoroacetyl)piperidin-4-yl)carbamate in 12 mL of methanol, 0.10 g of potassium carbonate and 3 mL of water were added, and the mixture was stirred at room temperature for 7 hours 30 minutes. To the reaction mixture, water, a saturated aqueous sodium hydrogen carbonate solution and chloroform were added, the organic layer was separated, and the aqueous layer was added with sodium chloride and extracted with chloroform. The organic layer and the extract were combined, the resultant solution was washed with a saturated aqueous sodium chloride solution and dried over anhydrous magnesium sulfate, and the solvent was distilled off under reduced pressure to obtain 0.24 g of tert-butyl ((7-oxo-5,6,7,8-tetrahydro-1,8-naphthyridin-2-yl)methyl)(piperidin-4-yl)carbamate as a colorless foam.

$^1$H-NMR (CDCl$_3$) δ: 1.28-1.78 (13H, m), 2.55-2.72 (4H, m), 2.87-2.97 (2H, m), 3.02-3.12 (2H, m), 4.15-4.50 (3H, m), 6.80-6.91 (1H, m), 7.41 (1H, d, J=7.6 Hz), 8.00-8.30 (1H, broad)

Reference Example 157

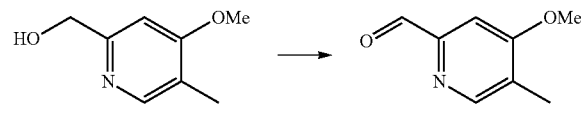

To a solution of 0.13 g of (4-methoxy-5-methylpyridin-2-yl)methanol in 2 mL of dichloromethane, 0.14 g of manganese dioxide was added. The mixture was stirred for 6 hours while dividedly further adding 0.36 g of manganese dioxide at room temperature. The insoluble substance was filtered off, the solvent was distilled off under reduced pressure, and the resultant residue was purified by flash column chromatography using gradient elution of hexane:ethyl acetate=9:1 to 4:1 to obtain 77 mg of 4-methoxy-5-methylpyridine-2-carbaldehyde as a white solid.

$^1$H-NMR (CDCl$_3$) δ: 2.26 (3H, s), 3.95 (3H, s), 7.43 (1H, s), 8.42 (1H, s), 10.00 (1H, s)

Reference Example 158

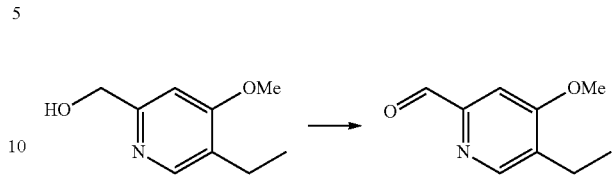

To a solution of 49 mg of (5-ethyl-4-methoxypyridin-2-yl)methanol in 1 mL of dichloromethane, 0.13 g of manganese dioxide was added. The mixture was stirred at room temperature for 1 hour 30 minutes, 0.13 g of manganese dioxide was then added thereto, and the mixture was stirred for 1 hour 30 minutes. Chloroform was added to the reaction mixture, the insoluble substance was filtered off, and the solvent was distilled off under reduced pressure to obtain 54 mg of 5-ethyl-4-methoxypyridine-2-carbaldehyde as a brown oily substance.

$^1$H-NMR (CDCl$_3$) δ: 1.24 (3H, t, J=7.5 Hz), 2.70 (2H, q, J=7.5 Hz), 3.95 (3H, s), 7.45 (1H, s), 8.43 (1H, s), 10.00 (1H, s)

Reference Example 159

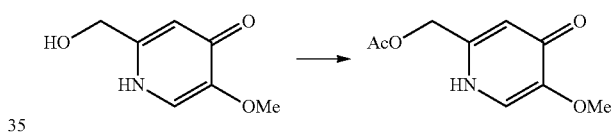

To a suspension of 8.3 g of 2-(hydroxymethyl)-5-methoxypyridin-4(1H)-one in 30 mL of pyridine, 5.7 mL of acetyl chloride was dropped under cooling with ice. After warming to room temperature, the mixture was stirred at 55 to 60° C. for 2 hours 30 minutes. After cooling to room temperature, the solvent was distilled off under reduced pressure, and the resultant residue was purified by flash silica gel column chromatography using gradient elution with chloroform:methanol=95:1 to 80:20 to obtain 6.7 g of (5-methoxy-4-oxo-1,4-dihydropyridin-2-yl)methyl acetate as a brown foam.

$^1$H-NMR (CDCl$_3$) δ: 2.15 (3H, s), 3.86 (3H, s), 5.15 (2H, s), 6.83 (1H, s), 7.68 (1H, s)

Reference Example 160

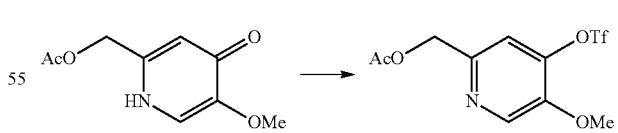

To a solution of 4.6 g of (5-methoxy-4-oxo-1,4-dihydropyridin-2-yl)methyl acetate in 120 mL of dichloromethane, 6.5 mL of triethylamine was added, 5.9 mL of trifluoromethanesulfonic anhydride was dropped under cooling with ice, and the mixture was stirred at the same temperature for 3 hours. Water and the chloroform were added to the reaction mixture, the organic layer was separated, and the aqueous layer was extracted with chloroform. The organic layer and the extract were combined, the resultant solution was dried over anhydrous magnesium sulfate, and the solvent was distilled off under reduced pressure. The resultant residue was purified by flash silica gel column chromatography using gradient elution with hexane:ethyl acetate=4:1 to 4:6 to obtain 5.2 g of (5-methoxy-4-(((trifluoromethyl)sulfonyl) oxy)pyridin-2-yl)methyl acetate as a yellow solid.

$^1$H-NMR (CDCl$_3$) δ: 2.16 (3H, S), 4.03 (3H, s), 5.18 (2H, s), 7.26 (1H, s), 8.43 (1H, s)

Reference Example 161

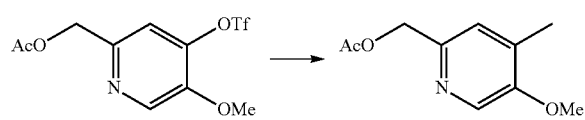 [SMILES: COc1cnc(COC(C)=O)cc1OS(=O)(=O)C(F)(F)F ; COc1cnc(COC(C)=O)cc1C]

To a solution of 0.50 g of (5-methoxy-4-(((trifluoromethyl) sulfonyl)oxy)pyridin-2-yl)methyl acetate in 5 mL of dioxane, 0.63 g of potassium carbonate, 0.21 mL of trimethylboroxin and 0.18 g of tetrakis(triphenylphosphine)palladium(0) were added, and the mixture was stirred at 70 to 90° C. for 3 hours under a nitrogen atmosphere. The mixture was heated under reflux while further stirring for 3 hours, after cooling to room temperature, water and ethyl acetate were added to the reaction mixture, and the organic layer was separated. The aqueous layer was extracted with ethyl acetate, the organic layer and the extract were combined, the resultant solution was dried over anhydrous magnesium sulfate, and the solvent was distilled off under reduced pressure. The resultant residue was purified by flash silica gel column chromatography using gradient elution with hexane:ethyl acetate=80:20 to 50:50 to obtain 0.22 g of (5-methoxy-4-methylpyridin-2-yl)methyl acetate as a yellow oily substance.

$^1$H-NMR (CDCl$_3$) δ: 2.13 (3H, s), 2.23 (3H, s), 3.92 (3H, s), 5.12 (2H, s), 7.15 (1H, s), 8.14 (1H, s)

Reference Example 162

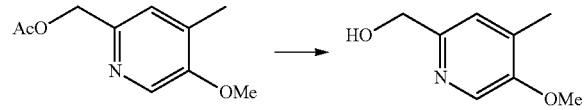

To a solution of 0.21 g of (5-methoxy-4-methylpyridin-2-yl)methyl acetate in 2 mL of methanol, 0.64 mL of a 20% aqueous sodium hydroxide solution was added, and the mixture was stirred at room temperature for 1 hour. The solvent was distilled off under reduced pressure, water and ethyl acetate were added to the resultant residue, the organic layer was separated, and the aqueous layer was extracted with ethyl acetate. The organic layer and the extract were combined, the resultant solution was dried over anhydrous magnesium sulfate, and the solvent was distilled off under reduced pressure to obtain 0.16 g of (5-methoxy-4-methylpyridin-2-yl)methanol as a white solid.

$^1$H-NMR (CDCl$_3$) δ: 2.24 (3H, s), 3.92 (3H, s), 4.66 (2H, s), 7.02 (1H, s), 8.09 (1H, s)

Reference Example 163

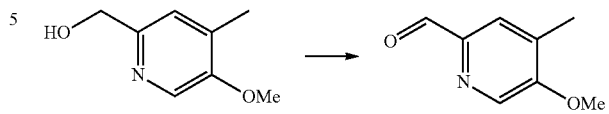

By the same technique as in Reference Example 67, 5-methoxy-4-methylpyridine-2-carbaldehyde was obtained from (5-methoxy-4-methylpyridin-2-yl)methanol.

$^1$H-NMR (CDCl$_3$) δ: 2.29 (3H, s), 4.03 (3H, s), 7.80 (1H, s), 8.31 (1H, s), 9.96 (1H, s)

Reference Example 164

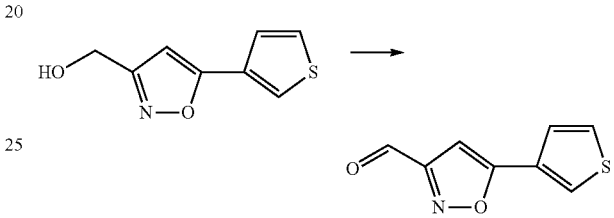

To a solution of 30 mg of (5-(3-thienyl)isoxazol-3-yl) methanol in 5 mL of dichloromethane, 84 mg of Dess-Martin periodinane was added under cooling with ice, and the mixture was stirred at room temperature for 1 hour 30 minutes. Thereto was further added 40 mg of Dess-Martin periodinane, and the mixture was stirred at room temperature for 1 hour 30 minutes. Diethyl ether was added to the reaction mixture, the insoluble substance was filtered off, and the solvent was distilled off under reduced pressure to obtain 30 mg of 5-(3-thienyl)isoxazole-3-carbaldehyde as a yellow solid.

$^1$H-NMR (CDCl$_3$) δ: 6.75 (1H, s), 7.42-7.49 (2H, m), 7.88 (1H, dd, J=2.8, 1.3 Hz), 10.18 (1H, s)

Reference Example 165

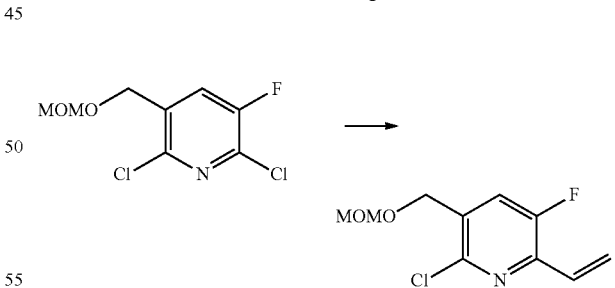

To a solution of 0.85 g of 2,6-dichloro-3-fluoro-5-((methoxymethoxy)methyl)pyridine in 8 mL of N,N-dimethylformamide, 0.45 g of lithium chloride was added at room temperature, one piece of 2,6-di-tert-butyl-4-methylphenol, 1.04 mL of tributyl(vinyl)tin and 50 mg of bis(triphenylphosphine)palladium (II) dichloride were added at room temperature. Under a nitrogen atmosphere, the mixture was stirred at 40 to 50° C. for 1 hour, and stirred at 50 to 60° C. for 1 hour 30 minutes, and then stirred at 70 to 80° C. for 1 hour. After cooling to room temperature, the solvent was distilled off under reduced pressure, and the resultant residue was purified by flash silica gel column chromatography using an eluent of chloroform:methanol=9:1 to obtain 0.51 g of a crude product of 2-chloro-5-fluoro-3-((methoxymethoxy)methyl)-6-vinylpyridine as a slightly yellow oily substance.

Reference Example 166

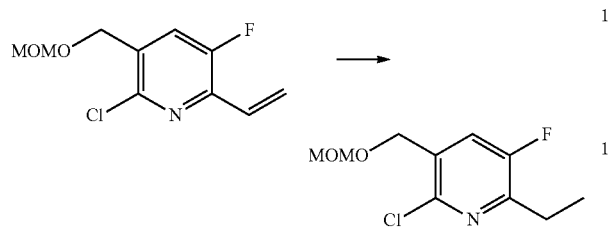

To a solution of 0.47 g of the crude product of 2-chloro-5-fluoro-3-((methoxymethoxy)methyl)-6-vinylpyridine obtained in Reference Example 165 in 5 mL of methanol, 0.24 g of 10% palladium-carbon was added, and the mixture was stirred at 40° C. for 1 hour under a hydrogen atmosphere. The insoluble substance was filtered off, the solvent was distilled off under reduced pressure, and the resultant residue was purified by flash silica gel column chromatography using an eluent of chloroform:methanol=19:1 to obtain 0.36 g of a crude product of 2-chloro-6-ethyl-5-fluoro-3-((methoxymethoxy)methyl)pyridine as a colorless oily substance.

Reference Example 167

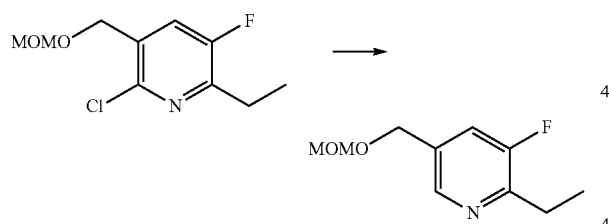

To a solution of 0.33 g of the crude product of 2-chloro-6-ethyl-5-fluoro-3-((methoxymethoxy)methyl)pyridine obtained in Reference Example 166 in 3 mL of N,N-dimethylformamide, 0.16 g of tetrakis(triphenylphosphine)palladium(0) and 0.98 mL of triethylamine were added at room temperature, and 0.27 mL of formic acid was dropped thereto. The mixture was stirred at 70 to 80° C. for 45 minutes under a nitrogen atmosphere. After cooling to room temperature, water and ethyl acetate were added to the reaction mixture, the insoluble substance was filtered off, the organic layer was separated, and the aqueous layer was extracted with ethyl acetate. The organic layer and the extract were combined, the resultant solution was washed with water and a saturated aqueous sodium chloride solution and dried over anhydrous magnesium sulfate, and the solvent was distilled off under reduced pressure. The resultant residue was purified by flash silica gel column chromatography using an eluent of chloroform:methanol=9:1 to obtain 0.11 g of 2-ethyl-3-fluoro-5-((methoxymethoxy)methyl)pyridine as a colorless oily substance.

$^1$H-NMR (CDCl$_3$) δ: 1.29 (3H, t, J=7.6 Hz), 2.87 (2H, qd, J=7.6, 2.3 Hz), 3.41 (3H, s), 4.59 (2H, s), 4.71 (2H, s), 7.35 (1H, dd, J=10.0, 1.7 Hz), 8.31 (1H, s)

Reference Example 168

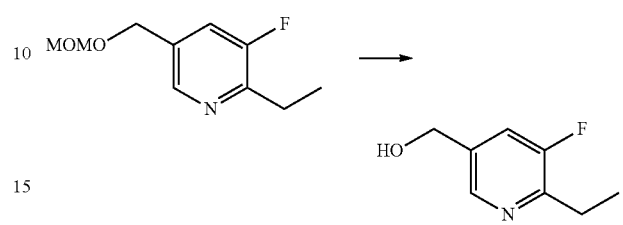

To a solution of 0.11 g of 2-ethyl-3-fluoro-5-((methoxymethoxy)methyl)pyridine in 2 mL of 1,4-dioxane, 1 mL of 6 mol/L hydrochloric acid was added, and the mixture was stirred at 30 to 40° C. for 1 hour. After cooling to room temperature, the reaction mixture was charged with water and ethyl acetate and adjusted to pH 7.9 with a 20% aqueous sodium hydroxide solution and a saturated aqueous sodium hydrogen carbonate solution. The organic layer was separated, and the aqueous layer was extracted with ethyl acetate. The organic layer and the extract were combined, the resultant solution was washed with water and a saturated aqueous sodium chloride solution and dried over anhydrous magnesium sulfate, and the solvent was distilled off under reduced pressure to obtain 87 mg of (6-ethyl-5-fluoropyridin-3-yl)methanol as a light yellow oily substance.

$^1$H-NMR (CDCl$_3$) δ: 1.29 (3H, t, J=7.6 Hz), 1.93-2.05 (1H, broad), 2.87 (1H, qd, J=7.6, 2.3 Hz), 4.72 (2H, d, J=3.4 Hz), 7.39 (1H, dd, J=10.1, 1.6 Hz), 8.30 (1H, s)

Reference Example 169

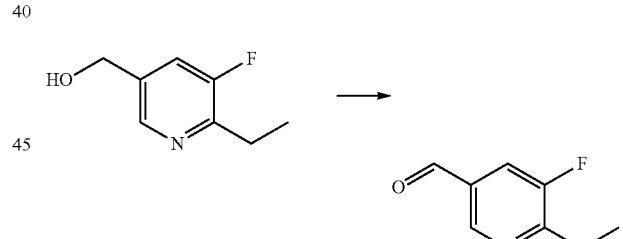

By the same technique as in Reference Example 67, 6-ethyl-5-fluoronicotinaldehyde was obtained from (6-ethyl-5-fluoropyridin-3-yl)methanol.

$^1$H-NMR (CDCl$_3$) δ: 1.34 (3H, t, J=7.6 Hz), 2.97 (2H, t, J=7.6, 2.4 Hz), 7.77 (1H, dd, J=9.0, 1.7 Hz), 8.80 (1H, s), 10.09 (1H, d, J=2.2 Hz)

Reference Example 170

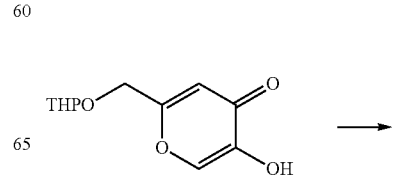

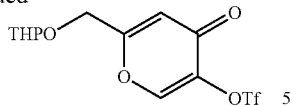

To a solution of 2.0 g of 5-hydroxy-2-((tetrahydro-2H-pyran-2-yloxy)methyl)-4H-pyran-4-one in 20 mL of dichloromethane, 2.1 mL of triethylamine was added, 1.9 mL of trifluoromethanesulfonic anhydride was dropped under cooling with ice, and the mixture was stirred for 40 minutes. Water and chloroform were added to the reaction mixture, the organic layer was separated, and the aqueous layer was extracted with chloroform. The resultant solution was dried over anhydrous magnesium sulfate, and the solvent was distilled off under reduced pressure. The resultant residue was purified by silica gel column chromatography using an eluent of hexane:ethyl acetate=2:1 to obtain 2.9 g of 4-oxo-6-((tetrahydro-2H-pyran-2-yloxy)methyl)-4H-pyran-3-yl trifluoromethanesulfonate as a light brown solid.

$^1$H-NMR (CDCl$_3$) δ: 1.53-1.90 (6H, m), 3.55-3.62 (1H, m), 3.77-3.85 (1H, m), 4.38 (1H, dd, J=14.9, 0.7 Hz), 4.57 (1H, dd, 14.9, 0.7 Hz), 4.74 (1H, t, J=3.2 Hz), 6.66 (1H, s), 8.05 (1H, s)

Reference Example 171

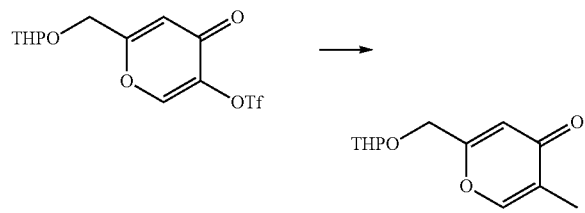

To a solution of 1.0 g of 4-oxo-6-((tetrahydro-2H-pyran-2-yloxy)methyl)-4H-pyran-3-yl trifluoromethanesulfonate in 10 mL of dioxane, 1.2 g of potassium carbonate, 0.4 mL of trimethylboroxin and 0.33 g of tetrakis(triphenylphosphine)palladium(0) were added, and the mixture was stirred at 70 to 80° C. for 2 hours under an argon atmosphere. After cooling to room temperature, water and ethyl acetate were added to the reaction mixture, and the organic layer was separated. The aqueous layer was extracted with ethyl acetate, the organic layer and the extract were combined, the resultant solution was dried over anhydrous magnesium sulfate, and the solvent was distilled off under reduced pressure. The resultant residue was purified by silica gel column chromatography using an eluent of hexane:ethyl acetate=1:1 to obtain 0.62 g of 5-methyl-2-((tetrahydro-2H-pyran-2-yloxy)methyl)-4H-pyran-4-one as a brown oily substance.

$^1$H-NMR (CDCl$_3$) δ: 1.20-1.66 (6H, m), 1.66 (3H, s), 3.25-3.35 (1H, m), 3.53-3.63 (1H, m), 4.06 (1H, d, J=14.4 Hz), 4.25 (1H, d, J=14.4 Hz), 4.47 (1H, t, J=3.3 Hz), 6.16 (1H, s), 7.43 (1H, s)

Reference Example 172

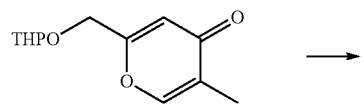

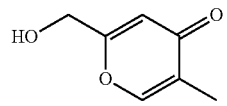

To a solution of 0.61 g of 5-methyl-2-((tetrahydro-2H-pyran-2-yloxy)methyl)-4H-pyran-4-one in 3 mL of methanol, 0.03 mL of concentrated hydrochloric acid was added, and the mixture was stirred at room temperature for 1 hour. To the reaction mixture, 0.5 g of potassium carbonate and chloroform were added, and the mixture was stirred for 30 minutes. The insoluble substance was filtered off, the solvent was distilled off under reduced pressure, and the resultant residue was purified by silica gel column chromatography using an eluent of chloroform:methanol=9:1 to obtain 0.26 g of 2-hydroxymethyl-5-methyl-4H-pyran-4-one as a white solid.

$^1$H-NMR (CDCl$_3$) δ: 1.92 (3H, d, J=1.1 Hz), 3.03 (1H, t, J=6.7 Hz), 4.47 (2H, d, J=6.7 Hz), 6.43 (1H, s), 7.66 (1H, d, J=1.1 Hz)

Reference Example 173

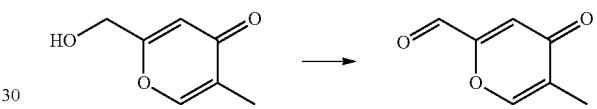

By the same technique as in Reference Example 67, 5-methyl-4-oxo-4H-pyran-2-carbaldehyde was obtained from 2-hydroxymethyl-5-methyl-4H-pyran-4-one.

$^1$H-NMR (CDCl$_3$) δ: 1.99 (3H, d, J=1.2 Hz), 6.89 (1H, s), 7.80 (1H, s), 9.67 (1H, s)

Reference Example 174

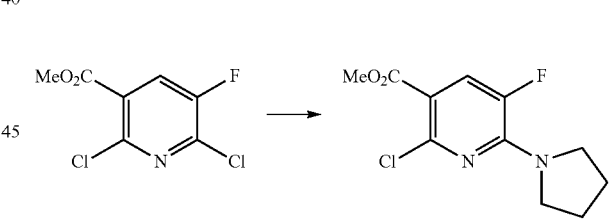

To a solution of 1.5 g of methyl 2,6-dichloro-5-fluoronicotinate in 15 mL of N,N-dimethylformamide, 0.93 mL of triethylamine was added at room temperature, and thereto was dropped 0.56 mL of pyrrolidine. The mixture was stirred at the same temperature for 1 hour, 56 μL of pyrrolidine was further added, and the mixture was stirred for 50 minutes. After leaving overnight, ethyl acetate and water were added to the reaction mixture. The organic layer was separated, and the aqueous layer was extracted with ethyl acetate. The organic layer and the extract were combined, the resultant solution was washed with water and a saturated aqueous sodium chloride solution, and dried over anhydrous magnesium sulfate, and the solvent was distilled off under reduced pressure to obtain 1.7 g of methyl 2-chloro-5-fluoro-6-(pyrrolidin-1-yl)nicotinate as a white solid.

$^1$H-NMR (CDCl$_3$) δ: 1.90-1.99 (4H, m), 3.66-3.74 (4H, m), 3.86 (3H, s), 7.73 (1H, dd, J=13.0, 0.6 Hz)

Reference Example 175

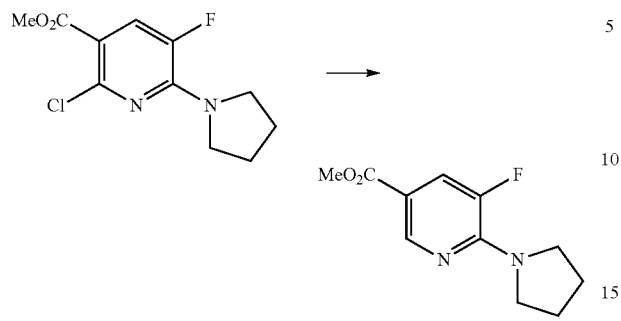

To a solution of 1.7 g of methyl 2-chloro-5-fluoro-6-(pyrrolidin-1-yl)nicotinate in 15 mL of N,N-dimethylformamide, 0.38 g of tetrakis(triphenylphosphine)palladium(0) and 1.4 mL of triethylamine were added at room temperature, and 0.37 mL of formic acid was dropped thereto. The mixture was stirred at 80 to 90° C. for 2 hours 30 minutes under a nitrogen atmosphere. After cooling to room temperature, water and ethyl acetate were added to the reaction mixture, the organic layer was separated, and the aqueous layer was extracted with ethyl acetate. The organic layer and the extract were combined, and the resultant solution was washed with a saturated aqueous sodium chloride solution. To the organic layer, a mixed solvent of chloroform:methanol was added, the organic layer was dried over anhydrous magnesium sulfate, and the solvent was distilled off under reduced pressure. To the resultant residue, a mixed solvent of diethyl ether:ethyl acetate (1:2) was added, the insoluble substance was filtered off, and the solvent was distilled off under reduced pressure. The resultant residue was purified by flash silica gel column chromatography using an eluent of chloroform to obtain 1.3 g of methyl 5-fluoro-6-(pyrrolidin-1-yl)nicotinate as a light yellow solid.

$^1$H-NMR (CDCl$_3$) δ: 1.95-1.99 (4H, m), 3.69-3.75 (4H, m), 3.86 (3H, s), 7.65 (1H, d, J=14.0, 1.8 Hz), 8.56 (1H, t, 1.8 Hz)

Reference Example 176

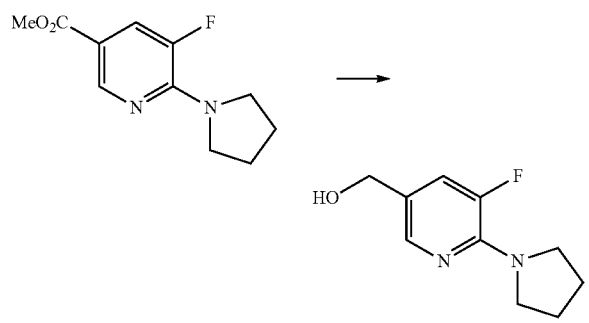

To a solution of 0.24 g of lithium aluminum hydride in 5 mL of THF, a solution of 0.70 g of methyl 5-fluoro-6-(pyrrolidin-1-yl)nicotinate in 5 mL of tetrahydrofuran was dropped under cooling with ice. After warming to room temperature, the mixture was stirred for 45 minutes, thereto was dropped a saturated aqueous sodium hydrogen carbonate solution under cooling with ice, and the mixture was stirred for 10 minutes. The reaction mixture was filtered, and the filtration residue was washed with ethyl acetate and water. The organic layer of the filtrate was separated, and the aqueous layer was extracted with ethyl acetate. The organic layer and the extract were combined, the resultant solution was washed with water and a saturated aqueous sodium chloride solution, and dried over anhydrous magnesium sulfate, and the solvent was distilled off under reduced pressure to obtain 0.68 g of (5-fluoro-6-(pyrrolidin-1-yl)pyridin-3-yl)methanol as a brown oily substance.

$^1$H-NMR (CDCl$_3$) δ: 1.52-1.57 (1H, m), 1.92-1.98 (4H, m), 3.61-3.66 (4H, m), 4.52-4.56 (2H, m), 7.21 (1H, dd, J=13.9, 1.8 Hz), 7.87 (1H, t, J=1.8 Hz)

Reference Example 177

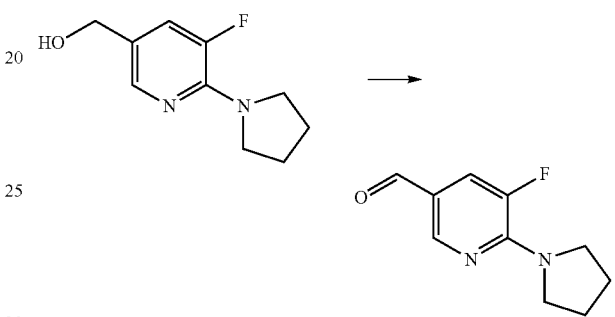

By the same technique as in Reference Example 67, 5-fluoro-6-(pyrrolidin-1-yl)nicotinaldehyde was obtained from (5-fluoro-6-(pyrrolidin-1-yl)pyridin-3-yl)methanol.

$^1$H-NMR (CDCl$_3$) δ: 1.97-2.03 (4H, m), 3.74-3.80 (4H, m), 7.56 (1H, dd, J=13.5, 1.8 Hz), 8.32 (1H, t, J=1.8 Hz), 9.76 (1H, d, J=3.2 Hz)

Reference Example 178

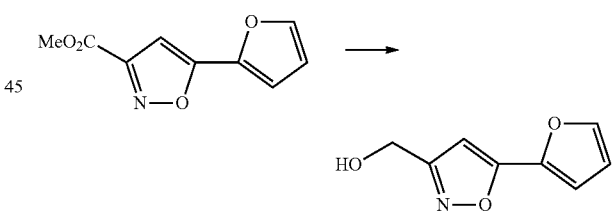

By the same technique as in Reference Example 58, (5-(2-furyl)isoxazol-3-yl)methanol was obtained from methyl 5-(2-furyl)isoxazole-3-carboxylate.

$^1$H-NMR (CDCl$_3$) δ: 1.94-1.99 (1H, m), 4.81 (2H, d, J=6.4 Hz), 6.50 (1H, s), 6.54 (1H, dd, J=3.6, 1.6 Hz), 6.91 (1H, d, J=3.6 Hz), 7.53-7.56 (1H, m)

Reference Example 179

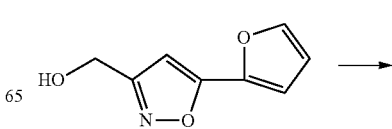

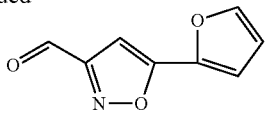

By the same technique as in Reference Example 164, 5-(2-furyl)isoxazole-3-carbaldehyde was obtained from (5-(2-furyl)isoxazol-3-yl)methanol.

¹H-NMR (CDCl₃) δ: 6.58 (1H, dd, J=3.6, 1.7 Hz), 6.80 (1H, s), 7.01 (1H, d, J=3.6 Hz), 7.60 (1H, d, J=1.7 Hz), 10.18 (1H, s)

Reference Example 180

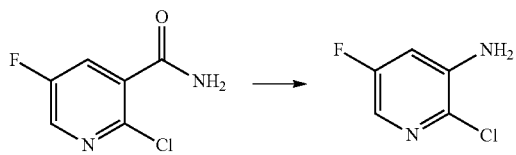 [SMILES: NC(=O)c1cc(F)cnc1Cl ; Nc1cc(F)cnc1Cl]

To a solution of 0.11 kg of sodium hydroxide in 1000 mL of water, 1.4 kg of a 12% aqueous sodium hypochlorite solution and 0.40 kg of 2-chloro-5-fluoronicotinamide were added, and the mixture was stirred at room temperature for 2 hours 30 minutes. The reaction mixture was heated to 45° C. and stirred for 4 hours. The reaction mixture was cooled to room temperature, and thereto were added ethyl acetate and a 6 mol/L aqueous hydrochloric acid solution. The organic layer was separated, and the aqueous layer was extracted with ethyl acetate. The organic layer and the extract were combined, anhydrous magnesium sulfate and active carbon were added thereto, and the mixture was stirred at room temperature for 30 minutes. The insoluble substance was filtered off, and the solvent was distilled off under reduced pressure to obtain 0.29 kg of 2-chloro-5-fluoropyridin-3-amine as a brown solid.

¹H-NMR (CDCl₃) δ: 4.22 (2H, s), 6.79 (1H, dd, J=9.3, 2.7 Hz), 7.67 (1H, d, J=2.7 Hz)

Reference Example 181

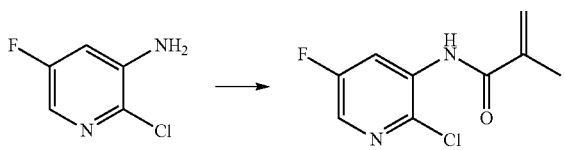

To a solution of 1.2 g of 2-chloro-5-fluoropyridin-3-amine in 5 mL of pyridine, 0.86 mL of 2-methylacryloyl chloride was added under cooling with ice, and the mixture was stirred at room temperature for 30 minutes. To the reaction mixture, water and ethyl acetate were added, the organic layer was separated, and the aqueous layer was extracted with ethyl acetate. The organic layer and the extract were combined, the resultant solution was washed sequentially with water and a saturated aqueous sodium chloride solution, and dried over anhydrous magnesium sulfate, and the solvent was distilled off under reduced pressure. The resultant residue was purified by flash silica gel column chromatography using gradient elution with hexane:ethyl acetate=100:0 to 50:50 to obtain 1.1 g of N-(2-chloro-5-fluoropyridin-3-yl)-2-methylacrylamide as a colorless oily substance.

¹H-NMR (CDCl₃) δ: 2.11 (3H, dd, J=1.5, 1.0 Hz), 5.60-5.63 (1H, m), 5.93-5.96 (1H, m), 7.99-8.02 (1H, m), 8.15 (1H, s), 8.72 (1H, dd, J=9.9, 2.8 Hz)

Reference Example 182

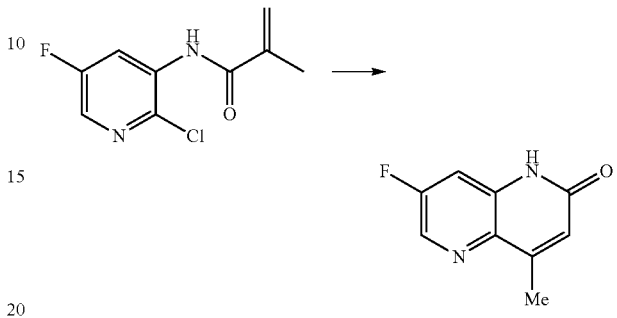

To a solution of 1.1 g of N-(2-chloro-5-fluoropyridin-3-yl)-2-methylacrylamide in 10 mL of N,N-dimethylformamide, 1.5 mL of triethylamine and 0.13 g of bis(tri-tert-butylphosphine)palladium(0) were added, and the mixture was stirred at 110° C. for 3 hours 40 minutes under a nitrogen flow. Thereto was further added 0.13 g of bis(tri-tert-butylphosphine)palladium(0), and the mixture was stirred for 2 hours. Thereto was further added 0.13 g of bis(tri-tert-butylphosphine)palladium(0), and the mixture was stirred for 2 hours. The reaction mixture was cooled to room temperature, the solvent was then distilled off under reduced pressure, and diisopropyl ether and ethyl acetate were added to the resultant residue, the solid was filtered off, and washed with ethyl acetate, to the solid thus obtained, water, chloroform and methanol were added, the organic layer was separated and the aqueous layer was extracted with chloroform. The organic layer and the extract were combined, the resultant solution was dried over anhydrous magnesium sulfate, and the solvent was distilled off under reduced pressure. To the resultant residue, diisopropyl ether was added, and the solid was filtered off to obtain 0.25 g of 7-fluoro-4-methyl-1,5-naphthyridin-2(1H)-one as a light brown solid.

¹H-NMR (DMSO-d₆) δ: 2.45 (3H, d, J=1.0 Hz), 6.61-6.64 (1H, m), 7.45 (1H, dd, J=9.6, 2.6 Hz), 8.51 (1H, d, J=2.6 Hz), 11.78-11.83 (1H, broad)

Reference Example 183

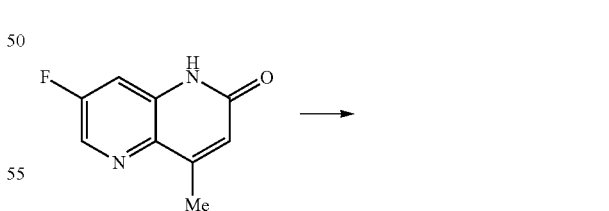

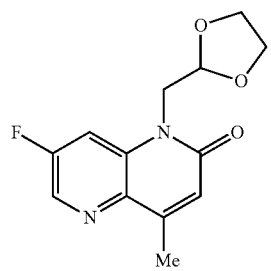

By the same technique as in Reference Example 3, 1-(1,3-dioxolan-2-ylmethyl)-7-fluoro-4-methyl-1,5-naphthyridin-2(1H)-one was obtained from 7-fluoro-4-methyl-1,5-naphthyridin-2(1H)-one and 2-bromomethyl-1,3-dioxolan.

¹H-NMR (CDCl₃) δ: 2.54 (3H, d, J=1.2 Hz), 3.82-4.06 (4H, m), 4.43 (2H, d, J=4.1 Hz), 5.18 (1H, t, J=4.1 Hz), 6.75-6.78 (1H, m), 7.67 (1H, dd, J=10.6, 2.4 Hz), 8.41 (1H, d, J=2.4 Hz)

Reference Example 184

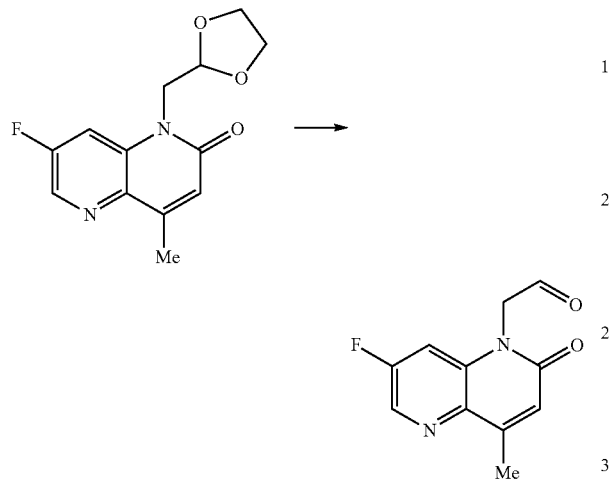

By the same technique as in Reference Example 4, (7-fluoro-4-methyl-2-oxo-1,5-naphthyridin-1(2H)-yl)acetaldehyde was obtained from 1-(1,3-dioxolan-2-ylmethyl)-7-fluoro-4-methyl-1,5-naphthyridin-2(1H)-one.

¹H-NMR (CDCl₃) δ: 2.58 (3H, s), 5.11 (2H, s), 6.80 (1H, s), 7.02 (1H, dd, J=9.6, 2.3 Hz), 8.45 (1H, d, J=2.3 Hz), 9.75 (1H, s)

Reference Example 185

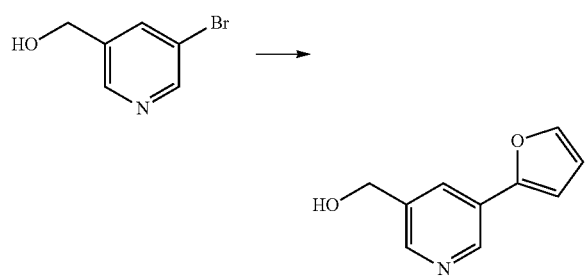

To a solution of 0.10 g of (5-bromopyridin-3-yl)methanol in 5 mL of dioxane, 72 mg of 2-furanboronic acid, 67 mg of lithium chloride, 0.51 g of cesium carbonate, 5.4 mg of palladium acetate and 20 mg of 2-dicyclohexylphosphino-2',6'-dimethoxybiphenyl were added at room temperature, and the mixture was heated under reflux for 1 hour 30 minutes under a nitrogen atmosphere. The reaction mixture was cooled to room temperature, and the solvent was then distilled off under reduced pressure. The resultant residue was purified by flash silica gel column chromatography using gradient elution with chloroform:methanol=95:5 to 90:10 to obtain 39 mg of (5-(2-furyl)pyridin-3-yl)methanol as a yellow oily substance.

¹H-NMR (CDCl₃) δ: 1.50-1.80 (1H, broad), 4.78 (2H, s), 6.52 (1H, dd, J=3.4, 1.7 Hz), 6.77 (1H, d, J=3.4 Hz), 7.53 (1H, d, J=1.7 Hz), 7.98 (1H, s), 8.47 (1H, d, J=1.8 Hz), 8.85 (1H, d, J=1.8 Hz)

Reference Example 186

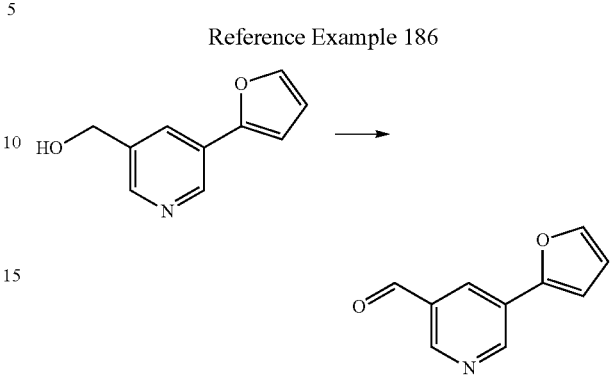

By the same technique as in Reference Example 164, 5-(2-furyl)nicotinaldehyde was obtained from (5-(2-furyl)pyridin-3-yl)methanol.

¹H-NMR (CDCl₃) δ: 6.56 (1H, dd, J=3.3, 1.7 Hz), 6.88 (1H, d, J=3.3 Hz), 7.58 (1H, d, J=1.7 Hz), 8.39 (1H, t, J=1.9 Hz), 8.95 (1H, d, J=1.9 Hz), 9.15 (1H, d, J=1.9 Hz), 10.16 (1H, s)

Reference Example 187

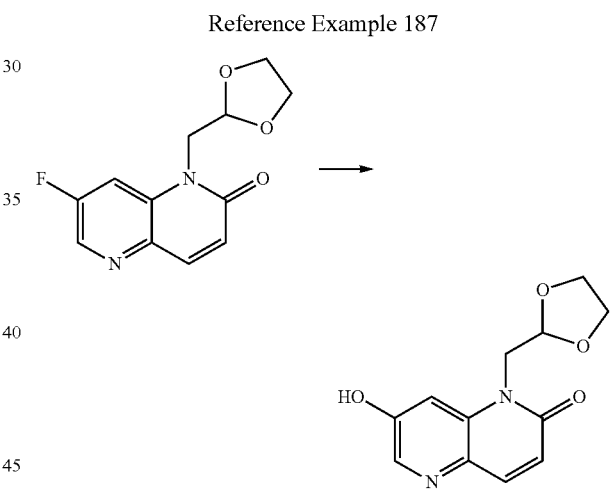

To a suspension of 0.50 g of 1-(1,3-dioxolan-2-ylmethyl)-7-fluoro-1,5-naphthyridin-2(1H)-one in 3 mL of tetrahydrofuran, 3 mL of a 20% aqueous sodium hydroxide solution was added, and the mixture was heated under reflux while stirring for 1 hour. Thereto was added 3 mL of water, and the mixture was heated under reflux while stirring for 3 hours 30 minutes. Thereto was added 3 mL of a 20% aqueous sodium hydroxide solution, and the mixture was heated under reflux while stirring for 4 hours. Tetrahydrofuran was distilled off under reduced pressure, and the mixture was then heated under reflux while stirring for 1 hour 30 minutes. After cooling to room temperature, the reaction mixture was added with 2 mol/L hydrochloric acid and adjusted to pH 5. Thereto was added ethyl acetate, the organic layer was separated, and the aqueous layer was extracted twice with ethyl acetate. The organic layer and the extract were combined, the resultant solution was washed with a saturated aqueous sodium chloride solution and dried over anhydrous magnesium sulfate, and the solvent was distilled off under reduced pressure. Diethyl ether was added to the resultant residue, and the solid was filtered off to obtain 0.32 g of 1-(1,3-dioxolan-2-ylmethyl)-7-hydroxy-1,5-naphthyridin-2(1H)-one as a yellow solid.

¹H-NMR (DMSO-d₆) δ: 3.76-3.86 (2H, m), 3.92-4.06 (2H, m), 4.32 (2H, d, J=4.6 Hz), 5.08 (1H, t, J=4.6 Hz), 6.61 (1H, d, J=9.6 Hz), 7.37 (1H, d, J=2.2 Hz), 7.84 (1H, d, J=9.6 Hz), 8.14 (1H, d, J=2.2 Hz), 10.6-11.0 (1H, broad)

Reference Example 188

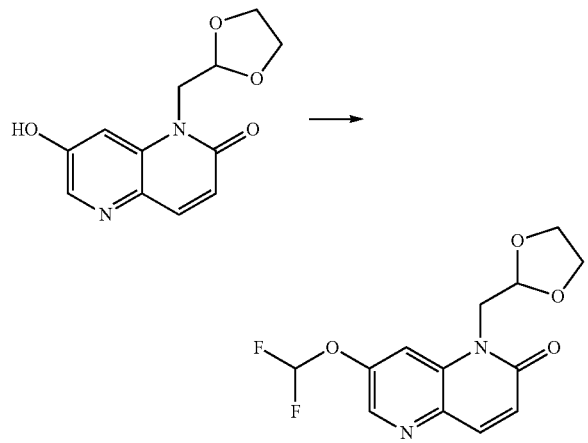

To a suspension of 0.15 g of 1-(1,3-dioxolan-2-ylmethyl)-7-hydroxy-1,5-naphthyridin-2(1H)-one in 1.5 mL of toluene, 1 mL of a 40% aqueous sodium hydroxide solution, 97 mg of tetrabutylammonium bromide and 0.25 mL of an N,N-dimethylformamide solution of 10 mol/L chloro(difluoro)methane were added, the mixture was stirred for 50 minutes, then, thereto was added 1 mL of an N,N-dimethylformamide solution of 10 mol/L chloro(difluoro)methane, and the mixture was stirred for 3 hours 40 minutes. Water and toluene were added to the reaction mixture, the organic layer was separated, and the aqueous layer was extracted with toluene. The organic layer and the extract were combined, the resultant solution was washed sequentially with water and a saturated aqueous sodium chloride solution and dried over anhydrous magnesium sulfate, and the solvent was distilled off under reduced pressure to obtain 95 mg of 7-(difluoromethoxy)-1-(1,3-dioxolan-2-ylmethyl)-1,5-naphthyridin-2(1H)-one as a light brown solid.

¹H-NMR (CDCl₃) δ: 3.83-4.04 (4H, m), 4.47 (2H, d, J=4.2 Hz), 5.20 (1H, t, J=4.2 Hz), 6.65 (1H, t, J=72.2 Hz), 6.90 (1H, d, J=9.9 Hz), 7.77 (1H, d, J=2.2 Hz), 7.90 (1H, dd, J=9.9, 0.7 Hz), 8.40 (1H, d, J=2.2 Hz)

Reference Example 189

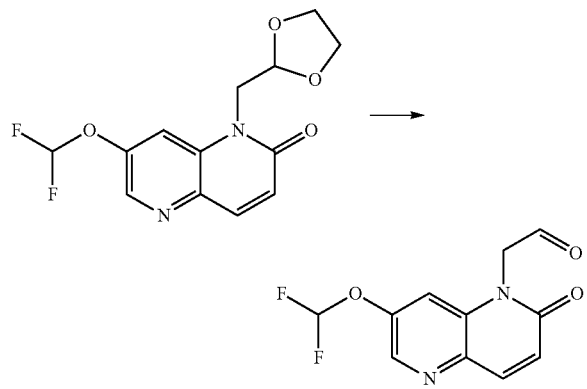

By the same technique as in Reference Example 4, (7-(difluoromethoxy)-2-oxo-1,5-naphthyridin-1(2H)-yl)acetaldehyde was obtained from 7-(difluoromethoxy)-1-(1,3-dioxolan-2-ylmethyl)-1,5-naphthyridin-2(1H)-one.

¹H-NMR (CDCl₃) δ: 5.13 (2H, s), 6.63 (1H, t, J=71.9 Hz), 6.94 (1H, d, J=9.8 Hz), 7.09 (1H, d, J=2.2 Hz), 7.95-8.00 (1H, m), 8.45 (1H, d, J=2.2 Hz), 9.77 (1H, s)

Reference Example 190

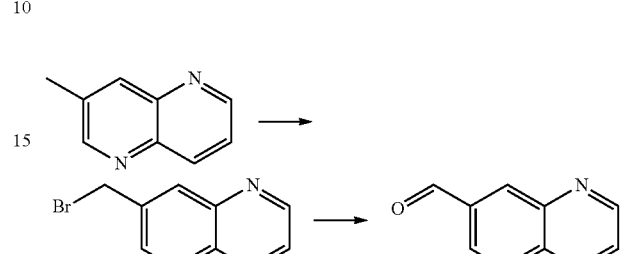

To a solution of 0.26 g of 3-methyl-1,5-naphthyridine in 4 mL of benzene, 0.35 g of N-bromosuccinimide and 29 mg of azobisisobutyronitrile were added, and the mixture was heated under reflux while stirring for 2 hours 15 minutes. Thereto was further added 0.13 g of N-bromosuccinimide, and the mixture was heated under reflux while stirring for 30 minutes. After cooling to room temperature, a solution of 0.50 g of hexamethylenetetramine in 1.5 mL of water was dropped to the reaction mixture under cooling with ice, thereto was added 1.5 mL of acetic acid, and the mixture was heated under reflux while stirring for 1 hour 20 minutes. After cooling to room temperature, chloroform and a 20% aqueous sodium hydroxide solution were added to the reaction mixture and the mixture was adjusted to pH 8.5. The organic layer was separated, and the aqueous layer was extracted with chloroform. The organic layer and the extract were combined, the resultant solution was washed with water and a saturated aqueous sodium chloride solution and dried over anhydrous magnesium sulfate. The solvent was distilled off under reduced pressure, and the resultant residue was purified by flash silica gel column chromatography using an eluent of hexane:ethyl acetate=1:1 to obtain 25 mg of 1,5-naphthyridine-3-carbaldehyde as a slightly yellow solid.

¹H-NMR (CDCl₃) δ: 7.80 (1H, dd, 8.5, 4.2 Hz), 8.49-8.52 (1H, m), 8.82-8.85 (1H, m), 9.12 (1H, dd, J=4.2, 1.5 Hz), 9.46 (1H, d, J=2.2 Hz), 10.35 (1H, s)

Reference Example 191

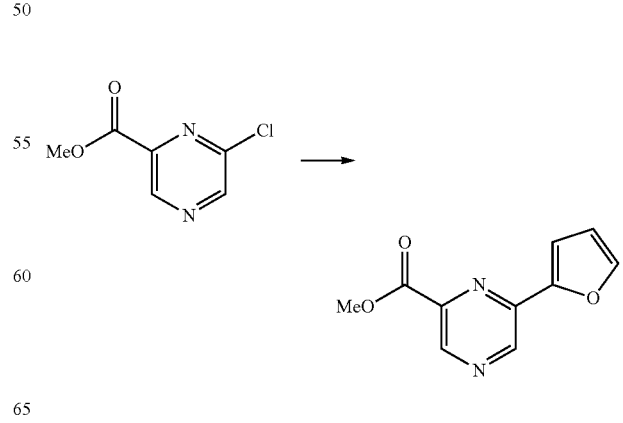

To a solution of 0.10 g of methyl 6-chloropyrazine-2-carboxylate in 2.9 mL of dioxane, 65 mg of 2-furanboronic acid, 74 mg of lithium chloride, 0.57 g of cesium carbonate, 21 mg of 2-dicyclohexylphosphino-2',6'-dimethoxybiphenyl and 24 mg of tris(dibenzylideneacetone)dipalladium(0) were added, and the mixture was heated under reflux for 2 hours. To the reaction mixture, water and ethyl acetate were added, the organic layer was separated, washed with a saturated aqueous sodium chloride solution and dried over anhydrous magnesium sulfate, and the solvent was then distilled off under reduced pressure. The resultant residue was purified by flash silica gel column chromatography using gradient elution with hexane:ethyl acetate=87:13 to 83:17 to obtain 74 mg of methyl 6-(2-furyl)pyrazine-2-carboxylate as a white solid.

$^1$H-NMR (CDCl$_3$) δ: 4.05 (3H, s), 6.60 (1H, dd, J=3.5, 1.8 Hz), 7.30-7.32 (1H, m), 7.62-7.65 (1H, m), 9.12 (1H, s), 9.12 (1H, s)

Reference Example 192

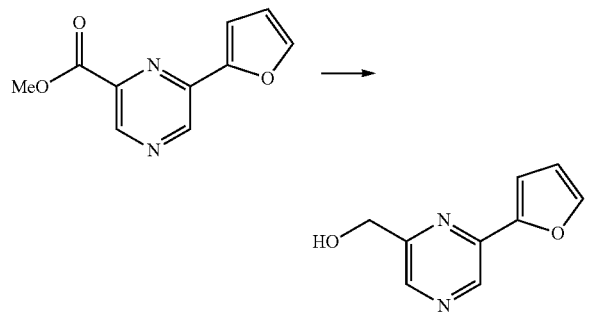

By the same technique as in Reference Example 58, 6-(2-furyl)pyrazin-2-yl)methanol was obtained from methyl 6-(2-furyl)pyrazine-2-carboxylate.

$^1$H-NMR (CDCl$_3$) δ: 3.08-3.24 (1H, m), 4.86 (2H, s), 6.59 (1H, dd, J=3.4, 1.7 Hz), 7.18 (1H, d, J=3.4 Hz), 7.58-7.62 (1H, m), 8.46 (1H, s), 8.89 (1H, s)

Reference Example 193

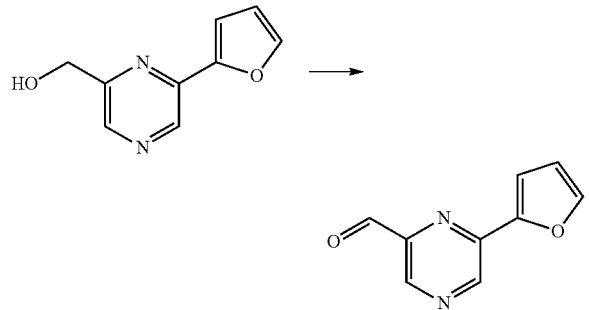

By the same technique as in Reference Example 67, 6-(2-furyl)pyrazine-2-carbaldehyde was obtained from (6-(2-furyl)pyrazin-2-yl)methanol.

$^1$H-NMR (CDCl$_3$) δ: 6.63 (1H, dd, J=3.4, 1.7 Hz), 7.30 (1H, dd, J=3.4, 0.7 Hz), 7.66 (1H, dd, J=1.7, 0.7 Hz), 8.99 (1H, s), 9.16 (1H, s), 10.18 (1H, s)

Reference Example 194

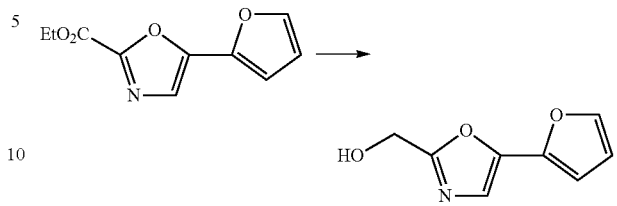

By the same technique as in Reference Example 58, (5-(2-furyl)-1,3-oxazol-2-yl)methanol was obtained from ethyl 5-(2-furyl)-1,3-oxazole-2-carboxylate.

$^1$H-NMR (CDCl$_3$) δ: 4.78 (2H, s), 6.50 (1H, dd, J=3.4, 2.0 Hz), 6.64 (1H, d, J=3.4 Hz), 7.21 (1H, s), 7.46-7.48 (1H, m)

Reference Example 195

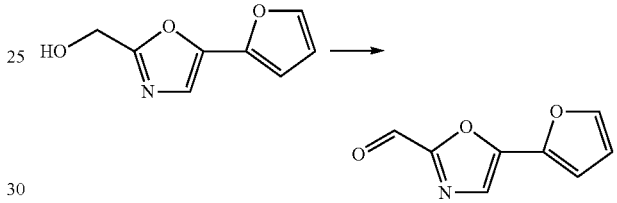

By the same technique as in Reference Example 164, 5-(2-furyl)-1,3-oxazole-2-carbaldehyde was obtained from (5-(2-furyl)-1,3-oxazol-2-yl)methanol.

$^1$H-NMR (CDCl$_3$) δ: 6.57 (1H, dd, J=3.5, 1.8 Hz), 6.94 (1H, d, J=3.5 Hz), 7.53 (1H, s), 7.56-7.58 (1H, m), 9.75 (1H, s)

Reference Example 196

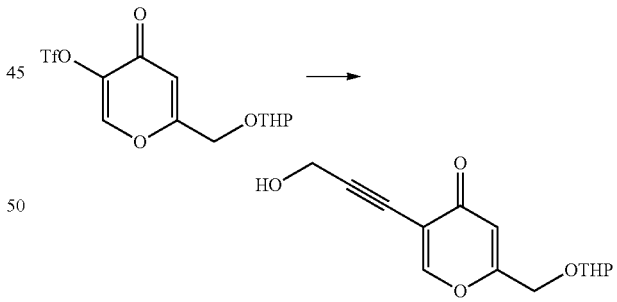

To a solution of 16 g of 4-oxo-6-((tetrahydro-2H-pyran-2-yloxy)methyl)-4H-pyran-3-yl trifluoromethanesulfonate in 100 mL of acetonitrile, 5.1 mL of propargyl alcohol, 18 mL of triethylamine, 0.62 g of dichlorobis(triphenylphosphine)palladium(II) and 0.42 g of copper (I) iodide were added under a nitrogen atmosphere, and the mixture was stirred at room temperature for 2 hours. The insoluble substance was filtered off, and the solvent was distilled off under reduced pressure. The resultant residue was purified by flash silica gel column chromatography using gradient elution with chloroform:methanol=100:0 to 97:3 to obtain 6.2 g of 5-(3-hydroxy-1-propyn-1-yl)-2-((tetrahydro-2H-pyran-2-yloxy)methyl)-4H-pyran-4-one as a brown oily substance.

¹H-NMR (CDCl₃) δ: 1.51-1.90 (6H, m), 2.27-2.40 (1H, broad), 3.52-3.60 (1H, m), 3.78-3.86 (1H, m), 4.34 (1H, d, J=14.9 Hz), 4.50 (2H, s), 4.54 (1H, d, J=14.9 Hz), 4.73 (1H, t, J=3.3 Hz), 6.51 (1H, s), 8.00 (1H, s)

Reference Example 197

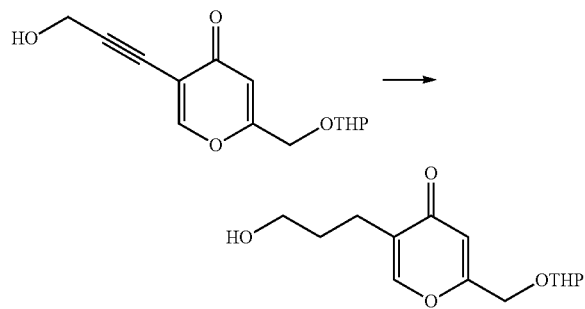

By the same technique as in Reference Example 151, 5-(3-hydroxypropyl)-2-((tetrahydro-2H-pyran-2-yloxy)methyl)-4H-pyran-4-one was obtained from 5-(3-hydroxy-1-propyn-1-yl)-2-((tetrahydro-2H-pyran-2-yloxy)methyl)-4H-pyran-4-one.

¹H-NMR (CDCl₃) δ: 1.52-1.92 (8H, m), 2.51 (2H, t, J=7.0 Hz), 2.85-3.17 (1H, broad), 3.52-3.60 (1H, m), 3.57 (2H, t, J=5.9 Hz), 3.80-3.88 (1H, m), 4.33 (1H, d, J=14.4 Hz), 4.53 (1H, d, J=14.4 Hz), 4.73 (1H, t, J=3.2 Hz), 6.46 (1H, s), 7.70 (1H, s)

Reference Example 198

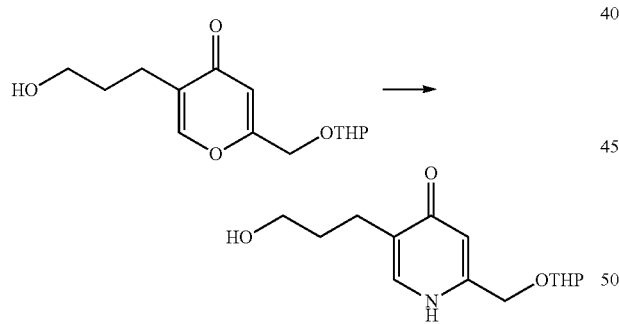

To a solution of 1.2 g of 5-(3-hydroxypropyl)-2-((tetrahydro-2H-pyran-2-yloxy)methyl)-4H-pyran-4-one in 5 mL of ethanol, 16 mL of 25% ammonium water was added, and the mixture was heated under reflux while stirring for 9 hours 30 minutes. The solvent was distilled off under reduced pressure, and the resultant residue was purified by flash silica gel column chromatography using gradient elution with chloroform: methanol=95:5 to 90:10 to obtain 0.42 g of 5-(3-hydroxypropyl)-2-((tetrahydro-2H-pyran-2-yloxy)methyl)pyridin-4(1H)-one as a brown oily substance.

¹H-NMR (CDCl₃) δ: 1.52-1.92 (8H, m), 2.64 (2H, t, J=6.5 Hz), 3.51 (2H, t, J=5.6 Hz), 3.55-3.62 (1H, m), 3.93-4.02 (1H, m), 4.55-4.68 (3H, m), 6.31 (1H, s), 7.47 (1H, s)

Reference Example 199

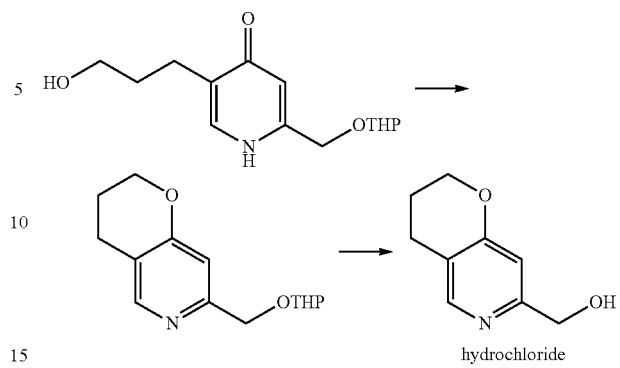

(1) To a solution of 0.42 g of 5-(3-hydroxypropyl)-2-((tetrahydro-2H-pyran-2-yloxy)methyl)pyridin-4(1H)-one in 8 mL of tetrahydrofuran, 0.54 g of triphenylphosphine and 0.89 g of a 40% diethyl azodicarboxylate/toluene solution were added, and the mixture was stirred for 10 minutes. The solvent was distilled off under reduced pressure to obtain 7-((tetrahydro-2H-pyran-2-yloxy)methyl)-3,4-dihydro-2H-pyrano(3,2-c)pyridine as a brown oily substance.

(2) By the same technique as in Reference Example 172, (3,4-dihydro-2H-pyrano(3,2-c)pyridin-7-yl)methanol hydrochloride was obtained from 7-((tetrahydro-2H-pyran-2-yloxy)methyl)-3,4-dihydro-2H-pyrano(3,2-c)pyridine.

¹H-NMR (DMSO-d₆) δ: 1.99 (2H, quint, J=5.8 Hz), 2.84 (2H, t, J=6.2 Hz), 4.46 (2H, t, J=5.2 Hz), 4.70 (2H, s), 6.06-6.36 (1H, broad), 7.22 (1H, s), 8.48 (1H, s)

Reference Example 200

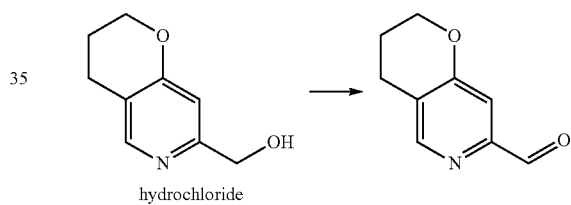

By the same technique as in Reference Example 123, 3,4-dihydro-2H-pyrano(3,2-c)pyridine-7-carbaldehyde was obtained from (3,4-dihydro-2H-pyrano(3,2-c)pyridin-7-yl)methanol hydrochloride.

¹H-NMR (CDCl₃) δ: 2.08 (2H, quint, J=5.8 Hz), 2.85 (2H, t, J=6.4 Hz), 4.30 (2H, t, J=5.1 Hz), 7.36 (1H, s), 8.38 (1H, s), 9.97 (1H, s)

Reference Example 201

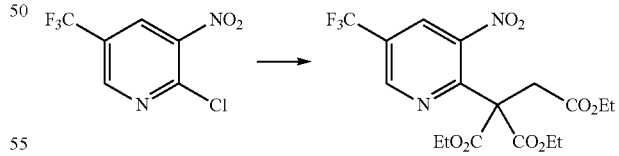

To a solution of 1.8 g of 2-chloro-3-nitro-5-(trifluoromethyl)pyridine in 8 mL of tetrahydrofuran, 2.0 mL of triethyl 1,1,2-ethanetricarboxylate and 0.63 g of 60% sodium hydroxide were added under cooling with ice, and the mixture was stirred at room temperature for 2 hours. Thereto were added water and ethyl acetate, the organic layer was separated, and washed with a saturated aqueous sodium chloride solution and dried over anhydrous magnesium sulfate, and the solvent was distilled off under reduced pressure to obtain 3.5 g of triethyl 1-(3-nitro-5-(trifluoromethyl)pyridin-2-yl)ethane-1,1,2-tricarboxylate as a brown oily substance.

¹H-NMR (CDCl₃) δ: 1.20-1.28 (9H, m), 3.57 (2H, s), 4.10 (2H, q, J=7.2 Hz), 4.25 (4H, q, J=7.2 Hz), 8.64-8.67 (1H, m), 8.96-8.99 (1H, m)

Reference Example 202

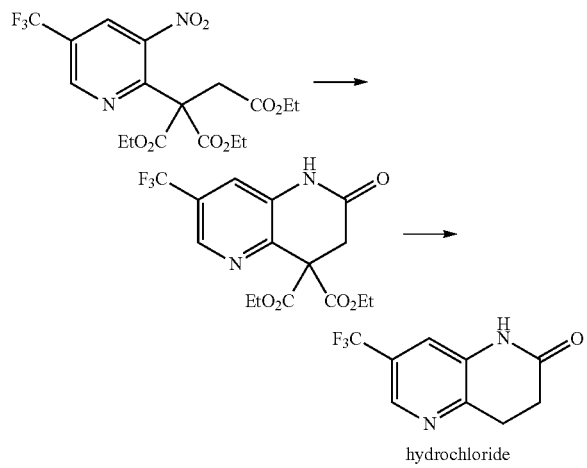

(1) To a solution of 3.5 g of triethyl 1-(3-nitro-5-(trifluoromethyl)pyridin-2-yl)ethane-1,1,2-tricarboxylate in a mixture of 35 mL of ethanol and 8.8 mL of water, 0.27 g of ammonium chloride and 1.6 g of iron powder were added, and the mixture was heated under reflux while stirring for 2 hours 20 minutes. After cooling to room temperature, the insoluble substance was filtered off, and washed with ethyl acetate and water. Thereto was added sodium chloride, the organic layer was separated, and the aqueous layer was extracted with ethyl acetate. The organic layer and the extract were combined, the resultant solution was washed with a saturated aqueous sodium chloride solution, and dried over anhydrous magnesium sulfate, and the solvent was distilled off under reduced pressure to obtain the residue as a brown oily substance.

(2) To a solution of the residue obtained in (1) in 8 mL of dioxane, 8.0 mL of hydrochloric acid was added, and the mixture was heated under reflux while stirring for 1 hour 30 minutes. The solvent was distilled off under reduced pressure, thereto were added ethanol and diethyl ether, and the deposit was filtered off to obtain 0.44 g of 7-(trifluoromethyl)-3,4-dihydro-1,5-naphthyridin-2(1H)-one hydrochloride as a light brown solid.

¹H-NMR (DMSO-d₆) δ: 2.65 (2H, t, J=7.7 Hz), 3.13 (2H, t, J=7.7 Hz), 7.46 (1H, d, J=1.3 Hz), 8.46 (1H, d, J=1.3 Hz), 10.43 (1H, s)

Reference Example 203

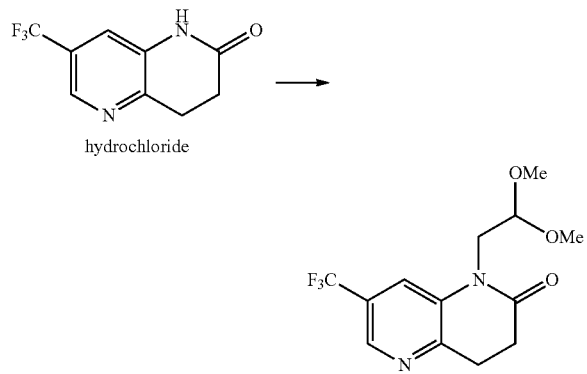

By the same technique as in Reference Example 3, 1-(2,2-dimethoxyethyl)-7-(trifluoromethyl)-3,4-dihydro-1,5-naphthyridin-2(1H)-one was obtained from 7-(trifluoromethyl)-3,4-dihydro-1,5-naphthyridin-2(1H)-one hydrochloride and 2-bromo-1,1-dimethoxyethane.

¹H-NMR (CDCl₃) δ: 2.82 (2H, t, J=7.5 Hz), 3.22 (2H, t, J=7.5 Hz), 3.43-3.46 (6H, m), 3.99 (2H, d, J=5.1 Hz), 4.61 (1H, t, J=5.1 Hz), 7.89-7.92 (1H, m), 8.45-8.48 (1H, m)

Reference Example 204

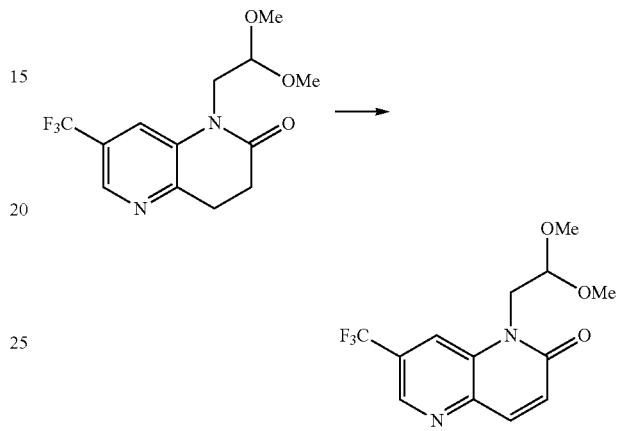

To a solution of 0.11 g of 1-(2,2-dimethoxyethyl)-7-(trifluoromethyl)-3,4-dihydro-1,5-naphthyridin-2(1H)-one in 2 mL of dioxane, 0.16 g of 2,3-dichloro-5,6-dicyano-p-benzoquinone was added, and the mixture was heated under reflux while stirring for 3 hours. Thereto were added water and ethyl acetate, the mixture was adjusted to pH 12 with a 2.0 mol/L aqueous sodium hydroxide solution, and the organic layer was separated. The organic layer was washed with an aqueous sodium hydroxide solution and a saturated aqueous sodium chloride solution, and dried over anhydrous magnesium sulfate, and the solvent was distilled off under reduced pressure to obtain 90 mg of 1-(2,2-dimethoxyethyl)-7-(trifluoromethyl)-1,5-naphthyridin-2(1H)-one as a brown solid.

¹H-NMR (CDCl₃) δ: 3.44 (6H, s), 4.38 (2H, d, J=5.1 Hz), 4.63 (1H, t, J=5.1 Hz), 7.03 (1H, d, J=9.8 Hz), 7.98 (1H, d, J=9.8 Hz), 8.24 (1H, s), 8.75 (1H, d, J=1.0 Hz)

Reference Example 205

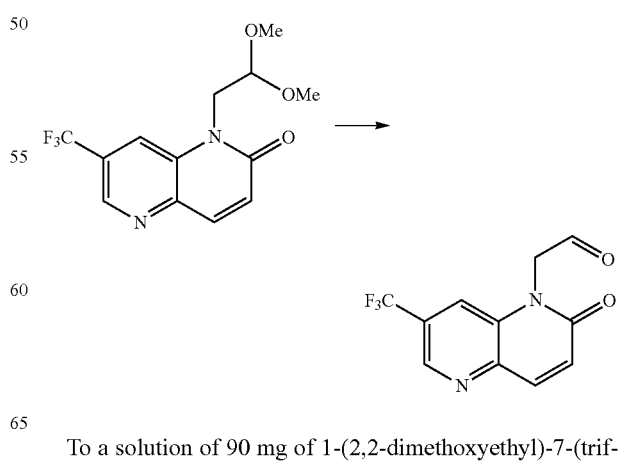

To a solution of 90 mg of 1-(2,2-dimethoxyethyl)-7-(trifluoromethyl)-1,5-naphthyridin-2(1H)-one in 0.72 mL of methyl ethyl ketone, 38 μL of concentrated hydrochloric acid was added, and the mixture was heated under reflux while stirring for 1 hour 30 minutes. The reaction mixture was cooled to room temperature, thereto were added chloroform and a saturated aqueous sodium hydrogen carbonate solution, the organic layer was separated, washed with a saturated aqueous sodium chloride solution and dried over anhydrous magnesium sulfate, and the solvent was distilled off under reduced pressure to obtain 67 mg of (2-oxo-7-(trifluoromethyl)-1,5-naphthyridin-1(2H)-yl)acetaldehyde as a brown oily substance.

$^1$H-NMR (CDCl$_3$) δ: 5.21 (2H, s), 7.09 (1H, d, J=9.8 Hz), 7.49 (1H, s), 8.04 (1H, d, J=9.8 Hz), 8.79-8.82 (1H, m), 9.82 (1H, s)

Reference Example 206

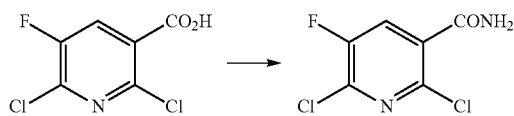 [SMILES: O=C(O)c1cc(F)c(Cl)nc1Cl ; NC(=O)c1cc(F)c(Cl)nc1Cl]

To a suspension of 10 g of 2,6-dichloro-5-fluoronicotinic acid in 30 mL of toluene, 8.5 g of thionyl chloride and 0.10 mL of N,N-dimethylformamide were added, and the mixture was stirred at 72° C. for 1 hour 30 minutes. The reaction mixture was cooled to room temperature, and the solvent was distilled off under reduced pressure. The resultant residue was dropped to 30 mL of 25% ammonium water at −20° C. The temperature was increased to 5 C.°, and the mixture was stirred for 30 minutes. The solid was filtered off to obtain 9.9 g of 2,6-dichloro-5-fluoronicotinamide as a white solid.

$^1$H-NMR (DMSO-d$_6$) δ: 7.94 (1H, s), 8.11 (1H, s), 8.23 (1H, d, J=7.8 Hz)

Reference Example 207

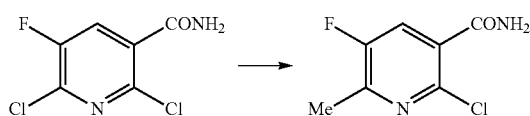 [SMILES: NC(=O)c1cc(F)c(Cl)nc1Cl ; Cc1nc(Cl)c(C(N)=O)cc1F]

By the same technique as in Reference Example 101, 2-chloro-5-fluoro-6-methylnicotinamide was obtained from 2,6-dichloro-5-fluoronicotinamide.

$^1$H-NMR (CDCl$_3$) δ: 2.56 (3H, d, J=2.9 Hz), 5.91 (1H, s), 6.85 (1H, s), 8.00 (1H, d, J=8.5 Hz)

Reference Example 208

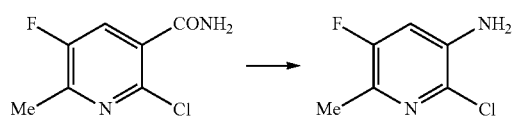 [SMILES: Cc1nc(Cl)c(C(N)=O)cc1F ; Cc1nc(Cl)c(N)cc1F]

By the same technique as in Reference Example 180, 2-chloro-5-fluoro-6-methylpyridin-3-amine was obtained from 2-chloro-5-fluoro-methylnicotinamide.

$^1$H-NMR (CDCl$_3$) δ: 2.37 (3H, d, J=2.7 Hz), 4.04 (2H, s), 6.78 (1H, d, J=9.5 Hz)

Reference Example 209

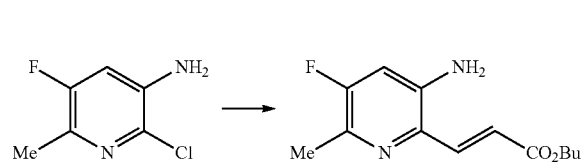

By the same technique as in Reference Example 1, butyl (2E)-3-(3-amino-5-fluoro-6-methylpyridin-2-yl)acrylate was obtained from 2-chloro-5-fluoro-6-methylpyridin-3-amine and butyl acrylate.

$^1$H-NMR (CDCl$_3$) δ: 0.95 (3H, t, J=7.3 Hz), 1.40-1.48 (2H, m), 1.68 (2H, quint, J=6.8 Hz), 2.40 (3H, d, J=2.7 Hz), 3.93 (2H, s), 4.21 (2H, t, J=6.8 Hz), 6.67 (1H, d, J=10.2 Hz), 6.87 (1H, d, J=15.2 Hz), 7.71 (1H, d, J=15.2 Hz)

Reference Example 210

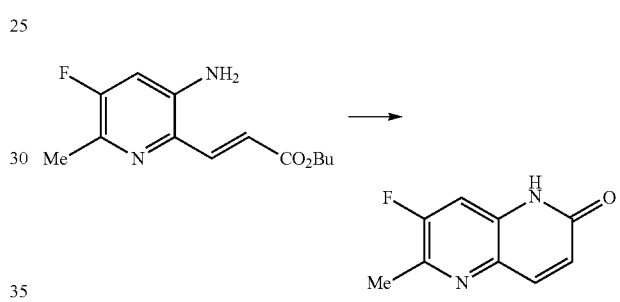

By the same technique as in Reference Example 2, 7-fluoro-6-methyl-1,5-naphthyridin-2(1H)-one was obtained from butyl (2E)-3-(3-amino-5-fluoro-6-methylpyridin-2-yl) acrylate.

$^1$H-NMR (DMSO-d$_6$) δ: 2.49 (3H, d, J=2.9 Hz), 6.68 (1H, d, J=9.8 Hz), 7.41 (1H, J=10.2 Hz), 7.89 (1H, d, J=9.8 Hz), 11.9 (1H, s)

Reference Example 211

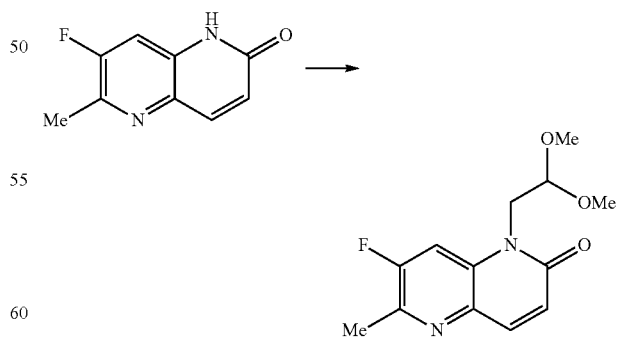

To a solution of 0.74 g of 7-fluoro-6-methyl-1,5-naphthyridin-2(1H)-one in 5 mL of N,N-dimethylformamide, 2.0 g of cesium carbonate and 0.84 g of 2-bromo-1,1-dimethoxyethane were added, the temperature was increased to 90 to 100° C., and the mixture was stirred for 2 hours 30 minutes.

The reaction mixture was cooled to room temperature, thereto was added ethyl acetate, the insoluble substance was filtered off, and the solvent was then distilled off under reduced pressure. The resultant residue was purified by silica gel column chromatography using an eluent of chloroform:methanol=100:1 to obtain 0.69 g of 1-(2,2-dimethoxyethyl)-7-fluoro-6-methyl-1,5-naphthyridin-2(1H)-one as a light yellow solid.

$^1$H-NMR (CDCl$_3$) δ: 2.58 (3H, d, J=2.7 Hz), 3.43 (6H, s), 4.28 (2H, d, J=5.2 Hz), 4.64 (1H, t, J=5.2 Hz), 6.83 (1H, d, J=9.8 Hz), 7.64 (1H, d, J=11.2 Hz), 7.86 (1H, d, J=9.8 Hz)

Reference Example 212

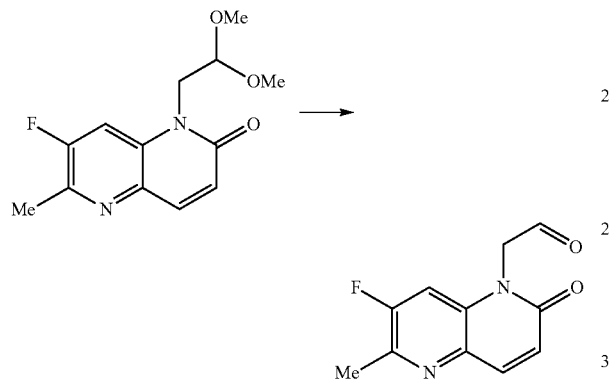

To a solution of 0.69 g of 1-(2,2-dimethoxyethyl)-7-fluoro-6-methyl-1,5-naphthyridin-2(1H)-one in 6 mL of methyl ethyl ketone, 0.35 mL of concentrated hydrochloric acid was added, and the temperature was increased to 74° C., and the mixture was stirred for 2 hours 50 minutes. The reaction mixture was cooled to room temperature, and the solvent was distilled off under reduced pressure. To the resultant residue, ethyl acetate and a saturated aqueous sodium hydrogen carbonate solution were added, the organic layer was separated, and the aqueous layer was extracted with ethyl acetate. The organic layer and the extract were combined, the resultant solution was dried over anhydrous magnesium sulfate to obtain 0.52 g of (7-fluoro-6-methyl-2-oxo-1,5-naphthyridin-1(2H)-yl)acetaldehyde as a light yellow solid.

$^1$H-NMR (CDCl$_3$) δ: 2.59 (3H, d, J=2.7 Hz), 5.10 (2H, s), 6.89 (1H, d, J=10.0 Hz), 7.00 (1H, d, J=10.0 Hz), 7.92 (1H, d, J=9.8 Hz), 9.75 (1H, s)

Reference Example 213

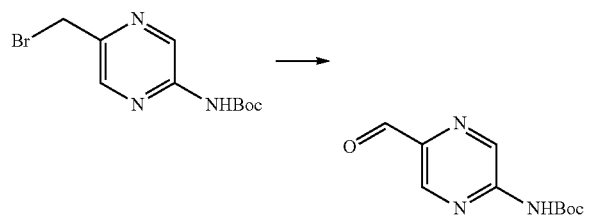

To a mixed solution of 0.17 g of tert-butyl (5-(bromomethyl)pyrazin-2-yl)carbamate in 4 mL of dimethyl sulfoxide and 2 mL of dichloromethane, 0.26 g of trimethylamine N-oxide dihydrate was added under cooling with ice, and the mixture was stirred for 2 hours. Thereto were added water and chloroform, the organic layer was separated, and washed with a saturated aqueous sodium hydrogen carbonate solution, water and a saturated aqueous sodium chloride solution. The organic layer was dried over anhydrous magnesium sulfate, and the solvent was distilled off under reduced pressure to obtain 0.10 g of tert-butyl (5-formylpyrazin-2-yl)carbamate as a white solid.

$^1$H-NMR (CDCl$_3$) δ: 1.55-1.59 (9H, m), 7.63-7.70 (1H, broad), 8.82 (1H, d, J=1.2 Hz), 9.44 (1H, d, J=1.2 Hz), 10.07 (1H, s)

Reference Example 214

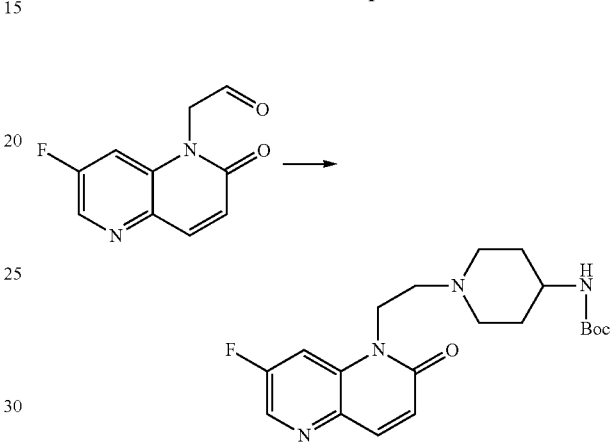

To a solution of 1.66 g of (7-fluoro-2-oxo-1,5-naphthyridin-1(2H)-yl)acetaldehyde in 42 mL of chloroform, 1.61 g of tert-butyl (piperidin-4-yl)carbamate and 0.48 g of acetic acid were added, and the mixture was stirred at room temperature for 7.5 hours. To the reaction mixture, 2.56 g of sodium triacetoxyborohydride was added, and the mixture was stirred for 10 hours. Thereto was added a saturated aqueous sodium hydrogen carbonate solution, and the organic layer was separated. The organic layer was washed with a saturated aqueous sodium chloride solution and dried over anhydrous magnesium sulfate, and the solvent was distilled off under reduced pressure. Ethanol was added to the resultant residue, and the solid was filtered off to obtain 0.59 g of tert-butyl (1-(2-(7-fluoro-2-oxo-1,5-naphthyridin-1(2H)-yl)ethyl)piperidin-4-yl)carbamate as a white solid.

$^1$H-NMR (CDCl$_3$) δ: 1.31-1.49 (11H, m), 1.84-2.04 (2H, m), 2.14-2.37 (2H, m), 2.56-2.71 (2H, m), 2.82-3.05 (2H, m), 3.35-3.60 (1H, m), 4.20-4.52 (3H, m), 6.79-6.93 (1H, m), 7.44-7.58 (1H, m), 7.79-7.96 (1H, m), 8.37-8.48 (1H, m)

Reference Example 215

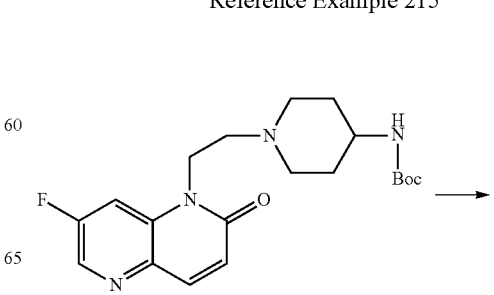

-continued

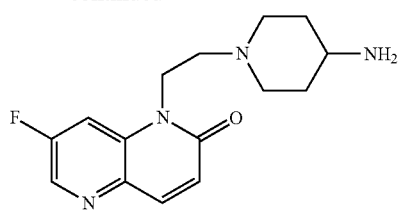

A solution of 0.59 g of tert-butyl (1-(2-(7-fluoro-2-oxo-1,5-naphthyridin-1(2H)-yl)ethyl)piperidin-4-yl)carbamate in 30 mL of a 2 mol/L hydrogen chloride/ethanol was stirred at room temperature for 18 hours. To the reaction mixture, 2 mL of chloroform was added, and the mixture was stirred at 40° C. for 4 hours, and stirred at room temperature for 18 hours. In the reaction mixture, the solvent was distilled off under reduced pressure, the mixture was neutralized with a saturated aqueous sodium hydrogen carbonate solution, and then the solvent was distilled off under reduced pressure. The resultant residue was washed with ethanol and, in the mother liquid, the solvent was distilled off under reduced pressure, and the resultant residue was purified with silica gel column chromatography using silica gel; Chromatorex-NH made by Fuji Silysia Chemical Ltd. and an eluent of chloroform:methanol=10:1 to obtain 421 mg of 1-(2-(4-aminopiperidin-1-yl)ethyl)-7-fluoro-1,5-naphthyridin-2(1H)-one as a light yellow solid.

$^1$H-NMR (CDCl$_3$) δ: 1.30-1.45 (2H, m), 1.54 (2H, s), 1.75-1.87 (2H, m), 2.11-2.24 (2H, m), 2.60-2.76 (3H, m), 2.86-2.99 (2H, m), 4.25-4.39 (2H, m), 6.86 (1H, d, J=9.6 Hz), 7.48-7.60 (1H, m), 7.89 (1H, d, J=9.6 Hz), 8.36-8.49 (1H, m)

Reference Example 216

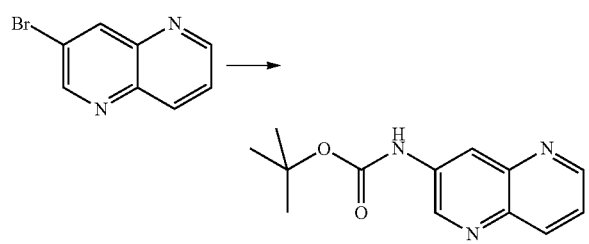

To a solution of 1.00 g of 3-bromo-1,5-naphthyridine in 5 mL of 1,4-dioxane, 0.67 g of tert-butylcarbamate, 2.18 g of cesium carbonate, 44 mg of tris(benzylideneacetone)dipalladium and 83 mg of 4,5-bis(diphenylphosphino)-9,9-dimethylxanthene were added, and the mixture was stirred at 80° C. for 12.5 hours under an argon atmosphere. Water and chloroform were added to the reaction mixture, and the organic layer was separated. The organic layer was washed with a saturated aqueous sodium chloride solution, and dried over anhydrous magnesium sulfate, and the solvent was distilled off under reduced pressure. The resultant residue was purified by silica gel column chromatography using silica gel; Silica Gel 60N made by KANTO CHEMICAL CO., INC., and an eluent of chloroform:methanol 10:1 to obtain 1.03 g of tert-butyl 1,5-naphthyridin-3-ylcarbamate as a yellow oily substance.

$^1$H-NMR (DMSO-d$_6$) δ: 1.53 (9H, s), 7.60-7.65 (1H, m), 8.32 (1H, d, J=4.1 Hz), 8.52 (1H, s), 8.90-8.93 (1H, m), 8.97-9.00 (1H, m), 10.08 (1H, s)

Reference Example 217

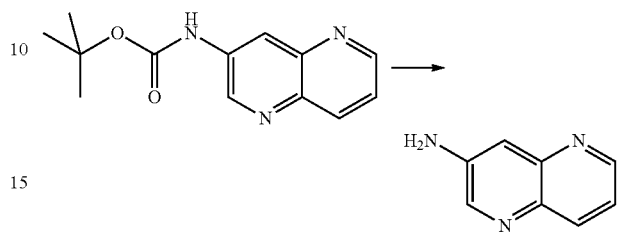

To a solution of 1.00 g of tert-butyl 1,5-naphthyridin-3-ylcarbamate in 6 mL of methanol, 1 mL of a 12 mol/L aqueous hydrogen chloride solution was added, and the mixture was stirred for 30 minutes. To the reaction mixture, 5 mL of methanol and 1 mL of a 12 mol/L aqueous hydrogen chloride solution were added, and the mixture was stirred at 40° C. for 40 minutes, and at 80° C. for 40 minutes. In the reaction mixture, the solvent was distilled off under reduced pressure, the mixture was neutralized with a saturated aqueous sodium hydrogen carbonate solution, and then the solvent was distilled off under reduced pressure. The resultant residue was washed with ethanol and, in the mother liquid, the solvent was distilled off under reduced pressure, and the resultant residue was purified with silica gel column chromatography using silica gel; Chromatorex-NH made by Fuji Silysia Chemical Ltd., and an eluent of chloroform:methanol=10:1 to obtain 0.50 g of 1,5-naphthyridin-3-amine as a yellow solid.

$^1$H-NMR (CDCl$_3$) δ: 4.18 (2H, s), 7.31-7.42 (1H, m), 7.43-7.50 (1H, m), 8.21-8.30 (1H, m), 8.51-8.62 (1H, m), 8.77-8.88 (1H, m)

Reference Example 218

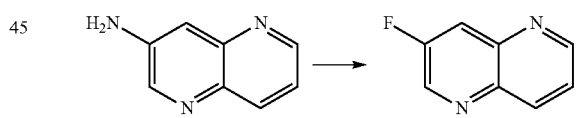

To 2 mL of hydrogen fluoride/pyridine, 145 mg of 1,5-naphthyridin-3-amine was added at 0° C., 76 mg of sodium nitrite was added to the reaction mixture, and stirred at 0° C. for 1 hour. The reaction mixture was stirred at 60° C. for 1 hour, and neutralized with a saturated aqueous sodium hydrogen carbonate solution at 0° C., chloroform was then added thereto, and the organic layer was separated. The organic layer was washed with a saturated aqueous sodium chloride solution, and dried over anhydrous magnesium sulfate, and the solvent was distilled off under reduced pressure. The resultant residue was purified by silica gel column chromatography using silica gel; Silica Gel 60N made by KANTO CHEMICAL CO., INC., and an eluent of chloroform:methanol=20:1 to obtain 77 mg of 3-fluoro-1,5-naphthyridine as a light yellow solid.

$^1$H-NMR (CDCl$_3$) δ: 7.62-7.67 (1H, m), 8.03-8.08 (1H, m), 8.42-8.47 (1H, m), 8.90-8.94 (1H, m), 8.98-9.03 (1H, m)

Reference Example 219

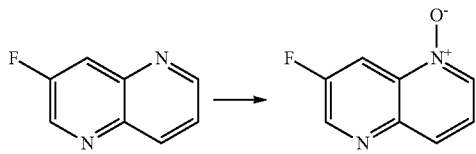 [SMILES: Fc1cnc2cccnc2c1 ; [O-][n+]1cccc2ncc(F)cc21]

To a solution of 76 mg of 3-fluoro-1,5-naphthyridine in 3 mL of chloroform, 136 mg of m-chloroperbenzoic acid was added, and the mixture was stirred at room temperature for 2.5 hours. Thereto was added 27 mg of m-chloroperbenzoic acid, and the mixture was stirred at room temperature for 1 hour. To the reaction mixture, a 5% aqueous sodium thiosulfate solution and chloroform were added, the organic layer was separated and dried over anhydrous magnesium sulfate, and the solvent was distilled off under reduced pressure. The resultant residue was purified by silica gel column chromatography using silica gel; Silica Gel 60N made by KANTO CHEMICAL CO., INC., and an eluent of chloroform:methanol=50:1 to obtain 60 mg of 7-fluoro-1,5-naphthyridine 1-oxide as a light yellow solid.

$^1$H-NMR (CDCl$_3$) δ: 7.53 (1H, dd, J=8.7, 6.0 Hz), 8.04 (1H, d, J=8.7 Hz), 8.59 (1H, d, J=6.0 Hz), 8.66-8.77 (1H, m), 8.91-9.02 (1H, m)

Reference Example 220

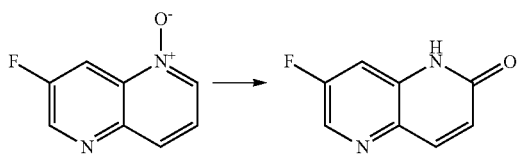 [SMILES: [O-][n+]1cccc2ncc(F)cc21 ; O=c1ccc2ncc(F)cc2[nH]1]

To a solution of 60 mg of 7-fluoro-1,5-naphthyridine 1-oxide in 1.6 mL of chloroform, 84 mg of p-toluenesulfonyl chloride, 171 mg of potassium carbonate and 0.5 mL of water were added, and the mixture was stirred at room temperature overnight. The solid was filtered off, and purified by silica gel column chromatography using silica gel; Chromatorex-NH made by Fuji Silysia Chemical Ltd., and an eluent of chloroform:methanol=10:1 to obtain 14 mg of 7-fluoro-1,5-naphthyridin-2(1H)-one as a white solid.

$^1$H-NMR (CDCl$_3$) δ: 6.71 (1H, d, J=10.1 Hz), 7.29-7.57 (1H, m), 7.94 (1H, d, J=10.1 Hz), 8.50 (1H, d, J=2.3 Hz), 12.00 (1H, s)

Reference Example 221

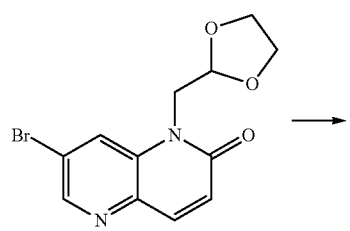

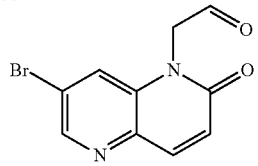

To 20.02 g of 7-bromo-1-(1,3-dioxolan-2-ylmeythyl)-1,5-naphthyridin-2(1H)-one, 400 mL of an 80% aqueous trifluoroacetic acid solution was added, and the mixture was stirred at 90° C. for 3.5 hours. The reaction mixture was cooled to room temperature, and the solvent was then distilled off under reduced pressure. The resultant residue was adjusted to pH 7.7 with a 2 mol/L aqueous sodium hydroxide solution. Then, the deposit was filtered off to obtain 13.43 g of (7-bromo-2-oxo-1,5-naphthyridin-1(2H)-yl)acetaldehyde as a brown solid.

$^1$H-NMR (CDCl$_3$) δ: 5.13 (2H, s), 6.98 (1H, d, J=9.6 Hz), 7.49 (1H, d, J=1.4 Hz), 7.95 (1H, d, J=9.6 Hz), 8.60 (1H, d, J=1.4 Hz), 9.78 (1H, s)

Example 1

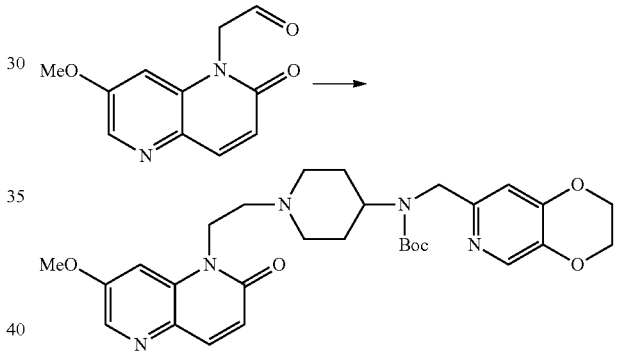

To 0.11 g of (7-methoxy-2-oxo-1,5-naphthyridin-1(2H)-yl)acetaldehyde, 0.15 g of tert-butyl (2,3-dihydro(1,4)dioxino(2,3-c)pyridin-7-ylmethyl)(piperidin-4-yl)carbamate in 4 mL of dichloromethane, 24 μL of acetic acid and 0.13 g of sodium triacetoxyborohydride were added, and the mixture was stirred at room temperature for 1 hour. To the reaction mixture, chloroform and a saturated aqueous sodium hydrogen carbonate solution were added, the organic layer was separated, and the aqueous layer was extracted with chloroform. The organic layer and the extract were combined, the resultant solution was washed with a saturated aqueous sodium chloride solution and dried over anhydrous magnesium sulfate, and the solvent was distilled off under reduced pressure. The resultant residue was purified by flash basic silica gel column chromatography using gradient elution with hexane:ethyl acetate=100:0 to 20:80, and then gradient eluent of chloroform:methanol=100:0 to 90:10 to obtain 0.18 g of tert-butyl (2,3-dihydro(1,4)dioxino(2,3-c)pyridin-7-ylmethyl)(1-(2-(7-methoxy-2-oxo-1,5-naphthyridin-1(2H)-yl)ethyl)piperidin-4-yl)carbamate as a light yellow foam.

$^1$H-NMR (CDCl$_3$) δ: 1.39 (9H, s), 1.40-1.72 (4H, m), 2.06-2.25 (2H, m), 2.57-2.64 (2H, m), 2.96-3.05 (2H, m), 3.96 (3H, s), 4.05-4.18 (1H, m), 4.23-4.50 (8H, m), 6.73 (1H, d, J=9.8 Hz), 6.73 (1H, s), 7.17 (1H, d, J=2.3 Hz), 7.83 (1H, d, J=9.8 Hz), 8.05 (1H, s), 8.27 (1H, d, J=2.3 Hz)

Example 2

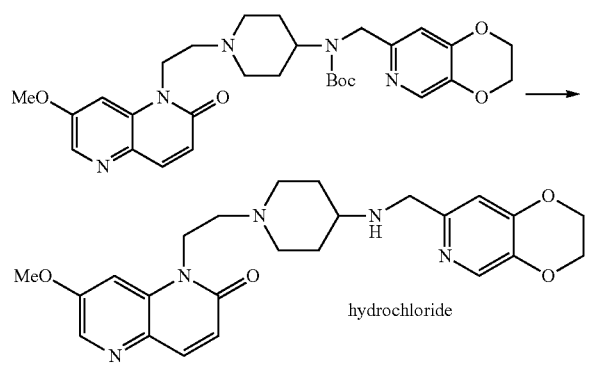

hydrochloride

To a solution of 0.17 g of tert-butyl (2,3-dihydro(1,4)dioxino(2,3-c)pyridin-7-ylmethyl)(1-(2-(7-methoxy-2-oxo-1,5-naphthyridin-1(2H)-yl)ethyl)piperidin-4-yl)carbamate in 3 mL of ethyl acetate, 6.0 mL of a 4.0 mol/L hydrogen chloride/ethyl acetate solution was added at room temperature. The mixture was stirred at the same temperature for 1 hour, and the solvent was distilled off under reduced pressure. Diethyl ether was added to the resultant residue, and the solid was filtered off to obtain 0.16 g of 1-(2-(4-((2,3-dihydro(1,4)dioxino(2,3-c)pyridin-7-ylmethyl)amino)piperidin-1-yl)ethyl)-7-methoxy-1,5-naphthyridin-2(1H)-one hydrochloride as a light yellow solid.

$^1$H-NMR (D$_2$O) δ: 1.98-2.13 (2H, m), 2.50-2.60 (2H, m), 3.21-3.34 (2H, m), 3.60-3.77 (3H, m), 3.95-4.08 (2H, m), 4.05 (3H, s), 4.42-4.49 (4H, m), 4.53-4.59 (2H, m), 4.72-4.87 (2H, m), 6.89 (1H, d, J=9.6 Hz), 7.37 (1H, s), 7.48-7.53 (1H, m), 8.06 (1H, d, J=9.6 Hz), 8.31 (1H, s), 8.40-8.44 (1H, m)

Example 3

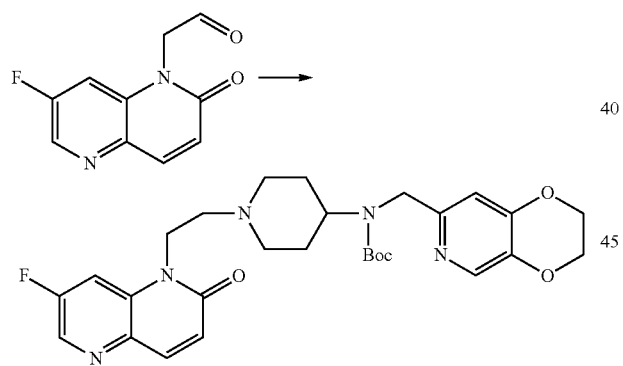

To 0.11 g of (7-fluoro-2-oxo-1,5-naphthyridin-1(2H)-yl)acetaldehyde, a solution of 0.19 g of tert-butyl (2,3-dihydro(1,4)dioxino(2,3-c)pyridin-7-ylmethyl(piperidin-4-yl)carbamate in 3 mL of dichloromethane, 31 μL of acetic acid and 0.17 g of sodium triacetoxyborohydride were added, and the mixture was stirred at room temperature for 1 hour, and then left overnight. Thereto were added chloroform and a saturated aqueous sodium hydrogen carbonate solution, the organic layer was separated, and the aqueous layer was extracted with chloroform. The organic layer and the extract were combined, the resultant solution was washed sequentially with water and a saturated aqueous sodium chloride solution and dried over anhydrous magnesium sulfate, and the solvent was distilled off under reduced pressure. The resultant residue was purified by basic silica gel column chromatography using an eluent of chloroform:methanol=19:1 to obtain 0.21 g of tert-butyl (2,3-dihydro(1,4)dioxino(2,3-c)pyridin-7-ylmethyl)(1-(2-(7-fluoro-2-oxo-1,5-naphthyridin-1(2H)-yl)ethyl)piperidin-4-yl)carbamate as a white foam.

$^1$H-NMR (CDCl$_3$) δ: 1.39 (9H, s), 1.33-1.71 (4H, m), 2.08-2.24 (2H, m), 2.57-2.63 (2H, m), 2.94-3.01 (2H, m), 4.02-4.18 (1H, m), 4.23-4.46 (8H, m), 6.73 (1H, s), 6.84 (1H, d, J=9.8 Hz), 7.47 (1H, dd, J=10.1, 2.4 Hz), 7.87 (1H, d, J=9.8 Hz), 8.05 (1H, s), 8.41 (1H, d, J=2.4 Hz)

Example 4

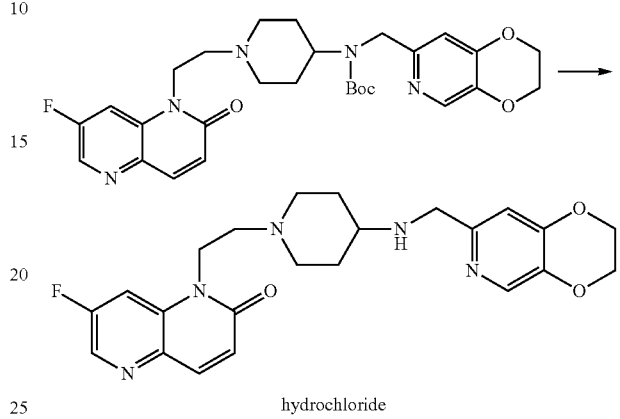

hydrochloride

To a solution of 0.21 g of tert-butyl (2,3-dihydro(1,4)dioxino(2,3-c)pyridin-7-ylmethyl)(1-(2-(7-fluoro-2-oxo-1,5-naphthyridin-1(2H)-yl)ethyl)piperidin-4-yl)carbamate in 4 mL of ethanol, 4 mL of a 6.0 mol/L hydrogen chloride/ethanol solution was added at room temperature, and the mixture was stirred for 1 hour 30 minutes. The solvent was distilled off under reduced pressure, diethyl ether was added to the resultant residue, and the solid was filtered off to obtain 0.21 g of 1-(2-(4-((2,3-dihydro(1,4)dioxino(2,3-c)pyridin-7-ylmethyl)amino)piperidin-1-yl)ethyl)-7-fluoro-1,5-naphthyridin-2(1H)-one hydrochloride as a light yellow solid.

$^1$H-NMR (D$_2$O) δ: 2.00-2.16 (2H, m), 2.52-2.61 (2H, m), 3.23-3.35 (2H, m), 3.61-3.67 (2H, m), 3.69-3.80 (1H, m), 3.98-4.07 (2H, m), 4.46-4.51 (2H, m), 4.53 (2H, s), 4.58-4.63 (2H, m), 4.71-4.96 (2H, m), 7.00 (1H, d, J=9.8 Hz), 7.47 (1H, s), 7.93-7.99 (1H, m), 8.10 (1H, d, J=9.8 Hz), 8.37 (1H, s), 8.56-8.58 (1H, m)

Example 4(2)

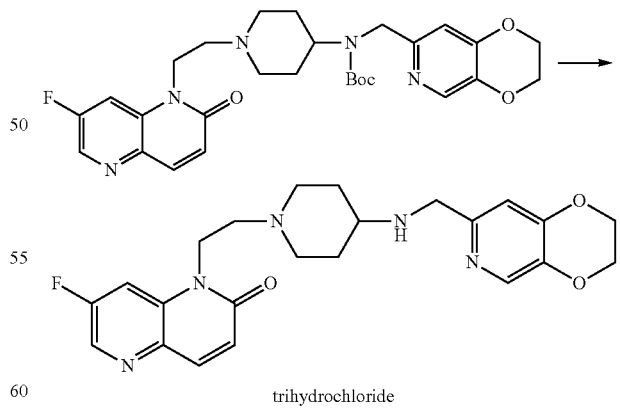

trihydrochloride

To a suspension of 0.30 g of tert-butyl (2,3-dihydro(1,4)dioxino(2,3-c)pyridin-7-ylmethyl)(1-(2-(7-fluoro-2-oxo-1,5-naphthyridin-1(2H)-yl)ethyl)piperidin-4-yl)carbamate in 1.8 mL of isopropyl alcohol, 0.23 mL of concentrated hydrochloride was added, and the mixture was heated under reflux while stirring for 1 hour 50 minutes. The reaction mixture was cooled to 5° C., and the solid was filtered off to obtain 0.28 g of 1-(2-(4-((2,3-dihydro(1,4)dioxino(2,3-c)pyridin-7-ylmethyl)amino)piperidin-1-yl)ethyl)-7-fluoro-1,5-naphthyridin-2(1H)-one trihydrochloride as a light yellow solid.

$^1$H-NMR (D$_2$O) δ: 2.00-2.16 (2H, m), 2.52-2.61 (2H, m), 3.23-3.35 (2H, m), 3.61-3.67 (2H, m), 3.69-3.80 (1H, m), 3.98-4.07 (2H, m), 4.46-4.51 (2H, m), 4.52 (2H, s), 4.55-4.63 (2H, m), 4.71-4.96 (2H, m), 6.99 (1H, d, J=9.8 Hz), 7.44 (1H, s), 7.93-7.99 (1H, m), 8.10 (1H, d, J=9.8 Hz), 8.36 (1H, s), 8.57 (1H, d, J=2.2 Hz)

Example 5

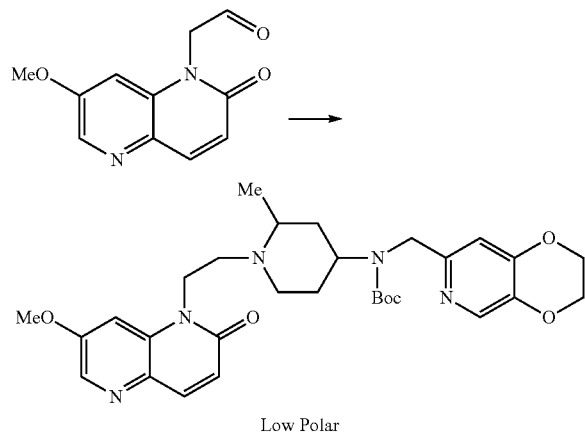

Low Polar

By the same technique as in Example 1, tert-butyl (2,3-dihydro(1,4)dioxino(2,3-c)pyridin-7-ylmethyl)(1-(2-(7-methoxy-2-oxo-1,5-naphthyridin-1(2H)-yl)ethyl)-2-methylpiperidin-4-yl)carbamate was obtained from (7-methoxy-2-oxo-1,5-naphthyridin-1(2H)-yl)acetaldehyde and tert-butyl (2,3-dihydro(1,4)dioxino(2,3-c)pyridin-7-ylmethyl)(2-methylpiperidin-4-yl)carbamate.

$^1$H-NMR (CDCl$_3$) δ: 0.99-1.10 (3H, m), 1.33-1.83 (13H, m), 2.57-2.78 (4H, m), 3.14-3.23 (1H, m), 3.96 (3H, s), 4.13-4.53 (9H, m), 6.73 (1H, s), 6.73 (1H, d, J=9.6 Hz), 7.19 (1H, d, J=2.2 Hz), 7.83 (1H, d, J=9.6 Hz), 8.05 (1H, s), 8.27 (1H, d, J=2.2 Hz)

Example 6

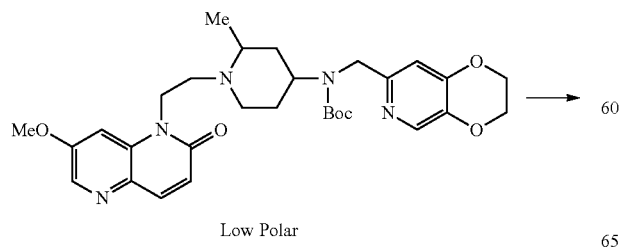

Low Polar

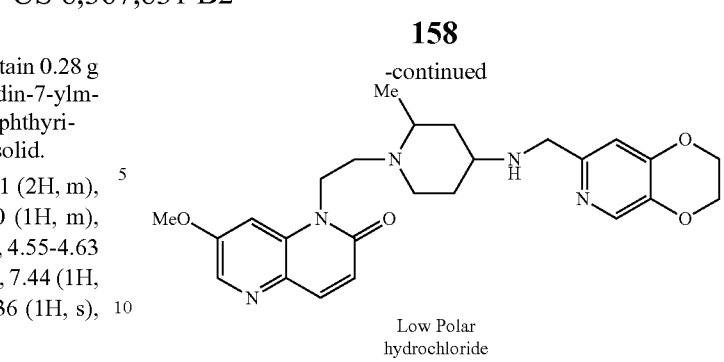

Low Polar hydrochloride

By the same technique as in Example 2, 1-(2-(4-((2,3-dihydro(1,4)dioxino(2,3-c)pyridin-7-ylmethyl)amino)-2-methylpiperidin-1-yl)ethyl)-7-methoxy-1,5-naphthyridin-2(1H)-one was obtained from tert-butyl (2,3-dihydro(1,4)dioxino(2,3-c)pyridin-7-ylmethyl)(1-(2-(7-methoxy-2-oxo-1,5-naphthyridin-1(2H)-yl)ethyl)-2-methylpiperidin-4-yl)carbamate.

$^1$H-NMR (CDCl$_3$) δ: 1.03 (3H, d, J=6.6 Hz), 1.20-1.90 (4H, m), 2.66-2.88 (5H, m), 2.95-3.05 (1H, m), 3.77 (2H, d, J=2.7 Hz), 3.97 (3H, s), 4.25-4.43 (6H, m), 6.74 (1H, d, J=9.6 Hz), 6.82 (1H, s), 7.20-7.25 (1H, m), 7.84 (1H, d, J=9.6 Hz), 8.10 (1H, s), 8.27 (1H, d, J=2.4 Hz)

To a solution of 53 mg of 1-(2-(4-((2,3-dihydro(1,4)dioxino(2,3-c)pyridin-7-ylmethyl)amino)-2-methylpiperidin-1-yl)ethyl)-7-methoxy-1,5-naphthyridin-2(1H)-one in 1 mL of ethyl acetate, 0.23 mL of a 4.0 mol/L hydrogen chloride/ethyl acetate solution was added at room temperature, and after stirring, the solid was filtered off to obtain 40 mg of 1-(2-(4-((2,3-dihydro(1,4)dioxino(2,3-c)pyridin-7-ylmethyl)amino)-2-methylpiperidin-1-yl)ethyl)-7-methoxy-1,5-naphthyridin-2(1H)-one hydrochloride as a light yellow solid.

$^1$H-NMR (DMSO-d$_6$-D$_2$O) δ: 1.03 (3H, d, J=6.6 Hz), 2.00-2.35 (4H, m), 3.12-3.60 (5H, m), 3.90-4.30 (3H, m), 4.07 (3H, s), 4.33-4.45 (4H, m), 4.58-4.86 (2H, m), 6.72 (1H, d, J=9.5 Hz), 7.22 (1H, s), 7.66-7.75 (1H, m), 7.96 (1H, d, J=9.5 Hz), 8.26 (1H, s), 8.34 (1H, d, J=1.9 Hz)

Example 7

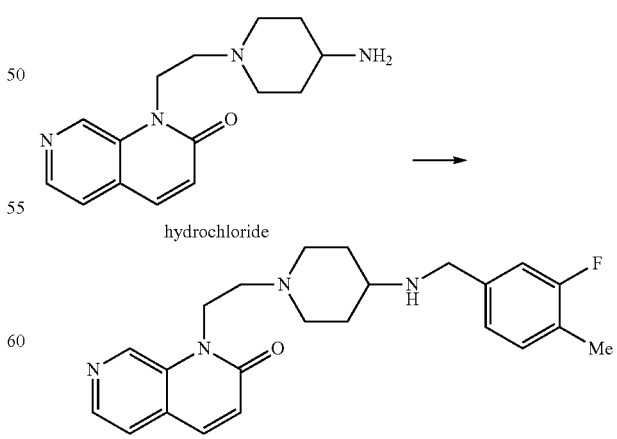

hydrochloride

To a suspension of 0.20 g of 1-(2-(4-(aminopiperidin-1-yl)ethyl)-1,7-naphthyridin-2(1H)-one hydrochloride in 3 mL of methanol, 66 mg of sodium cyanoborohydride, 64 µL of 3-fluoro-4-methylbenzaldehyde and 0.12 mL of acetic acid were added at room temperature, and the mixture was stirred at the same temperature for 1 hour 30 minutes. Thereto was added 64 µL of 3-fluoro-4-methylbenzaldehyde, and the mixture was stirred at the same temperature for 1 hour 30 minutes. Thereto were further added 33 mg of sodium cyanoborohydride and 64 µL of 3-fluoro-4-methylbenzaldehyde, and the mixture was stirred at the same temperature for 3 hours and then left overnight. The mixture was charged with chloroform and adjusted to pH 9.9 with a saturated aqueous sodium hydrogen carbonate solution and a 1 mol/L aqueous sodium hydroxide solution. The organic layer was separated, and the aqueous layer was extracted with chloroform. The organic layer and the extract were combined, the resultant solution was washed sequentially with water and a saturated aqueous sodium chloride solution and dried over anhydrous magnesium sulfate, and the solvent was distilled off under reduced pressure. The resultant residue was purified by basic silica gel column chromatography using an eluent of chloroform:methanol=10:1 to obtain 0.16 g of 1-(2-(4-((3-fluoro-4-methylbenzyl)amino)piperidin-1-yl)ethyl)-1,7-naphthyridin-2(1H)-one as a slightly yellow oily substance.

¹H-NMR (CDCl₃) δ: 1.37-1.49 (2H, m), 1.87-1.95 (2H, m), 2.17-2.25 (2H, m), 2.26 (3H, d, J=1.7 Hz), 2.48-2.57 (1H, m), 2.68-2.74 (2H, m), 2.97-3.04 (2H, m), 3.78 (2H, s), 4.45-4.51 (2H, m), 6.90 (1H, d, J=9.5 Hz), 6.97-7.02 (2H, m), 7.10-7.15 (1H, m), 7.43 (1H, d, J=5.1 Hz), 7.66 (1H, d, J=9.5 Hz), 8.46 (1H, d, J=5.1 Hz), 8.92 (1H, s)

Example 8

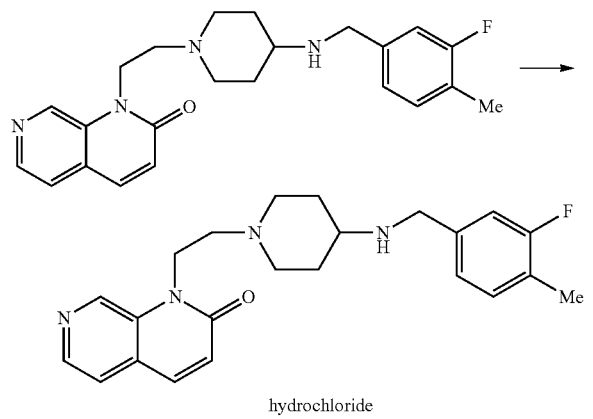

hydrochloride

To a solution of 0.16 g of 1-(2-(4-((3-fluoro-4-methylbenzyl)amino)piperidin-1-yl)ethyl)-1,7-naphthyridin-2(1H)-one in 3 mL of ethyl acetate, 5 mL of a 4.0 mol/L hydrogen chloride/ethyl acetate solution was added at room temperature. Thereto was added 2 mL of ethyl acetate, the mixture was stirred at the same temperature for 10 minutes, and the solvent was distilled off under reduced pressure. Ethyl acetate was added to the resultant residue, and the solid was filtered off to obtain 0.18 g of 1-(2-(4-((3-fluoro-4-methylbenzyl)amino)piperidin-1-yl)ethyl)-1,7-naphthyridin-2(1H)-one hydrochloride as a light yellow solid.

¹H-NMR (D₂O) δ: 1.98-2.11 (2H, m), 2.28 (3H, d, J=1.5 Hz), 2.50-2.58 (2H, m), 3.22-3.33 (2H, m), 3.60-3.70 (3H, m), 3.97-4.05 (2H, m), 4.30 (2H, s), 4.81-4.87 (2H, m), 7.17-7.22 (2H, m), 7.20 (1H, d, J=9.5 Hz), 7.36 (1H, t, J=7.7 Hz), 8.17 (1H, d, J=5.9 Hz), 8.17 (1H, d, J=9.5 Hz), 8.61 (1H, d, J=5.9 Hz), 9.12 (1H, s)

Example 9

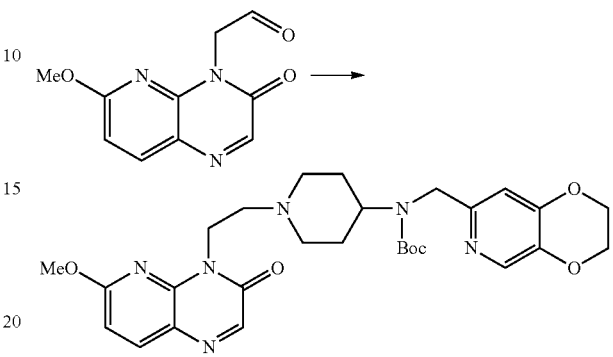

To a solution of 0.16 g of tert-butyl (2,3-dihydro(1,4)dioxino(2,3-c)pyridin-7-ylmethyl)(piperidin-4-yl)carbamate in 3 mL of dichloromethane, 0.10 g of (6-methoxy-3-oxopyrido(2,3-b)pyrazin-4(3H)-yl)acetaldehyde, 26 µL of acetic acid and 0.15 g of sodium triacetoxyborohydride were added, and the mixture was stirred at room temperature for 30 minutes. To the reaction mixture, chloroform and a saturated aqueous sodium hydrogen carbonate solution were added, the organic layer was separated, and the aqueous layer was extracted with chloroform. The organic layer and the extract were combined, the resultant solution was washed with a saturated aqueous sodium chloride solution and dried over anhydrous magnesium sulfate, and the solvent was distilled off under reduced pressure. The resultant residue was purified by flash basic silica gel column chromatography using an eluent of chloroform to obtain 0.15 g of tert-butyl (2,3-dihydro(1,4)dioxino(2,3-c)pyridin-7-ylmethyl)(1-(2-(6-methoxy-3-oxopyrido(2,3-b)pyrazin-4(3H)-yl)ethyl)piperidin-4-yl)carbamate as a light brown oily substance.

¹H-NMR (CDCl₃) δ: 1.38 (9H, s), 1.40-1.70 (4H, m), 2.03-2.23 (2H, m), 2.66-2.73 (2H, m), 3.02-3.10 (2H, m), 4.00 (3H, s), 4.03-4.20 (1H, m), 4.23-4.46 (6H, m), 4.48-4.55 (2H, m), 6.71 (1H, s), 6.72 (1H, d, J=8.5 Hz), 8.01 (1H, d, J=8.5 Hz), 8.04 (1H, s), 8.14 (1H, s)

Example 10

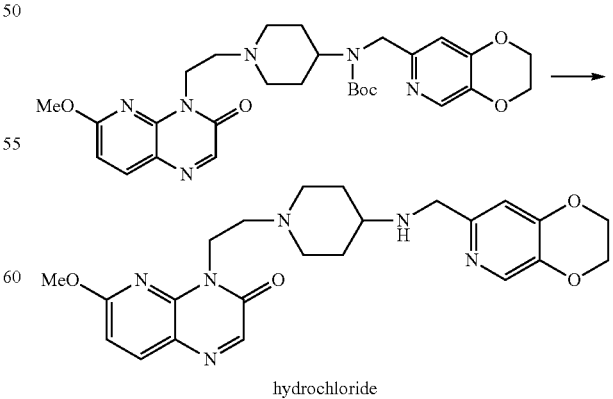

hydrochloride

To a solution of 0.14 g of tert-butyl (2,3-dihydro(1,4)dioxino(2,3-c)pyridin-7-ylmethyl)(1-(2-(6-methoxy-3-oxopyrido(2,3-b)pyrazin-4(3H)-yl)ethyl)piperidin-4-yl)carbamate in 3.0 mL of ethanol, 3 mL of a 6.0 mol/L hydrogen chloride/ethanol solution was added at room temperature. The mixture was stirred at the same temperature for 3 hours, and the solvent was distilled off under reduced pressure. Diethyl ether was added to the resultant residue, and the solid was filtered off to obtain 0.11 g of 4-(2-(4-((2,3-dihydro(1,4)dioxino(2,3-c)pyridin-7-ylmethyl)amino)piperidin-1-yl)ethyl)-6-methoxypyrido(2,3-b)pyrazin-3(4H)-one hydrochloride as a light brown solid.

$^1$H-NMR (D$_2$O) δ: 1.97-2.12 (2H, m), 2.49-2.58 (2H, m), 3.20-3.34 (2H, m), 3.66-3.78 (3H, m), 3.97-4.08 (2H, m), 4.07 (3H, s), 4.44-4.49 (2H, m), 4.49 (2H, s), 4.55-4.60 (2H, m), 4.88-4.94 (2H, m), 6.98 (1H, d, J=8.9 Hz), 7.41 (1H, s), 8.18 (1H, d, J=8.9 Hz), 8.19 (1H, s), 8.34 (1H, s)

Example 11

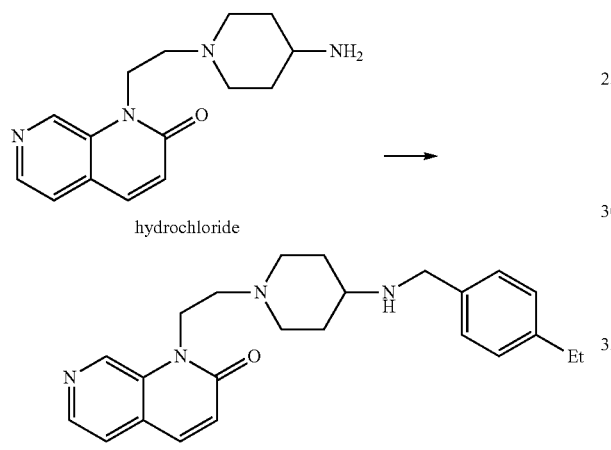

By the same technique as in Example 7, 1-(2-(4-((4-ethylbenzyl)amino)piperidin-1-yl)ethyl)-1,7-naphthyridin-2(1H)-one was obtained from 1-(2-(4-aminopiperidin-1-yl)ethyl)-1,7-naphthyridin-2(1H)-one hydrochloride and 4-ethylbenzaldehyde.

$^1$H-NMR (CDCl$_3$) δ: 1.23 (3H, t, J=7.6 Hz), 1.37-1.49 (2H, m), 1.87-1.95 (2H, m), 2.16-2.24 (2H, m), 2.49-2.58 (1H, m), 2.63 (2H, q, J=7.6 Hz), 2.67-2.73 (2H, m), 2.96-3.03 (2H, m), 3.78 (2H, s), 4.44-4.50 (2H, m), 6.89 (1H, d, J=9.5 Hz), 7.15 (2H, d, J=8.0 Hz), 7.23 (2H, d, J=8.0 Hz), 7.41 (1H, d, J=5.1 Hz), 7.65 (1H, d, J=9.5 Hz), 8.44 (1H, d, J=5.1 Hz), 8.91 (1H, s)

Example 12

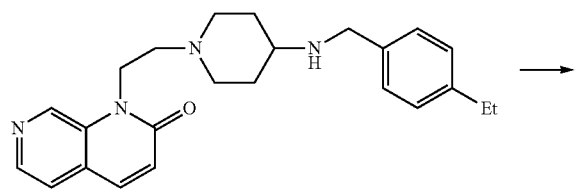

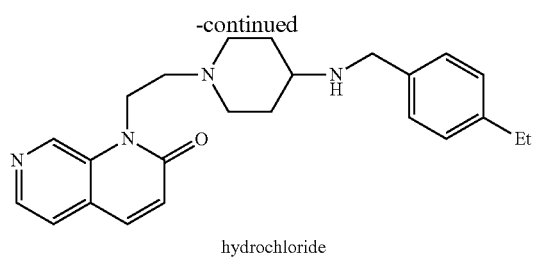

By the same technique as in Example 8, 1-(2-(4-((4-ethylbenzyl)amino)piperidin-1-yl)ethyl)-1,7-naphthyridin-2(1H)-one hydrochloride was obtained from 1-(2-(4-((4-ethylbenzyl)amino)piperidin-1-yl)ethyl)-1,7-naphthyridin-2(1H)-one.

$^1$H-NMR (D$_2$O) δ: 1.21 (3H, t, J=7.7 Hz), 1.99-2.12 (2H, m), 2.50-2.59 (2H, m), 2.68 (2H, q, J=7.7 Hz), 3.22-3.33 (2H, m), 3.58-3.71 (3H, m), 3.97-4.06 (2H, m), 4.30 (2H, s), 4.81-4.87 (2H, m), 7.24 (1H, d, J=9.8 Hz), 7.38 (2H, d, J=8.2 Hz), 7.42 (2H, d, J=8.2 Hz), 8.19 (1H, d, J=9.8 Hz), 8.24 (1H, d, J=5.9 Hz), 8.63 (1H, d, J=5.9 Hz), 9.16 (1H, s)

Example 13

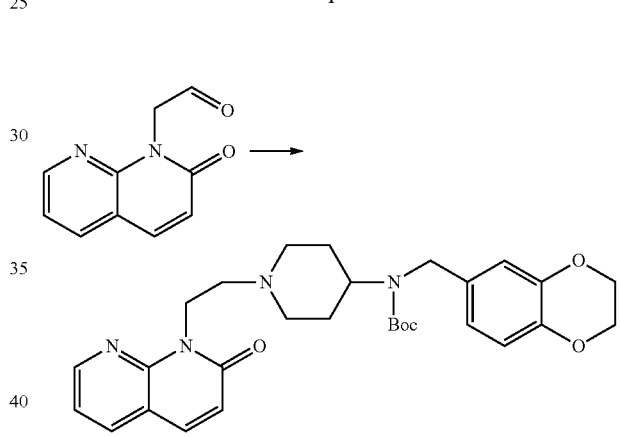

To a solution of 0.75 g of (2-oxo-1,8-naphthyridin-1(2H)-yl)acetaldehyde in 40 mL of dichloromethane, 1.4 g of tert-butyl (2,3-dihydro-1,4-benzodioxin-6-ylmethyl)(piperidin-4-yl)carbamate, 0.23 mL of acetic acid and 1.3 g of sodium triacetoxyborohydride were added, and the mixture was stirred at room temperature for 2 hours. Thereto were added water, a saturated aqueous sodium hydrogen carbonate solution and chloroform, the organic layer was separated, and the aqueous layer was extracted with chloroform. The organic layer and the extract were combined, the resultant solution was washed with a saturated aqueous sodium chloride solution and dried over anhydrous magnesium sulfate, and the solvent was distilled off under reduced pressure. The resultant residue was purified by silica gel column chromatography using an eluent of chloroform:methanol=200:3 to obtain 1.4 g of tert-butyl (2,3-dihydro-1,4-benzodioxin-6-ylmethyl)(1-(2-(2-oxo-1,8-naphthyridin-1(2H)-yl)ethyl)piperidin-4-yl)carbamate as a white foam.

$^1$H-NMR (CDCl$_3$) δ: 1.41 (9H, s), 1.55-1.70 (4H, m), 2.05-2.25 (2H, m), 2.62-2.68 (2H, m), 3.08-3.14 (2H, m), 4.00-4.18 (1H, m), 4.21-4.27 (6H, m), 4.62-4.67 (2H, m), 6.64-6.70 (1H, m), 6.72 (1H, d, J=1.7 Hz), 6.72 (1H, d, J=9.5 Hz), 6.77 (1H, d, J=8.3 Hz), 7.15 (1H, dd, J=7.7, 4.7 Hz), 7.61 (1H, d, J=9.5 Hz), 7.84 (1H, dd, J=7.7, 1.9 Hz), 8.56 (1H, dd, J=4.7, 1.9 Hz)

Example 14

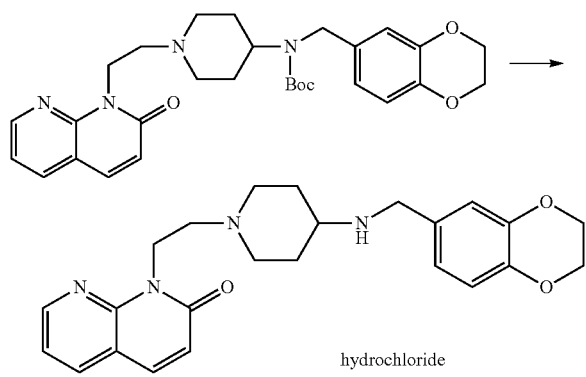

To 1.4 g of tert-butyl (2,3-dihydro-1,4-benzodioxin-6-yl-methyl)(1-(2-(2-oxo-1,8-naphthyridin-1(2H)-yl)ethyl)piperidin-4-yl)carbamate, 50 mL of a 4 mol/L hydrogen chloride/ethyl acetate solution was added, and the mixture was stirred at room temperature for 1 day. The solvent was distilled off under reduced pressure, thereto was added ethanol, and the solvent was distilled off under reduced pressure. Ethyl acetate was added to the resultant residue, and after stirring, the solid was filtered off to obtain 1.2 g of 1-(2-(4-((2,3-dihydro-1,4-benzodioxin-6-ylmethyl)amino)piperidin-1-yl)ethyl)-1,8-naphthyridin-2(1H)-one hydrochloride as a white solid.

$^1$H-NMR (D$_2$O) δ: 1.93-2.07 (2H, m), 2.48-2.58 (2H, m), 3.18-3.29 (2H, m), 3.57-3.78 (3H, m), 4.03-4.10 (2H, m), 4.20-4.27 (2H, m), 4.30-4.40 (4H, m), 4.90-4.95 (2H, m), 6.85 (1H, d, J=9.5 Hz), 6.98-7.06 (3H, m), 7.47 (1H, dd, J=7.7, 4.8 Hz), 8.06 (1H, d, J=9.5 Hz), 8.24 (1H, d, J=7.7 Hz), 8.70 (1H, d, J=4.8 Hz)

Example 15

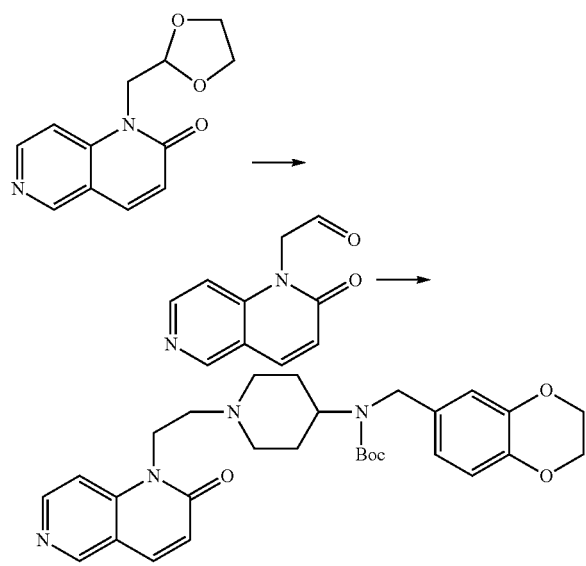

(1) To 0.60 g of 1-(1,3-dioxolan-2-ylmethyl)-1,6-naphthyridin-2(1H)-one, 6 mL of a 90% aqueous trifluoroacetic acid solution was added, and the mixture was stirred at room temperature for 12 hours. Thereto was added 1.0 mL of water, and the mixture was stirred for 1 hour, and stirred at 55 to 75° C. for 3 hours 30 minutes. The solvent was distilled off under reduced pressure, thereto were added a saturated aqueous sodium hydrogen carbonate solution and chloroform, and the mixture was stirred at room temperature for 1 hour 30 minutes. The organic layer was then separated, and the aqueous layer was extracted with chloroform. The organic layer and the extract were combined, the resultant solution was dried over anhydrous magnesium sulfate, and the solvent was distilled off under reduced pressure to obtain (2-oxo-1,6-naphthyridin-1(2H)-yl)acetaldehyde.

(2) To a solution of 0.38 g of (2-oxo-1,6-naphthyridin-1(2H)-yl)acetaldehyde in 14 mL of dichloromethane, 0.35 g of tert-butyl (2,3-dihydro-1,4-benzodioxin-6-ylmethyl)(piperidin-4-yl)carbamate and 0.12 mL of acetic acid were added, the mixture was stirred for 5 minutes, and then, 0.32 g of sodium triacetoxyborohydride was added to the reaction mixture and the mixture was stirred for 4 hours 20 minutes. To the reaction mixture, a saturated aqueous sodium hydrogen carbonate solution and chloroform were added, the organic layer was separated, and the aqueous layer was extracted with chloroform. The organic layer and the extract were combined, the resultant solution was washed with a saturated aqueous sodium chloride solution and dried over anhydrous magnesium sulfate, and the solvent was distilled off under reduced pressure. The resultant residue was purified by silica gel column chromatography using an eluent of chloroform:methanol=100:1 to obtain 0.36 g of tert-butyl (2,3-dihydro-1,4-benzodioxin-6-ylmethyl)(1-(2-(2-oxo-1,6-naphthyridin-1(2H)-yl)ethyl)piperidin-4-yl)carbamate as a colorless oily substance.

$^1$H-NMR (CDCl$_3$) δ: 1.43 (9H, s), 1.61-1.70 (4H, m), 2.09-2.23 (2H, m), 2.58-2.63 (2H, m), 2.98-3.04 (2H, m), 3.95-4.35 (9H, m), 6.64-6.70 (1H, m), 6.73 (1H, d, J=9.5 Hz), 6.74 (1H, d, J=2.4 Hz), 6.78 (1H, d, J=8.3 Hz), 7.24 (1H, d, J=5.9 Hz), 7.73 (1H, d, J=9.5 Hz), 8.58 (1H, d, J=5.9 Hz), 8.77 (1H, s)

Example 16

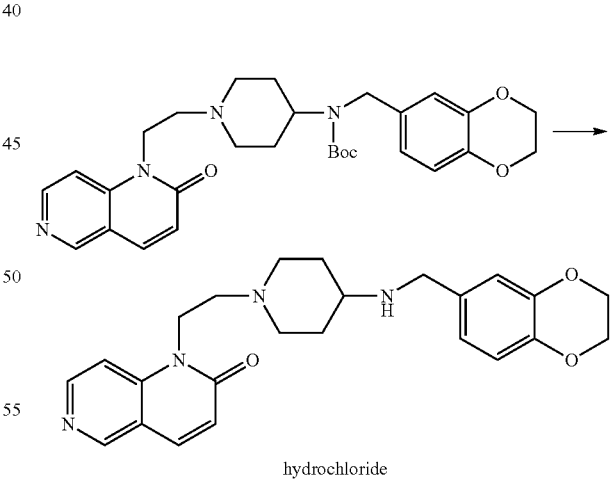

To 0.15 g of tert-butyl (2,3-dihydro-1,4-benzodioxin-6-ylmethyl)(1-(2-(2-oxo-1,6-naphthyridin-1(2H)-yl)ethyl)piperidin-4-yl)carbamate, 10 mL of a 4 mol/L hydrogen chloride/ethyl acetate solution was added, and the mixture was stirred at room temperature for 2 hours 30 minutes. Thereto was further added 5 mL of a 4 mol/L hydrogen chloride/ethyl acetate solution, the mixture was reacted at room temperature for 20 hours, and the solvent was distilled off under reduced pressure. The mixture was dissolved in 8 mL of 6 mol/L hydrochloric acid, and then the solvent was distilled off under reduced pressure. Ethanol was added to the resultant residue, and the solvent was distilled off under reduced pressure, and ethyl acetate was then added to the resultant residue, and the solid was filtered off to obtain 0.13 g of 1-(2-(4-((2,3-dihydro-1,4-benzodioxin-6-ylmethyl)amino)piperidin-1-yl)ethyl)-1,6-naphthyridin-2(1H)-one hydrochloride as a light yellow solid.

$^1$H-NMR (D$_2$O) δ: 2.02-2.14 (2H, m), 2.52-2.59 (2H, m), 3.27-3.36 (2H, m), 3.64-3.70 (3H, m), 3.99-4.07 (2H, m), 4.24-4.26 (2H, m), 4.35 (4H, s), 4.80-4.90 (2H, m), 6.98-7.07 (3H, m), 7.08 (1H, d, J=9.8 Hz), 8.06 (1H, d, J=7.3 Hz), 8.25 (1H, d, J=9.8 Hz), 8.79 (1H, d, J=7.1 Hz), 9.23 (1H, s)

Example 17

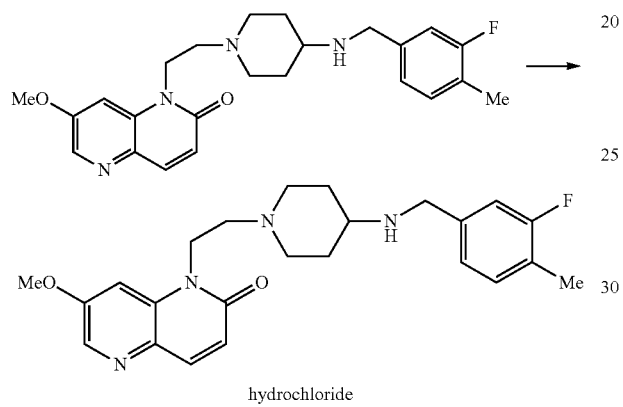

By the same technique as in Example 8, 1-(2-(4-((3-fluoro-4-methylbenzyl)amino)piperidin-1-yl)ethyl)-7-methoxy-1,5-naphthyridin-2(1H)-one hydrochloride was obtained from 1-(2-(4-((3-fluoro-4-methylbenzyl)amino)piperidin-1-yl)ethyl)-7-methoxy-1,5-naphthyridin-2(1H)-one.

$^1$H-NMR (D$_2$O) δ: 1.96-2.10 (2H, m), 2.28 (3H, s), 2.48-2.57 (2H, m), 3.18-3.31 (2H, m), 3.59-3.68 (3H, m), 3.95-4.06 (2H, m), 4.04 (3H, s), 4.29 (2H, s), 4.74-4.83 (2H, m), 6.87 (1H, d, J=9.8 Hz), 7.17-7.22 (2H, m), 7.36 (1H, t, J=7.8 Hz), 7.44 (1H, d, J=2.2 Hz), 8.06 (1H, d, J=9.8 Hz), 8.40 (1H, d, J=2.2 Hz)

Example 18

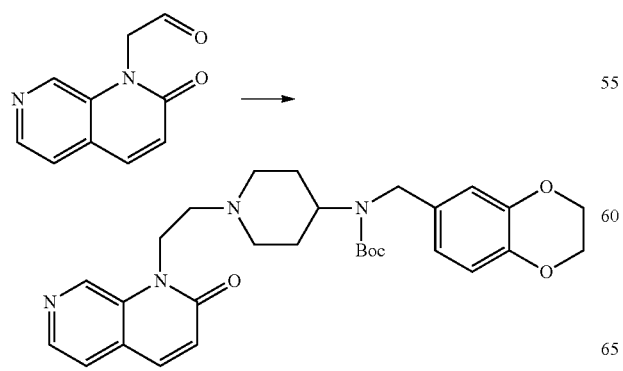

To a solution of 0.32 g of (2-oxo-1,7-naphthyridin-1(2H)-yl)acetaldehyde in 10 mL of dichloromethane, 0.59 g of tert-butyl (2,3-dihydro-1,4-benzodioxin-6-ylmethyl)(piperidin-4-yl)carbamate and 97 µL of acetic acid were added, then, 0.54 g of sodium triacetoxyborohydride was added to the reaction mixture, and the mixture was stirred at room temperature for 2 hours 30 minutes. Thereto were added water, a saturated aqueous sodium hydrogen carbonate solution and chloroform, the organic layer was separated, and the aqueous layer was extracted with chloroform. The organic layer and the extract were combined, the resultant solution was washed with a saturated aqueous sodium chloride solution and dried over anhydrous magnesium sulfate, and the solvent was distilled off under reduced pressure. The resultant residue was purified by silica gel column chromatography using an eluent of chloroform:methanol=100:1 to obtain 0.15 g of tert-butyl (2,3-dihydro-1,4-benzodioxin-6-ylmethyl)(1-(2-(2-oxo-1,7-naphthyridin-1(2H)-yl)ethyl)piperidin-4-yl)carbamate as a colorless oily substance.

$^1$H-NMR (CDCl$_3$) δ: 1.42 (9H, s), 1.62-1.72 (4H, m), 2.12-2.26 (2H, m), 2.63-2.69 (2H, m), 3.00-3.06 (2H, m), 3.98-4.15 (1H, m), 4.22-4.33 (6H, m), 4.41-4.46 (2H, m), 6.67-6.71 (1H, m), 6.74 (1H, d, J=2.0 Hz), 6.78 (1H, d, J=8.3 Hz), 6.89 (1H, d, J=9.5 Hz), 7.43 (1H, d, J=5.0 Hz), 7.66 (1H, d, J=9.5 Hz), 8.44 (1H, d, J=5.0 Hz), 8.87 (1H, s)

Example 19

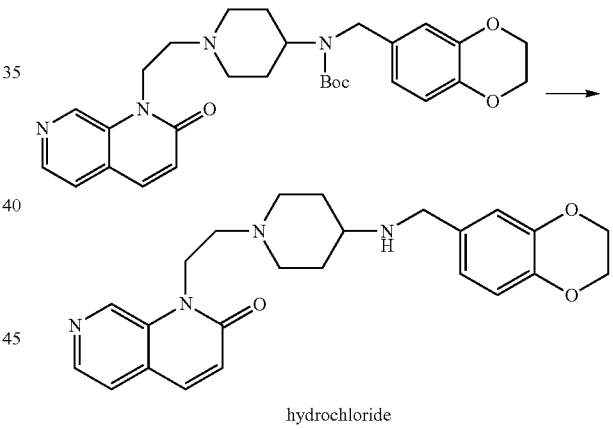

To 0.15 g of tert-butyl (2,3-dihydro-1,4-benzodioxin-6-ylmethyl)(1-(2-(2-oxo-1,7-naphthyridin-1(2H)-yl)ethyl)piperidin-4-yl)carbamate, 8 mL of a 4 mol/L hydrogen chloride/ethyl acetate solution was added, the mixture was reacted at room temperature for 21 hours, and the solvent was distilled off under reduced pressure. Ethanol was added to the resultant residue, the solvent was distilled off under reduced pressure, ethyl acetate was then added to the resultant residue, and the solid was filtered off to obtain 0.15 g of 1-(2-(4-((2,3-dihydro-1,4-benzodioxin-6-ylmethyl)amino)piperidin-1-yl)ethyl)-1,7-naphthyridin-2(1H)-one hydrochloride as a yellow solid.

$^1$H-NMR (D$_2$O) δ: 2.01-2.13 (2H, m), 2.52-2.58 (2H, m), 3.26-3.35 (2H, m), 3.61-3.72 (3H, m), 4.00-4.07 (2H, m), 4.25 (2H, s), 4.35 (4H, s), 4.82-4.89 (2H, m), 6.69-7.07 (3H, m), 7.27 (1H, d, J=9.0 Hz), 8.22 (1H, d, J=9.8 Hz), 8.28 (1H, d, J=5.7 Hz), 8.65 (1H, d, J=5.7 Hz), 9.19 (1H, s)

Example 20

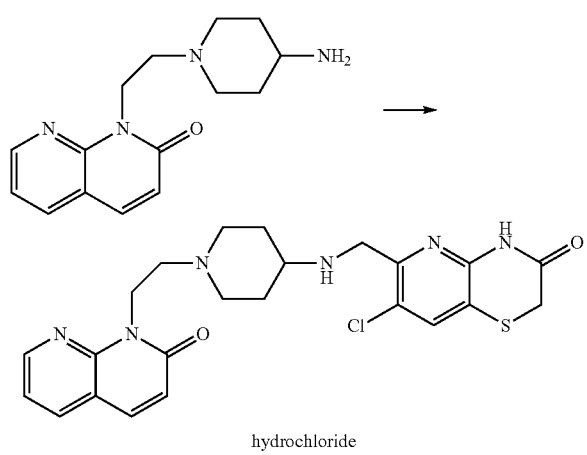

hydrochloride

To a solution of 0.07 g of 1-(2-(4-aminopiperidin-1-yl)ethyl)-1,8-naphthyridin-2(1H)-one in 3 mL of dichloromethane, 57 mg of 7-chloro-3-oxo-3,4-dihydro-2H-pyrido(3,2-b)(1,4)thiazine-6-carbaldehyde and 14 µL of acetic acid were added, the mixture was stirred for 10 minutes, and then, 79 mg of sodium triacetoxyborohydride was added to the reaction mixture, and the mixture was reacted for 1 day. Thereto was further added 7 µL of acetic acid, the mixture was stirred for 35 minutes, and then, 7 µL of acetic acid and 26 mg of sodium triacetoxyborohydride was added thereto, and the mixture was reacted for 20 minutes. To the reaction mixture, water, a saturated aqueous sodium hydrogen carbonate solution, chloroform and sodium chloride were added, the organic layer was separated, and the aqueous layer was extracted with chloroform while salting out. The organic layer and the extract were combined, the resultant solution was dried over anhydrous magnesium sulfate, and the solvent was distilled off under reduced pressure. The resultant residue was dissolved in 5 mL of 6 mol/L hydrochloric acid, and the solvent was distilled off under reduced pressure. The resultant residue was purified by reverse silica gel column chromatography using an eluent of water to obtain 71 mg of 7-chloro-6-(((1-(2-(2-oxo-1,8-naphthyridin-1(2H)-yl)ethyl)piperidin-4-yl)amino)methyl)-2H-pyrido(3,2-b)(1,4)thiazin-3(4H)-one hydrochloride as a light gray solid.

$^1$H-NMR (D$_2$O) δ: 2.03-2.19 (2H, m), 2.56-2.66 (2H, m), 3.22-3.34 (2H, m), 3.59-3.85 (5H, m), 4.03-4.15 (2H, m), 4.56 (2H, s), 4.70-5.02 (2H, m), 6.83 (1H, d, J=9.4 Hz), 7.44-7.49 (1H, m), 7.93 (1H, s), 8.05 (1H, d, J=9.4 Hz), 8.22 (1H, d, J=7.8 Hz), 8.68-8.73 (1H, m)

Example 21

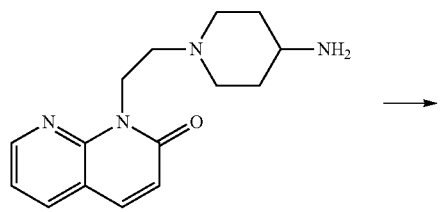

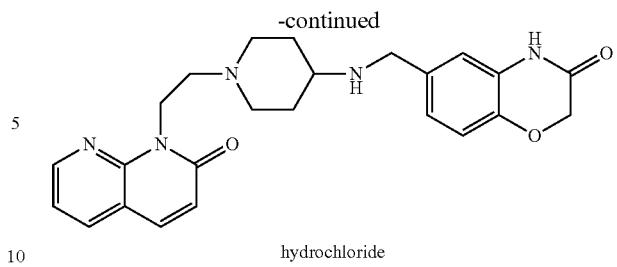

hydrochloride

To a solution of 83 mg of 1-(2-(4-aminopiperidin-1-yl)ethyl)-1,8-naphthyridin-2(1H)-one in 15 mL of dichloromethane, 54 mg of 3-oxo-3,4-dihydro-2H-1,4-benzoxazine-6-carbaldehyde, 86 µL of acetic acid and 0.36 g of sodium triacetoxyborohydride were dividedly added while reacting at room temperature for 1.5 days. To the reaction solution, water, a saturated aqueous sodium hydrogen carbonate solution, chloroform and sodium chloride were added, the organic layer was separated, and the aqueous layer was extracted with chloroform while salting out. The organic layer and the extract were combined, the resultant solution was dried over anhydrous magnesium sulfate, and the solvent was distilled off under reduced pressure. The resultant residue was purified by silica gel column chromatography using an eluent of chloroform:methanol=5:1, and the resultant residue was dissolved in 5 mL of 6 mol/L hydrochloric acid, and then, the solvent was distilled off under reduced pressure. Diethyl ether was added to the resultant residue, and the solid was filtered off to obtain 0.12 g of 6-(((1-(2-(2-oxo-1,8-naphthyridin-1(2H)-yl)ethyl)piperidin-4-yl)amino)methyl)-2H-1,4-benzoxazin-3(4H)-one hydrochloride as a light yellow solid.

$^1$H-NMR (D$_2$O) δ: 1.94-2.09 (2H, m), 2.50-2.58 (2H, m), 3.18-3.34 (2H, m), 3.59-3.70 (3H, m), 3.98-4.11 (2H, m), 4.27 (2H, s), 4.71 (2H, s), 4.91-4.97 (2H, m), 6.85 (1H, d, J=9.5 Hz), 7.06-7.11 (2H, m), 7.15 (1H, dd, J=8.4, 1.8 Hz), 7.47 (1H, dd, J=7.8, 4.8 Hz), 8.07 (1H, d, J=9.5 Hz), 8.23-8.26 (1H, m), 8.68-8.72 (1H, m)

Example 22

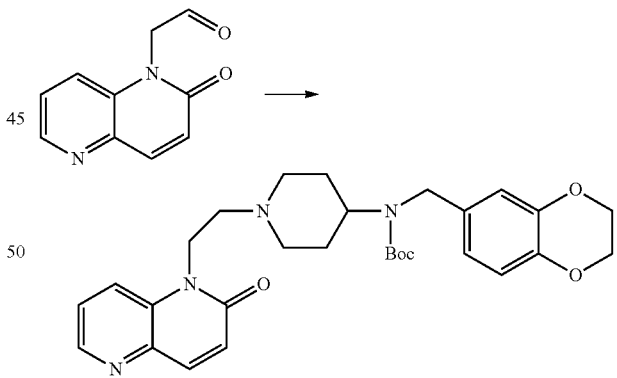

To a solution of 0.62 g of (2-oxo-1,5-naphthyridin-1(2H)-yl)acetaldehyde in 20 mL of dichloromethane, 1.5 g of tert-butyl (2,3-dihydro-1,4-benzodioxin-6-ylmethyl)(piperidin-4-yl)carbamate and 0.19 mL of acetic acid were added, and the mixture was stirred at room temperature for 30 minutes, and then 1.0 g of sodium triacetoxyborohydride was added to the reaction mixture, and the mixture was stirred at room temperature for 4 days. Thereto were added water, a saturated aqueous sodium hydrogen carbonate solution and chloroform, the organic layer was separated, and the aqueous layer was extracted with chloroform. The organic layer and the extract were combined, the resultant solution was dried over anhydrous magnesium sulfate, and the solvent was distilled off under reduced pressure. The resultant residue was purified by silica gel column chromatography using an eluent of chloroform:methanol=75:1 to obtain 0.70 g of tert-butyl (2,3-dihydro-1,4-benzodioxin-6-ylmethyl)(1-(2-(2-oxo-1,5-naphthyridin-1(2H)-yl)ethyl)piperidin-4-yl)carbamate as a light brown oily substance.

$^1$H-NMR (CDCl$_3$) δ: 1.43 (9H, s), 1.61-1.72 (4H, m), 2.10-2.21 (2H, m), 2.61 (2H, t, J=7.3 Hz), 2.97-3.03 (2H, m), 3.97-4.15 (1H, m), 4.20-4.38 (8H, m), 6.65-6.76 (2H, m), 6.78 (1H, d, J=8.3 Hz), 6.90 (1H, d, J=9.8 Hz), 7.45 (1H, dd, J=8.6, 4.5 Hz), 7.75 (1H, d, J=8.6 Hz), 7.90 (1H, d, J=9.8 Hz), 8.53 (1H, d, J=4.5 Hz)

Example 23

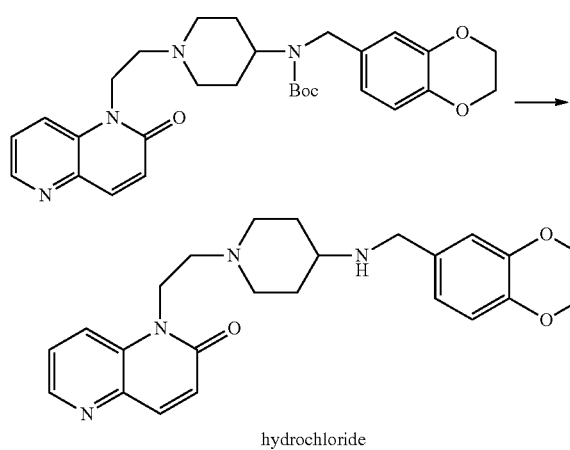

To 0.69 g of tert-butyl (2,3-dihydro-1,4-benzodioxin-6-ylmethyl)(1-(2-(2-oxo-1,5-naphthyridin-1(2H)-yl)ethyl)piperidin-4-yl)carbamate, 25 mL of a 4 mol/L hydrogen chloride/ethyl acetate solution was added, and the mixture was stirred at room temperature for 42 hours. The solvent was distilled off under reduced pressure, a mixed solution of ethyl acetate and ethanol (5:1) was added to the resultant residue, and the solid was filtered off to obtain 0.59 g of 1-(2-(4-((2,3-dihydro-1,4-benzodioxin-6-ylmethyl)amino)piperidin-1-yl)ethyl)-1,5-naphthyridin-2(1H)-one hydrochloride as a light yellow solid.

$^1$H-NMR (D$_2$O) δ: 1.98-2.12 (2H, m), 2.46-2.58 (2H, m), 3.21-3.36 (2H, m), 3.56-3.70 (3H, m), 3.97-4.07 (2H, m), 4.20-4.25 (2H, m), 4.33 (4H, s), 4.80-5.60 (2H, m), 6.96-7.05 (3H, m), 7.24 (1H, d, J=10.0 Hz), 8.09 (1H, dd, J=8.9, 5.2 Hz), 8.22 (1H, d, J=10.0 Hz), 8.54 (1H, d, J=8.9 Hz), 8.77 (1H, d, J=5.2 Hz)

Example 24

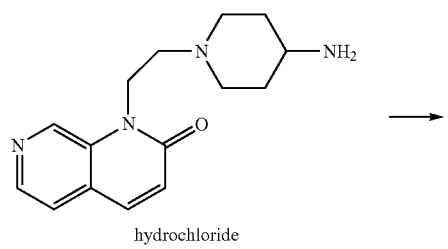

hydrochloride

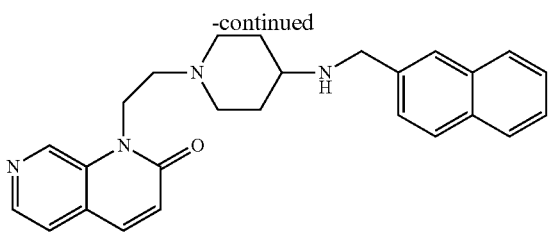

By the same technique as in Example 7, 1-(2-(4-((2-naphthylmethyl)amino)piperidin-1-yl)ethyl)-1,7-naphthyridin-2(1H)-one was obtained from 1-(2-(4-aminopiperidin-1-yl)ethyl)-1,7-naphthyridin-2(1H)-one hydrochloride and 2-naphthaldehyde.

$^1$H-NMR (CDCl$_3$) δ: 1.41-1.51 (2H, m), 1.91-1.99 (2H, m), 2.16-2.25 (2H, m), 2.54-2.62 (1H, m), 2.68-2.73 (2H, m), 2.98-3.04 (2H, m), 3.99 (2H, s), 4.45-4.50 (2H, m), 6.89 (1H, d, J=9.5 Hz), 7.42 (1H, d, J=5.0 Hz), 7.43-7.48 (3H, m), 7.65 (1H, d, J=9.5 Hz), 7.76 (1H, s), 7.79-7.84 (3H, m), 8.44 (1H, d, J=5.0 Hz), 8.91 (1H, s)

Example 25

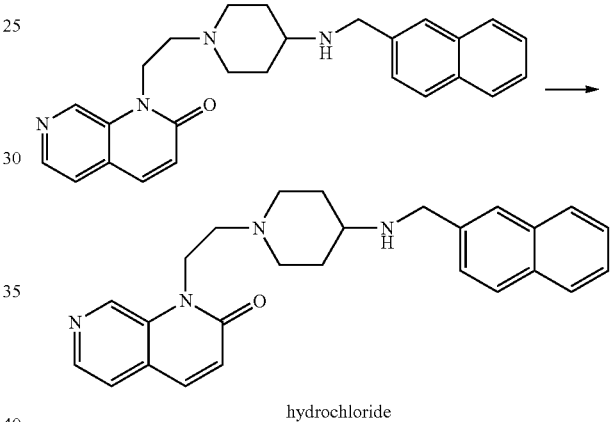

hydrochloride

By the same technique as in Example 8, 1-(2-(4-((2-naphthylmethyl)amino)piperidin-1-yl)ethyl)-1,7-naphthyridin-2(1H)-one hydrochloride was obtained from 1-(2-(4-((2-naphthylmethyl)amino)piperidin-1-yl)ethyl)-1,7-naphthyridin-2(1H)-one.

$^1$H-NMR (DMSO-d$_6$) δ: 2.08-2.22 (2H, m), 2.40-2.48 (2H, m), 3.08-3.20 (2H, m), 3.28-3.87 (5H, m), 4.34-4.43 (2H, m), 4.70-4.79 (2H, m), 7.01 (1H, d, J=9.5 Hz), 7.56-7.63 (2H, m), 7.78 (1H, d, J=8.3 Hz), 7.90-8.04 (4H, m), 8.09 (1H, d, J=9.5 Hz), 8.14 (1H, s), 8.55 (1H, d, J=5.4 Hz), 9.26 (1H, s), 9.78-9.97 (2H, m), 10.82-10.96 (1H, m)

Example 26

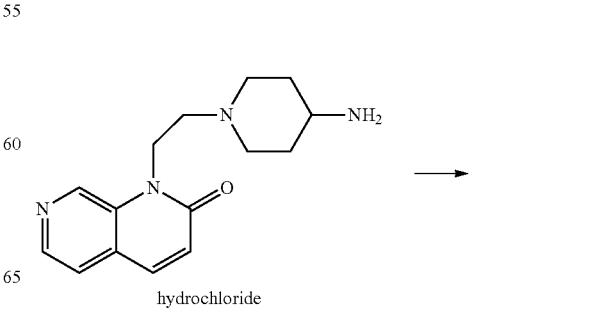

hydrochloride

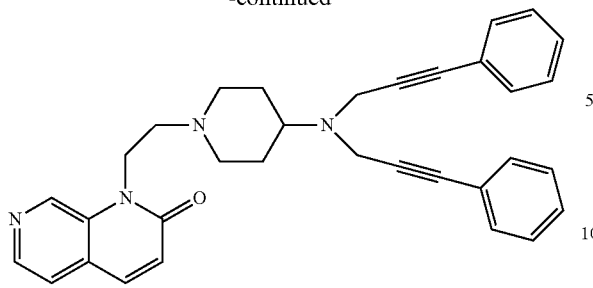

To a suspension of 0.20 g of 1-(2-(4-aminopiperidin-1-yl)ethyl)-1,7-naphthyridin-2(1H)-one hydrochloride in 6 mL of methanol, 99 mg of sodium cyanoborohydride and 0.40 g of molecular sieves 3 A were added, and the mixture was stirred at room temperature for 15 minutes. Thereto was added 68 mg of phenylpropargyl aldehyde, and the mixture was stirred at room temperature for 1 hour 30 minutes. Thereto was added 68 mg of phenylpropargyl aldehyde, and the mixture was stirred at room temperature for 2 hours. Thereto was added 68 mg of phenylpropargyl aldehyde, and the mixture was stirred at room temperature for 1 hour 30 minutes. A saturated aqueous sodium hydrogen carbonate solution and chloroform were added thereto, and the insoluble substance was filtered off. The organic layer was separated, washed sequentially with water and a saturated aqueous sodium chloride solution, and dried over anhydrous magnesium sulfate, and the solvent was distilled off under reduced pressure. The resultant residue was purified by basic silica gel column chromatography using an eluent of chloroform:methanol=50:1 to obtain 0.11 g of 1-(2-(4-(bis(3-phenyl-2-propynyl)amino)piperidin-1-yl)ethyl)-1,7-naphthyridin-2(1H)-one as a light yellow oily substance.

$^1$H-NMR (CDCl$_3$) δ: 1.59-1.72 (2H, m), 1.99-2.07 (2H, m), 2.18-2.26 (2H, m), 2.66-2.75 (3H, m), 3.06-3.14 (2H, m), 3.84 (4H, s), 4.45-4.52 (2H, m), 6.89 (1H, d, J=9.5 Hz), 7.27-7.46 (11H, m), 7.65 (1H, d, J=9.8 Hz), 8.44 (1H, d, J=5.1 Hz), 8.91 (1H, s)

Example 27

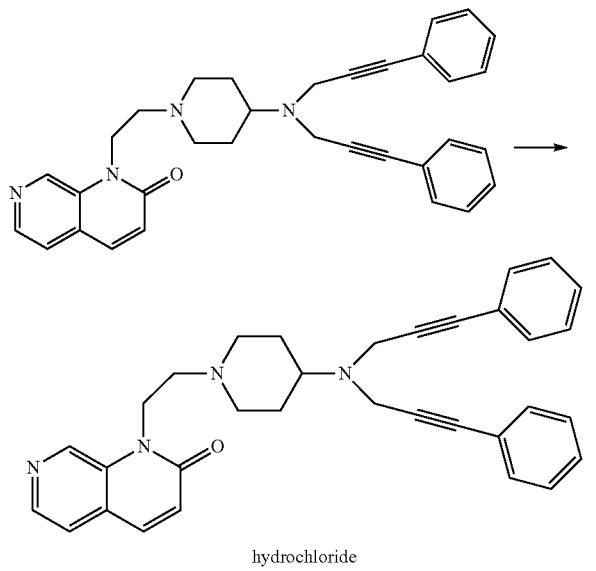

By the same technique as in Example 8, 1-(2-(4-(bis(3-phenyl-2-propynyl)amino)piperidin-1-yl)ethyl)-1,7-naphthyridin-2(1H)-one hydrochloride was obtained from 1-(2-(4-(bis(3-phenyl-2-propynyl)amino)piperidin-1-yl)ethyl)-1,7-naphthyridin-2(1H)-one.

$^1$H-NMR (DMSO-d$_6$) δ: 2.10-2.25 (2H, m), 2.38-2.50 (2H, m), 3.18-3.30 (2H, m), 3.38-3.92 (5H, m), 4.32-4.42 (4H, m), 4.71-4.79 (2H, m), 7.04 (1H, d, J=9.5 Hz), 7.34-7.54 (10H, m), 7.98 (1H, d, J=5.4 Hz), 8.11 (1H, d, J=9.5 Hz), 8.58 (1H, d, J=5.4 Hz), 9.31 (1H, s)

Example 28

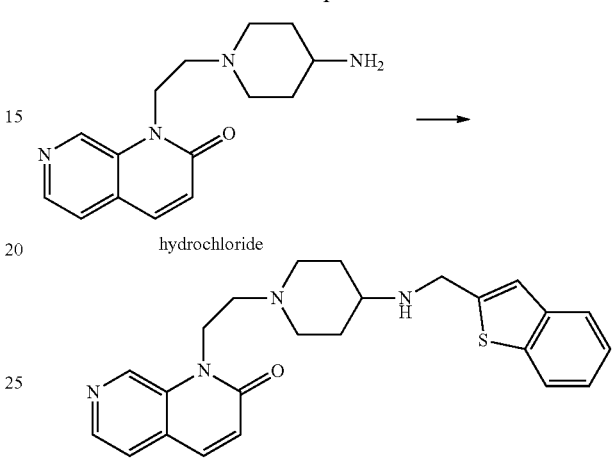

By the same technique as in Example 7, 1-(2-(4-((1-benzothiophen-2-ylmethyl)amino)piperidin-1-yl)ethyl)-1,7-naphthyridin-2(1H)-one was obtained from 1-(2-(4-aminopiperidin-1-yl)ethyl)-1,7-naphthyridin-2(1H)-one hydrochloride and 1-benzothiophene-2-carbaldehyde.

$^1$H-NMR (CDCl$_3$) δ: 1.39-1.50 (2H, m), 1.89-1.97 (2H, m), 2.15-2.24 (2H, m), 2.57-2.66 (1H, m), 2.68-2.73 (2H, m), 2.97-3.04 (2H, m), 4.11 (2H, d, J=0.8 Hz), 4.44-4.50 (2H, m), 6.89 (1H, d, J=9.5 Hz), 7.14 (1H, s), 7.27-7.34 (2H, m), 7.42 (1H, d, J=5.1 Hz), 7.65 (1H, d, J=9.5 Hz), 7.67-7.72 (1H, m), 7.79 (1H, d, J=7.6 Hz), 8.44 (1H, d, J=5.1 Hz), 8.90 (1H, s)

Example 29

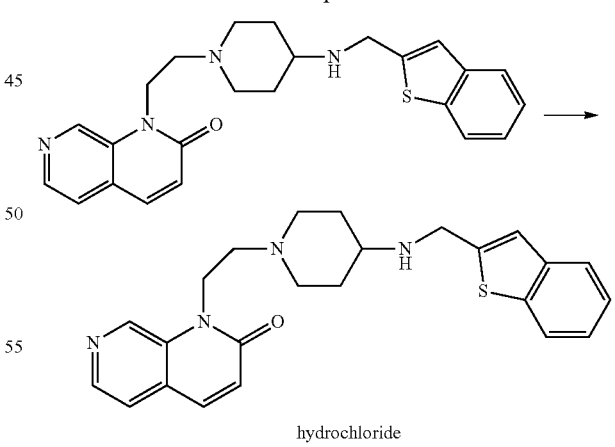

By the same technique as in Example 8, 1-(2-(4-((1-benzothiophen-2-ylmethyl)amino)piperidin-1-yl)ethyl)-1,7-naphthyridin-2(1H)-one hydrochloride was obtained from 1-(2-(4-((1-benzothiophen-2-ylmethyl)amino)piperidin-1-yl)ethyl)-1,7-naphthyridin-2(1H)-one.

$^1$H-NMR (DMSO-d$_6$) δ: 2.02-2.16 (2H, m), 2.38-2.46 (2H, m), 3.11-3.22 (2H, m), 3.35-3.46 (3H, m), 3.79-3.88 (2H, m), 4.58 (2H, s), 4.69-4.78 (2H, m), 7.06 (1H, d, J=9.6 Hz), 7.40-7.46 (2H, m), 7.72 (1H, s), 7.88-7.94 (1H, m), 8.00-8.05 (2H, m), 8.13 (1H, d, J=9.6 Hz), 8.59 (1H, d, J=5.4 Hz), 9.31 (1H, s)

Example 30

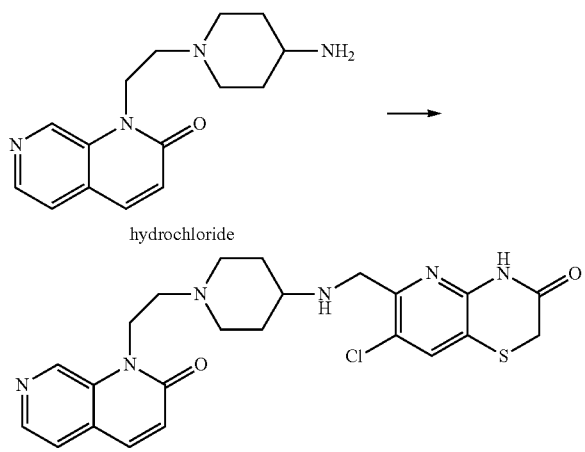

To a suspension of 0.10 g of 1-(2-(4-aminopiperidin-1-yl)ethyl)-1,7-naphthyridin-2(1H)-one hydrochloride in 3 mL of methanol, 0.15 mL of a 28% sodium methoxide/methanol solution and 15 μL of acetic acid were added. Thereto were added 51 mg of 7-chloro-3-oxo-3,4-dihydro-2H-pyrido(3,2-b)(1,4)thiazine-6-carbaldehyde and 0.20 g of molecular sieves 3 A, and the mixture was stirred at room temperature for 30 minutes. Thereto was added 33 mg of sodium cyanoborohydride, and the mixture was stirred at room temperature for 1 hour 30 minutes. Thereto was added 51 mg of 7-chloro-3-oxo-3,4-dihydro-2H-pyrido(3,2-b)(1,4)thiazine-6-carbaldehyde, and the mixture was stirred at room temperature for 2 hours. The insoluble substance was filtered off, and chloroform and a saturated aqueous sodium hydrogen carbonate solution were added thereto. The organic layer was separated, and washed sequentially with water and a saturated aqueous sodium chloride solution. The organic layer was dried over anhydrous magnesium sulfate, and the solvent was distilled off under reduced pressure. The resultant residue was purified by basic silica gel column chromatography using an eluent of chloroform:methanol=10:1 to obtain 97 mg of 7-chloro-6-(((1-(2-(2-oxo-1,7-naphthyridin-1(2H)-yl)ethyl)piperidin-4-yl)amino)methyl)-2H-pyrido(3,2-b)(1,4)thiazin-3(4H)-one as a white solid.

$^1$H-NMR (CDCl$_3$) δ: 1.43-1.60 (2H, m), 1.88-1.96 (2H, m), 2.18-2.26 (2H, m), 2.50-2.58 (1H, m), 2.69-2.76 (2H, m), 2.97-3.05 (2H, m), 3.48 (2H, s), 3.95 (2H, s), 4.44-4.50 (2H, m), 6.90 (1H, d, J=9.5 Hz), 7.42 (1H, d, J=4.9 Hz), 7.60 (1H, s), 7.65 (1H, d, J=9.5 Hz), 8.17 (1H, s), 8.45 (1H, d, J=4.9 Hz), 8.92 (1H, s)

Example 31

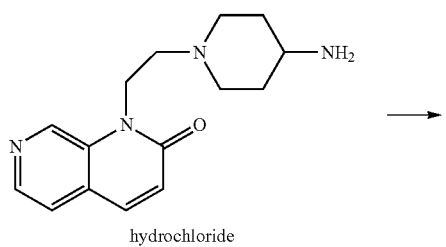

-continued

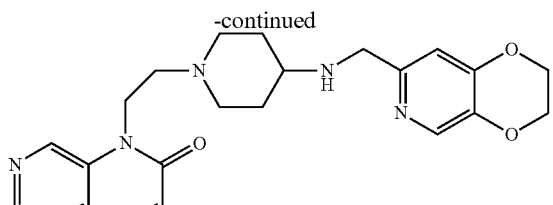

By the same technique as in Example 30, 1-(2-(4-((2,3-dihydro(1,4)dioxino(2,3-c)pyridin-7-ylmethyl)amino)piperidin-1-yl)ethyl)-1,7-naphthyridin-2(1H)-one was obtained from 1-(2-(4-aminopiperidin-1-yl)ethyl)-1,7-naphthyridin-2(1H)-one hydrochloride and 2,3-dihydro(1,4)dioxino(2,3-c)pyridine-7-carbaldehyde.

$^1$H-NMR (CDCl$_3$) δ: 1.40-1.52 (2H, m), 1.87-1.95 (2H, m), 2.16-2.25 (2H, m), 2.49-2.57 (1H, m), 2.67-2.74 (2H, m), 2.97-3.04 (2H, m), 3.80 (2H, s), 4.26-4.36 (4H, m), 4.44-4.51 (2H, m), 6.83 (1H, s), 6.89 (1H, d, J=9.5 Hz), 7.42 (1H, d, J=5.1 Hz), 7.65 (1H, d, J=9.5 Hz), 8.11 (1H, s), 8.45 (1H, d, J=5.1 Hz), 8.91 (1H, s)

Example 32

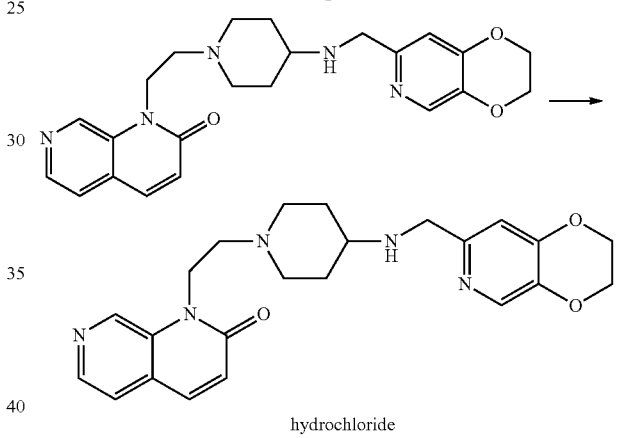

By the same technique as in Example 8, 1-(2-(4-((2,3-dihydro(1,4)dioxino(2,3-c)pyridin-7-ylmethyl)amino)piperidin-1-yl)ethyl)-1,7-naphthyridin-2(1H)-one hydrochloride was obtained from 1-(2-(4-((2,3-dihydro(1,4)dioxino(2,3-c)pyridin-7-ylmethyl)amino)piperidin-1-yl)ethyl)-1,7-naphthyridin-2(1H)-one.

$^1$H-NMR (D$_2$O) δ: 1.98-2.11 (2H, m), 2.49-2.57 (2H, m), 3.23-3.33 (2H, m), 3.62-3.72 (3H, m), 3.96-4.05 (2H, m), 4.38 (2H, s), 4.39-4.44 (2H, m), 4.46-4.51 (2H, m), 4.80-4.86 (2H, m), 7.19 (1H, d, J=9.5 Hz), 7.22 (1H, s), 8.15 (1H, d, J=5.7 Hz), 8.17 (1H, d, J=9.5 Hz), 8.23 (1H, s), 8.60 (1H, d, J=5.7 Hz), 9.10 (1H, s)

Example 33

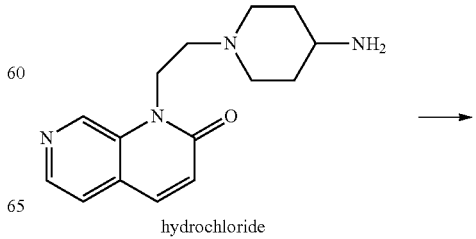

-continued

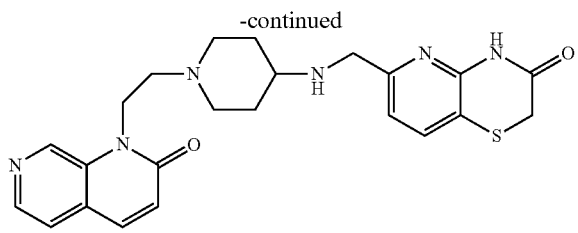

By the same technique as in Example 30, 6-(((1-(2-(2-oxo-1,7-naphthyridin-1(2H)-yl)ethyl)piperidin-4-yl)amino)methyl)-2H-pyrido(3,2-b)(1,4)thiazin-3(4H)-one was obtained from 1-(2-(4-aminopiperidin-1-yl)ethyl)-1,7-naphthyridin-2(1H)-one hydrochloride and 3-oxo-3,4-dihydro-2H-pyrido(3,2-b)(1,4)thiazine-6-carbaldehyde.

$^1$H-NMR (CDCl$_3$) δ: 1.39-1.51 (2H, m), 1.86-1.95 (2H, m), 2.16-2.25 (2H, m), 2.47-2.57 (1H, m), 2.68-2.74 (2H, m), 2.97-3.04 (2H, m), 3.48 (2H, s), 3.83 (2H, s), 4.44-4.50 (2H, m), 6.89 (1H, d, J=9.4 Hz), 6.98 (1H, d, J=7.8 Hz), 7.42 (1H, d, J=5.1 Hz), 7.57 (1H, d, J=7.8 Hz), 7.65 (1H, d, J=9.4 Hz), 8.02-8.10 (1H, broad), 8.45 (1H, d, J=5.1 Hz), 8.91 (1H, s)

Example 34

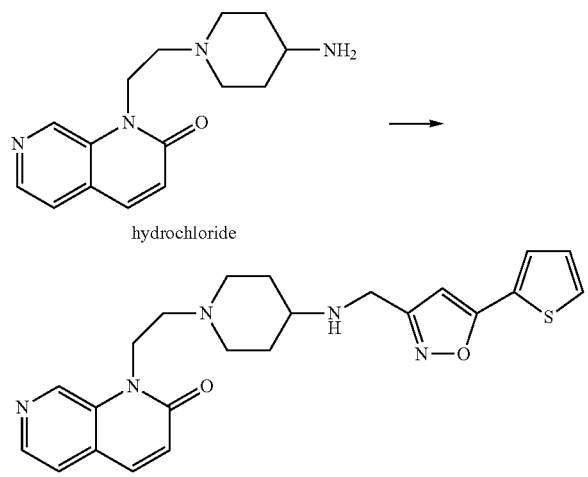

By the same technique as in Example 30, 1-(2-(4-(((5-(2-thienyl)isoxazol-3-yl)methyl)amino)piperidin-1-yl)ethyl)-1,7-naphthyridin-2(1H)-one was obtained from 1-(2-(4-aminopiperidin-1-yl)ethyl)-1,7-naphthyridin-2(1H)-one hydrochloride and 5-(2-thienyl)isoxazole-3-carbaldehyde.

$^1$H-NMR (CDCl$_3$) δ: 1.38-1.49 (2H, m), 1.88-1.96 (2H, m), 2.17-2.26 (2H, m), 2.52-2.62 (1H, m), 2.68-2.74 (2H, m), 2.97-3.04 (2H, m), 3.91 (2H, s), 4.44-4.50 (2H, m), 6.40 (1H, s), 6.89 (1H, d, J=9.5 Hz), 7.12 (1H, dd, J=5.1, 3.7 Hz), 7.40-7.46 (2H, m), 7.50 (1H, dd, J=3.7, 1.0 Hz), 7.65 (1H, d, J=9.5 Hz), 8.44 (1H, d, J=5.1 Hz), 8.90 (1H, s)

Example 35

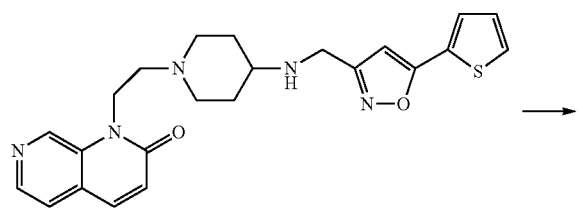

-continued

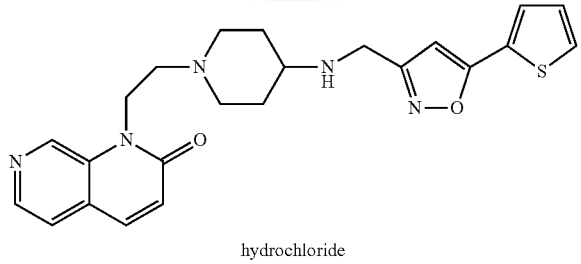

hydrochloride

By the same technique as in Example 8, 1-(2-(4-(((5-(2-thienyl)isoxazol-3-yl)methyl)amino)piperidin-1-yl)ethyl)-1,7-naphthyridin-2(1H)-one hydrochloride was obtained from 1-(2-(4-(((5-(2-thienyl)isoxazol-3-yl)methyl)amino)piperidin-1-yl)ethyl)-1,7-naphthyridin-2(1H)-one.

$^1$H-NMR (DMSO-d$_6$) δ: 2.05-2.18 (2H, m), 2.36-2.46 (2H, m), 3.10-3.22 (2H, m), 3.35-3.40 (3H, m), 3.60-3.88 (2H, m), 4.38-4.46 (2H, m), 4.70-4.79 (2H, m), 7.02 (1H, d, J=9.5 Hz), 7.15 (1H, s), 7.28 (1H, dd, J=5.1, 3.7 Hz), 7.74 (1H, d, J=3.7 Hz), 7.89 (1H, d, J=5.1 Hz), 7.94 (1H, d, J=5.1 Hz), 8.10 (1H, d, J=9.5 Hz), 8.56 (1H, d, J=5.1 Hz), 9.27 (1H, s), 10.20-10.40 (2H, broad), 10.73-10.90 (1H, broad)

Example 36

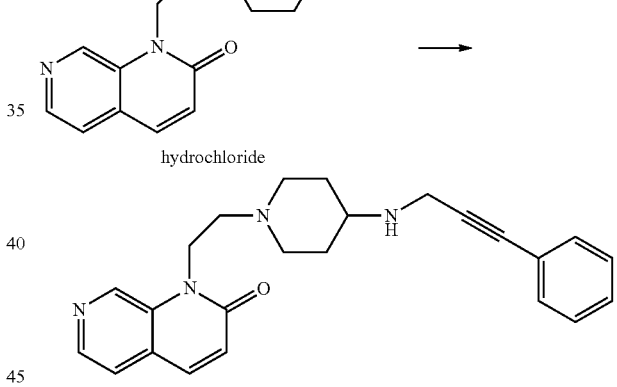

hydrochloride

By the same technique as in Example 30, 1-(2-(4-((3-phenyl-2-propynyl)amino)piperidin-1-yl)ethyl)-1,7-naphthyridin-2(1H)-one was obtained from 1-(2-(4-aminopiperidin-1-yl)ethyl)-1,7-naphthyridin-2(1H)-one hydrochloride and phenylpropargyl aldehyde.

$^1$H-NMR (CDCl$_3$) δ: 1.40-1.52 (2H, m), 1.88-1.96 (2H, m), 2.22-2.33 (2H, m), 2.70-2.85 (3H, m), 2.99-3.07 (2H, m), 3.68 (2H, s), 4.46-4.52 (2H, m), 6.89 (1H, d, J=9.5 Hz), 7.28-7.32 (3H, m), 7.38-7.44 (3H, m), 7.65 (1H, d, J=9.5 Hz), 8.44 (1H, d, J=5.1 Hz), 8.92 (1H, s)

Example 37

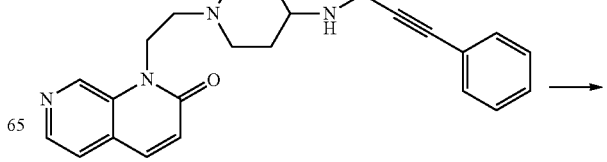

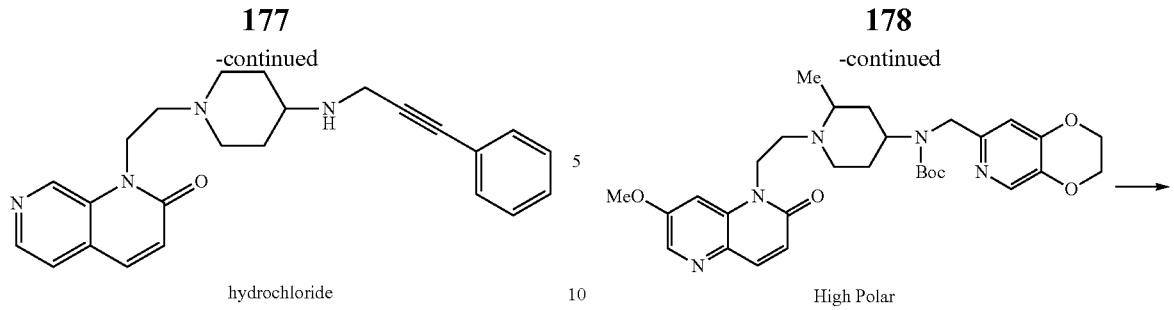

By the same technique as in Example 8, 1-(2-(4-((3-phenyl-2-propynyl)amino)piperidin-1-yl)ethyl)-1,7-naphthyridin-2(1H)-one hydrochloride was obtained from 1-(2-(4-((3-phenyl-2-propynyl)amino)piperidin-1-yl)ethyl)-1,7-naphthyridin-2(1H)-one.

$^1$H-NMR (DMSO-d$_6$) δ: 2.00-2.13 (2H, m), 2.32-2.41 (2H, m), 3.14-3.26 (2H, m), 3.35-3.75 (3H, m), 3.80-3.86 (2H, m), 4.20-4.28 (2H, m), 4.70-4.78 (2H, m), 7.01 (1H, d, J=9.5 Hz), 7.42-7.48 (3H, m), 7.51-7.56 (2H, m), 7.92 (1H, d, J=5.4 Hz), 8.09 (1H, d, J=9.5 Hz), 8.56 (1H, d, J=5.1 Hz), 9.26 (1H, s), 9.99-10.08 (2H, m), 10.70-10.82 (1H, m)

Example 38

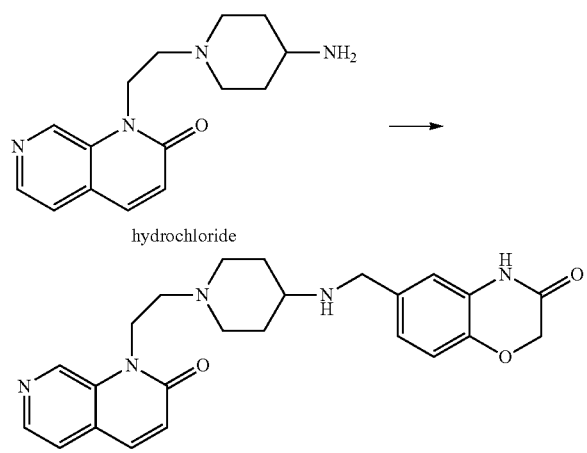

By the same technique as in Example 30, 6-(((1-(2-(2-oxo-1,7-naphthyridin-1(2H)-yl)ethyl)piperidin-4-yl)amino)methyl)-2H-1,4-benzoxazin-3(4H)-one was obtained from 1-(2-(4-aminopiperidin-1-yl)ethyl)-1,7-naphthyridin-2(1H)-one hydrochloride and 3-oxo-3,4-dihydro-2H-1,4-benzoxazine-6-carbaldehyde.

$^1$H-NMR (DMSO-d$_6$) δ: 1.13-1.25 (2H, m), 1.70-1.79 (2H, m), 1.97-2.06 (2H, m), 2.28-2.37 (1H, m), 2.46-2.57 (2H, m), 2.84-2.92 (2H, m), 3.59 (2H, s), 4.35-4.42 (2H, m), 4.50 (2H, s), 6.81-6.90 (4H, m), 7.67 (1H, d, J=5.0 Hz), 7.94 (1H, d, J=9.5 Hz), 8.40 (1H, d, J=5.0 Hz), 8.92 (1H, s), 10.61 (1H, s)

Example 39

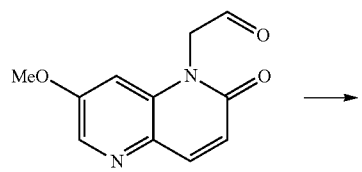

(1) By the same technique as in Example 1, tert-butyl (2,3-dihydro(1,4)dioxino(2,3-c)pyridin-7-ylmethyl)(1-(2-(7-methoxy-2-oxo-1,5-naphthyridin-1(2H)-yl)ethyl)-2-methylpiperidin-4-yl)carbamate was obtained from (7-methoxy-2-oxo-1,5-naphthyridin-1(2H)-yl)acetaldehyde and tert-butyl (2,3-dihydro(1,4)dioxino(2,3-c)pyridin-7-ylmethyl)(2-methylpiperidin-4-yl)carbamate.

(2) By the same technique as in Example 54, 1-(2-(4-((2,3-dihydro(1,4)dioxino(2,3-c)pyridin-7-ylmethyl)amino)-2-methylpiperidin-1-yl)ethyl)-7-methoxy-1,5-naphthyridin-2(1H)-one was obtained from tert-butyl (2,3-dihydro(1,4)dioxino(2,3-c)pyridin-7-ylmethyl)(1-(2-(7-methoxy-2-oxo-1,5-naphthyridin-1(2H)-yl)ethyl)-2-methylpiperidin-4-yl)carbamate.

$^1$H-NMR (CDCl$_3$) δ: 1.11 (3H, d, J=6.1 Hz), 1.22-1.44 (2H, m), 1.84-1.98 (2H, m), 2.28-2.44 (1H, m), 2.56-2.61 (2H, m), 2.68-2.90 (1H, m), 2.97-3.07 (1H, m), 3.08-3.16 (1H, m), 3.79 (2H, s), 3.97 (3H, s), 4.16-4.20 (1H, m), 4.34-4.38 (4H, m), 4.55-4.59 (1H, m), 6.74 (1H, d, J=9.6 Hz), 6.81 (1H, s), 7.24 (1H, d, J=2.3 Hz), 7.84 (1H, d, J=9.6 Hz), 8.10 (1H, s), 8.27 (1H, d, J=2.3 Hz)

Example 40

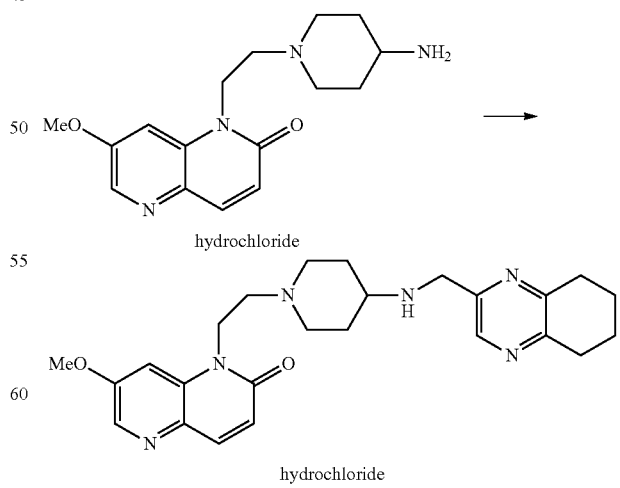

To a solution of 0.13 g of 1-(2-(4-aminopiperidin-1-yl)ethyl)-7-methoxy-1,5-naphthyridin-2(1H)-one hydrochloride in 2.6 mL of N,N-dimethylformamide, 75 mg of 5,6,7, 8-tetrahydroquinoxaline-2-carbaldehyde, 0.26 mL of acetic acid, 0.21 mL of triethylamine and 98 mg of sodium triacetoxyborohydride were added, and the mixture was stirred at room temperature for 9 hours 40 minutes. Thereto were added water, a saturated aqueous sodium hydrogen carbonate solution, and ethyl acetate, and the reaction mixture was adjusted to pH 11.5 with a 20% aqueous sodium hydroxide solution, the organic layer was then separated, and the aqueous layer was extracted with ethyl acetate. The organic layer and the extract were combined, the resultant solution was washed with a saturated aqueous sodium chloride solution and dried over anhydrous magnesium sulfate, and the solvent was distilled off under reduced pressure. The resultant residue was purified by basic silica gel column chromatography using an eluent of chloroform:methanol=10:1, and thereto were added ethyl acetate and a 4 mol/L hydrogen chloride/ethyl acetate solution. The solvent was distilled off under reduced pressure, diethyl ether was added thereto, and the solid was filtered off to obtain 92 mg of 7-methoxy-1-(2-(4-((5,6,7,8-tetrahydroquinoxalin-2-ylmethyl)amino)piperidin-1-yl)ethyl)-1,5-naphthyridin-2(1H)-one hydrochloride as a light brown solid.

$^1$H-NMR (D$_2$O) δ: 1.87-1.95 (4H, m), 2.01-2.14 (2H, m), 2.51-2.60 (2H, m), 2.92-3.00 (4H, m), 3.19-3.34 (2H, m), 3.59-3.78 (3H, m), 3.97-4.06 (2H, m), 4.04 (3H, s), 4.47 (2H, s), 4.76-4.79 (2H, m), 6.88 (1H, d, J=9.8 Hz), 7.47 (1H, d, J=2.1 Hz), 8.06 (1H, d, J=9.8 Hz), 8.39 (1H, s), 8.41 (1H, d, J=2.1 Hz)

Example 41

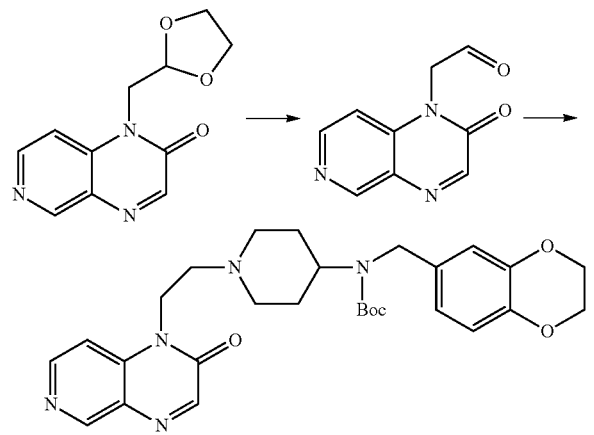

(1) To 95 mg of 1-(1,3-dioxolan-2-ylmethyl)pyrido(3,4-b)pyrazin-2(1H)-one, 4.0 mL of an 80% aqueous trifluoroacetic acid solution was added, and the mixture was stirred at room temperature for 2 hours, and then left overnight. Thereto was added 4.0 mL of an 80% aqueous trifluoroacetic acid solution, and the mixture was stirred at 50 to 70° C. for 6 hours. The reaction mixture was cooled to room temperature, and the solvent was distilled off under reduced pressure. The resultant residue was charged with chloroform and water and adjusted to pH 7.0 with a 1 mol/L aqueous sodium hydroxide solution. The organic layer was separated, and the aqueous layer was extracted with chloroform. The organic layer and the extract were combined, the resultant solution was dried over anhydrous magnesium sulfate, and the solvent was distilled off under reduced pressure to obtain 40 mg of (2-oxopyrido(3,4-b)pyrazin-1(2H)-yl)acetaldehyde as a light brown oily substance.

(2) To a suspension of 40 mg of (2-oxopyrido(3,4-b)pyrazin-1(2H)-yl)acetaldehyde in 2 mL of dichloromethane, a solution of 74 mg of tert-butyl (2,3-dihydro-1,4-benzodioxin-6-ylmethyl)(piperidin-4-yl)carbamate in 2 mL of dichloromethane, and 12 μL of acetic acid were added, and the mixture was stirred at room temperature for 10 minutes. Thereto was added 67 mg of sodium triacetoxyborohydride, and the mixture was stirred at room temperature for 30 minutes. To the reaction mixture, chloroform and a saturated aqueous sodium hydrogen carbonate solution were added, the organic layer was separated, and the aqueous layer was extracted with chloroform. The organic layer and the extract were combined, the resultant solution was washed with a saturated aqueous sodium chloride solution and dried over anhydrous magnesium sulfate, and the solvent was distilled off under reduced pressure. The resultant residue was purified by flash silica gel column chromatography using gradient elution with chloroform:methanol=100:0 to 90:10 to obtain 80 mg of tert-butyl (2,3-dihydro-1,4-benzodioxin-6-ylmethyl(1-(2-(2-oxopyrido(3,4-b)pyrazin-1(2H)-yl)ethyl)piperidin-4-yl)carbamate as a light brown oily substance.

$^1$H-NMR (CDCl$_3$) δ: 1.42 (9H, s), 1.54-1.72 (4H, m), 2.05-2.23 (2H, m), 2.59-2.66 (2H, m), 2.91-3.00 (2H, m), 3.95-4.14 (1H, m), 4.20-4.30 (8H, m), 6.64-6.70 (1H, m), 6.73 (1H, d, J=2.0 Hz), 6.78 (1H, d, J=8.3 Hz), 7.23 (1H, d, J=5.9 Hz), 8.30 (1H, s), 8.61 (1H, d, J=5.9 Hz), 9.08 (1H, s)

Example 42

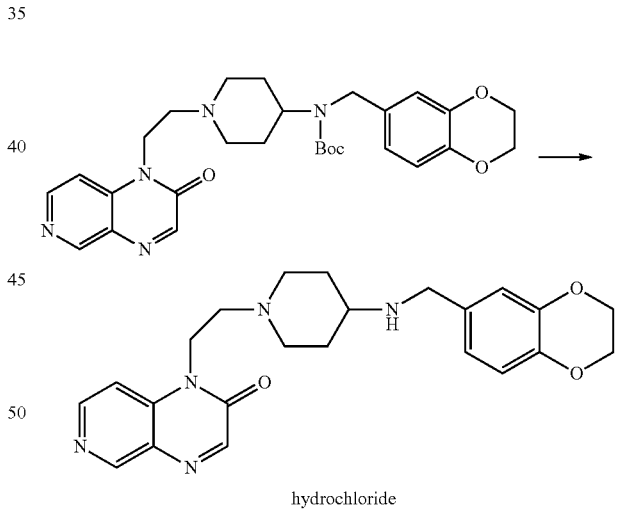

By the same technique as in Example 2, 1-(2-(4-((2,3-dihydro-1,4-benzodioxin-6-ylmethyl)amino)piperidin-1-yl)ethyl)pyrido(3,4-b)pyrazin-2(1H)-one hydrochloride was obtained from tert-butyl (2,3-dihydro-1,4-benzodioxin-6-ylmethyl)(1-(2-(2-oxopyrido(3,4-b)pyrazin-1(2H)-yl)ethyl)piperidin-4-yl)carbamate.

$^1$H-NMR (D$_2$O) δ: 1.83-1.98 (2H, m), 2.34-2.45 (2H, m), 3.09-3.21 (2H, m), 3.40-3.56 (3H, m), 3.82-3.90 (2H, m), 4.10 (2H, s), 4.21 (4H, s), 4.50-4.80 (2H, m), 6.85-6.92 (3H, m), 7.86 (1H, d, J=6.8 Hz), 8.40 (1H, s), 8.69 (1H, d, J=6.8 Hz), 9.16 (1H, s)

Example 43

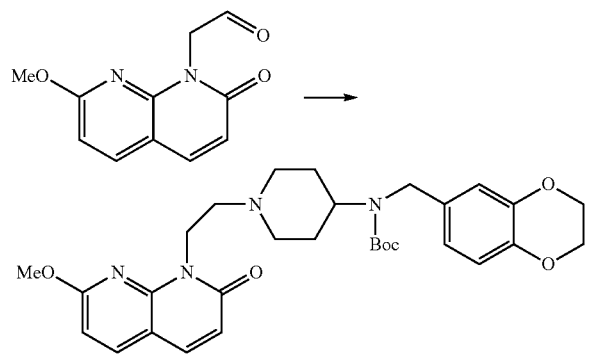

To a solution of 0.20 g of (7-methoxy-2-oxo-1,8-naphthyridin-1(2H)-yl)acetaldehyde in 20 mL of dichloromethane, 0.32 g of tert-butyl (2,3-dihydro-1,4-benzodioxin-6-ylmethyl)(piperidin-4-yl)carbamate and 53 μL of acetic acid were added, and the mixture was stirred at room temperature for 15 minutes. To the reaction mixture, 0.29 g of sodium triacetoxyborohydride was added, and the mixture was stirred at room temperature for 1 hour 40 minutes. Thereto were added water, a saturated aqueous sodium hydrogen carbonate solution was added, and chloroform, the organic layer was separated, and the aqueous layer was extracted with chloroform. The organic layer and the extract were combined, the resultant solution was washed with a saturated aqueous sodium chloride solution and dried over anhydrous magnesium sulfate, and the solvent was distilled off under reduced pressure. The resultant residue was purified by silica gel column chromatography using an eluent of chloroform:methanol=50:1 to obtain 0.50 g of tert-butyl (2,3-dihydro-1,4-benzodioxin-6-ylmethyl(1-(2-(7-methoxy-2-oxo-1,8-naphthyridin-1(2H)-yl)ethyl)piperidin-4-yl)carbamate as a white foam.

$^1$H-NMR (CDCl$_3$) δ: 1.41 (9H, s), 1.59-1.72 (4H, m), 2.09-2.25 (2H, m), 2.64-2.72 (2H, m), 3.07-3.14 (2H, m), 3.99 (3H, s), 4.00-4.15 (1H, m), 4.20-4.34 (6H, m), 4.57-4.63 (2H, m), 6.56 (1H, d, J=9.4 Hz), 6.60 (1H, d, J=8.3 Hz), 6.64-6.69 (1H, m), 6.71-6.73 (1H, m), 6.77 (1H, d, J=8.3 Hz), 7.55 (1H, d, J=9.4 Hz), 7.71 (1H, d, J=8.3 Hz)

Example 44

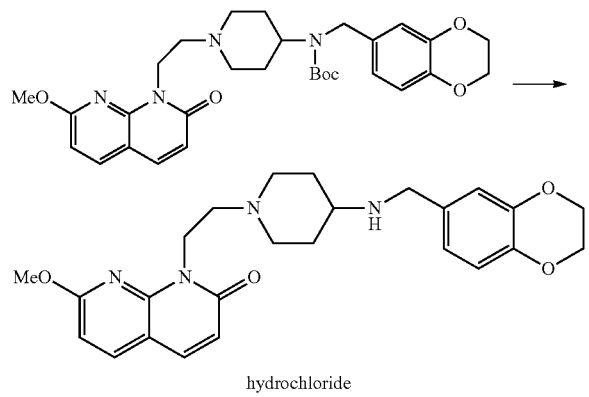

To 0.50 g of tert-butyl (2,3-dihydro-1,4-benzodioxin-6-ylmethyl(1-(2-(7-methoxy-2-oxo-1,8-naphthyridin-1(2H)-yl)ethyl)piperidin-4-yl)carbamate, 15 mL of a 4 mol/L hydrogen chloride/ethyl acetate solution was added, and the mixture was stirred at room temperature for 43 hours. The solvent was distilled off under reduced pressure, methanol was added to the resultant residue, and the solvent was distilled off under reduced pressure. Then, ethyl acetate was added to the resultant residue, and the solid was filtered off to obtain 0.41 g of 1-(2-(4-((2,3-dihydro-1,4-benzodioxin-6-ylmethyl)amino)piperidin-1-yl)ethyl)-7-methoxy-1,8-naphthyridin-2(1H)-one hydrochloride as a light yellow solid.

$^1$H-NMR (D$_2$O) δ: 1.92-2.08 (2H, m), 2.45-2.58 (2H, m), 3.16-3.31 (2H, m), 3.56-3.72 (3H, m), 3.96-4.10 (2H, m), 4.05 (3H, s), 4.17-4.28 (2H, m), 4.33 (4H, s), 4.82-4.98 (2H, m), 6.64 (1H, d, J=9.3 Hz), 6.85 (1H, d, J=8.4 Hz), 6.95-7.06 (3H, m), 7.96 (1H, d, J=9.3 Hz), 8.04 (1H, d, J=8.4 Hz)

Example 45

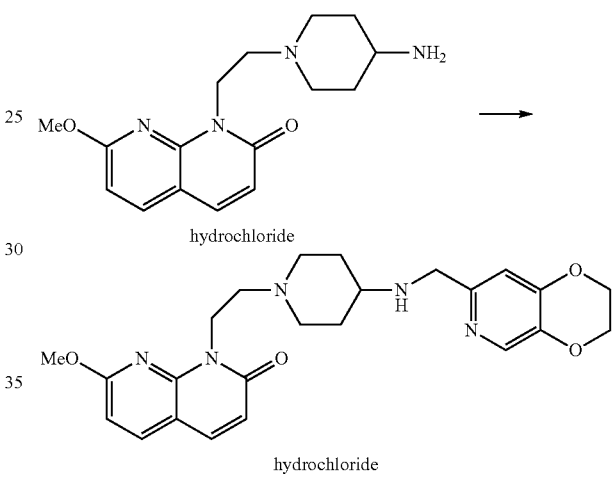

To a solution of 0.20 g of 1-(2-(4-(aminopiperidin-1-yl)ethyl)-7-methoxy-1,8-naphthyridin-2(1H)-one hydrochloride in 4 mL of methanol, 0.21 g of 28% sodium methoxide, 88 mg of 2,3-dihydro(1,4)dioxino(2,3-c)pyridine-7-carbaldehyde, 30 μL of acetic acid and 67 mg of sodium cyanoborohydride were added, and the mixture was stirred at room temperature for 6 hours 45 minutes. Thereto were added 27 mg of 2,3-dihydro(1,4)dioxino(2,3-c)pyridine-7-carbaldehyde and 9 μL of acetic acid, and the mixture was stirred for 1 hour 30 minutes. After leaving overnight, the mixture was stirred at room temperature for 2 hours, 27 mg of 2,3-dihydro(1,4)dioxino(2,3-c)pyridine-7-carbaldehyde and 9 μL of acetic acid were added, and the mixture was stirred for 2 hours 30 minutes. To the reaction mixture, water, a 1 mol/L aqueous sodium hydroxide solution and chloroform were added, the organic layer was separated, and the aqueous layer was extracted with chloroform. The organic layer and the extract were combined, the resultant solution was dried over anhydrous magnesium sulfate, and the solvent was distilled off under reduced pressure. The resultant residue was purified by silica gel column chromatography using an eluent of chloroform:methanol=5:1, the oily substance thus obtained was dissolved in a 4 mol/L hydrogen chloride/ethyl acetate solution and methanol, and the solvent was then distilled off under reduced pressure. Ethyl acetate was added to the resultant residue, and the solid was filtered off to obtain 0.18 g of 1-(2-(4-((2,3-dihydro(1,4)dioxino(2,3-c)pyridin-7-ylmethyl)amino)piperidin-1-yl)ethyl)-7-methoxy-1,8-naphthyridin-2(1H)-one hydrochloride as a white solid.

$^1$H-NMR (D$_2$O) δ: 2.00-2.13 (2H, m), 2.52-2.62 (2H, m), 3.21-3.33 (2H, m), 3.64-3.83 (3H, m), 3.98-4.15 (5H, m), 4.49-4.54 (2H, m), 4.59 (2H, s), 4.64-4.68 (2H, m), 4.89-4.94 (2H, m), 6.65 (1H, d, J=9.5 Hz), 6.86 (1H, d, J=8.6 Hz), 7.56 (1H, s), 7.97 (1H, d, J=9.5 Hz), 8.05 (1H, d, J=8.6 Hz), 8.43 (1H, s)

Example 46

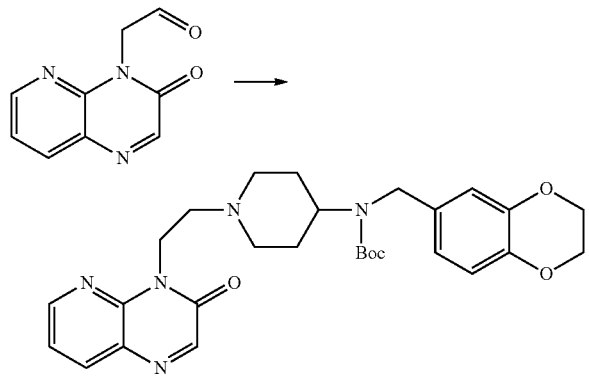

To 0.13 g of (3-oxopyrido(2,3-b)pyrazin-4(3H)-yl)acetaldehyde, a solution of 0.23 g of tert-butyl (2,3-dihydro-1,4-benzodioxin-6-ylmethyl)(piperidin-4-yl)carbamate in 4 mL of dichloromethane, 38 μL of acetic acid and 0.21 g of sodium triacetoxyborohydride were added, and the mixture was stirred at room temperature for 3 hours. Chloroform and a saturated aqueous sodium hydrogen carbonate solution were added to the reaction mixture, the organic layer was separated, and the aqueous layer was extracted with chloroform. The organic layer and the extract were combined, the resultant solution was washed with a saturated aqueous sodium chloride solution and dried over anhydrous magnesium sulfate, and the solvent was distilled off under reduced pressure. The resultant residue was purified by flash silica gel column chromatography using gradient elution with chloroform:methanol=100:0 to 90:10 to obtain 0.24 g of tert-butyl (2,3-dihydro-1,4-benzodioxin-6-ylmethyl)(1-(2-(3-oxopyrido(2,3-b)pyrazin-4(3H)-yl)ethyl)piperidin-4-yl)carbamate as a light brown oily substance.

$^1$H-NMR (CDCl$_3$) δ: 1.41 (9H, s), 1.50-1.66 (4H, m), 1.98-2.20 (2H, m), 2.64-2.72 (2H, m), 3.01-3.10 (2H, m), 3.95-4.14 (1H, m), 4.18-4.30 (6H, m), 4.54-4.61 (2H, m), 6.63-6.68 (1H, m), 6.69-6.72 (1H, m), 6.77 (1H, d, J=8.3 Hz), 7.31 (1H, dd, J=8.0, 4.6 Hz), 8.16 (1H, dd, J=8.0, 1.6 Hz), 8.31 (1H, s), 8.56 (1H, dd, J=4.6, 1.6 Hz)

Example 47

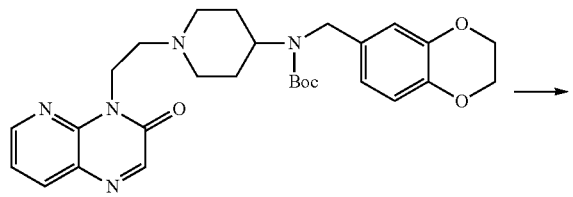

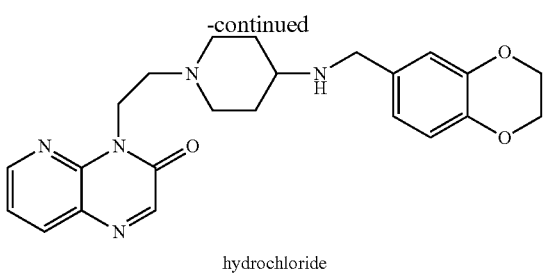

hydrochloride

By the same technique as in Example 2, 4-(2-(4-((2,3-dihydro-1,4-benzodioxin-6-ylmethyl)amino)piperidin-1-yl)ethyl)pyrido(2,3-b)pyrazin-3(4H)-one hydrochloride was obtained from tert-butyl (2,3-dihydro-1,4-benzodioxin-6-ylmethyl)(1-(2-(3-oxopyrido(2,3-b)pyrazin-4(3H)-yl)ethyl)piperidin-4-yl)carbamate.

$^1$H-NMR (D$_2$O) δ: 1.90-2.05 (2H, m), 2.45-2.55 (2H, m), 3.16-3.32 (2H, m), 3.55-3.71 (3H, m), 3.96-4.07 (2H, m), 4.21 (2H, s), 4.33 (4H, s), 4.88-4.93 (2H, m), 6.95-7.04 (3H, m), 7.58 (1H, dd, J=8.0, 4.8 Hz), 8.35 (1H, dd, J=8.0, 1.5 Hz), 8.39 (1H, s), 8.71 (1H, dd, J=4.8, 1.5 Hz)

Example 48

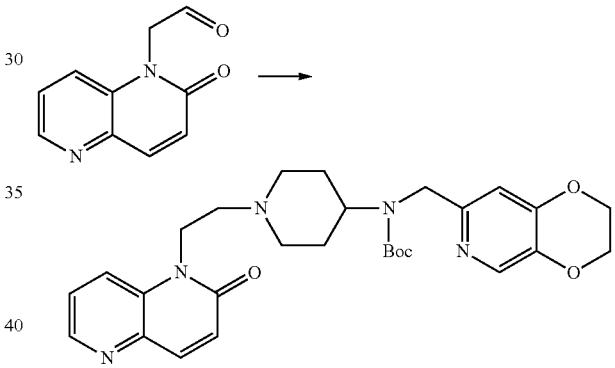

By the same technique as in Example 1, tert-butyl (2,3-dihydro(1,4)dioxino(2,3-c)pyridin-7-ylmethyl)(1-(2-(2-oxo-1,5-naphthyridin-1(2H)-yl)ethyl)piperidin-4-yl)carbamate was obtained from (2-oxo-1,5-naphthyridin-1(2H)-yl)acetaldehyde and tert-butyl (2,3-dihydro(1,4)dioxino(2,3-c)pyridin-7-ylmethyl)(piperidin-4-yl)carbamate.

$^1$H-NMR (CDCl$_3$-D$_2$O) δ: 1.34-1.52 (9H, m), 1.60-1.70 (4H, m), 2.08-2.22 (2H, m), 2.58-2.63 (2H, m), 2.95-3.04 (2H, m), 4.00-4.20 (1H, m), 4.24-4.40 (8H, m), 6.74 (1H, s), 6.91 (1H, d, J=9.8 Hz), 7.46 (1H, dd, J=8.6, 4.5 Hz), 7.76 (1H, d, J=8.6 Hz), 7.91 (1H, d, J=9.8 Hz), 8.05 (1H, s), 8.53-8.56 (1H, m)

Example 49

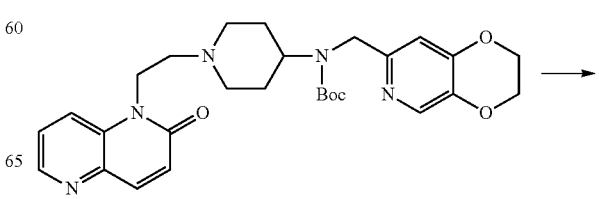

185

-continued

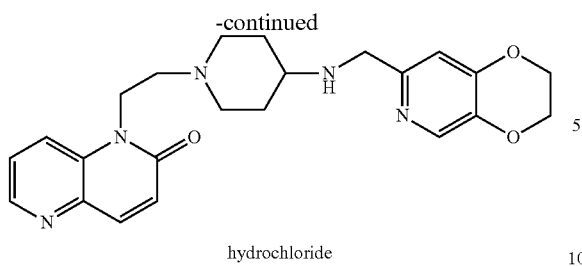

hydrochloride

By the same technique as in Example 2, 1-(2-(4-((2,3-dihydro(1,4)dioxino(2,3-c)pyridin-7-ylmethyl)amino)piperidin-1-yl)ethyl)-1,5-naphthyridin-2(1H)-one hydrochloride was obtained from tert-butyl (2,3-dihydro(1,4)dioxino(2,3-c)pyridin-7-ylmethyl)(1-(2-(2-oxo-1,5-naphthyridin-1(2H)-yl)ethyl)piperidin-4-yl)carbamate.

$^1$H-NMR (DMSO-d$_6$-D$_2$O) δ: 2.02-2.18 (2H, m), 2.36-2.48 (2H, m), 3.12-3.24 (2H, m), 3.30-3.50 (3H, m), 3.72-3.88 (2H, m), 4.36-4.46 (4H, m), 4.53 (2H, s), 4.65-4.73 (2H, m), 7.00 (1H, d, J=9.8 Hz), 7.62 (1H, s), 7.76 (1H, dd, J=8.6, 4.6 Hz), 8.08 (1H, d, J=9.8 Hz), 8.42 (1H, d, J=8.6 Hz), 8.50 (1H, s), 8.65 (1H, d, J=4.6 Hz)

Example 50

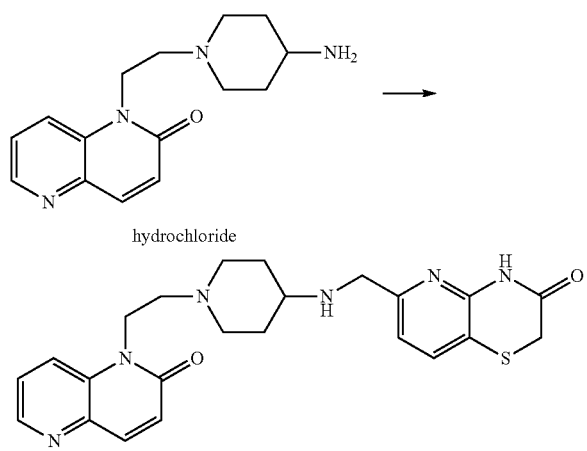

By the same technique as in Example 30, 6-(((1-(2-(2-oxo-1,5-naphthyridin-1(2H)-yl)ethyl)piperidin-4-yl)amino)methyl)-2H-pyrido(3,2-b)(1,4)thiazin-3(4H)-one was obtained from 1-(2-(4-aminopiperidin-1-yl)ethyl)-1,5-naphthyridin-2(1H)-one hydrochloride and 3-oxo-3,4-dihydro-2H-pyrido(3,2-b)(1,4)thiazine-6-carbaldehyde.

$^1$H-NMR (CDCl$_3$-D$_2$O) δ: 1.36-1.50 (2H, m), 1.82-1.92 (2H, m), 2.12-2.20 (2H, m), 2.44-2.54 (1H, m), 2.60-2.64 (2H, m), 2.90-3.00 (2H, m), 3.44 (2H, s), 3.79 (2H, s), 4.34-4.39 (2H, m), 6.89 (1H, d, J=9.6 Hz), 6.94 (1H, d, J=7.8 Hz), 7.44 (1H, dd, J=8.5, 4.4 Hz), 7.54 (1H, d, J=7.8 Hz), 7.78 (1H, d, J=8.5 Hz), 7.89 (1H, d, J=9.6 Hz), 8.52 (1H, d, J=4.4 Hz)

Example 51

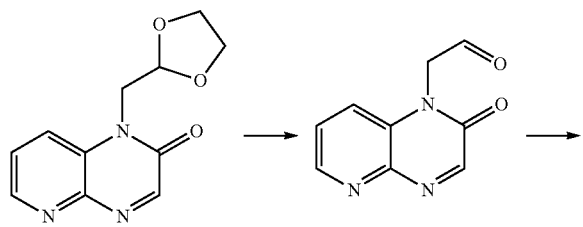

186

-continued

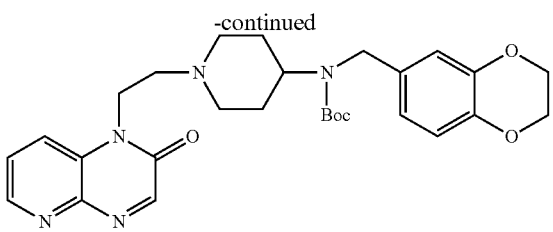

By the same technique as in Example 41, (2-oxopyrido(2,3-b)pyrazin-1(2H)-yl)acetaldehyde was obtained from 1-(1,3-dioxolan-2-ylmethyl)pyrido(2,3-b)pyrazin-2(1H)-one. Tert-butyl (2,3-dihydro-1,4-benzodioxin-6-ylmethyl)(1-(2-(2-oxopyrido(2,3-b)pyrazin-1(2H)-yl)ethyl)piperidin-4-yl)carbamate was obtained from (2-oxopyrido(2,3-b)pyrazin-1(2H)-yl)acetaldehyde and tert-butyl(2,3-dihydro-1,4-benzodioxin-6-ylmethyl)(piperidin-4-yl)carbamate.

$^1$H-NMR (CDCl$_3$) δ: 1.42 (9H, s), 1.53-1.72 (4H, m), 2.02-2.23 (2H, m), 2.49-2.66 (2H, m), 2.90-3.00 (2H, m), 3.94-4.13 (1H, m), 4.20-4.35 (8H, m), 6.64-6.80 (3H, m), 7.50 (1H, dd, J=8.6, 4.5 Hz), 7.77 (1H, dd, J=8.6, 1.3 Hz), 8.53 (1H, s), 8.66 (1H, dd, J=4.5, 1.3 Hz)

Example 52

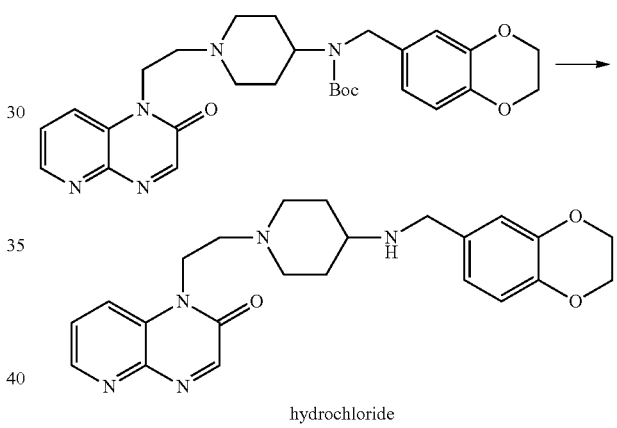

hydrochloride

By the same technique as in Example 2, 1-(2-(4-((2,3-dihydro-1,4-benzodioxin-6-ylmethyl)amino)piperidin-1-yl)ethyl)pyrido(2,3-b)pyrazin-2(1H)-one hydrochloride was obtained from tert-butyl (2,3-dihydro-1,4-benzodioxin-6-ylmethyl)(1-(2-(2-oxopyrido(2,3-b)pyrazin-1(2H)-yl)ethyl)piperidin-4-yl)carbamate.

$^1$H-NMR (DMSO-d$_6$) δ: 1.94-2.12 (2H, m), 2.27-2.40 (2H, m), 3.00-3.86 (7H, m), 4.02-4.13 (2H, m), 4.25 (4H, s), 4.60-4.69 (2H, m), 6.91 (1H, d, J=8.3 Hz), 7.00-7.07 (1H, m), 7.15 (1H, s), 7.66-7.79 (1H, m), 8.32-8.38 (1H, m), 8.50 (1H, s), 8.63 (1H, d, J=4.4 Hz), 9.40-9.60 (2H, broad), 10.65-10.85 (1H, broad)

Example 53

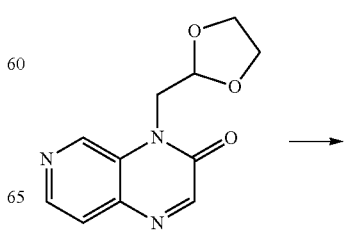

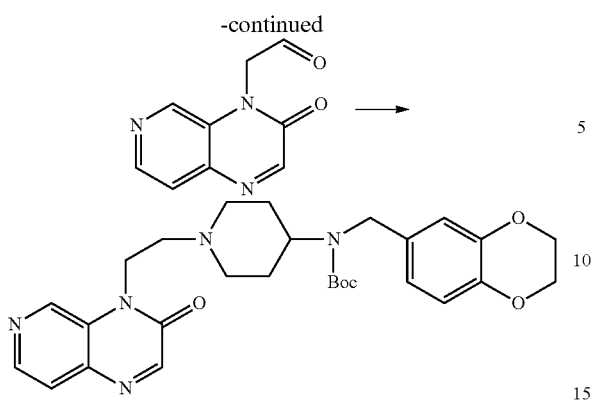

By the same technique as in Example 41, (3-oxopyrido(3,4-b)pyrazin-4(3H)-yl)acetaldehyde was obtained from 4-(1,3-dioxolan-2-ylmethyl)pyrido(3,4-b)pyrazin-3(4H)-one. Tert-butyl (2,3-dihydro-1,4-benzodioxin-6-ylmethyl)(1-(2-(3-oxopyrido(3,4-b)pyrazin-4(3H)-yl)ethyl)piperidin-4-yl)carbamate was obtained from (3-oxopyrido(3,4-b)pyrazin-4(3H)-yl)acetaldehyde and tert-butyl (2,3-dihydro-1,4-benzodioxin-6-ylmethyl)(piperidin-4-yl)carbamate.

$^1$H-NMR (CDCl$_3$) δ: 1.41 (9H, s), 1.53-1.69 (4H, m), 2.06-2.26 (2H, m), 2.65-2.72 (2H, m), 2.93-3.02 (2H, m), 3.96-4.12 (1H, m), 4.12-4.34 (6H, m), 4.34-4.40 (2H, m), 6.63-6.80 (3H, m), 7.74 (1H, d, J=5.1 Hz), 8.45 (1H, s), 8.58 (1H, d, J=5.1 Hz), 8.87 (1H, s)

Example 54

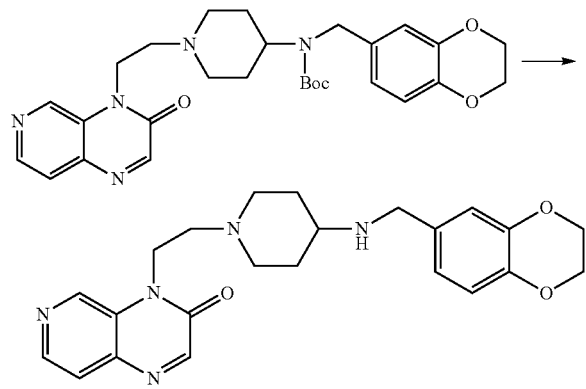

To a solution of 10 mg of tert-butyl (2,3-dihydro-1,4-benzodioxin-6-ylmethyl)(1-(2-(3-oxopyrido(3,4-b)pyrazin-4(3H)-yl)ethyl)piperidin-4-yl)carbamate in 1 mL of dichloromethane, 1.0 mL of trifluoroacetic acid was added at room temperature. The mixture was stirred at the same temperature for 4 hours, and the solvent was distilled off under reduced pressure. The resultant residue was charged with chloroform and water and adjusted to pH 0.5 with 1 mol/L hydrochloric acid, and the aqueous layer was separated. Chloroform was added to the aqueous layer, and the aqueous layer was adjusted to pH 12 with a 1 mol/L aqueous sodium hydroxide solution. The organic layer was separated, and the aqueous layer was extracted with chloroform. The organic layer and the extract were combined, the resultant solution was washed with a saturated aqueous sodium chloride solution and dried over anhydrous magnesium sulfate, and the solvent was distilled off under reduced pressure to obtain 2 mg of 4-(2-(4-(((2,3-dihydro-1,4-benzodioxin-6-ylmethyl)amino)piperidin-1-yl)ethyl)pyrido(3,4-b)pyrazin-3(4H)-one as a light brown oily substance.

$^1$H-NMR (CDCl$_3$) δ: 1.35-1.48 (2H, m), 1.83-1.95 (2H, m), 2.13-2.23 (2H, m), 2.50-2.65 (1H, m), 2.69-2.75 (2H, m), 2.91-3.00 (2H, m), 3.71 (2H, s), 4.24 (4H, s), 4.37-4.44 (2H, m), 6.76-6.86 (3H, m), 7.74 (1H, d, J=5.1 Hz), 8.45 (1H, s), 8.58 (1H, d, J=5.1 Hz), 8.90 (1H, s)

Example 55

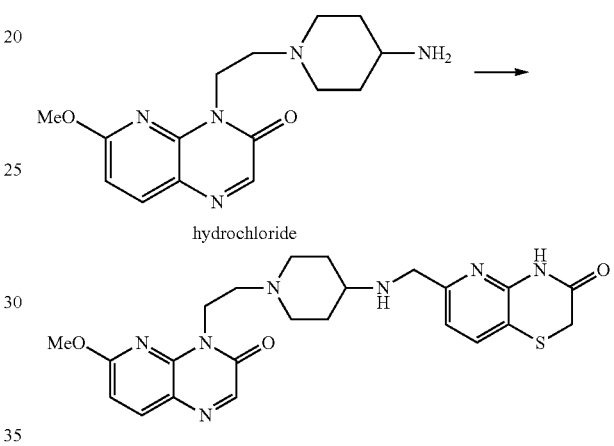

To a suspension of 0.21 g of 4-(2-(4-aminopiperidin-1-yl)ethyl)-6-methoxypyrido(2,3-b)pyrazin-3(4H)-one hydrochloride in 5 mL of methanol, 0.22 g of a 28% sodium methoxide/methanol solution, 0.11 g of 3-oxo-3,4-dihydro-2H-pyrido(3,2-b)(1,4)thiazine-6-carbaldehyde, 32 μL of acetic acid and 70 mg of sodium cyanoborohydride were added, and the mixture was stirred at room temperature for 3 hours. Chloroform and a saturated aqueous sodium hydrogen carbonate solution were added to the reaction mixture, the organic layer was separated, and the aqueous layer was extracted with chloroform. The organic layer and the extract were combined, the resultant solution was washed with a saturated aqueous sodium chloride solution and dried over anhydrous magnesium sulfate, and the solvent was distilled off under reduced pressure. The resultant residue was purified by basic silica gel column chromatography using an eluent of chloroform:methanol=10:1. Diethyl ether and hexane were added to the resultant residue, and the solid was filtered off to obtain 0.13 g of 6-(((1-(2-(6-methoxy-3-oxopyrido(2,3-b)pyrazin-4(3H)-yl)ethyl)piperidin-4-yl)amino)methyl)-2H-pyrido(3,2-b)(1,4)thiazin-3(4H)-one as a light brown solid.

$^1$H-NMR (CDCl$_3$) δ: 1.34-1.47 (2H, m), 1.82-1.93 (2H, m), 2.12-2.22 (2H, m), 2.46-2.56 (1H, m), 2.71-2.78 (2H, m), 3.00-3.08 (2H, m), 3.46 (2H, s), 3.83 (2H, s), 4.03 (3H, s), 4.54-4.61 (2H, m), 6.72 (1H, d, J=8.7 Hz), 6.97 (1H, d, J=7.8 Hz), 7.56 (1H, d, J=7.8 Hz), 8.01 (1H, d, J=8.7 Hz), 8.14 (1H, s), 8.60-8.80 (1H, broad)

Example 56

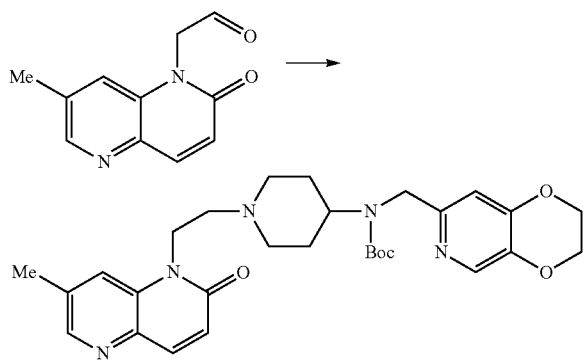

By the same technique as in Example 1, tert-butyl (2,3-dihydro(1,4)dioxino(2,3-c)pyridin-7-ylmethyl)(1-(2-(7-methyl-2-oxo-1,5-naphthyridin-1(2H)-yl)ethyl)piperidin-4-yl)carbamate was obtained from (7-methyl-2-oxo-1,5-naphthyridin-1(2H)-yl)acetaldehyde and tert-butyl (2,3-dihydro(1,4)dioxino(2,3-c)pyridin-7-ylmethyl)(piperidin-4-yl)carbamate.

$^1$H-NMR (CDCl$_3$) δ: 1.39 (9H, s), 1.40-1.72 (4H, m), 2.08-2.25 (2H, m), 2.49 (3H, s), 2.56-2.63 (2H, m), 2.97-3.06 (2H, m), 4.02-4.20 (1H, m), 4.24-4.48 (8H, m), 6.73 (1H, s), 6.83 (1H, d, J=9.6 Hz), 7.50-7.54 (1H, m), 7.86 (1H, d, J=9.6 Hz), 8.05 (1H, s), 8.36-8.39 (1H, m)

Example 57

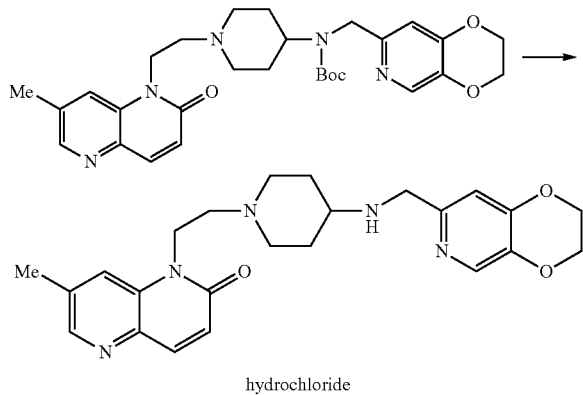

hydrochloride

By the same technique as in Example 2, 1-(2-(4-((2,3-dihydro(1,4)dioxino(2,3-c)pyridin-7-ylmethyl)amino)piperidin-1-yl)ethyl)-7-methyl-1,5-naphthyridin-2(1H)-one hydrochloride was obtained from tert-butyl (2,3-dihydro(1,4)dioxino(2,3-c)pyridin-7-ylmethyl)(1-(2-(7-methyl-2-oxo-1,5-naphthyridin-1(2H)-yl)ethyl)piperidin-4-yl)carbamate.

$^1$H-NMR (D$_2$O) δ: 2.02-2.16 (2H, m), 2.51-2.63 (2H, m), 2.65 (3H, s), 3.25-3.37 (2H, m), 3.63-3.69 (2H, m), 3.71-3.82 (1H, m), 3.99-4.08 (2H, m), 4.46-4.51 (2H, m), 4.54 (2H, s), 4.59-4.63 (2H, m), 4.76-4.86 (2H, m), 7.17 (1H, d, J=9.9 Hz), 7.48 (1H, s), 8.18 (1H, d, J=9.9 Hz), 8.38 (1H, s), 8.40 (1H, s), 8.64 (1H, m)

Example 58

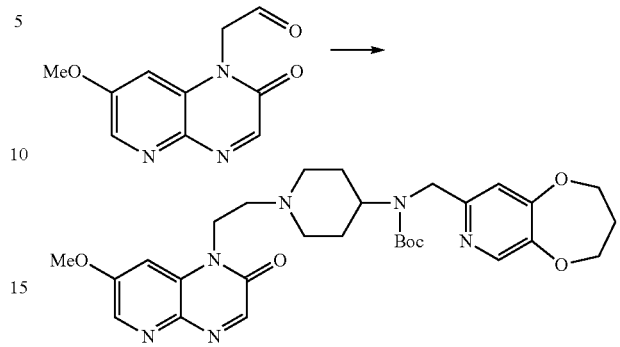

By the same technique as in Example 1, tert-butyl (3,4-dihydro-2H-(1,4)dioxepino(2,3-c)pyridin-8-ylmethyl)(1-(2-(7-methoxy-2-oxopyrido(2,3-b)pyrazin-1(2H)-yl)ethyl)piperidin-4-yl)carbamate was obtained from (7-methoxy-2-oxopyrido(2,3-b)pyrazin-1(2H)-yl)acetaldehyde and tert-butyl (3,4-dihydro-2H-(1,4)dioxepino(2,3-c)pyridin-8-ylmethyl)(piperidin-4-yl)carbamate.

$^1$H-NMR (CDCl$_3$) δ: 1.29-1.72 (4H, m), 1.37 (9H, s), 2.06-2.28 (4H, m), 2.58-2.66 (2H, m), 2.91-3.01 (2H, m), 3.99 (3H, s), 4.06-4.16 (1H, m), 4.20-4.38 (8H, m), 6.77 (1H, s), 7.15-7.21 (1H, m), 8.13 (1H, s), 8.33 (1H, s), 8.36 (1H, d, J=2.7 Hz)

Example 59

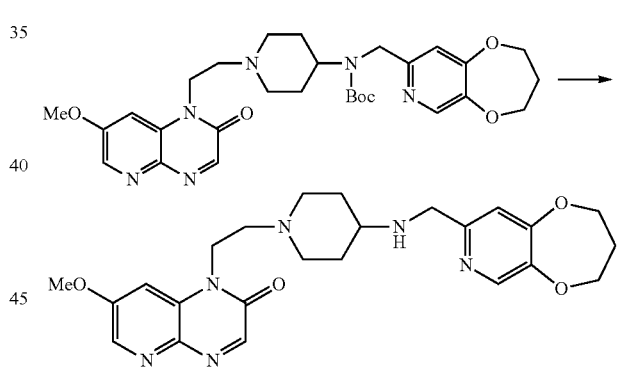

To a solution of 87 mg of tert-butyl (3,4-dihydro-2H-(1,4)dioxepino(2,3-c)pyridin-8-ylmethyl)(1-(2-(7-methoxy-2-oxopyrido(2,3-b)pyrazin-1(2H)-yl)ethyl)piperidin-4-yl)carbamate in 2 mL of dichloromethane, 2 mL of trifluoroacetic acid was added, and the mixture was stirred at room temperature for 1 hour. The solvent was distilled off under reduced pressure, and chloroform and water were added thereto. The aqueous layer was separated and adjusted to pH 13.1 with a 20% aqueous sodium hydroxide solution. Chloroform was added thereto, the organic layer was separated, and the aqueous layer was extracted with chloroform. The organic layer and the extract were combined, the resultant solution was washed sequentially with water and a saturated aqueous sodium chloride solution and dried over anhydrous magnesium sulfate, and the solvent was distilled off under reduced pressure to obtain 54 mg of 1-(2-(4-((3,4-dihydro-2H-(1,4)dioxepino(2,3-c)pyridin-8-ylmethyl)amino)piperidin-1-yl)ethyl)-7-methoxypyrido(2,3-b)pyrazin-2(1H)-one as a yellowish brown oily substance.

¹H-NMR (CDCl₃) δ: 1.36-1.48 (2H, m), 1.86-1.95 (2H, m), 2.13-2.28 (2H, m), 2.25 (2H, quint, J=5.8 Hz), 2.48-2.59 (1H, m), 2.64-2.70 (2H, m), 2.91-2.98 (2H, m), 3.80 (2H, s), 4.00 (3H, s), 4.24 (2H, t, J=5.8 Hz), 4.28-4.36 (2H, m), 4.33 (2H, t, J=5.8 Hz), 6.85 (1H, s), 7.24-7.28 (1H, m), 8.18 (1H, s), 8.34 (1H, s), 8.36 (1H, d, J=2.7 Hz)

Example 60

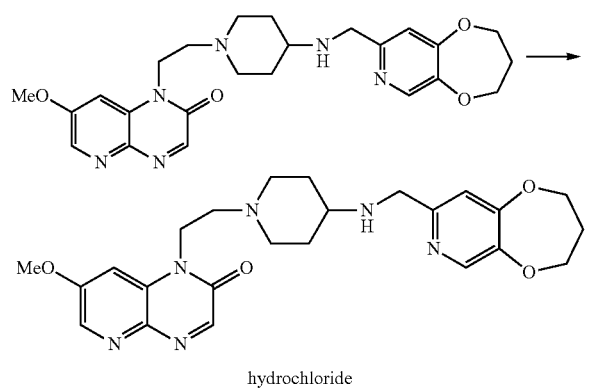

hydrochloride

By the same technique as in Example 8, 1-(2-(4-((3,4-dihydro-2H-(1,4)dioxepino(2,3-c)pyridin-8-ylmethyl)amino)piperidin-1-yl)ethyl)-7-methoxypyrido(2,3-b)pyrazin-2(1H)-one hydrochloride was obtained from 1-(2-(4-((3,4-dihydro-2H-(1,4)dioxepino(2,3-c)pyridin-8-ylmethyl)amino)piperidin-1-yl)ethyl)-7-methoxypyrido(2,3-b)pyrazin-2(1H)-one.

¹H-NMR (D₂O) δ: 1.97-2.10 (2H, m), 2.31 (2H, quint, J=5.7 Hz), 2.49-2.57 (2H, m), 3.21-3.31 (2H, m), 3.61-3.71 (3H, m), 3.95-4.04 (2H, m), 4.05 (3H, s), 4.36 (2H, t, J=5.9 Hz), 4.37 (2H, s), 4.48 (2H, t, J=5.9 Hz), 4.73-4.87 (2H, m), 7.20 (1H, s), 7.49 (1H, d, J=2.6 Hz), 8.28 (1H, s), 8.34 (1H, s), 8.42 (1H, d, J=2.6 Hz)

Example 61

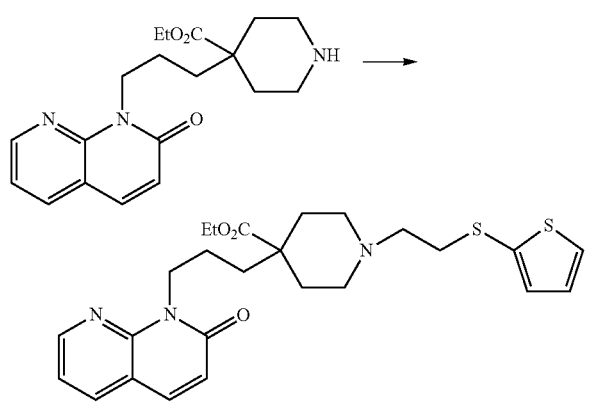

To a solution of 0.46 g of ethyl 4-(3-(2-oxo-1,8-naphthyridin-1(2H)-yl)propyl)piperidine-4-carboxylate in 10 mL of N,N-dimethylformamide, 0.37 g of potassium carbonate and 0.31 g of 2-((2-bromoethyl)thio)thiophene were added, and the mixture was stirred at 50 to 70° C. for 2 hours 10 minutes. The reaction mixture was cooled to room temperature, then, water and ethyl acetate were added thereto, the organic layer was separated, and the aqueous layer was extracted with ethyl acetate. The organic layer and the extract were combined, the resultant solution was dried over anhydrous magnesium sulfate, and the solvent was distilled off under reduced pressure. The resultant residue was purified by silica gel column chromatography using an eluent of chloroform:methanol=50:1 to obtain 0.39 g of ethyl 4-(3-(2-oxo-1,8-naphthyridin-1(2H)-yl)propyl)-1-(2-(2-thienylthio)ethyl)piperidine-4-carboxylate as a yellow oily substance.

¹H-NMR (CDCl₃) δ: 1.20 (3H, t, J=7.1 Hz), 1.42-1.52 (2H, m), 1.60-1.69 (4H, m), 2.00-2.14 (4H, m), 2.52-2.58 (2H, m), 2.64-2.71 (2H, m), 2.85-2.91 (2H, m), 4.10 (2H, q, J=7.1 Hz), 4.42-4.47 (2H, m), 6.71 (1H, d, J=9.4 Hz), 6.93-6.97 (1H, m), 7.08-7.10 (1H, m), 7.15 (1H, dd, J=7.6, 4.6 Hz), 7.30-7.33 (1H, m), 7.61 (1H, d, J=9.4 Hz), 7.84 (1H, dd, J=7.6, 1.7 Hz), 8.55 (1H, dd, J=4.6, 1.7 Hz)

Example 62

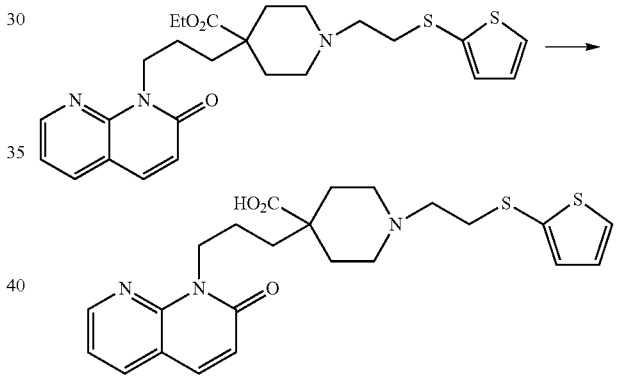

To a solution of 0.30 g of ethyl 4-(3-(2-oxo-1,8-naphthyridin-1(2H)-yl)propyl)-1-(2-(2-thienylthio)ethyl)piperidine-4-carboxylate in 5 mL of ethanol, 1.7 mL of a 20% aqueous sodium hydroxide solution was added at room temperature, and the mixture was heated under reflux while stirring for 7 hours. Thereto was further added 0.3 mL of a 20% aqueous sodium hydroxide solution, and mixture was stirred for 1 hour, and then cooled to room temperature, and the solvent was distilled off under reduced pressure. The resultant residue was charged with water and adjusted to pH 6.5 with 1 mol/L hydrochloric acid. The solid was filtered off to obtain 0.22 g of 4-(3-(2-oxo-1,8-naphthyridin-1(2H)-yl) propyl)-1-(2-(2-thienylthio)ethyl)piperidine-4-carboxylic acid as a white solid.

¹H-NMR (DMSO-d₆) δ: 1.24-1.34 (2H, m), 1.45-1.59 (4H, m), 1.86-1.98 (4H, m), 2.42-2.47 (2H, m), 2.55-2.62 (2H, m), 2.87-2.92 (2H, m), 4.30-4.35 (2H, m), 6.69 (1H, d, J=9.5 Hz), 7.03 (1H, dd, J=5.1, 3.6 Hz), 7.15-7.17 (1H, m), 7.32 (1H, dd, J=7.6, 4.8 Hz), 7.59 (1H, d, J=5.1 Hz), 7.95 (1H, d, J=9.5 Hz), 8.16-8.20 (1H, m), 8.63-8.66 (1H, m)

Example 63

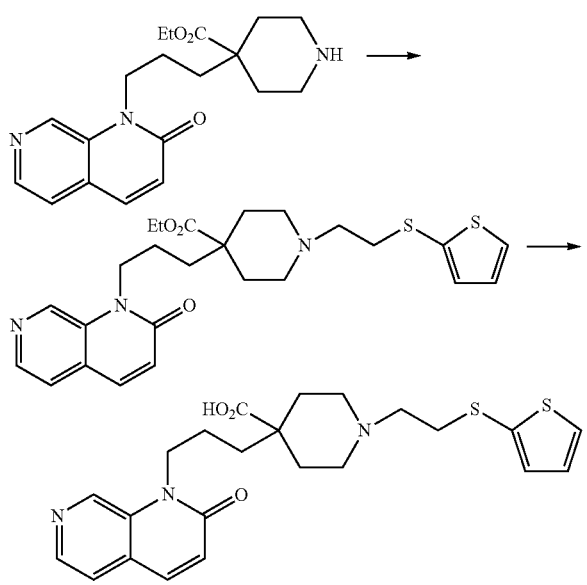

By the same technique as in Example 61, ethyl 4-(3-(2-oxo-1,7-naphthyridin-1(2H)-yl)propyl)-1-(2-(2-thienylthio)ethyl)piperidine-4-carboxylate was obtained from ethyl 4-(3-(2-oxo-1,7-naphthyridin-1(2H)-yl)propyl)piperidine-4-carboxylate and 2-(2-bromoethylthio)thiophene.

$^1$H-NMR (CDCl$_3$) δ: 1.21 (3H, t, J=7.2 Hz), 1.40-1.80 (6H, m), 2.00-2.18 (4H, m), 2.50-2.60 (2H, m), 2.62-2.74 (2H, m), 2.84-2.92 (2H, m), 4.12 (2H, q, J=7.2 Hz), 4.24-4.31 (2H, m), 6.88 (1H, d, J=9.5 Hz), 6.95 (1H, dd, J=5.3, 3.6 Hz), 7.10 (1H, dd, J=3.6, 1.2 Hz), 7.32 (1H, dd, J=5.3, 1.2 Hz), 7.42 (1H, d, J=5.0 Hz), 7.64 (1H, d, J=9.5 Hz), 8.44 (1H, d, J=5.0 Hz), 8.74 (1H, s)

By the same technique as in Example 62, 4-(3-(2-oxo-1,7-naphthyridin-1(2H)-yl)propyl)-1-(2-(2-thienylthio)ethyl)piperidine-4-carboxylic acid was obtained from ethyl 4-(3-(2-oxo-1,7-naphthyridin-1(2H)-yl)propyl)-1-(2-(2-thienylthio)ethyl)piperidine-4-carboxylate.

$^1$H-NMR (DMSO-d$_6$) δ: 1.22-1.36 (2H, m), 1.48-1.60 (4H, m), 1.86-2.02 (4H, m), 2.40-2.63 (4H, m), 2.86-2.93 (2H, m), 4.22-4.28 (2H, m), 6.85 (1H, d, J=9.5 Hz), 7.03 (1H, dd, J=5.4, 3.5 Hz), 7.16 (1H, dd, J=3.5, 1.1 Hz), 7.58 (1H, dd, J=5.4, 1.1 Hz), 7.69 (1H, d, J=5.0 Hz), 7.95 (1H, d, J=9.5 Hz), 8.42 (1H, d, J=5.0 Hz), 8.93 (1H, s)

Example 64

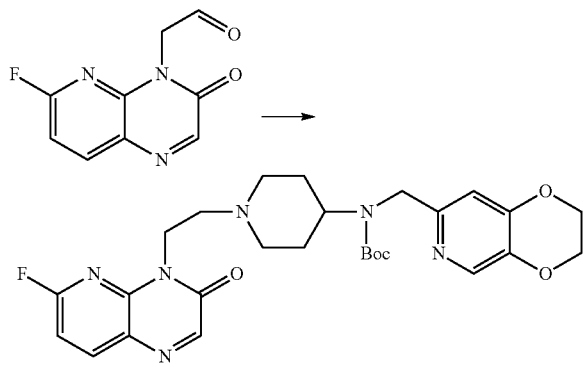

By the same technique as in Example 1, tert-butyl (2,3-dihydro(1,4)dioxino(2,3-c)pyridin-7-ylmethyl)(1-(2-(6-fluoro-3-oxopyrido(2,3-b)pyrazin-4(3H)-yl)ethyl)piperidin-4-yl)carbamate was obtained from tert-butyl (2,3-dihydro(1,4)dioxino(2,3-c)pyridin-7-ylmethyl)(piperidin-4-yl)carbamate and (6-fluoro-3-oxopyrido(2,3-b)pyrazin-4(3H)-yl)acetaldehyde.

$^1$H-NMR (CDCl$_3$) δ: 1.30-1.70 (4H, m), 1.38 (9H, s), 2.00-2.15 (2H, m), 2.64-2.70 (2H, m), 3.01-3.08 (2H, m), 4.02-4.16 (1H, m), 4.25-4.33 (6H, m), 4.42-4.48 (2H, m), 6.71 (1H, s), 6.89 (1H, dd, J=8.4, 2.8 Hz), 8.03 (1H, s), 8.21-8.27 (2H, m)

Example 65

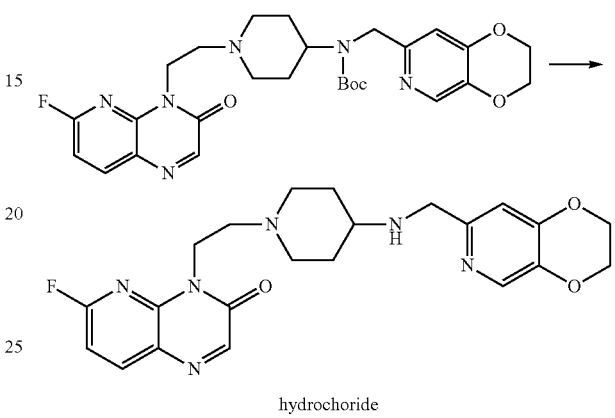

hydrochoride

To a solution of 90 mg of tert-butyl (2,3-dihydro(1,4)dioxino(2,3-c)pyridin-7-ylmethyl)(1-(2-(6-fluoro-3-oxopyrido(2,3-b)pyrazin-4(3H)-yl)ethyl)piperidin-4-yl)carbamate in 1 mL of methanol, 1 mL of a 4 mol/L hydrogen chloride/ethyl acetate solution was added, and the mixture was stirred at room temperature for 1 hour. The solid was filtered off to obtain 76 mg of 4-(2-(4-((2,3-dihydro(1,4)dioxino(2,3-c)pyridin-7-ylmethyl)amino)piperidin-1-yl)ethyl)-6-fluoropyrido(2,3-b)pyrazin-3(4H)-one hydrochloride.

$^1$H-NMR (DMSO-d$_6$) δ: 1.97-2.09 (2H, m), 2.28-2.37 (2H, m), 3.00-3.14 (2H, m), 3.26-3.36 (1H, m), 3.39-3.57 (2H, m), 3.80-4.00 (2H, m), 4.19-4.27 (2H, m), 4.33-4.45 (4H, m), 4.55-4.63 (2H, m), 7.25 (1H, dd, J=8.5, 2.2 Hz), 7.32 (1H, s), 8.26 (1H, s), 8.33 (1H, s), 8.46-8.51 (1H, m), 9.70-9.90 (2H, broad), 10.35-10.55 (1H, broad)

Example 66

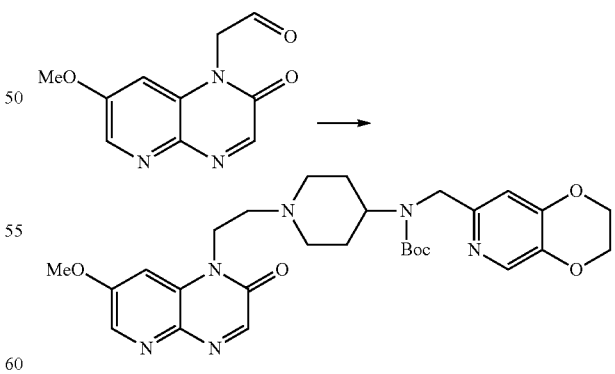

By the same technique as in Example 1, tert-butyl (2,3-dihydro(1,4)dioxino(2,3-c)pyridin-7-ylmethyl)(1-(2-(7-methoxy-2-oxopyrido(2,3-b)pyrazin-1(2H)-yl)ethyl)piperidin-4-yl)carbamate was obtained from (7-methoxy-2-oxopyrido(2,3-b)pyrazin-1(2H)-yl)acetaldehyde and tert-butyl (2,3-dihydro(1,4)dioxino(2,3-c)pyridin-7-ylmethyl)(piperidin-4-yl)carbamate.

¹H-NMR (CDCl₃) δ: 1.34-1.70 (4H, m), 1.39 (9H, s), 2.08-2.24 (2H, m), 2.60-2.66 (2H, m), 2.92-3.00 (2H, m), 3.99 (3H, s), 4.03-4.15 (1H, m), 4.23-4.37 (8H, m), 6.73 (1H, s), 7.18 (1H, d, J=2.4 Hz), 8.05 (1H, s), 8.33 (1H, s), 8.36 (1H, d, J=2.4 Hz)

Example 67

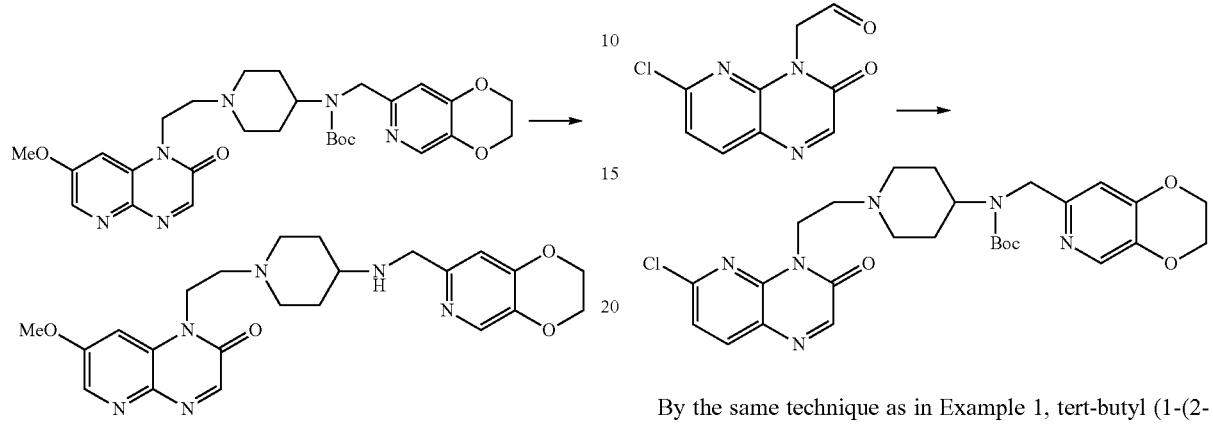

By the same technique as in Example 59, 1-(2-(4-((2,3-dihydro(1,4)dioxino(2,3-c)pyridin-7-ylmethyl)amino)piperidin-1-yl)ethyl)-7-methoxypyrido(2,3-b)pyrazin-2(1H)-one was obtained from tert-butyl (2,3-dihydro(1,4)dioxino(2,3-c)pyridin-7-ylmethyl)(1-(2-(7-methoxy-2-oxopyrido(2,3-b)pyrazin-1(2H)-yl)ethyl)piperidin-4-yl)carbamate.

¹H-NMR (CDCl₃) δ: 1.37-1.48 (2H, m), 1.86-1.99 (2H, m), 2.13-2.23 (2H, m), 2.48-2.58 (1H, m), 2.64-2.69 (2H, m), 2.91-2.98 (2H, m), 3.78 (2H, s), 4.00 (3H, s), 4.25-4.35 (6H, m), 6.81 (1H, s), 7.26 (1H, d, J=2.6 Hz), 8.10 (1H, s), 8.34 (1H, s), 8.36 (1H, d, J=2.6 Hz)

Example 68

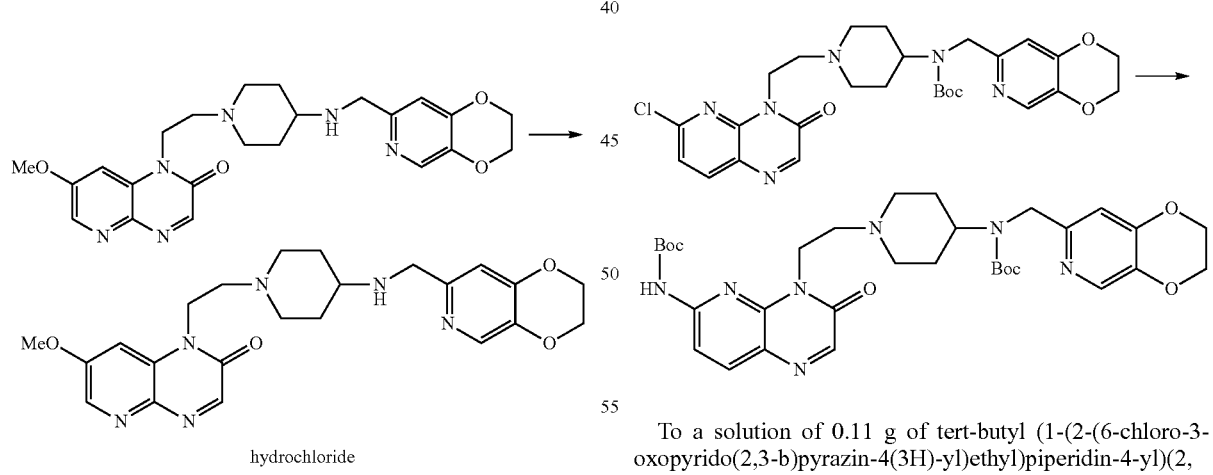

hydrochloride

By the same technique as in Example 8, 1-(2-(4-((2,3-dihydro(1,4)dioxino(2,3-c)pyridin-7-ylmethyl)amino)piperidin-1-yl)ethyl)-7-methoxypyrido(2,3-b)pyrazin-2(1H)-one hydrochloride was obtained from 1-(2-(4-((2,3-dihydro(1,4)dioxino(2,3-c)pyridin-7-ylmethyl)amino)piperidin-1-yl)ethyl)-7-methoxypyrido(2,3-b)pyrazin-2(1H)-one.

¹H-NMR (D₂O) δ: 1.96-2.10 (2H, m), 2.49-2.57 (2H, m), 3.21-3.32 (2H, m), 3.61-3.72 (3H, m), 3.95-4.04 (2H, m), 4.06 (3H, s), 4.39 (2H, s), 4.40-4.54 (4H, m), 4.75-4.81 (2H, m), 7.25 (1H, s), 7.48-7.51 (1H, m), 8.24 (1H, s), 8.34 (1H, s), 8.41-8.44 (1H, m)

Example 69

By the same technique as in Example 1, tert-butyl (1-(2-(6-chloro-3-oxopyrido(2,3-b)pyrazin-4(3H)-yl)ethyl)piperidin-4-yl)(2,3-dihydro(1,4)dioxino(2,3-c)pyridin-7-ylmethyl)carbamate was obtained from tert-butyl (2,3-dihydro(1,4)dioxino(2,3-c)pyridin-7-ylmethyl)(piperidin-4-yl)carbamate and (6-chloro-3-oxopyrido(2,3-b)pyrazin-4(3H)-yl)acetaldehyde.

¹H-NMR (CDCl₃) δ: 1.38 (9H, s), 1.40-1.65 (4H, m), 1.97-2.15 (2H, m), 2.64-2.70 (2H, m), 3.03-3.10 (2H, m), 4.02-4.14 (1H, m), 4.25-4.34 (6H, m), 4.46-4.52 (2H, m), 6.70 (1H, s), 7.26 (1H, d, J=8.2 Hz), 8.02 (1H, s), 8.09 (1H, d, J=8.2 Hz), 8.28 (1H, s)

Example 70

To a solution of 0.11 g of tert-butyl (1-(2-(6-chloro-3-oxopyrido(2,3-b)pyrazin-4(3H)-yl)ethyl)piperidin-4-yl)(2,3-dihydro(1,4)dioxino(2,3-c)pyridin-7-ylmethyl)carbamate in 3 mL of dioxane, 25 mg of tert-butyl carbamate and 82 mg of cesium carbonate were added. Thereto were added 2.5 mg of tris(dibenzylideneacetate)dipalladium(0) and 3.1 mg of 4,5-bis(diphenylphosphino)-9,9-dimethylxanthene under an argon atmosphere. The mixture was stirred at 80 to 90° C. for 2 hours under an argon atmosphere. The insoluble substance was filtered off, and the solvent was distilled off under reduced pressure. The resultant residue was purified by basic silica gel column chromatography using an eluent of chloroform:methanol=20:1 to obtain 78 mg of tert-butyl (1-(2-(6-((tert-butoxycarbonyl)amino)-3-oxopyrido(2,3-b)pyrazin-4(3H)-yl)ethyl)piperidin-4-yl)(2,3-dihydro(1,4)dioxino(2,3-c)pyridin-7-ylmethyl)carbamate as a light brown oily substance.

$^1$H-NMR (CDCl$_3$) δ: 1.35-1.70 (4H, m), 1.38 (9H, s), 1.56 (9H, s), 2.03-2.19 (2H, m), 2.58-2.64 (2H, m), 3.00-3.04 (2H, m), 4.06-4.19 (1H, m), 4.24-4.38 (6H, m), 4.40-4.48 (2H, m), 6.72 (1H, s), 7.37 (1H, s), 7.96 (1H, d, J=8.8 Hz), 8.05 (1H, s), 8.09 (1H, d, J=8.8 Hz), 8.15 (1H, s)

Example 71

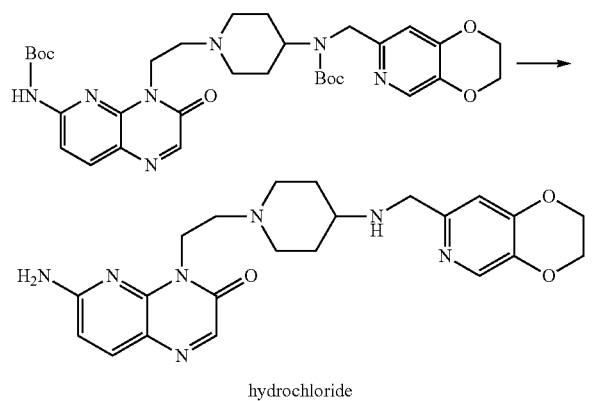

By the same technique as in Example 65, 6-amino-4-(2-(4-((2,3-dihydro(1,4)dioxino(2,3-c)pyridin-7-ylmethyl)amino)piperidin-1-yl)ethyl)pyrido(2,3-b)pyrazin-3(4H)-one hydrochloride was obtained from tert-butyl (1-(2-(6-((tert-butoxycarbonyl)amino)-3-oxopyrido(2,3-b)pyrazin-4(3H)-yl)ethyl)piperidin-4-yl)(2,3-dihydro(1,4)dioxino(2,3-c)pyridin-7-ylmethyl)carbamate.

$^1$H-NMR (DMSO-d$_6$-D$_2$O) δ: 1.85-1.97 (2H, m), 2.32-2.41 (2H, m), 3.04-3.14 (2H, m), 3.33-3.48 (3H, m), 3.92-4.00 (2H, m), 4.26 (2H, s), 4.35-4.46 (4H, m), 4.54-4.60 (2H, m), 6.56 (1H, d, J=8.8 Hz), 7.31 (1H, s), 7.83 (1H, d, J=8.8 Hz), 7.87 (1H, s), 8.30 (1H, s)

Example 72

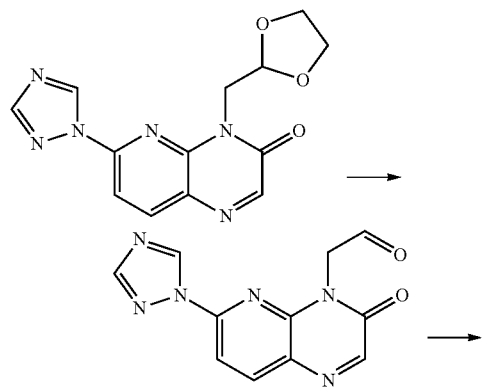

(1) To 98 mg of 4-(1,3-dioxolan-2-ylmethyl)-6-(1H-1,2,4-triazol-1-yl)pyrido(2,3-b)pyrazin-3(4H)-one, 3 mL of an 80% aqueous trifluoroacetic acid solution was added, and the mixture was stirred at room temperature for 6 hours 30 minutes. Thereto were added water and ethyl acetate, and the mixture was neutralized with a saturated aqueous sodium hydrogen carbonate solution and an aqueous sodium hydroxide solution. The organic layer was separated, and sodium chloride was added to the aqueous layer, and the mixture was extracted with chloroform. The organic layer and the extract were combined, the resultant solution was dried over anhydrous magnesium sulfate, and the solvent was distilled off under reduced pressure to obtain 0.12 g of (3-oxo-6-(1H-1,2,4-triazol-1-yl)pyrido(2,3-b)pyrazin-4(3H)-yl)acetaldehyde as a light red solid.

(2) To a solution of 48 mg of tert-butyl (2,3-dihydro(1,4)dioxino(2,3-c)pyridin-7-ylmethyl)(piperidin-4-yl)carbamate in 2 mL of methanol, 50 mg of (3-oxo-6-(1H-1,2,4-triazol-1-yl)pyrido(2,3-b)pyrazin-4(3H)-yl)acetaldehyde, 2.5 mL of dichloromethane and 20 μL of acetic acid were added, and the mixture was stirred at room temperature for 40 minutes. To the reaction mixture, 9.0 mg of sodium cyanoborohydride was added, and the mixture was stirred at room temperature for 1 hour 30 minutes. Thereto were added a saturated aqueous sodium hydrogen carbonate solution and chloroform, the organic layer was separated, washed sequentially with water and a saturated aqueous sodium chloride solution and dried over anhydrous magnesium sulfate, and the solvent was distilled off under reduced pressure. The resultant residue was purified by silica gel column chromatography using an eluent of chloroform:methanol=50:1 to obtain 35 mg of tert-butyl (2,3-dihydro(1,4)dioxino(2,3-c)pyridin-7-ylmethyl)(1-(2-(3-oxo-6-(1H-1,2,4-triazol-1-yl)pyrido(2,3-b)pyrazin-4(3H)-yl)ethyl)piperidin-4-yl)carbamate as a light yellow oily substance.

$^1$H-NMR (CDCl$_3$) δ: 1.38 (9H, s), 1.30-1.70 (4H, m), 2.05-2.21 (2H, m), 2.69-2.75 (2H, m), 3.00-3.08 (2H, m), 4.04-4.16 (1H, m), 4.25-4.34 (6H, m), 4.52-4.58 (2H, m), 6.70 (1H, s), 7.92 (1H, d, J=8.6 Hz), 8.02 (1H, s), 8.14 (1H, s), 8.31 (1H, s), 8.35 (1H, d, J=8.6 Hz), 9.09 (1H, s)

Example 73

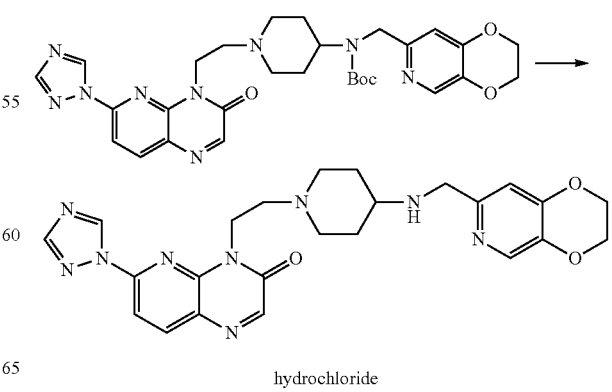

By the same technique as in Example 65, 4-(2-(4-((2,3-dihydro(1,4)dioxino(2,3-c)pyridin-7-ylmethyl)amino)piperidin-1-yl)ethyl)-6-(1H-1,2,4-triazol-1-yl)pyrido(2,3-b)pyrazin-3(4H)-one hydrochloride was obtained from tert-butyl (2,3-dihydro(1,4)dioxino(2,3-c)pyridin-7-ylmethyl)(1-(2-(3-oxo-6-(1H-1,2,4-triazol-1-yl)pyrido(2,3-b)pyrazin-4(3H)-yl)ethyl)piperidin-4-yl)carbamate.

$^1$H-NMR (DMSO-d$_6$) δ: 1.97-2.34 (4H, m), 3.02-3.14 (2H, m), 3.24-3.36 (1H, m), 3.40-3.50 (2H, m), 3.80-4.00 (2H, m), 4.19-4.26 (2H, m), 4.30-4.45 (4H, m), 4.80-4.83 (2H, m), 7.27 (1H, s), 7.90 (1H, d, J=8.4 Hz), 8.25 (1H, s), 8.35 (1H, s), 8.41 (1H, s), 8.52 (1H, d, J=8.4 Hz), 9.55-9.80 (2H, broad), 9.94 (1H, s), 10.95-11.00 (1H, m)

Example 74

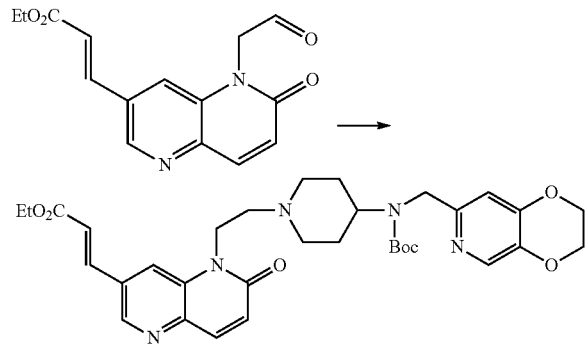

By the same technique as in Example 1, ethyl (2E)-3-(5-(2-(4-((tert-butoxycarbonyl)(2,3-dihydro(1,4)dioxino(2,3-c)pyridin-7-ylmethyl)amino)piperidin-1-yl)ethyl)-6-oxo-5,6-dihydro-1,5-naphthyridin-3-yl)acrylate was obtained from ethyl (2E)-3-(6-oxo-5-(2-oxoethyl)-5,6-dihydro-1,5-naphthyridin-3-yl)acrylate and tert-butyl (2,3-dihydro(1,4)dioxino(2,3-c)pyridin-7-ylmethyl)(piperidin-4-yl)carbamate.

$^1$H-NMR (CDCl$_3$) δ: 1.30-1.75 (13H, m), 1.38 (3H, t, J=7.2 Hz), 2.10-2.27 (2H, m), 2.58-2.65 (2H, m), 2.98-3.06 (2H, m), 4.04-4.20 (1H, m), 4.24-4.46 (10H, m), 6.62 (1H, d, J=16.2 Hz), 6.72-6.74 (1H, broad), 6.93 (1H, d, J=9.8 Hz), 7.75 (1H, d, J=16.2 Hz), 7.78 (1H, s), 7.89 (1H, d, J=9.8 Hz), 8.05 (1H, s), 8.68 (1H, d, J=1.2 Hz)

Example 75

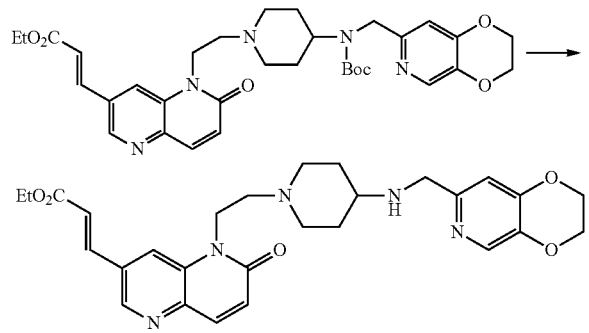

By the same technique as in Example 54, ethyl (2E)-3-(5-(2-(4-((2,3-dihydro(1,4)dioxino(2,3-c)pyridin-7-ylmethyl)amino)piperidin-1-yl)ethyl)-6-oxo-5,6-dihydro-1,5-naphthyridin-3-yl)acrylate was obtained from ethyl (2E)-3-(5-(2-(4-((tert-butoxycarbonyl)(2,3-dihydro(1,4)dioxino(2,3-c)pyridin-7-ylmethyl)amino)piperidin-1-yl)ethyl)-6-oxo-5,6-dihydro-1,5-naphthyridin-3-yl)acrylate.

$^1$H-NMR (CDCl$_3$) δ: 1.35-1.54 (2H, m), 1.37 (3H, t, J=7.2 Hz), 1.85-2.00 (2H, m), 2.12-2.28 (2H, m), 2.46-2.74 (3H, m), 2.93-3.04 (2H, m), 3.80 (2H, s), 4.24-4.44 (8H, m), 6.65 (1H, d, J=16.1 Hz), 6.82 (1H, s), 6.93 (1H, d, J=9.8 Hz), 7.76 (1H, d, J=16.1 Hz), 7.87-7.92 (1H, broad), 7.89 (1H, d, J=9.8 Hz), 8.10 (1H, s), 8.68 (1H, d, J=1.7 Hz)

Example 76

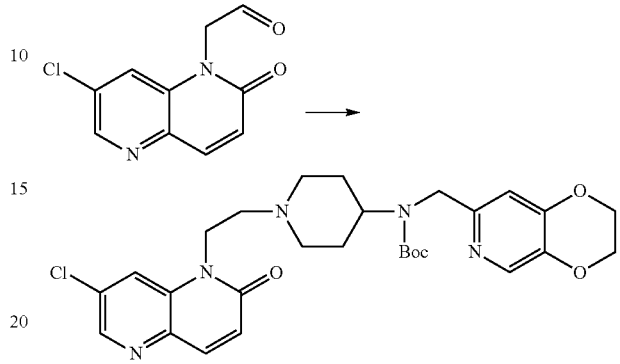

By the same technique as in Example 1, tert-butyl (1-(2-(7-chloro-2-oxo-1,5-naphthyridin-1(2H)-yl)ethyl)piperidin-4-yl)(2,3-dihydro(1,4)dioxino(2,3-c)pyridin-7-ylmethyl)carbamate was obtained from (7-chloro-2-oxo-1,5-naphthyridin-1(2H)-yl)acetaldehyde and tert-butyl (2,3-dihydro(1,4)dioxino(2,3-c)pyridin-7-ylmethyl)(piperidin-4-yl)carbamate.

$^1$H-NMR (CDCl$_3$) δ: 1.35-1.55 (13H, m), 2.08-2.27 (2H, m), 2.58-2.65 (2H, m), 2.93-3.02 (2H, m), 4.05-4.20 (1H, m), 4.22-4.50 (8H, m), 6.72 (1H, s), 6.88 (1H, d, J=9.8 Hz), 7.78-7.82 (1H, m), 7.86 (1H, d, J=9.8 Hz), 8.05 (1H, s), 8.46 (1H, d, J=2.0 Hz)

Example 77

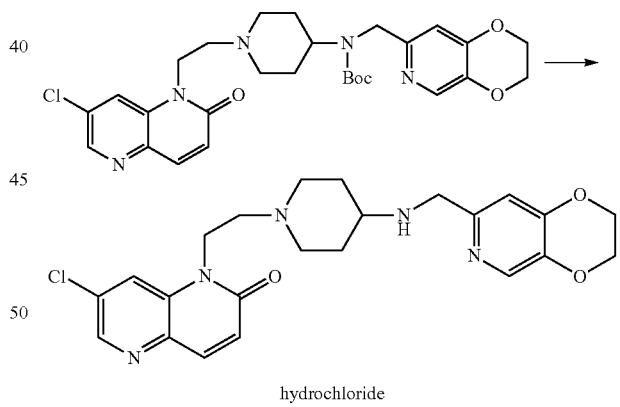

By the same technique as in Example 2, 7-chloro-1-(2-(4-((2,3-dihydro(1,4)dioxino(2,3-c)pyridin-7-ylmethyl)amino)piperidin-1-yl)ethyl)-1,5-naphthyridin-2(1H)-one hydrochloride was obtained from tert-butyl (1-(2-(7-chloro-2-oxo-1,5-naphthyridin-1(2H)-yl)ethyl)piperidin-4-yl)(2,3-dihydro(1,4)dioxino(2,3-c)pyridin-7-ylmethyl)carbamate.

$^1$H-NMR (D$_2$O) δ: 2.00-2.14 (2H, m), 2.51-2.61 (2H, m), 3.22-3.36 (2H, m), 3.60-3.80 (3H, m), 3.97-4.07 (2H, m), 4.45-4.50 (2H, m), 4.52 (2H, s), 4.57-4.62 (2H, m), 4.72-4.82 (2H, m), 7.03 (1H, d, J=9.8 Hz), 7.44 (1H, s), 8.08 (1H, d, J=9.8 Hz), 8.19-8.22 (1H, m), 8.36 (1H, s), 8.61 (1H, d, J=1.7 Hz)

Example 78

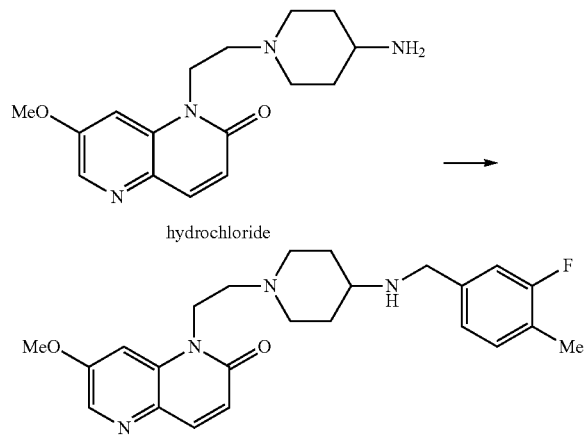

To a suspension of 0.22 g of 1-(2-(4-aminopiperidin-1-yl)ethyl)-7-methoxy-1,5-naphthyridin-2(1H)-one hydrochloride in 7 mL of methanol, 66 mg of sodium cyanoborohydride, 64 μL of 3-fluoro-4-methylbenzaldehyde, 0.30 g of a 28% sodium methoxide/methanol solution and 30 μL of acetic acid were added, and the mixture was stirred at room temperature for 3 hours. Thereto was added 22 mg of 3-fluoro-4-methylbenzaldehyde, and the mixture was stirred at the same temperature for 1 hour. Thereto was further added 33 mg of sodium cyanoborohydride, and the mixture was stirred at the same temperature for 1 hour. A saturated aqueous sodium hydrogen carbonate solution was added thereto, and the solvent was distilled off under reduced pressure. Thereto was added chloroform, the organic layer was separated, and the aqueous layer was extracted with chloroform. The organic layer and the extract were combined, the resultant solution was washed sequentially with water and a saturated aqueous sodium chloride solution, and dried over anhydrous magnesium sulfate, and the solvent was distilled off under reduced pressure. The resultant residue was purified by basic silica gel column chromatography using an eluent of chloroform:methanol=9:1 to obtain 20 mg of 1-(2-(4-((3-fluoro-4-methylbenzyl)amino)piperidin-1-yl)ethyl)-7-methoxy-1,5-naphthyridin-2(1H)-one as a colorless oily substance.

$^1$H-NMR (CDCl$_3$) δ: 1.36-1.57 (2H, m), 1.86-1.94 (2H, m), 2.13-2.22 (2H, m), 2.25 (3H, s), 2.48-2.56 (1H, m), 2.61-2.68 (2H, m), 2.94-3.01 (2H, m), 3.77 (2H, s), 3.97 (3H, s), 4.33-4.39 (2H, m), 6.74 (1H, d, J=9.6 Hz), 6.95-7.01 (2H, m), 7.11 (1H, t, J=8.0 Hz), 7.23 (1H, d, J=2.3 Hz), 7.84 (1H, d, J=9.6 Hz), 8.28 (1H, d, J=2.3 Hz)

Example 79

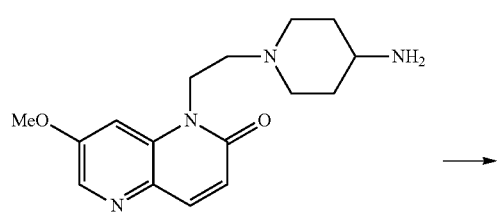

-continued

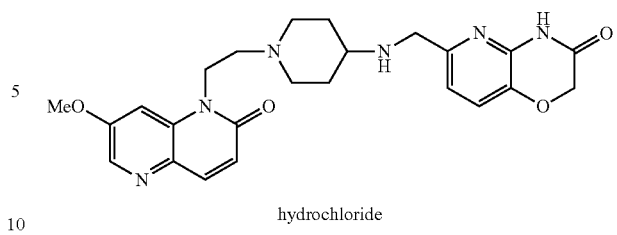

hydrochloride

To a solution of 297 mg of 1-(2-(4-aminopiperidin-1-yl)ethyl)-7-methoxy-1,5-naphthyridin-2(1H)-one and 159 mg of 3-oxo-3,4-dihydro-2H-pyrido(3,2-b)(1,4)oxazine-6-carbaldehyde in 4 mL of chloroform and 1 mL of methanol, 0.11 mL of acetic acid was added, and the mixture was stirred at room temperature for 16 hours. To the reaction mixture, 299 mg of sodium triacetoxyborohydride was added, and the mixture was stirred for 1.5 hours. Thereto was added a saturated aqueous sodium hydrogen carbonate solution, and the organic layer was separated. The organic layer was washed with a saturated aqueous sodium chloride solution, and dried over anhydrous magnesium sulfate, and the solvent was distilled off under reduced pressure. The resultant residue was purified by silica gel column chromatography using silica gel; Silica Gel 60 made by KANTO CHEMICAL CO., INC., and an eluent of chloroform:methanol (mixing 5% of 28% ammonium water)=87:13 to obtain 275 mg of 1-(2-(4-((3-oxo-3,4-dihydro-2H-pyrido(3,2-b)(1,4)oxazin-6-yl)methylamino)piperidin-1-yl)ethyl)-7-methoxy-1,5-naphthyridin-2(1H)-one as a yellow foam.

To a solution of 260 mg of 1-(2-(4-((3-oxo-3,4-dihydro-2H-pyrido(3,2-b)(1,4)oxazin-6-yl)methylamino)piperidin-1-yl)ethyl)-7-methoxy-1,5-naphthyridin-2(1H)-one in 4 mL of ethyl acetate and 2 mL of methanol, 3 mL of 4 mol/L hydrogen chloride/ethyl acetate was added, and the mixture was stirred at room temperature for 12 minutes. The solvent was distilled off under reduced pressure, thereto was added diethyl ether, and the solid was filtered off to obtain 304 mg of 1-(2-(4-((3-oxo-3,4-dihydro-2H-pyrido(3,2-b)(1,4)oxazin-6-yl)methylamino)piperidin-1-yl)ethyl)-7-methoxy-1,5-naphthyridin-2(1H)-one hydrochloride as a white solid.

$^1$H-NMR (DMSO-d$_6$) δ: 2.03-2.12 (2H, m), 2.37-2.44 (2H, m), 3.08-3.16 (2H, m), 3.27-3.33 (2H, m), 3.35-3.43 (1H, m), 3.78-3.82 (2H, m), 4.07 (3H, s), 4.19 (2H, t, J=5.5 Hz), 4.70-4.73 (4H, m), 6.72 (1H, d, J=9.6 Hz), 7.23 (1H, d, J=8.3 Hz), 7.46 (1H, d, J=8.3 Hz), 7.72 (1H, d, J=2.3 Hz), 7.94 (1H, d, J=9.6 Hz), 8.34 (1H, d, J=2.3 Hz), 9.54-9.68 (2H, m), 11.30-11.63 (2H, m)

Example 80

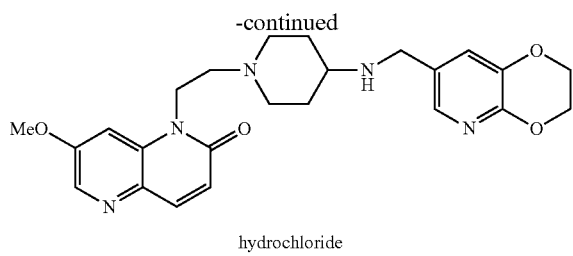

hydrochloride

To a solution of 150 mg of 1-(2-(4-(aminopiperidin-1-yl) ethyl)-7-methoxy-1,5-naphthyridin-2(1H)-one and 82 mg of 2,3-dihydro(1,4)dioxino(2,3-b)pyridine-7-carbaldehyde in 15 mL of chloroform, 60 mg of acetic acid was added, and the mixture was stirred at room temperature for 16.5 hours. To the reaction mixture, 158 mg of sodium triacetoxyborohydride was added, and the mixture was stirred for 2 hours. Thereto was added a saturated aqueous sodium hydrogen carbonate solution, and the organic layer was separated. The organic layer was washed with a saturated aqueous sodium chloride solution and dried over anhydrous magnesium sulfate, and the solvent was distilled off under reduced pressure. The resultant residue was purified by silica gel column chromatography using silica gel; Silica Gel 60N made by KANTO CHEMICAL CO., INC., and an eluent of chloroform:methanol=10:1 to obtain 103 mg of 1-(2-(4-((2,3-dihydro(1,4)dioxino(2,3-b)pyridin-7-yl)methylamino)piperidin-1-yl) ethyl)-7-methoxy-1,5-naphthyridin-2(1H)-one as a colorless viscous oily substance.

In a solution of 134 mg of 1-(2-(4-((2,3-dihydro(1,4)dioxino(2,3-b)pyridin-7-yl)methylamino)piperidin-1-yl) ethyl)-7-methoxy-1,5-naphthyridin-2(1H)-one in 1 mL of methanol and 5 mL of ethyl acetate, 2 mL of 4 mol/L hydrogen chloride/ethyl acetate was added, and the mixture was stirred at room temperature. The solid was filtered off to obtain 159 mg of 1-(2-(4-((2,3-dihydro(1,4)dioxino(2,3-b) pyridin-7-yl)methylamino)piperidin-1-yl)ethyl)-7-methoxy-1,5-naphthyridin-2(1H)-one hydrochloride as a light yellow solid.

$^1$H-NMR (DMSO-$d_6$) δ: 2.02-2.11 (2H, m), 2.35-2.42 (2H, m), 3.07-3.17 (2H, m), 3.24-3.32 (3H, m), 3.75-3.82 (2H, m), 4.07 (3H, s), 4.09-4.19 (2H, m), 4.25-4.31 (2H, m), 4.41-4.44 (2H, m), 4.67-4.74 (2H, m), 6.72 (1H, d, J=9.6 Hz), 7.64 (1H, d, J=2.3 Hz), 7.70 (1H, d, J=2.3 Hz), 7.92 (1H, d, J=2.3 Hz), 7.94 (1H, d, J=9.6 Hz), 8.33 (1H, d, J=2.3 Hz), 9.59-9.78 (3H, m), 11.26-11.52 (1H, m)

Example 81

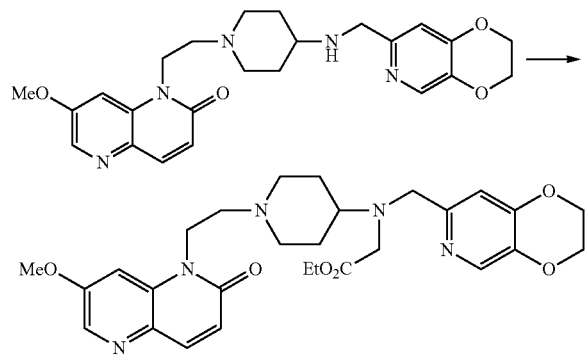

A solution of 150 mg of 1-(2-(4-((2,3-dihydro(1,4)dioxino (2,3-c)pyridin-7-yl)methylamino)piperidin-1-yl)ethyl)-7-methoxy-1,5-naphthyridin-2(1H)-one and 85 mg of bromo acetate in 15 mL of acetonitrile, 100 mg of potassium carbonate was added, and the mixture was stirred at room temperature for 18 hours, and stirred at 40° C. for 4 hours. The solvent was distilled off under reduced pressure, thereto were added chloroform and water, and the organic layer was separated. The organic layer was dried over anhydrous magnesium sulfate, and the solvent was distilled off under reduced pressure. The resultant residue was purified by silica gel column chromatography using silica gel; Silica Gel 60N made by KANTO CHEMICAL CO., INC., and an eluent of chloroform:methanol=20:1 to obtain 90 mg of ethyl ((2,3-dihydro(1,4)dioxino (2,3-c)pyridin-7-ylmethyl)(1-(2-(7-methoxy-2-oxo-1,5-naphthyridin-1(2H)-yl)ethyl)piperidin-4-yl)amino)acetate as an brown oily substance.

$^1$H-NMR (CDCl$_3$) δ: 1.26 (3H, m), 1.52-1.60 (2H, m), 1.84-1.89 (2H, m), 2.08-2.15 (2H, m), 2.59-2.64 (2H, m), 2.65-2.71 (1H, m), 3.01-3.07 (2H, m), 3.40-3.43 (2H, m), 3.84-3.87 (2H, m), 3.97 (3H, s), 4.12-4.17 (2H, m), 4.26-4.29 (2H, m), 4.31-4.37 (4H, m), 6.72-6.75 (1H, m), 7.13-7.15 (1H, m), 7.19-7.21 (1H, m), 7.82-7.85 (1H, m), 8.05-8.07 (1H, m), 8.27-8.29 (1H, m)

Example 82

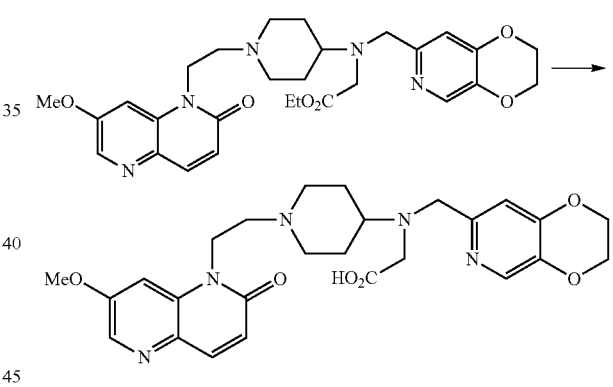

A solution of 90 mg of ethyl ((2,3-dihydro(1,4)dioxino(2, 3-c)pyridin-7-ylmethyl)(1-(2-(7-methoxy-2-oxo-1,5-naphthyridin-1(2H)-yl)ethyl)piperidin-4-yl)amino)acetate in 0.2 mL of methanol and 1 mL of tetrahydrofuran, 0.2 mL of a 10% aqueous sodium hydroxide solution was added, and the mixture was stirred at room temperature for 2 hours. The reaction mixture was added with a 1 mol/L aqueous hydrochloric acid solution and neutralized, and the solvent was distilled off under reduced pressure. The resultant residue was purified by a resin; HP-20, made by Mitsubishi Chemical Corporation and an eluent of acetone to obtain 54 mg of ((2,3-dihydro(1,4)dioxino(2,3-c) pyridin-7-ylmethyl)(1-(2-(7-methoxy-2-oxo-1,5-naphthyridin-1(2H)-yl)ethyl)piperidin-4-yl)amino)acetic acid as a light yellow solid.

$^1$H-NMR (DMSO-$d_6$) δ: 1.26-1.34 (2H, m), 1.66-1.71 (2H, m), 1.74-1.78 (2H, m), 1.90-1.97 (2H, m), 2.94-3.01 (3H, m), 3.58-3.62 (2H, m), 3.66-3.69 (2H, m), 3.96 (3H, s), 4.25-4.28 (2H, m), 4.31-4.35 (4H, m), 6.65 (1H, d, J=9.6 Hz), 7.08 (1H, s), 7.40 (1H, d, J=2.3 Hz), 7.86 (1H, d, J=9.6 Hz), 7.96 (1H, s), 8.27 (1H, d, J=2.3 Hz)

Example 83

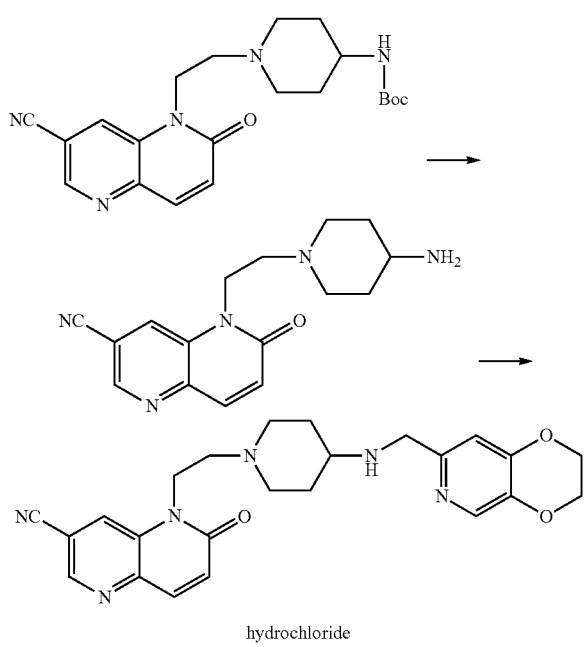

hydrochloride

To a solution of 75 mg of tert-butyl (1-(2-(7-cyano-2-oxo-1,5-naphthyridin-1(2H)-yl)ethyl)piperidin-4-yl)carbamate in 5 mL of ethyl acetate, 7 mL of a 4 mol/L hydrogen chloride/ethyl acetate was added, and the mixture was stirred at room temperature for 2 hours. The reaction mixture was alkalified with a saturated aqueous sodium hydrogen carbonate solution, the solvent was distilled off under reduced pressure, and the resultant residue was then purified by silica gel column chromatography using silica gel; Chromatorex-NH made by Fuji Silysia Chemical Ltd., and an eluent of chloroform to obtain 34 mg of 1-(2-(4-aminopiperidin-1-yl)ethyl)-7-cyano-1,5-naphthyridin-2(1H)-one as a light yellow solid.

To a solution of 32 mg of 1-(2-(4-aminopiperidin-1-yl)ethyl)-7-cyano-(1,5-naphthyridin)-2(1H)-one and 16 mg of 2,3-dihydro(1,4)dioxino(2,3-c)pyridine-7-carbaldehyde in 5 mL of chloroform, 9 μL of acetic acid was added, and the mixture was stirred at room temperature overnight. To the reaction mixture, 34 mg of sodium triacetoxyborohydride was added, and the mixture was stirred for 9 hours. Thereto was added a saturated aqueous sodium hydrogen carbonate solution, and the solvent was distilled off under reduced pressure. The resultant residue was purified by silica gel column chromatography using silica gel; Chromatorex-NH made by Fuji Silysia Chemical Ltd., and an eluent of chloroform to obtain 39 mg of 1-(2-(4-((2,3-dihydro(1,4)dioxino(2,3-c)pyridin-7-ylmethyl)amino)piperidin-1-yl)ethyl)-7-cyano-1,5-naphthyridin-2(1H)-one as a light yellow solid.

To a solution of 36 mg of 1-(2-(4-((2,3-dihydro (1,4)dioxino(2,3-c)pyridin-7-ylmethyl)amino)piperidin-1-yl)ethyl)-7-cyano-1,5-naphthyridin-2(1H)-one in 5 mL of acetic acid, 0.5 mL of a 4 mol/L hydrogen chloride/ethyl acetate and 5 mL of ethyl acetate were added, and the mixture was stirred at room temperature for 10 minutes. The solvent was distilled off under reduced pressure to obtain 44 mg of 1-(2-(4-((2,3-dihydro(1,4)dioxino(2,3-c)pyridin-7-ylmethyl)amino)piperidin-1-yl)ethyl)-7-cyano-1,5-naphthyridin-2(1H)-one hydrochloride as a white solid.

$^{1}$H-NMR (CDCl$_3$) δ: 2.03-2.09 (2H, m), 2.33-2.38 (2H, m), 3.07-3.15 (2H, m), 3.28-3.36 (3H, m), 3.76-3.81 (2H, m), 4.21-4.24 (2H, m), 4.34-4.36 (2H, m), 4.40-4.43 (2H, m), 4.62-4.66 (2H, m), 7.09 (1H, d, J=9.6 Hz), 7.26 (1H, s), 8.07 (1H, d, J=9.6 Hz), 8.23 (1H, s), 8.84-8.85 (1H, m), 8.96 (1H, d, J=1.8 Hz), 9.65-9.70 (2H, m), 10.74-10.78 (1H, m)

Example 84

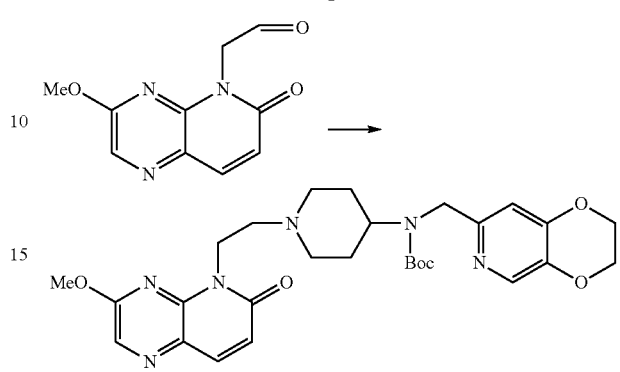

To a solution of 0.12 g of (3-methoxy-6-oxopyrido(2,3-b)pyrazin-5(6H)-yl)acetaldehyde in 5 mL of methylene chloride, 0.18 g of tert-butyl (2,3-dihydro(1,4)dioxino(2,3-c)pyridin-7-ylmethyl)(piperidin-4-yl)carbamate, 26 μL of acetic acid and 0.12 g of sodium triacetoxyborohydride were added, and the mixture was stirred at room temperature for 2 hours 30 minutes. To the reaction mixture, a saturated aqueous sodium hydrogen carbonate solution and chloroform were added, the organic layer was separated, and the aqueous layer was extracted with chloroform. The organic layer and the extract were combined, the resultant solution was washed with a saturated aqueous sodium chloride solution and dried over anhydrous magnesium sulfate, and the solvent was distilled off under reduced pressure. The resultant residue was purified by silica gel column chromatography using an eluent of chloroform:methanol=20:1 to obtain 0.32 g of tert-butyl (2,3-dihydro(1,4)dioxino(2,3-c)pyridin-7-ylmethyl)(1-(2-(3-methoxy-6-oxopyrido(2,3-b)pyrazin-5(6H)-yl)ethyl)piperidin-4-yl)carbamate as a colorless oily substance.

$^{1}$H-NMR (CDCl$_3$) δ: 1.27-1.72 (13H, m), 2.01-2.23 (2H, m), 2.59-2.69 (2H, m), 3.01-3.11 (2H, m), 3.98-4.18 (1H, m), 4.03 (3H, s), 4.19-4.39 (6H, m), 4.46-4.56 (2H, m), 6.71 (1H, s), 6.74 (1H, d, J=9.8 Hz), 7.83 (1H, d, J=9.8 Hz), 8.04 (1H, s), 8.10 (1H, s)

Example 85

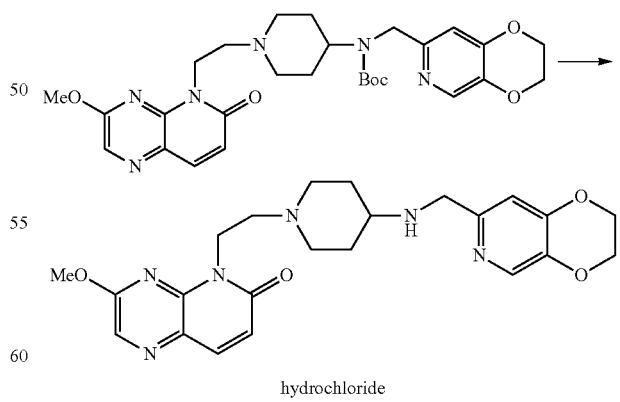

hydrochloride

To 0.32 g of tert-butyl (2,3-dihydro(1,4)dioxino(2,3-c)pyridin-7-ylmethyl)(1-(2-(3-methoxy-6-oxopyrido(2,3-b)pyrazin-5(6H)-yl)ethyl)piperidin-4-yl)carbamate, 15 mL of a 4 mol/L hydrogen chloride/ethyl acetate solution was added, and the mixture was stirred at room temperature for 2.5 days.

The solvent was distilled off under reduced pressure, 5 mL of ethyl acetate was added to the resultant residue, and the solid was filtered off to obtain 0.24 g of 5-(2-(4-((2,3-dihydro(1,4)dioxino(2,3-c)pyridin-7-ylmethyl)amino)piperidin-1-yl)ethyl-3-methoxypyrido(2,3-b)pyrazin-6(5H)-one hydrochloride as a yellow solid.

¹H-NMR (D₂O) δ: 1.98-2.13 (2H, m), 2.50-2.59 (2H, m), 3.19-3.35 (2H, m), 3.64-3.77 (3H, m), 3.97-4.09 (2H, m), 4.13 (3H, s), 4.45-4.52 (4H, m), 4.55-4.61 (2H, m), 4.90-4.94 (1H, m), 6.88 (1H, d, J=9.8 Hz), 7.40 (1H, s), 8.08 (1H, d, J=9.8 Hz), 8.26 (1H, s), 8.33 (1H, s)

Example 86

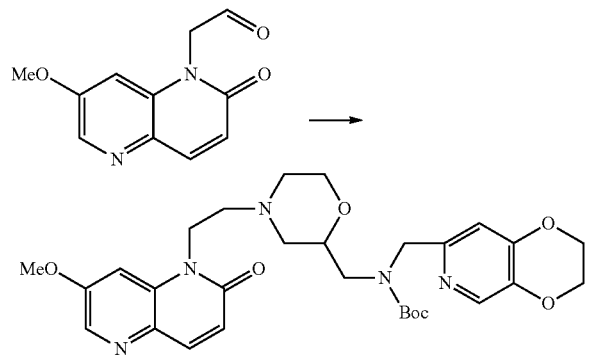

By the same technique as in Example 1, tert-butyl (2,3-dihydro(1,4)dioxino(2,3-c)pyridin-7-ylmethyl)(4-(2-(7-methoxy-2-oxo-1,5-naphthyridin-1(2H)-yl)ethyl)morpholin-2-ylmethyl)carbamate was obtained from tert-butyl (2,3-dihydro(1,4)dioxino(2,3-c)pyridin-7-ylmethyl)(morpholin-2-ylmethyl)carbamate and (7-methoxy-2-oxo-1,5-naphthyridin-1(2H)-yl)acetaldehyde.

¹H-NMR (CDCl₃) δ: 1.35-1.55 (9H, m), 1.95-2.10 (1H, m), 2.23-2.33 (1H, m), 2.58-2.71 (2H, m), 2.75-2.88 (2H, m), 3.17-3.50 (2H, m), 3.53-3.62 (1H, m), 3.65-3.79 (1H, m), 3.82-3.89 (1H, m), 3.98 (3H, s), 4.22-4.46 (7H, m), 4.52-4.68 (1H, m), 6.69-6.77 (1H, m), 6.74 (1H, d, J=9.6 Hz), 7.18 (1H, d, J=2.2 Hz), 7.85 (1H, d, J=9.6 Hz), 8.08 (1H, s), 8.26-8.31 (1H, m)

Example 87

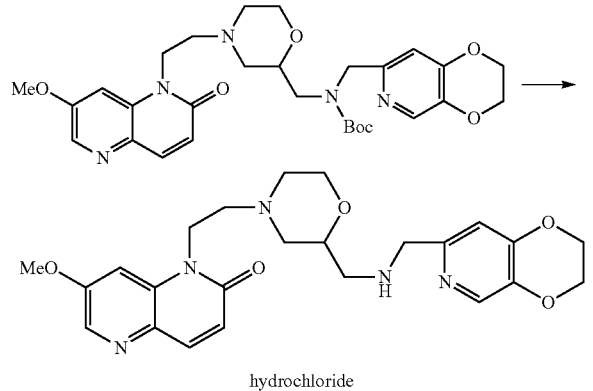

hydrochloride

By the same technique as in Example 2, 1-(2-(2-(((2,3-dihydro(1,4)dioxino(2,3-c)pyridin-7-ylmethyl)amino)methyl)morpholin-4-yl)ethyl)-7-methoxy-1,5-naphthyridin-2(1H)-one hydrochloride was obtained from tert-butyl (2,3-dihydro(1,4)dioxino(2,3-c)pyridin-7-ylmethyl)(4-(2-(7-methoxy-2-oxo-1,5-naphthyridin-1(2H)-yl)ethyl)morpholin-2-ylmethyl)carbamate.

¹H-NMR (D₂O) δ: 3.11-3.20 (1H, m), 3.27-3.39 (2H, m), 3.43-3.50 (1H, m), 3.65-3.74 (2H, m), 3.78-3.86 (1H, m), 3.87-3.97 (2H, m), 4.05 (3H, s), 4.21-4.32 (2H, m), 4.44-4.51 (4H, m), 4.56-4.61 (2H, m), 4.70-4.83 (2H, m), 6.89 (1H, d, J=9.8 Hz), 7.42 (1H, s), 7.49-7.53 (1H, m), 8.07 (1H, d, J=9.8 Hz), 8.35 (1H, s), 8.42 (1H, d, J=2.2 Hz)

Example 88

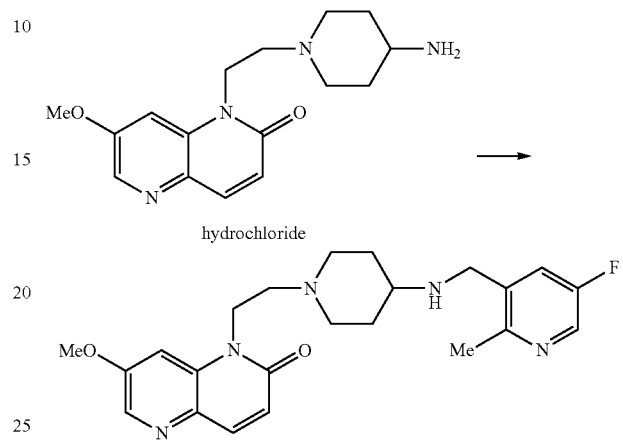

By the same technique as in Example 78, 1-(2-(4-(((5-fluoro-2-methylpyridin-3-yl)methyl)amino)piperidin-1-yl)ethyl)-7-methoxy-1,5-naphthyridin-2(1H)-one was obtained from 1-(2-(4-aminopiperidin-1-yl)ethyl)-7-methoxy-1,5-naphthyridin-2(1H)-one hydrochloride and 5-fluoro-2-methylnicotinaldehyde.

¹H-NMR (CDCl₃) δ: 1.39-1.51 (2H, m), 1.90-1.99 (2H, m), 2.17-2.28 (2H, m), 2.44-2.61 (1H, m), 2.51 (3H, s), 2.63-2.71 (2H, m), 2.96-3.05 (2H, m), 3.79 (2H, s), 3.98 (3H, s), 4.33-4.42 (2H, m), 6.75 (1H, d, J=9.8 Hz), 7.23 (1H, s), 7.47 (1H, dd, J=9.0, 2.6 Hz), 7.85 (1H, d, J=9.8 Hz), 8.23 (1H, d, J=2.6 Hz), 8.28 (1H, d, J=2.2 Hz)

Example 89

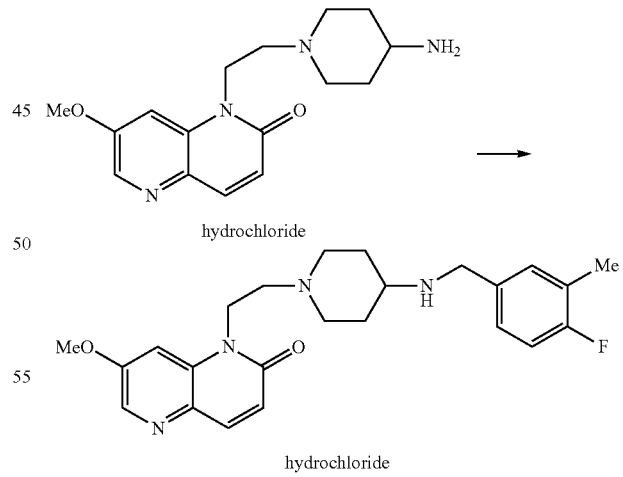

To a suspension of 0.10 g of 1-(2-(4-aminopiperidin-1-yl)ethyl)-7-methoxy-1,5-naphthyridin-2(1H)-one hydrochloride in 4 mL of methanol, 31 mg of sodium cyanoborohydride cyanoborohydride, 44 μL of 4-fluoro-3-methylbenzaldehyde, 39 mg of a 28% sodium methoxide/methanol solution and 42 μL of acetic acid were added, and the mixture was stirred at room temperature for 1 hour 15 minutes. Thereto were added 44 μL of 4-fluoro-3-methylbenzaldehyde and 31 mg of sodium cyanoborohydride cyanoborohydride, and the mixture was stirred at the same temperature for 45 minutes. Thereto were further added 44 μL of 4-fluoro-3-methylbenzaldehyde and 31 mg of sodium cyanoborohydride, and the mixture was stirred at the same temperature for 30 minutes. A saturated aqueous sodium hydrogen carbonate solution and ethyl acetate were added thereto, and the organic layer was separated, washed with a saturated aqueous sodium chloride solution, and dried over anhydrous magnesium sulfate, and the solvent was distilled off under reduced pressure. The resultant residue was purified by basic silica gel column chromatography using an eluent of chloroform:methanol=10:1. The resultant residue was dissolved in 2 mL of ethyl acetate, and thereto was added 1 mL of a 4.0 mol/L hydrogen chloride/ethyl acetate solution at room temperature. The solvent was distilled off under reduced pressure, ethyl acetate was added to the resultant residue and the solid was filtered off to obtain 54 mg of 1-(2-(4-((4-fluoro-3-methylbenzyl)amino)piperidin-1-yl)ethyl)-7-methoxy-1,5-naphthyridin-2(1H)-one hydrochloride as a light yellow solid.

$^1$H-NMR (D$_2$O) δ: 1.95-2.09 (2H, m), 2.28 (3H, d, J=1.5 Hz), 2.47-2.56 (2H, m), 3.16-3.26 (2H, m), 3.55-3.64 (3H, m), 3.92-4.00 (2H, m), 4.04 (3H, s), 4.27 (2H, s), 4.70-4.90 (2H, m), 6.87 (1H, d, J=9.8 Hz), 7.12-7.18 (1H, m), 7.28-7.39 (2H, m), 7.44 (1H, d, J=2.2 Hz), 8.06 (1H, d, J=9.8 Hz), 8.40 (1H, d, J=2.3 Hz)

Example 90

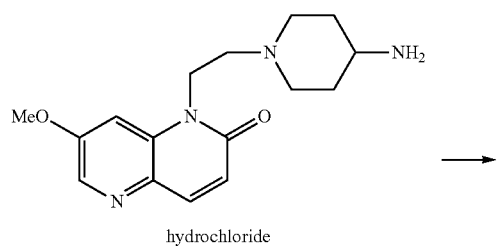

By the same technique as in Example 30, 6-(((1-(2-(7-methoxy-2-oxo-1,5-naphthyridin-1(2H)-yl)ethyl)piperidin-4-yl)amino)methyl)-2H-pyrido(3,2-b)(1,4)thiazin-3(4H)-one was obtained from 1-(2-(4-aminopiperidin-1-yl)ethyl)-7-methoxy-1,5-naphthyridin-2(1H)-one hydrochloride and 3-oxo-3,4-dihydro-2H-pyrido(3,2-b)(1,4)thiazine-6-carbaldehyde.

$^1$H-NMR (CDCl$_3$) δ: 1.40-1.53 (2H, m), 1.87-1.96 (2H, m), 2.14-2.24 (2H, m), 2.47-2.58 (1H, m), 2.62-2.69 (2H, m), 2.95-3.04 (2H, m), 3.48 (2H, s), 3.83 (2H, s), 3.98 (3H, s), 4.33-4.41 (2H, m), 6.74 (1H, d, J=9.6 Hz), 6.97 (1H, d, J=7.7 Hz), 7.24 (1H, d, J=2.2 Hz), 7.57 (1H, d, J=7.7 Hz), 7.85 (1H, d, J=9.6 Hz), 8.13-8.23 (1H, broad), 8.28 (1H, d, J=2.2 Hz)

Example 91

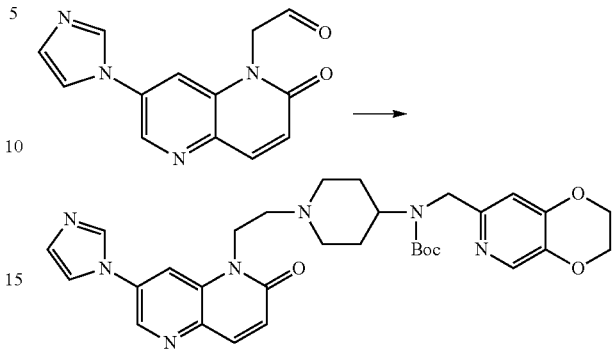

To a solution of 0.12 g of (7-(1H-imidazol-1-yl)-2-oxo-1,5-naphthyridin-1(2H)-yl)acetaldehyde in 1 mL of dichloromethane, a solution of 0.14 g of tert-butyl (2,3-dihydro(1,4)dioxino(2,3-c)pyridin-7-ylmethyl)(piperidin-4-yl)carbamate in 1.4 mL of dichloromethane, and 23 μL of acetic acid and 0.13 g of sodium triacetoxyborohydride were added, and the mixture was stirred at room temperature for 1 hour 40 minutes. The reaction mixture was charged with chloroform, and a saturated aqueous sodium hydrogen carbonate solution and adjusted to pH 8.6, the organic layer was separated and the aqueous layer was extracted with chloroform. The organic layer and the extract were combined, the resultant solution was washed with water and a saturated aqueous sodium chloride solution and dried over anhydrous magnesium sulfate, and the solvent was distilled off under reduced pressure. The resultant residue was purified by basic silica gel column chromatography using gradient elution with chloroform:methanol=19:1 to 93:7 to obtain 0.12 g of tert-butyl (2,3-dihydro(1,4)dioxino(2,3-c)pyridin-7-ylmethyl)(1-(2-(7-(1H-imidazol-1-yl)-2-oxo-1,5-naphthyridin-1(2H)-yl)ethyl)piperidin-4-yl)carbamate as a light yellow solid.

$^1$H-NMR (CDCl$_3$) δ: 1.32-1.72 (13H, m), 2.10-2.27 (2H, m), 2.60-2.69 (2H, m), 2.94-3.03 (2H, m), 4.05-4.15 (1H, m), 4.24-4.40 (8H, m), 6.72 (1H, s), 6.93 (1H, d, J=9.8 Hz), 7.32 (1H, s), 7.39 (1H, s), 7.75 (1H, s), 7.93 (1H, d, J=9.8 Hz), 7.97 (1H, s), 8.04 (1H, s), 8.65 (1H, d, J=1.9 Hz)

Example 92

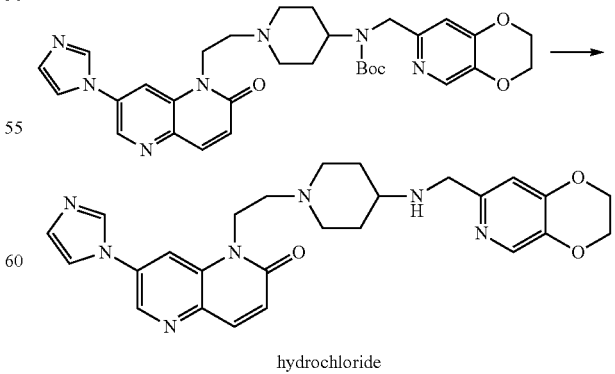

By the same technique as in Example 4, 1-(2-(4-(((2,3-dihydro(1,4)dioxino(2,3-c)pyridin-7-yl)methyl)amino)piperidin-1-yl)ethyl)-7-(1H-imidazol-1-yl)-1,5-naphthyridin-2 (1H)-one hydrochloride was obtained from tert-butyl (2,3-dihydro(1,4)dioxino(2,3-c)pyridin-7-ylmethyl)(1-(2-(7-(1H-imidazol-1-yl)-2-oxo-1,5-naphthyridin-1(2H)-yl)ethyl)piperidin-4-yl)carbamate.

$^1$H-NMR (D$_2$O) δ: 1.90-2.15 (2H, m), 2.52-2.61 (2H, m), 3.24-3.36 (2H, m), 3.66-3.80 (3H, m), 4.00-4.09 (2H, m), 4.40-4.50 (2H, m), 4.50-4.54 (2H, m), 4.57-4.88 (4H, m), 7.16 (1H, d, J=9.9 Hz), 7.45 (1H, s), 7.77 (1H, t, J=2.0 Hz), 8.09 (1H, t, J=1.6 Hz), 8.19 (1H, d, J=9.9 Hz), 8.36 (1H, s), 8.44 (1H, d, J=1.6 Hz), 8.93 (1H, d, J=2.0 Hz), 9.46 (1H, t, J=1.4 Hz)

Example 93

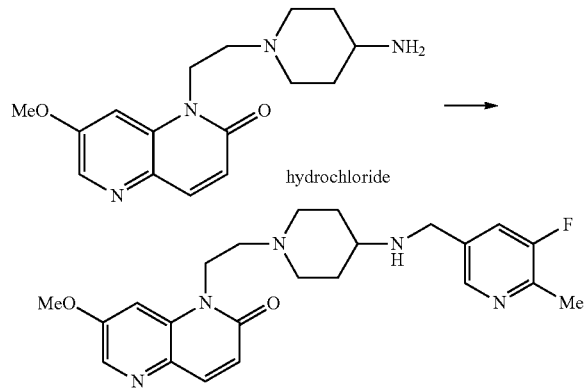

By the same technique as in Example 78, 1-(2-(4-(((5-fluoro-6-methylpyridin-3-yl)methyl)amino)piperidin-1-yl)ethyl)-7-methoxy-1,5-naphthyridin-2(1H)-one was obtained from 1-(2-(4-aminopiperidin-1-yl)ethyl)-7-methoxy-1,5-naphthyridin-2(1H)-one hydrochloride and 5-fluoro-6-methylnicotinaldehyde.

$^1$H-NMR (CDCl$_3$) δ: 1.35-1.47 (2H, m), 1.86-1.95 (2H, m), 2.14-2.24 (2H, m), 2.47-2.56 (1H, m), 2.51 (3H, d, J=2.9 Hz), 2.62-2.68 (2H, m), 2.94-3.02 (2H, m), 3.82 (2H, s), 3.98 (3H, s), 4.33-4.40 (2H, m), 6.74 (1H, d, J=9.8 Hz), 7.21 (1H, d, J=2.3 Hz), 7.36 (1H, dd, J=9.9, 1.4 Hz), 7.84 (1H, d, J=9.8 Hz), 8.23 (1H, s), 8.28 (1H, d, J=2.3 Hz)

Example 94

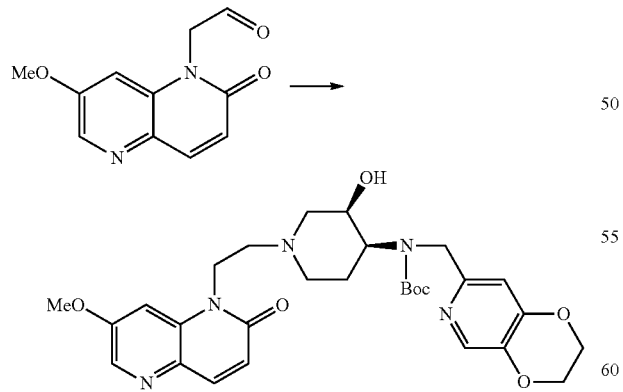

By the same technique as in Example 1, tert-butyl (2,3-dihydro(1,4)dioxino(2,3-c)pyridin-7-ylmethyl)((3R,4R)-3-hydroxy-1-(2-(7-methoxy-2-oxo-1,5-naphthyridin-1(2H)-yl)ethyl)piperidin-4-yl)carbamate was obtained from tert-butyl (2,3-dihydro(1,4)dioxino(2,3-c)pyridin-7-ylmethyl)((3R,4R)-3-hydroxypiperidin-4-yl)carbamate and (7-methoxy-2-oxo-1,5-naphthyridin-1(2H)-yl)acetaldehyde.

$^1$H-NMR (CDCl$_3$) δ: 1.22-1.42 (9H, m), 1.55-1.85 (3H, m), 2.18-2.36 (2H, m), 2.67-2.79 (2H, m), 2.98-3.07 (1H, m), 3.26-3.36 (1H, m), 3.62-3.73 (1H, m), 3.94 (3H, s), 4.00-4.52 (8H, m), 6.70-6.84 (2H, m), 7.13-7.17 (1H, m), 7.81-8.05 (2H, m), 8.24-8.32 (1H, m)

Example 95

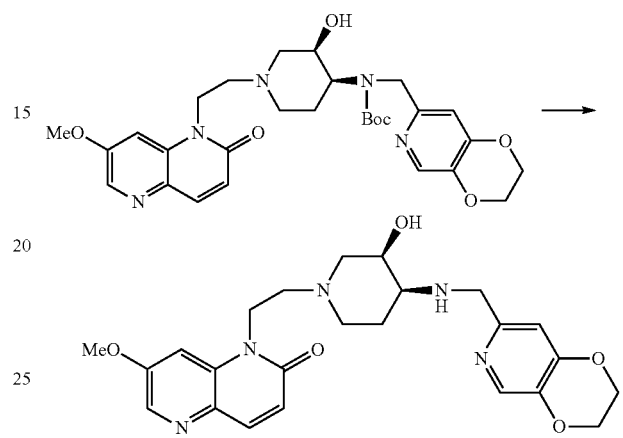

To a solution of 75 mg of tert-butyl (2,3-dihydro(1,4)dioxino(2,3-c)pyridin-7-ylmethyl)((3R,4R)-3-hydroxy-1-(2-(7-methoxy-2-oxo-1,5-naphthyridin-1(2H)-yl)ethyl)piperidin-4-yl)carbamate in 3 mL of ethanol, 3.0 mL of a hydrogen chloride/ethanol solution was added at room temperature. The mixture was stirred at the same temperature for 1 hour, and the solvent was distilled off under reduced pressure. Diethyl ether was added to the resultant residue, and the solid was filtered off. To the solid, chloroform and water were added, and the aqueous layer was separated. The aqueous layer was charged with chloroform and adjusted to pH 12 with a 1 mol/L aqueous sodium hydroxide solution. The organic layer was separated, washed with a saturated aqueous sodium chloride solution and dried over anhydrous magnesium sulfate, and the solvent was distilled off under reduced pressure to obtain 45 mg of 1-(2-((3R,4R)-4-((2,3-dihydro(1,4)dioxino(2,3-c)pyridin-7-ylmethyl)amino)-3-hydroxypiperidin-1-yl)ethyl)-7-methoxy-1,5-naphthyridin-2(1H)-one.

$^1$H-NMR (CDCl$_3$) δ: 1.35-1.47 (1H, m), 1.92-2.02 (1H, m), 2.07-2.23 (2H, m), 2.33-2.42 (1H, m), 2.65-2.73 (2H, m), 2.91-2.99 (1H, m), 3.14-3.22 (1H, m), 3.44-3.52 (1H, m), 3.72-3.84 (1H, m), 3.92-4.01 (1H, m), 3.97 (3H, s), 4.25-4.42 (6H, m), 6.73 (1H, d, J=9.8 Hz), 6.76 (1H, s), 7.18 (1H, d, J=2.4 Hz), 7.84 (1H, d, J=9.8 Hz), 8.09 (1H, s), 8.27 (1H, d, J=2.4 Hz)

Example 96

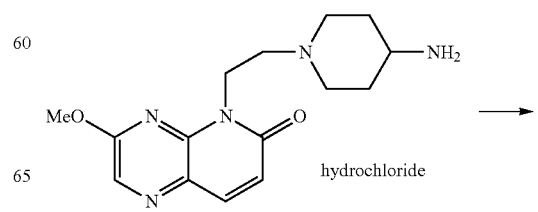

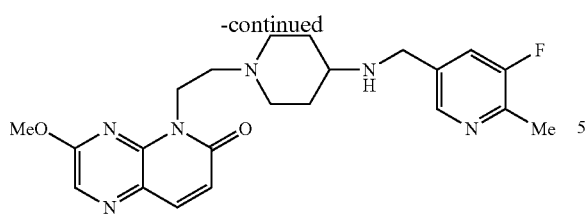

By the same technique as in Example 78, 5-(2-(4-(((5-fluoro-6-methylpyridin-3-yl)methyl)amino)piperidin-1-yl)ethyl)-3-methoxypyrido(2,3-b)pyrazin-6(5H)-one was obtained from 5-(2-(4-aminopiperidin-1-yl)ethyl)-3-methoxypyrido(2,3-b)pyrazin-6(5H)-one hydrochloride and 5-fluoro-6-methylnicotinaldehyde.

¹H-NMR (CDCl₃) δ: 1.31-1.43 (2H, m), 1.83-1.92 (2H, m), 2.12-2.22 (2H, m), 2.44-2.55 (1H, m), 2.50 (3H, d, J=2.7 Hz), 2.67-2.74 (2H, m), 2.99-3.08 (2H, m), 3.81 (2H, s), 4.06 (3H, s), 4.55-4.62 (2H, m), 6.76 (1H, d, J=9.8 Hz), 7.36 (1H, d, J=9.8 Hz), 7.84 (1H, d, J=9.8 Hz), 8.11 (1H, s), 8.22 (1H, s)

Example 97

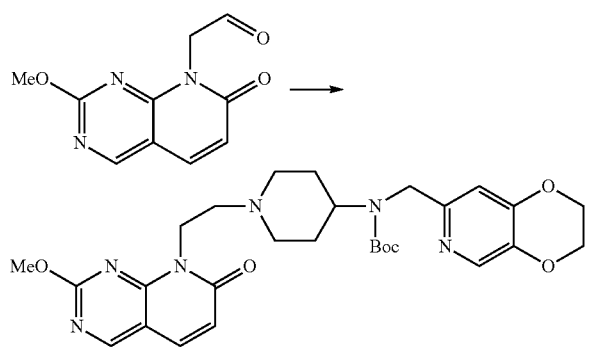

To a solution of 0.33 g of (2-methoxy-7-oxopyrido(2,3-d)pyrimidin-8(7H)-yl)acetaldehyde in 15 mL of dichloromethane, a solution of 0.53 g of tert-butyl (2,3-dihydro(1,4)dioxino(2,3-c)pyridin-7-ylmethyl)(piperidin-4-yl)carbamate in 5.3 mL of dichloromethane, and 87 μL of acetic acid were added, and the mixture was stirred at room temperature for 1 hour 30 minutes. To the reaction mixture, 0.40 g of sodium triacetoxyborohydride was added, and the mixture was stirred for 2 hours 30 minutes. After leaving overnight, the mixture was stirred at room temperature for 4 hours. Chloroform and a saturated aqueous sodium hydrogen carbonate solution were added to the reaction mixture, the organic layer was separated, and the aqueous layer was extracted with chloroform. The organic layer and the extract were combined, the resultant solution was washed with a saturated aqueous sodium chloride solution and dried over anhydrous magnesium sulfate, and the solvent was distilled off under reduced pressure. The resultant residue was purified by silica gel column chromatography using gradient elution with chloroform:methanol=50:1 to 10:1 to obtain 0.55 g of tert-butyl (2,3-dihydro(1,4)dioxino(2,3-c)pyridin-7-ylmethyl)(1-(2-(2-methoxy-7-oxopyrido(2,3-d)pyrimidin-8(7H)-yl)ethyl)piperidin-4-yl)carbamate as a light yellow foam.

¹H-NMR (CDCl₃) δ: 1.25-1.69 (13H), 2.01-2.23 (2H, m), 2.61-2.69 (2H, m), 3.02-3.11 (2H, m), 3.63-3.84 (1H, m), 4.06 (3H, s), 4.22-4.43 (6H, m), 4.45-4.53 (2H, m), 6.57 (1H, d, J=9.4 Hz), 6.71 (1H, s), 7.60 (1H, d, J=9.4 Hz), 8.04 (1H, s), 8.64 (1H, s)

Example 98

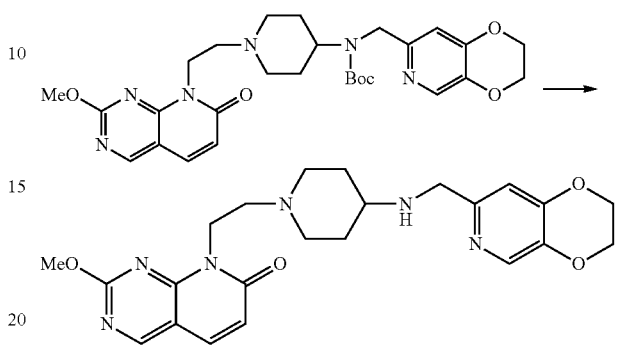

To a solution of 0.54 g of tert-butyl (2,3-dihydro(1,4)dioxino(2,3-c)pyridin-7-ylmethyl)(1-(2-(2-methoxy-7-oxopyrido(2,3-d)pyrimidin-8(7H)-yl)ethyl)piperidin-4-yl)carbamate in 15 mL of dichloromethane, 5 mL of trifluoroacetic acid was added, and the mixture was stirred at room temperature for 2 hours. A 2 mol/L aqueous sodium hydroxide solution was added under cooling with ice to adjust pH at 13, dichloromethane was added thereto, the organic layer was separated, and the aqueous layer was extracted with dichloromethane. The organic layer and the extract were combined, the resultant solution was washed with a saturated aqueous sodium chloride solution and dried over anhydrous magnesium sulfate, and the solvent was distilled off under reduced pressure. The resultant residue was purified by basic silica gel column chromatography using an eluent of chloroform:methanol=10:1 to obtain 0.34 g of 8-(2-(4-((2,3-dihydro(1,4)dioxino(2,3-c)pyridin-7-ylmethyl)amino)piperidin-1-yl)ethyl)-2-methoxypyrido(2,3-d)pyrimidin-7(8H)-one as a yellow oily substance.

¹H-NMR (CDCl₃) δ: 1.31-1.43 (2H, m), 1.81-1.90 (2H, m), 2.08-2.19 (2H, m), 2.41-2.55 (1H, m), 2.64-2.72 (2H, m), 2.97-3.06 (2H, m), 3.77 (2H, s), 4.07 (3H, s), 4.23-4.34 (4H, m), 4.50-4.58 (2H, m), 6.56 (1H, d, J=9.5 Hz), 6.80 (1H, s), 7.59 (1H, d, J=9.5 Hz), 8.08 (1H, s), 8.63 (1H, s)

Example 99

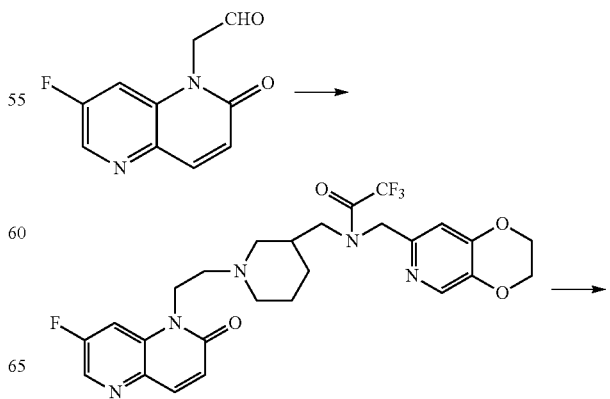

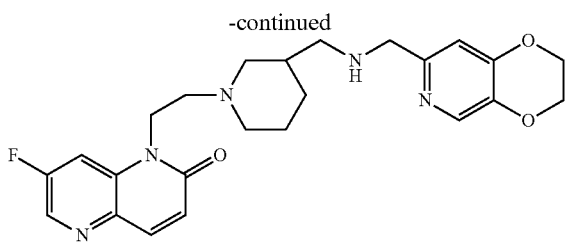

To a solution of 0.15 g of N-(2,3-dihydro(1,4)dioxino(2,3-c)pyridin-7-ylmethyl)-2,2,2-trifluoro-N-(piperidin-3-ylmethyl)acetamide in 2 mL of dichloromethane, 85 mg of (7-fluoro-2-oxo-1,5-naphthyridin-1(2H)-yl)acetaldehyde and 24 µL of acetic acid were added, subsequently, 0.13 g of sodium triacetoxyborohydride was added, and the mixture was stirred at room temperature for 2 hours. To the reaction mixture, chloroform was added, and a saturated aqueous sodium hydrogen carbonate solution was added thereto under cooling with ice and adjusted to pH 8.0. The organic layer was separated and the aqueous layer was extracted with chloroform. The organic layer and the extract were combined, the resultant solution was washed with water and a saturated aqueous sodium chloride solution and dried over anhydrous magnesium sulfate, and the solvent was distilled off under reduced pressure to obtain 0.21 g of N-(2,3-dihydro(1,4)dioxino(2,3-c)pyridin-7-ylmethyl)-2,2,2-trifluoro-N-(1-(2-(7-fluoro-2-oxo-1,5-naphthyridin-1(2H)-yl)ethyl)piperidin-3-ylmethyl)acetamide as a yellow solid. To 0.21 g of N-(2,3-dihydro(1,4)dioxino(2,3-c)pyridin-7-ylmethyl)-2,2,2-trifluoro-N-(1-(2-(7-fluoro-2-oxo-1,5-naphthyridin-1(2H)-yl)ethyl)piperidin-3-ylmethyl)acetamide, 3 mL of methanol and 0.7 mL of water were added, and thereto was added 62 mg of potassium carbonate. The mixture was stirred at room temperature for 1 hour 15 minutes, then stirred at 40 to 50° C. for 1 hour, and stirred at 50 to 60° C. for 1 hour 30 minutes. The solvent was distilled off under reduced pressure, chloroform and water were added to the resultant residue, the organic layer was separated, and the aqueous layer was extracted with chloroform. The organic layer and the extract were combined, the resultant solution was washed with a saturated aqueous sodium chloride solution and dried over anhydrous magnesium sulfate, and the solvent was distilled off under reduced pressure. The resultant residue was purified by basic silica gel column chromatography using gradient elution with hexane:ethyl acetate=92:8 to 88:12 to obtain 0.18 g of 1-(2-(3-(((2,3-dihydro(1,4)dioxino(2,3-c)pyridin-7-ylmethyl)amino)methyl)piperidin-1-yl)ethyl)-7-fluoro-1,5-naphthyridin-2(1H)-one as a light yellow oily substance.

$^1$H-NMR (CDCl$_3$) δ: 0.90-1.10 (1H, m), 1.45-1.92 (5H, m), 2.05-2.14 (1H, m), 2.46-2.52 (2H, m), 2.60-2.66 (2H, m), 2.85-2.92 (1H, m), 2.98-3.05 (1H, m), 3.74 (2H, s), 4.25-4.35 (6H, m), 6.81 (1H, s), 6.86 (1H, d, J=9.8 Hz), 7.60 (1H, dd, J=10.4, 2.2 Hz), 7.88 (1H, d, J=9.8 Hz), 8.10 (1H, s), 8.41 (1H, d, J=2.4 Hz)

Example 100

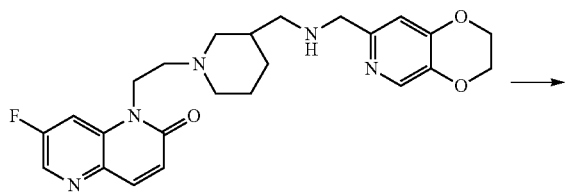

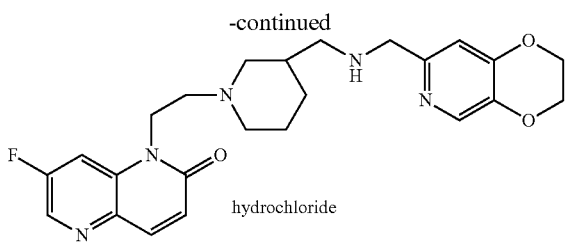

To a solution of 0.14 g of 1-(2-(3-(((2,3-dihydro(1,4)dioxino(2,3-c)pyridin-7-ylmethyl)amino)methyl)piperidin-1-yl)ethyl)-7-fluoro-1,5-naphthyridin-2(1H)-one in 4 mL of ethyl acetate, 1 mL of a 4 mol/L hydrogen chloride/ethyl acetate solution was added, and the mixture was stirred at room temperature for 20 minutes. The solvent was distilled off under reduced pressure, diethyl ether was added to the resultant residue, and the solid was filtered off to obtain 0.10 g of 1-(2-(3-(((2,3-dihydro(1,4)dioxino(2,3-c)pyridin-7-ylmethyl)amino)methyl)piperidin-1-yl)ethyl)-7-fluoro-1,5-naphthyridin-2(1H)-one hydrochloride as a light yellow solid.

$^1$H-NMR (D$_2$O) δ: 1.31-1.48 (1H, m), 1.76-1.90 (1H, m), 2.00-2.14 (2H, m), 2.32-2.44 (1H, m), 2.86-3.26 (4H, m), 3.56-4.00 (4H, m), 4.38-4.46 (4H, m), 4.52-4.56 (2H, m), 4.74-4.84 (2H, m), 6.99 (1H, d, J=10.4 Hz), 7.33 (1H, s), 7.94 (1H, dd, J=10.4, 2.1 Hz), 8.10 (1H, d, J=10.2 Hz), 8.29 (1H, s), 8.56 (1H, d, J=2.1 Hz)

Example 101

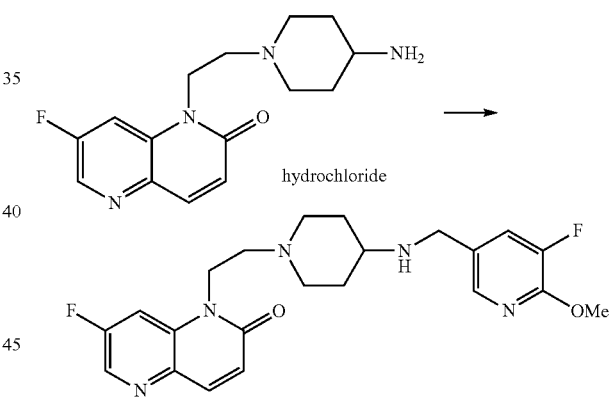

To a suspension of 0.10 g of 1-(2-(4-(aminopiperidin-1-yl)ethyl)-7-fluoro-1,5-naphthyridin-2(1H)-one hydrochloride in 2 mL of methanol, 0.15 g of a 28% sodium methoxide/methanol solution, 39 mg of (5-fluoro-6-methoxy)nicotinaldehyde and 14 µL of acetic acid were added. Thereto was added 31 mg of sodium cyanoborohydride, and the mixture was stirred at room temperature for 3 hours. After leaving for overnight, the mixture was stirred at room temperature for 35 minutes, 31 mg of sodium cyanoborohydride was added, and the mixture was stirred at the same temperature for 1 hour 40 minutes. To the reaction mixture, chloroform and a saturated aqueous sodium hydrogen carbonate solution were added, the organic layer was separated, washed with water and a saturated aqueous sodium chloride solution, and dried over anhydrous magnesium sulfate, and the solvent was distilled off under reduced pressure. The resultant residue was purified by basic silica gel column chromatography using gradient elution with chloroform:methanol=95:5 to 92:8 to obtain 43 mg of 7-fluoro-1-(2-(4-(((5-fluoro-6-methoxypyridin-3-yl)methyl)amino)piperidin-1-yl)ethyl)-1,5-naphthyridin-2(1H)-one as a white solid.

$^1$H-NMR (CDCl$_3$) δ: 1.32-1.46 (2H, m), 1.85-1.94 (2H, m), 2.13-2.22 (2H, m), 2.45-2.55 (1H, m), 2.62-2.68 (2H, m), 2.91-2.99 (2H, m), 3.75 (2H, s), 4.01 (3H, m), 4.28-4.34 (2H, m), 6.86 (1H, d, J=9.8 Hz), 7.38 (1H, dd, J=10.9, 2.0 Hz), 7.50-7.55 (1H, m), 7.83 (1H, d, J=2.0 Hz), 7.88 (1H, d, J=9.8 Hz), 8.42 (1H, d, 2.4 Hz)

Example 102

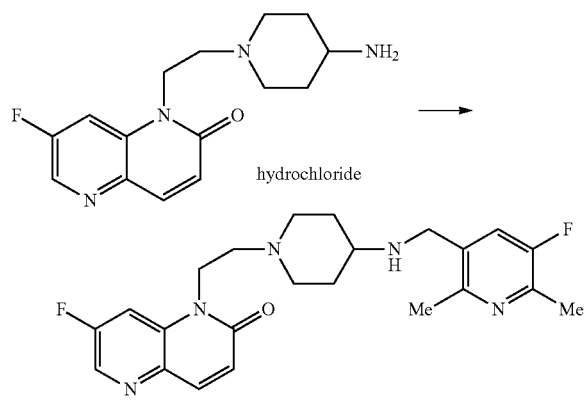

By the same technique as in Example 78, 7-fluoro-1-(2-(4-(((5-fluoro-2,6-dimethylpyridin-3-yl)methyl)amino)piperidin-1-yl)ethyl)-1,5-naphthyridin-2(1H)-one was obtained from 1-(2-(4-aminopiperidin-1-yl)ethyl)-7-fluoro-1,5-naphthyridin-2(1H)-one hydrochloride and 5-fluoro-2,6-dimethylnicotinaldehyde.

$^1$H-NMR (CDCl$_3$) δ: 1.36-1.48 (2H, m), 1.87-1.97 (2H, m), 2.16-2.26 (2H, m), 2.42-2.59 (7H, m), 2.62-2.70 (2H, m), 2.92-3.01 (2H, m), 3.74 (2H, s), 4.29-4.37 (2H, m), 6.86 (1H, d, J=9.5 Hz), 7.34 (1H, d, J=10.0 Hz), 7.54 (1H, dd, J=10.2, 2.0 Hz), 7.89 (1H, d, J=10.0 Hz), 8.42 (1H, d, J=2.2 Hz)

Example 103

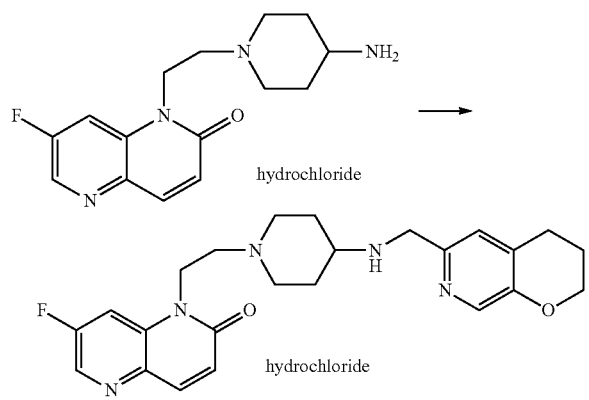

To a suspension of 0.10 g of 1-(2-(4-aminopiperidin-1-yl)ethyl)-7-fluoro-1,5-naphthyridin-2(1H)-one hydrochloride and 61 mg of 3,4-dihydro-2H-pyrano(2,3-c)pyridine-6-carbaldehyde in 2.5 mL of methanol, 62 mg of sodium cyanoborohydride, 0.14 g of a 28% sodium methoxide/methanol solution and 86 μL of acetic acid were added, and the mixture was stirred at room temperature for 1 hour 50 minutes. Thereto were added ethyl acetate, a saturated aqueous sodium hydrogen carbonate solution, and a 2 mol/L aqueous sodium hydroxide solution, the organic layer was separated, and the aqueous layer was extracted with ethyl acetate twice. The organic layer and the extract were combined, the resultant solution was washed with a saturated aqueous sodium chloride solution and dried over anhydrous magnesium sulfate, and the solvent was distilled off under reduced pressure. The resultant residue was purified by basic silica gel column chromatography using an eluent of chloroform:methanol=10:1. The resultant residue was dissolved in 1 mL of methanol and 1 mL of and ethyl acetate, and thereto was added 0.5 mL of a 4 mol/L hydrogen chloride/ethyl acetate solution at room temperature. The solvent was distilled off under reduced pressure, diethyl ether was added the resultant residue, and the solid was filtered off to obtain 0.11 g of 1-(2-(4-(((3,4-dihydro-2H-pyrano(2,3-c)pyridin-6-ylmethyl)amino)piperidin-1-yl)ethyl)-7-fluoro-1,5-naphthyridin-2(1H)-one hydrochloride as a light yellow solid.

$^1$H-NMR (D$_2$O) δ: 2.00-2.12 (4H, m), 2.50-2.59 (2H, m), 2.93 (2H, t, J=6.3 Hz), 3.22-3.32 (2H, m), 3.60-3.75 (1H, m), 3.63 (2H, t, J=5.9 Hz), 3.95-4.06 (2H, m), 4.33-4.36 (2H, m), 4.44 (2H, s), 4.72-4.92 (2H, m), 6.99 (1H, d, J=9.9 Hz), 7.52 (1H, s), 7.95 (1H, dd, J=10.3, 2.1 Hz), 8.10 (1H, d, J=9.9 Hz), 8.20 (1H, s), 8.57 (1H, d, J=2.1 Hz)

Example 104

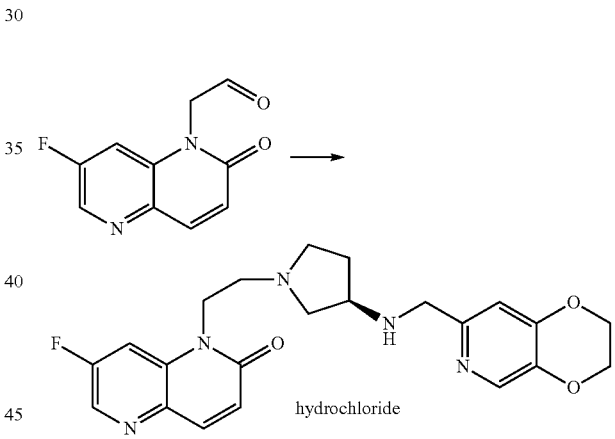

To a solution of 62 mg of (3S)—N-(2,3-dihydro(1,4)dioxino(2,3-c)pyridin-7-ylmethyl)pyrrolidin-3-amine hydrochloride in 3 mL of methanol, 0.10 g of a 28% sodium methoxide/methanol solution, 37 mg of (7-fluoro-2-oxo-1,5-naphthyridin-1(2H)-yl)acetaldehyde, 60 μL of acetic acid, 0.12 g of molecular sieves 3 A and 11 mg of sodium cyanoborohydride were added at room temperature, and the mixture was stirred at the same temperature for 1 hour 10 minutes. To the reaction mixture, a saturated aqueous sodium hydrogen carbonate solution and ethyl acetate were added, the organic layer was separated, and the aqueous layer was extracted with ethyl acetate. The organic layer and the extract were combined, the resultant solution was washed with a saturated aqueous sodium chloride solution and dried over anhydrous magnesium sulfate, and the solvent was distilled off under reduced pressure. The resultant residue was purified by basic silica gel column chromatography using an eluent of chloroform:methanol=30:1, thereto were added ethyl acetate and a 4 mol/L hydrogen chloride/ethyl acetate solution, and the solid was filtered off to obtain 33 mg of 1-(2-((3S)-3-((2, 3-dihydro(1,4)dioxino(2,3-c)pyridin-7-ylmethyl)amino)pyrrolidin-1-yl)ethyl)-7-fluoro-1,5-naphthyridin-2(1H)-one hydrochloride as a yellow solid.

$^1$H-NMR (D$_2$O) δ: 2.16-2.34 (1H, m), 2.55-2.70 (1H, m), 3.35-3.95 (6H, m), 4.16-4.26 (1H, m), 4.45-4.85 (8H, m), 6.98 (1H, d, J=10.0 Hz), 7.47 (1H, s), 7.94-7.98 (1H, m), 8.08 (1H, d, J=10.0 Hz), 8.36 (1H, s), 8.56 (1H, s)

Example 105

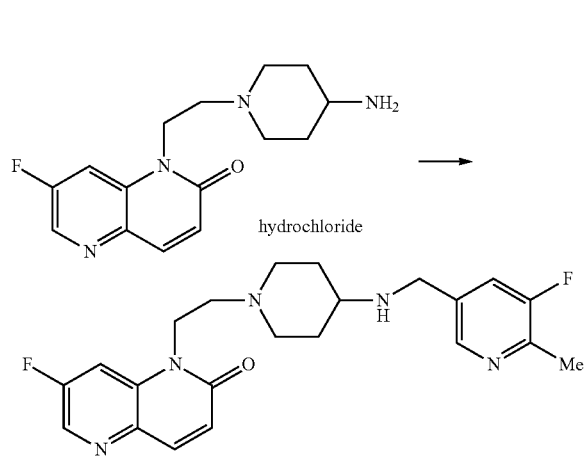

By the same technique as in Example 78, 7-fluoro-1-(2-(4-(((5-fluoro-6-methylpyridin-3-yl)methyl)amino)piperidin-1-yl)ethyl)-1,5-naphthyridin-2(1H)-one was obtained from 1-(2-(4-aminopiperidin-1-yl)ethyl)-7-fluoro-1,5-naphthyridin-2(1H)-one hydrochloride and 5-fluoro-6-methylnicotinaldehyde.

$^1$H-NMR (CDCl$_3$) δ: 1.33-1.45 (2H, m), 1.85-1.94 (2H, m), 2.14-2.23 (2H, m), 2.46-2.55 (1H, m), 2.51 (3H, d, J=2.7 Hz), 2.61-2.68 (2H, m), 2.91-3.00 (2H, m), 3.81 (2H, s), 4.28-4.35 (2H, m), 6.86 (1H, d, J=9.8 Hz), 7.36 (1H, dd, J=10.1, 1.6 Hz), 7.53 (1H, dd, J=10.2, 2.3 Hz), 7.88 (1H, d, J=9.8 Hz), 8.23 (1H, s), 8.42 (1H, d, J=2.3 Hz)

Example 106

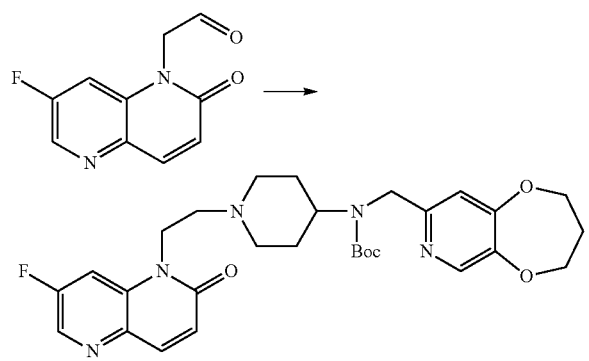

By the same technique as in Example 1, tert-butyl (3,4-dihydro-2H-(1,4)dioxepino(2,3-c)pyridin-8-ylmethyl)(1-(2-(7-fluoro-2-oxo-1,5-naphthyridin-1(2H)-yl)ethyl)piperidin-4-yl)carbamate was obtained from tert-butyl (3,4-dihydro-2H-(1,4)dioxepino(2,3-c)pyridin-8-ylmethyl)(piperidin-4-yl)carbamate and (7-fluoro-2-oxo-1,5-naphthyridin-1(2H)-yl)acetaldehyde.

$^1$H-NMR (CDCl$_3$) δ: 1.28-1.74 (13H, m), 2.07-2.30 (4H, m), 2.57-2.65 (2H, m), 2.94-3.03 (2H, m), 4.06-4.18 (1H, m), 4.20-4.40 (8H, m), 6.77 (1H, s), 6.85 (1H, d, J=9.8 Hz), 7.47 (1H, dd, J=10.4, 2.3 Hz), 7.87 (1H, d, J=9.8 Hz), 8.14 (1H, s), 8.41 (1H, d, J=2.3 Hz)

Example 107

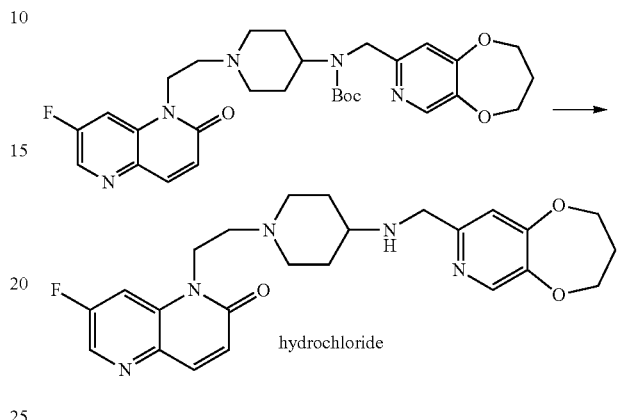

By the same technique as in Example 2, 1-(2-(4-((3,4-dihydro-2H-(1,4)dioxepino(2,3-c)pyridin-8-ylmethyl)amino)piperidin-1-yl)ethyl)-7-fluoro-1,5-naphthyridin-2(1H)-one hydrochloride was obtained from tert-butyl (3,4-dihydro-2H-(1,4)dioxepino(2,3-c)pyridin-8-ylmethyl)(1-(2-(7-fluoro-2-oxo-1,5-naphthyridin-1(2H)-yl)ethyl)piperidin-4-yl)carbamate.

$^1$H-NMR (D$_2$O) δ: 2.00-2.15 (2H, m), 2.37 (2H, quint, J=5.9 Hz), 2.51-2.60 (2H, m), 3.20-3.35 (2H, m), 3.60-3.78 (3H, m), 3.97-4.07 (2H, m), 4.42 (2H, t, J=5.9 Hz), 4.48 (2H, s), 4.60 (2H, t, J=5.9 Hz), 4.71-4.87 (2H, m), 6.99 (1H, d, J=10.0 Hz), 7.37 (1H, s), 7.96 (1H, dd, J=10.1, 2.1 Hz), 8.10 (1H, d, J=10.0 Hz), 8.37 (1H, s), 8.57 (1H, d, J=2.1 Hz)

Example 108

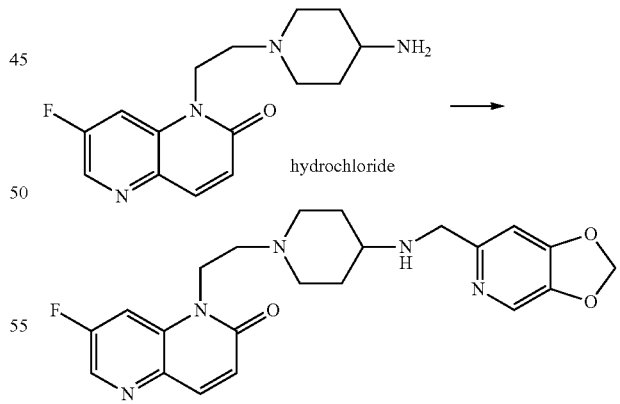

By the same technique as in Example 30, 1-(2-(4-(((1,3)dioxolo(4,5-c)pyridin-6-ylmethyl)amino)piperidin-1-yl)ethyl)-7-fluoro-1,5-naphthyridin-2(1H)-one was obtained from 1-(2-(4-aminopiperidin-1-yl)ethyl)-7-fluoro-1,5-naphthyridin-2(1H)-one hydrochloride and (1,3)dioxolo(4,5-c)pyridine-6-carbaldehyde.

$^1$H-NMR (CDCl$_3$) δ: 1.36-1.50 (2H, m), 1.80-1.97 (2H, m), 2.13-2.24 (2H, m), 2.47-2.57 (1H, m), 2.61-2.68 (2H, m), 2.91-3.00 (2H, m), 3.83 (2H, s), 4.28-4.36 (2H, m), 6.03 (2H, s), 6.86 (1H, d, J=9.8 Hz), 6.88 (1H, s), 7.56 (1H, dd, J=10.2, 2.1 Hz), 7.88 (1H, dd, J=9.8, 0.5 Hz), 8.00 (1H, s), 8.41 (1H, d, J=2.1 Hz)

Example 109

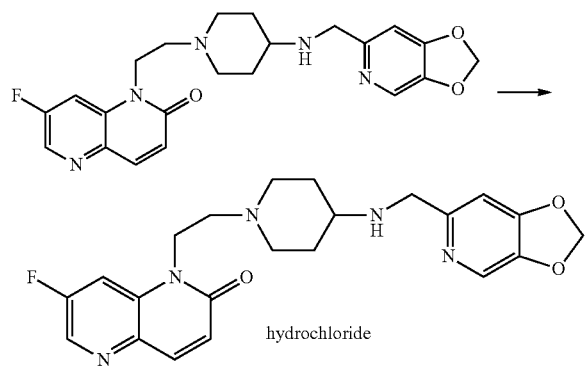

By the same technique as in Example 8, 1-(2-(4-(((1,3)dioxolo(4,5-c)pyridin-6-ylmethyl)amino)piperidin-1-yl)ethyl)-7-fluoro-1,5-naphthyridin-2(1H)-one hydrochloride was obtained from 1-(2-(4-((((1,3)dioxolo(4,5-c)pyridin-6-ylmethyl)amino)piperidin-1-yl)ethyl)-7-fluoro-1,5-naphthyridin-2(1H)-one.

$^1$H-NMR (D$_2$O) δ: 2.00-2.14 (2H, m), 2.50-2.60 (2H, m), 3.20-3.35 (2H, m), 3.60-3.78 (3H, m), 3.96-4.07 (2H, m), 4.48 (2H, s), 4.70-4.88 (2H, m), 6.34 (2H, s), 7.00 (1H, d, J=9.9 Hz), 7.32 (1H, s), 7.93-7.99 (1H, m), 8.10 (1H, d, J=9.9 Hz), 8.16 (1H, s), 8.57 (1H, d, J=2.2 Hz)

Example 110

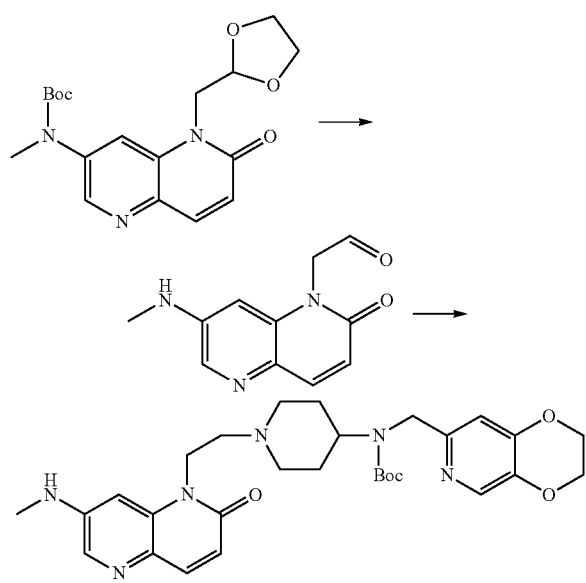

To 0.12 g of tert-butyl ((5-(1,3-dioxolan-2-yl)methyl)-6-oxo-5,6-dihydro-1,5-naphthyridin-3-yl)(methyl)carbamate, 2 mL of an 80% aqueous trifluoroacetic acid solution was added, and the mixture was stirred at room temperature for 2 hours. After leaving overnight, 2 mL of an 80% aqueous trifluoroacetic acid solution was added thereto, and the mixture was stirred at room temperature for 1 hour 30 minutes, and stirred at 40 to 50° C. for 35 minutes. The reaction mixture was charged with a 20% aqueous sodium hydroxide solution and chloroform and adjusted to pH 6.3. The organic layer was separated, and the aqueous layer was extracted with chloroform. Further, while keeping the aqueous layer around neutral, the aqueous layer was extracted with a mixed solvent of chloroform:methanol (5:95). The organic layer and the extract were combined, the resultant solution was dried over anhydrous magnesium sulfate, and the solvent was distilled off under reduced pressure to obtain 76 mg of (7-(methylamino)-2-oxo-1,5-naphthyridin-1(2H)-yl)acetaldehyde as a yellow solid.

To 76 mg of (7-(methylamino)-2-oxo-1,5-naphthyridin-1(2H)-yl)acetaldehyde, a solution of 0.11 g of tert-butyl (2,3-dihydro(1,4)dioxino(2,3-c)pyridin-7-ylmethyl)(piperidin-4-yl)carbamate in 2.5 mL of dichloromethane and 19 μL of acetic acid were added, and the mixture was stirred at room temperature for 5 minutes. To the reaction mixture, 0.10 g of sodium triacetoxyborohydride was added, and the mixture was stirred at the same temperature for 2 hours 20 minutes. Thereto was added chloroform and the reaction mixture was adjusted to pH 8.3 with a saturated aqueous sodium hydrogen carbonate solution. The organic layer was separated, and the aqueous layer was extracted with chloroform. The organic layer and the extract were combined, the resultant solution was washed with water and a saturated aqueous sodium chloride solution and dried over anhydrous magnesium sulfate, and the solvent was distilled off under reduced pressure. The resultant residue was purified by basic silica gel column chromatography using an eluent of chloroform:methanol=19:1 to obtain 55 mg of tert-butyl (2,3-dihydro(1,4)dioxino(2,3-c)pyridin-7-ylmethyl)(1-(2-(7-(methylamino)-2-oxo-1,5-naphthyridin-1(2H)-yl)ethyl)piperidin-4-yl)carbamate as a light yellow oily substance.

$^1$H-NMR (CDCl$_3$) δ: 1.34-1.73 (13H, m), 2.10-2.26 (2H, m), 2.58-2.64 (2H, m), 2.96 (3H, d, J=5.1 Hz), 2.98-3.05 (2H, m), 4.03-4.17 (1H, m), 4.25-4.45 (8H, m), 6.57 (1H, d, J=9.8 Hz), 6.70-6.76 (2H, m), 7.74 (1H, d, J=9.8 Hz), 7.98 (1H, d, J=2.2 Hz), 8.05 (1H, s)

Example 111

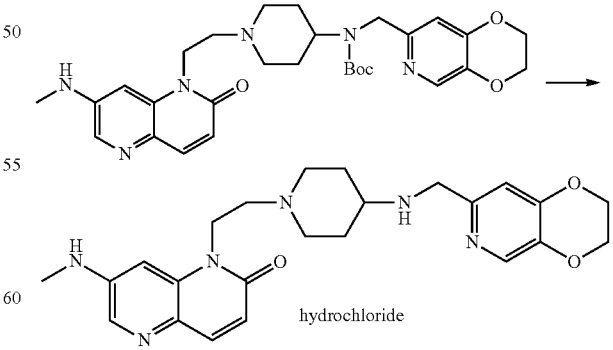

By the same technique as in Example 4, 1-(2-(4-((2,3-dihydro(1,4)dioxino(2,3-c)pyridin-7-ylmethyl)amino)piperidin-1-yl)ethyl)-7-(methylamino)-1,5-naphthyridin-2(1H)-one hydrochloride was obtained from tert-butyl (2,3- dihydro(1,4)dioxino(2,3-c)pyridin-7-ylmethyl)(1-(2-(7-(methylamino)-2-oxo-1,5-naphthyridin-1(2H)-yl)ethyl)piperidin-4-yl)carbamate.

$^1$H-NMR (D$_2$O) δ: 1.96-2.12 (2H, m), 2.48-2.57 (2H, m), 2.95 (3H, s), 3.20-3.32 (2H, m), 3.60-3.72 (3H, m), 3.95-4.04 (2H, m), 4.37-4.44 (4H, m), 4.47-4.52 (2H, m), 4.77-4.83 (2H, m), 6.75 (1H, d, J=9.8 Hz), 7.05-7.08 (1H, m), 7.23 (1H, s), 7.97 (1H, d, J=9.8 Hz), 8.16 (1H, d, J=2.2 Hz), 8.24 (1H, s)

Example 112

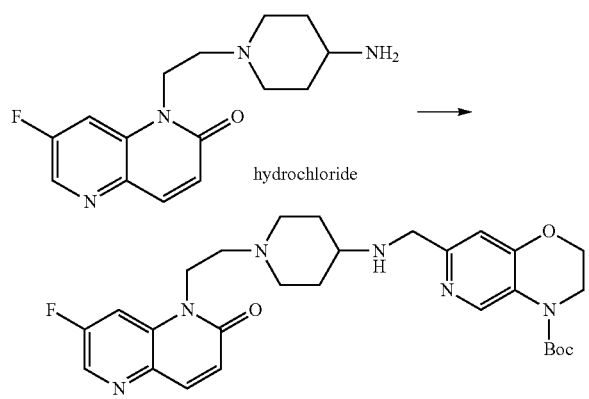

By the same technique as in Example 78, tert-butyl 7-(((1-(2-(7-fluoro-2-oxo-1,5-naphthyridin-1(2H)-yl)ethyl)piperidin-4-yl)amino)methyl)-2,3-dihydro-4H-pyrido(4,3-b)(1,4)oxazine-4-carboxylate was obtained from 1-(2-(4-aminopiperidin-1-yl)ethyl)-7-fluoro-1,5-naphthyridin-2(1H)-one hydrochloride and tert-butyl 7-formyl-2,3-dihydro-4H-pyrido(4,3-b)(1,4)oxazine-4-carboxylate.

$^1$H-NMR (CDCl$_3$) δ: 1.38-1.49 (2H, m), 1.59 (9H, s), 1.87-1.95 (2H, m), 2.13-2.23 (2H, m), 2.48-2.57 (1H, m), 2.61-2.66 (2H, m), 2.92-2.98 (2H, m), 3.81 (2H, s), 3.84-3.87 (2H, m), 4.28-4.34 (4H, m), 6.82 (1H, s), 6.86 (1H, d, J=9.9 Hz), 7.55 (1H, dd, J=10.5, 2.2 Hz), 7.88 (1H, d, J=9.9 Hz), 8.41 (1H, d, J=2.2 Hz), 8.79-8.87 (1H, m)

Example 113

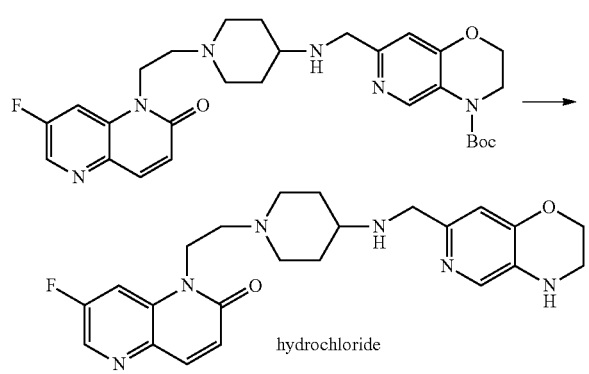

By the same technique as in Example 2, 1-(2-(4-((3,4-dihydro-2H-pyrido(4,3-b)(1,4)oxazin-7-ylmethyl)amino)piperidin-1-yl)ethyl)-7-fluoro-1,5-naphthyridin-2(1H)-one hydrochloride was obtained from tert-butyl 7-(((1-(2-(7-fluoro-2-oxo-1,5-naphthyridin-1(2H)-yl)ethyl)piperidin-4-yl)amino)methyl)-2,3-dihydro-4H-pyrido(4,3-b)(1,4)oxazine-4-carboxylate.

$^1$H-NMR (D$_2$O) δ: 2.00-2.12 (2H, m), 2.52-2.60 (2H, m), 3.23-3.36 (2H, m), 3.51 (2H, t, J=4.4 Hz), 3.64 (2H, t, J=6.0 Hz), 3.68-3.78 (1H, m), 3.98-4.06 (2H, m), 4.48-4.54 (4H, m), 4.66-4.92 (2H, m), 6.99 (1H, d, J=9.8 Hz), 7.30-7.36 (1H, m), 7.92-7.98 (1H, m), 8.01 (1H, s), 8.11 (1H, d, J=9.8 Hz), 8.57 (1H, s)

Example 114

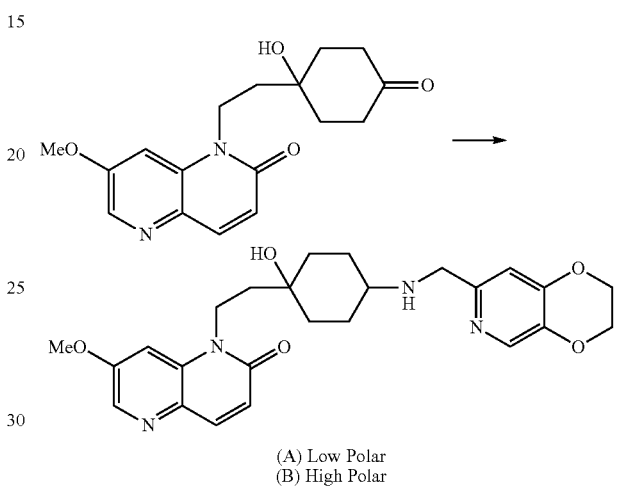

(A) Low Polar
(B) High Polar

To a solution of 40 mg of 1-(2-(1-hydroxy-4-oxocyclohexyl)ethyl)-7-methoxy-1,5-naphthyridin-2(1H)-one in 5 mL of dichloromethane, 25 mg of 1-(2,3-dihydro(1,4)dioxino(2,3-c)pyridin-7-yl)methanamine and 11 μL of acetic acid were added at room temperature, the mixture was stirred for 2 hours, then, 27 mg of sodium triacetoxyborohydride was added to the reaction mixture, and the mixture was stirred at room temperature for 1 hour. Thereto were added a saturated aqueous sodium hydrogen carbonate solution and chloroform, the organic layer was separated, and washed with a saturated aqueous sodium chloride solution and dried over anhydrous magnesium sulfate, and the solvent was distilled off under reduced pressure. The resultant residue was purified by basic silica gel column chromatography using an eluent of chloroform:methanol=30:1 to obtain 10 mg of (A)1-(2-(4-((2,3-dihydro(1,4)dioxino(2,3-c)pyridin-7-ylmethyl)amino)-1-hydroxycyclohexyl)ethyl)-7-methoxy-1,5-naphthyridin-2(1H)-one as a light yellow solid and 9 mg of (B) 1-(2-(4-((2,3-dihydro(1,4)dioxino(2,3-c)pyridin-7-ylmethyl)amino)-1-hydroxycyclohexyl)ethyl)-7-methoxy-1,5-naphthyridin-2(1H)-one as a light yellow solid.

(A) $^1$H-NMR (CDCl$_3$) δ: 1.35-1.55 (4H, m), 1.80-2.20 (6H, m), 2.65-2.75 (1H, m), 3.77 (2H, s), 3.97 (3H, s), 4.25-4.46 (6H, m), 6.75 (1H, d, J=9.6 Hz), 6.80 (1H, s), 7.32 (1H, d, J=2.4 Hz), 7.86 (1H, d, J=9.6 Hz), 8.10 (1H, s), 8.29 (1H, d, J=2.4 Hz)

(B) $^1$H-NMR (CDCl$_3$) δ: 1.40-1.60 (4H, m), 1.70-1.90 (6H, m), 2.48-2.58 (1H, m), 3.82 (2H, s), 3.96 (3H, s), 4.26-4.44 (6H, m), 6.74 (1H, d, J=9.6 Hz), 6.82 (1H, s), 7.38 (1H, d, J=2.4 Hz), 7.85 (1H, d, J=9.6 Hz), 8.11 (1H, s), 8.28 (1H, d, J=2.4 Hz)

Example 115

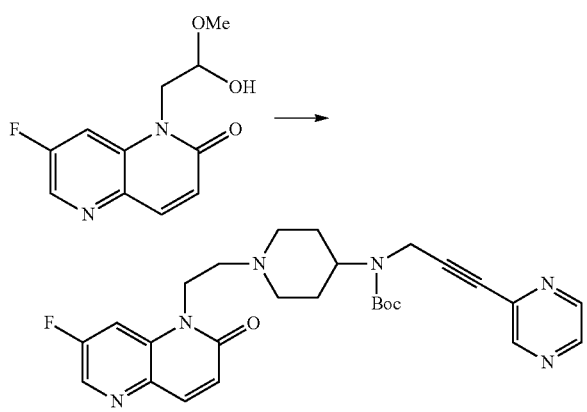

By the same technique as in Example 3, tert-butyl 1-(2-(7-fluoro-2-oxo-1,5-naphthyridin-1(2H)-yl)ethyl)piperidin-4-yl)(3-(pyrazin-2-yl)-2-propyn-1-yl)carbamate was obtained from 7-fluoro-1-(2-hydroxy-2-methoxyethyl)-1,5-naphthyridin-2(1H)-one and tert-butyl (piperidin-4-yl)(3-(pyrazin-2-yl)-2-propyn-1-yl)carbamate.

$^1$H-NMR (CDCl$_3$) δ: 1.50 (9H, s), 1.78-1.88 (4H, m), 2.16-2.28 (2H, m), 2.66 (2H, t, J=7.1 Hz), 3.03-3.12 (2H, m), 4.04-4.25 (3H, m), 4.32 (2H, t, J=7.1 Hz), 6.86 (1H, d, J=9.8 Hz), 7.48-7.54 (1H, m), 7.88 (1H, d, J=9.8 Hz), 8.41 (1H, d, J=2.4 Hz), 8.48 (1H, d, J=2.7 Hz), 8.51-8.54 (1H, m), 8.62 (1H, d, J=1.2 Hz)

Example 116

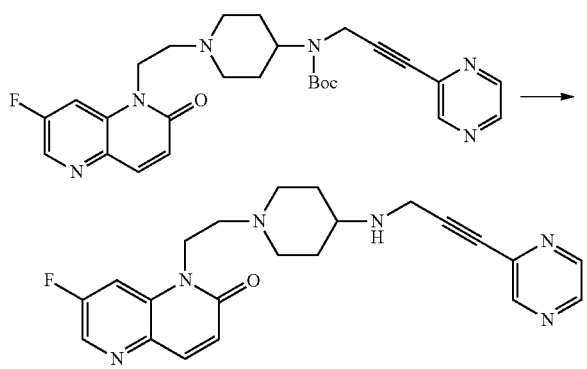

To a solution of 96 mg of tert-butyl 1-(2-(7-fluoro-2-oxo-1,5-naphthyridin-1(2H)-yl)ethyl)piperidin-4-yl)(3-(pyrazin-2-yl)-2-propyn-1-yl)carbamate in 2 mL of chloroform, 1 mL of trifluoroacetic acid was added at room temperature, and the mixture was stirred for 1 hour 30 minutes. Thereto was added a saturated aqueous sodium hydrogen carbonate solution, the organic layer was separated, and the aqueous layer was extracted with chloroform. The organic layer and the extract were combined, the resultant solution was dried over anhydrous magnesium sulfate, and the solvent was distilled off under reduced pressure. The resultant residue was purified by basic silica gel column chromatography using an eluent of chloroform:methanol=20:1 to obtain 20 mg of 7-fluoro-1-(2-(4-((3-(pyrazin-2-yl)prop-2-in-1-yl)amino)piperidin-1-yl)ethyl)-1,5-naphthyridin-2(1H)-one as a yellow oily substance.

$^1$H-NMR (CDCl$_3$) δ: 1.38-1.49 (2H, m), 1.86-1.95 (2H, m), 2.21-2.30 (2H, m), 2.67 (2H, t, J=7.1 Hz), 2.76-2.86 (1H, m), 2.93-3.01 (2H, m), 3.76 (2H, s), 4.33 (2H, t, J=7.1 Hz), 6.86 (1H, d, J=9.8 Hz), 7.56 (1H, dd, J=10.3, 2.2 Hz), 7.89 (1H, d, J=9.8 Hz), 8.42 (1H, d, J=2.2 Hz), 8.48 (1H, d, J=2.4 Hz), 8.52-8.55 (1H, m), 8.65 (1H, d, J=1.4 Hz)

Example 117

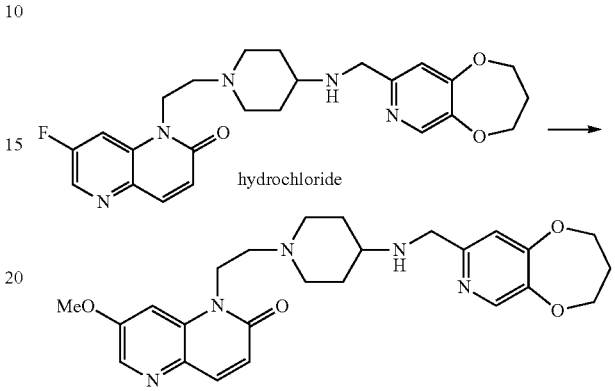

To 85 mg of 1-(2-(4-((3,4-dihydro-2H-(1,4)dioxepino(2,3-c)pyridin-8-ylmethyl)amino)piperidin-1-yl)ethyl)-7-fluoro-1,5-naphthyridin-2(1H)-one hydrochloride, chloroform and a saturated aqueous sodium hydrogen carbonate solution were added, the organic layer was separated, and the aqueous layer was extracted with chloroform. The organic layer and the extract were combined, the resultant solution was washed with a saturated aqueous sodium chloride solution and dried over anhydrous magnesium sulfate, and the solvent was distilled off under reduced pressure. To the resultant oily substance, 2 mL of methanol and 83 mg of a 28% sodium methoxide/methanol solution were added at room temperature, and the mixture was heated under reflux while stirring for 4 hours. After cooling to room temperature, water and chloroform were added to the reaction mixture, the organic layer was separated, and the aqueous layer was extracted with chloroform. The organic layer and the extract were combined, the resultant residue was washed with a saturated aqueous sodium chloride solution and dried over anhydrous magnesium sulfate, and the solvent was distilled off under reduced pressure to obtain 53 mg of 1-(2-(4-((3,4-dihydro-2H-(1,4) dioxepino(2,3-c)pyridin-8-ylmethyl)amino)piperidin-1-yl) ethyl)-7-methoxy-1,5-naphthyridin-2(1H)-one as a light brown oily substance.

$^1$H-NMR (CDCl$_3$) δ: 1.38-1.52 (2H, m), 1.86-1.97 (2H, m), 2.13-2.28 (4H, m), 2.46-2.59 (1H, m), 2.61-2.68 (2H, m), 2.94-3.02 (2H, m), 3.78-3.84 (2H, m), 3.97 (3H, s), 4.24 (2H, t, J=5.8 Hz), 4.31-4.40 (4H, m), 6.74 (1H, d, J=9.8 Hz), 6.86 (1H, s), 7.23-7.32 (1H, m), 7.84 (1H, d, J=9.8 Hz), 8.18 (1H, s), 8.27 (1H, d, J=2.4 Hz)

Example 118

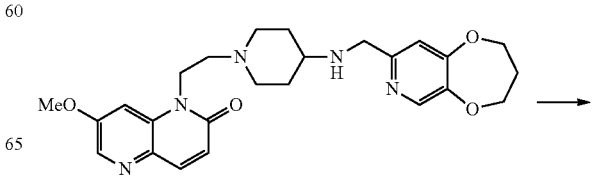

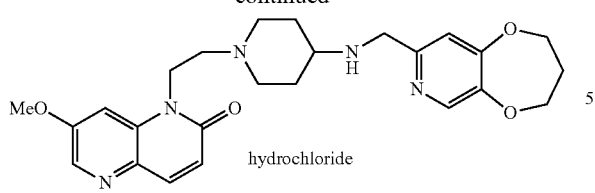

By the same technique as in Example 8, 1-(2-(4-((3,4-dihydro-2H-(1,4)dioxepino(2,3-c)pyridin-8-ylmethyl)amino)piperidin-1-yl)ethyl)-7-methoxy-1,5-naphthyridin-2(1H)-one hydrochloride was obtained from 1-(2-(4-((3,4-dihydro-2H-(1,4)dioxepino(2,3-c)pyridin-8-ylmethyl)amino)piperidin-1-yl)ethyl)-7-methoxy-1,5-naphthyridin-2(1H)-one.

$^1$H-NMR (D$_2$O) δ: 1.99-2.14 (2H, m), 2.35 (2H, quint, J=5.9 Hz), 2.50-2.60 (2H, m), 3.20-3.34 (2H, m), 3.60-3.76 (3H, m), 3.96-4.07 (2H, m), 4.06 (3H, s), 4.40 (2H, t, J=5.9 Hz), 4.44 (2H, s), 4.56 (2H, t, J=5.9 Hz), 4.71-4.87 (2H, m), 6.90 (1H, d, J=9.8 Hz), 7.31 (1H, s), 7.53 (1H, d, J=2.1 Hz), 8.07 (1H, d, J=9.8 Hz), 8.34 (1H, s), 8.43 (1H, d, J=2.1 Hz)

Example 119

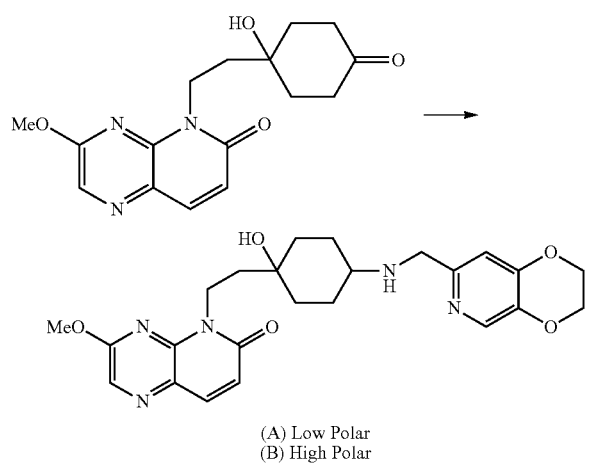

(A) Low Polar
(B) High Polar

By the same technique as in Example 114, (A) 5-(2-(4-((2,3-dihydro(1,4)dioxino(2,3-c)pyridin-7-ylmethyl)amino)-1-hydroxycyclohexyl)ethyl)-3-methoxypyrido(2,3-b)pyrazin-6(5H)-one as a yellow oily substance and (B) 5-(2-(4-((2,3-dihydro(1,4)dioxino(2,3-c)pyridin-7-ylmethyl)amino)-1-hydroxycyclohexyl)ethyl)-3-methoxypyrido(2,3-b)pyrazin-6(5H)-one as a light yellow solid were obtained from 5-(2-(1-hydroxy-4-oxocyclohexyl)ethyl)-3-methoxypyrido(2,3-b)pyrazin-6(5H)-one and 1-(2,3-dihydro(1,4)dioxino(2,3-c)pyridin-7-yl)methanamine.

(A) $^1$H-NMR (CDCl$_3$) δ: 1.33-1.56 (4H, m), 1.70-1.95 (4H, m), 1.99 (2H, t, J=7.3 Hz), 2.62-2.71 (1H, m), 3.75 (2H, s), 4.08 (3H, s), 4.25-4.35 (4H, m), 4.59 (2H, t, J=7.3 Hz), 6.77 (1H, d, J=9.6 Hz), 6.78 (1H, s), 7.86 (1H, d, J=9.6 Hz), 8.10 (1H, s), 8.13 (1H, s)

(B) $^1$H-NMR (CDCl$_3$) δ: 1.38-1.48 (2H, m), 1.50-1.90 (8H, m), 2.42-2.54 (1H, m), 3.82 (2H, s), 4.08 (3H, s), 4.24-4.35 (4H, m), 4.57-4.62 (2H, m), 6.77 (1H, d, J=10.0 Hz), 6.83 (1H, s), 7.85 (1H, d, J=10.0 Hz), 8.10 (1H, s), 8.13 (1H, s)

Example 120

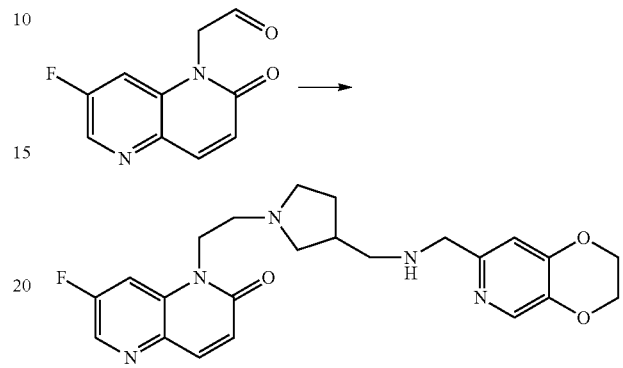

To a suspension of 0.10 g of 1-(2,3-dihydro(1,4)dioxino(2,3-c)pyridin-7-yl)-N-(pyrrolidin-3-ylmethyl)methanamine hydrochloride in 5 mL of methanol, 0.17 g of a 28% sodium methoxide/methanol solution, 66 mg of (7-fluoro-2-oxo-1,5-naphthyridin-1(2H)-yl)acetaldehyde, 0.10 g of molecular sieves 3 A, 33 μL of acetic acid and 18 mg of sodium cyanoborohydride were added at room temperature, and the mixture was stirred at the same temperature for 2 hours 30 minutes. To the reaction mixture, a saturated aqueous sodium hydrogen carbonate solution and ethyl acetate were added, the organic layer was separated, and the aqueous layer was extracted with ethyl acetate. The organic layer and the extract were combined, the resultant solution was washed with a saturated aqueous sodium chloride solution and dried over anhydrous magnesium sulfate, and the solvent was distilled off under reduced pressure. The resultant residue was purified by basic silica gel column chromatography using an eluent of chloroform:methanol=30:1 to obtain 20 mg of 1-(2-(3-(((2,3-dihydro(1,4)dioxino(2,3-c)pyridin-7-ylmethyl)amino)methyl)pyrrolidin-1-yl)ethyl)-7-fluoro-1,5-naphthyridin-2(1H)-one as a yellow oily substance.

$^1$H-NMR (CDCl$_3$) δ: 1.45-1.55 (1H, m), 1.96-2.07 (1H, m), 2.32-2.47 (2H, m), 2.59-2.88 (7H, m), 3.77 (2H, s), 4.25-4.37 (6H, m), 6.81 (1H, s), 6.86 (1H, d, J=9.8 Hz), 7.54 (1H, dd, J=10.2, 2.1 Hz), 7.88 (1H, d, J=9.8 Hz), 8.10 (1H, s), 8.41 (1H, d, J=2.1 Hz)

Example 121

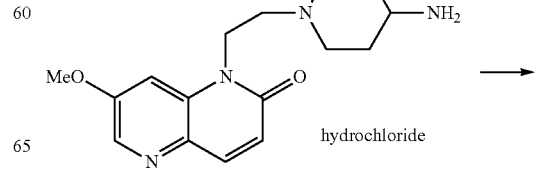

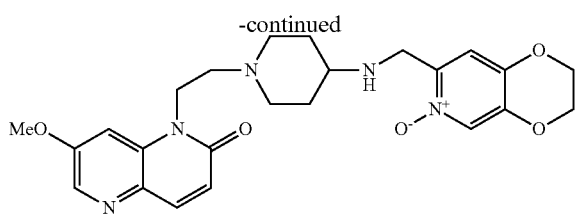

By the same technique as in Example 55, 7-methoxy-1-(2-(4-((((6-oxido-2,3-dihydro(1,4)dioxino(2,3-c)pyridin-7-yl)methyl)amino)piperidin-1-yl)ethyl)-1,5-naphthyridin-2(1H)-one was obtained from 1-(2-(4-aminopiperidin-1-yl)ethyl)-7-methoxy-1,5-naphthyridin-2(1H)-one hydrochloride and 2,3-dihydro(1,4)dioxino(2,3-c)pyridine-7-carbaldehyde 6-oxide.

$^1$H-NMR (CDCl$_3$) δ: 1.38-1.50 (2H, m), 1.85-1.96 (2H, m), 2.13-2.23 (2H, m), 2.44-2.54 (1H, m), 2.61-2.68 (2H, m), 2.93-3.02 (2H, m), 3.93 (2H, s), 3.98 (3H, s), 4.28-4.40 (6H, m), 6.74 (1H, d, J=9.8 Hz), 6.94 (1H, s), 7.23 (1H, d, J=2.2 Hz), 7.84 (1H, d, J=9.8 Hz), 7.97 (1H, s), 8.28 (1H, d, J=2.2 Hz)

Example 122

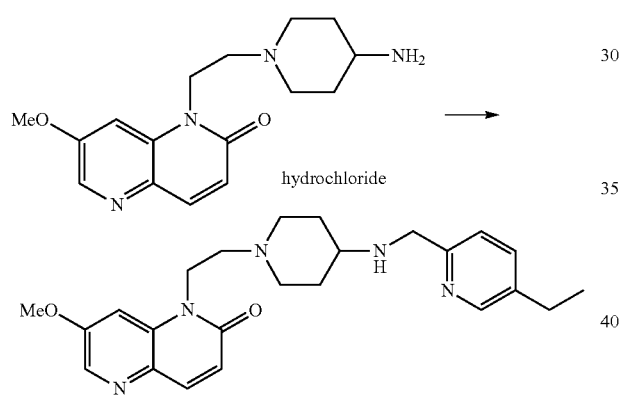

To a suspension of 0.20 g of 1-(2-(4-aminopiperidin-1-yl)ethyl)-7-methoxy-1,5-naphthyridin-2(1H)-one hydrochloride in 2 mL of methanol, 0.28 g of a 28% sodium methoxide/methanol solution, 66 mg of 5-ethylpyridine-2-carbaldehyde and 28 μL of acetic acid were added. Then, 61 mg of sodium cyanoborohydride was added thereto and the mixture was stirred at room temperature for 3 hours. Thereto was further added 31 mg of sodium cyanoborohydride, and the mixture was stirred at room temperature for 1 hour 30 minutes. To the reaction mixture, chloroform and a saturated aqueous sodium hydrogen carbonate solution were added. The organic layer was separated, washed with water and a saturated aqueous sodium chloride solution and dried over anhydrous magnesium sulfate, and the solvent was distilled off under reduced pressure. The resultant residue was purified by basic silica gel column chromatography using gradient elution with chloroform:methanol=93:7 to 9:1 to obtain 0.15 g of 1-(2-(4-(((5-ethylpyridin-2-yl)methyl)amino)piperidin-1-yl)ethyl)-7-methoxy-1,5-naphthyridin-2(1H)-one as a light yellow oily substance.

$^1$H-NMR (CDCl$_3$) δ: 1.24 (3H, t, J=6.6 Hz), 1.40-1.52 (2H, m), 1.89-1.97 (2H, m), 2.15-2.23 (2H, m), 2.50-2.59 (1H, m), 2.60-2.67 (4H, m), 2.95-3.02 (2H, m), 3.90 (2H, s), 3.97 (3H, s), 4.34-4.39 (2H, m), 6.74 (1H, d, J=9.6 Hz), 7.21 (1H, d, J=7.9 Hz), 7.25 (1H, d, J=2.2 Hz), 7.47 (1H, dd, J=7.9, 2.4 Hz), 7.84 (1H, d, J=9.7 Hz), 8.27 (1H, d, J=2.4 Hz), 8.39 (1H, d, J=2.2 Hz)

Example 123

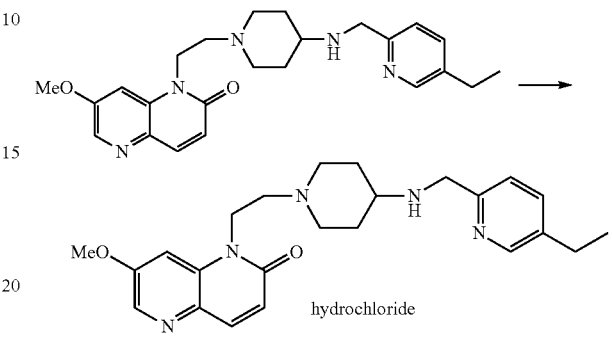

By the same technique as in Example 100, 1-(2-(4-(((5-ethylpyridin-2-yl)methyl)amino)piperidin-1-yl)ethyl)-7-methoxy-1,5-naphthyridin-2(1H)-one hydrochloride was obtained from 1-(2-(4-(((5-ethylpyridin-2-yl)methyl)amino)piperidin-1-yl)ethyl)-7-methoxy-1,5-naphthyridin-2(1H)-one.

$^1$H-NMR (D$_2$O) δ: 1.28 (3H, t, J=7.6 Hz), 2.02-2.17 (2H, m), 2.53-2.62 (2H, m), 2.83 (2H, t, J=7.6 Hz), 3.22-3.35 (2H, m), 3.62-3.82 (3H, m), 3.98-4.10 (2H, m), 4.06 (3H, s), 4.61 (2H, s), 4.70-4.92 (2H, m), 6.92 (1H, d, J=9.9 Hz), 7.56 (1H, d, J=2.1 Hz), 7.84 (1H, d, J=8.2 Hz), 8.08 (1H, d, J=9.9 Hz), 8.24 (1H, dd, J=8.2, 1.5 Hz), 8.44 (1H, d, J=2.1 Hz), 8.65 (1H, d, J=1.5 Hz)

Example 124

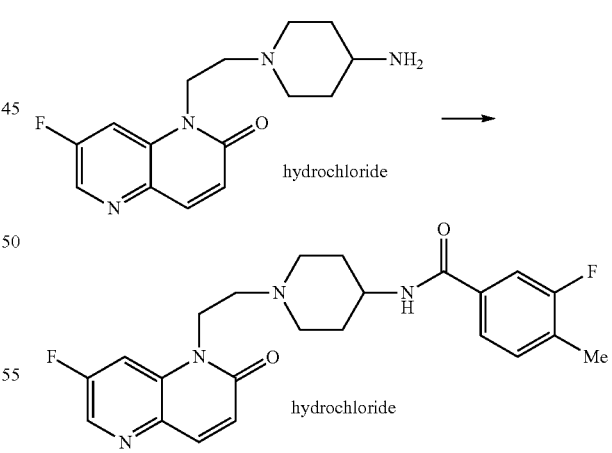

To a solution of 50 mg of 3-fluoro-4-methylbenzoic acid in 0.64 mL of thionyl chloride, 50 μL of N,N-dimethylformamide was added, and the mixture was heated under reflux while stirring for 1 hour. The solvent was distilled off under reduced pressure, and the mixture was dissolved in 4.0 mL of dichloromethane, thereto were added 0.13 mL of triethylamine and 64 mg of 1-(2-(4-aminopiperidin-1-yl)ethyl)-7-fluoro-1,5-naphthyridin-2(1H)-one hydrochloride under cooling with ice, and the mixture was stirred for 2 hours. Thereto were added chloroform and water, and the mixture was adjusted to pH 1 with 6 mol/L hydrochloric acid. The solid was filtered off to obtain 51 mg of 3-fluoro-N-(1-(2-(7-fluoro-2-oxo-1,5-naphthyridin-1(2H)-yl)ethyl)piperidin-4-yl)-4-methylbenzamide hydrochloride as a white solid.

$^1$H-NMR (DMSO-d$_6$) δ: 1.83-1.96 (2H, m), 2.00-2.11 (2H, m), 2.29 (3H, s), 3.00-3.50 (4H, m), 3.70-3.79 (2H, m), 3.99-4.11 (1H, m), 4.58-4.66 (2H, m), 6.90 (1H, d, J=9.9 Hz), 7.37-7.42 (1H, m), 7.62-7.68 (2H, m), 8.02 (1H, d, J=9.9 Hz), 8.27-8.36 (1H, m), 8.52-8.57 (1H, m), 8.61-8.65 (1H, m), 9.95-10.07 (1H, m)

Example 125

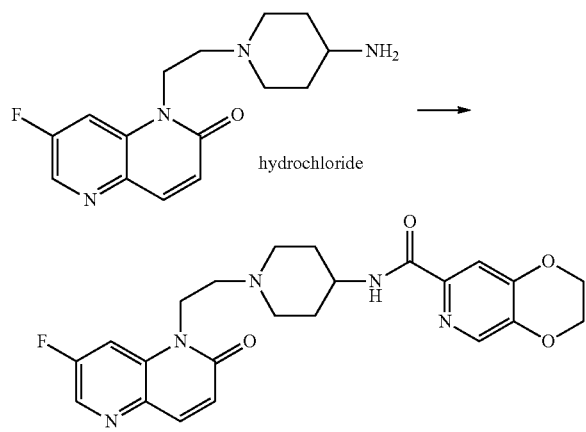

To a solution of 50 mg of 2,3-dihydro(1,4)dioxino(2,3-c)pyridine-7-carboxylic acid in 2.0 mL of thionyl chloride, one drop of N,N-dimethylformamide was added, and the mixture was heated under reflux while stirring for 1 hour 30 minutes. The solvent was distilled off under reduced pressure, the mixture was dissolved in 2.0 mL of dichloromethane, and 0.14 mL of triethylamine and 53 mg of 1-(2-(4-aminopiperidin-1-yl)ethyl)-7-fluoro-1,5-naphthyridin-2(1H)-one hydrochloride were added thereto, and the mixture was stirred for 1 hour. Chloroform and water were added, the organic layer was separated, and the aqueous layer was extracted with chloroform. The organic layer and the extract were combined, the resultant solution was washed with an aqueous sodium hydroxide solution and then with a saturated aqueous sodium chloride solution, and dried over anhydrous magnesium sulfate, and the solvent was distilled off under reduced pressure. To the resultant residue, a mixed solvent of ethyl acetate: diethyl ether was added to obtain 48 mg of N-(1-(2-(7-fluoro-2-oxo-1,5-naphthyridin-1(2H)-yl)ethyl)piperidin-4-yl)-2,3-dihydro(1,4)dioxino(2,3-c)pyridine-7-carboxamide as a light brown solid.

$^1$H-NMR (CDCl$_3$) δ: 1.50-3.20 (10H, m), 3.94-4.13 (1H, m), 4.30-4.40 (6H, m), 6.86 (1H, d, J=9.9 Hz), 7.70 (1H, s), 7.77-7.95 (1H, m), 7.91 (1H, d, J=9.9 Hz), 8.07 (1H, s), 8.43 (1H, d, J=2.2 Hz)

Example 126

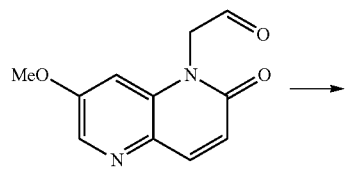

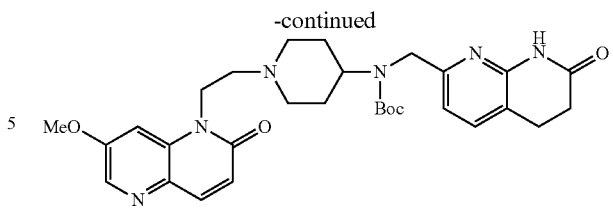

To a solution of 0.14 g of (7-methoxy-2-oxo-1,5-naphthyridin-1(2H)-yl)acetaldehyde in 12 mL of dichloromethane, 0.23 g of tert-butyl ((7-oxo-5,6,7,8-tetrahydro-1,8-naphthyridin-2-yl)methyl)(piperidin-4-yl)carbamate and 37 μL of acetic acid were added, and the mixture was stirred at room temperature for 30 minutes. Then, 0.17 g of sodium triacetoxyborohydride was added to the reaction mixture, and after stirring at room temperature for 30 minutes, the mixture was left overnight and further stirred for 5 hours. To the reaction mixture, water, a saturated aqueous sodium hydrogen carbonate solution and chloroform were added, the organic layer was separated, and the aqueous layer was extracted with chloroform. The organic layer and the extract were combined, the resultant solution was washed with a saturated aqueous sodium chloride solution and dried over anhydrous magnesium sulfate, and the solvent was distilled off under reduced pressure. The resultant residue was purified by silica gel column chromatography using an eluent of chloroform:methanol=50:1 to obtain 0.23 g of tert-butyl 1-(2-(7-methoxy-2-oxo-1,5-naphthyridin-1(2H)-yl)ethyl)piperidin-4-yl)((7-oxo-5,6,7,8-tetrahydro-1,8-naphthyridin-2-yl)methyl)carbamate as a light yellow foam.

$^1$H-NMR (CDCl$_3$) δ: 1.28-1.88 (13H, m), 2.10-2.28 (2H, m), 2.58-2.72 (4H, m), 2.87-3.09 (4H, m), 3.97 (3H, s), 4.06-4.23 (1H, m), 4.27-4.47 (4H, m), 6.73 (1H, d, J=9.6 Hz), 6.80-6.91 (1H, m), 7.18 (1H, s), 7.42 (1H, d, J=7.3 Hz), 7.84 (1H, d, J=9.6 Hz), 8.21 (1H, s), 8.28 (1H, d, J=2.2 Hz)

Example 127

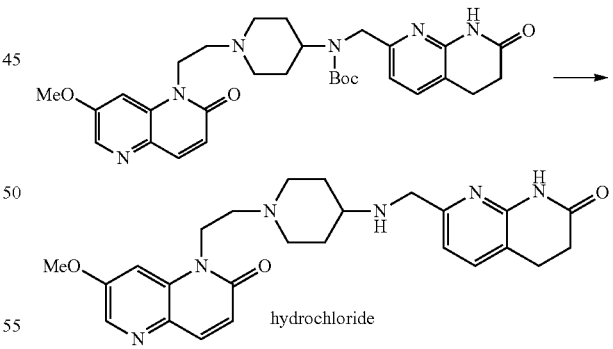

By the same technique as in Example 2, 7-methoxy-1-(2-(4-(((7-oxo-5,6,7,8-tetrahydro-1,8-naphthyridin-2-yl)methyl)amino)piperidin-1-yl)ethyl)-1,5-naphthyridin-2(1H)-one hydrochloride was obtained from tert-butyl 1-(2-(7-methoxy-2-oxo-1,5-naphthyridin-1(2H)-yl)ethyl)piperidin-4-yl)((7-oxo-5,6,7,8-tetrahydro-1,8-naphthyridin-2-yl)methyl)carbamate.

$^1$H-NMR (D$_2$O) δ: 2.01-2.21 (2H, m), 2.48-2.63 (2H, m), 2.65-2.75 (2H, m), 2.97-3.07 (2H, m), 3.19-3.41 (2H, m), 3.59-3.77 (3H, m), 3.97-4.11 (2H, m), 4.09 (3H, s), 4.40 (2H, s), 4.52-5.18 (2H, m), 6.95 (1H, d, J=9.5 Hz), 7.15 (1H, d, J=7.4 Hz), 7.66 (1H, s), 7.72 (1H, d, J=7.4 Hz), 8.07 (1H, d, J=9.5 Hz), 8.46 (1H, s)

Example 128

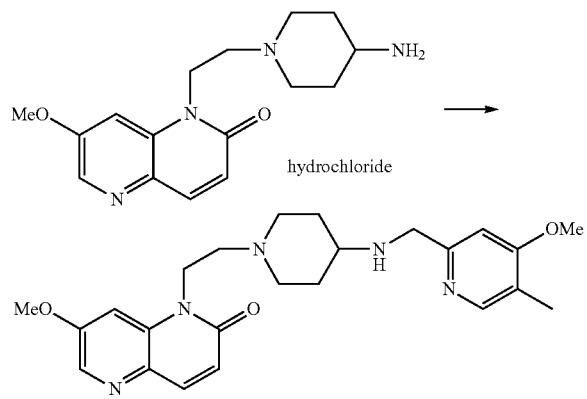

To a solution of 71 mg of 4-methoxy-5-methylpyridine-2-carbaldehyde in 2 mL of methanol, 0.27 g of a 28% sodium methoxide/methanol solution, 0.19 g of 1-(2-(4-aminopiperidin-1-yl)ethyl)-7-methoxy-1,5-naphthyridin-2(1H)-one hydrochloride and 27 µL of acetic acid were added. Then, 59 mg of sodium cyanoborohydride was added thereto and the mixture was stirred at room temperature for 4 hours. To the reaction mixture, chloroform and a saturated aqueous sodium hydrogen carbonate solution were added. The organic layer was separated, washed with water and a saturated aqueous sodium chloride solution and dried over anhydrous magnesium sulfate, and the solvent was distilled off under reduced pressure. The resultant residue was purified by basic silica gel column chromatography using gradient elution with chloroform:methanol=19:1 to 86:14 to obtain 0.13 g of 7-methoxy-1-(2-(4-(((4-methoxy-5-methylpyridin-2-yl)methyl)amino)piperidin-1-yl)ethyl)-1,5-naphthyridin-2(1H)-one as a yellow oily substance.

¹H-NMR (CDCl₃) δ: 1.40-1.52 (2H, m), 1.88-1.97 (2H, m), 2.14 (3H, s), 2.14-2.23 (2H, m), 2.50-2.60 (1H, m), 2.62-2.68 (2H, m), 2.94-3.03 (2H, m), 3.86 (2H, s), 3.88 (3H, s), 3.97 (3H, s), 4.34-4.40 (2H, m), 6.74 (1H, d, J=9.8 Hz), 6.79 (1H, s), 7.25 (1H, d, J=2.4 Hz), 7.84 (1H, d, J=9.8 Hz), 8.16 (1H, s), 8.28 (1H, d, J=2.4 Hz)

Example 129

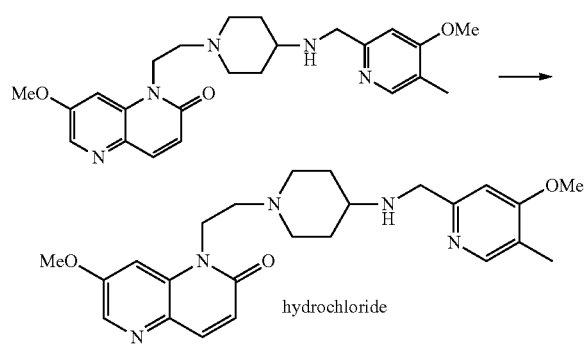

By the same technique as in Example 8, 7-methoxy-1-(2-(4-(((4-methoxy-5-methylpyridin-2-yl)methyl)amino)piperidin-1-yl)ethyl)-1,5-naphthyridin-2(1H)-one hydrochloride was obtained from 7-methoxy-1-(2-(4-(((4-methoxy-5-methylpyridin-2-yl)methyl)amino)piperidin-1-yl)ethyl)-1,5-naphthyridin-2(1H)-one.

¹H-NMR (D₂O) δ: 1.79-1.92 (2H, m), 2.22 (3H, s), 2.30-2.40 (2H, m), 3.02-3.17 (2H, m), 3.23-3.35 (1H, m), 3.42-3.53 (2H, m), 3.74-3.86 (2H, m), 4.03 (3H, s), 4.05 (3H, s), 4.26 (2H, s), 4.67-4.80 (2H, m), 6.87 (1H, d, J=9.8 Hz), 7.23-7.25 (1H, m), 7.44 (1H, d, J=2.2 Hz), 8.05 (1H, d, J=9.8 Hz), 8.25 (1H, s), 8.40 (1H, d, J=2.2 Hz)

Example 130

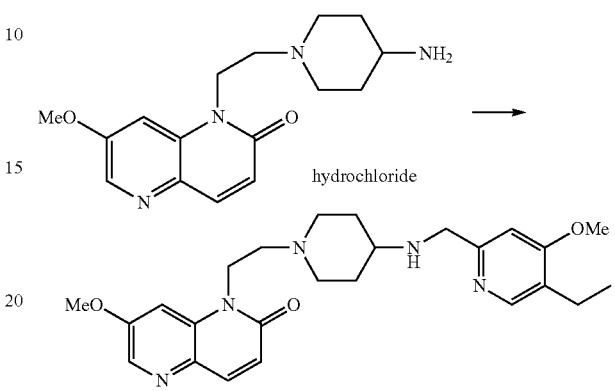

To a suspension of 0.10 g of 1-(2-(4-aminopiperidin-1-yl)ethyl)-7-methoxy-1,5-naphthyridin-2(1H)-one hydrochloride in 2 mL of methanol, 0.14 g of a 28% sodium methoxide/methanol solution, 40 mg of 5-ethyl-4-methoxypyridine-2-carbaldehyde and 14 µL of acetic acid were added. Then, 30 mg of sodium cyanoborohydride was added thereto, and the mixture was stirred at room temperature for 5 hours. To the reaction mixture, chloroform and a saturated aqueous sodium hydrogen carbonate solution were added. The organic layer was separated, washed with water and a saturated aqueous sodium chloride solution and dried over anhydrous magnesium sulfate, and the solvent was distilled off under reduced pressure. The resultant residue was purified by basic silica gel column chromatography using gradient elution with chloroform:methanol=9:1 to 86:14 to obtain 51 mg of 1-(2-(4-(((5-ethyl-4-methoxypyridin-2-yl)methyl)amino)piperidin-1-yl)ethyl)-7-methoxy-1,5-naphthyridin-2(1H)-one as a yellow oily substance.

¹H-NMR (CDCl₃) δ: 1.18 (3H, t, 7.6 Hz), 1.41-1.55 (2H, m), 1.89-1.98 (2H, m), 2.12-2.24 (2H, m), 2.51-2.68 (5H, m), 2.93-3.03 (2H, m), 3.83-3.90 (5H, m), 3.97 (3H, s), 4.33-4.40 (2H, m), 6.74 (1H, d, J=9.6 Hz), 6.79 (1H, s), 7.24-7.30 (1H, m), 7.84 (1H, d, J=9.6 Hz), 8.17 (1H, s), 8.28 (1H, d, J=2.4 Hz)

Example 131

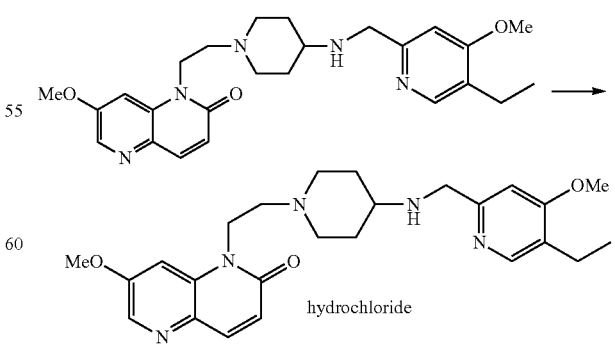

By the same technique as in Example 8, 1-(2-(4-(((5-ethyl-4-methoxypyridin-2-yl)methyl)amino)piperidin-1-yl)ethyl)-

7-methoxy-1,5-naphthyridin-2(1H)-one hydrochloride was obtained from 1-(2-(4-(((5-ethyl-4-methoxypyridin-2-yl)methyl)amino)piperidin-1-yl)ethyl)-7-methoxy-1,5-naphthyridin-2(1H)-one.

$^1$H-NMR (D$_2$O) δ: 1.20 (3H, t, J=7.6 Hz), 1.79-1.94 (2H, m), 2.32-2.40 (2H, m), 2.68 (2H, q, J=7.6 Hz), 3.12-3.32 (3H, m), 3.51-3.57 (2H, m), 3.80-3.89 (2H, m), 4.04 (6H, s), 4.26 (2H, s), 4.70-4.90 (2H, m), 6.86 (1H, d, J=9.9 Hz), 7.28 (1H, s), 7.42-7.45 (1H, m), 8.05 (1H, d, J=9.9 Hz), 8.26 (1H, s), 8.39 (1H, d, J=2.2 Hz)

Example 132

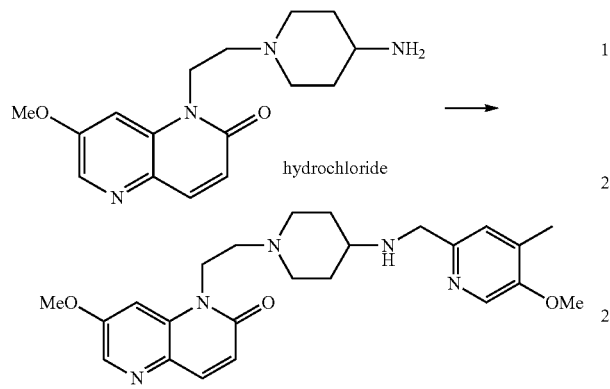

To a suspension of 0.20 g of 1-(2-(4-aminopiperidin-1-yl)ethyl)-7-methoxy-1,5-naphthyridin-2(1H)-one hydrochloride in 2 mL of methanol, 0.28 g of a 28% sodium methoxide/methanol solution, 73 mg of 5-methoxy-4-methylpyridine-2-carbaldehyde and 28 μL of acetic acid were added. Then, 61 mg of sodium cyanoborohydride was added thereto, and the mixture was stirred at room temperature for 1 hour 30 minutes. To the reaction mixture, chloroform, a saturated aqueous sodium hydrogen carbonate solution and water were added. The organic layer was separated, and the aqueous layer was extracted with chloroform. The organic layer and the extract were combined, the resultant solution was washed with water and a saturated aqueous sodium chloride solution and dried over anhydrous magnesium sulfate, and the solvent was distilled off under reduced pressure. The resultant residue was purified by basic silica gel column chromatography using gradient elution with chloroform:methanol=93:7 to 86:14 to obtain 82 mg of 7-methoxy-1-(2-(4-(((5-methoxy-4-methylpyridin-2-yl)methyl)amino)piperidin-1-yl)ethyl)-1,5-naphthyridin-2(1H)-one as a light yellow solid.

$^1$H-NMR (CDCl$_3$) δ: 1.40-1.53 (2H, m), 1.89-1.98 (2H, m), 2.13-2.23 (2H, m), 2.22 (3H, s), 2.50-2.60 (1H, m), 2.62-2.68 (2H, m), 2.93-3.03 (2H, m), 3.83 (2H, s), 3.90 (3H, s), 3.97 (3H, s), 4.34-4.39 (2H, m), 6.74 (1H, d, J=9.8 Hz), 7.08 (1H, s), 7.24-7.28 (1H, m), 7.84 (1H, d, J=9.8 Hz), 8.08 (1H, s), 8.27 (1H, d, J=2.2 Hz)

Example 133

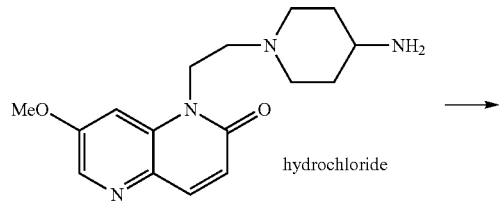

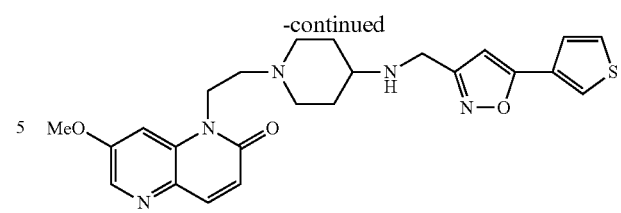

By the same technique as in Example 30, 7-methoxy-1-(2-(4-(((5-(3-thienyl)isoxazol-3-yl)methyl)amino)piperidin-1-yl)ethyl)-1,5-naphthyridin-2(1H)-one was obtained from 1-(2-(4-aminopiperidin-1-yl)ethyl)-7-methoxy-1,5-naphthyridin-2(1H)-one hydrochloride and 5-(3-thienyl)isoxazole-3-carbaldehyde.

$^1$H-NMR (CDCl$_3$) δ: 1.38-1.50 (2H, m), 1.89-1.97 (2H, m), 2.15-2.25 (2H, m), 2.54-2.68 (3H, m), 2.95-3.03 (2H, m), 3.93 (2H, s), 3.98 (3H, s), 4.35-4.39 (2H, m), 6.39 (1H, s), 6.74 (1H, d, J=9.6 Hz), 7.23 (1H, d, J=2.2 Hz), 7.38-7.43 (2H, m), 7.77 (1H, dd, J=2.8, 1.4 Hz), 7.84 (1H, d, J=9.6 Hz), 8.28 (1H, d, J=2.2 Hz)

Example 134

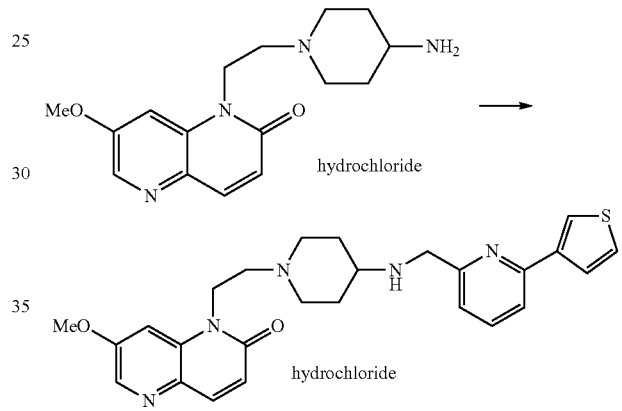

To a suspension of 0.14 g of 1-(2-(4-aminopiperidin-1-yl)ethyl)-7-methoxy-1,5-naphthyridin-2(1H)-one hydrochloride in 5 mL of methanol, 0.14 g of a 28% sodium methoxide/methanol solution, 46 mg of 6-(3-thienyl)pyridine-2-carbaldehyde, 0.10 g of molecular sieves 3 A, 28 μL of acetic acid and 15 mg of sodium cyanoborohydride were added at room temperature, and the mixture was stirred at the same temperature for 3 hours. To the reaction mixture, a saturated aqueous sodium hydrogen carbonate solution and chloroform were added, the organic layer was separated, washed with a saturated aqueous sodium chloride solution and dried over anhydrous magnesium sulfate, and the solvent was distilled off under reduced pressure. The resultant residue was purified by basic silica gel column chromatography using an eluent of chloroform:methanol=30:1. To a solution of the resultant residue in 2 mL of ethyl acetate, 2 mL of a 4 mol/L hydrogen chloride/ethyl acetate solution was added, and the mixture was stirred at room temperature for 30 minutes. The solid was filtered off to obtain 97 mg of 7-methoxy-1-(2-(4-(((6-(3-thienyl)pyridin-2-yl)methyl)amino)piperidin-1-yl)ethyl)-1,5-naphthyridin-2(1H)-one hydrochloride as a yellow solid.

$^1$H-NMR (D$_2$O) δ: 2.07-2.23 (2H, m), 2.54-2.66 (2H, m), 3.20-3.36 (2H, m), 3.59-3.67 (2H, m), 3.73-3.83 (1H, m), 3.98-4.10 (2H, m), 4.07 (3H, s), 4.54-4.61 (2H, m), 4.70-4.90 (2H, m), 6.92 (1H, d, J=9.8 Hz), 7.41-7.65 (3H, m), 7.70-7.80 (1H, m), 7.87-7.92 (1H, m), 7.97-8.10 (1H, m), 8.05 (1H, d, J=9.8 Hz), 8.14 (1H, s), 8.44 (1H, s)

Example 135

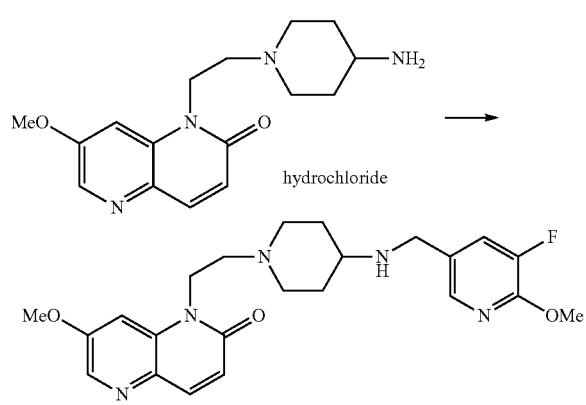

To a suspension of 0.20 g of 1-(2-(4-aminopiperidin-1-yl)ethyl)-7-methoxy-1,5-naphthyridin-2(1H)-one hydrochloride in 2 mL of methanol, 0.28 g of a 28% sodium methoxide/methanol solution and 28 μL of acetic acid were added. Thereto was added 75 mg of 5-fluoro-6-methoxynicotinaldehyde, then, 61 mg of sodium cyanoborohydride was added thereto, and the mixture was stirred at room temperature for 1 hour 20 minutes. Thereto was further added 62 mg of sodium cyanoborohydride, and the mixture was stirred at room temperature for 1 hour 30 minutes, and then stirred at 30 to 35° C. for 1 hour. To the reaction mixture, chloroform and a saturated aqueous sodium hydrogen carbonate solution were added. The organic layer was separated, and the aqueous layer was extracted with chloroform. The organic layer and the extract were combined, the resultant solution was washed with water and a saturated aqueous sodium chloride solution and dried over anhydrous magnesium sulfate, and the solvent was distilled off under reduced pressure. The resultant residue was purified by basic silica gel column chromatography using gradient elution with chloroform:methanol=19:1 to 9:1, diethyl ether was added to the resultant light yellow oily substance, and the solid was filtered off to obtain 97 mg of 1-(2-(4-(((5-fluoro-6-methoxypyridin-3-yl)methyl)amino)piperidin-1-yl)ethyl)-7-methoxy-1,5-naphthyridin-2(1H)-one as a slightly yellow solid.

$^1$H-NMR (CDCl$_3$) δ: 1.35-1.46 (2H, m), 1.86-1.95 (2H, m), 2.15-2.23 (2H, m), 2.47-2.58 (1H, m), 2.62-2.68 (2H, m), 2.92-3.02 (2H, m), 3.75 (2H, m), 3.98 (3H, s), 4.01 (3H, s), 4.33-4.40 (2H, m), 6.74 (1H, d, J=9.8 Hz), 7.23 (1H, d, J=2.3 Hz), 7.38 (1H, dd, J=11.0, 2.0 Hz), 7.82-7.86 (2H, m), 8.28 (1H, d, J=2.3 Hz)

Example 136

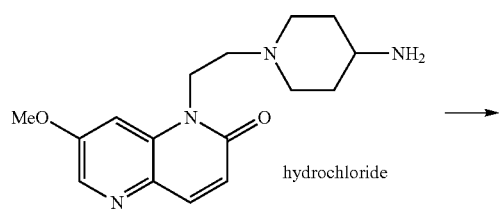

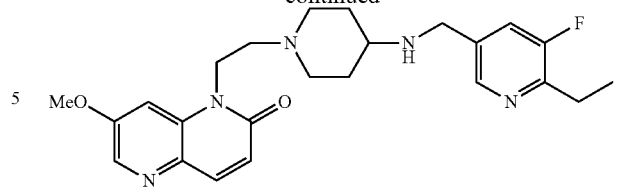

To a suspension of 0.14 g of 1-(2-(4-aminopiperidin-1-yl)ethyl)-7-methoxy-1,5-naphthyridin-2(1H)-one hydrochloride in 2 mL of methanol, 0.20 g of a 28% sodium methoxide/methanol solution, 53 mg of 6-ethyl-5-fluoronicotinaldehyde and 20 μL of acetic acid were added. Then, 43 mg of sodium cyanoborohydride was added thereto, and the mixture was stirred at room temperature for 1 hour 20 minutes. Thereto was further added 43 mg of sodium cyanoborohydride, and the mixture was stirred at room temperature for 1 hour, and then stirred at 30 to 40° C. for 1 hour. To the reaction mixture, chloroform and a saturated aqueous sodium hydrogen carbonate solution were added. The organic layer was separated, and the aqueous layer was extracted with chloroform. The organic layer and the extract were combined, the resultant solution was washed with water and a saturated aqueous sodium chloride solution and dried over anhydrous magnesium sulfate, and the solvent was distilled off under reduced pressure. The resultant residue was purified by basic silica gel column chromatography using gradient elution with chloroform:methanol=93:7 to 9:1 to obtain 53 mg of 1-(2-(4-(((6-ethyl-5-fluoropyridin-3-yl)methyl)amino)piperidin-1-yl)ethyl)-7-methoxy-1,5-naphthyridin-2(1H)-one as a light yellow oily substance.

$^1$H-NMR (CDCl$_3$) δ: 1.29 (3H, t, J=7.6 Hz), 1.36-1.47 (2H, m), 1.87-1.96 (2H, m), 2.15-2.24 (2H, m), 2.47-2.57 (1H, m), 2.62-2.68 (2H, m), 2.86 (2H, dd, J=7.6, 2.0 Hz), 2.95-3.02 (2H, m), 3.82 (2H, s), 3.98 (3H, s), 4.33-4.40 (2H, m), 6.75 (1H, d, J=9.6 Hz), 7.20-7.24 (1H, m), 7.34-7.39 (1H, m), 7.85 (1H, d, J=9.6 Hz), 8.25-8.27 (1H, m), 8.28 (1H, d, J=2.4 Hz)

Example 137

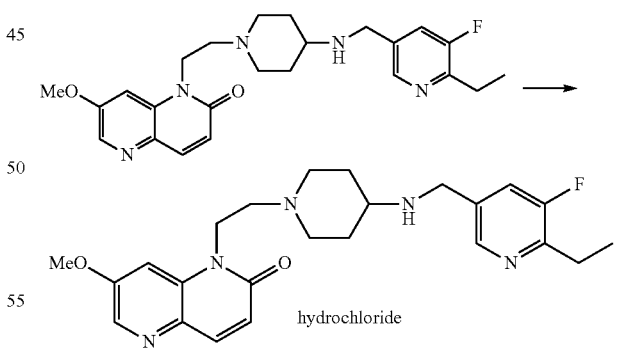

By the same technique as in Example 8, 1-(2-(4-(((6-ethyl-5-fluoropyridin-3-yl)methyl)amino)piperidin-1-yl)ethyl)-7-methoxy-1,5-naphthyridin-2(1H)-one hydrochloride was obtained from 1-(2-(4-(((6-ethyl-5-fluoropyridin-3-yl)methyl)amino)piperidin-1-yl)ethyl)-7-methoxy-1,5-naphthyridin-2(1H)-one.

$^1$H-NMR (D$_2$O) δ: 1.30 (3H, t, J=7.7 Hz), 2.00-2.14 (2H, m), 2.53-2.61 (2H, m), 2.99 (2H, q, J=7.7 Hz), 3.23-3.35 (2H, m), 3.61-3.77 (3H, m), 3.96-4.05 (2H, m), 4.05 (3H, s), 4.47

(2H, s), 4.64-4.90 (2H, m), 6.90 (1H, d, J=10.0 Hz), 7.51 (1H, s), 8.02 (1H, d, J=9.2 Hz), 8.07 (1H, d, J=10.0 Hz), 8.41-8.43 (1H, m), 8.51 (1H, s)

Example 138

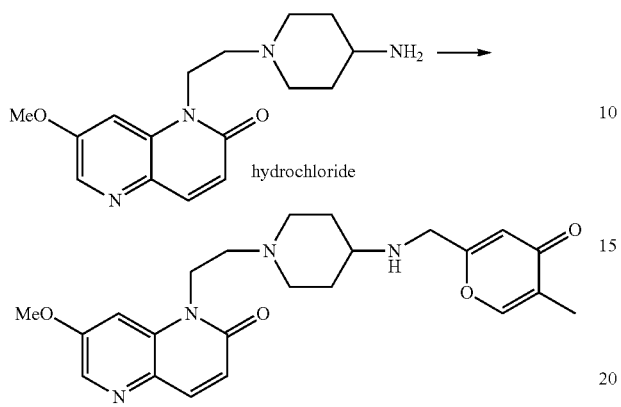

By the same technique as in Example 79, 7-methoxy-1-(2-(4-(((5-methyl-4-oxo-4H-pyran-2-yl)methyl)amino)piperidin-1-yl)ethyl)-1,5-naphthyridin-2(1H)-one was obtained from 1-(2-(4-aminopiperidin-1-yl)ethyl)-7-methoxy-1,5-naphthyridin-2(1H)-one hydrochloride and 5-methyl-4-oxo-4H-pyran-2-carbaldehyde.

$^1$H-NMR (CDCl$_3$) δ: 1.30-1.50 (2H, m), 1.80-1.95 (5H, m), 2.10-2.25 (2H, m), 2.45-2.55 (1H, m), 2.60-2.70 (2H, m), 2.90-3.05 (2H, m), 3.66 (2H, s), 3.98 (3H, s), 4.30-4.45 (2H, m), 6.33 (1H, s), 6.74 (1H, d, J=9.6 Hz), 7.21-7.25 (1H, m), 7.66 (1H, s), 7.85 (1H, d, J=9.6 Hz), 8.28 (1H, d, J=2.4 Hz)

Example 139

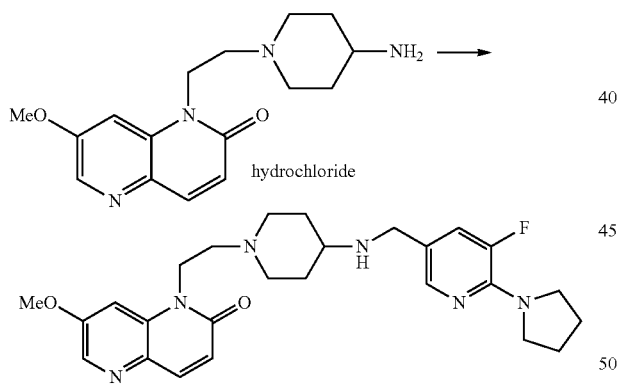

To a suspension of 0.20 g of 1-(2-(4-aminopiperidin-1-yl)ethyl)-7-methoxy-1,5-naphthyridin-2(1H)-one hydrochloride in 2 mL of methanol, 0.28 g of a 28% sodium methoxide/methanol solution, 94 mg of 5-fluoro-6-(pyrrolidin-1-yl)nicotinaldehyde and 28 μL of acetic acid were added. Then, 61 mg of sodium cyanoborohydride was added thereto, and the mixture was stirred at room temperature for 2 hours 20 minutes. To the reaction mixture, chloroform, a saturated aqueous sodium hydrogen carbonate solution and water were added. The organic layer was separated, and the aqueous layer was extracted with chloroform. The organic layer and the extract were combined, the resultant solution was washed with water and a saturated aqueous sodium chloride solution and dried over anhydrous magnesium sulfate, and the solvent was distilled off under reduced pressure. The resultant residue was purified by basic silica gel column chromatography using gradient elution with chloroform:methanol=95:5 to 9:1, thereto was added diethyl ether, and the solid was filtered off to obtain 91 mg of 1-(2-(4-(((5-fluoro-6-(pyrrolidin-1-yl)pyridin-3-yl)methyl)amino)piperidin-1-yl)ethyl)-7-methoxy-1,5-naphthyridin-2(1H)-one as a slightly yellow solid.

$^1$H-NMR (CDCl$_3$) δ: 1.34-1.47 (2H, m), 1.85-1.99 (6H, m), 2.12-2.23 (2H, m), 2.47-2.55 (1H, m), 2.61-2.67 (2H, m), 2.92-3.01 (2H, m), 3.58-3.65 (4H, m), 3.67 (2H, s), 3.98 (3H, s), 4.33-4.40 (2H, m), 6.74 (1H, d, J=9.6 Hz), 7.18 (1H, d, J=15.6 Hz), 7.22-7.25 (1H, m), 7.81 (1H, s), 7.84 (1H, d, J=9.6 Hz), 8.28 (1H, d, J=2.2 Hz)

Example 140

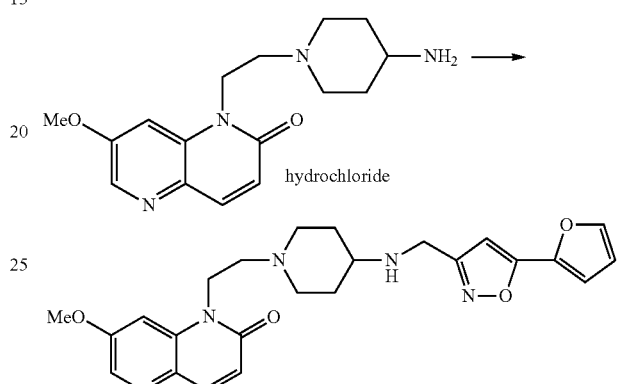

By the same technique as in Example 30, 1-(2-(4-(((5-(2-furyl)isoxazol-3-yl)methyl)amino)piperidin-1-yl)ethyl)-7-methoxy-1,5-naphthyridin-2(1H)-one was obtained from 1-(2-(4-aminopiperidin-1-yl)ethyl)-7-methoxy-1,5-naphthyridin-2(1H)-one hydrochloride and 5-(2-furyl)isoxazole-3-carbaldehyde.

$^1$H-NMR (CDCl$_3$) δ: 1.36-1.49 (2H, m), 1.87-1.97 (2H, m), 2.15-2.25 (2H, m), 2.52-2.62 (1H, m), 2.65 (2H, t, J=7.1 Hz), 2.94-3.02 (2H, m), 3.93 (2H, s), 3.97 (3H, s), 4.36 (2H, t, J=7.1 Hz), 6.44 (1H, s), 6.53 (1H, dd, J=3.4, 1.7 Hz), 6.74 (1H, d, J=9.6 Hz), 6.89 (1H, d, J=3.4 Hz), 7.21-7.24 (1H, m), 7.54 (1H, d, J=1.7 Hz), 7.84 (1H, d, J=9.6 Hz), 8.28 (1H, d, J=2.0 Hz)

Example 141

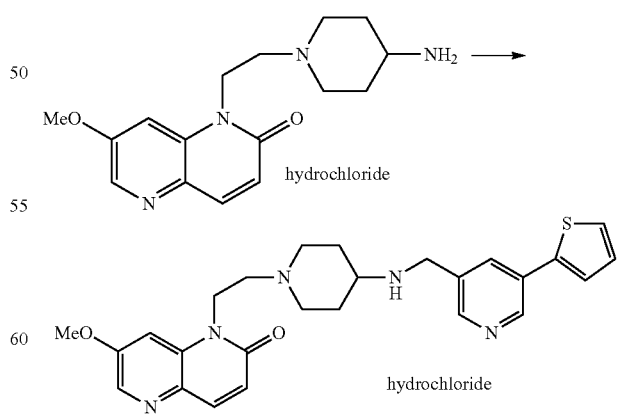

By the same technique as in Example 134, 7-methoxy-1-(2-(4-(((5-(2-thienyl)pyridin-3-yl)methyl)amino)piperidin-1-yl)ethyl)-1,5-naphthyridin-2(1H)-one hydrochloride was obtained from 1-(2-(4-aminopiperidin-1-yl)ethyl)-7-methoxy-1,5-naphthyridin-2(1H)-one hydrochloride and 5-(2-thienyl)nicotinaldehyde.

¹H-NMR (D₂O) δ: 2.04-2.19 (2H, m), 2.57-2.67 (2H, m), 3.24-3.38 (2H, m), 3.60-3.70 (2H, m), 3.75-3.86 (1H, m), 4.01-4.09 (2H, m), 4.06 (3H, s), 4.58-4.64 (2H, m), 4.71-4.87 (2H, m), 6.90 (1H, d, J=9.6 Hz), 7.29 (1H, dd, J=5.0, 3.8 Hz), 7.48-7.59 (1H, m), 7.71-7.79 (2H, m), 8.07 (1H, d, J=9.6 Hz), 8.43 (1H, d, J=2.2 Hz), 8.74-8.94 (2H, m), 9.10-9.20 (1H, m)

Example 142

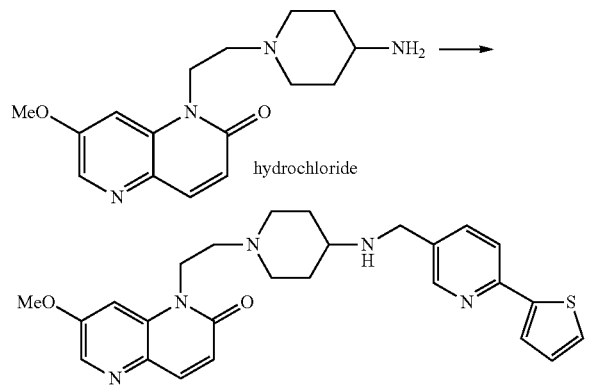

By the same technique as in Example 30, 7-methoxy-1-(2-(4-(((6-(2-thienyl)pyridin-3-yl)methyl)amino)piperidin-1-yl)ethyl)-1,5-naphthyridin-2(1H)-one was obtained from 1-(2-(4-aminopiperidin-1-yl)ethyl)-7-methoxy-1,5-naphthyridin-2(1H)-one hydrochloride and 6-(2-thienyl)nicotinaldehyde.

¹H-NMR (CDCl₃) δ: 1.38-1.50 (2H, m), 1.87-1.97 (2H, m), 2.14-2.25 (2H, m), 2.49-2.70 (3H, m), 2.95-3.03 (2H, m), 3.84 (2H, s), 3.98 (3H, s), 4.35-4.39 (2H, m), 6.74 (1H, d, J=9.6 Hz), 7.09-7.14 (1H, m), 7.20-7.25 (1H, m), 7.38 (1H, d, J=5.1 Hz), 7.57 (1H, d, J=3.6 Hz), 7.61-7.72 (2H, m), 7.84 (1H, d, J=9.6 Hz), 8.28 (1H, d, J=1.9 Hz), 8.48-8.52 (1H, m)

Example 143

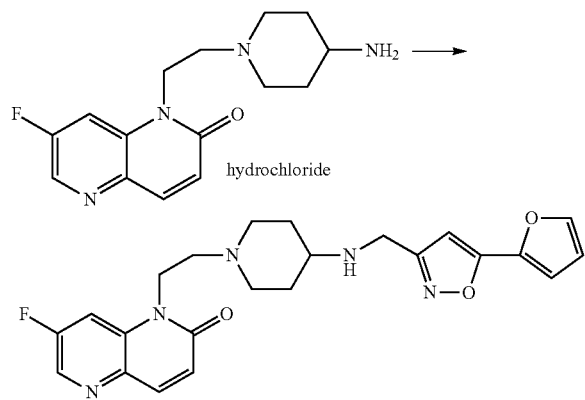

By the same technique as in Example 30, 7-fluoro-1-(2-(4-(((5-(2-furyl)isoxazol-3-yl)methyl)amino)piperidin-1-yl)ethyl)-1,5-naphthyridin-2(1H)-one was obtained from 1-(2-(4-aminopiperidin-1-yl)ethyl)-7-fluoro-1,5-naphthyridin-2(1H)-one hydrochloride and 5-(2-furyl)isoxazole-3-carbaldehyde.

¹H-NMR (CDCl₃) δ: 1.35-1.47 (2H, m), 1.87-1.96 (2H, m), 2.14-2.24 (2H, m), 2.53-2.60 (1H, m), 2.65 (2H, t, J=7.0 Hz), 2.92-2.99 (2H, m), 3.93 (2H, s), 4.32 (2H, t, J=7.0 Hz), 6.44 (1H, s), 6.53 (1H, dd, J=3.2, 2.0 Hz), 6.86 (1H, d, J=9.6 Hz), 6.89 (1H, d, J=3.2 Hz), 7.50-7.58 (2H, m), 7.88 (1H, d, J=9.6 Hz), 8.42 (1H, d, J=2.0 Hz)

Example 144

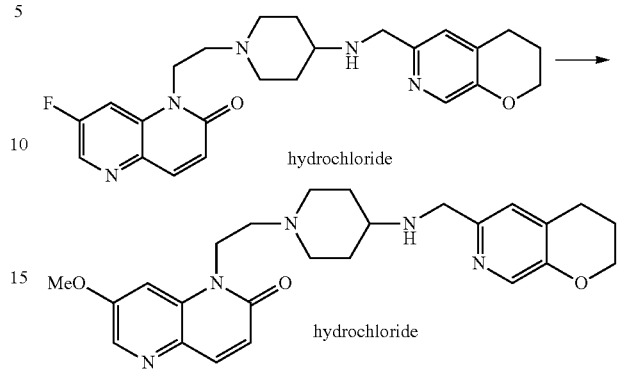

To a suspension of 60 mg of 1-(2-(4-((3,4-dihydro-2H-pyrano(2,3-c)pyridin-6-ylmethyl)amino)piperidin-1-yl)ethyl)-7-fluoro-1,5-naphthyridin-2(1H)-one hydrochloride in 2 mL of methanol, 60 mg of a 28% sodium methoxide/methanol solution, and the mixture was heated under reflux while stirring for 4 hours. Thereto were added water and ethyl acetate, the organic layer was separated, and the aqueous layer was saturated with sodium chloride, and then extracted with ethyl acetate twice. The organic layer and the extract were combined, the resultant solution was dried over anhydrous magnesium sulfate, and the solvent was distilled off under reduced pressure. To the resultant residue, 1 mL of ethyl acetate was added, and 1 mL of a 4.0 mol/L hydrogen chloride/ethyl acetate solution was added at room temperature. The solvent was distilled off under reduced pressure, ethyl acetate was added to the resultant residue, and the solid was filtered off to obtain 31 mg of 1-(2-(4-((3,4-dihydro-2H-pyrano(2,3-c)pyridin-6-ylmethyl)amino)piperidin-1-yl)ethyl)-7-methoxy-1,5-naphthyridin-2(1H)-one hydrochloride as a yellow solid.

¹H-NMR (D₂O) δ: 2.00-2.12 (4H, m), 2.50-2.60 (2H, m), 2.92 (2H, t, J=6.2 Hz), 3.20-3.34 (2H, m), 3.60-3.74 (3H, m), 3.98-4.07 (2H, m), 4.05 (3H, s), 4.34 (2H, t, J=5.2 Hz), 4.43 (2H, s), 4.70-4.90 (2H, m), 6.89 (1H, d, J=9.9 Hz), 7.48-7.52 (2H, m), 8.07 (1H, d, J=9.9 Hz), 8.18 (1H, s), 8.42 (1H, d, J=1.7 Hz)

Example 145

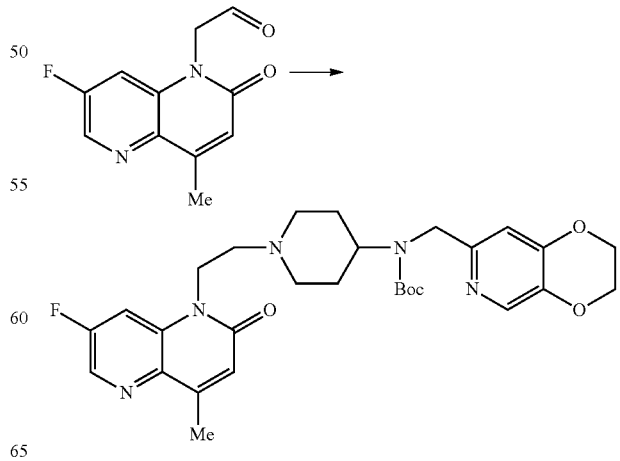

By the same technique as in Example 1, tert-butyl (2,3-dihydro(1,4)dioxino(2,3-c)pyridin-7-ylmethyl)(1-(2-(7- fluoro-4-methyl-2-oxo-1,5-naphthyridin-1(2H)-yl)ethyl)(piperidin-4-yl)carbamate was obtained from (7-fluoro-4-methyl-2-oxo-1,5-naphthyridin-1(2H)-yl)acetaldehyde and tert-butyl (2,3-dihydro(1,4)dioxino(2,3-c)pyridin-7-ylmethyl)(piperidin-4-yl)carbamate.

¹H-NMR (CDCl₃) δ: 1.30-1.70 (13H, m), 2.07-2.25 (2H, m), 2.53 (3H, d, J=1.0 Hz), 2.59 (2H, t, J=7.1 Hz), 2.94-3.02 (2H, m), 4.04-4.18 (1H, m), 4.20-4.48 (8H, m), 6.70-6.76 (2H, m), 7.41-7.48 (1H, m), 8.05 (1H, s), 8.41 (1H, d, J=2.2 Hz)

Example 146

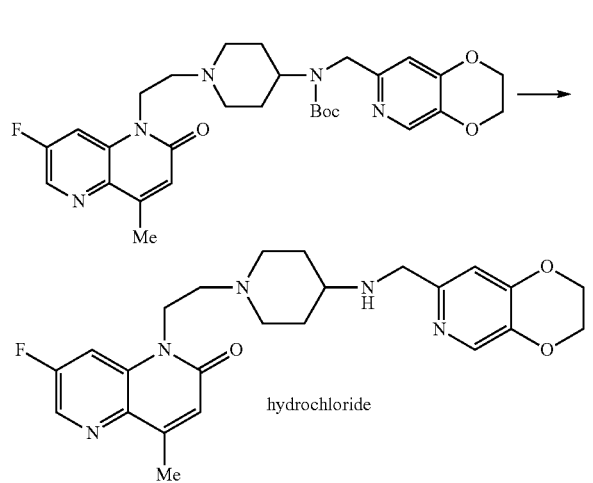

By the same technique as in Example 4, 1-(2-(4-((2,3-dihydro(1,4)dioxino(2,3-c)pyridin-7-ylmethyl)amino)piperidin-1-yl)ethyl)-7-fluoro-4-methyl-1,5-naphthyridin-2(1H)-one hydrochloride was obtained from tert-butyl (2,3-dihydro(1,4)dioxino(2,3-c)pyridin-7-ylmethyl)(1-(2-(7-fluoro-4-methyl-2-oxo-1,5-naphthyridin-1(2H)-yl)ethyl)piperidin-4-yl)carbamate.

¹H-NMR (D₂O) δ: 2.01-2.16 (2H, m), 2.53-2.62 (2H, m), 2.56 (3H, s), 3.22-3.36 (2H, m), 3.60-3.67 (2H, m), 3.72-3.82 (1H, m), 3.97-4.08 (2H, m), 4.48-4.53 (2H, m), 4.57 (2H, s), 4.61-4.66 (2H, m), 4.70-4.78 (2H, m), 6.89 (1H, s), 7.53 (1H, s), 7.93 (1H, dd, J=10.4, 2.2 Hz), 8.41 (1H, s), 8.55 (1H, d, J=2.2 Hz)

Example 147

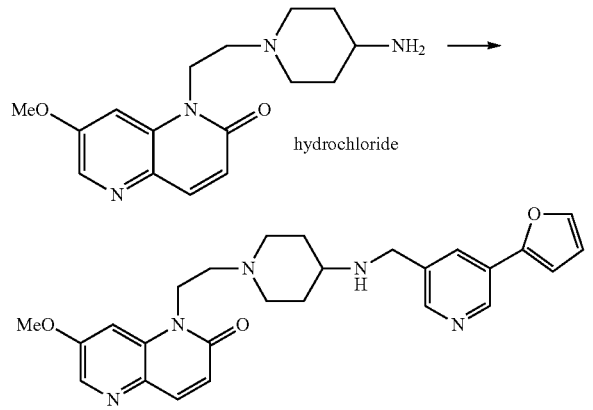

By the same technique as in Example 30, 1-(2-(4-(((5-(2-furyl)pyridin-3-yl)methyl)amino)piperidin-1-yl)ethyl)-7-methoxy-1,5-naphthyridin-2(1H)-one was obtained from 1-(2-(4-aminopiperidin-1-yl)ethyl)-7-methoxy-1,5-naphthyridin-2(1H)-one hydrochloride and 5-(2-furyl)nicotinaldehyde.

¹H-NMR (CDCl₃) δ: 1.38-1.54 (2H, m), 1.89-2.00 (2H, m), 2.14-2.28 (2H, m), 2.52-2.62 (1H, m), 2.66 (2H, t, J=7.3 Hz), 2.97-3.05 (2H, m), 3.87 (2H, s), 3.98 (3H, s), 4.38 (2H, t, J=7.3 Hz), 6.52 (1H, dd, J=3.3, 1.8 Hz), 6.73-6.77 (2H, m), 7.23-7.27 (1H, m), 7.53 (1H, d, J=1.4 Hz), 7.85 (1H, d, J=9.8 Hz), 7.92-7.96 (1H, s), 8.28 (1H, d, J=2.2 Hz), 8.44 (1H, d, J=2.0 Hz), 8.82 (1H, d, J=2.0 Hz)

Example 148

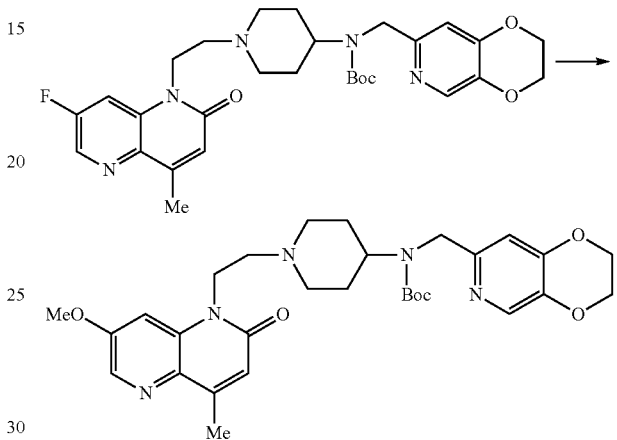

To a solution of 72 mg of tert-butyl (2,3-dihydro(1,4)dioxino(2,3-c)pyridin-7-ylmethyl)(1-(2-(7-fluoro-4-methyl-2-oxo-1,5-naphthyridin-1(2H)-yl)ethyl)piperidin-4-yl)carbamate in 2.5 mL of methanol, 77 mg of a 28% sodium methoxide/methanol solution was added at room temperature, and the mixture was heated under reflux while stirring for 2 hours. After cooling to room temperature, water and chloroform were added to the reaction mixture, the organic layer was separated, and the aqueous layer was extracted with chloroform. The organic layer and the extract were combined, the resultant solution was washed with a saturated aqueous sodium chloride solution and dried over anhydrous magnesium sulfate, and the solvent was distilled off under reduced pressure. The resultant residue was purified by basic silica gel column chromatography using an eluent of chloroform to obtain 82 mg of tert-butyl (2,3-dihydro(1,4)dioxino(2,3-c)pyridin-7-ylmethyl)(1-(2-(7-methoxy-4-methyl-2-oxo-1,5-naphthyridin-1(2H)-yl)ethyl)piperidin-4-yl)carbamate as a light brown oily substance.

¹H-NMR (CDCl₃) δ: 1.32-1.72 (13H, m), 2.07-2.25 (2H, m), 2.51 (3H, d, J=1.0 Hz), 2.56-2.62 (2H, m), 2.96-3.05 (2H, m), 3.95 (3H, s), 4.05-4.17 (1H, m), 4.25-4.45 (8H, m), 6.62 (1H, d, J=1.0 Hz), 6.71-6.76 (1H, m), 7.16 (1H, d, J=2.4 Hz), 8.05 (1H, s), 8.28 (1H, d, J=2.4 Hz)

Example 149

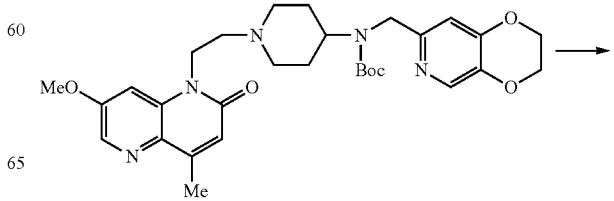

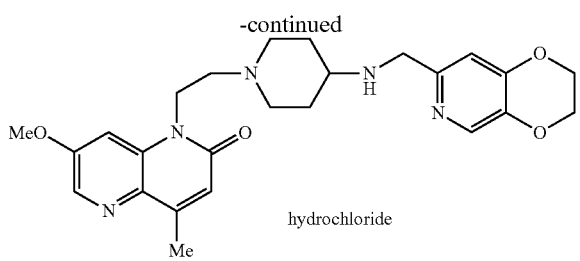

By the same technique as in Example 4, 1-(2-(4-((2,3-dihydro(1,4)dioxino(2,3-c)pyridin-7-ylmethyl)amino)piperidin-1-yl)ethyl)-7-methoxy-4-methyl-1,5-naphthyridin-2(1H)-one hydrochloride was obtained from tert-butyl (2,3-dihydro(1,4)dioxino(2,3-c)pyridin-7-ylmethyl)(1-(2-(7-methoxy-4-methyl-2-oxo-1,5-naphthyridin-1(2H)-yl)ethyl)piperidin-4-yl)carbamate.

$^1$H-NMR (D$_2$O) δ: 1.98-2.14 (2H, m), 2.50-2.61 (2H, m), 2.54 (3H, s), 3.20-3.35 (2H, m), 3.58-3.66 (2H, m), 3.68-3.79 (1H, m), 3.95-4.09 (2H, m), 4.05 (3H, s), 4.45-4.50 (2H, m), 4.51 (2H, s), 4.56-4.62 (2H, m), 4.71-4.89 (2H, m), 6.77-6.80 (1H, m), 7.43 (1H, s), 7.46 (1H, d, J=2.3 Hz), 8.35 (1H, s), 8.38 (1H, d, J=2.3 Hz)

Example 150

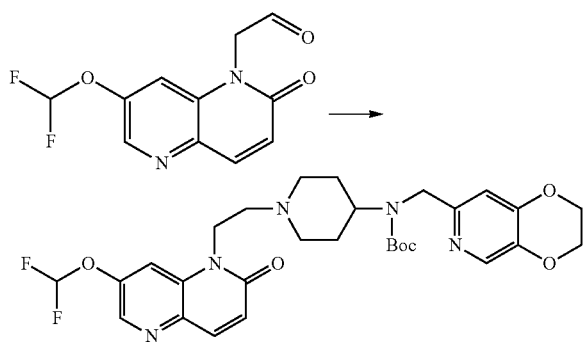

By the same technique as in Example 1, tert butyl (1-(2-(7-(difluoromethoxy)-2-oxo-1,5-naphthyridin-1(2H)-yl)ethyl)piperidin-4-yl)(2,3-dihydro(1,4)dioxino(2,3-c)pyridin-7-ylmethyl)carbamate was obtained from (7-(difluoromethoxy)-2-oxo-1,5-naphthyridin-1(2H)-yl)acetaldehyde and tert-butyl (2,3-dihydro(1,4)dioxino(2,3-c)pyridin-7-ylmethyl)(piperidin-4-yl)carbamate.

$^1$H-NMR (CDCl$_3$) δ: 1.30-1.70 (13H, m), 2.08-2.26 (2H, m), 2.58-2.65 (2H, m), 2.92-3.01 (2H, m), 4.00-4.18 (1H, m), 4.22-4.48 (8H, m), 6.70 (1H, t, J=72.1 Hz), 6.73 (1H, s), 6.86 (1H, d, J=9.9 Hz), 7.58 (1H, d, J=2.1 Hz), 7.88 (1H, d, J=9.8 Hz), 8.05 (1H, s), 8.41 (1H, d, J=2.1 Hz)

Example 151

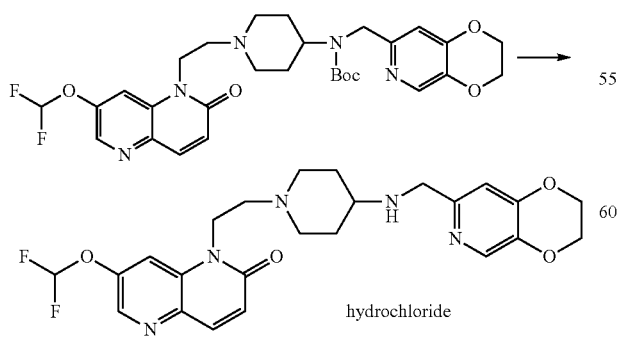

By the same technique as in Example 4, 7-(difluoromethoxy)-1-(2-(4-((2,3-dihydro(1,4)dioxino(2,3-c)pyridin-7-ylmethyl)amino)piperidin-1-yl)ethyl)-1,5-naphthyridin-2(1H)-one hydrochloride was obtained from tert-butyl (1-(2-(7-(difluoromethoxy)-2-oxo-1,5-naphthyridin-1(2H)-yl)ethyl)piperidin-4-yl)(2,3-dihydro(1,4)dioxino(2,3-c)pyridin-7-ylmethyl)carbamate.

$^1$H-NMR (D$_2$O) δ: 1.99-2.14 (2H, m), 2.50-2.60 (2H, m), 3.22-3.34 (2H, m), 3.59-3.78 (3H, m), 3.96-4.06 (2H, m), 4.44-4.50 (2H, m), 4.48 (2H, s), 4.54-4.60 (2H, m), 4.70-4.88 (2H, m), 7.01 (1H, d, J=9.8 Hz), 7.06 (1H, t, J=72.2 Hz), 7.39 (1H, s), 7.87 (1H, d, J=2.1 Hz), 8.10 (1H, d, J=9.8 Hz), 8.33 (1H, s), 8.57 (1H, d, J=2.1 Hz)

Example 152

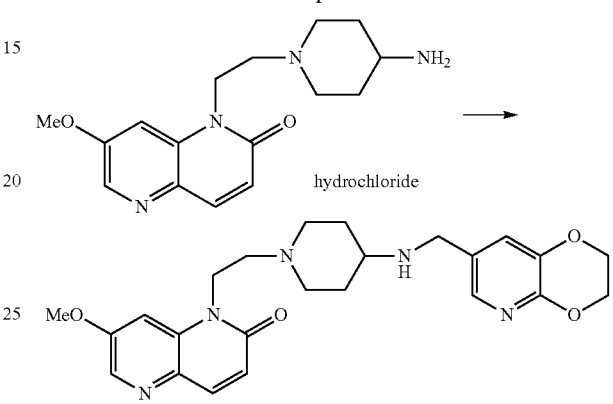

To a suspension of 86 mg of 1-(2-(4-aminopiperidin-1-yl)ethyl)-7-methoxy-1,5-naphthyridin-2(1H)-one hydrochloride in 4 mL of methanol, 33 mg of 1,5-naphthyridine-3-carbaldehyde, 0.12 g of a 28% sodium methoxide/methanol solution and 12 μL of acetic acid were added. Then, 26 mg of sodium cyanoborohydride was added thereto, and the mixture was stirred at room temperature for 4 hours. To the reaction mixture, chloroform, a saturated aqueous sodium hydrogen carbonate solution and water were added. The organic layer was separated and the aqueous layer was extracted with chloroform. The organic layer and the extract were combined, the resultant solution was washed with water and a saturated aqueous sodium chloride solution and dried over anhydrous magnesium sulfate, and the solvent was distilled off under reduced pressure. The resultant residue was purified by basic silica gel column chromatography using gradient elution with chloroform:methanol=87:13 to 85:15 to obtain 11 mg of 7-methoxy-1-(2-(4-(((1,5-naphthyridin-3-ylmethyl)amino)piperidin-1-yl)ethyl)-1,5-naphthyridin-2(1H)-one as a light yellow oily substance.

$^1$H-NMR (CDCl$_3$) δ: 1.42-1.53 (2H, m), 1.93-2.00 (2H, m), 2.14-2.26 (2H, m), 2.56-2.69 (3H, m), 2.96-3.40 (2H, m), 3.98 (3H, s), 4.10 (2H, s), 4.35-4.39 (2H, m), 6.74 (1H, d, J=9.8 Hz), 7.21-7.25 (1H, m), 7.62 (1H, dd, J=8.5, 4.3 Hz), 7.84 (1H, d, J=9.8 Hz), 8.28 (1H, d, J=2.4 Hz), 8.31-8.34 (1H, m), 8.38-8.42 (1H, m), 8.97 (1H, dd, J=4.3, 1.6 Hz), 8.99 (1H, d, J=2.0 Hz)

Example 153

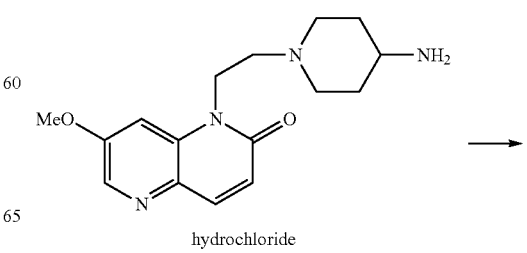

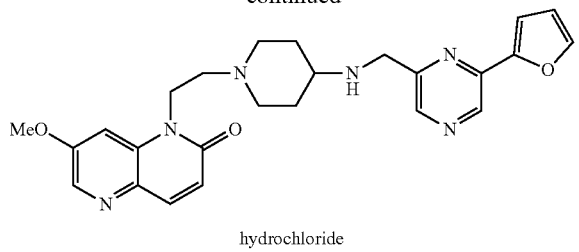

hydrochloride

By the same technique as in Example 103, 1-(2-(4-(((6-(2-furyl)pyrazin-2-yl)methyl)amino)piperidin-1-yl)ethyl)-7-methoxy-1,5-naphthyridin-2(1H)-one hydrochloride was obtained from 1-(2-(4-aminopiperidin-1-yl)ethyl)-7-methoxy-1,5-naphthyridin-2(1H)-one hydrochloride and 6-(2-furyl)pyrazine-2-carbaldehyde.

$^1$H-NMR (CD$_3$OD) δ: 2.06-2.20 (2H, m), 2.46-2.59 (2H, m), 3.04-3.70 (5H, m), 3.85-4.01 (2H, m), 4.08 (3H, s), 4.59 (2H, s), 4.70-5.08 (2H, m), 6.70 (1H, dd, J=3.6, 1.8 Hz), 6.80 (1H, d, J=9.6 Hz), 7.40 (1H, d, J=3.6 Hz), 7.53-7.59 (1H, m), 7.79-7.82 (1H, m), 7.99 (1H, d, J=9.6 Hz), 8.34 (1H, d, J=2.2 Hz), 8.58 (1H, s), 9.02 (1H, s)

Example 154

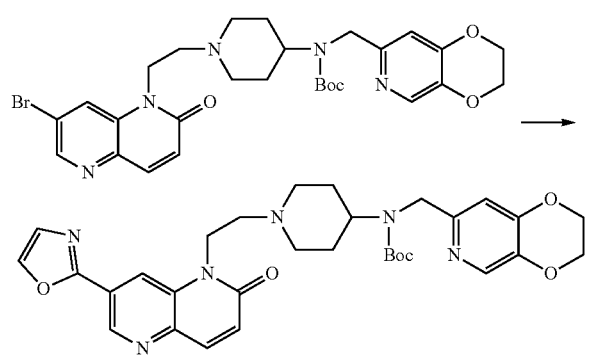

To a solution of 0.10 g of tert-butyl (1-(2-(7-bromo-2-oxo-1,5-naphthyridin-1(2H)-yl)ethyl)piperidin-4-yl)(2,3-dihydro(1,4)dioxino(2,3-c)pyridin-7-ylmethyl)carbamate in 2 mL of dioxane, 90 mg of 2-tributylstannyloxazole and 17 mg of bis(tri-tert-butylphosphine)palladium(0) were added under a nitrogen atmosphere, and the mixture was heated under reflux while stirring for 6 hours 30 minutes. The resultant residue was purified by flash silica gel column chromatography using gradient elution with chloroform:methanol=98:2 to 95:5 to obtain 87 mg of tert-butyl (2,3-dihydro(1,4)dioxino(2,3-c)pyridin-7-ylmethyl)(1-(2-(7-(1,3-oxazol-2-yl)-2-oxo-1,5-naphthyridin-1(2H)-yl)ethyl)piperidin-4-yl)carbamate as a yellow oily substance.

$^1$H-NMR (CDCl$_3$) δ: 1.30-1.86 (13H, m), 2.12-2.25 (2H, m), 2.67 (2H, t, J=6.7 Hz), 2.97-3.06 (2H, m), 4.00-4.42 (9H, m), 6.71 (1H, s), 6.95 (1H, d, J=9.8 Hz), 7.34 (1H, s), 7.86 (1H, s), 7.93 (1H, d, J=9.8 Hz), 8.05 (1H, s), 8.44 (1H, s), 9.18 (1H, d, J=1.5 Hz)

Example 155

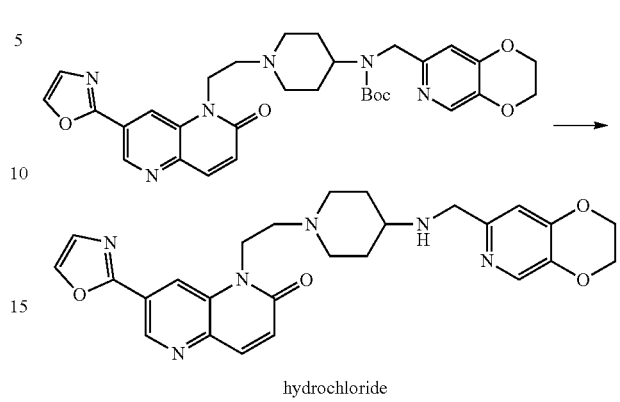

hydrochloride

By the same technique as in Example 2, 1-(2-(4-((2,3-dihydro(1,4)dioxino(2,3-c)pyridin-7-ylmethyl)amino)piperidin-1-yl)ethyl)-7-(1,3-oxazol-2-yl)-1,5-naphthyridin-2(1H)-one hydrochloride was obtained from tert-butyl (2,3-dihydro(1,4)dioxino(2,3-c)pyridin-7-ylmethyl)(1-(2-(7-(1,3-oxazol-2-yl)-2-oxo-1,5-naphthyridin-1(2H)-yl)ethyl)piperidin-4-yl)carbamate.

$^1$H-NMR (D$_2$O) δ: 2.00-2.15 (2H, m), 2.50-2.60 (2H, m), 3.24-3.36 (2H, m), 3.63-3.76 (3H, m), 3.95-4.15 (2H, m), 4.42-4.58 (6H, m), 4.70-4.95 (2H, m), 7.10 (1H, d, J=9.8 Hz), 7.35 (1H, s), 7.45 (1H, s), 8.10 (1H, s), 8.14 (1H, d, J=9.8 Hz), 8.31 (1H, s), 8.56 (1H, s), 9.19 (1H, d, J=1.5 Hz)

Example 156

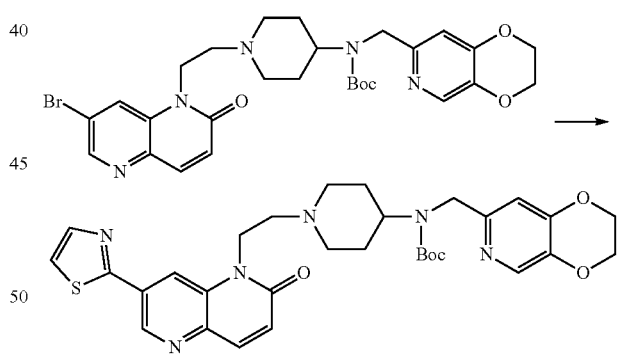

By the same technique as in Example 154, tert-butyl (2,3-dihydro(1,4)dioxino(2,3-c)pyridin-7-ylmethyl)(1-(2-(2-oxo-7-(1,3-thiazol-2-yl)-1,5-naphthyridin-1(2H)-yl)ethyl)piperidin-4-yl)carbamate was obtained from tert-butyl (1-(2-(7-bromo-2-oxo-1,5-naphthyridin-1(2H)-yl)ethyl)piperidin-4-yl)(2,3-dihydro(1,4)dioxino(2,3-c)pyridin-7-ylmethyl)carbamate.

$^1$H-NMR (CDCl$_3$) δ: 1.12-1.90 (13H, m), 2.10-2.23 (2H, m), 2.62-2.75 (2H, m), 2.98-3.08 (2H, m), 4.20-4.48 (9H, m), 6.70 (1H, s), 6.94 (1H, d, J=9.8 Hz), 7.46-7.52 (1H, m), 7.92 (1H, d, J=9.8 Hz), 7.95-7.99 (1H, m), 8.04 (1H, s), 8.42 (1H, s), 9.05 (1H, s)

Example 157

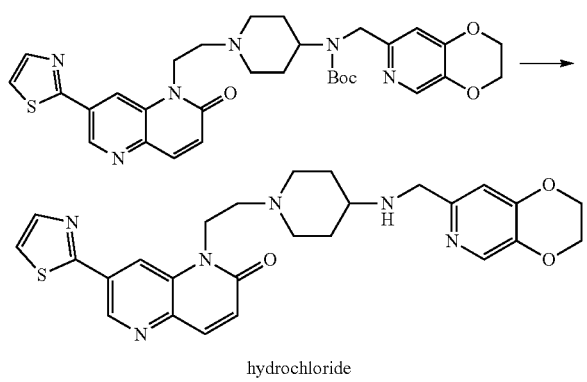

By the same technique as in Example 2, 1-(2-(4-((2,3-dihydro(1,4)dioxino(2,3-c)pyridin-7-ylmethyl)amino)piperidin-1-yl)ethyl)-7-(1,3-thiazol-2-yl)-1,5-naphthyridin-2(1H)-one hydrochloride was obtained from tert-butyl (2,3-dihydro(1,4)dioxino(2,3-c)pyridin-7-ylmethyl)(1-(2-(2-oxo-7-(1,3-thiazol-2-yl)-1,5-naphthyridin-1(2H)-yl)ethyl)piperidin-4-yl)carbamate.

$^1$H-NMR (D$_2$O) δ: 2.03-2.18 (2H, m), 2.53-2.64 (2H, m), 3.24-3.39 (2H, m), 3.62-3.84 (3H, m), 3.99-4.10 (2H, m), 4.48-4.64 (6H, m), 4.70-4.90 (2H, m), 7.09 (1H, d, J=9.9 Hz), 7.54 (1H, s), 7.84 (1H, d, J=3.2 Hz), 8.05 (1H, d, J=3.2 Hz), 8.12 (1H, d, J=9.9 Hz), 8.41 (1H, s), 8.48 (1H, s), 9.08 (1H, d, J=1.5 Hz)

Example 158

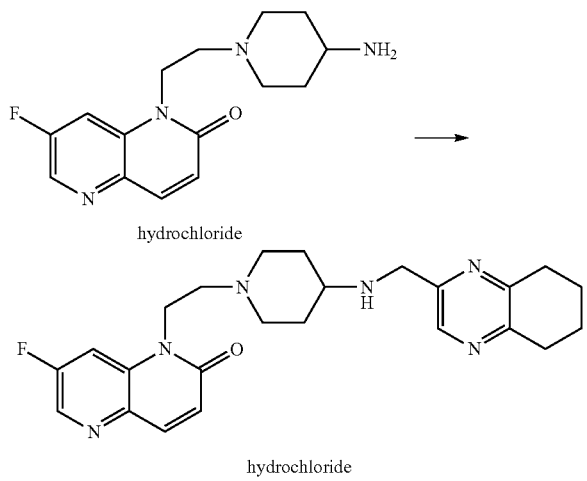

By the same technique as in Example 103, 7-fluoro-1-(2-(4-((5,6,7,8-tetrahydroquinoxalin-2-ylmethyl)amino)piperidin-1-yl)ethyl)-1,5-naphthyridin-2(1H)-one hydrochloride was obtained from 1-(2-(4-aminopiperidin-1-yl)ethyl)-7-fluoro-1,5-naphthyridin-2(1H)-one hydrochloride and 5,6,7,8-tetrahydroquinoxaline-2-carbaldehyde.

$^1$H-NMR (D$_2$O) δ: 1.89-1.97 (4H, m), 2.04-2.15 (2H, m), 2.52-2.62 (2H, m), 2.94-3.01 (4H, m), 3.20-3.36 (2H, m), 3.63 (2H, t, J=6.0 Hz), 3.68-3.78 (1H, m), 3.97-4.07 (2H, m), 4.49 (2H, s), 4.75-5.00 (2H, m), 7.00 (1H, d, J=9.8 Hz), 7.96 (1H, d, J=10.5 Hz), 8.10 (1H, d, J=9.8 Hz), 8.40 (1H, s), 8.57 (1H, s)

Example 159

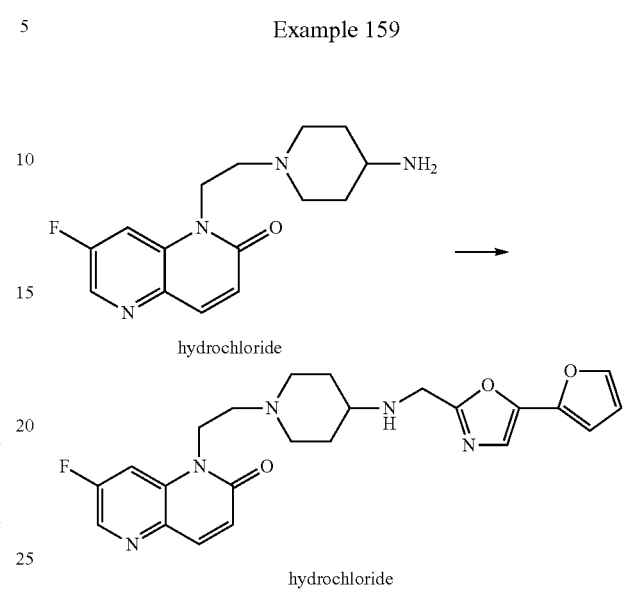

By the same technique as in Example 134, 7-fluoro-1-(2-(4-(((5-(2-furyl)-1,3-oxazol-2-yl)methyl)amino)piperidin-1-yl)ethyl)-1,5-naphthyridin-2(1H)-one hydrochloride was obtained from 1-(2-(4-aminopiperidin-1-yl)ethyl)-7-fluoro-1,5-naphthyridin-2(1H)-one hydrochloride and 5-(2-furyl)-1,3-oxazole-2-carbaldehyde.

$^1$H-NMR (D$_2$O) δ: 2.00-2.14 (2H, m), 2.50-2.60 (2H, m), 3.20-3.34 (2H, m), 3.63 (2H, t, J=6.1 Hz), 3.68-3.80 (1H, m), 3.98-4.06 (2H, m), 4.62 (2H, s), 4.70-4.88 (2H, m), 6.60-6.70 (1H, m), 6.85 (1H, d, J=3.4 Hz), 6.99 (1H, d, J=9.8 Hz), 7.40 (1H, s), 7.65 (1H, s), 7.95 (1H, d, J=9.8 Hz), 8.10 (1H, d, J=9.8 Hz), 8.56 (1H, s)

Example 160

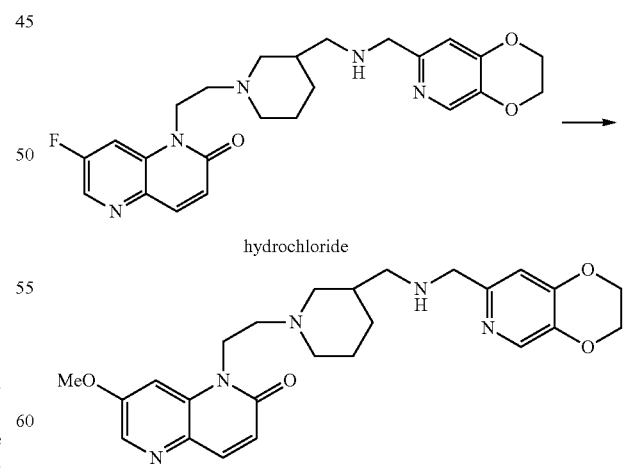

By the same technique as in Example 117, 1-(2-(3-(((2,3-dihydro(1,4)dioxino(2,3-c)pyridin-7-ylmethyl)amino)methyl)piperidin-1-yl)ethyl)-7-methoxy-1,5-naphthyridin-2(1H)-one was obtained from 1-(2-(3-(((2,3-dihydro(1,4)

dioxino(2,3-c)pyridin-7-ylmethyl)amino)methyl)piperidin-1-yl)ethyl)-7-fluoro-1,5-naphthyridin-2(1H)-one hydrochloride.

$^1$H-NMR (CDCl$_3$) δ: 0.90-1.04 (1H, m), 1.48-2.18 (6H, m), 2.47-2.54 (2H, m), 2.60-2.68 (2H, m), 2.89-2.98 (1H, m), 3.01-3.09 (1H, m), 3.74 (2H, s), 3.97 (3H, s), 4.24-4.43 (6H, m), 6.74 (1H, d, J=9.8 Hz), 6.81 (1H, s), 7.27-7.28 (1H, m), 7.84 (1H, d, J=9.8 Hz), 8.10 (1H, s), 8.27 (1H, d, J=2.4 Hz)

Example 161

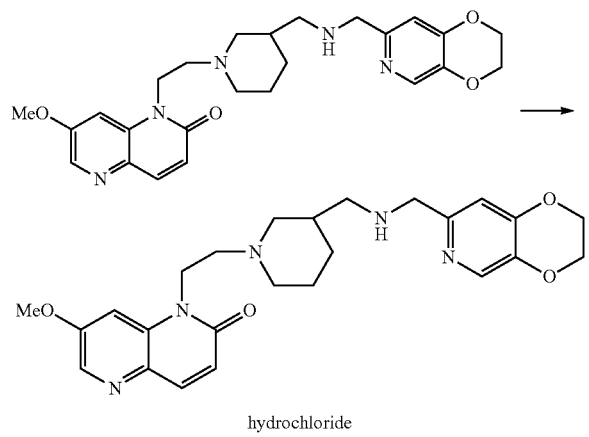

hydrochloride

By the same technique as in Example 8, 1-(2-(3-(((2,3-dihydro(1,4)dioxino(2,3-c)pyridin-7-ylmethyl)amino)methyl)piperidin-1-yl)ethyl)-7-methoxy-1,5-naphthyridin-2(1H)-one hydrochloride was obtained from 1-(2-(3-(((2,3-dihydro(1,4)dioxino(2,3-c)pyridin-7-ylmethyl)amino)methyl)piperidin-1-yl)ethyl)-7-methoxy-1,5-naphthyridin-2(1H)-one.

$^1$H-NMR (D$_2$O) δ: 1.33-1.50 (1H, m), 1.76-1.94 (1H, m), 1.99-2.17 (2H, m), 2.32-2.47 (1H, m), 2.88-3.13 (2H, m), 3.16-3.31 (2H, m), 3.54-3.68 (2H, m), 3.75-3.85 (1H, m), 3.95-4.04 (1H, m), 4.06 (3H, s), 4.44-4.65 (6H, m), 4.70-4.90 (2H, m), 6.91 (1H, d, J=9.8 Hz), 7.51 (1H, s), 7.55 (1H, d, J=2.3 Hz), 8.07 (1H, d, J=9.8 Hz), 8.38 (1H, s), 8.43 (1H, d, J=2.3 Hz)

Example 162

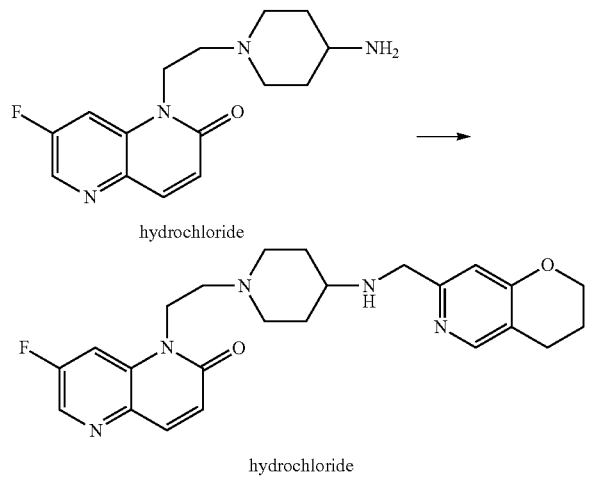

hydrochloride

By the same technique as in Example 103, 1-(2-(4-((3,4-dihydro-2H-pyrano(3,2-c)pyridin-7-ylmethyl)amino)piperidin-1-yl)ethyl)-7-fluoro-1,5-naphthyridin-2(1H)-one hydrochloride was obtained from 1-(2-(4-aminopiperidin-1-yl)ethyl)-7-fluoro-1,5-naphthyridin-2(1H)-one hydrochloride and 3,4-dihydro-2H-pyrano(3,2-c)pyridine-7-carbaldehyde.

$^1$H-NMR (D$_2$O) δ: 2.00-2.15 (4H, m), 2.50-2.64 (2H, m), 2.92 (2H, t, J=6.4 Hz), 3.24-3.36 (2H, m), 3.64 (2H, t, J=5.9 Hz), 3.68-3.80 (1H, m), 3.96-4.07 (2H, m), 4.51-4.59 (4H, m), 4.70-4.90 (2H, m), 7.00 (1H, d, J=9.8 Hz), 7.38 (1H, s), 7.96 (1H, dd, J=10.4, 2.2 Hz), 8.11 (1H, d, J=9.8 Hz), 8.44 (1H, s), 8.57 (1H, d, J=2.2 Hz)

Example 163

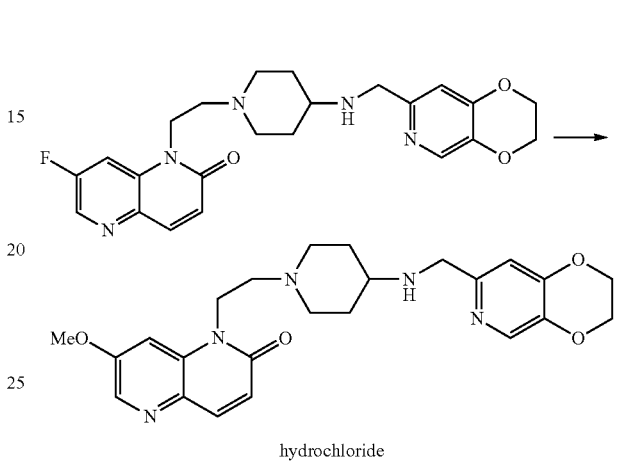

hydrochloride

By the same technique as in Example 144, 1-(2-(4-((3,4-dihydro-2H-pyrano(3,2-c)pyridin-7-ylmethyl)amino)piperidin-1-yl)ethyl)-7-methoxy-1,5-naphthyridin-2(1H)-one hydrochloride was obtained from 1-(2-(4-((3,4-dihydro-2H-pyrano(3,2-c)pyridin-7-ylmethyl)amino)piperidin-1-yl)ethyl)-7-fluoro-1,5-naphthyridin-2(1H)-one.

$^1$H-NMR (D$_2$O) δ: 2.00-2.15 (4H, m), 2.50-2.61 (2H, m), 2.92 (2H, t, J=6.2 Hz), 3.21-3.36 (2H, m), 3.64 (2H, t, J=5.9 Hz), 3.68-3.79 (1H, m), 3.98-4.08 (2H, m), 4.05 (3H, s), 4.51-4.58 (2H, m), 4.56 (2H, s), 4.77-4.90 (2H, m), 6.88 (1H, d, J=9.6 Hz), 7.37 (1H, s), 7.48 (1H, s), 8.06 (1H, d, J=9.6 Hz), 8.41 (1H, s), 8.44 (1H, s)

Example 164

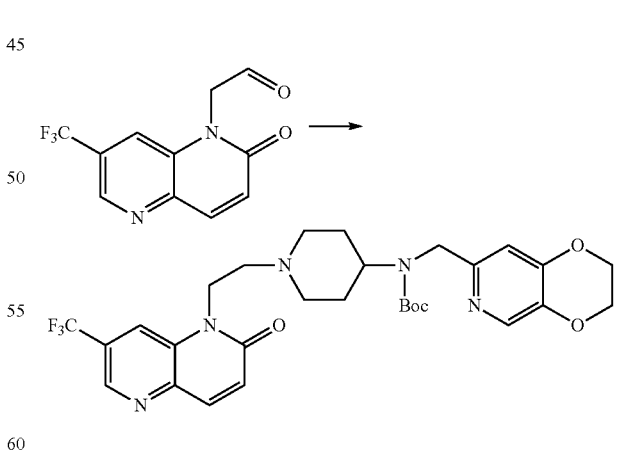

By the same technique as in Example 1, tert-butyl (2,3-dihydro(1,4)dioxino(2,3-c)pyridin-7-ylmethyl)(1-(2-(2-oxo-7-(trifluoromethyl)-1,5-naphthyridin-1(2H)-yl)ethyl)piperidin-4-yl)carbamate was obtained from (2-oxo-7-(trifluoromethyl)-1,5-naphthyridin-1(2H)-yl)acetaldehyde and tert-butyl (2,3-dihydro(1,4)dioxino(2,3-c)pyridin-7-ylmethyl)(piperidin-4-yl)carbamate.

¹H-NMR (CDCl₃) δ: 1.33-1.71 (13H, m), 2.10-2.26 (2H, m), 2.63 (2H, t, J=6.6 Hz), 2.93-3.01 (2H, m), 4.07-4.18 (1H, m), 4.25-4.37 (8H, m), 6.71 (1H, s), 7.02 (1H, d, J=9.8 Hz), 7.95 (1H, d, J=9.8 Hz), 8.02 (1H, s), 8.05 (1H, s), 8.75 (1H, s)

Example 165

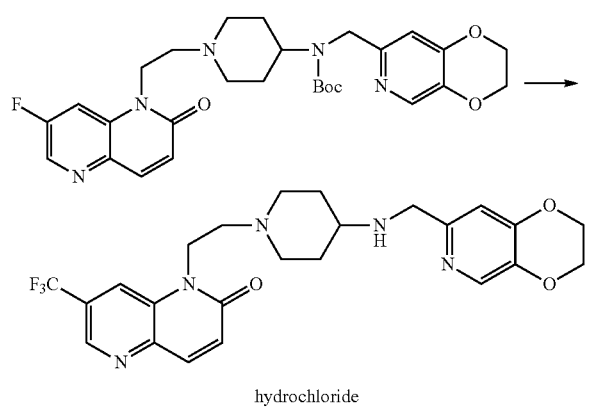

To a solution of 80 mg of tert-butyl (2,3-dihydro(1,4)dioxino(2,3-c)pyridin-7-ylmethyl)(1-(2-(2-oxo-7-(trifluoromethyl)-1,5-naphthyridin-1(2H)-yl)ethyl)piperidin-4-yl)carbamate in 1.4 mL of isopropyl alcohol, 57 μL of concentrated hydrochloric acid was added, and the mixture was heated under reflux while stirring for 1 hour 30 minutes. The reaction mixture was cooled to room temperature, and the solid was filtered off to obtain 70 mg of 1-(2-(4-((2,3-dihydro(1,4)dioxino(2,3-c)pyridin-7-ylmethyl)amino)piperidin-1-yl)ethyl)-7-(trifluoromethyl)-1,5-naphthyridin-2(1H)-one hydrochloride as a light brown solid.

¹H-NMR (D₂O) δ: 1.94-2.07 (2H, m), 2.44-2.52 (2H, m), 3.10-3.20 (2H, m), 3.50-3.63 (3H, m), 3.87-3.94 (2H, m), 4.29 (2H, s), 4.36-4.46 (4H, m), 4.75-4.85 (2H, m), 7.09 (1H, s), 7.17 (1H, d, J=10.0 Hz), 8.14-8.19 (2H, m), 8.39 (1H, s), 8.93 (1H, s)

Example 166

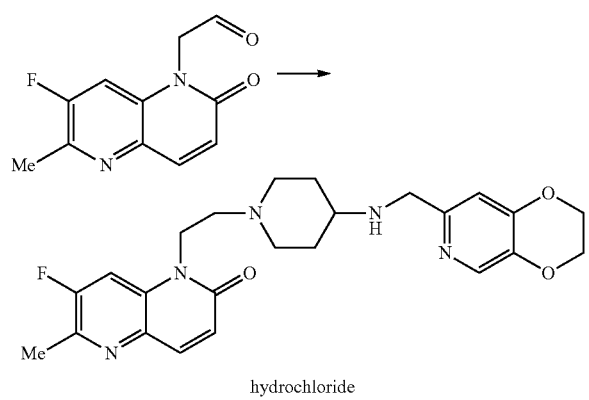

By the same technique as in Example 3, tert-butyl (2,3-dihydro(1,4)dioxino(2,3-c)pyridin-7-ylmethyl)(1-(2-(7-fluoro-6-methyl-2-oxo-1,5-naphthyridin-1(2H)-yl)ethyl)piperidin-4-yl)carbamate was obtained from (7-fluoro-6-methyl-2-oxo-1,5-naphthyridin-1(2H)-yl)acetaldehyde and tert-butyl (2,3-dihydro(1,4)dioxino(2,3-c)pyridin-7-ylmethyl)(piperidin-4-yl)carbamate.

¹H-NMR (CDCl₃) δ: 1.25-1.70 (13H, m), 2.05-2.25 (2H, m), 2.50-2.61 (2H, m), 2.58 (3H, d, J=2.9 Hz), 2.95-3.00 (2H, m), 4.01-4.20 (1H, m), 4.23-4.40 (8H, m), 6.72 (1H, s), 6.81 (1H, d, J=9.8 Hz), 7.41 (1H, d, J=10.7 Hz), 7.81 (1H, d, J=9.8 Hz), 8.05 (1H, s)

Example 167

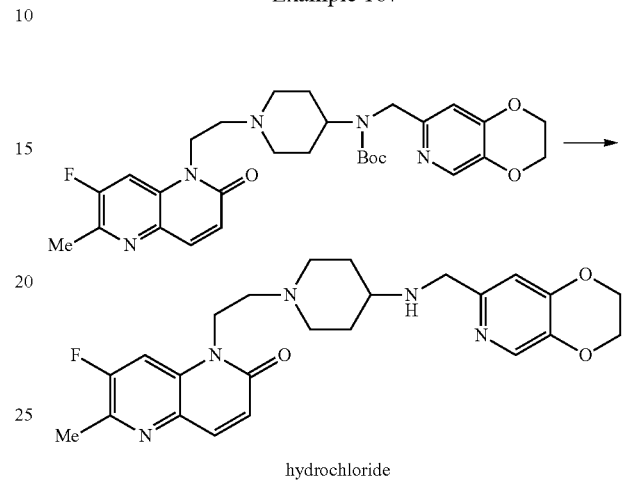

To a solution of 0.48 g of tert-butyl (2,3-dihydro(1,4)dioxino(2,3-c)pyridin-7-ylmethyl)(1-(2-(7-fluoro-6-methyl-2-oxo-1,5-naphthyridin-1(2H)-yl)ethyl)piperidin-4-yl)carbamate in 4.7 mL of isopropyl alcohol, 0.44 mL of concentrated hydrochloric acid was added, the temperature was increased to 60° C. and the mixture was stirred for 3 hours. The reaction mixture was cooled to room temperature, and the solid was filtered off to obtain 0.33 g of 1-(2-(4-((2,3-dihydro(1,4)dioxino(2,3-c)pyridin-7-ylmethyl)amino)piperidin-1-yl)ethyl)-7-fluoro-6-methyl-1,5-naphthyridin-2(1H)-one hydrochloride as a white solid.

¹H-NMR (D₂O) δ: 1.99-2.14 (2H, m), 2.49-2.61 (2H, m), 2.59 (3H, d, J=2.4 Hz), 3.19-3.34 (2H, m), 3.56-3.74 (3H, m), 3.94-4.04 (2H, m), 4.39 (2H, s), 4.39-4.54 (4H, m), 4.73 (2H, t, J=6.0 Hz), 6.96 (1H, d, J=9.9 Hz), 7.23 (1H, s), 7.88 (1H, d, J=10.5 Hz), 8.02 (1H, d, J=9.9 Hz), 8.23 (1H, s)

Example 168

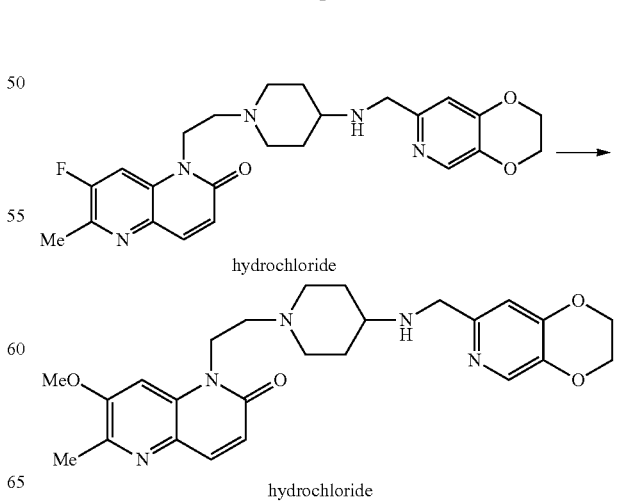

To 0.16 g of 1-(2-(4-((2,3-dihydro(1,4)dioxino(2,3-c)pyridin-7-ylmethyl)amino)piperidin-1-yl)ethyl)-7-fluoro-6-methyl-1,5-naphthyridin-2(1H)-one hydrochloride, chloroform and a saturated aqueous sodium hydrogen carbonate solution were added, the organic layer was separated and the aqueous layer was extracted with chloroform. The organic layer and the extract were combined, the resultant solution was dried over anhydrous magnesium sulfate, and the solvent was distilled off under reduced pressure. To the residue, 2.6 mL of methanol and 0.15 mL of a 28% sodium methoxide/methanol solution were added, and the mixture was heated under reflux while stirring for 2 hours. The reaction mixture was cooled to room temperature, thereto were added chloroform and a saturated aqueous sodium hydrogen carbonate solution, the organic layer was separated, and the aqueous layer was extracted with chloroform. The organic layer and the extract were combined, the resultant solution was dried over anhydrous magnesium sulfate, and the solvent was distilled off under reduced pressure. To the resultant residue, 1.4 mL of isopropyl alcohol and 93 μL of concentrated hydrochloric acid were added, and the mixture was stirred at room temperature for 30 minutes. The reaction mixture was cooled with ice, and the solid was filtered off to obtain 0.15 g of 1-(2-(4-((2,3-dihydro(1,4)dioxino(2,3-c)pyridin-7-ylmethyl)amino)piperidin-1-yl)ethyl)-7-methoxy-6-methyl-1,5-naphthyridin-2(1H)-one hydrochloride as a white solid.

$^1$H-NMR (D$_2$O) δ: 1.95-2.15 (2H, m), 2.50-2.60 (2H, m), 2.59 (3H, s), 3.30-3.35 (2H, m), 3.60-3.75 (3H, m), 3.95-4.10 (2H, m), 4.09 (3H, s), 4.38-4.55 (6H, m), 4.75-4.85 (2H, m), 6.91 (1H, d, J=9.8 Hz), 7.27 (1H, s), 7.49 (1H, s), 8.04 (1H, d, J=9.8 Hz), 8.26 (1H, s)

Example 169

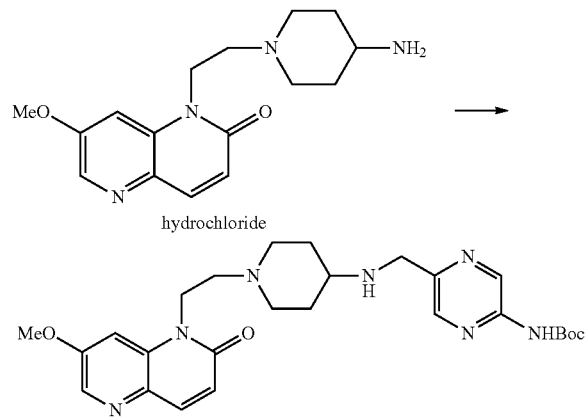

By the same technique as in Example 78, tert-butyl (5-(((1-(2-(7-methoxy-2-oxo-1,5-naphthyridin-1(2H)-yl)ethyl)piperidin-4-yl)amino)methyl)pyrazin-2-yl)carbamate was obtained from 1-(2-(4-aminopiperidin-1-yl)ethyl)-7-methoxy-1,5-naphthyridin-2(1H)-one hydrochloride and tert-butyl (5-formylpyrazin-2-yl)carbamate.

$^1$H-NMR (CDCl$_3$) δ: 1.40-1.60 (11H, m), 1.87-1.97 (2H, m), 2.13-2.25 (2H, m), 2.49-2.58 (1H, m), 2.61-2.70 (2H, m), 2.95-3.05 (2H, m), 3.91 (2H, s), 3.98 (3H, s), 4.33-4.42 (2H, m), 6.74 (1H, d, J=9.6 Hz), 7.15-7.19 (1H, m), 7.84 (1H, d, J=9.6 Hz), 8.20 (1H, s), 8.28 (1H, d, J=2.4 Hz), 9.19 (1H, s)

Example 170

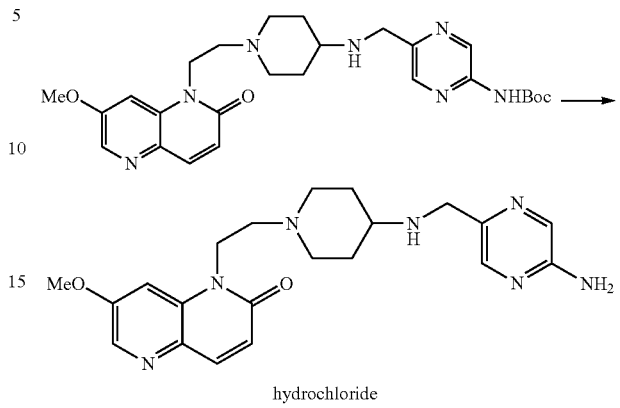

By the same technique as in Example 167, 1-(2-(4-(((5-aminopyrazin-2-yl)methyl)amino)piperidin-1-yl)ethyl)-7-methoxy-1,5-naphthyridin-2(1H)-one hydrochloride was obtained from tert-butyl (5-(((1-(2-(7-methoxy-2-oxo-1,5-naphthyridin-1(2H)-yl)ethyl)piperidin-4-yl)amino)methyl)pyrazin-2-yl)carbamate.

$^1$H-NMR (D$_2$O) δ: 1.97-2.13 (2H, m), 2.49-2.60 (2H, m), 3.19-3.34 (2H, m), 3.57-3.74 (3H, m), 3.96-4.07 (2H, m), 4.04 (3H, s), 4.30-4.38 (2H, m), 4.78-4.80 (2H, m), 6.85-6.91 (1H, m), 7.43-7.52 (1H, m), 7.98-8.32 (2H, m), 8.06 (1H, d, J=9.8 Hz), 8.40 (1H, d, J=2.2 Hz)

Example 171

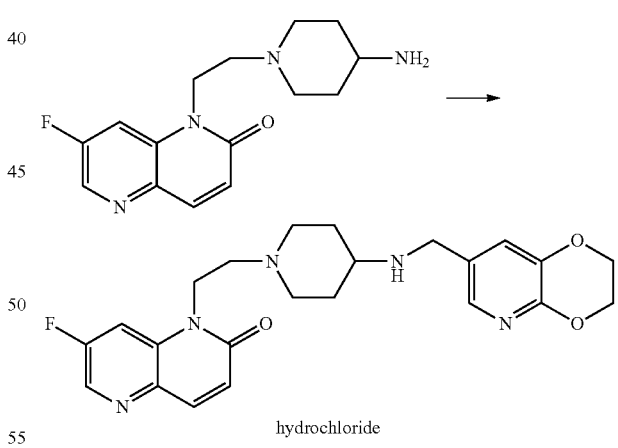

To a solution 211 mg of 1-(2-(4-aminopiperidin-1-yl)ethyl)-7-fluoro-1,5-naphthyridin-2(1H)-one and 120 mg of 2,3-dihydro(1,4)dioxino(2,3-b)pyridine-7-carbaldehyde in 22 mL of chloroform, 88 mg of acetic acid was added, and the mixture was stirred at room temperature for 14 hours. To the reaction mixture, 232 mg of sodium triacetoxyborohydride was added, and the mixture was stirred for 2 hours. Thereto was added a saturated aqueous sodium hydrogen carbonate solution, and the organic layer was separated. The organic layer was washed with a saturated aqueous sodium chloride solution, and dried over anhydrous magnesium sulfate, and the solvent was distilled off under reduced pressure. The resultant residue was purified by silica gel column chromatography using silica gel; Silica Gel 60N made by KANTO CHEMICAL CO., INC., and an eluent of chloroform:methanol=10:1 to obtain 185 mg of 1-(2-(4-((2,3-dihydro(1,4)dioxino(2,3-b)pyridin-7-ylmethyl)amino)piperidin-1-yl)ethyl)-7-fluoro-1,5-naphthyridin-2(1H)-one as a light yellow solid.

To a solution of 185 mg of 1-(2-(4-((2,3-dihydro(1,4)dioxino(2,3-b)pyridin-7-ylmethyl)amino)piperidin-1-yl)ethyl)-7-fluoro-1,5-naphthyridin-2(1H)-one in 4 mL of ethyl acetate, 2 mL of 4 mol/L hydrogen chloride/ethyl acetate was added, and the mixture was stirred at room temperature for 1 hour. The solid was filtered off to obtain 244 mg of 1-(2-(4-((2,3-dihydro(1,4)dioxino(2,3-b)pyridin-7-ylmethyl)amino)piperidin-1-yl)ethyl)-7-fluoro-1,5-naphthyridin-2(1H)-one hydrochloride as a white solid.

$^1$H-NMR (DMSO-$d_6$) δ: 2.01-2.12 (2H, m), 2.34-2.41 (2H, m), 3.17 (2H, s), 3.24-3.35 (3H, m), 3.75-3.82 (2H, m), 4.11-4.17 (2H, m), 4.25-4.30 (2H, m), 4.41-4.45 (2H, m), 4.59-4.65 (2H, m), 6.89 (1H, d, J=9.6 Hz), 7.61-7.67 (1H, m), 7.90-7.95 (1H, m), 8.01 (1H, d, J=9.6 Hz), 8.32-8.39 (1H, m), 8.60-8.65 (1H, m), 9.61-9.76 (3H, m), 10.79-11.02 (1H, m)

Example 172

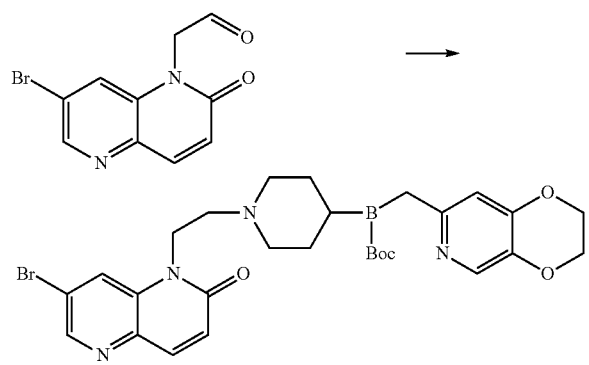

To 7.00 g of (7-bromo-2-oxo-1,5-naphthyridin-1(2H)-yl)acetaldehyde, a solution of 10.07 g of tert-butyl (2,3-dihydro(1,4)dioxino(2,3-c)pyridin-7-ylmethyl)(piperidin-4-yl)carbamate in 140 mL of chloroform and 1.57 g of acetic acid were added, and the mixture was stirred at room temperature for 19 hours, then, 8.77 g of sodium triacetoxyborohydride was added thereto and the mixture was stirred for 2 hours. To the reaction mixture, 140 mL of a saturated aqueous sodium hydrogen carbonate solution was added, the organic layer was separated, then washed with a saturated aqueous sodium chloride solution and dried over anhydrous magnesium sulfate, and the solvent was distilled off under reduced pressure. The resultant residue was purified by silica gel column chromatography using silica gel; Chromatorex-NH made by Fuji Silysia Chemical Ltd., and gradient elution with hexane:ethyl acetate=50:50 to 5:95, and then recrystallized in 24 mL of ethanol to obtain 11.26 g of tert-butyl (1-(2-(7-bromo-2-oxo-1,5-naphthyridin-1(2H)-yl)ethyl)piperidin-4-yl)(2,3-dihydro(1,4)dioxino(2,3-c)pyridin-7-ylmethyl)carbamate as a white solid.

$^1$H-NMR (CDCl$_3$) δ: 1.32-1.55 (9H, m), 1.69 (4H, m), 2.20 (2H, m), 2.62 (2H, t, J=6.6 Hz), 2.97 (2H, d, J=11.5 Hz), 4.12 (1H, s), 4.27 (4H, m), 4.32 (4H, m), 6.72 (1H, s), 6.90 (1H, d, J=9.6 Hz), 7.85 (1H, d, J=9.6 Hz), 8.01 (1H, s), 8.06 (1H, s), 8.54 (1H, d, J=1.4 Hz)

Example 173

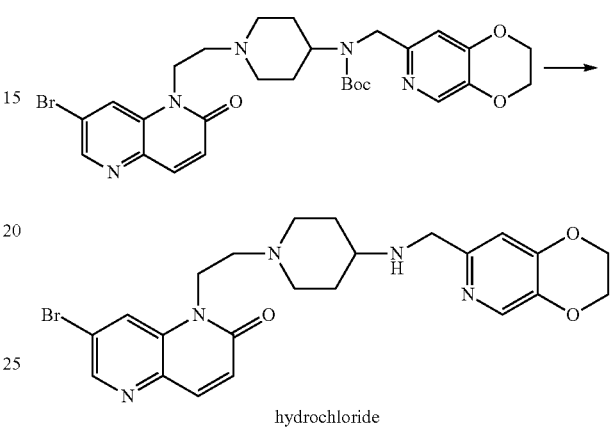

To 0.51 g of tert-butyl (1-(2-(7-bromo-2-oxo-1,5-naphthyridin-1(2H)-yl)ethyl)piperidin-4-yl)(2,3-dihydro(1,4)dioxino(2,3-c)pyridin-7-ylmethyl)carbamate, 18 mL of a 2 mol/L hydrogen chloride/ethanol solution was added at room temperature, the mixture was stirred at room temperature for 59 hours, and at 50° C. for 9 hours, and then, the generated solid was filtered off. Subsequently, the solid was suspended in 3 mL of chloroform, thereto was added 5 mL of trifluoroacetic acid, the mixture was stirred at room temperature for 100 minutes, and then the solvent was distilled off under reduced pressure. The residue was charged with 10 mL of chloroform and 3 mL of water and adjusted to pH 10 with a 2 mol/L aqueous sodium hydroxide solution, and then the organic layer was separated. The aqueous layer was extracted with chloroform twice, and combined with the organic layer, the resultant solution was washed with a saturated aqueous sodium chloride solution and dried over anhydrous magnesium sulfate, and the solvent was distilled off under reduced pressure. The residue was dissolved in 2 mL of ethyl acetate and 3 mL of ethanol, and 10 mL of a 2 mol/L hydrochloric acid/ethanol solution was added thereto, the mixture was stirred for 15 minutes, and the solvent was distilled off under reduced pressure. To the residue, 4 mL of ethyl acetate was added and suspended, and the solid was filtered off to obtain 0.41 g of 7-bromo-1-(2-(4-((2,3-dihydro(1,4)dioxino(2,3-c)pyridin-7-ylmethyl)amino)piperidin-1-yl)ethyl)-1,5-naphthyridin-2(1H)-one hydrochloride as a slightly yellow solid.

$^1$H-NMR (D$_2$O) δ: 2.03-2.15 (2H, m), 2.59 (2H, d, J=13.3 Hz), 3.30 (2H, s), 3.64 (2H, t, J=5.7 Hz), 3.79 (1H, tt, J=11.9, 4.1 Hz), 4.04 (2H, s), 4.51 (2H, dd), 4.59 (2H, s), 4.65 (2H, m), 4.75 (2H, t, J=6.2 Hz), 7.04 (1H, d, J=9.6 Hz), 7.56 (1H, s), 8.05 (1H, d, J=9.6 Hz), 8.37 (1H, d, J=0.9 Hz), 8.42 (1H, s), 8.70 (1H, d, J=1.8 Hz)

Example 174

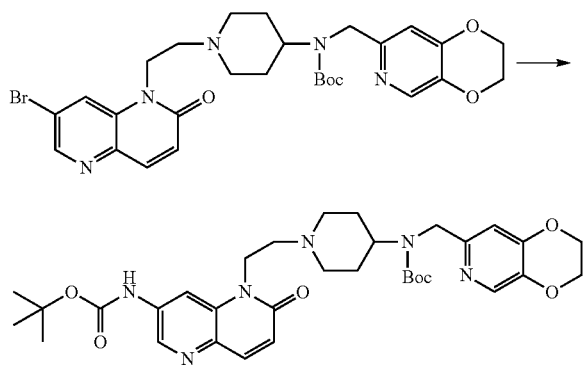

To a solution of 0.85 g of tert-butyl (1-(2-(7-bromo-2-oxo-1,5-naphthyridin-1(2H)-yl)ethyl)piperidin-4-yl)(2,3-dihydro(1,4)dioxino(2,3-c)pyridin-7-ylmethyl)carbamate in 5 mL of 1,4-dioxane, 0.20 g of tert-butyl carbamate, 0.69 g of cesium carbonate and 13 mg of tris(benzylideneacetone)dipalladium and 24 mg of 4,5-bis(diphenylphosphino)-9,9-dimethylxanthene were added, and the mixture was stirred at 90° C. for 38 hours under a nitrogen atmosphere. After cooling to room temperature, the insoluble substance was separated by filtration, and the filtrated solution was concentrated under reduced pressure. The residue was purified by silica gel column chromatography using silica gel; Silica Gel 60 made by KANTO CHEMICAL CO., INC., and an eluent of hexane:ethyl acetate=33:67 to 5:95 to obtain 0.68 g of tert-butyl (1-(2-(7-((tert-butoxycarbonyl)amino)-2-oxo-1,5-naphthyridin-1(2H)-yl)ethyl)piperidin-4-yl)(2,3-dihydro(1,4)dioxino(2,3-c)pyridin-7-ylmethyl)carbamate as a white solid.

$^1$H-NMR (CDCl$_3$) δ: 1.33-1.51 (9H, m), 1.53 (9H, s), 1.55-1.65 (2H, m), 1.78 (2H, s), 2.11-2.26 (2H, m), 2.66 (2H, t, J=7.1 Hz), 3.01 (2H, d, J=10.5 Hz), 4.06-4.15 (1H, m), 4.24-4.29 (2H, m), 4.29-4.37 (5H, m), 4.37-4.44 (1H, m), 6.72 (1H, s), 6.76 (1H, d, J=9.6 Hz), 7.09-7.24 (1H, m), 7.80 (1H, d, J=9.6 Hz), 8.04 (1H, s), 8.25 (1H, d, J=1.4 Hz), 8.32 (1H, s)

Example 175

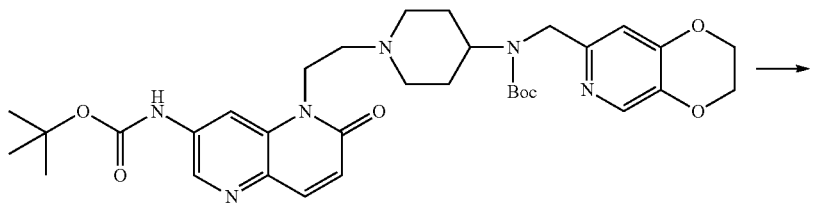

To a solution of 0.66 g of tert-butyl (1-(2-(7-((tert-butoxycarbonyl)amino)-2-oxo-1,5-naphthyridin-1(2H)-yl)ethyl)piperidin-4-yl)(2,3-dihydro(1,4)dioxino(2,3-c)pyridin-7-ylmethyl)carbamate in 8 mL of methanol, 8 mL of a 4 mol/L hydrogen chloride/ethyl acetate solution was added at room temperature, the mixture was stirred for 18 hours, and then the solid was filtered off. Subsequently, the solid was suspended in 3 mL of chloroform, thereto was added 6 mL of trifluoroacetic acid at room temperature, the mixture was stirred for 2 hours, and the solvent was then distilled off under reduced pressure. The residue was charged with chloroform and water and adjusted to pH 9 with a 2 mol/L aqueous sodium hydroxide solution, and the organic layer was separated. The aqueous layer was extracted with chloroform three times and combined with the organic layer, the resultant solution was washed with a saturated aqueous sodium chloride solution and dried over anhydrous magnesium sulfate, and the solvent was distilled off under reduced pressure to obtain 0.31 g of 7-amino-1-(2-(4-((2,3-dihydro(1,4)dioxino(2,3-c)pyridin-7-ylmethyl)amino)piperidin-1-yl)ethyl)-1,5-naphthyridin-2(1H)-one as a white foam.

$^1$H-NMR (CDCl$_3$) δ: 1.44-1.52 (2H, m), 1.94 (2H, d, J=12.4 Hz), 2.20 (2H, t, J=11.0 Hz), 2.51-2.57 (1H, m), 2.60-2.65 (2H, m), 2.98-3.03 (2H, m), 3.80 (2H, s), 4.20 (2H, s), 4.26-4.30 (2H, m), 4.30-4.35 (4H, m), 6.63 (1H, d, J=9.6 Hz), 6.82 (1H, s), 7.00 (1H, d, J=1.8 Hz), 7.76 (1H, d, J=9.6 Hz), 8.03 (1H, d, J=1.8 Hz), 8.11 (1H, s)

Example 176

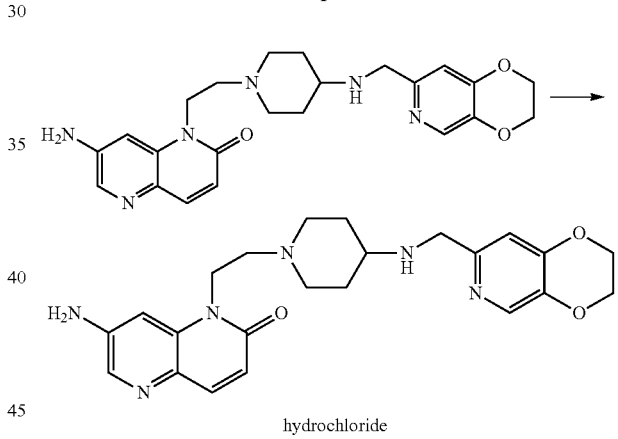

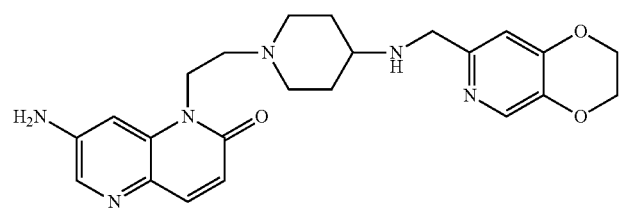

To a solution of 0.095 g of 7-amino-1-(2-(4-((2,3-dihydro(1,4)dioxino(2,3-c)pyridin-7-ylmethyl)amino)piperidin-1-yl)ethyl)-1,5-naphthyridin-2(1H)-one in 3 mL of ethanol and 2 mL of ethyl acetate, 4 mL of a 2 mol/L hydrogen chloride/ethanol solution was added at room temperature, and the mixture was stirred at room temperature for 20 minutes, and the solvent was distilled off under reduced pressure. To the residue, 8 mL of diethyl ether was added, the residue was suspended therein, and the solid was filtered off to obtain 0.41 g of 7-amino-1-(2-(4-((2,3-dihydro(1,4)dioxino(2,3-c)pyridin-7-ylmethyl)amino)piperidin-1-yl)ethyl)-1,5-naphthyridin-2(1H)-one hydrochloride as a yellow solid.

$^1$H-NMR (CDCl$_3$) δ: 2.02-2.12 (2H, m), 2.56 (2H, d, J=13.3 Hz), 3.28 (2H, t, J=10.5 Hz), 3.62 (2H, t, J=6.0 Hz), 3.69-3.76 (1H, m), 3.98-4.05 (2H, m), 4.44-4.49 (4H, m), 4.54-4.58 (2H, m), 4.71 (2H, t, J=6.0 Hz), 6.83 (1H, d, J=9.6 Hz), 7.37 (1H, s), 7.48 (1H, d, J=2.3 Hz), 7.99 (1H, d, J=9.6 Hz), 8.18 (1H, d, J=2.3 Hz), 8.31 (1H, s)

INDUSTRIAL APPLICABILITY

The present heterocyclic compound or salt thereof has strong antimicrobial activity and high safety and is therefore useful as an excellent antimicrobial agent.

The invention claimed is:

1. A compound represented by a formula (2):

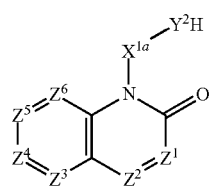

(2)

wherein
$X^{1a}$ denotes an optionally substituted $C_1$-$C_3$ alkylene group;
$Y^2$ denotes an optionally protected carbonyl group;
$Z^1$ is $CR^7$,
$Z^2$, $Z^3$, $Z^4$, $Z^5$ and $Z^6$ are the same or different and are each a nitrogen atom or a group represented by a formula $CR^7$, provided that at least one of $Z^3$, $Z^4$, $Z^5$ and $Z^6$ is a nitrogen atom,
wherein $R^7$ denotes a hydrogen atom, a halogen atom, a hydroxyl group, a cyano group, a nitro group, a formyl group, an optionally protected or substituted amino group, an optionally substituted lower alkyl, cycloalkyl, aryl, lower alkoxy, cycloalkyloxy, aralkyloxy, alkanoyl, ureido or monocyclic heterocyclic group, or a group represented by a formula $Q^1CONR^8R^9$, $Q^1CO_2R^{10}$ or $Q^1CN$, wherein $R^8$ and $R^9$ are the same or different and are each a hydrogen atom, an optionally substituted lower alkyl, cycloalkyl, aralkyl, aryl, lower alkoxy, alkanesulfonyl or monocyclic heterocyclic group, or form, together with the nitrogen atom to which $R^8$ and $R^9$ bind, an optionally substituted cyclic amino group; $R^{10}$ denotes a hydrogen atom or a carboxyl-protecting group; and $Q^1$ denotes an optionally substituted lower alkylene or lower alkenylene group or a bond.

2. The compound according to claim 1, wherein $Z^1$ is a group represented by a formula $CR^{7a}$,
wherein $R^{7a}$ denotes a hydrogen atom, a halogen atom, a hydroxyl group or an optionally substituted lower alkyl or lower alkoxy group.

3. The compound according to claim 1, wherein $X^{1a}$ is a methylene group; and $Y^2$ is a carbonyl group.

4. The compound according to claim 1, wherein $Z^1$, $Z^2$ and $Z^4$ are each CH; $Z^3$ is a nitrogen atom; $Z^5$ is a group represented by the formula $CR^{7d}$ (where $R^{7d}$ is a halogen atom or an optionally substituted lower alkyl or lower alkoxy group); and $Z^6$ is a nitrogen atom or CH.

5. The compound according to claim 1, wherein $Z^5$ is a group represented by the formula $CR^{7e}$,
wherein $R^{7e}$ is a halogen atom, a lower alkyl group or a lower alkoxy group.

6. A compound which is (7-fluoro-2-oxo-1,5-naphthyridin-1(2H)-yl)acetaldehyde.

* * * * *